US012221610B2

(12) United States Patent
Li et al.

(10) Patent No.: US 12,221,610 B2
(45) Date of Patent: Feb. 11, 2025

(54) **RNAi AGENTS FOR INHIBITING EXPRESSION OF HIF-2 ALPHA (*EPAS1*), COMPOSITIONS THEREOF, AND METHODS OF USE**

(71) Applicant: Arrowhead Pharmaceuticals, Inc., Pasadena, CA (US)

(72) Inventors: Zhen Li, San Diego, CA (US); Dongxu Shu, Madison, WI (US); Anthony Nicholas, Oregon, WI (US); Rui Zhu, San Diego, CA (US); Jeffrey Carlson, Madison, WI (US); So Wong, Oregon, WI (US); Xiaokai Li, Middleton, WI (US); Erich Altenhofer, Madison, WI (US); Matthew Fowler-Watters, Madison, WI (US); Bo Chen, Scarsdale, NY (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 887 days.

(21) Appl. No.: 17/420,460

(22) PCT Filed: Jan. 8, 2020

(86) PCT No.: PCT/US2020/012775

§ 371 (c)(1),
(2) Date: Jul. 2, 2021

(87) PCT Pub. No.: WO2020/146521

PCT Pub. Date: Jul. 16, 2020

(65) Prior Publication Data

US 2022/0204976 A1 Jun. 30, 2022

Related U.S. Application Data

(60) Provisional application No. 62/839,381, filed on Apr. 26, 2019, provisional application No. 62/827,564, filed on Apr. 1, 2019, provisional application No. 62/790,360, filed on Jan. 9, 2019.

(51) Int. Cl.

| | |
|---|---|
| ***C12N 15/11*** | (2006.01) |
| ***A61P 35/00*** | (2006.01) |
| ***C12N 15/113*** | (2010.01) |

(52) U.S. Cl.

CPC .......... *C12N 15/1138* (2013.01); *A61P 35/00* (2018.01); *C12N 2310/14* (2013.01); *C12N 2310/351* (2013.01); *C12N 2320/30* (2013.01)

(58) Field of Classification Search

None

See application file for complete search history.

(56) References Cited

U.S. PATENT DOCUMENTS

| | | | |
|---|---|---|---|
| 4,522,811 | A | 6/1985 | Eppstein et al. |
| 5,030,453 | A | 7/1991 | Lenk et al. |
| 5,962,016 | A | 10/1999 | Willis |
| 5,998,203 | A | 12/1999 | Matulic-adamic et al. |
| 6,017,926 | A | 1/2000 | Askew et al. |
| 6,680,068 | B2 | 1/2004 | Campbell et al. |
| 8,084,599 | B2 | 12/2011 | Rossi et al. |
| 8,084,600 | B2 | 12/2011 | Natt et al. |
| 8,097,716 | B2 | 1/2012 | Weiler et al. |
| 8,114,983 | B2 | 2/2012 | Davis et al. |
| 8,344,128 | B2 | 1/2013 | Natt et al. |
| 8,349,809 | B2 | 1/2013 | Brown |
| 8,513,207 | B2 | 8/2013 | Brown |
| 8,741,868 | B2 | 6/2014 | Chun et al. |
| 8,802,773 | B2 | 8/2014 | Rozema et al. |
| 9,487,556 | B2 | 11/2016 | Cheng et al. |
| 9,868,949 | B2 | 1/2018 | Bettencourt |
| 9,976,141 | B2 | 5/2018 | Wong |
| 2003/0012812 | A1 | 1/2003 | Tormo et al. |
| 2003/0036787 | A1 | 2/2003 | Vladimir et al. |
| 2004/0038921 | A1 | 2/2004 | Kreutzer et al. |
| 2004/0204377 | A1 | 10/2004 | Rana |

(Continued)

FOREIGN PATENT DOCUMENTS

| | | | |
|---|---|---|---|
| EP | 2213738 | A2 | 4/2010 |
| WO | 1999031061 | A1 | 6/1999 |

(Continued)

OTHER PUBLICATIONS

International Search Report and Written Opinion of corresponding International Application No. PCT/US/20/12775, dated Jun. 15, 2020.

(Continued)

*Primary Examiner* — Ekaterina Poliakova-Georgantas
(74) *Attorney, Agent, or Firm* — Paul VanderVelde; Meibo Chen; Darrin Flanigan

(57) ABSTRACT

The present disclosure relates to RNAi agents, for example, double stranded RNAi agents, able to inhibit HIF-2 alpha (EPAS1) gene expression. Also disclosed are pharmaceutical compositions that include HIF-2 alpha RNAi agents and methods of use thereof. The HIF-2 alpha RNAi agents disclosed herein may be linked or conjugated to targeting ligands (such as compounds that have affinity for integrins, including alpha-v-beta-3 and alpha-v-beta-5 integrins) and pharmacokinetic (PK) enhancers, to facilitate the delivery to cells and tissues, including to clear cell renal cell carcinoma (ccRCC) cells and tumors. Delivery of compositions comprising the HIF-2 alpha RNAi agents in vivo provides for inhibition of HIF-2 alpha gene expression. The HIF-2 alpha RNAi agents can be used in methods of treatment of various diseases and disorders, including ccRCC.

20 Claims, 10 Drawing Sheets

Specification includes a Sequence Listing.

(56) References Cited

U.S. PATENT DOCUMENTS

2006/0240093 A1 10/2006 Maclachlan et al.
2007/0039072 A1 2/2007 Khvorova et al.
2007/0135372 A1 6/2007 Maclachlan et al.
2008/0113351 A1 5/2008 Naito et al.
2008/0188430 A1 8/2008 Usman et al.
2009/0209626 A1 8/2009 Khvorova et al.
2010/0010071 A1 1/2010 Davis et al.
2011/0213008 A1 9/2011 Nakajima et al.
2012/0172412 A1 7/2012 Rozema et al.
2013/0236531 A1 9/2013 Chun et al.
2014/0303232 A1 10/2014 Baryza et al.
2015/0045573 A1 2/2015 Cheng et al.
2016/0272970 A1 9/2016 Rozema
2016/0348107 A1 12/2016 Wong et al.

FOREIGN PATENT DOCUMENTS

WO 2000044914 A1 8/2000
WO 2000053722 A2 9/2000
WO 2001068836 A2 9/2001
WO 2002100435 A1 12/2002
WO 2003015757 A1 12/2003
WO 2004002453 A2 1/2004
WO 2004029213 A2 4/2004
WO 2005021749 A1 3/2005
WO 2006020768 A2 2/2006
WO 2007107162 A2 9/2007
WO 2007128477 A2 11/2007
WO 2008022309 A2 2/2008
WO 2008147824 A2 12/2008
WO 2009082817 A1 7/2009
WO 2009114836 A1 9/2009
WO 2009117531 A1 9/2009
WO 2009123764 A2 10/2009
WO 2011076807 A2 6/2011
WO 2011104169 A1 9/2011
WO 2012083046 A2 6/2012
WO 2012083185 A2 6/2012
WO 2012174224 A2 12/2012
WO 2013032829 A1 3/2013
WO 2013158141 A1 10/2013
WO 2014134255 A2 9/2014
WO 2015021092 A1 2/2015
WO 2016196239 A1 12/2016
WO 2019161213 A1 8/2019
WO 2019210200 A1 10/2019

OTHER PUBLICATIONS

Bangoura et al.; "Expression of HIF-2α/EPAS1 in hepatocellular carcinoma"; World J. Gastroenterol; 2004; 10(4):525-530.

Bernstein et al.; "Role for a bidentate ribonuclease in the initiation step of RNA interference"; Nature; 2001; vol. 409:363-366.

Bertout et al.; "HIF2alpha inhibition promotes p53 pathway activity, tumor cell death, and radiation responses," Proceedings of the National Academy of Sciences; Aug. 25, 2009; vol. 206, No. 34, pp. 14391-14396.

Brooks, et al., "Integrin αvβ3 Antagonists Promote Tumor Regression by Inducing Apoptosis of Angiogenic Blood Vessels"; 79 Cell 1157-1164 (1994).

Burgin, et al.; "Chemically Modified Hammerhead Ribozymes with Improved Catalytic Rates" Biochemistry; 1996; 35:14090-14097.

Caplen, et al.; "Specific inhibition of gene expression by small double-stranded RNAs in invertebrate and vertebrate systems"; PNAS; 2001; 98: 9742-9747.

Chu and Rana; "Potent RNAi by short RNA triggers" 2008; RNA 14: 1714-1719.

Cleven, et al.; "Stromal expression of hypoxia regulated proteins is an adverse prognostic factor in colorectal carcinomas" Cellular Oncology; 29 (2007) 229-240.

Coleman, et al., "Nonpeptide αvβ3 Antagonists. Part 11: Discovery and Preclinical Evaluation of Potent αvβ3 Antagonists for the Prevention and Treatment of Osteoporosis"; J. Med. Chem.; 2004; 47, 4829-4837.

Covello, et al.; HIF-2α regulates Oct-4: effects of hypoxia on stem cell function, embryonic development, and tumor growth; 2006; Genes Dev. 20: 557-570.

Czauderna, et al.; "Structural variations and stablising modifications of synthetic siRNAs in mammalian cells"; Nucleic Acids Res.; 2003, 31(11), 2705-16.

Desgrosellier, JS et al., "Integrins in cancer: biological implications and therapeutic opportunities"; Nat Rev Cancer, 10(1):9-22 (2010).

Donze and Picard; "RNA interference in mammalian cells using siRNAs synthesized with T7 RNA polymerase"; Nucleic Acids Research; 2002; vol. 30, No. 10 e46.

Dowler, et al.; "Improvements in siRNA properties mediated by 2?-deoxy-2 ?-fluoro-B-D-arabinonucleic acid (FANA)"; Nucleic Acids Research; 2006; vol. 34, No. 6; 1669-1675.

Duxbury, et al.; "Retrovirally mediated RNA interference targeting the M2 subunit of ribonucleotide reductase: A novel therapeutic strategy in pancreatic cancer"; Surgery; 2004; 261-269.

Elbashir, et al.; "Duplexes of 21-nucleotide RNAs mediate RNA interference in cultured mammalian cells"; Nature; vol. 411; 494-498; 2001.

Elbashir, et al.; "Functional anatomy of siRNAs for mediating efficient RNAi in *Drosophila melanogaster* embryo lysate"; The EMBO Journal; vol. 20 No. 23; pp. 6877-6888; 2001.

Elbashir, et al.; "RNA interference is mediated by 21- and 22-nucleotide RNAs"; Genes & Development; 15:188-200; 2001.

Ema, et al.; "A novel bHLH-PAS factor with close sequence similarity to hypoxia-inducible factor 1α regulates the VEGF expression and is potentially involved in lung and vascular development"; Proc. Natl. Acad. Sci. USA; vol. 94: 4273-4278; 1997.

Farhood, et al.; "The role of dioleoyl phosphatidylethanolamine in cationic liposome mediated gene transfer"; Biochimica et Biophysica Acta; 1235; 1995; 289-295.

Flamme, et al.; "HRF, a putative basic helix-loop-helix-PAS-domain transcription factor is closely related to hypoxia-inducible factor-1α and developmentally expressed in blood vessels"; Mechanisms of Development; 63; 1997; 51-60.

Florczyk, et al.; "Opposite effects of HIF-1α and HIF-2α on the regulation of IL-8 expression in endothelial cells"; Free Radical Biology & Medicine; 51; 2011; 1882-1892.

Gambling, et al.; "Estrogen and progesterone regulate α, β, and γENaC subunit mRNA levels in female rat kidney"; Kidney International; vol. 65; 2004; 1774-1781.

Gautier, et al.; "α-DNA IV: α-anomeric and β-anomeric tetrathymidylates covalently linked to intercalating oxazolopyridocarbazole. Synthesis, physicochemical properties and poly (rA) binding"; Nucleic Acids Research; vol. 15, No. 16; 1987; 6625-6641.

Giatromanolaki, et al.; "Hypoxia-inducible factors 1α and 2α are related to vascular endothelial growth factor expression and a poorer prognosis in nodular malignant melanomas of the skin"; Melanoma Research; 2003; 13:493-501.

Giatromanolaki, et al.; "Hypoxia-Inducible Factor-2α (HIF-2α) Induces Angiogenesis in Breast Carcinomas"; Appl Immunohistochem Mol Morphol; vol. 14, No. 1; 2006; 78-82.

Giatromanolaki, et al.; "Phosphorylated pVEGFR2/KDR receptor expression in uveal melanomas: relation with HIF2α and survival"; Clin Exp Meatastasis; 29: 11-7; 2012.

Gossage, et al. "VHL, the story of a tumour suppressor gene" Nature Reviews 2015 vol. 15:55-64.

Griffiths, et al.; "Hypoxia-associated markers in gastric carcinogenesis and HIF-2α in gastric and gastro-oesophageal cancer prognosis"; British Journal of Cancer; 2008; 98:965-973.

Guo, JianFei; "Tumor Angiogenesis in Lung Adenocarcinomas: Correlation with FDG Uptake and Prognosis"; J. Kanazawa Med. Univ.; 31: 10-16; 2006.

Henschel, et al.; "DEQOR: a web-based tool for the design and quality control of siRNAs."; Nucleic Acids Research; vol. 32 (Web Server Issue): W113-W120); 2004.

(56) References Cited

OTHER PUBLICATIONS

Hogenesch, et al.; "Characterization of a Subset of the Basic-Helix-Loop-Helix-PAS Superfamily That Interacts with Components of the Dioxin Signaling Pathway"; The Journal of Biological Chemistry; vol. 272, No. 13; 1997.
Holmquist-Mengelbier, et al.; "Recruitment of HIF-1α and HIF-2α to common target genes is differentially regulated in neuroblastoma: HIF-2α promotes an aggressive phenotype"; Cancer Cell; 10: 413-23; 2006.
Horton, MA, "The αvβ3 Integrin 'vitronectin receptor'"; Int. J. Biochem. Cell Biol.; vol. 29, No. 5, pp. 721-725; 1997.
Hutvagner, et al.; "A Cellular Function for the RNA-Interference Enzyme Dicer in the Maturation of the let-7 Small Temporal RNA"; Science; 293: 834; 2001.
Inoue, et al.; "Synthesis and hybridization studies on two complementary nona(2'-O-methyl)ribonucleotides"; Nucleic Acids Res.; 15: 6131-6148; 1987.
Inoue, et al.; "Sequence-dependent hydrolysis of RNA using modified oligonucleotide splints and RNase H"; FEBS Lett.; 215: 327-330; 1987.
Ioachim, et al.; "Hypoxia-Inducible Factors HIF-1α and HIF-2α Expression in Bladder Cancer and Their Associations with Other Angiogenesis-Related Proteins"; Urol. Int.; 77: 255-263; 2006.
Jiang, et al.; "Dimerization, DNA Binding, and Transactivation Properties of Hypoxia-inducible Factor 1*"; J. Biol. Chem.; 271: 17771-17778; 1996.
Kamlah, F, et al.; "Intravenous injection of 1-12, 15 siRNA directed against hypoxia-inducible factors prolongs survival in a Lewis lung carcinoma cancer model"; Cancer Gene Therapy; vol. 16, No. 3; Mar. 1, 2009; pp. 195-205.
Kapp T. et al.; "A Comprehensive Evaluation of the Activity and Selectivity Profile of Ligands for RGD-binding Integrins"; Nature Scientific Reports; vol. 7; 1-13; 2017.
Ke, et al; Association Between Diversity of Hypoxia at Different Altitude and the Polymorphism of EPAS1 Gene; Clin J Med Genet; Oct. 2011, vol. 28, No. 6; 583-588.
Koh, et al.; "The Hypoxia-Associated Factor Switches Cells from HIF-1α-to HIF-2 α-Dependent Signaling Promoting Stem Cell Characteristics, Aggressive Tumor Growth and Invasion"; Cancer Research; 71:4015-4027; 2011.
Koh, et al. "Hypoxia-Induced SUMOylation of E3 Ligase HAF Determines Specific Activation of HIF2 in Clear-Cell Renal Cell Carcinoma" Cancer Research 75(2):316-329; 2015.
Kondo, et al.; "Inhibition of HIF is necessary for tumor suppression by the von Hippel-Lindau protein"; Cancer Cell; 1:237-246; 2002.
Kondo, et al.; "Inhibition of HIF2α Is Sufficient to Suppress pVHL-Defective Tumor Growth"; PLoS Biology; 1:439-444; 2003.
Kraynack, et al.; "Small interfering RNAs containing full 2'-O-methylribonucleotide-modified sense strands display Argonaute2/elF2C2-dependent activity"; RNA ; 12:163-176; 2006.
Ley, et al., "Integrin-based therapeutics: biological basis, clinical use and new drugs"; 15(3) Nat. Rev. Drug Discov.; vol. 15; pp. 173-183 (2016).
Loakes, David; "The applications of universal DNA base analogues"; Nucleic Acids Research; vol. 29, No. 12: 2437-2447; 2001.
Mas-Moruno, et al., "Cilengitide: The First Anti-Angiogenic Small Molecule Drug Candidate. Design, Synthesis and Clinical Evaluation"; Anticancer Agents Med Chem, 10:753-768; 2010.
Maynard, et al.; "The role of hypoxia-inducible factors in cancer"; Cell. Mol. Life Sci.; 64:2170-2180; 2007.
McCaffrey et al.; RNA interference in adult mice; Nature; vol. 418; Jul. 4, 2002; pp. 38-39.
Miller, et al.; "Liposome-Cell Interactions in Vitro: Effect of Liposome Surfact Charge on the Binding and Endocytosis of Conventional and Sterically Stabilized Liposomes"; Biochemistry; 1998; 37:12875-12883.
Monera, et al.; "Relationship of Sidechain Hydrophobicity and α-Helical Propensity on the Stability of the Single-stranded Amphipathic α-Helix"; Journal of Peptide Science; (1995) 1, 319-329.
Mutter, et al.; "Molecular mechanisms of preeclampsia"; Microvascular Research; 75; (2008) 1-8.
Nesbit, et al.; "MYC oncogenes and human neoplastic disease"; Oncogene; 1999; 18:3004-3016.
Nykanen, et al.; "ATP Requirements and Small Interfering RNA Structure in the RNA Interference Pathway"; Cell; vol. 107; 309-321; 2001.
Osada, et al.; "Expression of hypoxia-inducible factor 1α, hypoxia-inducible factor 2α, and von Hippel-Lindau protein in epithelial ovarian neoplasms and allelic loss of von Hippel-Lindau gene: nuclear expression of hypoxia-inducible factor 1α is an independent prognostic factor in ovarian carcinoma"; Human Pathology; 2007; 38:1310-1320.
Ovcharenko, D; "Efficient delivery of siRNAs to human primary cells."; Ambion TechNotes; 10 (5):15-16; 2003.
Parrish, et al.; "Functional Anatomy of a dsRNA Trigger: Differential Requirement for the Two Trigger Strands in RNA Interference"; Molecular Cell; 6:1077-1087; 2000.
Pelengaris, et al.; Reversible Activation of c-Myc in Skin: Induction of a Complex Neoplastic Phenotype by a Single Oncogenic Lesion; Colecular Cell; vol. 3; 565-577; 1999.
Pelengaris, et al.; "c-MYC: More Than Just a Matter of Life and Death"; Nature; 2:764-776; 2002.
Rasheed, et al.; "Hypoxia-inducible factor-1α and -2α are expressed in most rectal cancers but only hypoxia-inducible factor-1α is associated with prognosis"; British Journal of Cancer; 100:1666-1673; 2009.
Predicted: Pan paniscus endothelial PAS domain protein 1 (EPAS1), mRNA. Accession: XM_003822658, Version: XM_003822658.2, Data retrieved from NCBI Blast on Nov. 11, 2021.
Riches, AG et al.; "Scalable synthesis of an integrin-binding peptide mimetic for biomedical applications"; Tetrahedron (2012) 68, p. 9448-9455.
Roda, Julie, et al: "Hypoxia-inducible factor-2[alpha] regulates GM-CSF-derived soluble vascular endothelial growth factor receptor 1 production from macrophages and inhibits tumor growth and angiogenesis.", Journal of Immunology (Baltimore, MD.: 1950) Aug. 15, 2011, vol. 187, No. 4, Aug. 15, 2011 (Aug. 15, 2011), pp. 1970-1976.
Ross, et al., "Bone-Induced Expression of Integrin beta-3 Enables Targeted Nanotherapy of Breast Cancer Metastases", Cancer Research; vol. 77(22); pp. 6303-6313; 2017.
Rozema, DB et al. "Protease-triggered siRNA Delivery Vehicles."; J Control Release. 2015 vol. 209:57-66.
Schiffelers, et al.; "Cancer siRNA therapy by tumor selective delivery with ligand-targeted sterically stabilized nanoparticle"; Nucl. Acids Res.; 32: el49, 1-10; 2004.
Scortegagna, et al.; "Multiple organ pathology, metabolic abnormalities and impaired homeostasis of reactive oxygen species in Epas1-/- mice"; Nat. Genet.; vol. 35; No. 4; 331-340; 2003.
Sharp, Phillip A..; "RNA interference-2001"; Genes & Development; 15:485-490; 2001.
Sioud and Sorensen; "Cationic liposome-mediated delivery of siRNAs in adult mice"; Biochemical and Biophysical Research Communications; 312 (2003), 1220-12253.
Sioud, Mouldy; "Induction of Inflammatory Cytokines and Interferon Responses by Double-stranded and Single- stranded siRNAs is Sequence-dependent and Requires Endosomal Localization"; J. Mol. Biol.; 348:1079-1090; 2005.
Smith, et al.; "The human side of hypoxia-inducible factor"; Br. J. Haematol.; 141:325-34; 2008.
Song, et al.; "RNA interference targeting Fas protects mice from fulminant hepatitis"; (Nat Med. published online (Feb. 10, 2003; corrected Feb. 18, 2003) doi: 10.1038/nm828.
Song, et al.; "Antibody mediated in vivo delivery of small interfering RNAs via cell-surface receptors"; Nature Biotechnology; 23:709-717; 2005.
Sun, et al.; "Asymmetric RNA duplexes mediate RNA interference in mammalian cells"; Nature Biotechnology; 26:1379-1382; 2008.
Tian, et al.; "The hypoxia-responsive transcription factor EPAS1 is essential for catecholamine homeostasis and protection against heart failure during embryonic development"; Genes & Development; 12:3320-3324; 1998.

(56) References Cited

OTHER PUBLICATIONS

Usman and Cedergren; "Exploiting the chemical synthesis of RNA"; TIBS; 17:334-339; 1992.
Usman, et al.; "Chemical modification of hammerhead ribozymes: activity and nuclease resistance"; Nucleic Acids Symposium Series; No. 31: 163-164; 1994.
Van Patot, et al.; "Hypoxia: Adapting to High Altitude by Mutating EPAS-1, the Gene Encoding HIF-2α"; High Altitude Medicine & Biology; vol. 12, No. 2; 157-67; 2011.
Veeranna, et al.; "Kaposi's Sarcoma-Associated Herpesvirus Latency-Associated Nuclear Antigen Induction by Hypoxia and Hypoxia-Inducible Factors"; Journal of Virology; 1097-1108; 2012.
Wallace, et al., "Multi-Kiloscale Enantioselective Synthesis of a Vitronectin Receptor Antagonist", Organic Process Research & Development; vol. 8; pp. 738-743; (2004).
Wang, et al.; "Hypoxia-inducible factor 1 is a basic-helix-loop-helix-PAS heterodimer regulated by cellular O2 tension"; Proc. Natl. Acad. Sci. USA; 92:5510-14; 1995.
Xu, et al.; "Epigenetic regulation of HIF-1α in renal cancer cells involves HIF-1α/2α binding to a reverse hypoxia-response element"; Oncogene; 31:1065-72; 2012.
Yamato, et al.; "Enhanced specificity of HPV16 E6E7 siRNA by RNA-DNA chimera modification"; Cancer Gene Therapy; 18:587-597; 2011.
Zajac, et al., "An Application of Borane As a Protecting Group for Pyridine"; J. Org. Chem.; vol. 73; p. 6901; 2008.
Zimmer, et al.; "Inhibition of Hypoxia-Inducible Factor Is Sufficient for Growth Suppression of VHL-/- Tumors"; Molecular Cancer Research; 2:89-95; 2004.
GenBank NM_001430.4; 2018.

AD05971

Sense Strand (5' → 3')  (AM07939-SS)
Antisense Strand (3' ← 5')  (AM05815-AS)

AD06153

Sense Strand (5' → 3')  (AM08125-SS)
Antisense Strand (3' ← 5')  (AM07555-AS)

AD06157

Sense Strand (5' → 3')  (AM08129-SS)
Antisense Strand (3' ← 5')  (AM07745-AS)

SEQUENCE LISTING

```
<160> NUMBER OF SEQ ID NOS: 1049

<210> SEQ ID NO 1
<211> LENGTH: 5184
<212> TYPE: DNA
<213> ORGANISM: Artificial sequence
<220> FEATURE:
<223> OTHER INFORMATION: Homo Sapiens Endothelial PAS Domain Protein 1
      (EPAS1 or HIF-2 alpha), transcript, GenBank NM_001430.4

<400> SEQUENCE: 1

gctttacact cgcgagcgga ccgccacacg ggtccggtgc ccgctgcgct tccgccccag     60

cgctcctgag gcggccgtac aatcctcggc agtgtcctga gactgtatgg tcagctcagc    120

ccggcctccg actccttccg actcccagca ttcgagccac tttttttttt ctttgaaaac    180

tcagaaaagt gactcctttt ccagggaaaa aggaacttgg gttcccttct ctccgtcctc    240

ttttcgggtc tgacagcctc cacccactcc ttccccggac cccgcctccg cgcgcaggtt    300

cctcccagtc acctttctcc acccccgccc ccgcacctag cccgccgcgc gccaccttcc    360

acctgactgc gcggggcgct cgggacctgc gcgcacctcg gaccttcacc acccgcccgg    420

gccgcgggga gcggacgagg gccacagccc cccacccgcc agggagccca ggtgctcggc    480

gtctgaacgt ctcaaagggc cacagcgaca atgacagctg acaaggagaa gaaaaggagt    540

agctcggaga ggaggaagga gaagtcccgg gatgctgcgc ggtgccggcg gagcaaggag    600

acggaggtgt tctatgagct ggcccatgag ctgcctctgc cccacagtgt gagctcccat    660

ctggacaagg cctccatcat gcgactggca atcagcttcc tgcgaacaca caagctcctc    720

tcctcagttt gctctgaaaa cgagtccgaa gccgaagctg accagcagat ggacaacttg    780

tacctgaaag ccttggaggg tttcattgcc gtggtgaccc aagatggcga catgatcttt    840

ctgtcagaaa acatcagcaa gttcatggga cttacacagg tggagctaac aggacatagt    900

atctttgact tcactcatcc ctgcgaccat gaggagattc gtgagaacct gagtctcaaa    960

aatggctctg gttttgggaa aaaaagcaaa gacatgtcca cagagcggga cttcttcatg   1020

aggatgaagt gcacggtcac caacagaggc cgtactgtca acctcaagtc agccacctgg   1080

aaggtcttgc actgcacggg ccaggtgaaa gtctacaaca actgccctcc tcacaatagt   1140

ctgtgtggct acaaggagcc cctgctgtcc tgcctcatca tcatgtgtga accaatccag   1200

cacccatccc acatggacat ccccctggat agcaagacct tcctgagccg ccacagcatg   1260

gacatgaagt tcacctactg tgatgacaga atcacagaac tgattggtta ccaccctgag   1320

gagctgcttg gccgctcagc ctatgaattc taccatgcgc tagactccga gaacatgacc   1380

aagagtcacc agaacttgtg caccaagggt caggtagtaa gtggccagta ccggatgctc   1440
```

-continued

```
gcaaagcatg ggggctacgt gtggctggag acccagggga cggtcatcta caaccctcgc   1500
aacctgcagc cccagtgcat catgtgtgtc aactacgtcc tgagtgagat tgagaagaat   1560
gacgtggtgt tctccatgga ccagactgaa tccctgttca agccccacct gatggccatg   1620
aacagcatct ttgatagcag tggcaagggg gctgtgtctg agaagagtaa cttcctattc   1680
accaagctaa aggaggagcc cgaggagctg gcccagctgg ctcccacccc aggagacgcc   1740
atcatctctc tggatttcgg gaatcagaac ttcgaggagt cctcagccta tggcaaggcc   1800
atcctgcccc cgagccagcc atgggccacg gagttgagga gccacagcac ccagagcgag   1860
gctgggagcc tgcctgcctt caccgtgccc caggcagctg ccccgggcag caccaccccc   1920
agtgccacca gcagcagcag cagctgctcc acgcccaata gccctgaaga ctattacaca   1980
tctttggata acgacctgaa gattgaagtg attgagaagc tcttcgccat ggacacagag   2040
gccaaggacc aatgcagtac ccagacggat ttcaatgagc tggacttgga gacactggca   2100
ccctatatcc ccatggacgg ggaagacttc cagctaagcc ccatctgccc cgaggagcgg   2160
ctcttggcgg agaacccaca gtccaccccc cagcactgct tcagtgccat gacaaacatc   2220
ttccagccac tggcccctgt agccccgcac agtcccttcc tcctggacaa gtttcagcag   2280
cagctggaga gcaagaagac agagcccgag caccggccca tgtcctccat cttctttgat   2340
gccggaagca aagcatccct gccaccgtgc tgtggccagg ccagcacccc tctctcttcc   2400
atgggggggca gatccaatac ccagtggccc ccagatccac cattacattt tgggcccaca   2460
aagtgggccg tcggggatca gcgcacagag ttcttgggag cagcgccgtt ggggcccccct   2520
gtctctccac cccatgtctc caccttcaag acaaggtctg caaagggttt tggggctcga   2580
ggcccagacg tgctgagtcc ggccatggta gccctctcca acaagctgaa gctgaagcga   2640
cagctggagt atgaagagca agccttccag gacctgagcg gggggggaccc acctggtggc   2700
agcacctcac atttgatgtg gaaacggatg aagaacctca ggggtgggag ctgccctttg   2760
atgccggaca agccactgag cgcaaatgta cccaatgata agttcaccca aaaccccatg   2820
aggggcctgg gccatcccct gagacatctg ccgctgccac agcctccatc tgccatcagt   2880
cccggggaga acagcaagag caggttcccc ccacagtgct acgccaccca gtaccaggac   2940
tacagcctgt cgtcagccca caaggtgtca ggcatggcaa gccggctgct cgggccctca   3000
tttgagtcct acctgctgcc cgaactgacc agatatgact gtgaggtgaa cgtgcccgtg   3060
ctgggaagct ccacgctcct gcaaggaggg gacctcctca gagccctgga ccaggccacc   3120
tgagccaggc cttctacctg ggcagcacct ctgccgacgc cgtcccacca gcttcactct   3180
ctccgtctgt tttgcaact aggtatttct aacgccagca cactatttac aagatggact   3240
tacctggcag acttgcccag gtcaccaagc agtggccttt ttctgagatg ctcactttat   3300
tatccctatt tttaaagtac acaattgttt tacctgttct gaaatgttct taaattttgt   3360
aggatttttt tcctccccac cttcaatgac ttctaattta tattatccat aggtttctct   3420
ccctccttct ccttctcaca cacaactgtc catactaaca agtttggtgc atgtctgttc   3480
ttctgtaggg agaagcttta gcttcatttt actaaaaaga ttcctcgtta ttgttgttgc   3540
caaagagaaa caaaaatgat tttgctttcc aagcttggtt tgtggcgtct ccctcgcaga   3600
gcccttctcg tttcttttt aaactaatca ccatattgta aatttcaggg tttttttttt   3660
tttgtttaag ctgactcttt gctctaattt tggaaaaaaa gaaatgtgaa gggtcaactc   3720
caacgtatgt ggttatctgt gaaagttgca cagcgtggct tttcctaaac tggtgttttt   3780
cccccgcatt tggtggattt tttattatta ttcaaaaaca taactgagtt ttttaaaaga   3840
```

ggagaaaatt tatatctggg ttaagtgttt atcatatata tgggtacttt gtaatatcta 3900
aaaacttaga aacggaaatg gaatcctgct cacaaaatca ctttaagatc ttttcgaagc 3960
tgttaatttt tcttagtgtt gtggacactg cagacttgtc cagtgctccc acggcctgta 4020
cggacactgt ggaaggcctc cctctgtcgg ctttttgcca tctgtgatat gccataggtg 4080
tgacaatccg agcagtggag tcattcagcg ggagcactgc gcgctatccc ctcacattct 4140
ctatgtacta tgtatgtatg tattattatt attgctgcca agagggtctg atggcacgtt 4200
gtggggtcgg ggggtggggc ggggaagtgc tctaactttt cttaaggttt tgttgctagc 4260
ccttcaagtg cactgagcta tgtgactcgg atggtctttc acacggcaca tttggacatt 4320
tccagaacta ccatgagatg gtttagacgg gaattcatgc aaatgagggg tcaaaaatgg 4380
tatagtgacc ccgtccacgt cctccaagct cacgaccttg gagccccgtg gagctggact 4440
gaggaggagg ctgcacagcg ggagagcagc tggtccagac cagccctgca gcccccactc 4500
agccggcagc cagatggccc cgcaaggcct ccagggatgg cccctagcca caggccctgg 4560
ctgaggtctc tgggtcggtc agtgacatgt aggtaggaag cactgaaaat agtgttccca 4620
gagcactttg caactccctg ggtaagaggg acgacacctc tggtttttca ataccaatta 4680
catggaactt ttctgtaatg ggtacaatga agaagtttct aaaaacacac acaaagcaca 4740
ttgggccaac tatttagtaa gcccggatag acttattgcc aaaaacaaaa aatagctttc 4800
aaaagaaatt taagttctat gagaaattcc ttagtcatgg tgttgcgtaa atcatatttt 4860
agctgcacgg cattacccca cacagggtgg cagaacttga agggttactg acgtgtaaat 4920
gctggtattt gatttcctgt gtgtgttgcc ctggcattaa gggcatttta cccttgcagt 4980
tttactaaaa cactgaaaaa tattccaagc ttcatattaa ccctacctgt caacgtaacg 5040
atttcatgaa cgttattata ttgtcgaatt cctactgaca acattataac tgtatgggag 5100
cttaacttta taaggaaatg tattttgaca ctggtatctt attaaagtat tctgatccta 5160
ccactgaaaa aaaaaaaaaa aaaa 5184

<210> SEQ ID NO 2
<211> LENGTH: 19
<212> TYPE: RNA
<213> ORGANISM: Artificial sequence
<220> FEATURE:
<223> OTHER INFORMATION: Hif2-alpha mRNA (gene transcript) target sequence

<400> SEQUENCE: 2
acguaacgau uucaugaac 19

<210> SEQ ID NO 3
<211> LENGTH: 19
<212> TYPE: RNA
<213> ORGANISM: Artificial sequence
<220> FEATURE:
<223> OTHER INFORMATION: Hif2-alpha mRNA (gene transcript) target sequence

<400> SEQUENCE: 3
acaacugucc auacuaaca 19

<210> SEQ ID NO 4
<211> LENGTH: 19
<212> TYPE: RNA
<213> ORGANISM: Artificial sequence
<220> FEATURE:

<223> OTHER INFORMATION: Hif2-alpha mRNA (gene transcript) target
      sequence

<400> SEQUENCE: 4
cauucucuau guacuaugu 19

<210> SEQ ID NO 5
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 5
uuucaugaaa ucguuacgu 19

<210> SEQ ID NO 6
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 6
guucaugaaa ucguuacgu 19

<210> SEQ ID NO 7
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 7
auucaugaaa ucguuacgu 19

<210> SEQ ID NO 8
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 8
nuucaugaaa ucguuacgu 19

<210> SEQ ID NO 9
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 9
nuucaugaaa ucguuacgn 19

<210> SEQ ID NO 10
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 10
uguuaguaug gacaguugu 19

<210> SEQ ID NO 11
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 11
nguuaguaug gacaguugu 19

<210> SEQ ID NO 12
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 12
nguuaguaug gacaguugn 19

<210> SEQ ID NO 13
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 13
acauaguaca uagagaaug 19

<210> SEQ ID NO 14
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 14
ucauaguaca uagagaaug 19

<210> SEQ ID NO 15
<211> LENGTH: 19
<212> TYPE: RNA
<213> ORGANISM: Artificial sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 15
ncauaguaca uagagaaug 19

<210> SEQ ID NO 16
<211> LENGTH: 19
<212> TYPE: RNA
<213> ORGANISM: Artificial sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 16
ncauaguaca uagagaaun 19

<210> SEQ ID NO 17
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 17
acguaacgau uucaugaaa 19

<210> SEQ ID NO 18
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 18
acguaacgau uucaugaac 19

<210> SEQ ID NO 19
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 19
acguaacgau uucaugaau 19

<210> SEQ ID NO 20
<211> LENGTH: 19
<212> TYPE: RNA
<213> ORGANISM: Artificial sequence
<220> FEATURE:
<223> OTHER INFORMATION: RNAi agent sense strand core 19-mer base
sequence
<220> FEATURE:
<221> NAME/KEY: modified_base
<222> LOCATION: 19

<223> OTHER INFORMATION: n = any nucleobase

<400> SEQUENCE: 20
acguaacgau uucaugaan 19

<210> SEQ ID NO 21
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 21
ncguaacgau uucaugaan 19

<210> SEQ ID NO 22
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 22
acaacugucc auacuaaca 19

<210> SEQ ID NO 23
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 23
acaacugucc auacuaacn 19

<210> SEQ ID NO 24
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n =

<400> SEQUENCE: 24
ncaacugucc auacuaacn 19

<210> SEQ ID NO 25
<211> LENGTH: 19
<212> TYPE: RNA
<213> ORGANISM: Artificial sequence
<220> FEATURE:
<223> OTHER INFORMATION: RNAi agent sense strand core 19-mer base sequence

```
<400> SEQUENCE: 25

cauucucuau guacuaugu                                                 19


<210> SEQ ID NO 26
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 26

cauucucuau guacuauga                                                 19


<210> SEQ ID NO 27
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 27

cauucucuau guacuaugn                                                 19


<210> SEQ ID NO 28
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 28

nauucucuau guacuaugn                                                 19


<210> SEQ ID NO 29
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 29

uuucaugaaa ucguuacguu g                                              21


<210> SEQ ID NO 30
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 30

uuucaugaaa ucguuacguu g                                              21


<210> SEQ ID NO 31
<211> LENGTH: 21
<212> TYPE: RNA
```

<213> ORGANISM: Artificial sequence
<220> FEATURE:
<223> OTHER INFORMATION: RNAi agent antisense strand modified sequence

<400> SEQUENCE: 31
ugucaaagau acuaugucca g 21

<210> SEQ ID NO 32
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 32
uucucggagu cuagcgcaug g 21

<210> SEQ ID NO 33
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 33
uuugcgagca uccgguacug g 21

<210> SEQ ID NO 34
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 34
uuugcgaggg uuguagauga c 21

<210> SEQ ID NO 35
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 35
ucgaaguucu gauucccgaa g 21

<210> SEQ ID NO 36
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 36
uuucagggcu auugggcgug g 21

<210> SEQ ID NO 37
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 37
ugaaauccgu cuggguacug c 21

<210> SEQ ID NO 38
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 38
uaugcuuugc uuccggcauc 20

<210> SEQ ID NO 39
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 39
ugcuuguccg gcaucaaagg g 21

<210> SEQ ID NO 40
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 40
uuugcgcuca guggcuuguc c 21

<210> SEQ ID NO 41
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 41
uugacgacag gcuguagucc u 21

<210> SEQ ID NO 42
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 42
uagucugcca gguaaguccg 20

<210> SEQ ID NO 43
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 43
uuacguugga guugacccuu c 21

<210> SEQ ID NO 44
<211> LENGTH: 21
<212> TYPE: RNA
<213> ORGANISM: Artificial sequence
<220> FEATURE:

<223> OTHER INFORMATION: RNAi agent antisense strand modified sequence

<400> SEQUENCE: 44
uauacguugg aguugacccu g 21

<210> SEQ ID NO 45
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 45
uacauacguu ggaguugacc c 21

<210> SEQ ID NO 46
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 46
ugauaaccac auacguugga g 21

<210> SEQ ID NO 47
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 47
uggauuguca caccuauggc 20

<210> SEQ ID NO 48
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 48
uucggauugu cacaccuaug g 21

<210> SEQ ID NO 49
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 49
uacaacgugc caucagaccc 20

<210> SEQ ID NO 50
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 50
uauccgaguc acauagcuca g 21

-continued

<210> SEQ ID NO 51
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 51
uggugucguc ccucuuaccc 20

<210> SEQ ID NO 52
<211> LENGTH: 19
<212> TYPE: RNA
<213> ORGANISM: Artificial sequence
<220> FEATURE:
<223> OTHER INFORMATION: RNAi agent antisense strand modified sequence

<400> SEQUENCE: 52
uuuacguuga cagguaggg 19

<210> SEQ ID NO 53
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 53
uuuacguuga cagguagggu u 21

<210> SEQ ID NO 54
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 54
ucguuacguu gacagguagg g 21

<210> SEQ ID NO 55
<211> LENGTH: 20
<212> TYPE: RNA
<213> ORGANISM: Artificial sequence
<220> FEATURE:
<223> OTHER INFORMATION: RNAi agent antisense strand modified sequence

<400> SEQUENCE: 55
ucguuacguu gacagguagg 20

<210> SEQ ID NO 56
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 56
uaaaucguua cguugacagg u 21

<210> SEQ ID NO 57
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 57
uucguuuuca gagcaaacug c 21

<210> SEQ ID NO 58
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 58
aguuguugua gacuuucacc u 21

<210> SEQ ID NO 59
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 59
ucguuaucca aagauguguc c 21

<210> SEQ ID NO 60
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 60
aucacuucaa ucuucagguc g 21

<210> SEQ ID NO 61
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 61
uuuagcugga agucuucccg u 21

<210> SEQ ID NO 62
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 62
agauacuaug uccuguuagc u 21

<210> SEQ ID NO 63
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 63
uucaccucac agucauaucu g 21

<210> SEQ ID NO 64
<211> LENGTH: 21

<212> TYPE: RNA
<213> ORGANISM: Artificial sequence
<220> FEATURE:
<223> OTHER INFORMATION: RNAi agent antisense strand modified sequence

<400> SEQUENCE: 64
uguaaaacaa uuguguacuc c 21

<210> SEQ ID NO 65
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 65
ucacauacgu uggaguugac c 21

<210> SEQ ID NO 66
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 66
accacauacg uuggaguuga c 21

<210> SEQ ID NO 67
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 67
uauugucaca ccuauggcau c 21

<210> SEQ ID NO 68
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 68
aaaccaucuc augguaguuc c 21

<210> SEQ ID NO 69
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 69
ucuaaaccau cucaugguag c 21

<210> SEQ ID NO 70
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 70
aguuccaugu aauugguauc g 21

<210> SEQ ID NO 71
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 71
aucguuacgu ugacagguag g 21

<210> SEQ ID NO 72
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 72
uuucaugaaa ucguuacguu g 21

<210> SEQ ID NO 73
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 73
uuucaugaaa ucguuacguu g 21

<210> SEQ ID NO 74
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 74
uuucaugaaa ucguuacguu c 21

<210> SEQ ID NO 75
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 75
uuucaugaaa ucguuacguc c 21

<210> SEQ ID NO 76
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 76
uuucaugaaa ucguuacguc c 21

<210> SEQ ID NO 77
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 77
uuucaugaaa ucguuacguu g 21

<210> SEQ ID NO 78
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 78
aaggcuuuca gguacaaguu g 21

<210> SEQ ID NO 79
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 79
uuuagcucca ccuguguaag u 21

<210> SEQ ID NO 80
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 80
aagucaaaga uacuaugucc u 21

<210> SEQ ID NO 81
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 81
aguuacucuu cucagacaca g 21

<210> SEQ ID NO 82
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 82
uuuagcuugg ugaauaggaa g 21

<210> SEQ ID NO 83
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 83
aucuuguaaa uagugugcug g 21

<210> SEQ ID NO 84
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 84
uuguacuuua aaaauagggg c 21

<210> SEQ ID NO 85
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 85
agguaaaaca auuguguacu c 21

<210> SEQ ID NO 86
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 86
acuuguuagu auggacaguu g 21

<210> SEQ ID NO 87
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 87
ucaacuuuca cagauaacca c 21

<210> SEQ ID NO 88
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 88
uccauuuccg uuucuaaguu c 21

<210> SEQ ID NO 89
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 89
aaugacucca cugcucggau c 21

<210> SEQ ID NO 90
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 90
acauaguaca uagagaaugu g 21

<210> SEQ ID NO 91
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 91
ucuaccuaca ugucacugac c 21

<210> SEQ ID NO 92
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 92
ucaaugugcu uugugugugu c 21

<210> SEQ ID NO 93
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 93
uuggcaauaa gucuauccgg u 21

<210> SEQ ID NO 94
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 94
aggaauuucu cauagaacuu c 21

<210> SEQ ID NO 95
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 95
agcauuuaca cgucaguaac c 21

<210> SEQ ID NO 96
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 96
acguucauga aaucguuacg u 21

<210> SEQ ID NO 97

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 97
uaacguucau gaaaucguua c 21

<210> SEQ ID NO 98
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 98
auaacguuca ugaaaucguu c 21

<210> SEQ ID NO 99
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 99
uuccuuauaa aguuaagcuc c 21

<210> SEQ ID NO 100
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 100
uuucaugaaa ucguuacgu ug 21

<210> SEQ ID NO 101
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 101
uuucaugaaa ucguuacgu ug 21

<210> SEQ ID NO 102
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 102
uuucaugaaa ucguuacguu g 21

<210> SEQ ID NO 103
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 103
acauaguaca uagagaaugu c 21

<210> SEQ ID NO 104
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 104
acauaguaca uagagaaugc g 21

<210> SEQ ID NO 105
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 105
acauaguaca uagagaaugg g 21

<210> SEQ ID NO 106
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 106
acauaguaca uagagaaugc c 21

<210> SEQ ID NO 107
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 107
ugaaucuccu cauggucgcu u 21

<210> SEQ ID NO 108
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 108
ugaauucaua ggcugagcgu u 21

<210> SEQ ID NO 109
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 109
ucacuuacua ccugacccuu g 21

<210> SEQ ID NO 110
<211> LENGTH: 21
<212> TYPE: RNA
<213> ORGANISM: Artificial sequence
<220> FEATURE:

<223> OTHER INFORMATION: RNAi agent antisense strand modified sequence

<400> SEQUENCE: 110
ugcuugaaca gggauucagu c 21

<210> SEQ ID NO 111
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 111
agauguuugu cauggcacug a 21

<210> SEQ ID NO 112
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 112
uccacaucaa augugaggug c 21

<210> SEQ ID NO 113
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 113
uguuaguaug gacaguugug u 21

<210> SEQ ID NO 114
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 114
ugaagucaaa gauacuaugc c 21

<210> SEQ ID NO 115
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 115
uguuaguaug gacaguugug c 21

<210> SEQ ID NO 116
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 116
uguuaguaug gacaguugug g 21

<210> SEQ ID NO 117
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 117
uguuaguaug gacaguuguc c 21

<210> SEQ ID NO 118
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 118
uuucaugaaa ucguuacguu g 21

<210> SEQ ID NO 119
<211> LENGTH: 23
<212> TYPE: DNA
<213> ORGANISM: Artificial sequence
<220> FEATURE:
<223> OTHER INFORMATION: RNAi agent sense strand modified sequence

<400> SEQUENCE: 119
uauacguaac gauuucauga aat 23

<210> SEQ ID NO 120
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 120
caacguaacg auuucaugaa a 21

<210> SEQ ID NO 121
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 121
caacguaacg auuucaugaa a 21

<210> SEQ ID NO 122
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 122
cuggacauag uaucuuugac a 21

<210> SEQ ID NO 123
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 123
ccaugcgcua gacuccgaga a 21

<210> SEQ ID NO 124
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 124
ccaguaccgg augcucgcaa a 21

<210> SEQ ID NO 125
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 125
gucaucuaca acccucgcaa a 21

<210> SEQ ID NO 126
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 126
cuucgggaau cagaacuucg a 21

<210> SEQ ID NO 127
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 127
ccacgcccaa uagcccugaa a 21

<210> SEQ ID NO 128
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 128
gcaguaccca gacggauuuc a 21

<210> SEQ ID NO 129
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 129
gaugccggaa gcaaagcaua 20

<210> SEQ ID NO 130
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 130
cccuuugaug ccggacaagc a 21

<210> SEQ ID NO 131
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 131
ggacaagcca cugagcgcaa a 21

<210> SEQ ID NO 132
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 132
aggacuacag ccugucguca a 21

<210> SEQ ID NO 133
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 133
cggacuuacc uggcagacua 20

<210> SEQ ID NO 134
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 134
gaagggucaa cuccaacgua a 21

<210> SEQ ID NO 135
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 135
cagggucaac uccaacguau a 21

<210> SEQ ID NO 136
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 136
gggucaacuc caacguaugu a 21

<210> SEQ ID NO 137
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 137
cuccaacgua ugugguuauc a 21

<210> SEQ ID NO 138
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 138
gccauaggug ugacaaucca 20

<210> SEQ ID NO 139
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 139
ccauaggugu gacaauccga a 21

<210> SEQ ID NO 140
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 140
gggucugaug gcacguugua 20

<210> SEQ ID NO 141
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 141
cugagcuaug ugacucggau a 21

<210> SEQ ID NO 142
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 142
ggguaagagg gacgacacca 20

<210> SEQ ID NO 143
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 143
cccuaccugu caacguaaa 19

<210> SEQ ID NO 144
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 144
cccuaccugu caacguaaa 19

<210> SEQ ID NO 145
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 145
cccuaccugu caacguaacg a 21

<210> SEQ ID NO 146
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 146
ccuaccuguc aacguaacga 20

<210> SEQ ID NO 147
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 147
accugucaac guaacgauuu a 21

<210> SEQ ID NO 148
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 148
gcaguuugcu cugaaaacga a 21

<210> SEQ ID NO 149
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 149
aggugaaagu cuacaacaac u 21

<210> SEQ ID NO 150
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 150
ggacacaucu uuggauaacg a 21

<210> SEQ ID NO 151
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 151
cgaccugaag auugaaguga u 21

<210> SEQ ID NO 152
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 152
acgggaagac uuccagcuaa a 21

<210> SEQ ID NO 153
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 153
agcuaacagg acauaguauc u 21

<210> SEQ ID NO 154
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 154
cagauaugac ugugagguga a 21

<210> SEQ ID NO 155
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 155
ggaguacaca auuguuuuac a 21

<210> SEQ ID NO 156
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 156
ggucaacucc aacguaugug a 21

<210> SEQ ID NO 157
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 157
gucaacucca acguaugugg u 21

<210> SEQ ID NO 158
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 158
gaugccauag gugugacaau a 21

<210> SEQ ID NO 159
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 159
ggaacuacca ugagaugguu u 21

<210> SEQ ID NO 160
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 160
gcuaccauga gaugguuuag a 21

<210> SEQ ID NO 161
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 161
cgauaccaau uacauggaac u 21

<210> SEQ ID NO 162
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 162
ccuaccuguc aacguaacga u 21

<210> SEQ ID NO 163

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 163
caacguaacg auuucaugaa a 21

<210> SEQ ID NO 164
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 164
caacguaacg auuucaugaa a 21

<210> SEQ ID NO 165
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 165
caacguaacg auuucaugaa a 21

<210> SEQ ID NO 166
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 166
caacguaacg auuucaugaa a 21

<210> SEQ ID NO 167
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 167
caacguaacg auuucaugaa a 21

<210> SEQ ID NO 168
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 168
caacguaacg auuucaugaa a 21

<210> SEQ ID NO 169
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 169
gaacguaacg auuucaugaa a 21

<210> SEQ ID NO 170
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 170
gnacguaacg auuucaugaa a 21

<210> SEQ ID NO 171
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 171
ggacguaacg auuucaugaa a 21

<210> SEQ ID NO 172
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine (hypoxanthine)

<400> SEQUENCE: 172
ggacguaacg auuucaunaa a 21

<210> SEQ ID NO 173
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 173
ggacguaacg auuucaugaa a 21

<210> SEQ ID NO 174
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 174
caacguaacg auuucaugaa a 21

<210> SEQ ID NO 175
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 175
caacguaacg auuucaugaa a 21

<210> SEQ ID NO 176
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 176
gaacguaacg auuucaugaa a 21

<210> SEQ ID NO 177
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 177
gnacguaacg auuucaugaa a 21

<210> SEQ ID NO 178
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 178
ggacguaacg auuucaugaa a 21

<210> SEQ ID NO 179
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine (hypoxanthine)

<400> SEQUENCE: 179
ggacguaacg auuucaunaa a 21

<210> SEQ ID NO 180
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 180
ggacguaacg auuucaugaa a 21

<210> SEQ ID NO 181
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 181
caacguaacg auuucaugaa a 21

<210> SEQ ID NO 182
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 182
caacguaacg auuucaugaa a 21

<210> SEQ ID NO 183
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 183
caacguaacg auuucaugaa a 21

<210> SEQ ID NO 184
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 184
caacguaacg auuucaugaa a 21

<210> SEQ ID NO 185
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 185
caacguaacg auuucaugaa a 21

<210> SEQ ID NO 186
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 186
caacguaacg auuucaugaa a 21

<210> SEQ ID NO 187
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 187
caacguaacg auuucaugaa a 21

<210> SEQ ID NO 188

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 188
caacguaacg auuucaugaa a 21

<210> SEQ ID NO 189
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 189
caacguaacg auuucaugaa a 21

<210> SEQ ID NO 190
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 190
caacguaacg auuucaugaa a 21

<210> SEQ ID NO 191
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 191
caacguaacg auuucaugaa a 21

<210> SEQ ID NO 192
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 192
caacguaacg auuucaugaa a 21

<210> SEQ ID NO 193
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 193
caacguaacg auuucaugaa a 21

<210> SEQ ID NO 194
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 194
caacguaacg auuucaugaa a 21

<210> SEQ ID NO 195
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 195
caacguaacg auuucaugaa a 21

<210> SEQ ID NO 196
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 196
caacguaacg auuucaugaa a 21

<210> SEQ ID NO 197
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 197
caacguaacg auuucaugaa a 21

<210> SEQ ID NO 198
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 198
caacguaacg auuucaugaa a 21

<210> SEQ ID NO 199
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 199
caacguaacg auuucaugaa a 21

<210> SEQ ID NO 200
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 200
caacguaacg auuucaugaa a 21

<210> SEQ ID NO 201
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 201
caacguaacg auuucaugaa a 21

<210> SEQ ID NO 202
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 202
caacguaacg auuucaugaa a 21

<210> SEQ ID NO 203
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 203
caacguaacg auuucaugaa a 21

<210> SEQ ID NO 204
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 204
caacguaacg auuucaugaa a 21

<210> SEQ ID NO 205
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 205
caacguaacg auuucaugaa a 21

<210> SEQ ID NO 206
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 206
caacuuguac cugaaanccu u 21

<210> SEQ ID NO 207
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 207
acuuacacag guggagcuaa a 21

<210> SEQ ID NO 208
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 208
aggacauagu aucuuugacu u 21

<210> SEQ ID NO 209
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 209
cugugucuga gaagaguaac u 21

<210> SEQ ID NO 210
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 210
cuuccuauuc accaagcuaa a 21

<210> SEQ ID NO 211
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 211
ccagcacacu auuuacaaga u 21

<210> SEQ ID NO 212
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 212
gccccuauuu uuaaaguaca a 21

<210> SEQ ID NO 213
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 213
gaguacacaa uuguuuuacc u 21

<210> SEQ ID NO 214

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 214
caacugucca uacuaacaag u 21

<210> SEQ ID NO 215
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 215
gugguuaucu gugaaaguug a 21

<210> SEQ ID NO 216
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 216
gaacuuagaa acggaaaugg a 21

<210> SEQ ID NO 217
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 217
gauccgagca guggagucau u 21

<210> SEQ ID NO 218
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 218
cacauucucu auguacuaug u 21

<210> SEQ ID NO 219
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 219
ggucagugac auguagguag a 21

<210> SEQ ID NO 220
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 220
gacacacaca aagcacauug a 21

<210> SEQ ID NO 221
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 221
accggauaga cuuauuncca a 21

<210> SEQ ID NO 222
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 222
gaaguucuau gagaaauucc u 21

<210> SEQ ID NO 223
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 223
gguuacugac guguaaaugc u 21

<210> SEQ ID NO 224
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 224
acguaacgau uucaugaacg u 21

<210> SEQ ID NO 225
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 225
guaacgauuu caugaacguu a 21

<210> SEQ ID NO 226
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 226
gaacgauuuc augaacguua u 21

<210> SEQ ID NO 227
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 227
ggagcuuaac uuuauaagga a 21

<210> SEQ ID NO 228
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 228
caacguaacg auuucaugaa a 21

<210> SEQ ID NO 229
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 229
caacguaacg auuucaugaa a 21

<210> SEQ ID NO 230
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 230
caacguaacg auuucaugaa a 21

<210> SEQ ID NO 231
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 231
caacguaacg auuucaugaa a 21

<210> SEQ ID NO 232
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 232
caacguaacg auuucaugaa a 21

<210> SEQ ID NO 233
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 233
caacguaacg auuucaugaa a 21

<210> SEQ ID NO 234
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 234
caacguaacg auuucaugaa a 21

<210> SEQ ID NO 235
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 235
caacguaacg auuucaugaa a 21

<210> SEQ ID NO 236
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 236
caacguaacg auuucaugaa a 21

<210> SEQ ID NO 237
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 237
caacguaacg auuucaugaa a 21

<210> SEQ ID NO 238
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 238
caacguaacg auuucaugaa a 21

<210> SEQ ID NO 239
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 239
cacauucucu auguacuaug u 21

<210> SEQ ID NO 240

-continued

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 240
gacauucucu auguacuaug u 21

<210> SEQ ID NO 241
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 241
cgcauucucu auguacuaug u 21

<210> SEQ ID NO 242
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 242
cccauucucu auguacuaug u 21

<210> SEQ ID NO 243
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 243
ggcauucucu auguacuaug u 21

<210> SEQ ID NO 244
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2-aminoadenosine

<400> SEQUENCE: 244
cacnuucucu auguacuaug u 21

<210> SEQ ID NO 245
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2-aminoadenosine

<400> SEQUENCE: 245
cccnuucucu auguacuaug u 21

<210> SEQ ID NO 246
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 246
gcgaccauga ggagauucau u 21

<210> SEQ ID NO 247
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 247
cgcucagccu augaauucau u 21

<210> SEQ ID NO 248
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 248
caagggucag guaguaagug a 21

<210> SEQ ID NO 249
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 249
gacugaaucc cuguucaagc a 21

<210> SEQ ID NO 250
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 250
ucagugccau gacaaacauc u 21

<210> SEQ ID NO 251
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 251
gcaccucaca uuugaugugg a 21

<210> SEQ ID NO 252
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 252
acacaacugu ccauacuaac a 21

<210> SEQ ID NO 253
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 253
ggcauaguau cuuugacuuc a 21

<210> SEQ ID NO 254
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 254
gaguacacaa uuguuuuacc u 21

<210> SEQ ID NO 255
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 255
cuuccuauuc accaagcuaa a 21

<210> SEQ ID NO 256
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 256
ggucagugac auguagguag a 21

<210> SEQ ID NO 257
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 257
caacguaacg auuucaugaa a 21

<210> SEQ ID NO 258
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 258
caacguaacg auuucaugaa a 21

<210> SEQ ID NO 259
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 259
caacguaacg auuucaugaa a 21

<210> SEQ ID NO 260
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 260
caacguaacg auuucaugaa a 21

<210> SEQ ID NO 261
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 261
caacguaacg auuucaugaa a 21

<210> SEQ ID NO 262
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 262
caacguaacg auuucaugaa a 21

<210> SEQ ID NO 263
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 263
caacguaacg auuucaugaa a 21

<210> SEQ ID NO 264
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 264
caacguaacg auuucaugaa a 21

<210> SEQ ID NO 265
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 265
caacguaacg auuucaugaa a 21

<210> SEQ ID NO 266
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 266
caacguaacg auuucaugaa a 21

<210> SEQ ID NO 267
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 267
caacguaacg auuucaugaa a 21

<210> SEQ ID NO 268
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 268
caacguaacg auuucaugaa a 21

<210> SEQ ID NO 269
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 269
caacguaacg auuucaugaa a 21

<210> SEQ ID NO 270
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 270
caacguaacg auuucaugaa a 21

<210> SEQ ID NO 271
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 271
caacguaacg auuucaugaa a 21

<210> SEQ ID NO 272
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 272
caacguaacg auuucaugaa a 21

<210> SEQ ID NO 273
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 273
caacguaacg auuucaugaa a 21

<210> SEQ ID NO 274
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 274
caacguaacg auuucaugaa a 21

<210> SEQ ID NO 275
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 275
caacguaacg auuucaugaa a 21

<210> SEQ ID NO 276
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 276
caacguaacg auuucaugaa a 21

<210> SEQ ID NO 277
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 277
caacguaacg auuucaugaa a 21

<210> SEQ ID NO 278
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 278
caacguaacg auuucaugaa a 21

<210> SEQ ID NO 279
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 279
caacguaacg auuucaugaa a 21

<210> SEQ ID NO 280
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 280
caacguaacg auuucaugaa a 21

<210> SEQ ID NO 281
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 281
gcacaacugu ccauacuaac a 21

<210> SEQ ID NO 282
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 282
ccacaacugu ccauacuaac a 21

<210> SEQ ID NO 283
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 283
ggacaacugu ccauacuaac a 21

<210> SEQ ID NO 284
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 284
caacguaacg auuucaugaa a 21

<210> SEQ ID NO 285
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 285
caacguaacg auuucaugaa a 21

<210> SEQ ID NO 286
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 286
caacguaacg auuucaugaa a 21

<210> SEQ ID NO 287
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 287
caacguaacg auuucaugaa a 21

<210> SEQ ID NO 288
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 288
caacguaacg auuucaugaa a 21

<210> SEQ ID NO 289
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 289
caacguaacg auuucaugaa a 21

<210> SEQ ID NO 290
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 290
caacguaacg auuucaugaa a 21

<210> SEQ ID NO 291
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 291
caacguaacg auuucaugaa a 21

<210> SEQ ID NO 292

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 292
caacguaacg auuucaugaa a 21

<210> SEQ ID NO 293
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 293
caacguaacg auuucaugaa a 21

<210> SEQ ID NO 294
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 294
caacguaacg auuucaugaa a 21

<210> SEQ ID NO 295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 295
caacguaacg auuucaugaa a 21

<210> SEQ ID NO 296
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 296
caacguaacg auuucaugaa a 21

<210> SEQ ID NO 297
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 297
caacguaacg auuucaugaa a 21

<210> SEQ ID NO 298
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 298
caacguaacg auuucaugaa at 22

<210> SEQ ID NO 299
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 299
caacguaacg auuucaugaa a 21

<210> SEQ ID NO 300
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 300
caacguaacg auuucaugaa a 21

<210> SEQ ID NO 301
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 301
caacguaacg auuucaugaa a 21

<210> SEQ ID NO 302
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 302
caacguaacg auuucaugaa a 21

<210> SEQ ID NO 303
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 303
caacguaacg auuucaugaa a 21

<210> SEQ ID NO 304
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 304
caacguaacg auuucaugaa a 21

<210> SEQ ID NO 305
<211> LENGTH: 22
<212> TYPE: DNA

<213> ORGANISM: Artificial sequence
<220> FEATURE:
<223> OTHER INFORMATION: RNAi agent sense strand modified sequence

<400> SEQUENCE: 305
caacguaacg auuucaugaa at 22

<210> SEQ ID NO 306
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 306
caacguaacg auuucaugaa at 22

<210> SEQ ID NO 307
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 307
caacguaacg auuucaugaa at 22

<210> SEQ ID NO 308
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 308
caacguaacg auuucaugaa at 22

<210> SEQ ID NO 309
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 309
caacguaacg auuucaugaa at 22

<210> SEQ ID NO 310
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 310
caacguaacg auuucaugaa at 22

<210> SEQ ID NO 311
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 311
caacguaacg auuucaugaa at 22

<210> SEQ ID NO 312
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 312
caacguaacg auuucaugaa at 22

<210> SEQ ID NO 313
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 313
caacguaacg auuucaugaa at 22

<210> SEQ ID NO 314
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 314
caacguaacg auuucaugaa at 22

<210> SEQ ID NO 315
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 315
caacguaacg auuucaugaa at 22

<210> SEQ ID NO 316
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 316
caacguaacg auuucaugaa at 22

<210> SEQ ID NO 317
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 317
caacguaacg auuucaugaa at 22

<210> SEQ ID NO 318
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 318
caacguaacg auuucaugaa a 21

<210> SEQ ID NO 319
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 319
caacguaacg auuucaugaa a 21

<210> SEQ ID NO 320
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 320
caacguaacg auuucaugaa a 21

<210> SEQ ID NO 321
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 321
caacguaacg auuucaugaa a 21

<210> SEQ ID NO 322
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 322
caacguaacg auuucaugaa a 21

<210> SEQ ID NO 323
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 323
cacauucucu auguacuaug ut 22

<210> SEQ ID NO 324
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 324
cacauucucu auguacuaug ut 22

<210> SEQ ID NO 325
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 325
cacauucucu auguacuaug ut 22

<210> SEQ ID NO 326
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 326
cacauucucu auguacuaug ut 22

<210> SEQ ID NO 327
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 327
acacaacugu ccauacuaac at 22

<210> SEQ ID NO 328
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 328
acacaacugu ccauacuaac at 22

<210> SEQ ID NO 329
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 329
acacaacugu ccauacuaac at 22

<210> SEQ ID NO 330
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 330
acacaacugu ccauacuaac at 22

<210> SEQ ID NO 331
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 331
caacguaacg auuucaugaa at 22

<210> SEQ ID NO 332
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 332
caacguaacg auuucaugaa at 22

<210> SEQ ID NO 333
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 333
caacguaacg auuucaugaa at 22

<210> SEQ ID NO 334
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 334
caacguaacg auuucaugaa at 22

<210> SEQ ID NO 335
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 335
caacguaacg auuucaugaa a 21

<210> SEQ ID NO 336
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 336
caacguaacg auuucaugaa a 21

<210> SEQ ID NO 337
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 337
caacguaacg auuucaugaa a 21

<210> SEQ ID NO 338
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 338
caacguaacg auuucaugaa a 21

<210> SEQ ID NO 339
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 339
caacguaacg auuucaugaa at 22

<210> SEQ ID NO 340
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 340
caacguaacg auuucaugaa a 21

<210> SEQ ID NO 341
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 341
caacguaacg auuucaugaa at 22

<210> SEQ ID NO 342
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 342
caacguaacg auuucaugaa at 22

<210> SEQ ID NO 343
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 343
caacguaacg auuucaugaa a 21

<210> SEQ ID NO 344
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 344

-continued caacguaacg auuucaugaa at 22

<210> SEQ ID NO 345
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 345
caacguaacg auuucaugaa a 21

<210> SEQ ID NO 346
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 346
caacguaacg auuucaugaa a 21

<210> SEQ ID NO 347
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 347
caacguaacg auuucaugaa a 21

<210> SEQ ID NO 348
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 348
caacguaacg auuucaugaa a 21

<210> SEQ ID NO 349
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 349
caacguaacg auuucaugaa a 21

<210> SEQ ID NO 350
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 350
caacguaacg auuucaugaa a 21

<210> SEQ ID NO 351
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 351
caacguaacg auuucaugaa a 21

<210> SEQ ID NO 352
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 352
caacguaacg auuucaugaa a 21

<210> SEQ ID NO 353
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 353
caacguaacg auuucaugaa a 21

<210> SEQ ID NO 354
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 354
caacguaacg auuucaugaa a 21

<210> SEQ ID NO 355
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 355
caacguaacg auuucaugaa a 21

<210> SEQ ID NO 356
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 356
caacguaacg auuucaugaa a 21

<210> SEQ ID NO 357
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 357
caacguaacg auuucaugaa a 21

<210> SEQ ID NO 358
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 358
caacguaacg auuucaugaa a 21

<210> SEQ ID NO 359
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 359
cacauucucu auguacuaug u 21

<210> SEQ ID NO 360
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 360
cacauucucu auguacuaug u 21

<210> SEQ ID NO 361
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 361
cacauucucu auguacuaug u 21

<210> SEQ ID NO 362
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 362
cacauucucu auguacuaug u 21

<210> SEQ ID NO 363
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 363
acacaacugu ccauacuaac a 21

<210> SEQ ID NO 364
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 364
acacaacugu ccauacuaac a 21

<210> SEQ ID NO 365
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 365
acacaacugu ccauacuaac a 21

<210> SEQ ID NO 366
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 366
acacaacugu ccauacuaac a 21

<210> SEQ ID NO 367
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 367
caacguaacg auuucaugaa a 21

<210> SEQ ID NO 368
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 368
caacguaacg auuucaugaa a 21

<210> SEQ ID NO 369
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 369
caacguaacg auuucaugaa a 21

<210> SEQ ID NO 370
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 370
caacguaacg auuucaugaa a 21

<210> SEQ ID NO 371

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 371
caacguaacg auuucaugaa a 21

<210> SEQ ID NO 372
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 372
caacguaacg auuucaugaa a 21

<210> SEQ ID NO 373
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 373
caacguaacg auuucaugaa a 21

<210> SEQ ID NO 374
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 374
caacguaacg auuucaugaa a 21

<210> SEQ ID NO 375
<211> LENGTH: 23
<212> TYPE: DNA
<213> ORGANISM: Artificial sequence
<220> FEATURE:
<223> OTHER INFORMATION: RNAi agent sense strand modified sequence

<400> SEQUENCE: 375
uauacguaac gauuucauga aat 23

<210> SEQ ID NO 376
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 376
caacguaacg auuucaugaa a 21

<210> SEQ ID NO 377
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 377
caacguaacg auuucaugaa a 21

<210> SEQ ID NO 378
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 378
cuggacauag uaucuuugac a 21

<210> SEQ ID NO 379
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 379
ccaugcgcua gacuccgaga a 21

<210> SEQ ID NO 380
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 380
ccaguaccgg augcucgcaa a 21

<210> SEQ ID NO 381
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 381
gucaucuaca acccucgcaa a 21

<210> SEQ ID NO 382
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 382
cuucgggaau cagaacuucg a 21

<210> SEQ ID NO 383
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 383
ccacgcccaa uagcccugaa a 21

<210> SEQ ID NO 384
<211> LENGTH: 21
<212> TYPE: RNA

-continued

<213> ORGANISM: Artificial sequence
<220> FEATURE:
<223> OTHER INFORMATION: RNAi agent sense strand modified sequence

<400> SEQUENCE: 384
gcaguaccca gacggauuuc a 21

<210> SEQ ID NO 385
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 385
gaugccggaa gcaaagcaua 20

<210> SEQ ID NO 386
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 386
cccuuugaug ccggacaagc a 21

<210> SEQ ID NO 387
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 387
ggacaagcca cugagcgcaa a 21

<210> SEQ ID NO 388
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 388
aggacuacag ccugucguca a 21

<210> SEQ ID NO 389
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 389
cggacuuacc uggcagacua 20

<210> SEQ ID NO 390
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 390
gaagggucaa cuccaacgua a 21

<210> SEQ ID NO 391
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 391
cagggucaac uccaacguau a 21

<210> SEQ ID NO 392
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 392
gggucaacuc caacguaugu a 21

<210> SEQ ID NO 393
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 393
cuccaacgua ugugguuauc a 21

<210> SEQ ID NO 394
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 394
gccauaggug ugacaaucca 20

<210> SEQ ID NO 395
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 395
ccauaggugu gacaauccga a 21

<210> SEQ ID NO 396
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 396
gggucugaug gcacguugua 20

<210> SEQ ID NO 397
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 397
cugagcuaug ugacucggau a 21

<210> SEQ ID NO 398
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 398
ggguaagagg gacgacacca 20

<210> SEQ ID NO 399
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 399
cccuaccugu caacguaaa 19

<210> SEQ ID NO 400
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 400
cccuaccugu caacguaaa 19

<210> SEQ ID NO 401
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 401
cccuaccugu caacguaacg a 21

<210> SEQ ID NO 402
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 402
ccuaccuguc aacguaacga 20

<210> SEQ ID NO 403
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 403
accugucaac guaacgauuu a 21

<210> SEQ ID NO 404
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 404
gcaguuugcu cugaaaacga a 21

<210> SEQ ID NO 405
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 405
aggugaaagu cuacaacaac u 21

<210> SEQ ID NO 406
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 406
ggacacaucu uuggauaacg a 21

<210> SEQ ID NO 407
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 407
cgaccugaag auugaaguga u 21

<210> SEQ ID NO 408
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 408
acgggaagac uuccagcuaa a 21

<210> SEQ ID NO 409
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 409
agcuaacagg acauaguauc u 21

<210> SEQ ID NO 410
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 410
cagauaugac ugugagguga a 21

<210> SEQ ID NO 411
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 411
ggaguacaca auuguuuuac a 21

<210> SEQ ID NO 412
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 412
ggucaacucc aacguaugug a 21

<210> SEQ ID NO 413
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 413
gucaacucca acguaugugg u 21

<210> SEQ ID NO 414
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 414
gaugccauag gugugacaau a 21

<210> SEQ ID NO 415
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 415
ggaacuacca ugagaugguu u 21

<210> SEQ ID NO 416
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 416
gcuaccauga gaugguuuag a 21

<210> SEQ ID NO 417
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 417
cgauaccaau uacauggaac u 21

<210> SEQ ID NO 418
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 418
ccuaccuguc aacguaacga u 21

<210> SEQ ID NO 419
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 419
caacguaacg auuucaugaa a 21

<210> SEQ ID NO 420
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 420
caacguaacg auuucaugaa a 21

<210> SEQ ID NO 421
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 421
caacguaacg auuucaugaa a 21

<210> SEQ ID NO 422
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 422
caacguaacg auuucaugaa a 21

<210> SEQ ID NO 423
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 423
caacguaacg auuucaugaa a 21

<210> SEQ ID NO 424
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 424
caacguaacg auuucaugaa a 21

<210> SEQ ID NO 425
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 425
gaacguaacg auuucaugaa a 21

<210> SEQ ID NO 426
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 426
gnacguaacg auuucaugaa a 21

<210> SEQ ID NO 427
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 427
ggacguaacg auuucaugaa a 21

<210> SEQ ID NO 428
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine (hypoxanthine)

<400> SEQUENCE: 428
ggacguaacg auuucaunaa a 21

<210> SEQ ID NO 429
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 429
ggacguaacg auuucaugaa a 21

<210> SEQ ID NO 430
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 430
caacguaacg auuucaugaa a 21

<210> SEQ ID NO 431
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 431
caacguaacg auuucaugaa a 21

<210> SEQ ID NO 432
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 432
gaacguaacg auuucaugaa a 21

<210> SEQ ID NO 433
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 433
gnacguaacg auuucaugaa a 21

<210> SEQ ID NO 434
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 434
ggacguaacg auuucaugaa a 21

<210> SEQ ID NO 435
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine

<400> SEQUENCE: 435
ggacguaacg auuucaunaa a 21

<210> SEQ ID NO 436
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 436
ggacguaacg auuucaugaa a 21

<210> SEQ ID NO 437
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 437
caacguaacg auuucaugaa a 21

<210> SEQ ID NO 438
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 438
caacguaacg auuucaugaa a 21

<210> SEQ ID NO 439
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 439
caacguaacg auuucaugaa a 21

<210> SEQ ID NO 440
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 440
caacguaacg auuucaugaa a 21

<210> SEQ ID NO 441
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 441
caacguaacg auuucaugaa a 21

<210> SEQ ID NO 442
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 442
caacguaacg auuucaugaa a 21

<210> SEQ ID NO 443
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 443
caacguaacg auuucaugaa a 21

<210> SEQ ID NO 444
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 444
caacguaacg auuucaugaa a 21

<210> SEQ ID NO 445
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 445
caacguaacg auuucaugaa a 21

<210> SEQ ID NO 446
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 446
caacguaacg auuucaugaa a 21

<210> SEQ ID NO 447
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 447
caacguaacg auuucaugaa a 21

<210> SEQ ID NO 448
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 448
caacguaacg auuucaugaa a 21

<210> SEQ ID NO 449
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 449
caacguaacg auuucaugaa a 21

<210> SEQ ID NO 450
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 450
caacguaacg auuucaugaa a 21

<210> SEQ ID NO 451
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 451
caacguaacg auuucaugaa a 21

<210> SEQ ID NO 452
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 452
caacguaacg auuucaugaa a 21

<210> SEQ ID NO 453
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 453
caacguaacg auuucaugaa a 21

<210> SEQ ID NO 454
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 454
caacguaacg auuucaugaa a 21

<210> SEQ ID NO 455
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 455
caacguaacg auuucaugaa a 21

<210> SEQ ID NO 456
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 456
caacguaacg auuucaugaa a 21

<210> SEQ ID NO 457
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 457
caacguaacg auuucaugaa a 21

<210> SEQ ID NO 458
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 458
caacguaacg auuucaugaa a 21

<210> SEQ ID NO 459
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 459
caacguaacg auuucaugaa a 21

<210> SEQ ID NO 460
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 460
caacguaacg auuucaugaa a 21

<210> SEQ ID NO 461
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 461
caacguaacg auuucaugaa a 21

<210> SEQ ID NO 462
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 462
caacuuguac cugaaanccu u 21

<210> SEQ ID NO 463
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 463
acuuacacag guggagcuaa a 21

<210> SEQ ID NO 464
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 464
aggacauagu aucuuugacu u 21

<210> SEQ ID NO 465
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 465
cugugucuga gaagaguaac u 21

<210> SEQ ID NO 466
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 466
cuuccuauuc accaagcuaa a 21

<210> SEQ ID NO 467
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 467
ccagcacacu auuuacaaga u 21

<210> SEQ ID NO 468
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 468
gccccuauuu uuaaaguaca a 21

<210> SEQ ID NO 469
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 469
gaguacacaa uuguuuuacc u 21

<210> SEQ ID NO 470
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 470
caacugucca uacuaacaag u 21

<210> SEQ ID NO 471
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 471
gugguuaucu gugaaaguug a 21

<210> SEQ ID NO 472
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 472
gaacuuagaa acggaaaugg a 21

<210> SEQ ID NO 473
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 473
gauccgagca guggagucau u 21

<210> SEQ ID NO 474
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 474
cacauucucu auguacuaug u 21

<210> SEQ ID NO 475
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 475
ggucagugac auguagguag a 21

<210> SEQ ID NO 476
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 476
gacacacaca aagcacauug a 21

<210> SEQ ID NO 477
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 477
accggauaga cuuauuncca a 21

<210> SEQ ID NO 478
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 478
gaaguucuau gagaaauucc u 21

<210> SEQ ID NO 479
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 479
gguuacugac guguaaaugc u 21

<210> SEQ ID NO 480
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 480
acguaacgau uucaugaacg u 21

<210> SEQ ID NO 481
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 481
guaacgauuu caugaacguu a 21

<210> SEQ ID NO 482
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 482
gaacgauuuc augaacguua u 21

<210> SEQ ID NO 483
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 483
ggagcuuaac uuuauaagga a 21

<210> SEQ ID NO 484
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 484
caacguaacg auuucaugaa a 21

<210> SEQ ID NO 485
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 485
caacguaacg auuucaugaa a 21

<210> SEQ ID NO 486
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 486
caacguaacg auuucaugaa a 21

<210> SEQ ID NO 487
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 487
caacguaacg auuucaugaa a 21

<210> SEQ ID NO 488
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 488
caacguaacg auuucaugaa a 21

<210> SEQ ID NO 489
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 489
caacguaacg auuucaugaa a 21

<210> SEQ ID NO 490
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 490
caacguaacg auuucaugaa a 21

<210> SEQ ID NO 491
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 491
caacguaacg auuucaugaa a 21

<210> SEQ ID NO 492
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 492
caacguaacg auuucaugaa a 21

<210> SEQ ID NO 493
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 493
caacguaacg auuucaugaa a 21

<210> SEQ ID NO 494
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 494
caacguaacg auuucaugaa a 21

<210> SEQ ID NO 495
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 495
cacauucucu auguacuaug u 21

<210> SEQ ID NO 496
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 496
gacauucucu auguacuaug u 21

<210> SEQ ID NO 497
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 497
cgcauucucu auguacuaug u 21

<210> SEQ ID NO 498
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 498
cccauucucu auguacuaug u 21

<210> SEQ ID NO 499
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 499
ggcauucucu auguacuaug u 21

<210> SEQ ID NO 500
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4

<223> OTHER INFORMATION: n = 2-aminoadenosine

<400> SEQUENCE: 500
cacnuucucu auguacuaug u 21

<210> SEQ ID NO 501
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2-aminoadenosine

<400> SEQUENCE: 501
cccnuucucu auguacuaug u 21

<210> SEQ ID NO 502
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 502
gcgaccauga ggagauucau u 21

<210> SEQ ID NO 503
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 503
cgcucagccu augaauucau u 21

<210> SEQ ID NO 504
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 504
caagggucag guaguaagug a 21

<210> SEQ ID NO 505
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 505
gacugaaucc cuguucaagc a 21

<210> SEQ ID NO 506
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 506
ucagugccau gacaaacauc u 21

<210> SEQ ID NO 507
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 507
gcaccucaca uuugaugugg a 21

<210> SEQ ID NO 508
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 508
acacaacugu ccauacuaac a 21

<210> SEQ ID NO 509
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 509
ggcauaguau cuuugacuuc a 21

<210> SEQ ID NO 510
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 510
gaguacacaa uuguuuuacc u 21

<210> SEQ ID NO 511
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 511
cuuccuauuc accaagcuaa a 21

<210> SEQ ID NO 512
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 512
ggucagugac auguagguag a 21

<210> SEQ ID NO 513
<211> LENGTH: 21
<212> TYPE: RNA

-continued

<213> ORGANISM: Artificial sequence
<220> FEATURE:
<223> OTHER INFORMATION: RNAi agent sense strand modified sequence

<400> SEQUENCE: 513
caacguaacg auuucaugaa a 21

<210> SEQ ID NO 514
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 514
caacguaacg auuucaugaa a 21

<210> SEQ ID NO 515
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 515
caacguaacg auuucaugaa a 21

<210> SEQ ID NO 516
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 516
caacguaacg auuucaugaa a 21

<210> SEQ ID NO 517
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 517
caacguaacg auuucaugaa a 21

<210> SEQ ID NO 518
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 518
caacguaacg auuucaugaa a 21

<210> SEQ ID NO 519
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 519
caacguaacg auuucaugaa a 21

<210> SEQ ID NO 520
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 520
caacguaacg auuucaugaa a 21

<210> SEQ ID NO 521
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 521
caacguaacg auuucaugaa a 21

<210> SEQ ID NO 522
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 522
caacguaacg auuucaugaa a 21

<210> SEQ ID NO 523
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 523
caacguaacg auuucaugaa a 21

<210> SEQ ID NO 524
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 524
caacguaacg auuucaugaa a 21

<210> SEQ ID NO 525
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 525
caacguaacg auuucaugaa a 21

<210> SEQ ID NO 526
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 526
caacguaacg auuucaugaa a 21

<210> SEQ ID NO 527
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 527
caacguaacg auuucaugaa a 21

<210> SEQ ID NO 528
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 528
caacguaacg auuucaugaa a 21

<210> SEQ ID NO 529
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 529
caacguaacg auuucaugaa a 21

<210> SEQ ID NO 530
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 530
caacguaacg auuucaugaa a 21

<210> SEQ ID NO 531
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 531
caacguaacg auuucaugaa a 21

<210> SEQ ID NO 532
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 532
caacguaacg auuucaugaa a 21

<210> SEQ ID NO 533
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 533
caacguaacg auuucaugaa a 21

<210> SEQ ID NO 534
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 534
caacguaacg auuucaugaa a 21

<210> SEQ ID NO 535
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 535
caacguaacg auuucaugaa a 21

<210> SEQ ID NO 536
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 536
caacguaacg auuucaugaa a 21

<210> SEQ ID NO 537
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 537
gcacaacugu ccauacuaac a 21

<210> SEQ ID NO 538
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 538
ccacaacugu ccauacuaac a 21

<210> SEQ ID NO 539
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 539
ggacaacugu ccauacuaac a 21

<210> SEQ ID NO 540
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 540
caacguaacg auuucaugaa a 21

<210> SEQ ID NO 541
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 541
caacguaacg auuucaugaa a 21

<210> SEQ ID NO 542
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 542
caacguaacg auuucaugaa a 21

<210> SEQ ID NO 543
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 543
caacguaacg auuucaugaa a 21

<210> SEQ ID NO 544
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 544
caacguaacg auuucaugaa a 21

<210> SEQ ID NO 545
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 545
caacguaacg auuucaugaa a 21

<210> SEQ ID NO 546
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 546
caacguaacg auuucaugaa a 21

<210> SEQ ID NO 547
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 547
caacguaacg auuucaugaa a 21

<210> SEQ ID NO 548
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 548
caacguaacg auuucaugaa a 21

<210> SEQ ID NO 549
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 549
caacguaacg auuucaugaa a 21

<210> SEQ ID NO 550
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 550
caacguaacg auuucaugaa a 21

<210> SEQ ID NO 551
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 551
caacguaacg auuucaugaa a 21

<210> SEQ ID NO 552
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 552
caacguaacg auuucaugaa a 21

<210> SEQ ID NO 553
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 553
caacguaacg auuucaugaa a 21

<210> SEQ ID NO 554
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 554
caacguaacg auuucaugaa a 21

<210> SEQ ID NO 555
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 555
caacguaacg auuucaugaa a 21

<210> SEQ ID NO 556
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 556
caacguaacg auuucaugaa a 21

<210> SEQ ID NO 557
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 557
caacguaacg auuucaugaa a 21

<210> SEQ ID NO 558
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 558
caacguaacg auuucaugaa a 21

<210> SEQ ID NO 559
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 559
caacguaacg auuucaugaa a 21

<210> SEQ ID NO 560
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 560
caacguaacg auuucaugaa a 21

<210> SEQ ID NO 561
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 561
caacguaacg auuucaugaa a 21

<210> SEQ ID NO 562
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 562
caacguaacg auuucaugaa a 21

<210> SEQ ID NO 563
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 563
caacguaacg auuucaugaa a 21

<210> SEQ ID NO 564
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 564
caacguaacg auuucaugaa a 21

<210> SEQ ID NO 565
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 565
caacguaacg auuucaugaa a 21

-continued

<210> SEQ ID NO 566
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 566
caacguaacg auuucaugaa a 21

<210> SEQ ID NO 567
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 567
caacguaacg auuucaugaa a 21

<210> SEQ ID NO 568
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 568
caacguaacg auuucaugaa a 21

<210> SEQ ID NO 569
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 569
caacguaacg auuucaugaa a 21

<210> SEQ ID NO 570
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 570
caacguaacg auuucaugaa a 21

<210> SEQ ID NO 571
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 571
caacguaacg auuucaugaa a 21

<210> SEQ ID NO 572
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 572
caacguaacg auuucaugaa a 21

<210> SEQ ID NO 573
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 573
caacguaacg auuucaugaa a 21

<210> SEQ ID NO 574
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 574
caacguaacg auuucaugaa a 21

<210> SEQ ID NO 575
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 575
caacguaacg auuucaugaa a 21

<210> SEQ ID NO 576
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 576
caacguaacg auuucaugaa a 21

<210> SEQ ID NO 577
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 577
caacguaacg auuucaugaa a 21

<210> SEQ ID NO 578
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 578
caacguaacg auuucaugaa a 21

<210> SEQ ID NO 579

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 579
cacauucucu auguacuaug u 21

<210> SEQ ID NO 580
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 580
cacauucucu auguacuaug u 21

<210> SEQ ID NO 581
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 581
cacauucucu auguacuaug u 21

<210> SEQ ID NO 582
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 582
cacauucucu auguacuaug u 21

<210> SEQ ID NO 583
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 583
acacaacugu ccauacuaac a 21

<210> SEQ ID NO 584
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 584
acacaacugu ccauacuaac a 21

<210> SEQ ID NO 585
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 585
acacaacugu ccauacuaac a 21

<210> SEQ ID NO 586
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 586
acacaacugu ccauacuaac a 21

<210> SEQ ID NO 587
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 587
caacguaacg auuucaugaa a 21

<210> SEQ ID NO 588
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 588
caacguaacg auuucaugaa a 21

<210> SEQ ID NO 589
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 589
caacguaacg auuucaugaa a 21

<210> SEQ ID NO 590
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 590
caacguaacg auuucaugaa a 21

<210> SEQ ID NO 591
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 591
caacguaacg auuucaugaa a 21

<210> SEQ ID NO 592
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 592
caacguaacg auuucaugaa a 21

<210> SEQ ID NO 593
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 593
caacguaacg auuucaugaa a 21

<210> SEQ ID NO 594
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 594
caacguaacg auuucaugaa a 21

<210> SEQ ID NO 595
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 595
caacguaacg auuucaugaa a 21

<210> SEQ ID NO 596
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 596
caacguaacg auuucaugaa a 21

<210> SEQ ID NO 597
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 597
caacguaacg auuucaugaa a 21

<210> SEQ ID NO 598
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 598
caacguaacg auuucaugaa a 21

<210> SEQ ID NO 599
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 599
caacguaacg auuucaugaa a 21

<210> SEQ ID NO 600
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 600
caacguaacg auuucaugaa a 21

<210> SEQ ID NO 601
<211> LENGTH: 23
<212> TYPE: DNA
<213> ORGANISM: Artificial sequence
<220> FEATURE:
<223> OTHER INFORMATION: RNAi agent sense strand modified sequence

<400> SEQUENCE: 601
uauacguaac gauuucauga aat 23

<210> SEQ ID NO 602
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 602
caacguaacg auuucaugaa a 21

<210> SEQ ID NO 603
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 603
caacguaacg auuucaugaa a 21

<210> SEQ ID NO 604
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 604
cuggacauag uaucuuugac a 21

<210> SEQ ID NO 605
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 605
ccaugcgcua gacuccgaga a 21

<210> SEQ ID NO 606
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 606
ccaguaccgg augcucgcaa a 21

<210> SEQ ID NO 607
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 607
gucaucuaca acccucgcaa a 21

<210> SEQ ID NO 608
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 608
cuucgggaau cagaacuucg a 21

<210> SEQ ID NO 609
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 609
ccacgcccaa uagcccugaa a 21

<210> SEQ ID NO 610
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 610
gcaguaccca gacggauuuc a 21

<210> SEQ ID NO 611
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 611
gaugccggaa gcaaagcaua 20

<210> SEQ ID NO 612
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 612
cccuuugaug ccggacaagc a 21

<210> SEQ ID NO 613
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 613
ggacaagcca cugagcgcaa a 21

<210> SEQ ID NO 614
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 614
aggacuacag ccugucguca a 21

<210> SEQ ID NO 615
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 615
cggacuuacc uggcagacua 20

<210> SEQ ID NO 616
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 616
gaagggucaa cuccaacgua a 21

<210> SEQ ID NO 617
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 617
cagggucaac uccaacguau a 21

<210> SEQ ID NO 618
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 618
gggucaacuc caacguaugu a 21

<210> SEQ ID NO 619
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 619
cuccaacgua ugugguuauc a 21

<210> SEQ ID NO 620
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 620
gccauaggug ugacaaucca 20

<210> SEQ ID NO 621
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 621
ccauaggugu gacaauccga a 21

<210> SEQ ID NO 622
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 622
gggucugaug gcacguugua 20

<210> SEQ ID NO 623
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 623
cugagcuaug ugacucggau a 21

<210> SEQ ID NO 624
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 624
ggguaagagg gacgacacca 20

<210> SEQ ID NO 625
<211> LENGTH: 19

<212> TYPE: RNA
<213> ORGANISM: Artificial sequence
<220> FEATURE:
<223> OTHER INFORMATION: RNAi agent sense strand modified sequence

<400> SEQUENCE: 625
cccuaccugu caacguaaa 19

<210> SEQ ID NO 626
<211> LENGTH: 19
<212> TYPE: RNA
<213> ORGANISM: Artificial sequence
<220> FEATURE:
<223> OTHER INFORMATION: RNAi agent sense strand modified sequence

<400> SEQUENCE: 626
cccuaccugu caacguaaa 19

<210> SEQ ID NO 627
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 627
cccuaccugu caacguaacg a 21

<210> SEQ ID NO 628
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 628
ccuaccuguc aacguaacga 20

<210> SEQ ID NO 629
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 629
accugucaac guaacgauuu a 21

<210> SEQ ID NO 630
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 630
gcaguuugcu cugaaaacga a 21

<210> SEQ ID NO 631
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 631
aggugaaagu cuacaacaac u 21

<210> SEQ ID NO 632
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 632
ggacacaucu uuggauaacg a 21

<210> SEQ ID NO 633
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 633
cgaccugaag auugaaguga u 21

<210> SEQ ID NO 634
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 634
acgggaagac uuccagcuaa a 21

<210> SEQ ID NO 635
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 635
agcuaacagg acauaguauc u 21

<210> SEQ ID NO 636
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 636
cagauaugac ugugagguga a 21

<210> SEQ ID NO 637
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 637
ggaguacaca auuguuuuac a 21

<210> SEQ ID NO 638
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 638
ggucaacucc aacguaugug a 21

<210> SEQ ID NO 639
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 639
gucaacucca acguaugugg u 21

<210> SEQ ID NO 640
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 640
gaugccauag gugugacaau a 21

<210> SEQ ID NO 641
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 641
ggaacuacca ugagaugguu u 21

<210> SEQ ID NO 642
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 642
gcuaccauga gaugguuuag a 21

<210> SEQ ID NO 643
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 643
cgauaccaau uacauggaac u 21

<210> SEQ ID NO 644
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 644
ccuaccuguc aacguaacga u 21

<210> SEQ ID NO 645
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 645
caacguaacg auuucaugaa a 21

<210> SEQ ID NO 646
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 646
caacguaacg auuucaugaa a 21

<210> SEQ ID NO 647
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 647
caacguaacg auuucaugaa a 21

<210> SEQ ID NO 648
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 648
caacguaacg auuucaugaa a 21

<210> SEQ ID NO 649
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 649
caacguaacg auuucaugaa a 21

<210> SEQ ID NO 650
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 650
caacguaacg auuucaugaa a 21

<210> SEQ ID NO 651
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 651
gaacguaacg auuucaugaa a 21

<210> SEQ ID NO 652
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 652
gnacguaacg auuucaugaa a 21

<210> SEQ ID NO 653
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 653
ggacguaacg auuucaugaa a 21

<210> SEQ ID NO 654
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine

<400> SEQUENCE: 654
ggacguaacg auuucaunaa a 21

<210> SEQ ID NO 655
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 655
ggacguaacg auuucaugaa a 21

<210> SEQ ID NO 656
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 656
caacguaacg auuucaugaa a 21

<210> SEQ ID NO 657
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 657
caacguaacg auuucaugaa a 21

<210> SEQ ID NO 658
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 658
gaacguaacg auuucaugaa a 21

<210> SEQ ID NO 659
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2-aminoadenosine

<400> SEQUENCE: 659
gnacguaacg auuucaugaa a 21

<210> SEQ ID NO 660
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 660
ggacguaacg auuucaugaa a 21

<210> SEQ ID NO 661
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = inosine

<400> SEQUENCE: 661
ggacguaacg auuucaunaa a 21

<210> SEQ ID NO 662
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 662
ggacguaacg auuucaugaa a 21

<210> SEQ ID NO 663
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 663
caacguaacg auuucaugaa a 21

<210> SEQ ID NO 664
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 664
caacguaacg auuucaugaa a 21

<210> SEQ ID NO 665
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 665
caacguaacg auuucaugaa a 21

<210> SEQ ID NO 666
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 666
caacguaacg auuucaugaa a 21

<210> SEQ ID NO 667
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 667
caacguaacg auuucaugaa a 21

<210> SEQ ID NO 668
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 668
caacguaacg auuucaugaa a 21

<210> SEQ ID NO 669
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 669
caacguaacg auuucaugaa a 21

<210> SEQ ID NO 670
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 670
caacguaacg auuucaugaa a 21

<210> SEQ ID NO 671
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 671
caacguaacg auuucaugaa a 21

<210> SEQ ID NO 672
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 672
caacguaacg auuucaugaa a 21

<210> SEQ ID NO 673
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 673
caacguaacg auuucaugaa a 21

<210> SEQ ID NO 674
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 674
caacguaacg auuucaugaa a 21

<210> SEQ ID NO 675
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 675
caacguaacg auuucaugaa a 21

<210> SEQ ID NO 676
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 676
caacguaacg auuucaugaa a 21

<210> SEQ ID NO 677
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 677
caacguaacg auuucaugaa a 21

<210> SEQ ID NO 678
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 678
caacguaacg auuucaugaa a 21

<210> SEQ ID NO 679
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 679
caacguaacg auuucaugaa a 21

<210> SEQ ID NO 680
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 680
caacguaacg auuucaugaa a 21

<210> SEQ ID NO 681
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 681
caacguaacg auuucaugaa a 21

<210> SEQ ID NO 682
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 682
caacguaacg auuucaugaa a 21

<210> SEQ ID NO 683

-continued

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 683
caacguaacg auuucaugaa a 21

<210> SEQ ID NO 684
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 684
caacguaacg auuucaugaa a 21

<210> SEQ ID NO 685
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 685
caacguaacg auuucaugaa a 21

<210> SEQ ID NO 686
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 686
caacguaacg auuucaugaa a 21

<210> SEQ ID NO 687
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 687
caacguaacg auuucaugaa a 21

<210> SEQ ID NO 688
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 688
caacuuguac cugaaanccu u 21

<210> SEQ ID NO 689
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 689
acuuacacag guggagcuaa a 21

<210> SEQ ID NO 690
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 690
aggacauagu aucuuugacu u 21

<210> SEQ ID NO 691
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 691
cugugucuga gaagaguaac u 21

<210> SEQ ID NO 692
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 692
cuuccuauuc accaagcuaa a 21

<210> SEQ ID NO 693
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 693
ccagcacacu auuuacaaga u 21

<210> SEQ ID NO 694
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 694
gccccuauuu uuaaaguaca a 21

<210> SEQ ID NO 695
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 695
gaguacacaa uuguuuuacc u 21

<210> SEQ ID NO 696
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 696
caacugucca uacuaacaag u 21

<210> SEQ ID NO 697
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 697
gugguuaucu gugaaaguug a 21

<210> SEQ ID NO 698
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 698
gaacuuagaa acggaaaugg a 21

<210> SEQ ID NO 699
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 699
gauccgagca guggagucau u 21

<210> SEQ ID NO 700
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 700
cacauucucu auguacuaug u 21

<210> SEQ ID NO 701
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 701
ggucagugac auguagguag a 21

<210> SEQ ID NO 702
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 702
gacacacaca aagcacauug a 21

<210> SEQ ID NO 703
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = inosine (hypoxanthine)

<400> SEQUENCE: 703
accggauaga cuuauuncca a 21

<210> SEQ ID NO 704
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 704
gaaguucuau gagaaauucc u 21

<210> SEQ ID NO 705
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 705
gguuacugac guguaaaugc u 21

<210> SEQ ID NO 706
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 706
acguaacgau uucaugaacg u 21

<210> SEQ ID NO 707
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 707
guaacgauuu caugaacguu a 21

<210> SEQ ID NO 708
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 708
gaacgauuuc augaacguua u 21

<210> SEQ ID NO 709
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 709
ggagcuuaac uuuauaagga a 21

<210> SEQ ID NO 710
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 710
caacguaacg auuucaugaa a 21

<210> SEQ ID NO 711
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 711
caacguaacg auuucaugaa a 21

<210> SEQ ID NO 712
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 712
caacguaacg auuucaugaa a 21

<210> SEQ ID NO 713
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 713
caacguaacg auuucaugaa a 21

<210> SEQ ID NO 714
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 714
caacguaacg auuucaugaa a 21

<210> SEQ ID NO 715
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 715
caacguaacg auuucaugaa a 21

<210> SEQ ID NO 716
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 716
caacguaacg auuucaugaa a 21

<210> SEQ ID NO 717
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 717
caacguaacg auuucaugaa a 21

<210> SEQ ID NO 718
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 718
caacguaacg auuucaugaa a 21

<210> SEQ ID NO 719
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 719
caacguaacg auuucaugaa a 21

<210> SEQ ID NO 720
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 720
caacguaacg auuucaugaa a 21

<210> SEQ ID NO 721
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 721
cacauucucu auguacuaug u 21

<210> SEQ ID NO 722
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 722
gacauucucu auguacuaug u 21

<210> SEQ ID NO 723
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 723
cgcauucucu auguacuaug u 21

<210> SEQ ID NO 724
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 724
cccauucucu auguacuaug u 21

<210> SEQ ID NO 725
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 725
ggcauucucu auguacuaug u 21

<210> SEQ ID NO 726
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2-aminoadenosine

<400> SEQUENCE: 726
cacnuucucu auguacuaug u 21

<210> SEQ ID NO 727
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2-aminoadenosine

<400> SEQUENCE: 727
cccnuucucu auguacuaug u 21

<210> SEQ ID NO 728
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 728
gcgaccauga ggagauucau u 21

<210> SEQ ID NO 729
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 729
cgcucagccu augaauucau u 21

<210> SEQ ID NO 730
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 730
caagggucag guaguaagug a 21

<210> SEQ ID NO 731
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 731
gacugaaucc cuguucaagc a 21

<210> SEQ ID NO 732
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 732
ucagugccau gacaaacauc u 21

<210> SEQ ID NO 733
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 733
gcaccucaca uuugaugugg a 21

<210> SEQ ID NO 734
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 734
acacaacugu ccauacuaac a 21

<210> SEQ ID NO 735
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 735
ggcauaguau cuuugacuuc a 21

<210> SEQ ID NO 736
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 736
gaguacacaa uuguuuuacc u 21

<210> SEQ ID NO 737
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 737
cuuccuauuc accaagcuaa a 21

<210> SEQ ID NO 738
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 738
ggucagugac auguagguag a 21

<210> SEQ ID NO 739
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 739
caacguaacg auuucaugaa a 21

<210> SEQ ID NO 740
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 740
caacguaacg auuucaugaa a 21

<210> SEQ ID NO 741
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 741
caacguaacg auuucaugaa a 21

<210> SEQ ID NO 742
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 742
caacguaacg auuucaugaa a 21

<210> SEQ ID NO 743
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 743
caacguaacg auuucaugaa a 21

<210> SEQ ID NO 744
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 744
caacguaacg auuucaugaa a 21

<210> SEQ ID NO 745
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 745
caacguaacg auuucaugaa a 21

<210> SEQ ID NO 746
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 746
caacguaacg auuucaugaa a 21

<210> SEQ ID NO 747
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 747
caacguaacg auuucaugaa a 21

<210> SEQ ID NO 748
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 748
caacguaacg auuucaugaa a 21

<210> SEQ ID NO 749
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 749
caacguaacg auuucaugaa a 21

<210> SEQ ID NO 750
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 750
caacguaacg auuucaugaa a 21

<210> SEQ ID NO 751
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 751
caacguaacg auuucaugaa a 21

<210> SEQ ID NO 752
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 752
caacguaacg auuucaugaa a 21

<210> SEQ ID NO 753
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 753
caacguaacg auuucaugaa a 21

<210> SEQ ID NO 754
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 754
caacguaacg auuucaugaa a 21

<210> SEQ ID NO 755
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 755
caacguaacg auuucaugaa a 21

<210> SEQ ID NO 756
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 756
caacguaacg auuucaugaa a 21

<210> SEQ ID NO 757
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 757
caacguaacg auuucaugaa a 21

<210> SEQ ID NO 758
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 758
caacguaacg auuucaugaa a 21

<210> SEQ ID NO 759
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 759
caacguaacg auuucaugaa a 21

<210> SEQ ID NO 760
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 760
caacguaacg auuucaugaa a 21

<210> SEQ ID NO 761
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 761
caacguaacg auuucaugaa a 21

<210> SEQ ID NO 762
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 762
caacguaacg auuucaugaa a 21

<210> SEQ ID NO 763
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 763
gcacaacugu ccauacuaac a 21

<210> SEQ ID NO 764
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 764
ccacaacugu ccauacuaac a 21

<210> SEQ ID NO 765
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 765
ggacaacugu ccauacuaac a 21

<210> SEQ ID NO 766
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 766
caacguaacg auuucaugaa a 21

<210> SEQ ID NO 767
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 767
caacguaacg auuucaugaa a 21

<210> SEQ ID NO 768
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 768
caacguaacg auuucaugaa a 21

<210> SEQ ID NO 769
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 769
caacguaacg auuucaugaa a 21

<210> SEQ ID NO 770
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 770
caacguaacg auuucaugaa a 21

<210> SEQ ID NO 771
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 771
caacguaacg auuucaugaa a 21

<210> SEQ ID NO 772
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 772
caacguaacg auuucaugaa a 21

<210> SEQ ID NO 773
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 773
caacguaacg auuucaugaa a 21

<210> SEQ ID NO 774
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 774
caacguaacg auuucaugaa a 21

<210> SEQ ID NO 775
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 775
caacguaacg auuucaugaa a 21

<210> SEQ ID NO 776
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 776
caacguaacg auuucaugaa a 21

<210> SEQ ID NO 777
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 777
caacguaacg auuucaugaa a 21

<210> SEQ ID NO 778
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 778
caacguaacg auuucaugaa a 21

<210> SEQ ID NO 779
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 779
caacguaacg auuucaugaa a 21

<210> SEQ ID NO 780
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 780
caacguaacg auuucaugaa a 21

<210> SEQ ID NO 781
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 781
caacguaacg auuucaugaa a 21

<210> SEQ ID NO 782
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 782
caacguaacg auuucaugaa a 21

<210> SEQ ID NO 783
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 783
caacguaacg auuucaugaa a 21

<210> SEQ ID NO 784
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 784
caacguaacg auuucaugaa a 21

<210> SEQ ID NO 785
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 785
caacguaacg auuucaugaa a 21

<210> SEQ ID NO 786
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 786
caacguaacg auuucaugaa a 21

<210> SEQ ID NO 787

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 787
caacguaacg auuucaugaa a 21

<210> SEQ ID NO 788
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 788
caacguaacg auuucaugaa a 21

<210> SEQ ID NO 789
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 789
caacguaacg auuucaugaa a 21

<210> SEQ ID NO 790
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 790
caacguaacg auuucaugaa a 21

<210> SEQ ID NO 791
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 791
caacguaacg auuucaugaa a 21

<210> SEQ ID NO 792
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 792
caacguaacg auuucaugaa a 21

<210> SEQ ID NO 793
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 793
caacguaacg auuucaugaa a 21

<210> SEQ ID NO 794
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 794
caacguaacg auuucaugaa a 21

<210> SEQ ID NO 795
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 795
caacguaacg auuucaugaa a 21

<210> SEQ ID NO 796
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 796
caacguaacg auuucaugaa a 21

<210> SEQ ID NO 797
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 797
caacguaacg auuucaugaa a 21

<210> SEQ ID NO 798
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 798
caacguaacg auuucaugaa a 21

<210> SEQ ID NO 799
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 799
caacguaacg auuucaugaa a 21

<210> SEQ ID NO 800
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 800
caacguaacg auuucaugaa a 21

<210> SEQ ID NO 801
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 801
caacguaacg auuucaugaa a 21

<210> SEQ ID NO 802
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 802
caacguaacg auuucaugaa a 21

<210> SEQ ID NO 803
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 803
caacguaacg auuucaugaa a 21

<210> SEQ ID NO 804
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 804
caacguaacg auuucaugaa a 21

<210> SEQ ID NO 805
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 805
cacauucucu auguacuaug u 21

<210> SEQ ID NO 806
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 806
cacauucucu auguacuaug u 21

<210> SEQ ID NO 807
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 807
cacauucucu auguacuaug u 21

<210> SEQ ID NO 808
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 808
cacauucucu auguacuaug u 21

<210> SEQ ID NO 809
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 809
acacaacugu ccauacuaac a 21

<210> SEQ ID NO 810
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 810
acacaacugu ccauacuaac a 21

<210> SEQ ID NO 811
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 811
acacaacugu ccauacuaac a 21

<210> SEQ ID NO 812
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 812
acacaacugu ccauacuaac a 21

<210> SEQ ID NO 813
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 813
caacguaacg auuucaugaa a 21

<210> SEQ ID NO 814
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 814
caacguaacg auuucaugaa a 21

<210> SEQ ID NO 815
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 815
caacguaacg auuucaugaa a 21

<210> SEQ ID NO 816
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 816
caacguaacg auuucaugaa a 21

<210> SEQ ID NO 817
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 817
caacguaacg auuucaugaa a 21

<210> SEQ ID NO 818
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 818
caacguaacg auuucaugaa a 21

<210> SEQ ID NO 819
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 819
caacguaacg auuucaugaa a 21

<210> SEQ ID NO 820
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 820
caacguaacg auuucaugaa a 21

<210> SEQ ID NO 821
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 821
caacguaacg auuucaugaa a 21

<210> SEQ ID NO 822
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 822
caacguaacg auuucaugaa a 21

<210> SEQ ID NO 823
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 823
caacguaacg auuucaugaa a 21

<210> SEQ ID NO 824
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 824
caacguaacg auuucaugaa a 21

<210> SEQ ID NO 825
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 825
caacguaacg auuucaugaa a 21

<210> SEQ ID NO 826
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 826
caacguaacg auuucaugaa a 21

<210> SEQ ID NO 827
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 827
uuucaugaaa ucguuacguu g 21

<210> SEQ ID NO 828
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 828
ugucaaagau acuaugucca g 21

<210> SEQ ID NO 829
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 829
uucucggagu cuagcgcaug g 21

<210> SEQ ID NO 830
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 830
uuugcgagca uccgguacug g 21

<210> SEQ ID NO 831
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 831
uuugcgaggg uuguagauga c 21

<210> SEQ ID NO 832
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 832
ucgaaguucu gauucccgaa g                                             21

<210> SEQ ID NO 833
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 833
uuucagggcu auugggcgug g                                             21

<210> SEQ ID NO 834
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 834
ugaaauccgu cuggguacug c                                             21

<210> SEQ ID NO 835
<211> LENGTH: 20
<212> TYPE: RNA
<213> ORGANISM: Artificial sequence
<220> FEATURE:
<223> OTHER INFORMATION: RNAi agent antisense strand underlying base
      sequence

<400> SEQUENCE: 835
uaugcuuugc uuccggcauc                                               20

<210> SEQ ID NO 836
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 836
ugcuuguccg gcaucaaagg g                                             21

<210> SEQ ID NO 837
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 837
uuugcgcuca guggcuuguc c                                             21

<210> SEQ ID NO 838
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 838
uugacgacag gcuguagucc u 21

<210> SEQ ID NO 839
<211> LENGTH: 20
<212> TYPE: RNA
<213> ORGANISM: Artificial sequence
<220> FEATURE:
<223> OTHER INFORMATION: RNAi agent antisense strand underlying base sequence

<400> SEQUENCE: 839
uagucugcca gguaaguccg 20

<210> SEQ ID NO 840
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 840
uuacguugga guugacccuu c 21

<210> SEQ ID NO 841
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 841
uauacguugg aguugacccu g 21

<210> SEQ ID NO 842
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 842
uacauacguu ggaguugacc c 21

<210> SEQ ID NO 843
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 843
ugauaaccac auacguugga g 21

<210> SEQ ID NO 844
<211> LENGTH: 20
<212> TYPE: RNA
<213> ORGANISM: Artificial sequence
<220> FEATURE:
<223> OTHER INFORMATION: RNAi agent antisense strand underlying base sequence

<400> SEQUENCE: 844
uggauuguca caccuauggc 20

<210> SEQ ID NO 845
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 845
uucggauugu cacaccuaug g 21

<210> SEQ ID NO 846
<211> LENGTH: 20
<212> TYPE: RNA
<213> ORGANISM: Artificial sequence
<220> FEATURE:
<223> OTHER INFORMATION: RNAi agent antisense strand underlying base sequence

<400> SEQUENCE: 846
uacaacgugc caucagaccc 20

<210> SEQ ID NO 847
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 847
uauccgaguc acauagcuca g 21

<210> SEQ ID NO 848
<211> LENGTH: 20
<212> TYPE: RNA
<213> ORGANISM: Artificial sequence
<220> FEATURE:
<223> OTHER INFORMATION: RNAi agent antisense strand underlying base sequence

<400> SEQUENCE: 848
uggugucguc ccucuuaccc 20

<210> SEQ ID NO 849
<211> LENGTH: 19
<212> TYPE: RNA
<213> ORGANISM: Artificial sequence
<220> FEATURE:
<223> OTHER INFORMATION: RNAi agent antisense strand underlying base sequence

<400> SEQUENCE: 849
uuuacguuga cagguaggg 19

<210> SEQ ID NO 850
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 850
uuuacguuga cagguagggu u 21

```
<210> SEQ ID NO 851
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 851

ucguuacguu gacagguagg g                                               21


<210> SEQ ID NO 852
<211> LENGTH: 20
<212> TYPE: RNA
<213> ORGANISM: Artificial sequence
<220> FEATURE:
<223> OTHER INFORMATION: RNAi agent antisense strand underlying base
      sequence

<400> SEQUENCE: 852

ucguuacguu gacagguagg                                                 20


<210> SEQ ID NO 853
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 853

uaaaucguua cguugacagg u                                               21


<210> SEQ ID NO 854
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 854

uucguuuuca gagcaaacug c                                               21


<210> SEQ ID NO 855
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 855

aguuguugua gacuuucacc u                                               21


<210> SEQ ID NO 856
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 856

ucguuaucca aagauguguc c                                               21
```

-continued

<210> SEQ ID NO 857
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 857
aucacuucaa ucuucagguc g 21

<210> SEQ ID NO 858
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 858
uuuagcugga agucuucccg u 21

<210> SEQ ID NO 859
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 859
agauacuaug uccuguuagc u 21

<210> SEQ ID NO 860
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 860
uucaccucac agucauaucu g 21

<210> SEQ ID NO 861
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 861
uguaaaacaa uuguguacuc c 21

<210> SEQ ID NO 862
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 862
ucacauacgu uggaguugac c 21

<210> SEQ ID NO 863

<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 863
accacauacg uuggaguuga c 21

<210> SEQ ID NO 864
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 864
uauugucaca ccuauggcau c 21

<210> SEQ ID NO 865
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 865
aaaccaucuc augguaguuc c 21

<210> SEQ ID NO 866
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 866
ucuaaaccau cucaugguag c 21

<210> SEQ ID NO 867
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 867
aguuccaugu aauugguauc g 21

<210> SEQ ID NO 868
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 868
aucguuacgu ugacagguag g 21

<210> SEQ ID NO 869
<211> LENGTH: 21

<212> TYPE: RNA
<213> ORGANISM: Artificial sequence
<220> FEATURE:
<223> OTHER INFORMATION: RNAi agent antisense strand underlying base sequence

<400> SEQUENCE: 869
uuucaugaaa ucguuacguu c 21

<210> SEQ ID NO 870
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 870
uuucaugaaa ucguuacguc c 21

<210> SEQ ID NO 871
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 871
aaggcuuuca gguacaaguu g 21

<210> SEQ ID NO 872
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 872
uuuagcucca ccuguguaag u 21

<210> SEQ ID NO 873
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 873
aagucaaaga uacuaugucc u 21

<210> SEQ ID NO 874
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 874
aguuacucuu cucagacaca g 21

<210> SEQ ID NO 875
<211> LENGTH: 21
<212> TYPE: RNA

<213> ORGANISM: Artificial sequence
<220> FEATURE:
<223> OTHER INFORMATION: RNAi agent antisense strand underlying base sequence

<400> SEQUENCE: 875
uuuagcuugg ugaauaggaa g 21

<210> SEQ ID NO 876
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 876
aucuuguaaa uagugugcug g 21

<210> SEQ ID NO 877
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 877
uuguacuuua aaaauagggg c 21

<210> SEQ ID NO 878
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 878
agguaaaaca auuguguacu c 21

<210> SEQ ID NO 879
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 879
acuuguuagu auggacaguu g 21

<210> SEQ ID NO 880
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 880
ucaacuuuca cagauaacca c 21

<210> SEQ ID NO 881
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 881
uccauuuccg uuucuaaguu c 21

<210> SEQ ID NO 882
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 882
aaugacucca cugcucggau c 21

<210> SEQ ID NO 883
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 883
acauaguaca uagagaaugu g 21

<210> SEQ ID NO 884
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 884
ucuaccuaca ugucacugac c 21

<210> SEQ ID NO 885
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 885
ucaaugugcu uugugugugu c 21

<210> SEQ ID NO 886
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 886
uuggcaauaa gucuauccgg u 21

<210> SEQ ID NO 887
<211> LENGTH: 21
<212> TYPE: RNA
<213> ORGANISM: Artificial sequence
<220> FEATURE:

<223> OTHER INFORMATION: RNAi agent antisense strand underlying base
      sequence

<400> SEQUENCE: 887
aggaauuucu cauagaacuu c 21

<210> SEQ ID NO 888
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 888
agcauuuaca cgucaguaac c 21

<210> SEQ ID NO 889
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 889
acguucauga aaucguuacg u 21

<210> SEQ ID NO 890
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 890
uaacguucau gaaaucguua c 21

<210> SEQ ID NO 891
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 891
auaacguuca ugaaaucguu c 21

<210> SEQ ID NO 892
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 892
uuccuuauaa aguuaagcuc c 21

<210> SEQ ID NO 893
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 893
uuucaugaaa ucguuacguu g 21

<210> SEQ ID NO 894
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 894
acauaguaca uagagaaugu c 21

<210> SEQ ID NO 895
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 895
acauaguaca uagagaaugc g 21

<210> SEQ ID NO 896
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 896
acauaguaca uagagaaugg g 21

<210> SEQ ID NO 897
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 897
acauaguaca uagagaaugc c 21

<210> SEQ ID NO 898
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 898
ugaaucuccu cauggucgcu u 21

<210> SEQ ID NO 899
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 899
ugaauucaua ggcugagcgu u 21

<210> SEQ ID NO 900
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 900
ucacuuacua ccugacccuu g 21

<210> SEQ ID NO 901
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 901
ugcuugaaca gggauucagu c 21

<210> SEQ ID NO 902
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 902
agauguuugu cauggcacug a 21

<210> SEQ ID NO 903
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 903
uccacaucaa augugaggug c 21

<210> SEQ ID NO 904
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 904
uguuaguaug gacaguugug u 21

<210> SEQ ID NO 905
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 905
ugaagucaaa gauacuaugc c 21

<210> SEQ ID NO 906
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 906
uguuaguaug gacaguugug c 21

<210> SEQ ID NO 907
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 907
uguuaguaug gacaguugug g 21

<210> SEQ ID NO 908
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 908
uguuaguaug gacaguuguc c 21

<210> SEQ ID NO 909
<211> LENGTH: 23
<212> TYPE: DNA
<213> ORGANISM: Artificial sequence
<220> FEATURE:
<223> OTHER INFORMATION: RNAi agent sense strand underlying base sequence

<400> SEQUENCE: 909
uauacguaac gauuucauga aat 23

<210> SEQ ID NO 910
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 910
caacguaacg auuucaugaa a 21

<210> SEQ ID NO 911
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 911
cuggacauag uaucuuugac a 21

<210> SEQ ID NO 912
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 912
ccaugcgcua gacuccgaga a 21

<210> SEQ ID NO 913
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 913
ccaguaccgg augcucgcaa a 21

<210> SEQ ID NO 914
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 914
gucaucuaca acccucgcaa a 21

<210> SEQ ID NO 915
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 915
cuucgggaau cagaacuucg a 21

<210> SEQ ID NO 916
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 916
ccacgcccaa uagcccugaa a 21

<210> SEQ ID NO 917
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 917
gcaguaccca gacggauuuc a 21

<210> SEQ ID NO 918
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 918
gaugccggaa gcaaagcaua 20

<210> SEQ ID NO 919
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 919
cccuuugaug ccggacaagc a 21

<210> SEQ ID NO 920
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 920
ggacaagcca cugagcgcaa a 21

<210> SEQ ID NO 921
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 921
aggacuacag ccugucguca a 21

<210> SEQ ID NO 922
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 922
cggacuuacc uggcagacua 20

<210> SEQ ID NO 923
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 923
gaagggucaa cuccaacgua a 21

<210> SEQ ID NO 924
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 924
cagggucaac uccaacguau a 21

<210> SEQ ID NO 925
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 925
gggucaacuc caacguaugu a 21

<210> SEQ ID NO 926
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 926
cuccaacgua ugugguuauc a 21

<210> SEQ ID NO 927
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 927
gccauaggug ugacaaucca 20

<210> SEQ ID NO 928
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 928
ccauaggugu gacaauccga a 21

<210> SEQ ID NO 929
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 929
gggucugaug gcacguugua 20

<210> SEQ ID NO 930
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 930
cugagcuaug ugacucggau a 21

<210> SEQ ID NO 931
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 931
ggguaagagg gacgacacca 20

<210> SEQ ID NO 932
<211> LENGTH: 19
<212> TYPE: RNA
<213> ORGANISM: Artificial sequence
<220> FEATURE:
<223> OTHER INFORMATION: RNAi agent sense strand underlying base sequence

<400> SEQUENCE: 932
cccuaccugu caacguaaa 19

<210> SEQ ID NO 933
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 933
cccuaccugu caacguaacg a 21

<210> SEQ ID NO 934
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 934
ccuaccuguc aacguaacga 20

<210> SEQ ID NO 935
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 935
accugucaac guaacgauuu a 21

-continued

<210> SEQ ID NO 936
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 936
gcaguuugcu cugaaaacga a 21

<210> SEQ ID NO 937
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 937
aggugaaagu cuacaacaac u 21

<210> SEQ ID NO 938
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 938
ggacacaucu uuggauaacg a 21

<210> SEQ ID NO 939
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 939
cgaccugaag auugaaguga u 21

<210> SEQ ID NO 940
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 940
acgggaagac uuccagcuaa a 21

<210> SEQ ID NO 941
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 941
agcuaacagg acauaguauc u 21

<210> SEQ ID NO 942

<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 942
cagauaugac ugugagguga a 21

<210> SEQ ID NO 943
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 943
ggaguacaca auuguuuuac a 21

<210> SEQ ID NO 944
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 944
ggucaacucc aacguaugug a 21

<210> SEQ ID NO 945
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 945
gucaacucca acguaugugg u 21

<210> SEQ ID NO 946
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 946
gaugccauag gugugacaau a 21

<210> SEQ ID NO 947
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 947
ggaacuacca ugagaugguu u 21

<210> SEQ ID NO 948
<211> LENGTH: 21

<212> TYPE: RNA
<213> ORGANISM: Artificial sequence
<220> FEATURE:
<223> OTHER INFORMATION: RNAi agent sense strand underlying base sequence

<400> SEQUENCE: 948
gcuaccauga gaugguuuag a 21

<210> SEQ ID NO 949
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 949
cgauaccaau uacauggaac u 21

<210> SEQ ID NO 950
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 950
ccuaccuguc aacguaacga u 21

<210> SEQ ID NO 951
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 951
gaacguaacg auuucaugaa a 21

<210> SEQ ID NO 952
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 952
gaacguaacg auuucaugaa a 21

<210> SEQ ID NO 953
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 953
ggacguaacg auuucaugaa a 21

<210> SEQ ID NO 954
<211> LENGTH: 21
<212> TYPE: RNA

<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 954
ggacguaacg auuucaunaa a 21

<210> SEQ ID NO 955
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 955
caacuuguac cugaaanccu u 21

<210> SEQ ID NO 956
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 956
acuuacacag guggagcuaa a 21

<210> SEQ ID NO 957
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 957
aggacauagu aucuuugacu u 21

<210> SEQ ID NO 958
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 958
cugugucuga gaagaguaac u 21

<210> SEQ ID NO 959
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 959
cuuccuauuc accaagcuaa a 21

<210> SEQ ID NO 960
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 960
ccagcacacu auuuacaaga u 21

<210> SEQ ID NO 961
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 961
gccccuauuu uuaaaguaca a 21

<210> SEQ ID NO 962
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 962
gaguacacaa uuguuuuacc u 21

<210> SEQ ID NO 963
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 963
caacugucca uacuaacaag u 21

<210> SEQ ID NO 964
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 964
gugguuaucu gugaaaguug a 21

<210> SEQ ID NO 965
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 965
gaacuuagaa acggaaaugg a 21

<210> SEQ ID NO 966
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 966
gauccgagca guggagucau u 21

<210> SEQ ID NO 967
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 967
cacauucucu auguacuaug u 21

<210> SEQ ID NO 968
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 968
ggucagugac auguagguag a 21

<210> SEQ ID NO 969
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 969
gacacacaca aagcacauug a 21

<210> SEQ ID NO 970
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 970
accggauaga cuuauuncca a 21

<210> SEQ ID NO 971
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 971
gaaguucuau gagaaauucc u 21

<210> SEQ ID NO 972
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 972
gguuacugac guguaaaugc u 21

<210> SEQ ID NO 973
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 973
acguaacgau uucaugaacg u 21

<210> SEQ ID NO 974
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 974
guaacgauuu caugaacguu a 21

<210> SEQ ID NO 975
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 975
gaacgauuuc augaacguua u 21

<210> SEQ ID NO 976
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 976
ggagcuuaac uuuauaagga a 21

<210> SEQ ID NO 977
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 977
gacauucucu auguacuaug u 21

<210> SEQ ID NO 978
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 978
cgcauucucu auguacuaug u 21

<210> SEQ ID NO 979
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 979
cccauucucu auguacuaug u 21

<210> SEQ ID NO 980
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 980
ggcauucucu auguacuaug u 21

<210> SEQ ID NO 981
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 981
cacauucucu auguacuaug u 21

<210> SEQ ID NO 982
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 982
cccauucucu auguacuaug u 21

<210> SEQ ID NO 983
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 983
gcgaccauga ggagauucau u 21

<210> SEQ ID NO 984
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 984
cgcucagccu augaauucau u 21

<210> SEQ ID NO 985
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 985
caagggucag guaguaagug a 21

<210> SEQ ID NO 986
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 986
gacugaaucc cuguucaagc a 21

<210> SEQ ID NO 987
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 987
ucagugccau gacaaacauc u 21

<210> SEQ ID NO 988
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 988
gcaccucaca uuugaugugg a 21

<210> SEQ ID NO 989
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 989

-continued acacaacugu ccauacuaac a 21

<210> SEQ ID NO 990
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 990
ggcauaguau cuuugacuuc a 21

<210> SEQ ID NO 991
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 991
gcacaacugu ccauacuaac a 21

<210> SEQ ID NO 992
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 992
ccacaacugu ccauacuaac a 21

<210> SEQ ID NO 993
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 993
ggacaacugu ccauacuaac a 21

<210> SEQ ID NO 994
<211> LENGTH: 22
<212> TYPE: DNA
<213> ORGANISM: Artificial sequence
<220> FEATURE:
<223> OTHER INFORMATION: RNAi agent sense strand underlying base sequence

<400> SEQUENCE: 994
caacguaacg auuucaugaa at 22

<210> SEQ ID NO 995
<211> LENGTH: 22
<212> TYPE: DNA
<213> ORGANISM: Artificial sequence
<220> FEATURE:
<223> OTHER INFORMATION: RNAi agent sense strand underlying base sequence

<400> SEQUENCE: 995
cacauucucu auguacuaug ut 22

<210> SEQ ID NO 996
<211> LENGTH: 22
<212> TYPE: DNA
<213> ORGANISM: Artificial sequence
<220> FEATURE:
<223> OTHER INFORMATION: RNAi agent sense strand underlying base
sequence

<400> SEQUENCE: 996
acacaacugu ccauacuaac at 22

<210> SEQ ID NO 997
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 997
caacguaacg auuucaugaa a 21

<210> SEQ ID NO 998
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 998
caacguaacg auuucaugaa a 21

<210> SEQ ID NO 999
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 999
caacguaacg auuucaugaa a 21

<210> SEQ ID NO 1000
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1000
caacguaacg auuucaugaa a 21

<210> SEQ ID NO 1001
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1001
caacguaacg auuucaugaa a 21

<210> SEQ ID NO 1002
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1002
caacguaacg auuucaugaa a 21

<210> SEQ ID NO 1003
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1003
caacguaacg auuucaugaa a 21

<210> SEQ ID NO 1004
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1004
caacguaacg auuucaugaa a 21

<210> SEQ ID NO 1005
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1005
caacguaacg auuucaugaa a 21

<210> SEQ ID NO 1006
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1006
caacguaacg auuucaugaa a 21

<210> SEQ ID NO 1007
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1007
caacguaacg auuucaugaa a 21

<210> SEQ ID NO 1008
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1008
cacauucucu auguacuaug u 21

<210> SEQ ID NO 1009
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1009
cacauucucu auguacuaug u 21

<210> SEQ ID NO 1010
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1010
cacauucucu auguacuaug u 21

<210> SEQ ID NO 1011
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1011
acacaacugu ccauacuaac a 21

<210> SEQ ID NO 1012
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1012
acacaacugu ccauacuaac a 21

<210> SEQ ID NO 1013
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1013
acacaacugu ccauacuaac a 21

<210> SEQ ID NO 1014

<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1014
caacguaacg auuucaugaa a 21

<210> SEQ ID NO 1015
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1015
caacguaacg auuucaugaa a 21

<210> SEQ ID NO 1016
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1016
caacguaacg auuucaugaa a 21

<210> SEQ ID NO 1017
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1017
caacguaacg auuucaugaa a 21

<210> SEQ ID NO 1018
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1018
caacguaacg auuucaugaa a 21

<210> SEQ ID NO 1019
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1019
caacguaacg auuucaugaa a 21

<210> SEQ ID NO 1020
<211> LENGTH: 21

<212> TYPE: RNA
<213> ORGANISM: Artificial sequence
<220> FEATURE:
<223> OTHER INFORMATION: RNAi agent sense strand underlying base
sequence

<400> SEQUENCE: 1020
caacguaacg auuucaugaa a 21

<210> SEQ ID NO 1021
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1021
caacguaacg auuucaugaa a 21

<210> SEQ ID NO 1022
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1022
caacguaacg auuucaugaa a 21

<210> SEQ ID NO 1023
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1023
caacguaacg auuucaugaa a 21

<210> SEQ ID NO 1024
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1024
caacguaacg auuucaugaa a 21

<210> SEQ ID NO 1025
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1025
caacguaacg auuucaugaa a 21

<210> SEQ ID NO 1026
<211> LENGTH: 21
<212> TYPE: RNA

<213> ORGANISM: Artificial sequence
<220> FEATURE:
<223> OTHER INFORMATION: RNAi agent sense strand underlying base
      sequence

<400> SEQUENCE: 1026
caacguaacg auuucaugaa a 21

<210> SEQ ID NO 1027
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1027
caacguaacg auuucaugaa a 21

<210> SEQ ID NO 1028
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1028
caacguaacg auuucaugaa a 21

<210> SEQ ID NO 1029
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1029
caacguaacg auuucaugaa a 21

<210> SEQ ID NO 1030
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1030
caacguaacg auuucaugaa a 21

<210> SEQ ID NO 1031
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1031
caacguaacg auuucaugaa a 21

<210> SEQ ID NO 1032
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1032
caacguaacg auuucaugaa a 21

<210> SEQ ID NO 1033
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1033
caacguaacg auuucaugaa a 21

<210> SEQ ID NO 1034
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1034
caacguaacg auuucaugaa a 21

<210> SEQ ID NO 1035
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1035
caacguaacg auuucaugaa a 21

<210> SEQ ID NO 1036
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1036
caacguaacg auuucaugaa a 21

<210> SEQ ID NO 1037
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1037
caacguaacg auuucaugaa a 21

<210> SEQ ID NO 1038
<211> LENGTH: 21
<212> TYPE: RNA
<213> ORGANISM: Artificial sequence
<220> FEATURE:

<223> OTHER INFORMATION: RNAi agent sense strand underlying base
      sequence

<400> SEQUENCE: 1038
caacguaacg auuucaugaa a 21

<210> SEQ ID NO 1039
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1039
caacguaacg auuucaugaa a 21

<210> SEQ ID NO 1040
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1040
caacguaacg auuucaugaa a 21

<210> SEQ ID NO 1041
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1041
caacguaacg auuucaugaa a 21

<210> SEQ ID NO 1042
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1042
caacguaacg auuucaugaa a 21

<210> SEQ ID NO 1043
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1043
caacguaacg auuucaugaa a 21

<210> SEQ ID NO 1044
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1044
caacguaacg auuucaugaa a 21

<210> SEQ ID NO 1045
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1045
caacguaacg auuucaugaa a 21

<210> SEQ ID NO 1046
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1046
caacguaacg auuucaugaa a 21

<210> SEQ ID NO 1047
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1047
caacguaacg auuucaugaa a 21

<210> SEQ ID NO 1048
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1048
caacguaacg auuucaugaa a 21

<210> SEQ ID NO 1049
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1049
caacguaacg auuucaugaa a 21

RNAi AGENTS FOR INHIBITING EXPRESSION OF HIF-2 ALPHA (*EPAS1*), COMPOSITIONS THEREOF, AND METHODS OF USE

CROSS REFERENCE TO RELATED APPLICATIONS

This application is a U.S. National Phase Application under 35 U.S.C. § 371 of International Patent Application No. PCT/US2020/012775, filed Jan. 8, 2020 which claims priority to U.S. Provisional Application Ser. No. 62/790,360, filed Jan. 9, 2019; 62/827,564, filed Apr. 1, 2019; and 62/839,381, filed Apr. 26, 2019; all of which are incorporated by reference herein in their entirety.

SEQUENCE LISTING

This application contains a Sequence Listing which has been submitted in ASCII format and is hereby incorporated by reference in its entirety. The ASCII copy is named 30663_SEQ_LISTING.txt and is 227 kb in size.

FIELD OF THE INVENTION

The present disclosure relates to RNA interference (RNAi) agents, for example, double stranded RNAi agents, for inhibition of HIF-2 alpha (EPAS1) gene expression, compositions that include HIF-2 alpha RNAi agents, and methods of use thereof.

BACKGROUND

Hypoxia-inducible factor-2 alpha (referred to as HIF-2 alpha, HIF2-alpha, Hif2alpha, or Hif2a), which is also known as endothelial PAS domain-containing protein 1 (EPAS1), is a hypoxia-inducible transcription factor that responds to decreases in available oxygen (hypoxia). HIF-2 alpha is encoded by the EPAS1 gene (alternatively referred to herein as the "HIF-2 alpha gene"), and its expression is known to be upregulated under low oxygen conditions.

In certain human populations residing in high altitudes (such as Tibetans), it has been discovered that a high proportion of the population has evolved to carry certain allele variants of the HIF-2 alpha gene that serve to improve oxygen transport in the body in low oxygen environments. In more typical altitude environments, however, over-expression of wild-type EPAS1 has been associated with increased hypertension and stroke, and with symptoms similar to mountain sickness due to excess production of red blood cells. Mutations in this gene have also been associated with erythrocytosis familial type 4 and pulmonary hypertension.

Notably, while HIF-2 alpha is broadly expressed in a variety of tissues in humans, HIF-2 alpha protein has been identified as being required for expression of, or to enhance the expression of, various genes involved in an assortment of diseases, including tumor progression. For example, HIF-2 alpha is thought to play a role in the progression of uveal melanomas by promoting the autocrine loop VEGF-pVEGFR2/KDR, and by enhancing the expression of LDHA, thus conferring a growth advantage.

EPAS1 has also been shown to be associated with, or upregulate the expression of, other factors, including: cMyc (which favors cell proliferation, transformation, neoplasia and tumorigenesis, and which is highly expressed in most cancers); Interleukin 8 (a pro-inflammatory mediator, for example, in gingivitis and psoriasis); SP-1 (a transcription factor involved in IL-8 regulation and a coactivator of cMyc); LDH5 (which is linked with tumor necrosis and increased tumor size); and LANA (Latency Associated Nuclear Antigen, which is associated with Kaposi's sarcoma-associated Herpesvirus). In addition, HIF (hypoxia induced factor) activity in general may play a role in angiogenesis required for cancer tumor growth. For example, HIF-2 alpha is believed to be involved in several other diseases, including renal cancer, clear cell renal cell carcinoma (and metastases of this and other cancers), melanoma, inflammation, chronic inflammation, neovascular diseases, rheumatoid arthritis, uveal melanoma, chondrosarcoma, and multiple myeloma. Mutations in EPAS1 gene have also been correlated to early onset of neuroendocrine tumors such as paragangliomas, somatostatinomas and/or pheochromocytomas. The mutations are commonly somatic missense mutations located in the primary hydroxylation site of HIF-2a. These mutations are believed to disrupt the protein hydroxylation/degradation mechanism and lead to protein stabilization and pseudohypoxic signaling. In addition, neuroendocrine tumors release erythropoietin (EPO) into circulating blood, and lead to polycythemia.

More specifically, HIF-2 alpha has been linked to tumor progression and metastasis in clear cell renal cell carcinoma (ccRCC). It is believed that a high proportion of ccRCC tumors express a mutant form of the Von Hippel-Landau protein that is incapable of degrading HIF-2 alpha, which leads to accumulation of HIF-2 alpha and activation of HIF-2 alpha-regulated genes that promote tumor growth and metastasis.

There continues to be a need for viable therapeutic treatments to treat various diseases, including carcinomas such as ccRCC. Similarly, there continues to be a need for therapeutic drug products that are capable of inhibiting the expression and/or reducing the production of HIF-2 alpha. As just one example, a substantial reduction of HIF-2 alpha expression in ccRCC cells may be able to inhibit the undesired growth or otherwise slow the progression of these cancer cells.

One known method of inhibiting gene expression is through RNA interference (RNAi), by administering oligonucleotide-based drug products that are capable of inhibiting or silencing gene expression (for example, RNAi agents). However, great challenges remain in both identifying potent and stable oligonucleotide sequences capable of silencing gene expression in vivo, as well as determining therapeutically viable methods to safely and selectively deliver the therapeutic to the desired cells or tissues. Oligonucleotide-based drug products tend to readily and rapidly be degraded or filtered through the body when administered in vivo due to, among other things, their relatively small size and inherent organic properties, which often prevent them from reaching the intended target cells and/or tissues. Various attempts have been proposed to try to overcome this limitation including, for example, by encapsulation in liposomes, by iontophoresis, by incorporation into other vehicles such as hydrogels, cyclodextrins, biodegradable nanocapsules, bioadhesive microspheres, proteinaceous vectors, or Dynamic Polyconjugates™ (DPCs) (see, for example WO 2000/053722, WO 2008/0022309, WO 2011/104169, and WO 2012/083185, each of which is incorporated herein by reference). Alternatively, conjugation of the oligonucleotides to targeting ligands, such as compounds having affinity to cell surface molecules, cell receptor ligands, haptens, antibodies, monoclonal antibodies, antibody fragments, or antibody mimics with affinity to cell surface molecules, have seen some recent success in delivering oligonucleotide-based therapeutics to hepatocytes in the liver. To date, however, efforts to target oligonucleotide-based drug products to extrahepatic cells have largely failed either due to a lack of efficacy, toxicities, or a combination of both.

Despite certain advances in the field, there continues to exist a need for improved delivery mechanisms to facilitate the delivery of therapeutics, including oligonucleotides and oligonucleotide-based drug products, in vivo. Further, there remains a need for potent and selective inhibitors of HIF-2 alpha.

SUMMARY

Disclosed herein are RNA interference (RNAi) agents (also herein termed RNAi agent, RNAi trigger, or trigger), for example, double-stranded RNAi agents, that are able to selectively and efficiently inhibit the expression of a HIF-2 alpha (EPAS1) gene. Further disclosed herein are compositions that include an RNAi agent for inhibiting expression of HIF-2 alpha, wherein the HIF-2 alpha RNAi agent is linked to at least one targeting ligand that has affinity for a cell receptor present on a targeted cell, and, optionally, to at least one pharmacokinetic (PK) enhancer. The HIF-2 alpha RNAi agents disclosed herein can selectively and efficiently decrease or inhibit expression of a HIF-2 alpha (EPAS1) gene in a subject, for example, a human or animal subject.

In general, the present disclosure features HIF-2 alpha gene-specific RNAi agents, compositions that include HIF-2 alpha RNAi agents, and methods for inhibiting expression of a HIF-2 alpha (EPAS1) gene in vivo and/or in vitro using the HIF-2 alpha RNAi agents and compositions that include HIF-2 alpha RNAi agents described herein.

The described HIF-2 alpha RNAi agents can be used in methods for therapeutic treatment (including prophylactic and preventative treatment) of conditions and diseases that can be mediated at least in part by the reduction in HIF-2 alpha expression, including, for example, carcinomas such as clear cell renal cell carcinoma (ccRCC). The HIF-2 alpha RNAi agents disclosed herein can selectively reduce HIF-2 alpha gene expression in cells in a subject. The methods disclosed herein include the administration of one or more HIF-2 alpha RNAi agents to a subject, for example, a human or animal subject, using any suitable methods known in the art, such as intravenous infusion, intravenous injection, or subcutaneous injection.

In one aspect, the disclosure features RNAi agents for inhibiting expression of the human HIF-2 alpha (EPAS1) gene, wherein the RNAi agent includes a sense strand and an antisense strand. The HIF-2 alpha RNAi agents can further be linked or conjugated to one or more targeting ligands and/or one or more PK enhancers.

Also described herein are pharmaceutical compositions that include an RNAi agent capable of inhibiting the expression of a HIF-2 alpha (EPAS1) gene, wherein the composition further includes at least one pharmaceutically acceptable excipient. The pharmaceutical compositions described herein that include one or more of the disclosed HIF-2 alpha RNAi agents are able to selectively and efficiently decrease or inhibit expression of a HIF-2 alpha gene in vivo. The compositions that include one or more HIF-2 alpha RNAi agents can be administered to a subject, such as a human or animal subject, for the treatment (including prophylactic treatment or inhibition) of conditions and diseases that can be mediated at least in part by a reduction in HIF-2 alpha expression, including, for example, carcinomas such as ccRCC.

One aspect described herein is an RNAi agent for inhibiting expression of a HIF-2 alpha (EPAS1) gene, comprising:

(i) an antisense strand comprising at least 17 contiguous nucleotides differing by 0 or 1 nucleotides from any one of the sequences provided in Table 3;

(ii) a sense strand comprising a nucleotide sequence that is at least partially complementary to the antisense strand; and (iii) one or more targeting ligands.

In another aspect described is an RNAi agent capable of inhibiting expression of a HIF-2 alpha (EPAS1) gene comprising:

(i) an antisense strand that is between 18 and 49 nucleotides in length that is at least partially complementary to a HIF-2 alpha (EPAS1) gene (SEQ ID NO:1);

(ii) a sense strand that is at least partially complementary to the antisense strand;

(iii) a targeting ligand linked to the sense strand; and (iv) a PK enhancer linked to the sense strand.

In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') UUUCAUGAAAUCGUUACGUUG (SEQ ID NO: 827). In some embodiments, a HIF-2 alpha RNAi agent disclosed herein includes an antisense strand that consists of, consists essentially of, or comprises a nucleotide sequence differing by no more than 1 nucleotide from the nucleotide sequence (5'→3') UUUCAUGAAAUCGUUACGUUG (SEQ ID NO: 827), wherein all or substantially all of the nucleotides are modified nucleotides. In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') UUUCAUGAAAUCGUUACGUUG (SEQ ID NO: 827), wherein SEQ ID NO: 827 is located at positions 1-21 (5'→3') of the antisense strand.

In some embodiments, a HIF-2 alpha RNAi agent disclosed herein includes an antisense strand that consists of, consists essentially of, or comprises a modified nucleotide sequence differing by no more than 1 nucleotide from the nucleotide sequence (5'→3') usUfsusCfaUfgAfaAfuCfgUfuAfcGfuUfsg (SEQ ID NO: 30), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 7A through 7G showing all internucleoside linkages). In some embodiments, a HIF-2 alpha RNAi agent disclosed herein includes an antisense strand that consists of, consists essentially of, or comprises the nucleotide sequence (5'→3') usUfsusCfaUfgAfaAfuCfgUfuAfcGfuUfsg (SEQ ID NO: 30), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a HIF-2 alpha RNAi agent disclosed herein includes an antisense strand that consists of, consists essentially of, or comprises a modified nucleotide sequence differing by no more than 1 nucleotide from the nucleotide sequence (5'→3') asCfsasUfaGfuAfcAfuAfgAfgAfaUfgUfsg (SEQ ID NO: 90), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. In some embodiments, a HIF-2 alpha RNAi agent disclosed herein includes an antisense strand that consists of, consists essentially of, or comprises the nucleotide sequence (5'→3') asCfsasUfaGfuAfcAfuAfgAfgAfaUfgUfsg (SEQ ID NO: 90), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a HIF-2 alpha RNAi agent disclosed herein includes an antisense strand that consists of, consists essentially of, or comprises a modified nucleotide sequence differing by no more than 1 nucleotide from the nucleotide sequence (5'→3') usGfsusUfaGfuAfuGfgAfcAfgUfuGfuGfsu (SEQ ID NO: 113), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. In some embodiments, a HIF-2 alpha RNAi agent disclosed herein includes an antisense strand that consists of, consists essentially of, or comprises the nucleotide sequence (5'→3') usGfsusUfaGfuAfuGfgAfcAfgUfuGfuGfsu (SEQ ID NO: 113), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') ACAUAGUACAUAGAGAAUGUG (SEQ ID NO: 883). In some embodiments, a HIF-2 alpha RNAi agent disclosed herein includes an antisense strand that consists of, consists essentially of, or comprises a nucleotide sequence differing by no more than 1 nucleotide from the nucleotide sequence (5'→3') ACAUAGUACAUAGAGAAUGUG (SEQ ID NO: 883), wherein all or substantially all of the nucleotides are modified nucleotides. In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') ACAUAGUACAUAGAGAAUGUG (SEQ ID NO: 883), wherein SEQ ID NO: 883 is located at positions 1-21 (5'→3') of the antisense strand.

In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') UGUUAGUAUGGACAGUUGUGU (SEQ ID NO: 902). In some embodiments, a HIF-2 alpha RNAi agent disclosed herein includes an antisense strand that consists of, consists essentially of, or comprises a nucleotide sequence differing by no more than 1 nucleotide from the nucleotide sequence (5'→3') UGUUAGUAUGGACAGUUGUGU (SEQ ID NO: 902), wherein all or substantially all of the nucleotides are modified nucleotides. In some embodiments, a HIF-2 alpha RNAi agent disclosed herein includes an antisense strand that consists of, consists essentially of, or comprises a nucleobase sequence differing by 0 or 1 nucleobases from the nucleotide sequence (5'→3') UGUUAGUAUGGACAGUUGUGU (SEQ ID NO: 902), wherein SEQ ID NO: 902 is located at positions 1-21 (5'→3') of the antisense strand.

In some embodiments, a HIF-2 alpha RNAi agent disclosed herein includes an antisense strand that consists of, consists essentially of, or comprises the modified nucleotide sequence (5'→3') usUfsusCfaUfgAfaAfuCfgUfuAfcGfuUfsg (SEQ ID NO: 30), and a sense strand that consists of, consists essentially of, or comprises the modified nucleotide sequence (5'→3') Y-(NH-C6)scsaacguaaCfGfAfuuu$^{Z}$ca$^{Z}$ug$^{Z}$aa$^{Z}$sa(invAb)(6-S)-X (SEQ ID NO:761), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); u$^{Z}$, a$^{Z}$, g$^{Z}$, and c$^{Z}$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (NH2-C6) is as defined in Table 7, and s represents a phosphorothioate linkage. In some embodiments, a HIF-2 alpha RNAi agent disclosed herein includes an antisense strand that consists of, consists essentially of, or comprises the modified nucleotide sequence (5'→3') usUfsusCfaUfgAfaAfuCfgUfuAfcGfuUfsg (SEQ ID NO: 30), and a sense strand that consists of, consists essentially of, or comprises the modified nucleotide sequence (5'→3') Y-(NH-C6)scsaacguaaCfGfAfuuu$^{Z}$ca$^{Z}$ug$^{Z}$aa$^{Z}$sa(invAb)(6-S)-X (SEQ ID NO:761), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that consists of, consists essentially of, or comprises the modified nucleotide sequence (5'→3') asCfsasUfaGfuAfcAfuAfgAfgAfaUfgUfsg (SEQ ID NO:90), and a sense strand that consists of, consists essentially of, or comprises the modified nucleotide sequence (5'→3') $(Z)_3$-(TriAlk14)s(invAb)scacauucuCfUfAfugu$^{Z}$ac$^{Z}$ua$^{Z}$ug$^{Z}$us(invAb)(C6-S)-X (SEQ ID NO:806), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); u$^{Z}$, a$^{Z}$, g$^{Z}$, and c$^{Z}$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (TriAlk14), (C6-S), and (invAb) are as defined in Table 7, and s represents a phosphorothioate linkage. In some embodiments, a HIF-2 alpha RNAi agent disclosed herein includes an antisense strand that consists of, consists essentially of, or comprises the modified nucleotide sequence (5'→3') asCfsasUfaGfuAfcAfuAfgAfgAfaUfgUfsg (SEQ ID NO:90), and a sense strand that consists of, consists essentially of, or comprises the modified nucleotide sequence (5'→3') (Z)$_3$-(TriAlk14)s(invAb)scacauucuCfUfAfugu$^Z$ac$^Z$ua$^Z$ug$^Z$us(invAb)(C6-S)-X (SEQ ID NO:806), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that consists of, consists essentially of, or comprises the modified nucleotide sequence (5'→3') usGfsusUfaGfuAfuGfgAfcAfgUfuGfuGfsu (SEQ ID NO:113), and a sense strand that consists of, consists essentially of, or comprises the modified nucleotide sequence (5'→3')(Z)$_3$-(TriAlk14)s(invAb)sacacaacuGfUfCfcau$^Z$ac$^Z$ua$^Z$ac$^Z$ as(invAbxC6-S)-X (SEQ ID NO:810), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); u$^Z$, a$^Z$, g$^Z$, and c$^Z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (TriAlk14), (C6-S), and (invAb), as defined in Table 7, and s represents a phosphorothioate linkage. In some embodiments, a HIF-2 alpha RNAi agent disclosed herein includes an antisense strand that consists of, consists essentially of, or comprises the modified nucleotide sequence (5'→3') usGfsusUfaGfuAfuGfgAfcAfgUfuGfuGfsu (SEQ ID NO:113), and a sense strand that consists of, consists essentially of, or comprises the modified nucleotide sequence (5'→3') (Z)$_3$-(TriAlk14)s(invAb)sacacaacuGfUfCfcau$^Z$ac$^Z$ua$^Z$ac$^Z$as(invAb)(C6-S)-X (SEQ ID NO:810), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that consists of, consists essentially of, or comprises the modified nucleotide sequence (5'→3') usUfsusCfaUfgAfaAfuCfgUfuAfcGfuUfsg (SEQ ID NO:30), and a sense strand that consists of, consists essentially of, or comprises the modified nucleotide sequence (5'→3') selected from the group consisting of: Y-(NH-C6)scsaa$^Z$cgua$^Z$aCfGfAfuuuca$^Z$ugaa$^Z$sa(invAb)(6-S)-X (SEQ ID NO:740), Y-(NH-C6)scsaac$^Z$guaa$^Z$CfGfAfuuu$^Z$caug$^Z$aasa(invAb)(6-S)-X (SEQ ID NO:756), Y-(NH-C6)scsaacg$^Z$uaa$^Z$CfGfAfu$^Z$uuc$^Z$augaasa(invAb)(6-S)-X (SEQ ID NO:757), and Y-(NH-C6)scsaacguaaCfGfAfuuucau$^Z$g$^Z$a$^Z$a$^Z$sa(invAb)(6-S)-X (SEQ ID NO:762), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); u$^Z$, a$^Z$, g$^Z$, and c$^Z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (NH2-C6), (invAb), and (6-S) are as defined in Table 7, and s represents a phosphorothioate linkage. In some embodiments, a HIF-2 alpha RNAi agent disclosed herein includes an antisense strand that consists of, consists essentially of, or comprises the modified nucleotide sequence (5'→3') usUfsusCfaUfgAfaAfuCfgUfuAfcGfuUfsg (SEQ ID NO:30), and a sense strand that consists of, consists essentially of, or comprises the modified nucleotide sequence (5'→3') selected from the group consisting of: Y-(NH-C6)scsaa$^Z$cgua$^Z$aCfGfAfuuuca$^Z$ugaa$^Z$sa(invAb)(6-S)-X (SEQ ID NO:740), Y-(NH-C6)scsaac$^Z$guaa$^Z$CfGfAfuuu$^Z$caug$^Z$aasa(invAb)(6-S)-X (SEQ ID NO:756), Y-(NH-C6)scsaacg$^Z$uaa$^Z$CfGfAfu$^Z$uuc$^Z$augaasa(invAb)(6-S)-X (SEQ ID NO:757), and Y-(NH-C6)scsaacguaaCfGfAfuuucau$^Z$g$^Z$a$^Z$a$^Z$sa(invAb)(6-S)-X (SEQ ID NO:762), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that consists of, consists essentially of, or comprises a nucleotide sequence that differs by 0 or 1 nucleotides from one of the following nucleotide sequences (5'→3'):

```
UUUCAUGAAAUCGUUACGUUG;      (SEQ ID NO: 827)

ACAUAGUACAUAGAGAAUGUG;      (SEQ ID NO: 883)
or

UGUUAGUAUGGACAGUUGUGU;      (SEQ ID NO: 902)
```

wherein the HIF-2 alpha RNAi agent further includes a sense strand that is at least partially complementary to the antisense strand; and wherein all or substantially all of the nucleotides on both the antisense strand and the sense strand are modified nucleotides.

In some embodiments, a HIF-2 alpha RNAi agent disclosed herein includes an antisense strand that consists of, consists essentially of, or comprises a nucleotide sequence that differs by 0 or 1 nucleotides from one of the following nucleotide sequences (5'→3'):

```
UUUCAUGAAAUCGUUACGUUG;      (SEQ ID NO: 827)

ACAUAGUACAUAGAGAAUGUG;      (SEQ ID NO: 883)
or

UGUUAGUAUGGACAGUUGUGU;      (SEQ ID NO: 902)
```

wherein the HIF-2 alpha RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor.

In some embodiments, a HIF-2 alpha RNAi agent disclosed herein includes an antisense strand that consists of, consists essentially of, or comprises a nucleotide sequence that differs by 0 or 1 nucleotides from one of the following nucleotide sequences (5'→3'):

```
UUUCAUGAAAUCGUUACGUUG;      (SEQ ID NO: 827)

ACAUAGUACAUAGAGAAUGUG;      (SEQ ID NO: 883)
or

UGUUAGUAUGGACAGUUGUGU;      (SEQ ID NO: 902)
```

wherein the HIF-2 alpha RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor; and wherein the respective antisense strand sequence is located at positions 1-21 of the antisense strand.

In some embodiments, a HIF-2 alpha RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

```
UUUCAUGAAAUCGUUACGUUG       (SEQ ID NO: 827)
and

CAACGUAACGAUUUCAUGAAA;      (SEQ ID NO: 428)

ACAUAGUACAUAGAGAAUGUG       (SEQ ID NO: 883)
and

CACAUUCUCUAUGUACUAUGU;      (SEQ ID NO: 485)
or

UGUUAGUAUGGACAGUUGUGU       (SEQ ID NO: 902)
and

ACACAACUGUCCAUACUAACA;      (SEQ ID NO: 507)
```

wherein all or substantially all of the nucleotides on both the antisense strand and the sense strand are modified nucleotides.

In some embodiments, a HIF-2 alpha RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

```
UUUCAUGAAAUCGUUACGUUG       (SEQ ID NO: 827)
and

CAACGUAACGAUUUCAUGAAA;      (SEQ ID NO: 428)

ACAUAGUACAUAGAGAAUGUG       (SEQ ID NO: 883)
and

CACAUUCUCUAUGUACUAUGU;      (SEQ ID NO: 485)
or

UGUUAGUAUGGACAGUUGUGU       (SEQ ID NO: 902)
and

ACACAACUGUCCAUACUAACA;      (SEQ ID NO: 507)
```

wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that consists of, consists essentially of, or comprises a modified nucleotide sequence that differs by 0 or 1 nucleotides from one of the following nucleotide sequences (5'→3'):

```
                               (SEQ ID NO: 30)
usUfsusCfaUfgAfaAfuCfgUfuAfcGfuUfsg;

                               (SEQ ID NO: 90)
asCfsasUfaGfuAfcAfuAfgAfgAfaUfgUfsg;
or

                              (SEQ ID NO: 113)
usGfsusUfaGfuAfuGfgAfcAfgUfuGfuGfsu;
```

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; s represents a phosphorothioate linkage; and wherein the HIF-2 alpha RNAi agent further includes the sense strand that is at least partially complementary to the antisense strand; and wherein all or substantially all of the nucleotides of the sense strand are modified nucleotides.

In some embodiments, a HIF-2 alpha RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 30)
usUfsusCfaUfgAfaAfuCfgUfuAfcGfuUfsg;

(SEQ ID NO: 90)
asCfsasUfaGfuAfcAfuAfgAfgAfaUfgUfsg;
or (SEQ ID NO: 113)
usGfsusUfaGfuAfuGfgAfcAfgUfuGfuGfsu;

wherein the HIF-2 alpha RNAi agent further includes the sense strand that is at least partially complementary to the antisense strand; wherein all or substantially all of the nucleotides of the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

(SEQ ID NO: 30)
usUfsusCfaUfgAfaAfuCfgUfuAfcGfuUfsg
and (SEQ ID NO: 761)
Y-(NH-C6)scsaacguaaCfGfAfuuu$^{z}$ca$^{z}$ug$^{z}$aa$^{z}$sa(invAb)

(6-S)-X;

(SEQ ID NO: 90)
asCfsasUfaGfuAfcAfuAfgAfgAfaUfgUfsg
and (SEQ ID NO: 806)
(Z)$_{3}$-(TriAlk14)s(invAb)scacauucuCfUfAfugu$^{z}$ac$^{z}$ua$^{z}$ ug$^{z}$us(invAb)(C6-S)-X;

(SEQ ID NO: 113)
usGfsusUfaGfuAfuGfgAfcAfgUfuGfuGfsu
and (SEQ ID NO: 328)
(Z)$_{3}$-(TriAlk14)s(invAb)sacacaacuGfUfCfcau$^{z}$ac$^{z}$ua$^{z}$ ac$^{z}$as(invAb)(C6-S)-X;

(SEQ ID NO: 810)
usUfsusCfaUfgAfaAfuCfgUfuAfcGfuUfsg
and (SEQ ID NO: 740)
Y-(NH-C6)scsaa$^{z}$cgua$^{z}$aCfGfAfuuuca$^{z}$ugaa$^{z}$sa(invAb)

(6-S)-X;

(SEQ ID NO: 30)
usUfsusCfaUfgAfaAfuCfgUfuAfcGfuUfsg
and (SEQ ID NO: 756)
Y-(NH-C6)scsaac$^{z}$guaa$^{z}$CfGfAfuuu$^{z}$caug$^{z}$aasa(invAb)

(6-S)-X;

-continued (SEQ ID NO: 30)
usUfsusCfaUfgAfaAfuCfgUfuAfcGfuUfsg
and (SEQ ID NO: 757)
Y-(NH-C6)scsaacg$^{z}$uaa$^{z}$CfGfAfu$^{z}$uuc$^{z}$augaasa(invAb)

(6-S)-X;

(SEQ ID NO: 30)
usUfsusCfaUfgAfaAfuCfgUfuAfcGfuUfsg
and (SEQ ID NO: 762)
Y-(NH-C6)scsaacguaaCfGfAfuuucau$^{z}$g$^{z}$a$^{z}$a$^{z}$sa(invAb)

(6-S)-X;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); $u^Z$, $a^Z$, $g^Z$, and $c^Z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (TriAlk14), (NH2-C6), (C6-S), (6-S), and (invAb), as defined in Table 7, and s represents a phosphorothioate linkage.

In some embodiments, a HIF-2 alpha RNAi agent disclosed herein includes an antisense strand and a sense strand that consists of, consists essentially of, or comprises one of the following nucleotide sequence pairs (5'→3'):

(SEQ ID NO: 30)
usUfsusCfaUfgAfaAfuCfgUfuAfcGfuUfsg
and (SEQ ID NO: 761)
Y-(NH-C6)scsaacguaaCfGfAfuuu$^{z}$ca$^{z}$ug$^{z}$aa$^{z}$sa(invAb)

(6-S)-X;

(SEQ ID NO: 90)
asCfsasUfaGfuAfcAfuAfgAfgAfaUfgUfsg
and (SEQ ID NO: 806)
(Z)$_{3}$-(TriAlk14)s(invAb)scacauucuCfUfAfugu$^{z}$ac$^{z}$ua$^{z}$ ug$^{z}$us(invAb)(C6-S)-X;

(SEQ ID NO: 113)
usGfsusUfaGfuAfuGfgAfcAfgUfuGfuGfsu
and (SEQ ID NO: 810)
(Z)$_{3}$-(TriAlk14)s(invAb)sacacaacuGfUfCfcau$^{z}$ac$^{z}$ua $^{z}$ac$^{z}$as(invAb)(C6-S)-X;

(SEQ ID NO: 30)
usUfsusCfaUfgAfaAfuCfgUfuAfcGfuUfsg
and (SEQ ID NO: 740)
Y-(NH-C6)scsaa$^{z}$cgua$^{z}$aCfGfAfuuuca$^{z}$ugaa$^{z}$sa(invAb)

(6-S)-X;

-continued (SEQ ID NO: 30)
usUfsusCfaUfgAfaAfuCfgUfuAfcGfuUfsg
and (SEQ ID NO: 756)
Y-(NH-C6)scsaac$^{z}$guaa$^{z}$CfGfAfuuu$^{z}$caug$^{z}$aasa(invAb)

(6-S)-X;

(SEQ ID NO: 30)
usUfsusCfaUfgAfaAfuCfgUfuAfcGfuUfsg
and (SEQ ID NO: 757)
Y-(NH-C6)scsaacg$^{z}$uaa$^{z}$CfGfAfu$^{z}$uuc$^{z}$augaasa(invAb)

(6-S)-X;

(SEQ ID NO: 30)
usUfsusCfaUfgAfaAfuCfgUfuAfcGfuUfsg
and (SEQ ID NO: 762)
Y-(NH-C6)scsaacguaaCfGfAfuuucau$^{z}$g$^{z}$a$^{z}$a$^{z}$sa(invAb)

(6-S)-X;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and each X, Y and Z is independently a pharmacological moiety (for example, targeting ligand, targeting group, and/or PK enhancer); $u^Z$, $a^Z$, $g^Z$, and $c^Z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group), (TriAlk14), (NH2-C6), (C6-S), (6-S), and (invAb), as defined in Table 7, and s represents a phosphorothioate linkage; and the sense strand also includes a targeting ligand that is covalently linked to the 5' terminal end, wherein the targeting ligand includes a compound with affinity for an integrin receptor.

In some embodiments, a HIF-2 alpha RNAi agent disclosed herein includes an antisense strand that includes a nucleobase sequence that differs by 0 or 1 nucleobases from the nucleotide sequences selected from the group consisting of (5'→3'):

(SEQ ID NO: 5)
UUUCAUGAAAUCGUUACGU;

(SEQ ID NO: 10)
UGUUAGUAUGGACAGUUGU;
and (SEQ ID NO: 13)
ACAUAGUACAUAGAGAAUG.

In some embodiments, a HIF-2 alpha RNAi agent disclosed herein includes an antisense strand that includes a nucleobase sequence that differs by 0 or 1 nucleobases from the nucleotide sequences selected from the group consisting of (5'→3'):

(SEQ ID NO: 5)
UUUCAUGAAAUCGUUACGU;

(SEQ ID NO: 10)
UGUUAGUAUGGACAGUUGU;
and (SEQ ID NO: 13)
ACAUAGUACAUAGAGAAUG.

wherein all or substantially all of the nucleotides are modified nucleotides.

In some embodiments, a HIF-2 alpha RNAi agent disclosed herein includes an antisense strand that includes a nucleobase sequence that differs by 0 or 1 nucleobases from the nucleotide sequences selected from the group consisting of (5'→3'):

(SEQ ID NO: 5)
UUUCAUGAAAUCGUUACGU;

(SEQ ID NO: 10)
UGUUAGUAUGGACAGUUGU;
and (SEQ ID NO: 13)
ACAUAGUACAUAGAGAAUG;

wherein all or substantially all of the nucleotides are modified nucleotides, and wherein SEQ ID NO:5, SEQ ID NO: 10 and SEQ ID NO: 13, respectively, is located at nucleotide positions 1-19 (5'→3') of the antisense strand.

In some embodiments, a HIF-2 alpha RNAi agent disclosed herein includes an antisense strand and a sense strand that each include a nucleobase sequences that differs by 0 or 1 nucleobases from the nucleotide sequence pairs selected from the group consisting of (5'→3'):

(SEQ ID NO: 5)
UUUCAUGAAAUCGUUACGU and (SEQ ID NO: 17)
ACGUAACGAUUUCAUGAAA;

(SEQ ID NO: 10)
UGUUAGUAUGGACAGUUGU;
and (SEQ ID NO: 22)
ACAACUGUCCAUACUAACA;
or (SEQ ID NO: 13)
ACAUAGUACAUAGAGAAUG
and (SEQ ID NO:25)
CAUUCUCUAUGUACUAUGU.

In some embodiments, a HIF-2 alpha RNAi agent disclosed herein includes an antisense strand and a sense strand that each include a nucleobase sequences that differs by 0 or 1 nucleobases from the nucleotide sequence pairs selected from the group consisting of (5'→3'):

(SEQ ID NO: 5)
UUUCAUGAAAUCGUUACGU
and (SEQ ID NO: 17)
ACGUAACGAUUUCAUGAAA;

-continued (SEQ ID NO: 10)
UGUUAGUAUGGACAGUUGU;
and (SEQ ID NO: 22)
ACAACUGUCCAUACUAACA;
or (SEQ ID NO: 13)
ACAUAGUACAUAGAGAAUG
and (SEQ ID NO:25)
CAUUCUCUAUGUACUAUGU;
and wherein all or substantially all of the nucleotides are modified nucleotides.

In some embodiments, the compositions described herein comprising one or more HIF-2 alpha RNAi agents are packaged in a kit, container, pack, dispenser, pre-filled syringes, or vials. In some embodiments, the compositions described herein are administered parenterally, e.g., by intravenous injection, intravenous infusion, or subcutaneous injection.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

BRIEF DESCRIPTION OF THE DRAWINGS

FIG. 4A shows the tumor size from the vehicle control group (D5W), with the left kidney being the contralateral kidney and the right kidney (larger) the tumor kidney. FIG. 4B shows the tumor size from the mice administered with HIF-2 alpha RNAi agent, with the left kidney being the contralateral kidney and the right kidney being the tumor kidney.

FIG. 5A shows the vehicle control group (D5W), with darkened spots showing the presence of HIF-2 alpha protein. FIG. 5B shows the treatment group mice administered with HIF-2 alpha RNAi agent.

DETAILED DESCRIPTION

RNAi Agents

Figure 1:
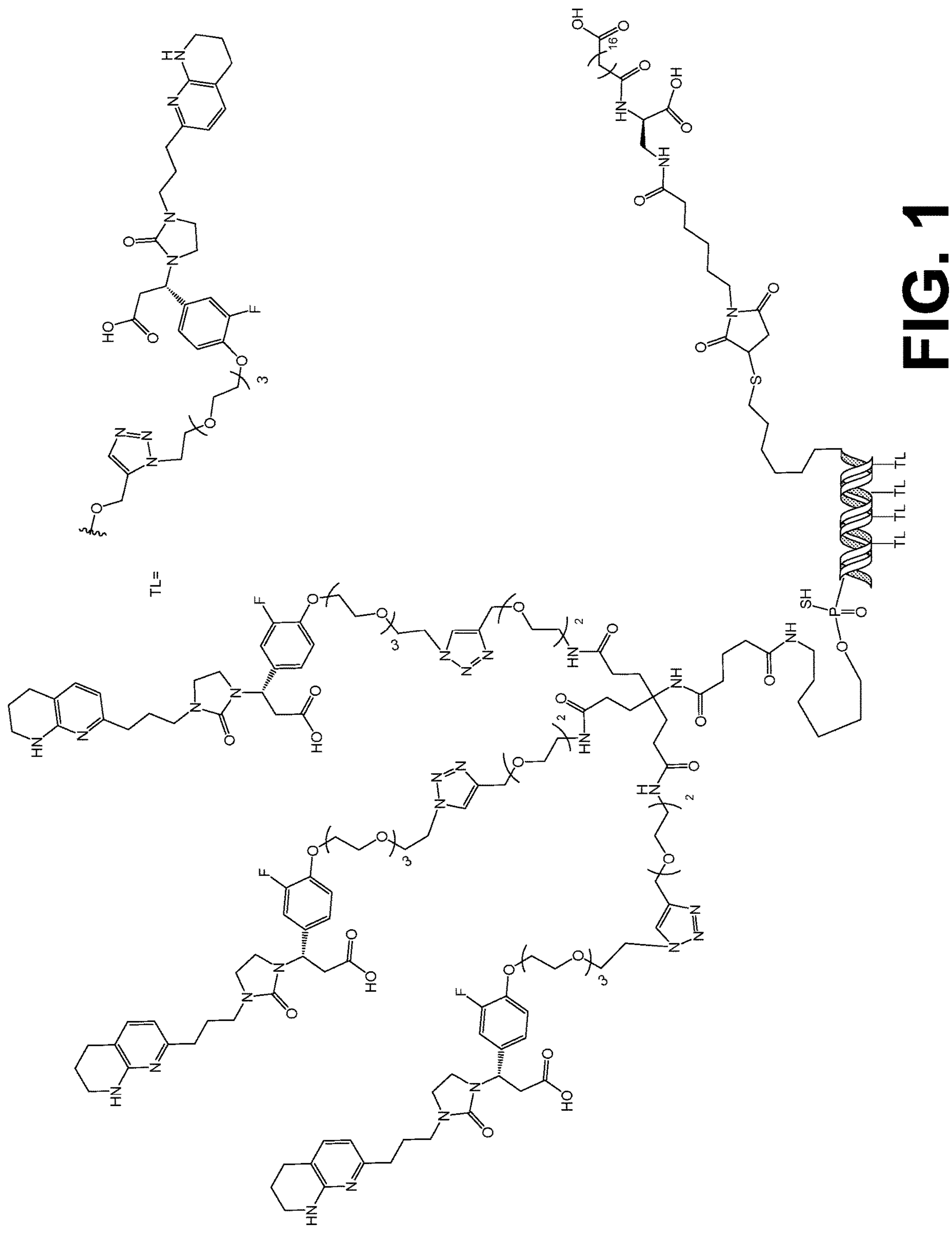
FIG. 1. Schematic diagram of a HIF-2 alpha RNAi agent (shown as the double-helix) linked to a tridentate targeting group that includes three Structure 2-avb3 targeting ligands, a C18-diacid PK enhancer, and four internal Structure 2-abv3 targeting ligands linked shown linked to internal nucleotides on the HIF-2 alpha RNAi agent. Chemical structures for the targeting ligands, targeting group, and PK enhancer are shown.

Described herein are RNAi agents for inhibiting expression of a HIF-2 alpha (EPAS1) gene (referred to herein as HIF-2 alpha or HIF2α RNAi agents, or HIF-2 alpha or HIF2α RNAi triggers). A HIF-2 alpha RNAi agent described herein includes a sense strand (also referred to as a passenger strand), and an antisense strand (also referred to as a guide strand). The sense strand and the antisense strand can be partially, substantially, or fully complementary to each other. The length of the RNAi agent sense and antisense strands described herein each can be 16 to 49 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the sense and/or antisense strands are independently 16, 17, 18, 19, 20, 21, 22, 23, 24, 25, 26, 27, 28, 29, or 30 nucleotides in length. The RNAi agents described herein, upon delivery to a cell expressing HIF-2 alpha, inhibit the expression of one or more HIF-2 alpha (EPAS1) genes in vivo or in vitro.

One aspect described herein is an RNAi agent for inhibiting expression of a HIF-2 alpha (EPAS1) gene, comprising:

(i) an antisense strand comprising at least 17 contiguous nucleotides differing by 0 or 1 nucleotides from any one of the sequences provided in Table 3;

(ii) a sense strand comprising a nucleotide sequence that is at least partially complementary to the antisense strand; and (iii) one or more targeting ligands.

In another aspect described is an RNAi agent capable of inhibiting expression of a HIF-2 alpha (EPAS1) gene comprising:

(i) an antisense strand that is between 18 and 49 nucleotides in length that is at least partially complementary to a HIF-2 alpha (EPAS1) gene (SEQ ID NO:1);

(ii) a sense strand that is at least partially complementary to the antisense strand;

(iii) a targeting ligand linked to the sense strand; and (iv) a PK enhancer linked to the sense strand.

An antisense strand of a HIF-2 alpha RNAi agent described herein includes at least 16 consecutive nucleotides that have at least 85% complementarity to a core stretch sequence (also referred to herein as a "core stretch" or "core sequence") of the same number of nucleotides in a HIF-2 alpha mRNA and to a core stretch of the same number of nucleotides in the corresponding sense strand. In some embodiments, this antisense strand core stretch is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length.

A sense strand of the HIF-2 alpha RNAi agents described herein includes at least 16 consecutive nucleotides that have at least 85% identity to a core stretch of the same number of nucleotides in a HIF-2 alpha mRNA. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

In some embodiments, the HIF-2 alpha RNAi agents disclosed herein target a portion of a HIF-2 alpha gene having the sequence of any of the sequences disclosed in Table 1.

Examples of HIF-2 alpha RNAi agent antisense strands that can be included in the HIF-2 alpha RNAi agents disclosed herein are provided in Table 3. Examples of HIF-2 alpha RNAi agent antisense strands that can be included in the HIF-2 alpha RNAi agents disclosed herein are provided in Tables 4, 4.1, 4.2, and 4.3. Examples of HIF-2 alpha RNAi agent duplexes are provided in Table 5. Examples of 19-nucleotide core stretch sequences that consist of or are included in the sense strands and antisense strands of HIF-2 alpha RNAi agents disclosed herein, are provided in Table 2.

In some embodiments, described herein are compositions that include one or more HIF-2 alpha RNAi agents that have the duplex structures disclosed in Table 5.

In a further aspect, the HIF-2 alpha RNAi agents disclosed herein can be delivered to target cells or tissues by covalently linking or conjugating the RNAi agent to one or more targeting ligands (for example, a ligand that includes a compound having affinity for one or more cell receptors located on a cell that expresses HIF-2 alpha). In some embodiments, a suitable targeting ligand includes or consists of a compound having affinity for one or more integrins (alternatively referred to as "integrin receptors").

The HIF-2 alpha RNAi agents can be delivered to cells, including but not limited to carcinoma cells such as (ccRCC) cells, using any oligonucleotide delivery technology known in the art. Nucleic acid delivery methods include, but are not limited to, by linking or conjugating to a targeting ligand, by encapsulation in liposomes, by iontophoresis, or by incorporation into other vehicles, such as hydrogels, cyclodextrins, biodegradable nanocapsules, and bioadhesive microspheres, proteinaceous vectors, or Dynamic Polyconjugates™ (DPCs).

In some embodiments, a HIF-2 alpha RNAi agent is linked to a targeting ligand comprising a compound that has affinity for one or more integrins (hereinafter referred to as an "integrin targeting ligand"). In some embodiments, a suitable targeting ligand for use with the HIF-2 alpha RNAi agents disclosed herein has affinity for integrin alpha-v-beta 3, integrin alpha-v-beta-5, or both of these integrins. Targeting ligands can be present individually (just one targeting compound present), or two or more targeting ligands may be linked via a branch point or scaffold, together forming a targeting group, and the branch point or scaffold of the targeting group is then singularly linked to the RNAi agent. Targeting groups may include two targeting ligands (referred to as "bidentate"), three targeting ligands ("tridentate"), four targeting ligands ("tetradentate"), or more than four targeting ligands. In some embodiments, a HIF-2 alpha RNAi agent is linked to two or more targeting ligands. In some embodiments, a HIF-2 alpha RNAi agent is linked to two to ten targeting ligands. In some embodiments, a HIF-2 alpha RNAi agent is liked to seven targeting ligands. In some embodiments, a HIF-2 alpha RNAi agent is liked to 1, 2, 3, 4, 5, 6, 7, 8, 9, 10, or more than 10 targeting ligands.

In some embodiments, when HIF-2 alpha RNAi agents are conjugated to targeting ligands that include compounds having affinity for integrin alpha-v-beta 3 and/or integrin alpha-v-beta-5, the RNAi agents are selectively internalized by ccRCC cells, either through receptor-mediated endocytosis or by other means. Examples of targeting ligands and targeting groups that have affinity for integrin alpha-v-beta 3 and/or integrin alpha-v-beta-5 that are useful for delivering HIF-2 alpha RNAi agents are disclosed, for example, in PCT Patent Publication No. WO 2019/210200, which is incorporated by reference herein in its entirety.

A targeting ligand can be linked to the 3' or 5' end of a sense strand, the 3' or 5' end of an antisense strand, and/or internally to one or more individual nucleotides of the sense strand and/or the antisense strand of a HIF-2 alpha RNAi agent. In some embodiments, a targeting ligand or targeting group is linked to the 3' or 5' end of the sense strand. In some embodiments, a targeting ligand or targeting group is linked to the 5' end of the sense strand. In some embodiments, a targeting ligand or targeting group is linked internally to a nucleotide of the sense strand and/or the antisense strand of the RNAi agent. In some embodiments, a targeting ligand or targeting group is linked to the 5' terminal end of the sense strand, and one or more targeting ligands are linked to one or more internal nucleotides of the sense strand. In some embodiments, a targeting ligand or targeting group is linked to the RNAi agent via a linker.

A targeting ligand or a targeting group, with or without a linker, can be linked to the 5' or 3' end of any of the sense and/or antisense strands disclosed in Tables 2, 3, or 4, 4.1, 4.2, or 4.3. A linker, with or without a targeting ligand or targeting group, can be attached to the 5' or 3' end of any of the sense and/or antisense strands disclosed in Tables 2, 3, or 4, 4.1, 4.2, or 4.3.

In a further aspect, the HIF-2 alpha RNAi agents disclosed herein can be linked or conjugated to one or more pharmacokinetic/pharmacodynamic (PK) enhancers. As used herein, a PK enhancer (also referred to as a "pharmacokinetic (PK) modifier") is a compound that, when linked to an oligonucleotide-based drug product or other therapeutic, may increase systemic circulation time of the therapeutic in vivo (increased half-life or plasma residence time) versus the free form of the therapeutic by limiting renal excretion without impeding delivery of the therapeutic to the targeted cells or tissues, or that otherwise provides a pharmacodynamic improvement over the therapeutic without a PK enhancer. Exemplary PK enhancers suitable for use with HIF-2 alpha RNAi agents are disclosed herein are disclosed. The person of ordinary skill in the art, in view of the selected therapeutic, would be able to readily design relevant in vivo and/or in vitro studies to identify additional suitable PK enhancers. For example, studies may be readily designed comparing the therapeutic both with and without the PK enhancer that quantify the amount of drug product remaining in systemic circulation of the subject at various time intervals, or that evaluate the effect or potency or duration of effect of the therapeutic at relevant time points. Such is within the knowledge of the person of ordinary skill in the art.

In another aspect, the disclosure features methods for inhibiting expression of a HIF-2 alpha (EPAS1) gene, wherein the methods include administering to a subject or to a cell of a subject an amount of a HIF-2 alpha RNAi agent capable of inhibiting the expression of a HIF-2 alpha gene, wherein the HIF-2 alpha RNAi agent comprises a sense strand and an antisense strand, and wherein the antisense strand includes the sequence of any one of the antisense strand nucleotide sequences in Table 2 or Table 3. In some embodiments, disclosed herein are methods of inhibiting expression of a HIF-2 alpha gene, wherein the methods include administering to a subject or to a cell an amount of a HIF-2 alpha RNAi agent capable of inhibiting the expression of a HIF-2 alpha gene, wherein the HIF-2 alpha RNAi agent comprises a sense strand and an antisense strand, and wherein the sense strand includes the sequence of any one of the sense strand nucleotide sequences in Tables 2, 4, 4.1, 4.2, or 4.3. Also described herein are compositions for use in such methods.

Methods for delivering HIF-2 alpha RNAi agents to cells that express integrins (also referred to herein as "integrin receptors") in a subject, such as a mammal, in vivo, are also disclosed herein. In some embodiments, the delivery of the HIF-2 alpha RNAi agents to the desired cells is facilitated by linking the HIF-2 RNAi agent to one or more targeting ligands and/or one or more PK enhancers. Compositions for use in such methods are also described.

In a further aspect, the disclosure features methods of treatment (including preventative or prophylactic treatment) of diseases, conditions, or symptoms that can be mediated at least in part by a reduction in HIF-2 alpha expression, including ccRCC, wherein the methods include administering to a subject in need thereof a HIF-2 alpha RNAi agent having an antisense strand that includes the sequence of any of the sequences in Tables 2 or 3. In some embodiments, described herein are methods of treatment (including preventative treatment) of diseases, symptoms, or conditions that can be mediated at least in part by a reduction in HIF-2 alpha expression, including ccRCC, wherein the methods include administering to a subject in need thereof a HIF-2 alpha RNAi agent having a sense strand comprising the sequence of any of the sequences in Tables 2, 4, 4.1, 4.2, or 4.3. Also described herein are compositions for use in such methods.

Also described are methods of treating a human subject having a pathological state (such as a condition or disease), or being at risk of developing a pathological state, that is mediated at least in part by HIF-2 alpha gene expression, the methods comprising the step of administering to the subject a therapeutically effective amount of a HIF-2 alpha RNAi agent and/or HIF-2 alpha RNAi agent-containing composition. The method of treating a subject with a HIF-2 alpha RNAi agent and/or HIF-2 alpha RNAi agent-containing composition can optionally be combined with one or more steps of administering one or more additional (for example, a second, third, etc.) therapeutics or treatments. An additional therapeutic can be another HIF-2 alpha RNAi agent (for example, a HIF-2 alpha RNAi agent that targets a different sequence within the HIF-2 alpha gene). An additional therapeutic can also be a small molecule drug, antibody, antibody fragment, and/or aptamer.

In a further aspect, described herein are pharmaceutical compositions that include one or more described HIF-2 alpha RNAi agent(s), optionally combined with one or more additional (second, third, etc.) therapeutics. In some embodiments, the pharmaceutical compositions that include one or more described HIF-2 alpha RNAi agent(s), optionally combined with one or more additional (for example second, third, etc.) therapeutics, can be formulated in a pharmaceutically acceptable carrier or diluent. In some embodiments, these compositions can be administered to a subject, such as a mammal. In some embodiments, the mammal is a human. In some embodiments, the optional one or more additional therapeutics is a drug product indicated for the treatment of cancer, such as one or more carcinomas. The HIF-2 alpha RNAi agent and additional therapeutic(s) can be administered in a single composition or they can be administered separately. In some embodiments, the one or more additional therapeutics is administered separately in separate dosage forms from the RNAi agent (for example, the HIF-2 alpha RNAi agent is administered by intravenous infusion or injection, while the additional therapeutic involved in the method of treatment dosing regimen is administered orally). In some embodiments, the described HIF-2 alpha RNAi agent(s) are administered to a subject in need thereof via intravenous infusion or injection, and the one or more optional additional therapeutics are also administered by intravenous infusion, injection, or orally, and together the administration provides for a treatment regimen for diseases and conditions that can be mediated by HIF-2 alpha gene expression, such as ccRCC. In some embodiments, the HIF-2 alpha RNAi agent and one or more additional therapeutics are combined into a single dosage form (for example, a "cocktail" formulated into a single composition for intravenous infusion or injection). The HIF-2 alpha RNAi agents, with or without the one or more additional therapeutics, can be combined with one or more excipients to form pharmaceutical compositions.

In some embodiments, disclosed herein are methods for inhibiting expression of a HIF-2 alpha gene in a cell or a subject, wherein the methods include administering to the cell or subject a HIF-2 alpha RNAi agent having a sense strand comprising the sequence of any of the sequences in Tables 4, 4.1, 4.2, or 4.3, and an antisense strand comprising the sequence of any of the sequences in Table 3.

In some embodiments, compositions for delivering a HIF-2 alpha RNAi agent to a ccRCC cell, in vivo, are described, the compositions comprising: a HIF-2 alpha RNAi agent linked or conjugated to one or more targeting ligands. In some embodiments, the targeting ligand includes a compound having affinity for integrin alpha-v-beta-3 and/or integrin alpha-v-beta-5. In some embodiments, the HIF-2 alpha RNAi agent linked or conjugated to one or more targeting ligands is further linked or conjugated to one or more PK enhancers.

In some embodiments, disclosed herein are compositions for delivering a HIF-2 alpha RNAi agent to a ccRCC cell in vivo, the composition including a HIF-2 alpha RNAi agent conjugated or linked to one or more targeting ligands and/or targeting groups. In some embodiments, the targeting ligands and/or targeting groups comprise compounds having affinity to one or more integrins. In some embodiments, compositions for delivering a HIF-2 alpha RNAi agent to a ccRCC cell in vivo are described, the composition including a HIF-2 alpha RNAi agent linked to an alpha-v-beta-3 and/or alpha-v-beta-5 integrin targeting ligand.

In some embodiments, disclosed herein are methods for inhibiting expression of a HIF-2 alpha (EPAS1) gene in a cell, wherein the methods include administering to the cell a HIF-2 alpha RNAi agent that includes an antisense strand that is at least partially complementary to the portion of the HIF-2 alpha mRNA having the sequence in Table 1. In some embodiments, disclosed herein are methods of inhibiting expression of a HIF-2 alpha gene in a cell, wherein the methods include administering to a cell a HIF-2 alpha RNAi agent that includes an antisense strand comprising the sequence of any of the sequences in Tables 2 or 3, and a sense strand that comprises any of the sequences in Table 2 or Table 4, 4.1, 4.2, or 4.3, that is at least partially complementary to the antisense strand. In some embodiments, disclosed herein are methods of inhibiting expression of a HIF-2 alpha gene in a cell, wherein the methods include administering a HIF-2 alpha RNAi agent that includes a sense strand that comprises any of the sequences in Table 2 or Table 4, 4.1, 4.2, or 4.3, and an antisense strand that includes the sequence of any of the sequences in Tables 2 or 3 that is at least partially complementary to the sense strand.

In some embodiments, disclosed herein are compositions for inhibiting expression of a HIF-2 alpha gene in a cell, wherein the methods include administering a composition that comprises a HIF-2 alpha RNAi agent having the duplex structure of a duplex set forth in Table 5.

The HIF-2 alpha RNAi agents disclosed herein are designed to target specific positions on a HIF-2 alpha (EPAS1) gene (SEQ ID NO:1). As defined herein, an antisense strand sequence is designed to target a HIF-2 alpha gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target a HIF-2 alpha gene at position 5033 requires that when base pairing to the gene, the 5' terminal nucleobase of the antisense strand is aligned with position 5051 of the HIF-2 alpha (EPAS1) gene.

As provided herein, a HIF-2 alpha RNAi agent does not require that the nucleobase at position 1 (5'→3') of the antisense strand be complementary to the gene, provided that there is at least 85% complementarity (for example, at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a HIF-2 alpha RNAi agent disclosed herein that is designed to target position 5033 of a HIF-2 alpha gene, the 5' terminal nucleobase of the antisense strand of the of the HIF-2 alpha RNAi agent must be aligned with position 5051 of the gene; however, the 5' terminal nucleobase of the antisense strand may be, but is not required to be, complementary to position 5051 of a HIF-2 alpha gene, provided that there is at least 85% complementarity (for example, at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, examples disclosed herein, the specific site of binding of the gene by the antisense strand of the HIF-2 alpha RNAi agent (for example, whether the HIF-2 alpha RNAi agent is designed to target a HIF-2 alpha (EPAS1) gene at position 5033 or at some other position) is important to the level of inhibition achieved by the HIF-2 alpha RNAi agent.

The described HIF-2 alpha RNAi agents can mediate RNA interference to inhibit the expression of one or more genes necessary for production of HIF-2 alpha protein. HIF-2 alpha RNAi agents can also be used to treat or prevent various diseases, disorders, or conditions, including ccRCC. Furthermore, compositions for delivery of HIF-2 alpha RNAi agents to ccRCC cells in vivo are described.

The pharmaceutical compositions including one or more HIF-2 alpha RNAi agents can be administered in a number of ways depending upon whether local or systemic treatment is desired. Administration can be, but is not limited to, intravenous, intraarterial, subcutaneous, intraperitoneal, subdermal (for example, via an implanted device), and intraparenchymal administration. In some embodiments, the pharmaceutical compositions described herein are administered by intravenous infusion or injection.

In some embodiments, the compositions described herein comprising one or more HIF-2 alpha RNAi agents are packaged in a kit, container, pack, dispenser, pre-filled syringes, infusion bag, or vials. In some embodiments, the compositions described herein are administered parenterally.

Each HIF-2 alpha RNAi agent comprises a sense strand and an antisense strand. The sense strand and the antisense strand each can be 16 to 30 nucleotides in length. The sense and antisense strands can be either the same length or they can be different lengths. In some embodiments, the sense and antisense strands are each independently 17 to 27 nucleotides in length. In some embodiments, the sense and antisense strands are each independently 17-21 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, 26, or 27 nucleotides in length. In some embodiments, a double-stranded RNAi agent has a duplex length of about 16, 17, 18, 19, 20, 21, 22, 23 or 24 nucleotides.

In some embodiments, the region of perfect, substantial, or partial complementarity between the sense strand and the antisense strand is 16-26 (for example, 16, 17, 18, 19, 20, 21, 22, 23, 24, 25, or 26) nucleotides in length and occurs at or near the 5' end of the antisense strand (for example, this region may be separated from the 5' end of the antisense strand by 0, 1, 2, 3, or 4 nucleotides that are not perfectly, substantially, or partially complementary).

The sense strand and antisense strand each contain a core stretch (also referred to herein as a “core sequence” or a “core stretch sequence”) that is 16 to 23 nucleotides in length. An antisense strand core stretch is 100% (perfectly) complementary or at least about 85% (substantially) complementary to a nucleotide sequence (sometimes referred to, for example, as a target sequence) present in the HIF-2 alpha (EPAS1) mRNA target. A sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence (target sequence) present in the HIF-2 alpha mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of nucleotide sequences used in forming HIF-2 alpha RNAi agents are provided in Tables 2, 3, and 4 (as well as 4.1, 4.2, and 4.3). Examples of RNAi agent duplexes, that include the sense strand and antisense strand sequences in Tables 2, 3, and 4, are shown in Table 5.

The HIF-2 alpha RNAi agent sense and antisense strands anneal to form a duplex. A sense strand and an antisense strand of a HIF-2 alpha RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (for example, the sense and antisense core stretch sequences of a HIF-2 alpha RNAi agent may have a region of at least 16, at least 17, at least 18, at least 19, at least 20, at least 21, at least 22, or at least 23 nucleotides that is at least 85% base paired or 100% base paired.)

In some embodiments, the antisense strand of a HIF-2 alpha RNAi agent disclosed herein differs by 0, 1, 2, or 3 nucleotides from any of the antisense strand sequences in Table 2 or Table 3. In some embodiments, the sense strand of a HIF-2 alpha RNAi agent disclosed herein differs by 0, 1, 2, or 3 nucleotides from any of the sense strand sequences in Table 2 or Table 4, 4.1, 4.2, or 4.3.

The sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the HIF-2 alpha mRNA. The sense strand additional nucleotides, if present, may or may not be identical to the corresponding sequence in the HIF-2 alpha mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a HIF-2 alpha RNAi agent has an antisense strand having a 3' extension and a sense strand having a 5' extension. In some embodiments, the extension nucleotide(s) are unpaired and form an overhang. As used herein, an “overhang” refers to a stretch of one or more unpaired nucleotides located at a terminal end of either the sense strand or the antisense strand that does not form part of the hybridized or duplexed portion of an RNAi agent disclosed herein.

In some embodiments, a HIF-2 alpha RNAi agent comprises an antisense strand having a 3' extension of 1, 2, 3, 4, 5, or 6 nucleotides in length. In other embodiments, a HIF-2 alpha RNAi agent comprises an antisense strand having a 3' extension of 1, 2, or 3 nucleotides in length. In some embodiments, one or more of the antisense strand extension nucleotides comprise nucleotides that are complementary to the corresponding HIF-2 alpha mRNA sequence. In some embodiments, one or more of the antisense strand extension nucleotides comprise nucleotides that are not complementary to the corresponding HIF-2 alpha mRNA sequence.

In some embodiments, the 5' and/or 3' end of the antisense strand can include abasic residues (Ab), which can also be referred to as an “abasic site” or “abasic nucleotide.” An abasic residue (Ab) is a nucleotide or nucleoside that lacks a nucleobase at the 1' position of the sugar moiety. (See, for example. U.S. Pat. No. 5,998,203, which is incorporated by reference herein). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (for example, (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, the sense strand or the antisense strand may include a “terminal cap,” which as used herein is a non-nucleotide compound or other moiety that can be incorporated at one or more termini of a strand of an RNAi agent disclosed herein, and can provide the RNAi agent, in some instances, with certain beneficial properties, such as, for example, protection against exonuclease degradation. In some embodiments, inverted abasic residues (invAb) are added as terminal caps (see Table 7). (See, for example, F. Czaudema, Nucleic Acids Res., 2003, 31(11), 2705-16). Terminal caps are generally known in the art, and include, for example, inverted abasic residues as well as carbon chains such as a terminal $C_3H_7$ (propyl), $C_6H_{13}$ (hexyl), or $C_{12}H_{25}$ (dodecyl) group. In some embodiments, a terminal cap is present at either the 5' terminal end, the 3' terminal end, or both the 5' and 3' terminal ends of the sense strand. In some embodiments, the 3' end of the sense strand may include additional abasic residues or inverted abasic terminal caps.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue.

In some embodiments, the 3' end of the antisense strand core stretch sequence, or the 3' end of the antisense strand sequence, may include an inverted abasic residue (invAb (see Table 7)).

In some embodiments, a HIF-2 alpha RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the HIF-2 alpha mRNA sequence. In some embodiments, the 3' sense strand extension includes or consists of one of the following sequences, but is not limited to: T, UT, TT, UU, UUT, TTT, or TTTT (each listed 5' to 3').

In some embodiments, a HIF-2 alpha RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the HIF-2 alpha mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand can have a 3' extension and/or a 5' extension.

Examples of sequences used in forming HIF-2 alpha RNAi agents are provided in Tables 2, 3, and 4, 4.1, 4.2, and 4.3. In some embodiments, a HIF-2 alpha RNAi agent antisense strand includes a sequence of any of the sequences in Tables 2 or 3. In certain embodiments, a HIF-2 alpha RNAi agent antisense strand comprises or consists of any one of the modified sequences in Table 3. In some embodiments, a HIF-2 alpha RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2 or 3. In some embodiments, a HIF-2 alpha RNAi agent sense strand includes the sequence of any of the sequences in Tables 2 or 4. In some embodiments, a HIF-2 alpha RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2 or 4. In certain embodiments, a HIF-2 alpha RNAi agent sense strand comprises or consists of a modified sequence of any one of the modified sequences in Table 4, 4.1, 4.2, or 4.3.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (do not form an overhang) but are not complementary (form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

Modified nucleotides, when used in various polynucleotide or oligonucleotide constructs, can preserve activity of the compound in cells while at the same time increasing the serum stability of these compounds, and can also minimize the possibility of activating interferon activity in humans upon administering of the polynucleotide or oligonucleotide construct.

In some embodiments, a HIF-2 alpha RNAi agent is prepared or provided as a salt, mixed salt, or a free-acid. In some embodiments, a HIF-2 alpha RNAi agent is prepared as a sodium salt. Such forms that are well known in the art are within the scope of the inventions disclosed herein.

Definitions

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (for example, chemically modified RNA) oligonucleotide molecule that is capable of degrading or inhibiting (for example, degrades or inhibits under appropriate conditions) translation of messenger RNA (mRNA) transcripts of a target mRNA in a sequence specific manner. As used herein, RNAi agents may operate through the RNA interference mechanism (for example, by inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (HIF-2 alpha mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, for example, Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (for example, RNAi agent sense strand or targeted mRNA) in relation to a second nucleobase or nucleotide sequence (for example, RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of a HIF-2 alpha (EPAS1) mRNA.

As used herein, the term "substantially identical" or "substantial identity," as applied to a nucleic acid sequence means the nucleotide sequence (or a portion of a nucleotide sequence) has at least about 85% sequence identity or more, for example, at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the preventative treatment, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, for example, sequence-specific inhibition of gene expression.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (for example, N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

As used herein, the term "linked" or "conjugated" when referring to the connection between two compounds or molecules means that two molecules are joined by a covalent bond or are associated via noncovalent bonds (for example, hydrogen bonds or ionic bonds). In some examples, where the term "linked" or "conjugated" refers to the association between two molecules via noncovalent bonds, the association between the two different molecules has a $K_D$ of less than $1\times10^{-4}$ M (for example, less than $1\times10^{-5}$ M, less than $1\times10^{-6}$ M, or less than $1\times10^{-7}$ M) in physiologically acceptable buffer (for example, buffered saline). Unless stated, the terms "linked" and "conjugated" as used herein may refer to the connection between a first compound and a second compound either with or without any intervening atoms or groups of atoms.

As used herein, a linking group is one or more atoms that connects one molecule or portion of a molecule to another to second molecule or second portion of a molecule. Similarly, as used in the art, the term scaffold is sometimes used interchangeably with a linking group. Linking groups may comprise any number of atoms or functional groups. In some embodiments, linking groups may not facilitate any biological or pharmaceutical response, and merely serve to link two biologically active molecules.

Unless stated otherwise, use of the symbol  as used herein means that any group or groups may be linked thereto that is in accordance with the scope of the inventions described herein.

As used herein, the term "including" is used to herein mean, and is used interchangeably with, the phrase "including but not limited to." The term "or" is used herein to mean, and is used interchangeably with, the term "and/or," unless the context clearly indicates otherwise.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Modified Nucleotides

In some embodiments, a HIF-2 alpha RNAi agent contains one or more modified nucleotides. As used herein, a "modified nucleotide" is a nucleotide other than a ribonucleotide (2'-hydroxyl nucleotide). In some embodiments, at least 50% (for example, at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides, 2'-fluoro nucleotides (also referred to herein as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single HIF-2 alpha RNAi agent or even in a single nucleotide thereof. The HIF-2 alpha RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and O-6 substituted purines, (for example, 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (for example, 6-methyl, 6-ethyl, 6-isopropyl, or 6-n-butyl) derivatives of adenine and guanine, 2-alkyl (for example, 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (for example, 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (0, 1, 2, 3, or 4) nucleotides in both the sense strand and the antisense strand being ribonucleotides (unmodified). As used herein, a sense strand wherein substantially all of the nucleotides present are modified nucleotides is a sense strand having two or fewer (0, 1, or 2) nucleotides in the sense strand being unmodified ribonucleotides. As used herein, an antisense sense strand wherein substantially all of the nucleotides present are modified nucleotides is an antisense strand having two or fewer (0, 1, or 2) nucleotides in the sense strand being unmodified ribonucleotides. In some embodiments, one or more nucleotides of an RNAi agent is an unmodified ribonucleotide.

As mentioned elsewhere herein, in some embodiments, the HIF-2 alpha RNAi agents disclosed herein can be linked to one or more targeting ligands and/or one or more PK enhancers on internal nucleotides of the sense strand or antisense strand of the RNAi agent to facilitate the delivery of the HIF-2 alpha RNAi agent in vivo. In some embodiments, the targeting ligands or PK enhancers are linked or conjugated to one or more internal nucleotides of the sense strand of the HIF-2 alpha RNAi agent. For example, a targeting ligand may be linked to an individual nucleotide at the 2' position of the ribose ring, the 3' position of the ribose ring, the 1' position of the ribose ring or to the nucleobase of the nucleotide, the 4' position of the ribose ring, the 5' position of the nucleotide, or to the oxygen atom on the ribose ring. The following depicts a hypothetical ribose nucleotide, with the carbons numbered:

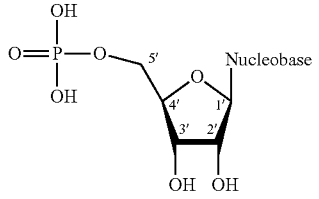

In some embodiments, to facilitate the linkage of one or more targeting ligands to internal nucleotides, 2'-O-propargyl modified nucleotides are incorporated to the nucleotide sequence (See, for example, Table 7 and Tables 4, 4.1, 4.2, and 4.3). The 2'-O-propargyl modified nucleotides, after synthesis of the respective strand, can be linked or conjugated to targeting ligands, targeting groups, and/or PK enhancers at the 2' position using standard coupling techniques as known in the art.

In some embodiments, a HIF-2 alpha RNAi agents disclosed herein may be synthesized to have at least one 2'-O-propargyl modified nucleotide in the sense strand to facilitate the linkage to a targeting ligand or targeting group. In some embodiments, the sense strand of an RNAi agent is synthesized to include at least 2, at least 3, at least 4, at least 5, at least 6, at least 7, at least 8, at least 9, at least 10, or more than 10 2'-O-propargyl modified nucleotides, in order to facilitate the linkage to at least 2, at least 3, at least 4, at least 5, at least 6, at least 7, at least 8, at least 9, at least 10, or more than 10 targeting ligands and/or targeting groups, respectively, to internal nucleotides. In some embodiments, the HIF-2 alpha RNAi agents disclosed herein may be synthesized with one 2'-O-propargyl modified nucleotide in the sense strand. In some embodiments, the HIF-2 alpha RNAi agent disclosed herein may be synthesized with two 2'-O-propargyl modified nucleotides in the sense strand. In some embodiments, the HIF-2 alpha RNAi agent disclosed herein may be synthesized with three 2'-O-propargyl modified nucleotides in the sense strand. In some embodiments, the HIF-2 alpha RNAi agent disclosed herein may be synthesized with four 2'-O-propargyl modified nucleotides in the sense strand. In some embodiments, the HIF-2 alpha RNAi agent disclosed herein may be synthesized with five 2'-O-propargyl modified nucleotides in the sense strand. In some embodiments, the HIF-2 alpha RNAi agent disclosed herein may be synthesized with more than five 2'-O-propargyl modified nucleotides in the sense strand.

Modified Internucleoside Linkages

In some embodiments, one or more nucleotides of a HIF-2 alpha RNAi agent are linked by non-standard linkages or backbones (for example, modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (for example, methyl phosphonates or 3'-alkylene phosphonates), chiral phosphonates, phosphinates, phosphoramidates (for example, 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a HIF-2 alpha RNAi agent can contain 1, 2, 3, 4, 5, or 6 phosphorothioate linkages, an antisense strand of a HIF-2 alpha RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a HIF-2 alpha RNAi agent can contain 1, 2, 3, or 4 phosphorothioate linkages, an antisense strand of a HIF-2 alpha RNAi agent can contain 1, 2, 3, or 4 phosphorothioate linkages, or both the sense strand and the antisense strand independently can contain 1, 2, 3, or 4 phosphorothioate linkages.

In some embodiments, a HIF-2 alpha RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, one phosphorothioate internucleoside linkage is at the 5' end of the sense strand, and another phosphorothioate linkage is at the 3' end of the sense strand. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a HIF-2 alpha RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a HIF-2 alpha RNAi agent contains at least three or four phosphorothioate internucleoside linkages in the antisense strand.

In some embodiments, a HIF-2 alpha RNAi agent contains one or more modified nucleotides and one or more modified internucleoside linkages. In some embodiments, a 2'-modified nucleoside is combined with modified internucleoside linkage.

HIF-2 Alpha RNAi Agents

In some embodiments, the HIF-2 alpha RNAi agents disclosed herein target a HIF-2 alpha gene at or near the positions of the HIF-2 alpha gene sequence shown in Table 1. In some embodiments, the antisense strand of a HIF-2 alpha RNAi agent disclosed herein includes a core stretch sequence that is fully, substantially, or at least partially complementary to a target HIF-2 alpha 19-mer sequence disclosed in Table 1.

TABLE 1

HIF-2 alpha 19-mer mRNA Target Sequences (taken from *homo sapiens* endothelial PAS domain protein 1 (EPAS1 or HIF-2 alpha) transcript. GenBank NM_001430.4 (SEQ ID NO: 1))

| SEQ ID No. | HIF-2 alpha 19-mer Target Sequences (5'→3') | Corresponding Positions on SEQ ID NO: 1 |
|---|---|---|
| 2 | ACGUAACGAUUUCAUGAAC | 5033-5051 |
| 3 | ACAACUGUCCAUACUAACA | 3442-3460 |
| 4 | CAUUCUCUAUGUACUAUGU | 4135-4153 |

In some embodiments, a HIF-2 alpha RNAi agent includes an antisense strand wherein position 19 of the antisense strand (5'→3') is capable of forming a base pair with position 1 of a 19-mer target sequence disclosed in Table 1. In some embodiments, a HIF-2 alpha RNAi agent includes an antisense strand wherein position 1 of the antisense strand (5'→3') is capable of forming a base pair with position 19 of the 19-mer target sequence disclosed in Table 1.

In some embodiments, a HIF-2 alpha RNAi agent includes an antisense strand wherein position 2 of the antisense strand (5'→3') is capable of forming a base pair with position 18 of the 19-mer target sequence disclosed in Table 1. In some embodiments, a HIF-2 alpha RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the HIF-2 alpha gene, or can be non-complementary to the HIF-2 alpha gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a HIF-2 alpha RNAi agent antisense strand comprises the sequence of nucleotides (from 5' end→3' end) 2-18 or 2-19 of any of the antisense strand sequences in Table 2 or Table 3. In some embodiments, a HIF-2 alpha RNAi sense strand comprises the sequence of nucleotides (from 5' end→3' end) 1-17, 1-18, or 2-18 of any of the sense strand sequences in Table 2 or Table 4, 4.1, 4.2, or 4.3.

In some embodiments, a HIF-2 alpha RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4, 4.1, 4.2, or 4.3.

In some embodiments, the HIF-2 alpha RNAi agents include core 19-mer nucleotide sequences shown in the following Table 2.

TABLE 2

HIF-2 alpha RNAi Agent Antisense Strand and Sense Strand Core Stretch Base Sequences (N = any nucleobase)

| SEQ ID NO: | Antisense Strand Base Sequence (5'→3') (Shown as an Unmodified Nucleotide Sequence) | SEQ ID NO: | Sense Strand Base Sequence (5'→3') (Shown as an Unmodified Nucleotide Sequence) | Corresponding Positions on SEQ ID NO: 1 |
|---|---|---|---|---|
| 5 | UUUCAUGAAAUCGUUACGU | 17 | ACGUAACGAUUUCAUGAAA | 5033-5051 |
| 6 | GUUCAUGAAAUCGUUACGU | 18 | ACGUAACGAUUUCAUGAAC | 5033-5051 |
| 7 | AUUCAUGAAAUCGUUACGU | 19 | ACGUAACGAUUUCAUGAAU | 5033-5051 |
| 8 | NUUCAUGAAAUCGUUACGU | 20 | ACGUAACGAUUUCAUGAAN | 5033-5051 |
| 9 | NUUCAUGAAAUCGUUACGN | 21 | NCGUAACGAUUUCAUGAAN | 5033-5051 |
| 10 | UGUUAGUAUGGACAGUUGU | 22 | ACAACUGUCCAUACUAACA | 3442-3460 |
| 11 | NGUUAGUAUGGACAGUUGU | 23 | ACAACUGUCCAUACUAACN | 3442-3460 |
| 12 | NGUUAGUAUGGACAGUUGN | 24 | NCAACUGUCCAUACUAACN | 3442-3460 |

TABLE 2-continued

HIF-2 alpha RNAi Agent Antisense Strand and Sense Strand Core Stretch Base Sequences (N = any nucleobase)

| SEQ ID NO: | Antisense Strand Base Sequence (5'→3') (Shown as an Unmodified Nucleotide Sequence) | SEQ ID NO: | Sense Strand Base Sequence (5'→3') (Shown as an Unmodified Nucleotide Sequence) | Corresponding Positions on SEQ ID NO: 1 |
|---|---|---|---|---|
| 13 | ACAUAGUACAUAGAGAAUG | 25 | CAUUCUCUAUGUACUAUGU | 4135-4153 |
| 14 | UCAUAGUACAUAGAGAAUG | 26 | CAUUCUCUAUGUACUAUGA | 4135-4153 |
| 15 | NCAUAGUACAUAGAGAAUG | 27 | CAUUCUCUAUGUACUAUGN | 4135-4153 |
| 16 | NCAUAGUACAUAGAGAAUN | 28 | NAUUCUCUAUGUACUAUGN | 4135-4153 |

The HIF-2 alpha RNAi agent sense strands and antisense strands that comprise or consist of the sequences in Table 2 can be modified nucleotides or unmodified nucleotides. In some embodiments, the HIF-2 alpha RNAi agents having the sense and antisense strand sequences that comprise or consist of the sequences in Table 2 are all or substantially all modified nucleotides.

In some embodiments, the antisense strand of a HIF-2 alpha RNAi agent disclosed herein differs by 0, 1, 2, or 3 nucleotides from any of the antisense strand sequences in Table 2. In some embodiments, the sense strand of a HIF-2 alpha RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified HIF-2 alpha RNAi agent antisense strands, as well as their underlying unmodified nucleobase sequences, are provided in Table 3. Certain modified HIF-2 alpha RNAi agent sense strands, as well as their underlying unmodified nucleobase sequences, are provided in Table 4 (as well as reflected in 4.1, 4.2, and 4.3). In forming HIF-2 alpha RNAi agents, each of the nucleotides in each of the underlying base sequences listed in Tables 3 and 4, as well as in Table 2, above, can be a modified nucleotide.

The HIF-2 alpha RNAi agents described herein are formed by annealing an antisense strand with a sense strand. A sense strand containing a sequence listed in Table 2 or Table 4, 4.1, 4.2, or 4.3, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, a HIF-2 alpha RNAi agent antisense strand comprises a nucleotide sequence of any of the sequences in Table 2 or Table 3.

In some embodiments, a HIF-2 alpha RNAi agent comprises or consists of a duplex having the nucleobase sequences of the sense strand and the antisense strand of any of the sequences in Table 2, Table 3 or Table 4, 4.1, 4.2, or 4.3.

Examples of antisense strands containing modified nucleotides are provided in Table 3. Examples of sense strands containing modified nucleotides are provided in Table 4.

As used in Tables 3 and 4 and 4.1, 4.2, and 4.3, the following notations are used to indicate modified nucleotides, targeting groups, and linking groups:

A=adenosine-3'-phosphate;
C=cytidine-3'-phosphate;
G=guanosine-3'-phosphate;
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
i=2'-O-methylinosine-3'-phosphate
is =2'-O-methylinosine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dA=2'-deoxyadenosine-3'-phosphate
dAs=2'-deoxyadenosine-3'-phosphorothioate
dC=2'-deoxycytidine-3'-phosphate
dCs=2'-deoxycytidine-3'-phosphorothioate
dG=2'-deoxyguanosine-3'-phosphate
dGs=2'-deoxyguanosine-3'-phosphorothioate
dT=2'-deoxythymidine-3'-phosphate
dTs=2'-deoxythymidine-3'-phosphorothioate
dU=2'-deoxyuridine-3'-phosphate
dUs=2'-deoxyuridine-3'-phosphorothioate
$A_{UNA}$=2',3'-seco-adenosine-3'-phosphate
$A_{UNAS}$=2',3'-seco-adenosine-3'-phosphorothioate
$C_{UNA}$=2',3'-seco-cytidine-3'-phosphate
$C_{UNAS}$=2',3'-seco-cytidine-3'-phosphorothioate
$G_{UNA}$=2',3'-seco-guanosine-3'-phosphate
$G_{UNAS}$=2',3'-seco-guanosine-3'-phosphorothioate
$U_{UNA}$=2',3'-seco-uridine-3'-phosphate
$U_{UNAS}$=2',3'-seco-uridine-3'-phosphorothioate
aAlk=2'-O-propargyladenosine-3'-phosphate, see Table 7 aAlks=2'-O-propargyladenosine-3'-phosphorothioate, see Table 7
cAlk=2'-O-propargylcytidine-3'-phosphate, see Table 7
cAlks=2'-O-propargylcytidine-3'-phosphorothioate, see Table 7
gAlk=2'-O-propargylguanosine-3'-phosphate, see Table 7
gAlks=2'-O-propargylguanosine-3'-phosphorothioate, see Table 7
tAlk=2'-O-propargyl-5-methyluridine-3'-phosphate, see Table 7
tAlks=2'-O-propargyl-5-methyluridine-3'-phosphorothioate, see Table 7
uAlk=2'-O-propargyluridine-3'-phosphate, see Table 7
uAlks=2'-O-propargyluridine-3'-phosphorothioate, see Table 7
a_2N=see Table 7
a_2Ns=see Table 7
(invAb)=inverted abasic deoxyribonucleotide, see Table 7
(invAb)s=inverted abasic deoxyribonucleotide-5'-phosphorothioate, see Table 7
s=phosphorothioate linkage
(C6-SS-Alk)=see Table 7
(C6-SS-C6)=see Table 7
(C3-SS-C3)=see Table 7
(6-SS-6)=see Table 7
(NH2-C6)=see Table 7
(C6-NH2)=see Table 7
(TriAlk #)=see Table 7
(TriAlk #)s=see Table 7

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasics are inserted such that the 3' position of the deoxyribose is linked at the 3' end of the preceding monomer on the respective strand. Moreover, as the person of ordinary skill would readily understand and appreciate, while the phosphorothioate chemical structures depicted herein typically show the anion on the sulfur atom, the inventions disclosed herein encompass all phosphorothioate tautomers (for example, where the sulfur atom has a double-bond and the anion is on an oxygen atom). Unless expressly indicated otherwise herein, such understandings of the person of ordinary skill in the art are used when describing the HIF-2 alpha RNAi agents and compositions of HIF-2 alpha RNAi agents disclosed herein.

Certain specific examples of linking groups used with the HIF-2 alpha RNAi agents disclosed herein are provided below in Table 7. Certain examples of targeting ligands and/or targeting groups, and PK enhancers, that can be linked or conjugated to the HIF-2 alpha RNAi agents disclosed herein, are also disclosed herein. For example, certain example PK enhancing compounds are provided below in Table 6. Further, in some embodiments, the PK enhancer can be positioned at the 3' terminal end of the sense strand of a HIF-2 alpha RNAi agent.

Linking groups include but are not limited to the following, for which their chemical structures are provided below in Table 7: (NH2-C6), (C6-NH2), (C6-SS-C6), (6-SS-6), (TriAlk1), (TriAlk1)s, (TriAlk2), (TriAlk2)s, (TriAlk3), (TriAlk3)s, (TriAlk4), (TriAlk4)s, (TriAlk5), (TriAlk5)s, (TriAlk6), (TriAlk6)s, (TriAlk7), (TriAlk7)s, (TriAlk8), (TriAlk8)s, (TriAlk9), (TriAlk9)s, (TriAlk10), (TriAlk10)s, (TriAlk11), (TriAlk11)s, (TriAlk12), (TriAlk12)s, (TriAlk13), (TriAlk13)s, (TriAlk14), or (TriAlk14)s. Each sense strand and/or antisense strand can have any targeting ligands or targeting groups, linking groups, and/or PK enhancers listed herein, as well as other targeting ligand/groups, other linking groups, and/or other PK enhancers, conjugated to the 5' and/or 3' end of the sequence.

TABLE 3

HIF-2 alpha RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM03465-AS | usUfsuCfaUfgAfaAfucgUfuAfcGfususg | 29 | UUUCAUGAAAUCGUUACGUUG | 827 |
| AM05815-AS | usUfsusCfaUfgAfaAfuCfgUfuAfcGfuUfsg | 30 | UUUCAUGAAAUCGUUACGUUG | 827 |
| AM06491-AS | usGfsusCfaAfaGfaUfaCfuAfuGfuCfcAfsg | 31 | UGUCAAAGAUACUAUGUCCAG | 828 |
| AM06493-AS | usUfscsUfcGfgagucUfaGfcGfcAfuGfsg | 32 | UUCUCGGAGUCUAGCGCAUGG | 829 |
| AM06495-AS | usUfsusGfcGfagcauCfcGfgUfaCfuGfsg | 33 | UUUGCGAGCAUCCGGUACUGG | 830 |
| AM06497-AS | usUfsusGfcGfaGfgGfuUfgUfaGfaUfgAfsc | 34 | UUUGCGAGGGUUGUAGAUGAC | 831 |
| AM06499-AS | usCfsgsAfaGfuUfcUfgAfuUfcCfcGfaAfsg | 35 | UCGAAGUUCUGAUUCCCGAAG | 832 |
| AM06501-AS | usUfsusCfaGfggcuaUfuGfgGfcGfuGfsg | 36 | UUUCAGGGCUAUUGGGCGUGG | 833 |
| AM06503-AS | usGfsasAfaUfcCfgUfcUfgGfgUfaCfuGfsc | 37 | UGAAAUCCGUCUGGGUACUGC | 834 |
| AM06505-AS | usAfsusGfcUfuUfgCfuUfcCfgGfcAfusCf | 38 | UAUGCUUUGCUUCCGGCAUC | 835 |
| AM06525-AS | usGfscsUfuGfuccggCfaUfcAfaAfgGfsg | 39 | UGCUUGUCCGGCAUCAAAGGG | 836 |
| AM06527-AS | usUfsusGfcGfcucagUfgGfcUfuGfuCfsc | 40 | UUUGCGCUCAGUGGCUUGUCC | 837 |

TABLE 3-continued

HIF-2 alpha RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06529-AS | usUfsgsAfcGfaCfaGfgCfuGfuAfgUfcCfsu | 41 | UUGACGACAGGCUGUAGUCCU | 838 |
| AM06531-AS | usAfsgsUfcUfgCfcAfgGfuAfaGfuCfcsg | 42 | UAGUCUGCCAGGUAAGUCCG | 839 |
| AM06533-AS | usUfsasCfgUfuGfgAfgUfuGfaCfcCfuUfsc | 43 | UUACGUUGGAGUUGACCCUUC | 840 |
| AM06535-AS | usAfsusAfcGfuUfgGfaGfuUfgAfcCfcUfsg | 44 | UAUACGUUGGAGUUGACCCUG | 841 |
| AM06537-AS | usAfscsAfuAfcGfuUfgGfaGfuUfgAfcCfsc | 45 | UACAUACGUUGGAGUUGACCC | 842 |
| AM06539-AS | usGfsasUfaAfcCfaCfaUfaCfgUfuGfgAfsg | 46 | UGAUAACCACAUACGUUGGAG | 843 |
| AM06551-AS | usGfsgsAfuUfgUfcAfcAfcCfuAfuGfgsc | 47 | UGGAUUGUCACACCUAUGGC | 844 |
| AM06553-AS | usUfscsGfgAfuUfgUfcAfcAfcCfuAfuGfsg | 48 | UUCGGAUUGUCACACCUAUGG | 845 |
| AM06555-AS | usAfscsAfaCfgUfgCfcAfuCfaGfaCfcsc | 49 | UACAACGUGCCAUCAGACCC | 846 |
| AM06557-AS | usAfsusCfcGfaGfuCfaCfaUfaGfcUfcAfsg | 50 | UAUCCGAGUCACAUAGCUCAG | 847 |
| AM06559-AS | usGfsgsUfgUfcGfuCfcCfuCfuUfaCfcsc | 51 | UGGUGUCGUCCCUCUUACCC | 848 |
| AM06561-AS | usUfsusAfcGfuUfgAfcAfgGfuAfgGfsg | 52 | UUUACGUUGACAGGUAGGG | 849 |
| AM06563-AS | usUfsusAfcGfuUfgAfcAfgGfuAfgGfgusu | 53 | UUUACGUUGACAGGUAGGGU | 850 |
| AM06565-AS | usCfsgsUfuAfcGfuUfgAfcAfgGfuAfgGfsg | 54 | UCGUUACGUUGACAGGUAGGG | 851 |
| AM06567-AS | usCfsgsUfuAfcGfuUfgAfcAfgGfuAfgsg | 55 | UCGUUACGUUGACAGGUAGG | 852 |
| AM06569-AS | usAfsasAfuCfgUfuAfcGfuUfgAfcAfgGfsu | 56 | UAAAUCGUUACGUUGACAGGU | 853 |
| AM06878-AS | usUfscsGfuUfuUfcAfgAfgCfaAfaCfuGfsc | 57 | UUCGUUUUCAGAGCAAACUGC | 854 |
| AM06880-AS | asGfsusUfgUfuGfuAfgAfcUfuUfcAfcCfsu | 58 | AGUUGUUGUAGACUUUCACCU | 855 |
| AM06882-AS | usCfsgsUfuAfuCfcAfaAfgAfuGfuGfuCfsc | 59 | UCGUUAUCCAAAGAUGUGUCC | 856 |
| AM06884-AS | asUfscsAfcUfuCfaAfuCfuUfcAfgGfuCfsg | 60 | AUCACUUCAAUCUUCAGGUCG | 857 |
| AM06886-AS | usUfsusAfgCfuGfgAfaGfuCfuUfcCfcGfsu | 61 | UUUAGCUGGAAGUCUUCCCGU | 858 |
| AM06888-AS | asGfsasUfaCfuAfuGfuCfcUfgUfuAfgCfsu | 62 | AGAUACUAUGUCCUGUUAGCU | 859 |
| AM06890-AS | usUfscsAfcCfuCfaCfaGfuCfaUfaUfcUfsg | 63 | UUCACCUCACAGUCAUAUCUG | 860 |
| AM06892-AS | usGfsusAfaAfaCfaAfuUfgUfgUfaCfuCfsc | 64 | UGUAAAACAAUUGUGUACUCC | 861 |
| AM06894-AS | usCfsasCfaUfaCfgUfuGfgAfgUfuGfaCfsc | 65 | UCACAUACGUUGGAGUUGACC | 862 |
| AM06896-AS | asCfscsAfcAfuAfcGfuUfgGfaGfuUfgAfsc | 66 | ACCACAUACGUUGGAGUUGAC | 863 |
| AM06898-AS | usAfsusUfgUfcAfcAfcCfuAfuGfgCfaUfsc | 67 | UAUUGUCACACCUAUGGCAUC | 864 |
| AM06900-AS | asAfsasCfcAfuCfuCfaUfgGfuAfgUfuCfsc | 68 | AAACCAUCUCAUGGUAGUUCC | 865 |
| AM06902-AS | usCfsusAfaAfcCfaUfcUfcAfuGfgUfaGfsc | 69 | UCUAAACCAUCUCAUGGUAGC | 866 |
| AM06904-AS | asGfsusUfcCfaUfgUfaAfuUfgGfuAfuCfsg | 70 | AGUUCCAUGUAAUUGGUAUCG | 867 |
| AM06906-AS | asUfscsGfuUfaCfgUfuGfaCfaGfgUfaGfsg | 71 | AUCGUUACGUUGACAGGUAGG | 868 |
| AM06982-AS | usUfsusCfaUfgAfaAfuCfgUfuAfcGfusUfsg | 72 | UUUCAUGAAAUCGUUACGUUG | 827 |
| AM06985-AS | usUfsusCfsasUfgAfaAfuCfgUfuAfscsGfsusUfsg | 73 | UUUCAUGAAAUCGUUACGUUG | 827 |
| AM07140-AS | usUfsusCfaUfgAfaAfuCfgUfuAfcGfuUfsc | 74 | UUUCAUGAAAUCGUUACGUUC | 869 |

TABLE 3-continued

HIF-2 alpha RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07143-AS | usUfsusCfaUfgAfaAfuCfgUfuAfcGfuCfsc | 75 | UUUCAUGAAAUCGUUACGUCC | 870 |
| AM07144-AS | usUfsusCfaUfGuNAAfaAfuCfgUfuAfcGfuCfsc | 76 | UUUCAUGAAAUCGUUACGUCC | 870 |
| AM07511-AS | usUfsuCfaUfgAfaAfuCfgUfuAfcGfuUfsg | 77 | UUUCAUGAAAUCGUUACGUUG | 827 |
| AM07531-AS | asAfsgsGfcUfuUfcAfgGfuAfcAfaGfuUfsg | 78 | AAGGCUUUCAGGUACAAGUUG | 871 |
| AM07533-AS | usUfsusAfgCfuCfcAfcCfuGfuGfuAfaGfsu | 79 | UUUAGCUCCACCUGUGUAAGU | 872 |
| AM07535-AS | asAfsgsUfcAfaAfgAfuAfcUfaUfgUfcCfsu | 80 | AAGUCAAAGAUACUAUGUCCU | 873 |
| AM07537-AS | asGfsusUfaCfuCfuUfcUfcAfgAfcAfcAfsg | 81 | AGUUACUCUUCUCAGACACAG | 874 |
| AM07539-AS | usUfsusAfgCfuUfgGfuGfaAfuAfgGfaAfsg | 82 | UUUAGCUUGGUGAAUAGGAAG | 875 |
| AM07541-AS | asUfscsUfuGfuAfaAfuAfgUfgUfgCfuGfsg | 83 | AUCUUGUAAAUAGUGUGCUGG | 876 |
| AM07543-AS | usUfsgsUfaCfuUfuAfaAfaAfuAfgGfgGfsc | 84 | UUGUACUUUAAAAAUAGGGGC | 877 |
| AM07545-AS | asGfsgsUfaAfaAfcAfaUfuGfuGfuAfcUfsc | 85 | AGGUAAAACAAUUGUGUACUC | 878 |
| AM07547-AS | asCfsusUfgUfuAfgUfaUfgGfaCfaGfuUfsg | 86 | ACUUGUUAGUAUGGACAGUUG | 879 |
| AM07549-AS | usCfsasAfcUfuUfcAfcAfgAfuAfaCfcAfsc | 87 | UCAACUUUCACAGAUAACCAC | 880 |
| AM07551-AS | usCfscsAfuUfuCfcGfuUfuCfuAfaGfuUfsc | 88 | UCCAUUUCCGUUUCUAAGUUC | 881 |
| AM07553-AS | asAfsusGfaCfuccacUfgCfuCfgGfaUfsc | 89 | AAUGACUCCACUGCUCGGAUC | 882 |
| AM07555-AS | asCfsasUfaGfuAfcAfuAfgAfgAfaUfgUfsg | 90 | ACAUAGUACAUAGAGAAUGUG | 883 |
| AM07557-AS | usCfsusAfcCfuacauGfuCfaCfuGfaCfsc | 91 | UCUACCUACAUGUCACUGACC | 884 |
| AM07559-AS | usCfsasAfuGfuGfcUfuUfgUfgUfgUfgUfsc | 92 | UCAAUGUGCUUUGUGUGUGUC | 885 |
| AM07561-AS | usUfsgsGfcAfaUfaAfgUfcUfaUfcCfgGfsu | 93 | UUGGCAAUAAGUCUAUCCGGU | 886 |
| AM07563-AS | asGfsgsAfaUfuUfcUfcAfuAfgAfaCfuUfsc | 94 | AGGAAUUUCUCAUAGAACUUC | 887 |
| AM07565-AS | asGfscsAfuUfuAfcAfcGfuCfaGfuAfaCfsc | 95 | AGCAUUUACACGUCAGUAACC | 888 |
| AM07567-AS | asCfsgsUfuCfaUfgAfaAfuCfgUfuAfcGfsu | 96 | ACGUUCAUGAAAUCGUUACGU | 889 |
| AM07569-AS | usAfsasCfgUfuCfaUfgAfaAfuCfgUfuAfsc | 97 | UAACGUUCAUGAAAUCGUUAC | 890 |
| AM07571-AS | asUfsasAfcGfuUfcAfuGfaAfaUfcGfuUfsc | 98 | AUAACGUUCAUGAAAUCGUUC | 891 |
| AM07573-AS | usUfscsCfuUfaUfaAfaGfuUfaAfgCfuCfsc | 99 | UUCCUUAUAAAGUUAAGCUCC | 892 |
| AM07603-AS | usUfsusCfaUfgAfaAfucgUfuAfcGfuUfsg | 102 | UUUCAUGAAAUCGUUACGUUG | 893 |
| AM07723-AS | asCfsasUfaGfuAfcAfuAfgAfgAfaUfgUfsc | 103 | ACAUAGUACAUAGAGAAUGUC | 894 |
| AM07725-AS | asCfsasUfaGfuAfcAfuAfgAfgAfaUfgCfsg | 104 | ACAUAGUACAUAGAGAAUGCG | 827 |
| AM07727-AS | asCfsasUfaGfuAfcAfuAfgAfgAfaUfgGfsg | 105 | ACAUAGUACAUAGAGAAUGGG | 894 |
| AM07729-AS | asCfsasUfaGfuAfcAfuAfgAfgAfaUfgCfsc | 106 | ACAUAGUACAUAGAGAAUGCC | 895 |
| AM07733-AS | usGfsasAfuCfuccucAfuGfgUfcGfcusu | 107 | UGAAUCUCCUCAUGGUCGCUU | 896 |
| AM07735-AS | usGfsasAfuUfcAfuAfgGfcUfgAfgCfgusu | 108 | UGAAUUCAUAGGCUGAGCGUU | 897 |
| AM07737-AS | usCfsasCfuUfacuacCfuGfaCfcCfuUfsg | 109 | UCACUUACUACCUGACCCUUG | 898 |
| AM07739-AS | usGfscsUfuGfaacagGfaUfuCfaGfuCfsc | 110 | UGCUUGAACAGGAUUCAGUCC | 899 |

TABLE 3-continued

HIF-2 alpha RNAi Agent Antisense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07741-AS | asGfsasUfgUfuuguсAfuGfgCfaCfuGfsa | 111 | AGAUGUUUGUCAUGGCACUGA | 900 |
| AM07743-AS | usCfscsAfcAfucaaaUfgUfgAfgGfuGfsc | 112 | UCCACAUCAAAUGUGAGGUGC | 901 |
| AM07745-AS | usGfsusUfaGfuAfuGfgAfcAfgUfuGfuGfsu | 113 | UGUUAGUAUGGACAGUUGUGU | 902 |
| AM07747-AS | usGfsasAfgUfcAfaAfgAfuAfcUfaUfgCfsc | 114 | UGAAGUCAAAGAUACUAUGCC | 903 |
| AM07891-AS | usGfsusUfaGfuauggAfcAfgUfuGfuGfsc | 115 | UGUUAGUAUGGACAGUUGUGC | 904 |
| AM07893-AS | usGfsusUfaGfuauggAfcAfgUfuGfuGfsg | 116 | UGUUAGUAUGGACAGUUGUGG | 905 |
| AM07895-AS | usGfsusUfaGfuauggAfcAfgUfuGfuCfsc | 117 | UGUUAGUAUGGACAGUUGUCC | 906 |
| AM08400-AS | usUfsusCfaUfgAfaAfuCfgUfuAfcGfuusg | 118 | UUUCAUGAAAUCGUUACGUUG | 907 |

TABLE 4

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM05339-SS | (NH2-C6)uAuascguaaCfGfAfuuuCfaugaaa(invdT)(C6-SS-C6)(C12) | 119 | UAUACGUAACGAUUUCAUGAAAT | 909 |
| AM05814-SS | (NH2-C6)scsaacguaaCfGfAfuuucaugaasa(invAb) | 120 | CAACGUAACGAUUUCAUGAAA | 910 |
| AM05816-SS | (NH2-C6)scsaacguaaCfGfAfuuucaugaasa(invAb)(C6-SS-C6) | 121 | CAACGUAACGAUUUCAUGAAA | 910 |
| AM06490-SS | (NH2-C6)scsuggacauAfGfUfaucuuugacas(invAb)(C6-SS-C6) | 122 | CUGGACAUAGUAUCUUUGACA | 911 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06492-SS | (NH2-C6)scscaugcgcUfAfGfacuccgagaas(invAb)(C6-SS-C6) | 123 | CCAUGCGCUAGACUCCGAGAA | 912 |
| AM06494-SS | (NH2-C6)scscaguaccGfGfAfugcucgcaaas(invAb)(C6-SS-C6) | 124 | CCAGUACCGGAUGCUCGCAAA | 913 |
| AM06496-SS | (NH2-C6)sgsucaucuaCfAfAfcccucgcaaas(invAb)(C6-SS-C6) | 125 | GUCAUCUACAACCCUCGCAAA | 914 |
| AM06498-SS | (NH2-C6)scsuucgggaAfUfCfagaacuucgas(invAb)(C6-SS-C6) | 126 | CUUCGGGAAUCAGAACUUCGA | 915 |
| AM06500-SS | (NH2-C6)scscacgcccAfAfUfagcccugaaas(invAb)(C6-SS-C6) | 127 | CCACGCCCAAUAGCCCUGAAA | 916 |
| AM06502-SS | (NH2-C6)sgscaguaccCfAfGfacggauuucas(invAb)(C6-SS-C6) | 128 | GCAGUACCCAGACGGAUUUCA | 917 |
| AM06504-SS | (NH2-C6)sgsaugccgGfAfAfgcaaagcauas(invAb)(C6-SS-C6) | 129 | GAUGCCGGAAGCAAAGCAUA | 918 |
| AM06524-SS | (NH2-C6)scsccuuugaUfGfCfcggacaagcas(invAb)(C6-SS-C6) | 130 | CCCUUUGAUGCCGGACAAGCA | 919 |
| AM06526-SS | (NH2-C6)sgsgacaagcCfAfCfugagcgcaaas(invAb)(C6-SS-C6) | 131 | GGACAAGCCACUGAGCGCAAA | 920 |
| AM06528-SS | (NH2-C6)sasggacuacAfGfCfcugucgucaas(invAb)(C6-SS-C6) | 132 | AGGACUACAGCCUGUCGUCAA | 921 |
| AM06530-SS | (NH2-C6)scsggacuuAfCfCfuggcagacuas(invAb)(C6-SS-C6) | 133 | CGGACUUACCUGGCAGACUA | 922 |
| AM06532-SS | (NH2-C6)sgsaaggucAfAfCfuccaacguaas(invAb)(C6-SS-C6) | 134 | GAAGGGUCAACUCCAACGUAA | 923 |
| AM06534-SS | (NH2-C6)scsagggucaAfCfUfccaacguauas(invAb)(C6-SS-C6) | 135 | CAGGGUCAACUCCAACGUAUA | 924 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06536-SS | (NH2-C6)sgsggucaacUfCfCfaacguauguas(invAb)(C6-SS-C6) | 136 | GGGUCAACUCCAACGUAUGUA | 925 |
| AM06538-SS | (NH2-C6)scsuccaacgUfAfUfgugguuaucas(invAb)(C6-SS-C6) | 137 | CUCCAACGUAUGUGGUUAUCA | 926 |
| AM06550-SS | (NH2-C6)sgsccauagGfUfGfugacaauccas(invAb)(C6-SS-C6) | 138 | GCCAUAGGUGUGACAAUCCA | 927 |
| AM06552-SS | (NH2-C6)scscauagguGfUfGfacaauccgaas(invAb)(C6-SS-C6) | 139 | CCAUAGGUGUGACAAUCCGAA | 928 |
| AM06554-SS | (NH2-C6)sgsggucugAfUfGfgcacguuguas(invAb)(C6-SS-C6) | 140 | GGGUCUGAUGGCACGUUGUA | 929 |
| AM06556-SS | (NH2-C6)scsugagcuaUfGfUfgacucggauas(invAb)(C6-SS-C6) | 141 | CUGAGCUAUGUGACUCGGAUA | 930 |
| AM06558-SS | (NH2-C6)sgsgguaagAfGfGfgacgacaccas(invAb)(C6-SS-C6) | 142 | GGGUAAGAGGGACGACACCA | 931 |
| AM06560-SS | (NH2-C6)scsccuacCfUfGfucaacguaaas(invAb)(C6-SS-C6) | 143 | CCCUACCUGUCAACGUAAA | 932 |
| AM06562-SS | (NH2-C6)s(invAb)scccuacCfUfGfucaacguaaas(invAb)(C6-SS-C6) | 144 | CCCUACCUGUCAACGUAAA | 932 |
| AM06564-SS | (NH2-C6)scsccuaccuGfUfCfaacguaacgas(invAb)(C6-SS-C6) | 145 | CCCUACCUGUCAACGUAACGA | 933 |
| AM06566-SS | (NH2-C6)scscuaccuGfUfCfaacguaacgas(invAb)(C6-SS-C6) | 146 | CCUACCUGUCAACGUAACGA | 934 |
| AM06568-SS | (NH2-C6)sasccugucaAfCfGfuaacgauuuas(invAb)(C6-SS-C6) | 147 | ACCUGUCAACGUAACGAUUUA | 935 |
| AM06877-SS | (NH2-C6)s(invAb)sgcaguuugCfUfCfugaaaacgaas(invAb)(C6-SS-C6) | 148 | GCAGUUUGCUCUGAAAACGAA | 936 |
| AM06879-SS | (NH2-C6)s(invAb)saggugaaaGfUfCfuacaacaacus(invAb)(C6-SS-C6) | 149 | AGGUGAAAGUCUACAACAACU | 937 |
| AM06881-SS | (NH2-C6)s(invAb)sggacacauCfUfUfuggauaacgas(invAb)(C6-SS-C6) | 150 | GGACACAUCUUUGGAUAACGA | 938 |
| AM06883-SS | (NH2-C6)s(invAb)scgaccugaAfGfAfuugaagugaus(invAb)(C6-SS-C6) | 151 | CGACCUGAAGAUUGAAGUGAU | 939 |
| AM06885-SS | (NH2-C6)s(invAb)sacgggaagAfCfUfuccagcuaaas(invAb)(C6-SS-C6) | 152 | ACGGGAAGACUUCCAGCUAAA | 940 |
| AM06887-SS | (NH2-C6)s(invAb)sagcuaacaGfGfAfcauaguaucus(invAb)(C6-SS-C6) | 153 | AGCUAACAGGACAUAGUAUCU | 941 |
| AM06889-SS | (NH2-C6)s(invAb)scagauaugAfCfUfgugaggugaas(invAb)(C6-SS-C6) | 154 | CAGAUAUGACUGUGAGGUGAA | 942 |
| AM06891-SS | (NH2-C6)s(invAb)sggaguacaCfAfAfuugummacas(invAb)(C6-SS-C6) | 155 | GGAGUACACAAUUGUUUACA | 943 |
| AM06893-SS | (NH2-C6)s(invAb)sggucaacuCfCfAfacguaugugas(invAb)(C6-SS-C6) | 156 | GGUCAACUCCAACGUAUGUGA | 944 |
| AM06895-SS | (NH2-C6)s(invAb)sgucaacucCfAfAfcguauguggus(invAb)(C6-SS-C6) | 157 | GUCAACUCCAACGUAUGUGGU | 945 |
| AM06897-SS | (NH2-C6)s(invAb)sgaugccauAfGfGfugugacaauas(invAb)(C6-SS-C6) | 158 | GAUGCCAUAGGUGUGACAAUA | 946 |
| AM06899-SS | (NH2-C6)s(invAb)sggaacnacCfAfUfgaganggunns(invAb)(C6-SS-C6) | 159 | GGAACUACCAUGAGAUGGUUU | 947 |
| AM06901-SS | (NH2-C6)s(invAb)sgcnaccanGfAfGfauggunuagas(invAb)(C6-SS-C6) | 160 | GCUACCAUGAGAUGGUUUAGA | 948 |
| AM06903-SS | (NH2-C6)s(invAb)scganaccaAfUfUfacauggaacus(invAb)(C6-SS-C6) | 161 | CGAUACCAAUUACAUGGAACU | 949 |
| AM06905-SS | (NH2-C6)s(invAb)sccuaccugUfCfAfacguaacgans(invAb)(C6-SS-C6) | 162 | CCUACCUGUCAACGUAACGAU | 950 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06981-SS | (NH2-C6)scsasascsguaaCfGfAfnuncausgsasasas(invAb)(C6-SS-C6) | 163 | CAACGUAACGAUUUCAUGAAA | 910 |
| AM06983-SS | (NH2-C6)scsaascgsnasaCfsGfAfsunsucsausgasaas(invAb)(C6-SS-C6) | 164 | CAACGUAACGAUUUCAUGAAA | 910 |
| AM06984-SS | (NH2-C6)scsasacguaaCfGfAfnuncaugasasas(invAb)(C6-SS-C6) | 165 | CAACGUAACGAUUUCAUGAAA | 910 |
| AM06986-SS | (NH2-C6)scasacsgusaasCfGfsAfusunscasugsaasas(invAb)(C6-SS-C6) | 166 | CAACGUAACGAUUUCAUGAAA | 910 |
| AM07071-SS | (NH2-C6)csaacguaaCfGfAfunucaugaasa(invAb)(C6-SS-C6) | 167 | CAACGUAACGAUUUCAUGAAA | 910 |
| AM07138-SS | (NH2-C6)s(invAb)scaacguaaCfGfAfnuncaugaaas(invAb)(C6-SS-C6) | 168 | CAACGUAACGAUUUCAUGAAA | 910 |
| AM07139-SS | (NH2-C6)s(invAb)sgaacguaaCfGfAfnuncaugaaas(invAb)(C6-SS-C6) | 169 | GAACGUAACGAUUUCAUGAAA | 951 |
| AM07141-SS | (NH2-C6)s(invAb)sga_2NacguaaCfGfAfnuncaugaaas(invAb)(C6-SS-C6) | 170 | GAACGUAACGAUUUCAUGAAA | 952 |
| AM07142-SS | (NH2-C6)s(invAb)sggacguaaCfGfAfnuncaugaaas(invAb)(C6-SS-C6) | 171 | GGACGUAACGAUUUCAUGAAA | 953 |
| AM07145-SS | (NH2-C6)s(invAb)sggacguaaCfGfAfnuncaniaaas(invAb)(C6-SS-C6) | 172 | GGACGUAACGAUUUCAUIAAA | 954 |
| AM07146-SS | (NH2-C6)s(invAb)sggacguaaCfGfAfnUncaugaaas(invAb)(C6-SS-C6) | 173 | GGACGUAACGAUUUCAUGAAA | 953 |
| AM07224-SS | (NH2-C6)scsaacguaaCfGfAfnuncaugaasa(invAb)(6-SS-6) | 174 | CAACGUAACGAUUUCAUGAAA | 910 |
| AM07225-SS | (NH2-C6)s(invAb)scaacguaaCfGfAfnuncaugaaas(invAb)(6-SS-6) | 175 | CAACGUAACGAUUUCAUGAAA | 910 |
| AM07226-SS | (NH2-C6)s(invAb)sgaacguaaCfGfAfnuncaugaaas(invAb)(6-SS-6) | 176 | GAACGUAACGAUUUCAUGAAA | 951 |
| AM07227-SS | (NH2-C6)s(invAb)sga_2NacguaaCfGfAfnuncaugaaas(invAb)(6-SS-6) | 177 | GAACGUAACGAUUUCAUGAAA | 952 |
| AM07228-SS | (NH2-C6)s(invAb)sggacguaaCfGfAfnuncaugaaas(invAb)(6-SS-6) | 178 | GGACGUAACGAUUUCAUGAAA | 953 |
| AM07229-SS | (NH2-C6)s(invAb)sggacguaaCfGfAfuuucauiaaas(invAb)(6-SS-6) | 179 | GGACGUAACGAUUUCAUIAAA | 954 |
| AM07230-SS | (NH2-C6)s(invAb)sggacguaaCfGfAfuUucaugaaas(invAb)(6-SS-6) | 180 | GGACGUAACGAUUUCAUGAAA | 953 |
| AM07231-SS | (NH2-C6)scsaacguaaCfGfAfuuucaugaasa(invAb)(C3-SS-C3) | 181 | CAACGUAACGAUUUCAUGAAA | 910 |
| AM07268-SS | (NH2-C6)scsaacguaaCfGfAfuusucsausgasaas(invAb)(C6-SS-C6) | 182 | CAACGUAACGAUUUCAUGAAA | 910 |
| AM07269-SS | (NH2-C6)scsaascgsuasaCfGfAfuuucaugaaas(invAb)(C6-SS-C6) | 183 | CAACGUAACGAUUUCAUGAAA | 910 |
| AM07270-SS | (NH2-C6)scsaacguaaCfGfAfuuucausgsasasas(invAb)(C6-SS-C6) | 184 | CAACGUAACGAUUUCAUGAAA | 910 |
| AM07271-SS | (NH2-C6)scsasascsgsuaaCfGfAfuuucaugaaas(invAb)(C6-SS-C6) | 185 | CAACGUAACGAUUUCAUGAAA | 910 |
| AM07272-SS | (NH2-C6)scsaacguasaCfsGfAfsuusucaugaaas(invAb)(C6-SS-C6) | 186 | CAACGUAACGAUUUCAUGAAA | 910 |
| AM07273-SS | (NH2-C6)scsaacgusaasCfGfsAfusuucaugaaas(invAb)(C6-SS-C6) | 187 | CAACGUAACGAUUUCAUGAAA | 910 |
| AM07274-SS | (NH2-C6)scsaascgsuaaCfGfAfuuucausgasaas(invAb)(C6-SS-C6) | 188 | CAACGUAACGAUUUCAUGAAA | 910 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07275-SS | (NH2-C6)scsasascguaaCfGfAfuuucaugasasas(invAb)(C6-SS-C6) | 189 | CAACGUAACGAUUUCAUGAAA | 910 |
| AM07301-SS | (NH2-C6)scsaacguaaCfGfAfuusucsausgasaas(invAb) | 190 | CAACGUAACGAUUUCAUGAAA | 910 |
| AM07302-SS | (NH2-C6)scsaascgsuasaCfGfAfuuucaugaaas(invAb) | 191 | CAACGUAACGAUUUCAUGAAA | 910 |
| AM07303-SS | (NH2-C6)scsaacguaaCfGfAfuuucausgsasasas(invAb) | 192 | CAACGUAACGAUUUCAUGAAA | 910 |
| AM07304-SS | (NH2-C6)scsasascsgsuaaCfGfAfuuucaugaaas(invAb) | 193 | CAACGUAACGAUUUCAUGAAA | 910 |
| AM07305-SS | (NH2-C6)scsaacguasaCfsGfAfsuusucaugaaas(invAb) | 194 | CAACGUAACGAUUUCAUGAAA | 910 |
| AM07306-SS | (NH2-C6)scsaacgusaasCfGfsAfusuucaugaaas(invAb) | 195 | CAACGUAACGAUUUCAUGAAA | 910 |
| AM07307-SS | (NH2-C6)scsaascgsuaaCfGfAfuuucausgasaas(invAb) | 196 | CAACGUAACGAUUUCAUGAAA | 910 |
| AM07308-SS | (NH2-C6)scsasascguaaCfGfAfuuucaugasasas(invAb) | 197 | CAACGUAACGAUUUCAUGAAA | 910 |
| AM07403-SS | (TriAlk1)scsaacguaaCfGfAfuuucaugaasa(invAb)(6-SS-6) | 198 | CAACGUAACGAUUUCAUGAAA | 910 |
| AM07404-SS | (TriAlk2)scsaacguaaCfGfAfuuucaugaasa(invAb)(6-SS-6) | 199 | CAACGUAACGAUUUCAUGAAA | 910 |
| AM07405-SS | (TriAlk3)scsaacguaaCfGfAfuuucaugaasa(invAb)(6-SS-6) | 200 | CAACGUAACGAUUUCAUGAAA | 910 |
| AM07406-SS | (TriAlk6)scsaacguaaCfGfAfuuucaugaasa(invAb)(6-SS-6) | 201 | CAACGUAACGAUUUCAUGAAA | 910 |
| AM07407-SS | (TriAlk4)scsaacguaaCfGfAfuuucaugaasa(invAb)(6-SS-6) | 202 | CAACGUAACGAUUUCAUGAAA | 910 |
| AM07408-SS | (TriAlk5)scsaacguaaCfGfAfuuucaugaasa(invAb)(6-SS-6) | 203 | CAACGUAACGAUUUCAUGAAA | 910 |
| AM07493-SS | (NH2-C6)scsaacguasaCfsGfAfsuusucaugaaas(invAb)(6-SS-6) | 204 | CAACGUAACGAUUUCAUGAAA | 910 |
| AM07528-SS | (NH2-C6)scsaacguaaCfGfAfuusucsausgasaas(invAb)(6-SS-6) | 205 | CAACGUAACGAUUUCAUGAAA | 910 |
| AM07530-SS | (NH2-C6)s(invAb)scaacuuguAfCfCfugaaaiccuus(invAb)(C6-SS-C6)(invAb) | 206 | CAACUUGUACCUGAAAICCUU | 955 |
| AM07532-SS | (NH2-C6)s(invAb)sacuuacacAfGfGfuggagcuaaas(invAb)(C6-SS-C6)(invAb) | 207 | ACUUACACAGGUGGAGCUAAA | 956 |
| AM07534-SS | (NH2-C6)s(invAb)saggacauaGfUfAfucuuugacuus(invAb)(C6-SS-C6)(invAb) | 208 | AGGACAUAGUAUCUUUGACUU | 957 |
| AM07536-SS | (NH2-C6)s(invAb)scugugucuGfAfGfaagaguaacus(invAb)(C6-SS-C6)(invAb) | 209 | CUGUGUCUGAGAAGAGUAACU | 958 |
| AM07538-SS | (NH2-C6)s(invAb)scuuccuauUfCfAfccaagcuaaas(invAb)(C6-SS-C6)(invAb) | 210 | CUUCCUAUUCACCAAGCUAAA | 959 |
| AM07540-SS | (NH2-C6)s(invAb)sccagcacaCfUfAfuuuacaagaus(invAb)(C6-SS-C6)(invAb) | 211 | CCAGCACACUAUUUACAAGAU | 960 |
| AM07542-SS | (NH2-C6)s(invAb)sgccccuauUfUfUfuaaaguacaas(invAb)(C6-SS-C6)(invAb) | 212 | GCCCCUAUUUUUAAAGUACAA | 961 |
| AM07544-SS | (NH2-C6)s(invAb)sgaguacacAfAfUfuguuuuaccus(invAb)(C6-SS-C6)(invAb) | 213 | GAGUACACAAUUGUUUUACCU | 962 |
| AM07546-SS | (NH2-C6)s(invAb)scaacugucCfAfUfacuaacaagus(invAb)(C6-SS-C6)(invAb) | 214 | CAACUGUCCAUACUAACAAGU | 963 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07548-SS | (NH2-C6)s(invAb)sgugguuauCfUfGfugaaaguugas(invAb)(C6-SS-C6)(invAb) | 215 | GUGGUUAUCUGUGAAAGUUGA | 964 |
| AM07550-SS | (NH2-C6)s(invAb)sgaacuuagAfAfAfcggaaauggas(invAb)(C6-SS-C6)(invAb) | 216 | GAACUUAGAAACGGAAAUGGA | 965 |
| AM07552-SS | (NH2-C6)s(invAb)sgauccgagCfAfGfuggagucauus(invAb)(C6-SS-C6)(invAb) | 217 | GAUCCGAGCAGUGGAGUCAUU | 966 |
| AM07554-SS | (NH2-C6)s(invAb)scacauucuCfUfAfuguacuaugus(invAb)(C6-SS-C6)(invAb) | 218 | CACAUUCUCUAUGUACUAUGU | 967 |
| AM07556-SS | (NH2-C6)s(invAb)sggucagugAfCfAfuguagguagas(invAb)(C6-SS-C6)(invAb) | 219 | GGUCAGUGACAUGUAGGUAGA | 968 |
| AM07558-SS | (NH2-C6)s(invAb)sgacacacaCfAfAfagcacaungas(invAb)(C6-SS-C6)(invAb) | 220 | GACACACACAAAGCACAUUGA | 969 |
| AM07560-SS | (NH2-C6)s(invAb)saccggauaGfAfCfuuauuiccaas(invAb)(C6-SS-C6)(invAb) | 221 | ACCGGAUAGACUUAUUICCAA | 970 |
| AM07562-SS | (NH2-C6)s(invAb)sgaaguucuAfUfGfagaaauuccus(invAb)(C6-SS-C6)(invAb) | 222 | GAAGUUCUAUGAGAAAUUCCU | 971 |
| AM07564-SS | (NH2-C6)s(invAb)sgguuacugAfCfGfuguaaaugcus(invAb)(C6-SS-C6)(invAb) | 223 | GGUUACUGACGUGUAAAUGCU | 972 |
| AM07566-SS | (NH2-C6)s(invAb)sacguaacgAfUfUfucaugaacgus(invAb)(C6-SS-C6)(invAb) | 224 | ACGUAACGAUUUCAUGAACGU | 973 |
| AM07568-SS | (NH2-C6)s(invAb)sguaacgauUfUfCfaugaacguuas(invAb)(C6-SS-C6)(invAb) | 225 | GUAACGAUUUCAUGAACGUUA | 974 |
| AM07570-SS | (NH2-C6)s(invAb)sgaacgauuUfCfAfugaacguuaus(invAb)(C6-SS-C6)(invAb) | 226 | GAACGAUUUCAUGAACGUUAU | 975 |
| AM07572-SS | (NH2-C6)s(invAb)sggagcuuaAfCfUfuuauaaggaas(invAb)(C6-SS-C6)(invAb) | 227 | GGAGCUUAACUUUAUAAGGAA | 976 |
| AM07619-SS | (NH2-C6)scsaaAlkcguaAlkaCfGfAfuuucaAlkugaaAlksa(invAb)(C6-SS-C6)(invAb) | 228 | CAACGUAACGAUUUCAUGAAA | 910 |
| AM07621-SS | (C6-SS-C6)scsaaAlkcguaAlkaCfGfAfuuucaAlkugaaAlksa(invAb)(C6-SS-C6)(invAb) | 229 | CAACGUAACGAUUUCAUGAAA | 910 |
| AM07705-SS | (TriAlk7)scsaacguaaCfGfAfuuucaugaasa(invAb)(6-SS-6) | 230 | CAACGUAACGAUUUCAUGAAA | 910 |
| AM07706-SS | (TriAlk8)scsaacguaaCfGfAfuuucaugaasa(invAb)(6-SS-6) | 231 | CAACGUAACGAUUUCAUGAAA | 910 |
| AM07707-SS | (TriAlk10)scsaacguaaCfGfAfuuucaugaasa(invAb)(6-SS-6) | 232 | CAACGUAACGAUUUCAUGAAA | 910 |
| AM07708-SS | (TriAlk11)scsaacguaaCfGfAfuuucaugaasa(invAb)(6-SS-6) | 233 | CAACGUAACGAUUUCAUGAAA | 910 |
| AM07709-SS | (TriAlk12)scsaacguaaCfGfAfuuucaugaasa(invAb)(6-SS-6) | 234 | CAACGUAACGAUUUCAUGAAA | 910 |
| AM07710-SS | (NH2-C6)scsaacguaaCfGfAfuuucaAlkugaasa(invAb)(6-SS-6) | 235 | CAACGUAACGAUUUCAUGAAA | 910 |
| AM07711-SS | (NH2-C6)scsaacguaAlkaCfGfAfuuucaugaasa(invAb)(6-SS-6) | 236 | CAACGUAACGAUUUCAUGAAA | 910 |
| AM07712-SS | (NH2-C6)scsaacguaAlkaCfGfAfuuucaAlkugaasa(invAb)(6-SS-6) | 237 | CAACGUAACGAUUUCAUGAAA | 910 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07713-SS | (NH2-C6)scsaaAlkcguaAlkaCfGfAfuuucaAlkugaaAlksa(invAb)(C6-NH2) | 238 | CAACGUAACGAUUUCAUGAAA | 910 |
| AM07721-SS | (NH2-C6)s(invAb)scacauucuCfUfAfuguacuaugus(invAb)(6-SS-6) | 239 | CACAUUCUCUAUGUACUAUGU | 967 |
| AM07722-SS | (NH2-C6)s(invAb)sgacauucuCfUfAfuguacuaugus(invAb)(6-SS-6) | 240 | GACAUUCUCUAUGUACUAUGU | 977 |
| AM07724-SS | (NH2-C6)s(invAb)scgcauucuCfUfAfuguacuaugus(invAb)(6-SS-6) | 241 | CGCAUUCUCUAUGUACUAUGU | 978 |
| AM07726-SS | (NH2-C6)s(invAb)scccauucuCfUfAfuguacuaugus(invAb)(6-SS-6) | 242 | CCCAUUCUCUAUGUACUAUGU | 979 |
| AM07728-SS | (NH2-C6)s(invAb)sggcauucuCfUfAfuguacuaugus(invAb)(6-SS-6) | 243 | GGCAUUCUCUAUGUACUAUGU | 980 |
| AM07730-SS | (NH2-C6)s(invAb)scaca_2NuucuCfUfAfuguacuaugus(invAb)(6-SS-6) | 244 | CACAUUCUCUAUGUACUAUGU | 981 |
| AM07731-SS | (NH2-C6)s(invAb)sccca_2NuucuCfUfAfuguacuaugus(invAb)(6-SS-6) | 245 | CCCAUUCUCUAUGUACUAUGU | 982 |
| AM07732-SS | (NH2-C6)s(invAb)sgcgaccAfUfGfaggagauucauus(invAb)(6-SS-6) | 246 | GCGACCAUGAGGAGAUUCAUU | 983 |
| AM07734-SS | (NH2-C6)s(invAb)scgcucaGfCfCfnaugaanucauus(invAb)(6-SS-6) | 247 | CGCUCAGCCUAUGAAUUCAUU | 984 |
| AM07736-SS | (NH2-C6)s(invAb)scaagggucAfGfGfuaguaagugas(invAb)(6-SS-6) | 248 | CAAGGGUCAGGUAGUAAGUGA | 985 |
| AM07738-SS | (NH2-C6)s(invAb)sgacugaauCfCfCfuguucaagcas(invAb)(6-SS-6) | 249 | GACUGAAUCCCUGUUCAAGCA | 986 |
| AM07740-SS | (NH2-C6)s(invAb)sucagugccAfUfGfacaaacaucus(invAb)(6-SS-6) | 250 | UCAGUGCCAUGACAAACAUCU | 987 |
| AM07742-SS | (NH2-C6)s(invAb)sgcaccucaCfAfUfuugauguggas(invAb)(6-SS-6) | 251 | GCACCUCACAUUUGAUGUGGA | 988 |
| AM07744-SS | (NH2-C6)s(invAb)sacacaacuGfUfCfcauacuaacas(invAb)(6-SS-6) | 252 | ACACAACUGUCCAUACUAACA | 989 |
| AM07746-SS | (NH2-C6)s(invAb)sggcauaguAfUfCfuuugacuucas(invAb)(6-SS-6) | 253 | GGCAUAGUAUCUUUGACUUCA | 990 |
| AM07776-SS | (NH2-C6)s(invAb)sgaguacacAfAfUfuguuuuaccus(invAb)(6-SS-6) | 254 | GAGUACACAAUUGUUUUACCU | 962 |
| AM07777-SS | (NH2-C6)s(invAb)scuuccuauUfCfAfccaagcuaaas(invAb)(6-SS-6) | 255 | CUUCCUAUUCACCAAGCUAAA | 959 |
| AM07778-SS | (NH2-C6)s(invAb)sggucagugAfCfAfuguagguagas(invAb)(6-SS-6) | 256 | GGUCAGUGACAUGUAGGUAGA | 968 |
| AM07801-SS | (TriAlk13)scsaacguaaCfGfAfuuucaugaaasa(invAb)(6-SS-6) | 257 | CAACGUAACGAUUUCAUGAAA | 910 |
| AM07813-SS | (NH2-C6)scsaaAlkcguaAlkaCfGfAfuuucaAlkugaaAlksa(invAb)(6-SS-6) | 258 | CAACGUAACGAUUUCAUGAAA | 910 |
| AM07814-SS | (C6-SS-C6)scsaaAlkcguaAlkaCfGfAfuuucaAlkugaaAlksa(invAb)(6-SS-6) | 259 | CAACGUAACGAUUUCAUGAAA | 910 |
| AM07817-SS | (NH2-C6)scsaAlkaAlkcguAlkaAlkaCfGfAfuuucaAlkuAlkgaAlkaAlksa(invAb)(6-SS-6) | 260 | CAACGUAACGAUUUCAUGAAA | 910 |
| AM07818-SS | (C6-SS-C6)scsaacguaaCfGfAfuuucaugaaasa(invAb)(6-SS-6) | 261 | CAACGUAACGAUUUCAUGAAA | 910 |
| AM07822-SS | (NH2-C6)scsaacguaAlkaCfGfAfuuucaAlkugaaAlksa(invAb)(6-SS-6) | 262 | CAACGUAACGAUUUCAUGAAA | 910 |
| AM07823-SS | (NH2-C6)scsaaAlkcguaaCfGfAfuuucaAlkugaaAlksa(invAb)(6-SS-6) | 263 | CAACGUAACGAUUUCAUGAAA | 910 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07824-SS | (NH2-C6)scsaaAlkcguaAlkaCfGfAfuuucaugaaAlksa(invAb)(6-SS-6) | 264 | CAACGUAACGAUUUCAUGAAA | 910 |
| AM07825-SS | (NH2-C6)scsaaAlkcguaAlkaCfGfAfuuucaAlkugaasa(invAb)(6-SS-6) | 265 | CAACGUAACGAUUUCAUGAAA | 910 |
| AM07826-SS | (NH2-C6)scsaaAlkcguaAlkaCfGfAfuuucaugaasa(invAb)(6-SS-6) | 266 | CAACGUAACGAUUUCAUGAAA | 910 |
| AM07827-SS | (NH2-C6)scsaacguaaCfGfAfuuucaAlkugaaAlksa(invAb)(6-SS-6) | 267 | CAACGUAACGAUUUCAUGAAA | 910 |
| AM07828-SS | (NH2-C6)scsaaAlkcguaaCfGfAfuuucaugaaAlksa(invAb)(6-SS-6) | 268 | CAACGUAACGAUUUCAUGAAA | 910 |
| AM07829-SS | (NH2-C6)scsaaAlkcguaaCfGfAfuuucaAlkugaasa(invAb)(6-SS-6) | 269 | CAACGUAACGAUUUCAUGAAA | 910 |
| AM07830-SS | (NH2-C6)scsaacguaAlkaCfGfAfuuucaugaaAlksa(invAb)(6-SS-6) | 270 | CAACGUAACGAUUUCAUGAAA | 910 |
| AM07831-SS | (NH2-C6)scsaacguaaCfGfAfuuucaugaaAlksa(invAb)(6-SS-6) | 271 | CAACGUAACGAUUUCAUGAAA | 910 |
| AM07832-SS | (NH2-C6)scsaaAlkcguaaCfGfAfuuucaugaasa(invAb)(6-SS-6) | 272 | CAACGUAACGAUUUCAUGAAA | 910 |
| AM07833-SS | (NH2-C6)scsaAlkaAlkcguaaCfGfAfuuucaugaAlkaAlksa(invAb)(6-SS-6) | 273 | CAACGUAACGAUUUCAUGAAA | 910 |
| AM07834-SS | (NH2-C6)scsaacAlkguaaAlkCfGfAfuuuAlkcaugAlkaasa(invAb)(6-SS-6) | 274 | CAACGUAACGAUUUCAUGAAA | 910 |
| AM07835-SS | (NH2-C6)scsaacgAlkuaaAlkCfGfAfuAlkuucAlkaugaasa(invAb)(6-SS-6) | 275 | CAACGUAACGAUUUCAUGAAA | 910 |
| AM07836-SS | (NH2-C6)scsaacguaAlkaAlkCfGfAfuAlkuAlkucaugaasa(invAb)(6-SS-6) | 276 | CAACGUAACGAUUUCAUGAAA | 910 |
| AM07837-SS | (NH2-C6)scsaAlkacAlkguAlkaaAlkCfGfAfuuucaugaasa(invAb)(6-SS-6) | 277 | CAACGUAACGAUUUCAUGAAA | 910 |
| AM07838-SS | (NH2-C6)scsaAlkaAlkcAlkgAlkuaaCfGfAfuuucaugaasa(invAb)(6-SS-6) | 278 | CAACGUAACGAUUUCAUGAAA | 910 |
| AM07839-SS | (NH2-C6)scsaacguaaCfGfAfiumAlkcaAlkugAlkaaAlksa(invAb)(6-SS-6) | 279 | CAACGUAACGAUUUCAUGAAA | 910 |
| AM07840-SS | (NH2-C6)scsaacguaaCfGfAfunucauAlkgAlkaAlkaAlksa(invAb)(6-SS-6) | 280 | CAACGUAACGAUUUCAUGAAA | 910 |
| AM07890-SS | (NH2-C6)s(invAb)sgcacaacuGfUfCfcauacuaacas(invAb)(6-SS-6) | 281 | GCACAACUGUCCAUACUAACA | 991 |
| AM07892-SS | (NH2-C6)s(invAb)sccacaacuGfUfCfcauacuaacas(invAb)(6-SS-6) | 282 | CCACAACUGUCCAUACUAACA | 992 |
| AM07894-SS | (NH2-C6)s(invAb)sggacaacuGfUfCfcauacuaacas(invAb)(6-SS-6) | 283 | GGACAACUGUCCAUACUAACA | 993 |
| AM08018-SS | (NH2-C6)scsaacguaaCfGfAfunucaAlkuAlkgaAlkaAlksa(invAb)(6-SS-6) | 284 | CAACGUAACGAUUUCAUGAAA | 910 |
| AM08019-SS | (NH2-C6)scsaacAlkguaaAlkCfGfAfunuAlkcaAlkugAlkaaAlksa(invAb)(6-SS-6) | 285 | CAACGUAACGAUUUCAUGAAA | 910 |
| AM08020-SS | (NH2-C6)scsaacguaaCfGfAfunucaugAlkaasa(invAb)(6-SS-6) | 286 | CAACGUAACGAUUUCAUGAAA | 910 |
| AM08021-SS | (NH2-C6)scsaacguaaCfGfAfunucaAlkuAlkgAlkaAlkasa(invAb)(6-SS-6) | 287 | CAACGUAACGAUUUCAUGAAA | 910 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08022-SS | (NH2-C6)scsaacguaaCfGfAfunucAlkaAlkuAlkgAlkaasa(invAb)(6-SS-6) | 288 | CAACGUAACGAUUUCAUGAAA | 910 |
| AM08023-SS | (NH2-C6)scsaacguaaCfGfAfunuAlkcAlkaAlkuAlkgaasa(invAb)(6-SS-6) | 289 | CAACGUAACGAUUUCAUGAAA | 910 |
| AM08024-SS | (NH2-C6)scsaacguaaCfGfAfunAlkuAlkcAlkaAlkugaasa(invAb)(6-SS-6) | 290 | CAACGUAACGAUUUCAUGAAA | 910 |
| AM08025-SS | (NH2-C6)scsaacguaaCfGfAfuAlkuAlkuAlkcAlkaugaasa(invAb)(6-SS-6) | 291 | CAACGUAACGAUUUCAUGAAA | 910 |
| AM08026-SS | (NH2-C6)scsaacguaaCfGfAfuAlkuuAlkcaAlkugAlkaaAlksa(invAb)(6-SS-6) | 292 | CAACGUAACGAUUUCAUGAAA | 910 |
| AM08027-SS | (NH2-C6)scsaacguaaCfGfAfunucaAlkugAlkaaAlksa(invAb)(6-SS-6) | 293 | CAACGUAACGAUUUCAUGAAA | 910 |
| AM08028-SS | (NH2-C6)scsaacguaaCfGfAfunuAlkcaugAlkaaAlksa(invAb)(6-SS-6) | 294 | CAACGUAACGAUUUCAUGAAA | 910 |
| AM08029-SS | (NH2-C6)scsaacguaaCfGfAfunuAlkcaAlkugaaAlksa(invAb)(6-SS-6) | 295 | CAACGUAACGAUUUCAUGAAA | 910 |
| AM08030-SS | (NH2-C6)scsaacguaaCfGfAfunuAlkcaAlkugAlkaasa(invAb)(6-SS-6) | 296 | CAACGUAACGAUUUCAUGAAA | 910 |
| AM08031-SS | (NH2-C6)scsaacguaaCfGfAfunucaugAlkaAlkaAlksa(invAb)(6-SS-6) | 297 | CAACGUAACGAUUUCAUGAAA | 910 |
| AM08032-SS | (NH2-C6)scsaacguaaCfGfAfunucauAlkgaAlkaAlksa(invAb)(C6-SS-C6)dT | 298 | CAACGUAACGAUUUCAUGAAAT | 994 |
| AM080 33-SS | (NH2-C6)scsaacguaaCfGfAfuuucauAlkgAlkaaAlksa(invAb)(6-SS-6) | 299 | CAACGUAACGAUUUCAUGAAA | 910 |
| AM080 34-SS | (NH2-C6)scsaacguaaCfGfAfuuucauAlkgAlkaAlkasa(invAb)(6-SS-6) | 300 | CAACGUAACGAUUUCAUGAAA | 910 |
| AM080 35-SS | (NH2-C6)scsaacguaaAlkCfGfAfiumAlkcaugAlkaasa(invAb)(6-SS-6) | 301 | CAACGUAACGAUUUCAUGAAA | 910 |
| AM080 36-SS | (NH2-C6)scsaacAlkguaaCfGfAfiumAlkcaugAlkaasa(invAb)(6-SS-6) | 302 | CAACGUAACGAUUUCAUGAAA | 910 |
| AM080 37-SS | (NH2-C6)scsaacAlkguaaAlkCfGfAfuuucaugAlkaasa(invAb)(6-SS-6) | 303 | CAACGUAACGAUUUCAUGAAA | 910 |
| AM080 38-SS | (NH2-C6)scsaacAlkguaaAlkCfGfAfimuAlkcaugaasa(invAb)(6-SS-6) | 304 | CAACGUAACGAUUUCAUGAAA | 910 |
| AM08092-SS | (NH2-C6)scsaaAlkcguaaCfGfAfuuucaugaasa(invAb)(C6-SS-C6)dT | 305 | CAACGUAACGAUUUCAUGAAAT | 994 |
| AM08093-SS | (NH2-C6)scsaacguaaCfGfAfuuucaugaaAlksa(invAb)(C6-SS-C6)dT | 306 | CAACGUAACGAUUUCAUGAAAT | 994 |
| AM08108-SS | (TriAlk14)scsaacguaaCfGfAfuuucaAlkuAlkgaAlkaAlksa(invAb)(C6-SS-C6)dT | 307 | CAACGUAACGAUUUCAUGAAAT | 994 |
| AM08109-SS | (TriAlk14)scsaacguaaCfGfAfuuucauAlkgaAlkaAlksa(invAb)(C6-SS-C6)dT | 308 | CAACGUAACGAUUUCAUGAAAT | 994 |
| AM08110-SS | (TriAlk14)scsaacguaaCfGfAfuuucaAlkugaAlkaAlksa(invAb)(C6-SS-C6)dT | 309 | CAACGUAACGAUUUCAUGAAAT | 994 |
| AM08111-SS | (TriAlk14)scsaacguaaCfGfAfuuucaAlkuAlkgaaAlksa(invAb)(C6-SS-C6)dT | 310 | CAACGUAACGAUUUCAUGAAAT | 994 |
| AM08112-SS | (TriAlk14)scsaacguaaCfGfAfuuucaAlkuAlkgaAlkasa(invAb)(C6-SS-C6)dT | 311 | CAACGUAACGAUUUCAUGAAAT | 994 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08113-SS | (TriA1k14)scsaacguaaCfGfAfuuucaugaAlkaAlksa(invAb)(C6-SS-C6)dT | 312 | CAACGUAACGAUUUCAUGAAAT | 994 |
| AM08114-SS | (TriA1k14)scsaacguaaCfGfAfuuucaAlkuAlkgaasa(invAb)(C6-SS-C6)dT | 313 | CAACGUAACGAUUUCAUGAAAT | 994 |
| AM08115-SS | (TriA1k14)scsaacguaaCfGfAfuuucauAlkgaAlkasa(invAb)(C6-SS-C6)dT | 314 | CAACGUAACGAUUUCAUGAAAT | 994 |
| AM08116-SS | (TriAlk14)scsaacguaaCfGfAfuuucaAlkugaAlkasa(invAb)(C6-SS-C6)dT | 315 | CAACGUAACGAUUUCAUGAAAT | 994 |
| AM08117-SS | (TriAlk14)scsaacguaaCfGfAfuuucauAlkgaaAlksa(invAb)(C6-SS-C6)dT | 316 | CAACGUAACGAUUUCAUGAAAT | 994 |
| AM08118-SS | (TriAlk14)scsaacguaaCfGfAfuuuAlkcaugAlkaasa(invAb)(C6-SS-C6)dT | 317 | CAACGUAACGAUUUCAUGAAAT | 994 |
| AM08119-SS | (C6-SS-C6)scsaacguaaCfGfAfuuucaugaasa(invAb)(C6-NH2) | 318 | CAACGUAACGAUUUCAUGAAA | 910 |
| AM08120-SS | (C6-SS-C6)scsaacguaaCfGfAfuuuAlkcaAlkugAlkaaAlksa(invAb)(C6-NH2) | 319 | CAACGUAACGAUUUCAUGAAA | 910 |
| AM08121-SS | (C6-SS-C6)scsaacguaaCfGfAfuuucaAlkuAlkgaAlkaAlksa(invAb)(C6-NH2) | 320 | CAACGUAACGAUUUCAUGAAA | 910 |
| AM08122-SS | (C6-SS-C6)scsaAlkacAlkguAlkaaAlkCfGfAfuuucaugaasa(invAb)(C6-NH2) | 321 | CAACGUAACGAUUUCAUGAAA | 910 |
| AM08123-SS | (C6-SS-C6)scsaAlkaAlkcgAlkuAlkaaCfGfAfuuucaugaasa(invAb)(C6-NH2) | 322 | CAACGUAACGAUUUCAUGAAA | 910 |
| AM08124-SS | (TriAlk14)s(invAb)scacauucuCfUfAfuguacuaugus(invAb)(C6-SS-C6)dT | 323 | CACAUUCUCUAUGUACUAUGUT | 995 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08125-SS | (TriAlk14)s(invAb)scacauucuCfUfAfuguAlkacAlkuaAlkugAlkus(invAb)(C6-SS-C6)dT | 324 | CACAUUCUCUAUGUACUAUGUT | 995 |
| AM08126-SS | (TriAlk14)s(invAb)scaAlkcaAlkuuAlkcuAlkCfUfAfuguacuaugus(invAb)(C6-SS-C6)dT | 325 | CACAUUCUCUAUGUACUAUGUT | 995 |
| AM08127-SS | (TriAlk14)s(invAb)scacauucuCfUfAfuguacAlkuAlkauAlkgAlkus(invAb)(C6-SS-C6)dT | 326 | CACAUUCUCUAUGUACUAUGUT | 995 |
| AM08128-SS | (TriAlk14)s(invAb)sacacaacuGfUfCfcauacuaacas(invAb)(C6-SS-C6)dT | 327 | ACACAACUGUCCAUACUAACAT | 996 |
| AM08129-SS | (TriAlk14)s(invAb)sacacaacuGfUfCfcauAlkacAlkuaAlkacAlkas(invAb)(C6-SS-C6)dT | 328 | ACACAACUGUCCAUACUAACAT | 996 |
| AM08130-SS | (TriAlk14)s(invAb)sacAlkacAlkaaAlkcuAlkGfUfCfcauacuaacas(invAb)(C6-SS-C6)dT | 329 | ACACAACUGUCCAUACUAACAT | 996 |
| AM08131-SS | (TriAlk14)s(invAb)sacacaacuGfUfCfcauacAlkuAlkaaAlkcAlkas(invAb)(C6-SS-C6)dT | 330 | ACACAACUGUCCAUACUAACAT | 996 |
| AM08132-SS | (TriA1k14)scsaacguaaCfGfAfuuucaugAlkaaAlksa(invAb)(C6-SS-C6)dT | 331 | CAACGUAACGAUUUCAUGAAAT | 994 |
| AM08133-SS | (TriA1k14)scsaacguaaCfGfAfuuucaAlkugAlkaasa(invAb)(C6-SS-C6)dT | 332 | CAACGUAACGAUUUCAUGAAAT | 994 |

TABLE 4-continued

HIF-2 alpha RNAi Agent Sense Strand Sequences

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08134-SS | (TriA1k14)scsaacguaaCfGfAfuuuAlkcaAlkugaasa(invAb)(C6-SS-C6)dT | 333 | CAACGUAACGAUUUCAUGAAAT | 994 |
| AM08135-SS | (TriA1k14)scsaacguaaCfGfAfuuuAlkcaugaaAlksa(invAb)(C6-SS-C6)dT | 334 | CAACGUAACGAUUUCAUGAAAT | 994 |
| AM08233-SS | (TriAlk14)scsaacguaaCfGfAfuuuAlkcaAlkugAlkaaAlksa(invAb)(Orn-C18-DA) | 335 | CAACGUAACGAUUUCAUGAAA | 910 |
| AM08234-SS | (TriAlk14)scsaacguaaCfGfAfuuuAlkcaAlkugAlkaaAlksa(invAb)(Dap-C18-DA) | 336 | CAACGUAACGAUUUCAUGAAA | 910 |
| AM08372-SS | (TriA1k14)scsaacguaaCfGfAfuuuAlkcaAlkugAlkaaAlksa(invAb)(Lys-C18-DA) | 337 | CAACGUAACGAUUUCAUGAAA | 910 |
| AM08394-SS | (TriAlk14)scsaacguaaCfGfAfuuuAlkcaAlkugAlkaaAlksa(invAb)s(Lys-C18-DA) | 338 | CAACGUAACGAUUUCAUGAAA | 910 |
| AM08395-SS | (TriAlk14)scsaacguaaCfGfAfuuuAlkcaAllcugAlkaaAlksa(invAb)(C6-SS-C6)dT | 339 | CAACGUAACGAUUUCAUGAAAT | 994 |
| AM08396-SS | (TriAlk14)scsaacguaaCfGfAfiumAlkcaAlkugAlkaaAlksas(invAb)s(Lys-C18-DA) | 340 | CAACGUAACGAUUUCAUGAAA | 910 |
| AM08397-SS | (TriAlk14)scsasacguaaCfGfAfuuuAlkcaAllcugAlkaaAlksas(invAb)s(C6-SS-C6)dT | 341 | CAACGUAACGAUUUCAUGAAAT | 994 |
| AM08398-55 | (TriAlk14)s(invAb)scsasacguaaCfGfAfuuuAlkcaAllcugAlkaaAlksas(invAb)s(C6-SS-C6)dT | 342 | CAACGUAACGAUUUCAUGAAAT | 994 |
| AM08399-55 | (TriAlk14)scsasacguaaCfGfAfuuuAlkcaAllcugAlkaaAlksas(invAb)s(Lys-C18-DA) | 343 | CAACGUAACGAUUUCAUGAAA | 910 |
| AM10042-SS | (NH2-C6)scsaacguaaCfGfAfuuucaugaasa(invAb)(C6-SS-C6)dT | 344 | CAACGUAACGAUUUCAUGAAAT | 994 |

As shown in Table 4, above, many of the example HIF-2 alpha nucleotide sequences are shown to further include reactive linking groups at 5' terminal end, the 3' terminal end, or both the 5' and the 3' terminal ends of the nucleotide sequence of the sense strand. For example, several HIF-2 alpha nucleotide sequences shown in Table 4 above have an (NH2-C6) linking group or a (TriAlk) linking group at the 5' end of the nucleotide sequence. Similarly, several of the HIF-2 alpha nucleotide sequences shown in Table 4 above have a (C6-SS-C6) or (6-SS-6) linking group at the 3' end of the nucleotide sequence. Such reactive linking groups are positioned to facilitate the linking of targeting ligands, targeting groups, and/or PK enhancers to the HIF-2 alpha RNAi agents disclosed herein. Linking or conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction and click chemistry cycloaddition reaction.

In some embodiments, targeting ligands can be synthesized as a tetrafluorophenyl (TFP) ester, which can be displaced by a reactive amino group (for example, NH2-C6) to attach the targeting ligand to the HIF-2 alpha RNAi agents disclosed herein. In some embodiments, targeting ligands are synthesized as azides, which can be conjugated to a propargyl or DBCO group, for example, via click chemistry cycloaddition reaction.

Additionally, several of the nucleotide sequences were synthesized with a dT nucleotide at the 3' terminal end of the sense strand, followed by (3'→5') a linker (for example. C6-SS-C6), which can in some embodiments be used after cleavage from the resin to facilitate the linkage to additional components, such as, for example, a PK enhancer or one or more targeting ligands. Synthesis in this manner involves dT attached to the resin, followed by the coupling of the linker and the remaining nucleotides of the sense strand. As described herein, upon conjugation of the desired PK enhancer (or targeting ligand(s)) the terminal dT is cleaved off the molecule. Table 4.1 below shows the nucleotide sequences identified in Table 4, above, but without the inclusion of the 3' terminal dT nucleotide.

Further, Table 4.2 below, shows the nucleotide sequences identified in Table 4, above, but without the terminal linking groups present.

TABLE 4.1

HIF-2 alpha RNAi Agent Sense Strand Sequences Shown Without 3' Terminal dT

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08032-SS | (NH2-C6)scsaacguaaCfGfAfunucauAlkgaAlkaAlksa(invAb)(C6-SS-C6) | 345 | CAACGUAACGAUUUCAUGAAA | 428 |
| AM08092-SS | (NH2-C6)scsaaAlkcguaaCfGfAfunucaugaasa(invAb)(C6--SSC6) | 346 | CAACGUAACGAUUUCAUGAAA | 428 |
| AM08093-SS | (NH2-C6)scsaacguaaCfGfAfunucaugaaAlksa(invAb)(C6-SS-C6) | 347 | CAACGUAACGAUUUCAUGAAA | 428 |
| AM08108-SS | (TriAlk14)scsaacguaaCfGfAfunucaAlkuAlkgaAlkaAlksa(invAb)(C6-SS-C6) | 348 | CAACGUAACGAUUUCAUGAAA | 428 |
| AM08109-SS | (TriAlk14)scsaacguaaCfGfAfunucauAlkgaAlkaAlksa(invAb)(C6-SS-C6) | 349 | CAACGUAACGAUUUCAUGAAA | 428 |
| AM08110-SS | (TriAlk14)scsaacguaaCfGfAfunucaAlkugaAlkaAlksa(invAb)(C6-SS-C6) | 350 | CAACGUAACGAUUUCAUGAAA | 428 |
| AM08111-SS | (TriAlk14)scsaacguaaCfGfAfunucaAlkuAlkgaaAlksa(invAb)(C6-SS-C6) | 351 | CAACGUAACGAUUUCAUGAAA | 428 |
| AM08112-SS | (TriAlk14)scsaacguaaCfGfAfunucaAlkuAlkgaAlkasa(invAb)(C6-SS-C6) | 352 | CAACGUAACGAUUUCAUGAAA | 428 |
| AM08113-SS | (TriAlk14)scsaacguaaCfGfAfunucaugaAlkaAlksa(invAb)(C6-SS-C6) | 353 | CAACGUAACGAUUUCAUGAAA | 428 |
| AM08114-SS | (TriAlk14)scsaacguaaCfGfAfunucaAlkuAlkgaasa(invAb)(C6-SS-C6) | 354 | CAACGUAACGAUUUCAUGAAA | 428 |
| AM08115-SS | (TriAlk14)scsaacguaaCfGfAfunucauAlkgaAlkasa(invAb)(C6-SS-C6) | 355 | CAACGUAACGAUUUCAUGAAA | 428 |
| AM08116-SS | (TriAlk14)scsaacguaaCfGfAfunucaAlkugaAlkasa(invAb)(C6-SS-C6) | 356 | CAACGUAACGAUUUCAUGAAA | 428 |
| AM08117-SS | (TriAlk14)scsaacguaaCfGfAfunucauAlkgaaAlksa(invAb)(C6-SS-C6) | 357 | CAACGUAACGAUUUCAUGAAA | 428 |

TABLE 4.1-continued

HIF-2 alpha RNAi Agent Sense Strand Sequences Shown Without 3' Terminal dT

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08118-SS | (TriAlk14)scsaacguaaCfGfAfunuAlkcaugAlkaasa(invAb)(C6-SS-C6) | 358 | CAACGUAACGAUUUCAUGAAA | 428 |
| AM08124-SS | (TriAlk14)s(invAb)scacauucuCfUfAfuguacuaugus(invAb)(C6-SS-C6) | 359 | CACAUUCUCUAUGUACUAUGU | 485 |
| AM08125-SS | (TriAlk14)s(invAb)scacauucuCfUfAfuguAlkacAlkuaAlkugAlkus(invAb)(C6-SS-C6) | 360 | CACAUUCUCUAUGUACUAUGU | 485 |
| AM08126-SS | (TriAlk14)s(invAb)scaAlkcaAlkuuAlkcuAlkCfUfAfuguacuaugus(invAb)(C6-SS-C6) | 361 | CACAUUCUCUAUGUACUAUGU | 485 |
| AM08127-SS | (TriAlk14)s(invAb)scacauucuCfUfAfuguacAlkuAlkauAlkgAlkus(invAb)(C6-SS-C6) | 362 | CACAUUCUCUAUGUACUAUGU | 485 |
| AM08128-SS | (TriAlk14)s(invAb)sacacaacuGfUfCfcauacuaacas(invAb)(C6-SS-C6) | 363 | ACACAACUGUCCAUACUAACA | 507 |
| AM08129-SS | (TriAlk14)s(invAb)sacacaacuGfUfCfcauAlkacAlkuaAlkacAlkas(invAb)(C6-SS-C6) | 364 | ACACAACUGUCCAUACUAACA | 507 |
| AM08130-SS | (TriAlk14)s(invAb)sacAlkacAlkaaAlkcuAlkGfUfCfcauacuaacas(invAb)(C6-SS-C6) | 365 | ACACAACUGUCCAUACUAACA | 507 |
| AM08131-SS | (TriAlk14)s(invAb)sacacaacuGfUfCfcauacAlkuAlkaaAlkcAlkas(invAb)(C6-SS-C6) | 366 | ACACAACUGUCCAUACUAACA | 507 |
| AM08132-SS | (TriAlk14)scsaacguaaCfGfAfuuucaugAlkaaAlksa(invAb)(C6-SS-C6) | 367 | CAACGUAACGAUUUCAUGAAA | 428 |
| AM08133-SS | (TriAlk14)scsaacguaaCfGfAfuuucaAlkugAlkaasa(invAb)(C6-SS-C6) | 368 | CAACGUAACGAUUUCAUGAAA | 428 |
| AM08134-SS | (TriAlk14)scsaacguaaCfGfAfuuuAlkcaAlkugaasa(invAb)(C6-SS-C6) | 369 | CAACGUAACGAUUUCAUGAAA | 428 |

TABLE 4.1-continued

HIF-2 alpha RNAi Agent Sense Strand Sequences Shown Without 3' Terminal dT

| Antisense Strand ID: | Modified Antisense Strand (5'→3') | SEQ ID NO. | Under lying Base Sequence (5'→3') (Shown as an Unmodified Nucleotide Sequence) | SEQ ID NO. |
|---|---|---|---|---|
| AM08135-SS | (TriAlk14)scsaacguaaCfGfAfuuuAlkcaugaaAlksa(invAb)(C6-SS-C6) | 370 | CAACGUAACGAUUUCAUGAAA | 428 |
| AM08395-SS | (TriAlk14)scsaacguaaCfGfAfuuuAlkcaAlkugAlkaaAlksa(invAb)(C6-SS-C6) | 371 | CAACGUAACGAUUUCAUGAAA | 428 |
| AM08397-SS | (TriAlk14)scsasacguaaCfGfAfuuuAlkcaAlkugAlkaaAlksas(invAb)s(C6-SS-C6) | 372 | CAACGUAACGAUUUCAUGAAA | 428 |
| AM08398-SS | (TriAlk14)s(invAb)scsasacguaaCfGfAfuuuAlkcaAlkugAlkaaAlksas(invAb)s(C6-SS-C6) | 373 | CAACGUAACGAUUUCAUGAAA | 428 |
| AM10024-SS | (NH2-C6)scsaacguaaCfGfAfuuucaugaasa(invAb)(C6-SS-C6) | 374 | CAACGUAACGAUUUCAUGAAA | 428 |

TABLE 4.2

HIF-2 alpha RNAi Agent Sense Strand Sequences Shown Without Terminal Linking Groups

| Antisense Strand ID: | Modified Antisense Strand (5'→3') | SEQ ID NO. | Under lying Base Sequence (5'→3') (Shown as an Unmodified Nucleotide Sequence) | SEQ ID NO. |
|---|---|---|---|---|
| AM05339-SS | uAuascguaaCfGfAfuuuCfaugaaa(invdT) | 375 | UAUACGUAACGAUUUCAUGAAT | 909 |
| AM05814-SS | scsaacguaaCfGfAfuuucaugaasa(invAb) | 376 | CAACGUAACGAUUUCAUGAAA | 910 |
| AM05816-SS | csaacguaaCfGfAfuuucaugaasa(invAb) | 377 | CAACGUAACGAUUUCAUGAAA | 910 |
| AM06490-SS | csuggacauAfGfUfaucuuugacas(invAb) | 378 | CUGGACAUAGUAUCUUUGACA | 911 |
| AM06492-SS | cscaugcgcUfAfGfacuccgagaas(invAb) | 379 | CCAUGCGCUAGACUCCGAGAA | 912 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Under lying Base Sequence (5'→3') (Shown as an Unmodified Nucleotide Sequence) | SEQ ID NO. |
|---|---|---|---|---|
| AM06494-SS | cscaguaccGfGfAfugcucgcaaas(invAb) | 380 | CCAGUACCGGAUGCUCGCAAA | 913 |
| AM06496-SS | gsucaucuaCfAfAfcccucgcaaas(invAb) | 381 | GUCAUCUACAACCCUCGCAAA | 914 |
| AM06498-SS | csuucgggaAfUfCfagaacuucgas(invAb) | 382 | CUUCGGGAAUCAGAACUUCGA | 915 |
| AM06500-SS | cscacgcccAfAfUfagcccugaaas(invAb) | 383 | CCACGCCCAAUAGCCCUGAAA | 916 |
| AM06502-SS | gscaguaccCfAfGfacggauuncas(invAb) | 384 | GCAGUACCCAGACGGAUUUCA | 917 |
| AM06504-SS | gsaugccgGfAfAfgcaaagcauas(invAb) | 385 | GAUGCCGGAAGCAAAGCAUA | 918 |
| AM06524-SS | cscccuuugaUfGfCfcggacaagcas(invAb) | 386 | CCCUUUGAUGCCGGACAAGCA | 919 |
| AM06526-SS | gsgacaagcCfAfCfugagcgcaaas(invAb) | 387 | GGACAAGCCACUGAGCGCAAA | 920 |
| AM06528-SS | asggacuacAfGfCfcugucgucaas(invAb) | 388 | AGGACUACAGCCUGUCGUCAA | 921 |
| AM06530-SS | csggacunAfCfCfuggcagacuas(invAb) | 389 | CGGACUUACCUGGCAGACUA | 922 |
| AM06532-SS | gsaagggucAfAfCfuccaacguaas(invAb) | 390 | GAAGGGUCAACUCCAACGUAA | 923 |
| AM06534-SS | csagggucaAfCfUfccaacguauas(invAb) | 391 | CAGGGUCAACUCCAACGUAUA | 924 |
| AM06536-SS | gsggucaacUfCfCfaacguauguas(invAb) | 392 | GGGUCAACUCCAACGUAUGUA | 925 |
| AM06538-SS | csuccaacgUfAfUfgugguuaucas(invAb) | 393 | CUCCAACGUAUGUGGUUAUCA | 926 |
| AM06550-SS | gsccauagGfUfGfugacaauccas(invAb) | 394 | GCCAUAGGUGUGACAAUCCA | 927 |
| AM06552-SS | cscauagguGfUfGfacaauccgaas(invAb) | 395 | CCAUAGGUGUGACAAUCCGAA | 928 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM06554-SS | gsggucugAfUfGfgcacguuguas(invAb) | 396 | GGGUCUGAUGGCACGUUGUA | 929 |
| AM06556-SS | csugagcuaUfGfUfgacucggauas(invAb) | 397 | CUGAGCUAUGUGACUCGGAUA | 930 |
| AM06558-SS | gsgguaagAfGfGfacgacaccas(invAb) | 398 | GGGUAAGAGGGACGACACCA | 931 |
| AM06560-SS | csccuacCfUfGfucaacguaaas(invAb) | 399 | CCCUACCUGUCAACGUAAA | 932 |
| AM06562-SS | (invAb)scccuacCfUfGfucaacguaaas(invAb) | 400 | CCCUACCUGUCAACGUAAA | 932 |
| AM06564-SS | csccuaccuGfUfCfaacguaacgas(invAb) | 401 | CCCUACCUGUCAACGUAACGA | 933 |
| AM06566-SS | cscuaccuGfUfCfaacguaacgas(invAb) | 402 | CCUACCUGUCAACGUAACGA | 934 |
| AM06568-SS | asccugucaAfCfGfuaacgauuuas(invAb) | 403 | ACCUGUCAACGUAACGAUUUA | 935 |
| AM06877-SS | (invAb)sgcaguuugCfUfCfugaaaacgaas(invAb) | 404 | GCAGUUUGCUCUGAAAACGAA | 936 |
| AM06879-SS | (invAb)saggugaaaGfUfCfuacaacaacus(invAb) | 405 | AGGUGAAAGUCUACAACAACU | 937 |
| AM06881-SS | (invAb)sggacacauCfUfUfuggauaacgas(invAb) | 406 | GGACACAUCUUUGGAUAACGA | 938 |
| AM06883-SS | (invAb)scgaccugaAfGfAfuugaagugaus(invAb) | 407 | CGACCUGAAGAUUGAAGUGAU | 939 |
| AM06885-SS | (invAb)sacgggaagAfCfUfuccagcuaaas(invAb) | 408 | ACGGGAAGACUUCCAGCUAAA | 940 |
| AM06887-SS | (invAb)sagcuacaGfGfAfcauaguaucus(invAb) | 409 | AGCUAACAGGACAUAGUAUCU | 941 |
| AM06889-SS | (invAb)scagauaugAfCfUfgugaggugaas(invAb) | 410 | CAGAUAUGACUGUGAGGUGAA | 942 |
| AM06891-SS | (invAb)sggaguacaCfAfAfuuguuuuacas(invAb) | 411 | GGAGUACACAAUUGUUUUACA | 943 |
| AM06893-SS | (invAb)sggucaacuCfCfAfacguaugugas(invAb) | 412 | GGUCAACUCCAACGUAUGUGA | 944 |
| AM06895-SS | (invAb)sgucaacucCfAfAfcguaugugus(invAb) | 413 | GUCAACUCCAACGUAUGUGGU | 945 |
| AM06897-SS | (invAb)sgaugccauAfGfGfugugacaauas(invAb) | 414 | GAUGCCAUAGGUGUGACAAUA | 946 |
| AM06899-SS | (invAb)sggaacuacCfAfUfgagauggu uus(invAb) | 415 | GGAACUACCAUGAGAUGGUUU | 947 |
| AM06901-SS | (invAb)sgcuaccauGfAfGfaugguuuagas(invAb) | 416 | GCUACCAUGAGAUGGUUUAGA | 948 |
| AM06903-SS | (invAb)scganaccaAfUfUfacauggaacus(invAb) | 417 | CGAUACCAAUUACAUGGAACU | 949 |
| AM06905-SS | (invAb)sccuaccugUfCfAfacguaacgaus(invAb) | 418 | CCUACCUGUCAACGUAACGAU | 950 |
| AM06981-SS | csasascsguaaCfGfAfuuucausgsasasas(invAb) | 419 | CAACGUAACGAUUUCAUGAAA | 910 |
| AM06983-SS | csaascgsuasaCfsGfAfsuusucsausgasaas(invAb) | 420 | CAACGUAACGAUUUCAUGAAA | 910 |
| AM06984-SS | csasacguaaCfGfAfuuucaugasasas(invAb) | 421 | CAACGUAACGAUUUCAUGAAA | 910 |
| AM06986-SS | casacsgusaasCfGfsAfusuuscasugsaasas(invAb) | 422 | CAACGUAACGAUUUCAUGAAA | 910 |
| AM07071-SS | csaacguaaCfGfAfuuucaugaaa(invAb) | 423 | CAACGUAACGAUUUCAUGAAA | 910 |
| AM07138-SS | (invAb)scaacguaaCfGfAfuuucaugaaas(invAb) | 424 | CAACGUAACGAUUUCAUGAAA | 910 |
| AM07139-SS | (invAb)sgaacguaaCfGfAfuuucaugaaas(invAb) | 425 | GAACGUAACGAUUUCAUGAAA | 951 |
| AM07141-SS | (invAb)sga_2NacguaaCfGfAfuuucaugaaas(invAb) | 426 | GAACGUAACGAUUUCAUGAAA | 952 |
| AM07142-SS | (invAb)sggacguaaCfGfAfuuucaugaaas(invAb) | 427 | GGACGUAACGAUUUCAUGAAA | 953 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07145-SS | (invAb)sggacguaaCfGfAfuuucauiaaas(invAb) | 428 | GGACGUAACGAUUUCAUIAA A | 954 |
| AM07146-SS | (invAb)sggacguaaCfGfAfuUucaugaaas(invAb) | 429 | GGACGUAACGAUUUCAUGAA A | 953 |
| AM07224-SS | csaacguaaCfGfAfuuucaugaasa(invAb)(6-SS-6) | 430 | CAACGUAACGAUUUCAUGAA A | 910 |
| AM07225-SS | (invAb)scaacguaaCfGfAfuuucaugaaas(invAb) | 431 | CAACGUAACGAUUUCAUGAA A | 910 |
| AM07226-SS | (invAb)sgaacguaaCfGfAfuuucaugaaas(invAb) | 432 | GAACGUAACGAUUUCAUGAA A | 951 |
| AM07227-SS | (invAb)sga_2NacguaaCfGfAfuuucaugaaas(invAb) | 433 | GAACGUAACGAUUUCAUGAA A | 952 |
| AM07228-SS | (invAb)sggacguaaCfGfAfuuucaugaaas(invAb) | 434 | GGACGUAACGAUUUCAUGAA A | 953 |
| AM07229-SS | (invAb)sggacguaaCfGfAfuuucauiaaas(invAb) | 435 | GGACGUAACGAUUUCAUIAA A | 954 |
| AM07230-SS | (invAb)sggacguaaCfGfAfuUucaugaaas(invAb) | 436 | GGACGUAACGAUUUCAUGAA A | 953 |
| AM07231-SS | csaacguaaCfGfAfuuucaugaasa(invAb) | 437 | CAACGUAACGAUUUCAUGAA A | 910 |
| AM07268-SS | csaacguaaCfGfAfuusucsausgasaas(invAb) | 438 | CAACGUAACGAUUUCAUGAA A | 910 |
| AM07269-SS | csaascgsuasaCfGfAfuuucaugaaas(invAb) | 439 | CAACGUAACGAUUUCAUGAA A | 910 |
| AM07270-SS | csaacguaaCfGfAfuuucausgsasasas(invAb) | 440 | CAACGUAACGAUUUCAUGAA A | 910 |
| AM07271-SS | csasascsgsuaaCfGfAfuuucaugaaas(invAb) | 441 | CAACGUAACGAUUUCAUGAA A | 910 |
| AM07272-SS | csaacguasaCfsGfAfsuusucaugaaas(invAb) | 442 | CAACGUAACGAUUUCAUGAA A | 910 |
| AM07273-SS | csaacgusaasCfGfsAfusuucaugaaas(invAb) | 443 | CAACGUAACGAUUUCAUGAA A | 910 |
| AM07274-SS | csaascgsuaaCfGfAfuuucausgasaas(invAb) | 444 | CAACGUAACGAUUUCAUGAA A | 910 |
| AM07275-SS | csasascguaaCfGfAfuuucaugasasas(invAb) | 445 | CAACGUAACGAUUUCAUGAA A | 910 |
| AM07301-SS | csaacguaaCfGfAfuusucsausgasaas(invAb) | 446 | CAACGUAACGAUUUCAUGAA A | 910 |
| AM07302-SS | csaascgsuasaCfGfAfuuucaugaaas(invAb) | 447 | CAACGUAACGAUUUCAUGAA A | 910 |
| AM07303-SS | csaacguaaCfGfAfuuucausgsasasas(invAb) | 448 | CAACGUAACGAUUUCAUGAA A | 910 |
| AM07304-SS | csasascsgsuaaCfGfAfuuucaugaaas(invAb) | 449 | CAACGUAACGAUUUCAUGAA A | 910 |
| AM07305-SS | csaacguasaCfsGfAfsuusucaugaaas(invAb) | 450 | CAACGUAACGAUUUCAUGAA A | 910 |
| AM07306-SS | csaacgusaasCfGfsAfusuucaugaaas(invAb) | 451 | CAACGUAACGAUUUCAUGAA A | 910 |
| AM07307-SS | csaascgsuaaCfGfAfuuucausgasaas(invAb) | 452 | CAACGUAACGAUUUCAUGAA A | 910 |
| AM07308-SS | csasascguaaCfGfAfuuucaugasasas(invAb) | 453 | CAACGUAACGAUUUCAUGAA A | 910 |
| AM07403-SS | csaacguaaCfGfAfuuucaugaasa(invAb) | 454 | CAACGUAACGAUUUCAUGAA A | 910 |
| AM07404-SS | csaacguaaCfGfAfuuucaugaasa(invAb) | 455 | CAACGUAACGAUUUCAUGAA A | 910 |
| AM07405-SS | csaacguaaCfGfAfuuucaugaasa(invAb) | 456 | CAACGUAACGAUUUCAUGAA A | 910 |
| AM07406-SS | csaacguaaCfGfAfuuucaugaasa(invAb) | 457 | CAACGUAACGAUUUCAUGAA A | 910 |
| AM07407-SS | csaacguaaCfGfAfuuucaugaasa(invAb) | 458 | CAACGUAACGAUUUCAUGAA A | 910 |
| AM07408-SS | csaacguaaCfGfAfuuucaugaasa(invAb) | 459 | CAACGUAACGAUUUCAUGAA A | 910 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07493-SS | csaacguasaCfsGfAfsuusucaugaaas(invAb) | 460 | CAACGUAACGAUUUCAUGAAA | 910 |
| AM07528-SS | csaacguaaCfGfAfuusucsausgasaas(invAb) | 461 | CAACGUAACGAUUUCAUGAAA | 910 |
| AM07530-SS | (invAb)scaacuuguAfCfCfugaaaiccuus(invAb)(invAb) | 462 | CAACUUGUACCUGAAAICCUU | 955 |
| AM07532-SS | (invAb)sacunacacAfGfGfuggagcuaaas(invAb)(invAb) | 463 | ACUUACACAGGUGGAGCUAAA | 956 |
| AM07534-SS | (invAb)saggacauaGfUfAfucuuugacuus(invAb)(invAb) | 464 | AGGACAUAGUAUCUUUGACUU | 957 |
| AM07536-SS | (invAb)scuguqucuGfAfGfaagaguaacus(invAb)(invAb) | 465 | CUGUGUCUGAGAAGAGUAACU | 958 |
| AM07538-SS | (invAb)scuuccuauUfCfAfccaagcuaaas(invAb)(invAb) | 466 | CUUCCUAUUCACCAAGCUAAA | 959 |
| AM07540-SS | (invAb)sccagcacaCfUfAfuuuacaagaus(invAb)(invAb) | 467 | CCAGCACACUAUUUACAAGAU | 960 |
| AM07542-SS | (invAb)sgccccuauMfUfuaaaguacaas(invAb)(invAb) | 468 | GCCCCUAUUUUUAAAGUACAA | 961 |
| AM07544-SS | (invAb)sgaguacacAfAfUfuguuuuaccus(invAb)(invAb) | 469 | GAGUACACAAUUGUUUUACCU | 962 |
| AM07546-SS | (invAb)scaacuguccCfAfUfacuaacaagus(invAb)(invAb) | 470 | CAACUGUCCAUACUAACAAGU | 963 |
| AM07548-SS | (invAb)sgugguuauCfUfGfugaaaguugas(invAb)(invAb) | 471 | GUGGUUAUCUGUGAAAGUUGA | 964 |
| AM07550-SS | (invAb)sgaacuuagAfAfAfcggaaauggas(invAb)(invAb) | 472 | GAACUUAGAAACGGAAAUGGA | 965 |
| AM07552-SS | (invAb)sgauccgagCfAfGfuggagucauus(invAb)(invAb) | 473 | GAUCCGAGCAGUGGAGUCAUU | 966 |
| AM07554-SS | (invAb)scacauucuCfUfAfuguacuaugus(invAb)(invAb) | 474 | CACAUUCUCUAUGUACUAUGU | 967 |
| AM07556-SS | (invAb)sggucagugAfCfAfuguagguagas(invAb)(invAb) | 475 | GGUCAGUGACAUGUAGGUAGA | 968 |
| AM07558-SS | (invAb)sgacacacaCfAfAfagcacaungas(invAb)(invAb) | 476 | GACACACACAAAGCACAUUGA | 969 |
| AM07560-SS | (invAb)saccggauaGfAfCfuuauuiccaas(invAb)(invAb) | 477 | ACCGGAUAGACUUAUUICCAA | 970 |
| AM07562-SS | (invAb)sgaaguucuAfUfGfagaaauuccus(invAb)(invAb) | 478 | GAAGUUCUAUGAGAAAUUCCU | 971 |
| AM07564-SS | (invAb)sgguuacugAfCfGfuguaaaugcus(invAb)(invAb) | 479 | GGUUACUGACGUGUAAAUGCU | 972 |
| AM07566-SS | (invAb)sacguaacgAfUfUfucaugaacgus(invAb)(invAb) | 480 | ACGUAACGAUUUCAUGAACGU | 973 |
| AM07568-SS | (invAb)sguaacgauUTUfCfaugaacguuas(invAb)(invAb) | 481 | GUAACGAUUUCAUGAACGUUA | 974 |
| AM07570-SS | (invAb)sgaacgauuUfCfAfugaacguuaus(invAb)(invAb) | 482 | GAACGAUUUCAUGAACGUUAU | 975 |
| AM07572-SS | (invAb)sggagcuuaAfCfUfuuauaaggaas(invAb)(invAb) | 483 | GGAGCUUAACUUUAUAAGGAA | 976 |
| AM07619-SS | csaaAlkcguaAlkaCfGfAfuuucaAlkugaaAlksa(invAb)(invAb) | 484 | CAACGUAACGAUUUCAUGAAA | 1016 |
| AM07621-SS | scsaaAlkcguaAlkaCfGfAfuuucaAlkugaaAlksa(invAb)(invAb) | 485 | CAACGUAACGAUUUCAUGAAA | 1016 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07705-SS | csaacguaaCfGfAfuuucaugaasa(invAb) | 486 | CAACGUAACGAUUUCAUGAAA | 910 |
| AM07706-SS | csaacguaaCfGfAfuuucaugaasa(invAb) | 487 | CAACGUAACGAUUUCAUGAAA | 910 |
| AM07707-SS | csaacguaaCfGfAfuuucaugaasa(invAb) | 488 | CAACGUAACGAUUUCAUGAAA | 910 |
| AM07708-SS | csaacguaaCfGfAfuuucaugaasa(invAb) | 489 | CAACGUAACGAUUUCAUGAAA | 910 |
| AM07709-SS | csaacguaaCfGfAfuuucaugaasa(invAb) | 490 | CAACGUAACGAUUUCAUGAAA | 910 |
| AM07710-SS | csaacguaaCfGfAfuuucaAlkugaasa(invAb) | 491 | CAACGUAACGAUUUCAUGAAA | 1017 |
| AM07711-SS | csaacguaAlkaCfGfAfuuucaugaasa(invAb) | 492 | CAACGUAACGAUUUCAUGAAA | 1018 |
| AM07712-SS | csaacguaAlkaCfGfAfuuucaAlkugaasa(invAb) | 493 | CAACGUAACGAUUUCAUGAAA | 1019 |
| AM07713-SS | csaaAlkcguaAlkaCfGfAfuuucaAlkugaaAlksa(invAb) | 494 | CAACGUAACGAUUUCAUGAAA | 1016 |
| AM07721-SS | (invAb)scacauucuCfUfAfuguacuaugus(invAb) | 495 | CACAUUCUCUAUGUACUAUGU | 967 |
| AM07722-SS | (invAb)sgacauucuCfUfAfuguacuaugus(invAb) | 496 | GACAUUCUCUAUGUACUAUGU | 977 |
| AM07724-SS | (invAb)scgcauucuCfUfAfuguacuaugus(invAb) | 497 | CGCAUUCUCUAUGUACUAUGU | 978 |
| AM07726-SS | (invAb)scccauucuCfUfAfuguacuaugus(invAb) | 498 | CCCAUUCUCUAUGUACUAUGU | 979 |
| AM07728-SS | (invAb)sggcauucuCfUfAfuguacuaugus(invAb) | 499 | GGCAUUCUCUAUGUACUAUGU | 980 |
| AM07730-SS | (invAb)scaca_2NuucuCfUfAfuguacuaugus(invAb) | 500 | CACAUUCUCUAUGUACUAUGU | 981 |
| AM07731-SS | (invAb)sccca_2NuucuCfUfAfuguacuaugus(invAb) | 501 | CCCAUUCUCUAUGUACUAUGU | 982 |
| AM07732-SS | (invAb)sgcgaccAfUfGfaggagauucauus(invAb) | 502 | GCGACCAUGAGGAGAUUCAUU | 983 |
| AM07734-SS | (invAb)scgcucaGfCfCfuaugaanucauus(invAb) | 503 | CGCUCAGCCUAUGAAUUCAUU | 984 |
| AM07736-SS | (invAb)scaagggucAfGfGfuaguaagugas(invAb) | 504 | CAAGGGUCAGGUAGUAAGUGA | 985 |
| AM07738-SS | (invAb)sgacugaauCfCfCfuguucaagcas(invAb) | 505 | GACUGAAUCCCUGUUCAAGCA | 986 |
| AM07740-SS | (invAb)sucagugccAfUfGfacaaacaucus(invAb) | 506 | UCAGUGCCAUGACAAACAUCU | 987 |
| AM07742-SS | (invAb)sgcaccucaCfAfUfuugaugugas(invAb) | 507 | GCACCUCACAUUUGAUGUGGA | 988 |
| AM07744-SS | (invAb)sacacaacuGfUfCfcauacuaacas(invAb) | 508 | ACACAACUGUCCAUACUAACA | 989 |
| AM07746-SS | (invAb)sggcauaguAfUfCfuuugacuucas(invAb) | 509 | GGCAUAGUAUCUUUGACUUCA | 990 |
| AM07776-SS | (invAb)sgaguacacAfAfUfuguuuuaccus(invAb) | 510 | GAGUACACAAUUGUUUUACCU | 962 |
| AM07777-SS | (invAb)scuuccuauUfCfAfccaagcuaaas(invAb) | 511 | CUUCCUAUUCACCAAGCUAAA | 959 |
| AM07778-SS | (invAb)sggucagugAfCfAfuguaggguagas(invAb) | 512 | GGUCAGUGACAUGUAGGUAGA | 968 |
| AM07801-SS | csaacguaaCfGfAfuuucaugaasa(invAb) | 513 | CAACGUAACGAUUUCAUGAAA | 910 |
| AM07813-SS | csaaAlkcguaAlkaCfGfAfuuucaAlkugaaAlksa(invAb) | 514 | CAACGUAACGAUUUCAUGAAA | 1016 |
| AM07814-SS | csaaAlkcguaAlkaCfGfAfuuucaAlkugaaAlksa(invAb) | 515 | CAACGUAACGAUUUCAUGAAA | 1016 |
| AM07817-SS | csaAlkaAlkcguAlkaAlkaCfGfAfuuucaAlkuAlkgaAlkaAlksa(invAb) | 516 | CAACGUAACGAUUUCAUGAAA | 1020 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM07818-SS | scsaacguaaCfGfAfuuucaugaasa(invAb) | 517 | CAACGUAACGAUUUCAUGAAA | 910 |
| AM07822-SS | csaacguaAlkaCfGfAfuuucaAlkugaaAlksa(invAb) | 518 | CAACGUAACGAUUUCAUGAAA | 1021 |
| AM07823-SS | csaaAlkcguaaCfGfAfuuucaAlkugaaAlksa(invAb) | 519 | CAACGUAACGAUUUCAUGAAA | 1022 |
| AM07824-SS | csaaAlkcguaAlkaCfGfAfuuucaugaaAlksa(invAb) | 520 | CAACGUAACGAUUUCAUGAAA | 1023 |
| AM07825-SS | csaaAlkcguaAlkaCfGfAfuuucaAlkugaasa(invAb) | 521 | CAACGUAACGAUUUCAUGAAA | 1024 |
| AM07826-SS | csaaAlkcguaAlkaCfGfAfuuucaugaasa(invAb) | 522 | CAACGUAACGAUUUCAUGAAA | 1025 |
| AM07827-SS | csaacguaaCfGfAfuuucaAlkugaaAlksa(invAb) | 523 | CAACGUAACGAUUUCAUGAAA | 1006 |
| AM07828-SS | csaaAlkcguaaCfGfAfuuucaugaaAlksa(invAb) | 524 | CAACGUAACGAUUUCAUGAAA | 1026 |
| AM07829-SS | csaaAlkcguaaCfGfAfuuucaAlkugaasa(invAb) | 525 | CAACGUAACGAUUUCAUGAAA | 1027 |
| AM07830-SS | csaacguaAlkaCfGfAfuuucaugaaAlksa(invAb) | 526 | CAACGUAACGAUUUCAUGAAA | 1028 |
| AM07831-SS | csaacguaaCfGfAfuuucaugaaAlksa(invAb) | 527 | CAACGUAACGAUUUCAUGAAA | 999 |
| AM07832-SS | csaaAlkcguaaCfGfAfuuucaugaasa(invAb) | 528 | CAACGUAACGAUUUCAUGAAA | 998 |
| AM07833-SS | csaAlkaAlkcguaaCfGfAfuuucaugaAlkaAlksa(invAb) | 529 | CAACGUAACGAUUUCAUGAAA | 1029 |
| AM07834-SS | csaacAlkguaaAlkCfGfAfuuuAlkcaugAlkaasa(invAb) | 530 | CAACGUAACGAUUUCAUGAAA | 1030 |
| AM07835-SS | csaacgAlkuaaAlkCfGfAfuAlkuucAlkaugaasa(invAb) | 531 | CAACGUAACGAUUUCAUGAAA | 1031 |
| AM07836-SS | csaacguaAlkaAlkCfGfAfuAlkuAlkucaugaasa(invAb) | 532 | CAACGUAACGAUUUCAUGAAA | 1032 |
| AM07837-SS | csaAlkacAlkguAlkaaAlkCfGfAfuuucaugaasa(invAb) | 533 | CAACGUAACGAUUUCAUGAAA | 1033 |
| AM07838-SS | csaAlkaAlkcAlkgAlkuaaCfGfAfuuucaugaasa(invAb) | 534 | CAACGUAACGAUUUCAUGAAA | 1034 |
| AM07839-SS | csaacguaaCfGfAfuuuAlkcaAlkugAlkaaAlksa(invAb) | 535 | CAACGUAACGAUUUCAUGAAA | 1015 |
| AM07840-SS | csaacguaaCfGfAfuuucauAlkgAlkaAlkaAlksa(invAb) | 536 | CAACGUAACGAUUUCAUGAAA | 1035 |
| AM07890-SS | (invAb)sgcacaacuGfUfCfcauacuaacas(invAb) | 537 | GCACAACUGUCCAUACUAACA | 991 |
| AM07892-SS | (invAb)sccacaacuGfUfCfcauacuaacas(invAb) | 538 | CCACAACUGUCCAUACUAACA | 992 |
| AM07894-SS | (invAb)sggacaacuGfUfCfcauacuaacas(invAb) | 539 | GGACAACUGUCCAUACUAACA | 993 |
| AM08018-SS | csaacguaaCfGfAfuuucaAlkuAlkgaAlkaAlksa(invAb) | 540 | CAACGUAACGAUUUCAUGAAA | 1000 |
| AM08019-SS | csaacAlkguaaAlkCfGfAfuuuAlkcaAlkugAlkaaAlksa(invAb) | 541 | CAACGUAACGAUUUCAUGAAA | 1036 |
| AM08020-SS | csaacguaaCfGfAfuuucaugAlkaasa(invAb) | 542 | CAACGUAACGAUUUCAUGAAA | 999 |
| AM08021-SS | csaacguaaCfGfAfuuucaAlkuAlkgAlkaAlkasa(invAb) | 543 | CAACGUAACGAUUUCAUGAAA | 1000 |
| AM08022-SS | csaacguaaCfGfAfuuucAlkaAlkuAlkgAlkaasa(invAb) | 544 | CAACGUAACGAUUUCAUGAAA | 1037 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08023-SS | csaacguaaCfGfAfuuuAlkcAlkaAlkuAlkgaasa(invAb) | 545 | CAACGUAACGAUUUCAUGAAA | 1038 |
| AM08024-SS | csaacguaaCfGfAfuuAlkuAlkcAlkaAlkugaasa(invAb) | 546 | CAACGUAACGAUUUCAUGAAA | 1039 |
| AM08025-SS | csaacguaaCfGfAfuAlkuAlkuAlkcAlkaugaasa(invAb) | 547 | CAACGUAACGAUUUCAUGAAA | 1040 |
| AM08026-SS | csaacguaaCfGfAfuAlkuuAlkcaAlkugAlkaaAlksa(invAb) | 548 | CAACGUAACGAUUUCAUGAAA | 1041 |
| AM08027-SS | csaacguaaCfGfAfuuucaAlkugAlkaaAlksa(invAb) | 549 | CAACGUAACGAUUUCAUGAAA | 1001 |
| AM08028-SS | csaacguaaCfGfAfuuuAlkcaugAlkaaAlksa(invAb) | 550 | CAACGUAACGAUUUCAUGAAA | 1042 |
| AM08029-SS | csaacguaaCfGfAfuuuAlkcaAlkugaaAlksa(invAb) | 551 | CAACGUAACGAUUUCAUGAAA | 1043 |
| AM08030-SS | csaacguaaCfGfAfuuuAlkcaAlkugAlkaasa(invAb) | 552 | CAACGUAACGAUUUCAUGAAA | 1043 |
| AM08031-SS | csaacguaaCfGfAfuuucaugAlkaAlkaAlksa(invAb) | 553 | CAACGUAACGAUUUCAUGAAA | 1044 |
| AM08032-SS | csaacguaaCfGfAfuuucauAlkgaAlkaAlksa(invAb) | 554 | CAACGUAACGAUUUCAUGAAA | 997 |
| AM08033-SS | csaacguaaCfGfAfuuucauAlkgAlkaaAlksa(invAb) | 555 | CAACGUAACGAUUUCAUGAAA | 997 |
| AM08034-SS | csaacguaaCfGfAfuuucauAlkgAlkaAlkasa(invAb) | 556 | CAACGUAACGAUUUCAUGAAA | 997 |
| AM08035-SS | csaacguaaAlkCfGfAfuuuAlkcaugAlkaasa(invAb) | 557 | CAACGUAACGAUUUCAUGAAA | 1045 |
| AM08036-SS | csaacAlkguaaCfGfAfuuuAlkcaugAlkaasa(invAb) | 558 | CAACGUAACGAUUUCAUGAAA | 1046 |
| AM08037-SS | csaacAlkguaaAlkCfGfAfuuucaugAlkaasa(invAb) | 559 | CAACGUAACGAUUUCAUGAAA | 1047 |
| AM08038-SS | csaacAlkguaaAlkCfGfAfimuAlkcaugaasa(invAb) | 560 | CAACGUAACGAUUUCAUGAAA | 1048 |
| AM08092-SS | csaaAlkcguaaCfGfAfuuucaugaasa(invAb) | 561 | CAACGUAACGAUUUCAUGAAA | 998 |
| AM08093-SS | csaacguaaCfGfAfuuucaugaaAlksa(invAb) | 562 | CAACGUAACGAUUUCAUGAAA | 999 |
| AM08108-SS | csaacguaaCfGfAfuuucaAlkuAlkgaAlkaAlksa(invAb) | 563 | CAACGUAACGAUUUCAUGAAA | 1000 |
| AM08109-SS | csaacguaaCfGfAfuuucauAlkgaAlkaAlksa(invAb) | 564 | CAACGUAACGAUUUCAUGAAA | 997 |
| AM08110-SS | csaacguaaCfGfAfuuucaAlkugaAlkaAlksa(invAb) | 565 | CAACGUAACGAUUUCAUGAAA | 1001 |
| AM08111-SS | csaacguaaCfGfAfuuucaAlkuAlkgaaAlksa(invAb) | 566 | CAACGUAACGAUUUCAUGAAA | 1002 |
| AM08112-SS | csaacguaaCfGfAfuuucaAlkuAlkgaAlkasa(invAb) | 567 | CAACGUAACGAUUUCAUGAAA | 1002 |
| AM08113-SS | csaacguaaCfGfAfuuucaugaAlkaAlksa(invAb) | 568 | CAACGUAACGAUUUCAUGAAA | 1003 |
| AM08114-SS | csaacguaaCfGfAfuuucaAlkuAlkgaasa(invAb) | 569 | CAACGUAACGAUUUCAUGAAA | 1004 |
| AM08115-SS | csaacguaaCfGfAfuuucauAlkgaAlkasa(invAb) | 570 | CAACGUAACGAUUUCAUGAAA | 1005 |
| AM08116-SS | csaacguaaCfGfAfuuucaAlkugaAlkasa(invAb) | 571 | CAACGUAACGAUUUCAUGAAA | 1006 |
| AM08117-SS | csaacguaaCfGfAfuuucauAlkgaaAlksa(invAb) | 572 | CAACGUAACGAUUUCAUGAAA | 1005 |
| AM08118-SS | csaacguaaCfGfAfuuuAlkcaugAlkaasa(invAb) | 573 | CAACGUAACGAUUUCAUGAAA | 1007 |
| AM08119-SS | csaacguaaCfGfAfunucaugaasa(invAb) | 574 | CAACGUAACGAUUUCAUGAAA | 910 |
| AM08120-SS | csaacguaaCfGfAfunuAlkcaAlkugAlkaaAlksa(invAb) | 575 | CAACGUAACGAUUUCAUGAAA | 1015 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08121-SS | csaacguaaCfGfAfunucaAlkuAlkgaAlkaAlksa(invAb) | 576 | CAACGUAACGAUUUCAUGAAA | 1000 |
| AM08122-SS | csaAlkacAlkguAlkaaAlkCfGfAfunucaugaasa(invAb) | 577 | CAACGUAACGAUUUCAUGAAA | 1033 |
| AM08123-SS | csaAlkaAlkcgAlkuAlkaaCfGfAfunucaugaasa(invAb) | 578 | CAACGUAACGAUUUCAUGAAA | 1049 |
| AM08124-SS | (invAb)scacauucuCfUfAfuguacuaugus(invAb) | 579 | CACAUUCUCUAUGUACUAUGU | 967 |
| AM08125-SS | (invAb)scacauucuCfUfAfuguAlkacAlkuaAlkugAlkus(invAb) | 580 | CACAUUCUCUAUGUACUAUGU | 1008 |
| AM08126-SS | (invAb)scaAlkcaAlkuuAlkcuAlkCfUfAfuguacuaugus(invAb) | 581 | CACAUUCUCUAUGUACUAUGU | 1009 |
| AM08127-SS | (invAb)scacauucuCfUfAfuguacAlkuAlkauAlkgAlkus(invAb) | 582 | CACAUUCUCUAUGUACUAUGU | 1010 |
| AM08128-SS | (invAb)sacacaacuGfUfCfcauacuaacas(invAb) | 583 | ACACAACUGUCCAUACUAACA | 989 |
| AM08129-SS | (invAb)sacacaacuGfUfCfcauAlkacAlkuaAlkacAlkas(invAb) | 584 | ACACAACUGUCCAUACUAACA | 1011 |
| AM08130-SS | (invAb)sacAlkacAlkaaAlkcuAlkGfUfCfcauacuaacas(invAb) | 585 | ACACAACUGUCCAUACUAACA | 1012 |
| AM08131-SS | (invAb)sacacaacuGfUfCfcauacAlkuAlkaaAlkcAlkas(invAb) | 586 | ACACAACUGUCCAUACUAACA | 1013 |
| AM08132-SS | csaacguaaCfGfAfunucaugAlkaaAlksa(invAb) | 587 | CAACGUAACGAUUUCAUGAAA | 1003 |
| AM08133-SS | csaacguaaCfGfAfunucaAlkugAlkaasa(invAb) | 588 | CAACGUAACGAUUUCAUGAAA | 1006 |

TABLE 4.2-continued

HIF-2 alpha RNAi Agent Sense Strand Sequences Shown Without Terminal Linking Groups

| Antisense Strand ID: | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM08134-SS | csaacguaaCfGfAfunuAlkcaAlkugaasa(invAb) | 589 | CAACGUAACGAUUUCAUGAAA | 1014 |
| AM08135-SS | csaacguaaCfGfAfunuAlkcaugaaAlksa(invAb) | 590 | CAACGUAACGAUUUCAUGAAA | 1007 |
| AM08233-SS | csaacguaaCfGfAfunuAlkcaAlkugAlkaaAlksa(invAb) | 591 | CAACGUAACGAUUUCAUGAAA | 1015 |
| AM08234-SS | csaacguaaCfGfAfunuAlkcaAlkugAlkaaAlksa(invAb) | 592 | CAACGUAACGAUUUCAUGAAA | 1015 |
| AM08372-SS | csaacguaaCfGfAfunuAlkcaAlkugAlkaaAlksa(invAb) | 593 | CAACGUAACGAUUUCAUGAAA | 1015 |
| AM08394-SS | csaacguaaCfGfAfuuuAlkcaAllcugAlkaaAlksa(invAb)s | 594 | CAACGUAACGAUUUCAUGAAA | 1015 |
| AM08395-SS | csaacguaaCfGfAfuuuAlkcaAllcugAlkaaAlksa(invAb) | 595 | CAACGUAACGAUUUCAUGAAA | 1015 |
| AM08396-SS | csaacguaaCfGfAfuuuAlkcaAllcugAlkaaAlksas(invAb)s | 596 | CAACGUAACGAUUUCAUGAAA | 1015 |
| AM08397-SS | csasacguaaCfGfAfuuuAlkcaAllcugAlkaaAlksas(invAb)s | 597 | CAACGUAACGAUUUCAUGAAA | 1015 |
| AM08398-SS | (invAb)scsasacguaaCfGfAfimuAlkcaAlkugAlkaaAlksas(invAb)s | 598 | CAACGUAACGAUUUCAUGAAA | 1015 |
| AM08399-SS | csasacguaaCfGfAfuuuAlkcaAllcugAlkaaAlksas(invAb)s | 599 | CAACGUAACGAUUUCAUGAAA | 1015 |
| AM10024-SS | csaacguaaCfGfAfuuucaugaasa(invAb) | 600 | CAACGUAACGAUUUCAUGAAA | 910 |

As discussed herein, in some embodiments, one or more targeting ligands and/or PK enhancers are linked or conjugated to the RNAi agent. In some embodiments, a targeting ligand (or targeting group) and/or a PK enhancer is linked to the 5' end of the sense strand, the 3' end of the sense strand, and/or to one or more internal nucleotides. The synthesis of the sense strand and/or the antisense strand can be designed such that reactive groups are readily available to facilitate linkage to additional components, such as a targeting ligand or PK enhancer. The following Table 4.3 depicts the sense strand of the HIF-2 alpha RNAi agents disclosed above in Table 4 after linking to one or more targeting ligands and/or PK enhancers (collectively, shown below, as Z).

TABLE 4.3

HIF-2 alpha RNAi Agent Sense Strand Sequences Showing Targeting Ligand and/or PK enhancer Positions (each X, Y and Z is independently a pharmacological moiety (for example, targeting ligand, targeting group, and/or PK enhancer); $(Z)_3$ = three Ligands linked (for example, a tridentate targeting group); $u^z$, $a^z$, $g^z$, and $c^z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group.)

| Sense Strand ID: | Modified Sense Strand (5' → 3') | SEQ ID NO. |
|---|---|---|
| AM05339-SS | Y-(NH-C6)uAuascguaaCfGfAfuuuCfaugaaa(invdT)(C6-S)-X | 601 |
| AM05814-SS | Y-(NH-C6)scsaacguaaCfGfAfuuucaugaasa(invAb)-X | 602 |
| AM05816-SS | Y-(NH-C6)scsaacguaaCfGfAfuuucaugaasa(invAb)(C6-S)-X | 603 |
| AM06490-SS | Y-(NH-C6)scsuggacauAfGfUfaucuuugacas(invAb)(C6-S)-X | 604 |
| AM06492-SS | Y-(NH-C6)scscaugcgcUfAfGfacuccgagaas(invAb)(C6-S)-X | 605 |
| AM06494-SS | Y-(NH-C6)scscaguaccGfGfAfugcucgcaaas(invAb)(C6-S)-X | 606 |
| AM06496-SS | Y-(NH-C6)sgsucaucuaCfAfAfcccucgcaaas(invAb)(C6-S)-X | 607 |
| AM06498-SS | Y-(NH-C6)scsuucgggaAfUfCfagaacuucgas(invAb)(C6-S)-X | 608 |
| AM06500-SS | Y-(NH-C6)scscacgcccAfAfUfagcccugaaas(invAb)(C6-S)-X | 609 |
| AM06502-SS | Y-(NH-C6)sgscaguaccCfAfGfacggauuucas(invAb)(C6-S)-X | 610 |
| AM06504-SS | Y-(NH-C6)sgsaugccgGfAfAfgcaaagcauas(invAb)(C6-S)-X | 611 |
| AM06524-SS | Y-(NH-C6)scsccuuugaUfGfCfcggacaagcas(invAb)(C6-S)-X | 612 |
| AM06526-SS | Y-(NH-C6)sgsgacaagcCfAfCfugagcgcaaas(invAb)(C6-S)-X | 613 |
| AM06528-SS | Y-(NH-C6)sasggacuacAfGfCfcugucgucaas(invAb)(C6-S)-X | 614 |
| AM06530-SS | Y-(NH-C6)scsggacuuAfCfCfuggcagacuas(invAb)(C6-S)-X | 615 |
| AM06532-SS | Y-(NH-C6)sgsaaggucAfAfCfuccaacguaas(invAb)(C6-S)-X | 616 |
| AM06534-SS | Y-(NH-C6)scsaggucaAfCfUfccaacguauas(invAb)(C6-S)-X | 617 |
| AM06536-SS | Y-(NH-C6)sgsggucaacUfCfCfaacguauguas(invAb)(C6-S)-X | 618 |
| AM06538-SS | Y-(NH-C6)scsuccaacgUfAfUfgugguuaucas(invAb)(C6-S)-X | 619 |
| AM06550-SS | Y-(NH-C6)sgsccauagGfUfGfugacaauccas(invAb)(C6-S)-X | 620 |
| AM06552-SS | Y-(NH-C6)scscauagguGfUfGfacaauccgaas(invAb)(C6-S)-X | 621 |
| AM06554-SS | Y-(NH-C6)sgsggucugAfUfGfgcacguuguas(invAb)(C6-S)-X | 622 |
| AM06556-SS | Y-(NH-C6)scsugagcuaUfGfUfgacucggauas(invAb)(C6-S)-X | 623 |
| AM06558-SS | Y-(NH-C6)sgsgguaagAfGfGfgacgacaccas(invAb)(C6-S)-X | 624 |
| AM06560-SS | Y-(NH-C6)scsccuacCfUfGfucaacguaaas(invAb)(C6-S)-X | 625 |
| AM06562-SS | Y-(NH-C6)s(invAb)scccuacCfUfGfucaacguaaas(invAb)(C6-S)-X | 626 |
| AM06564-SS | Y-(NH-C6)scsccuaccuGfUfCfaacguaacgas(invAb)(C6-S)-X | 627 |
| AM06566-SS | Y-(NH-C6)scscuaccuGfUfCfaacguaacgas(invAb)(C6-S)-X | 628 |
| AM06568-SS | Y-(NH-C6)sasccugucaAfCfGfuaacgauuuas(invAb)(C6-S)-X | 629 |
| AM06877-SS | Y-(NH-C6)s(invAb)sgcaguuugCfUfCfugaaaacgaas(invAb)(C6-S)-X | 630 |
| AM06879-SS | Y-(NH-C6)s(invAb)saggugaaaGfUfCfuacaacaacus(invAb)(C6-S)-X | 631 |
| AM06881-SS | Y-(NH-C6)s(invAb)sggacacauCfUfUfuggauaacgas(invAb)(C6-S)-X | 632 |
| AM06883-SS | Y-(NH-C6)s(invAb)scgaccugaAfGfAfuugaagugaus(invAb)(C6-S)-X | 633 |
| AM06885-SS | Y-(NH-C6)s(invAb)sacgggaagAfCfUfuccagcuaaas(invAb)(C6-S)-X | 634 |
| AM06887-SS | Y-(NH-C6)s(invAb)sagcuaacaGfGfAfcauaguaucus(invAb)(C6-S)-X | 635 |
| AM06889-SS | Y-(NH-C6)s(invAb)scagauaugAfCfUfgugaggugaas(invAb)(C6-S)-X | 636 |
| AM06891-SS | Y-(NH-C6)s(invAb)sggaguacaCfAfAfuuguuuuacas(invAb)(C6-S)-X | 637 |
| AM06893-SS | Y-(NH-C6)s(invAb)sggucaacuCfCfAfacguaugugas(invAb)(C6-S)-X | 638 |
| AM06895-SS | Y-(NH-C6)s(invAb)sgucaacucCfAfAfcguauguggus(invAb)(C6-S)-X | 639 |
| AM06897-SS | Y-(NH-C6)s(invAb)sgaugccauAfGfGfugugacaauas(invAb)(C6-S)-X | 640 |
| AM06899-SS | Y-(NH-C6)s(invAb)sggaacuacCfAfUfgagaugguuus(invAb)(C6-S)-X | 641 |
| AM06901-SS | Y-(NH-C6)s(invAb)sgcuaccauGfAfGfaugguuuagas(invAb)(C6-S)-X | 642 |
| AM06903-SS | Y-(NH-C6)s(invAb)scgauaccaAfUfUfacauggaacus(invAb)(C6-S)-X | 643 |
| AM06905-SS | Y-(NH-C6)s(invAb)sccuaccugUfCfAfacguaacgaus(invAb)(C6-S)-X | 644 |
| AM06981-SS | Y-(NH-C6)scsasascsguaaCfGfAfuuucausgsasasas(invAb)(C6-S)-X | 645 |
| AM06983-SS | Y-(NH-C6)scsaascgsuasaCfsGfAfsuusucsausgasaas(invAb)(C6-S)-X | 646 |
| AM06984-SS | Y-(NH-C6)scsasacguaaCfGfAfuuucaugasasas(invAb)(C6-S)-X | 647 |
| AM06986-SS | Y-(NH-C6)scasacsgusaasCfGfsAfusuuscasugsaasas(invAb)(C6-S)-X | 648 |
| AM07071-SS | Y-(NH-C6)csaacguaaCfGfAfuuucaugaasa(invAb)(C6-S)-X | 649 |
| AM07138-SS | Y-(NH-C6)s(invAb)scaacguaaCfGfAfuuucaugaaas(invAb)(C6-S)-X | 650 |
| AM07139-SS | Y-(NH-C6)s(invAb)sgaacguaaCfGfAfuuucaugaaas(invAb)(C6-S)-X | 651 |
| AM07141-SS | Y-(NH-C6)s(invAb)sga__2NacguaaCfGfAfuuucaugaaas(invAb)(C6-S)-X | 652 |
| AM07142-SS | Y-(NH-C6)s(invAb)sggacguaaCfGfAfuuucaugaaas(invAb)(C6-S)-X | 653 |

TABLE 4.3-continued

HIF-2 alpha RNAi Agent Sense Strand Sequences Showing Targeting Ligand and/or PK enhancer Positions (each X, Y and Z is independently a pharmacological moiety (for example, targeting ligand, targeting group, and/or PK enhancer); $(Z)_3$ = three Ligands linked (for example, a tridentate targeting group); $u^z$, $a^z$, $g^z$, and $c^z$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group.)

| Sense Strand ID: | Modified Sense Strand (5' → 3') | SEQ ID NO. |
|---|---|---|
| AM07145-SS | Y-(NH-C6)s(invAb)sggacguaaCfGfAfuuucauiaaas(invAb)(C6-S)-X | 654 |
| AM07146-SS | Y-(NH-C6)s(invAb)sggacguaaCfGfAfuUucaugaaas(invAb)(C6-S)-X | 655 |
| AM07224-SS | Y-(NH-C6)scsaacguaaCfGfAfuuucaugaasa(invAb)(6-S)-X | 656 |
| AM07225-SS | Y-(NH-C6)s(invAb)scaacguaaCfGfAfuuucaugaaas(invAb)(6-S)-X | 657 |
| AM07226-SS | Y-(NH-C6)s(invAb)sgaacguaaCfGfAfuuucaugaaas(invAb)(6-S)-X | 658 |
| AM07227-SS | Y-(NH-C6)s(invAb)sga__2NacguaaCfGfAfuuucaugaaas(invAb)(6-S)-X | 659 |
| AM07228-SS | Y-(NH-C6)s(invAb)sggacguaaCfGfAfuuucaugaaas(invAb)(6-S)-X | 660 |
| AM07229-SS | Y-(NH-C6)s(invAb)sggacguaaCfGfAfuuucauiaaas(invAb)(6-S)-X | 661 |
| AM07230-SS | Y-(NH-C6)s(invAb)sggacguaaCfGfAfuUucaugaaas(invAb)(6-S)-X | 662 |
| AM07231-SS | Y-(NH-C6)scsaacguaaCfGfAfuuucaugaasa(invAb)(C3-S)-X | 663 |
| AM07268-SS | Y-(NH-C6)scsaacguaaCfGfAfuusucsausgasaas(invAb)(C6-S)-X | 664 |
| AM07269-SS | Y-(NH-C6)scsaascgsuasaCfGfAfuuucaugaaas(invAb)(C6-S)-X | 665 |
| AM07270-SS | Y-(NH-C6)scsaacguaaCfGfAfuuucausgsasasas(invAb)(C6-S)-X | 666 |
| AM07271-SS | Y-(NH-C6)scsasascsgsuaaCfGfAfuuucaugaaas(invAb)(C6-S)-X | 667 |
| AM07272-SS | Y-(NH-C6)scsaacguasaCfsGfAfsuusucaugaaas(invAb)(C6-S)-X | 668 |
| AM07273-SS | Y-(NH-C6)scsaacgusaasCfGfsAfusuucaugaaas(invAb)(C6-S)-X | 669 |
| AM07274-SS | Y-(NH-C6)scsaascgsuaaCfGfAfuuucausgasaas(invAb)(C6-S)-X | 670 |
| AM07275-SS | Y-(NH-C6)scsasascguaaCfGfAfuuucaugasasas(invAb)(C6-S)-X | 671 |
| AM07301-SS | Y-(NH-C6)scsaacguaaCfGfAfuusucsausgasaas(invAb) | 672 |
| AM07302-SS | Y-(NH-C6)scsaascgsuasaCfGfAfuuucaugaaas(invAb) | 673 |
| AM07303-SS | Y-(NH-C6)scsaacguaaCfGfAfuuucausgsasasas(invAb) | 674 |
| AM07304-SS | Y-(NH-C6)scsasascsgsuaaCfGfAfuuucaugaaas(invAb) | 675 |
| AM07305-SS | Y-(NH-C6)scsaacguasaCfsGfAfsuusucaugaaas(invAb) | 676 |
| AM07306-SS | Y-(NH-C6)scsaacgusaasCfGfsAfusuucaugaaas(invAb) | 677 |
| AM07307-SS | Y-(NH-C6)scsaascgsuaaCfGfAfuuucausgasaas(invAb) | 678 |
| AM07308-SS | Y-(NH-C6)scsasascguaaCfGfAfuuucaugasasas(invAb) | 679 |
| AM07403-SS | $(Z)_3$-(TriAik1)scsaacguaaCfGfAfuuucaugaasa(invAb)(6-S)-X | 680 |
| AM07404-SS | $(Z)_3$-(TriAlk2)scsaacguaaCfGfAfuuucaugaasa(invAb)(6-S)-X | 681 |
| AM07405-SS | $(Z)_3$-(TriAlk3)scsaacguaaCfGfAfuuucaugaasa(invAb)(6-S)-X | 682 |
| AM07406-SS | $(Z)_3$-(TriAlk6)scsaacguaaCfGfAfuuucaugaasa(invAb)(6-S)-X | 683 |
| AM07407-SS | $(Z)_3$-(TriAlk4)scsaacguaaCfGfAfuuucaugaasa(invAb)(6-S)-X | 684 |
| AM07408-SS | $(Z)_3$-(TriAlk5)scsaacguaaCfGfAfuuucaugaasa(invAb)(6-S)-X | 685 |
| AM07493-SS | Y-(NH-C6)scsaacguasaCfsGfAfsuusucaugaaas(invAb)(6-S)-X | 686 |
| AM07528-SS | Y-(NH-C6)scsaacguaaCfGfAfuusucsausgasaas(invAb)(6-S)-X | 687 |
| AM07530-SS | Y-(NH-C6)s(invAb)scaacuuguAfCfCfugaaaiccuus(invAb)(C6-S)-X | 688 |
| AM07532-SS | Y-(NH-C6)s(invAb)sacuuacacAfGfGfuggagcuaaas(invAb)(C6-S)-X | 689 |
| AM07534-SS | Y-(NH-C6)s(invAb)saggacauaGfUfAfucuuugacuus(invAb)(C6-S)-X | 690 |
| AM07536-SS | Y-(NH-C6)s(invAb)scugugucuGfAfGfaagaguaacus(invAb)(C6-S)-X | 691 |
| AM07538-SS | Y-(NH-C6)s(invAb)scuuccuauUfCfAfccaagcuaaas(invAb)(C6-S)-X | 692 |
| AM07540-SS | Y-(NH-C6)s(invAb)sccagcacaCfUfAfuuuacaagaus(invAb)(C6-S)-X | 693 |
| AM07542-SS | Y-(NH-C6)s(invAb)sgccccuauUfUfUfuaaaguacaas(invAb)(C6-S)-X | 694 |
| AM07544-SS | Y-(NH-C6)s(invAb)sgaguacacAfAfUfuguuuuaccus(invAb)(C6-S)-X | 695 |
| AM07546-SS | Y-(NH-C6)s(invAb)scaacugucCfAfUfacuaacaagus(invAb)(C6-S)-X | 696 |
| AM07548-SS | Y-(NH-C6)s(invAb)sgugguuauCfUfGfugaaaguugas(invAb)(C6-S)-X | 697 |
| AM07550-SS | Y-(NH-C6)s(invAb)sgaacuuagAfAfAfcggaaauggas(invAb)(C6-S)-X | 698 |
| AM07552-SS | Y-(NH-C6)s(invAb)sgauccgagCfAfGfuggagucauus(invAb)(C6-S)-X | 699 |
| AM07554-SS | Y-(NH-C6)s(invAb)scacauucuCfUfAfuguacuaugus(invAb)(C6-S)-X | 700 |
| AM07556-SS | Y-(NH-C6)s(invAb)sggucagugAfCfAfuguagguagas(invAb)(C6-S)-X | 701 |
| AM07558-SS | Y-(NH-C6)s(invAb)sgacacacaCfAfAfagcacauugas(invAb)(C6-S)-X | 702 |
| AM07560-SS | Y-(NH-C6)s(invAb)saccggauaGfAfCfuuauuiccaas(invAb)(C6-S)-X | 703 |
| AM07562-SS | Y-(NH-C6)s(invAb)sgaaguucuAfUfGfagaaauuccus(invAb)(C6-S)-X | 704 |
| AM07564-SS | Y-(NH-C6)s(invAb)sgguuacugAfCfGfuguaaaugcus(invAb)(C6-S)-X | 705 |
| AM07566-SS | Y-(NH-C6)s(invAb)sacguaacgAfUfUfucaugaacgus(invAb)(C6-S)-X | 706 |
| AM07568-SS | Y-(NH-C6)s(invAb)sguaacgauUfUfCfaugaacguuas(invAb)(C6-S)-X | 707 |
| AM07570-SS | Y-(NH-C6)s(invAb)sgaacgauuUfCfAfugaacguuaus(invAb)(C6-S)-X | 708 |
| AM07572-SS | Y-(NH-C6)s(invAb)sggagcuuaAfCfUfuuauaaggaas(invAb)(C6-S)-X | 709 |
| AM07619-SS | Y-(NH-C6)scsaa$^z$cgua$^z$aCfGfAfuuuca$^z$ugaa$^z$sa(invAb)(C6-S)-X | 710 |
| AM07621-SS | Y-(S-C6)scsaa$^z$cgua$^z$aCfGfAfuuuca$^z$ugaa$^z$sa(invAb)(C6-S)-X | 711 |
| AM07705-SS | $(Z)_3$-(TriAlk7)scsaacguaaCfGfAfuuucaugaasa(invAb)(6-S)-X | 712 |
| AM07706-SS | $(Z)_3$-(TriAlk8)scsaacguaaCfGfAfuuucaugaasa(invAb)(6-S)-X | 713 |
| AM07707-SS | $(Z)_3$-(TriAlk10)scsaacguaaCfGfAfuuucaugaasa(invAb)(6-S)-X | 714 |
| AM07708-SS | $(Z)_3$-(TriAlk11)scsaacguaaCfGfAfuuucaugaasa(invAb)(6-S)-X | 715 |
| AM07709-SS | $(Z)_3$-(TriAlk12)scsaacguaaCfGfAfuuucaugaasa(invAb)(6-S)-X | 716 |
| AM07710-SS | Y-(NH-C6)scsaacguaaCfGfAfuuuca$^z$ugaasa(invAb)(6-S)-X | 717 |
| AM07711-SS | Y-(NH-C6)scsaacgua$^z$aCfGfAfuuucaugaasa(invAb)(6-S)-X | 718 |
| AM07712-SS | Y-(NH-C6)scsaacgua$^z$aCfGfAfuuuca$^z$ugaasa(invAb)(6-S)-X | 719 |
| AM07713-SS | Y-(NH-C6)scsaa$^z$cgua$^z$aCfGfAfuuuca$^z$ugaa$^z$sa(invAb)(C6-NH2)-X | 720 |
| AM07721-SS | Y-(NH-C6)s(invAb)scacauucuCfUfAfuguacuaugus(invAb)(6-S)-X | 721 |
| AM07722-SS | Y-(NH-C6)s(invAb)sgacauucuCfUfAfuguacuaugus(invAb)(6-S)-X | 722 |

TABLE 4.3-continued

HIF-2 alpha RNAi Agent Sense Strand Sequences Showing Targeting Ligand and/or PK enhancer Positions (each X, Y and Z is independently a pharmacological moiety (for example, targeting ligand, targeting group, and/or PK enhancer); $(Z)_3$ = three Ligands linked (for example, a tridentate targeting group); u$^{z}$, a$^{z}$, g$^{z}$, and c$^{z}$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group.)

| Sense Strand ID: | Modified Sense Strand (5' → 3') | SEQ ID NO. |
|---|---|---|
| AM07724-SS | Y-(NH-C6)s(invAb)scgcauucuCfUfAfuguacuaugus(invAb)(6-S)-X | 723 |
| AM07726-SS | Y-(NH-C6)s(invAb)scccauucuCfUfAfuguacuaugus(invAb)(6-S)-X | 724 |
| AM07728-SS | Y-(NH-C6)s(invAb)sggcauucuCfUfAfuguacuaugus(invAb)(6-S)-X | 725 |
| AM07730-SS | Y-(NH-C6)s(invAb)scaca_2NuucuCfUfAfuguacuaugus(invAb)(6-S)-X | 726 |
| AM07731-SS | Y-(NH-C6)s(invAb)sccca_2NuucuCfUfAfuguacuaugus(invAb)(6-S)-X | 727 |
| AM07732-SS | Y-(NH-C6)s(invAb)sgcgaccAfUfGfaggagauucauus(invAb)(6-S)-X | 728 |
| AM07734-SS | Y-(NH-C6)s(invAb)scgcucaGfCfCfuaugaauucauus(invAb)(6-S)-X | 729 |
| AM07736-SS | Y-(NH-C6)s(invAb)scaaggucAfGfGfuaguaagugas(invAb)(6-S)-X | 730 |
| AM07738-SS | Y-(NH-C6)s(invAb)sgacugaauCfCfCfuguucaagcas(invAb)(6-S)-X | 731 |
| AM07740-SS | Y-(NH-C6)s(invAb)sucagugccAfUfGfacaaacaucus(invAb)(6-S)-X | 732 |
| AM07742-SS | Y-(NH-C6)s(invAb)sgcaccucaCfAfUfuugauguggas(invAb)(6-S)-X | 733 |
| AM07744-SS | Y-(NH-C6)s(invAb)sacacaacuGfUfCfcauacuaacas(invAb)(6-S)-X | 734 |
| AM07746-SS | Y-(NH-C6)s(invAb)sggcauaguAfUfCfuuugacuucas(invAb)(6-S)-X | 735 |
| AM07776-SS | Y-(NH-C6)s(invAb)sgaguacacAfAfUfuguuuuaccus(invAb)(6-S)-X | 736 |
| AM07777-SS | Y-(NH-C6)s(invAb)scuuccuauUfCfAfccaagcuaaas(invAb)(6-S)-X | 737 |
| AM07778-SS | Y-(NH-C6)s(invAb)sggucagugAfCfAfuguagguagas(invAb)(6-S)-X | 738 |
| AM07801-SS | $(Z)_3$-(TriAlk13)scsaacguaaCfGfAfuuucaugaasa(invAb)(6-S)-X | 739 |
| AM07813-SS | Y-(NH-C6)scsaa$^{z}$cgua$^{z}$aCfGfAfuuuca$^{z}$ugaa$^{z}$sa(invAb)(6-S)-X | 740 |
| AM07814-SS | Y-(S-C6)scsaa$^{z}$cgua$^{z}$aCfGfAfuuuca$^{z}$ugaa$^{z}$sa(invAb)(6-S)-X | 741 |
| AM07817-SS | Y-(NH-C6)scsa$^{z}$a$^{z}$cgu$^{z}$a$^{z}$aCfGfAfuuuca$^{z}$u$^{z}$ga$^{z}$a$^{z}$sa(invAb)(6-S)-X | 742 |
| AM07818-SS | Y-(S-C6)scsaacguaaCfGfAfuuucaugaasa(invAb)(6-S)-X | 743 |
| AM07822-SS | Y-(NH-C6)scsaacgua$^{z}$aCfGfAfuuuca$^{z}$ugaa$^{z}$sa(invAb)(6-S)-X | 744 |
| AM07823-SS | Y-(NH-C6)scsaa$^{z}$cguaaCfGfAfuuuca$^{z}$ugaa$^{z}$sa(invAb)(6-S)-X | 745 |
| AM07824-SS | Y-(NH-C6)scsaa$^{z}$cgua$^{z}$aCfGfAfuuucaugaa$^{z}$sa(invAb)(6-S)-X | 746 |
| AM07825-SS | Y-(NH-C6)scsaa$^{z}$cgua$^{z}$aCfGfAfuuuca$^{z}$ugaasa(invAb)(6-S)-X | 747 |
| AM07826-SS | Y-(NH-C6)scsaa$^{z}$cgua$^{z}$aCfGfAfuuucaugaasa(invAb)(6-S)-X | 748 |
| AM07827-SS | Y-(NH-C6)scsaacguaaCfGfAfuuuca$^{z}$ugaa$^{z}$sa(invAb)(6-S)-X | 749 |
| AM07828-SS | Y-(NH-C6)scsaa$^{z}$cguaaCfGfAfuuucaugaa$^{z}$sa(invAb)(6-S)-X | 750 |
| AM07829-SS | Y-(NH-C6)scsaa$^{z}$cguaaCfGfAfuuuca$^{z}$ugaasa(invAb)(6-S)-X | 751 |
| AM07830-SS | Y-(NH-C6)scsaacgua$^{z}$aCfGfAfuuucaugaa$^{z}$sa(invAb)(6-S)-X | 752 |
| AM07831-SS | Y-(NH-C6)scsaacguaaCfGfAfuuucaugaa$^{z}$sa(invAb)(6-S)-X | 753 |
| AM07832-SS | Y-(NH-C6)scsaa$^{z}$cguaaCfGfAfuuucaugaasa(invAb)(6-S)-X | 754 |
| AM07833-SS | Y-(NH-C6)scsa$^{z}$a$^{z}$cguaaCfGfAfuuucauga$^{z}$a$^{z}$sa(invAb)(6-S)-X | 755 |
| AM07834-SS | Y-(NH-C6)scsaac$^{z}$guaa$^{z}$CfGfAfuuu$^{z}$caug$^{z}$aasa(invAb)(6-S)-X | 756 |
| AM07835-SS | Y-(NH-C6)scsaacg$^{z}$uaa$^{z}$CfGfAfu$^{z}$uuc$^{z}$augaasa(invAb)(6-S)-X | 757 |
| AM07836-SS | Y-(NH-C6)scsaacgua$^{z}$a$^{z}$CfGfAfu$^{z}$u$^{z}$ucaugaasa(invAb)(6-S)-X | 758 |
| AM07837-SS | Y-(NH-C6)scsa$^{z}$ac$^{z}$gu$^{z}$aa$^{z}$CfGfAfuuucaugaasa(invAb)(6-S)-X | 759 |
| AM07838-SS | Y-(NH-C6)scsa$^{z}$a$^{z}$c$^{z}$g$^{z}$uaaCfGfAfuuucaugaasa(invAb)(6-S)-X | 760 |
| AM07839-SS | Y-(NH-C6)scsaacguaaCfGfAfuuu$^{z}$ca$^{z}$ug$^{z}$aa$^{z}$sa(invAb)(6-S)-X | 761 |
| AM07840-SS | Y-(NH-C6)scsaacguaaCfGfAfuuucau$^{z}$g$^{z}$a$^{z}$a$^{z}$sa(invAb)(6-S)-X | 762 |
| AM07890-SS | Y-(NH-C6)s(invAb)sgcacaacuGfUfCfcauacuaacas(invAb)(6-S)-X | 763 |
| AM07892-SS | Y-(NH-C6)s(invAb)sccacaacuGfUfCfcauacuaacas(invAb)(6-S)-X | 764 |
| AM07894-SS | Y-(NH-C6)s(invAb)sggacaacuGfUfCfcauacuaacas(invAb)(6-S)-X | 765 |
| AM08018-SS | Y-(NH-C6)scsaacguaaCfGfAfuuuca$^{z}$u$^{z}$ga$^{z}$a$^{z}$sa(invAb)(6-S)-X | 766 |
| AM08019-SS | Y-(NH-C6)scsaac$^{z}$guaa$^{z}$CfGfAfuuu$^{z}$ca$^{z}$ug$^{z}$aa$^{z}$sa(invAb)(6-S)-X | 767 |
| AM08020-SS | Y-(NH-C6)scsaacguaaCfGfAfuuucaug$^{z}$aasa(invAb)(6-S)-X | 768 |
| AM08021-SS | Y-(NH-C6)scsaacguaaCfGfAfuuuca$^{z}$u$^{z}$g$^{z}$a$^{z}$asa(invAb)(6-S)-X | 769 |
| AM08022-SS | Y-(NH-C6)scsaacguaaCfGfAfuuuc$^{z}$a$^{z}$u$^{z}$g$^{z}$aasa(invAb)(6-S)-X | 770 |
| AM08023-SS | Y-(NH-C6)scsaacguaaCfGfAfuuu$^{z}$c$^{z}$a$^{z}$u$^{z}$gaasa(invAb)(6-S)-X | 771 |
| AM08024-SS | Y-(NH-C6)scsaacguaaCfGfAfuu$^{z}$u$^{z}$c$^{z}$a$^{z}$ugaasa(invAb)(6-S)-X | 772 |
| AM08025-SS | Y-(NH-C6)scsaacguaaCfGfAfu$^{z}$u$^{z}$u$^{z}$c$^{z}$augaasa(invAb)(6-S)-X | 773 |
| AM08026-SS | Y-(NH-C6)scsaacguaaCfGfAfu$^{z}$uu$^{z}$ca$^{z}$ug$^{z}$aa$^{z}$sa(invAb)(6-S)-X | 774 |
| AM08027-SS | Y-(NH-C6)scsaacguaaCfGfAfuuuca$^{z}$ug$^{z}$aa$^{z}$sa(invAb)(6-S)-X | 775 |
| AM08028-SS | Y-(NH-C6)scsaacguaaCfGfAfuuu$^{z}$caug$^{z}$aa$^{z}$sa(invAb)(6-S)-X | 776 |
| AM08029-SS | Y-(NH-C6)scsaacguaaCfGfAfuuu$^{z}$ca$^{z}$ugaa$^{z}$sa(invAb)(6-S)-X | 777 |
| AM08030-SS | Y-(NH-C6)scsaacguaaCfGfAfuuu$^{z}$ca$^{z}$ug$^{z}$aasa(invAb)(6-S)-X | 778 |
| AM08031-SS | Y-(NH-C6)scsaacguaaCfGfAfuuucaug$^{z}$a$^{z}$a$^{z}$sa(invAb)(6-S)-X | 779 |
| AM08032-SS | Y-(NH-C6)scsaacguaaCfGfAfuuucau$^{z}$ga$^{z}$a$^{z}$sa(invAb)(C6-S)-X | 780 |
| AM08033-SS | Y-(NH-C6)scsaacguaaCfGfAfuuucau$^{z}$g$^{z}$aa$^{z}$sa(invAb)(6-S)-X | 781 |
| AM08034-SS | Y-(NH-C6)scsaacguaaCfGfAfuuucau$^{z}$g$^{z}$a$^{z}$asa(invAb)(6-S)-X | 782 |
| AM08035-SS | Y-(NH-C6)scsaacguaa$^{z}$CfGfAfuuu$^{z}$caug$^{z}$aasa(invAb)(6-S)-X | 783 |
| AM08036-SS | Y-(NH-C6)scsaac$^{z}$guaaCfGfAfuuu$^{z}$caug$^{z}$aasa(invAb)(6-S)-X | 784 |
| AM08037-SS | Y-(NH-C6)scsaac$^{z}$guaa$^{z}$CfGfAfuuucaug$^{z}$aasa(invAb)(6-S)-X | 785 |
| AM08038-SS | Y-(NH-C6)scsaac$^{z}$guaa$^{z}$CfGfAfuuu$^{z}$caugaasa(invAb)(6-S)-X | 786 |
| AM08092-SS | Y-(NH-C6)scsaa$^{z}$cguaaCfGfAfuuucaugaasa(invAb)(C6-S)-X | 787 |
| AM08093-SS | Y-(NH-C6)scsaacguaaCfGfAfuuucaugaa$^{z}$sa(invAb)(C6-S)-X | 788 |
| AM08108-SS | $(Z)_3$-(TriAlk14)scsaacguaaCfGfAfuuuca$^{z}$u$^{z}$ga$^{z}$a$^{z}$sa(invAb)(C6-S)-X | 789 |
| AM08109-SS | $(Z)_3$-(TriAlk14)scsaacguaaCfGfAfuuucau$^{z}$ga$^{z}$a$^{z}$sa(invAb)(C6-S)-X | 790 |
| AM08110-SS | $(Z)_3$-(TriAlk14)scsaacguaaCfGfAfuuuca$^{z}$uga$^{z}$a$^{z}$sa(invAb)(C6-S)-X | 791 |

TABLE 4.3-continued

HIF-2 alpha RNAi Agent Sense Strand Sequences Showing Targeting Ligand and/or PK enhancer Positions (each X, Y and Z is independently a pharmacological moiety (for example, targeting ligand, targeting group, and/or PK enhancer); (Z)$_3$ = three Ligands linked (for example, a tridentate targeting group); u$^{z}$, a$^{z}$, g$^{z}$, and c$^{z}$ represent uridine, adenosine, guanosine and cytidine, respectively, with a pharmacological moiety (for example, targeting ligand, targeting group, and/or PK enhancer) linked to the 2' position of a nucleotide (which for the HIF-2 alpha RNAi agents disclosed in the Examples herein was completed by coupling to a 2'-O-propargyl group.)

| Sense Strand ID: | Modified Sense Strand (5' → 3') | SEQ ID NO. |
|---|---|---|
| AM08111-SS | (Z)$_3$-(TriAlk14)scsaacguaaCfGfAfuuuca$^{z}$u$^{z}$gaa$^{z}$sa(invAb)(C6-S)-X | 792 |
| AM08112-SS | (Z)$_3$-(TriAlk14)scsaacguaaCfGfAfuuuca$^{z}$u$^{z}$ga$^{z}$asa(invAb)(C6-S)-X | 793 |
| AM08113-SS | (Z)$_3$-(TriAlk14)scsaacguaaCfGfAfuuucauga$^{z}$a$^{z}$sa(invAb)(C6-S)-X | 794 |
| AM08114-SS | (Z)$_3$-(TriAlk14)scsaacguaaCfGfAfuuuca$^{z}$u$^{z}$gaasa(invAb)(C6-S)-X | 795 |
| AM08115-SS | (Z)$_3$-(TriAlk14)scsaacguaaCfGfAfuuucau$^{z}$ga$^{z}$asa(invAb)(C6-S)-X | 796 |
| AM08116-SS | (Z)$_3$-(TriAlk14)scsaacguaaCfGfAfuuuca$^{z}$uga$^{z}$asa(invAb)(C6-S)-X | 797 |
| AM08117-SS | (Z)$_3$-(TriAlk14)scsaacguaaCfGfAfuuucau$^{z}$gaa$^{z}$sa(invAb)(C6-S)-X | 798 |
| AM08118-SS | (Z)$_3$-(TriAlk14)scsaacguaaCfGfAfuuu$^{z}$caug$^{z}$aasa(invAb)(C6-S)-X | 799 |
| AM08119-SS | Y-(S-C6)scsaacguaaCfGfAfuuucaugaasa(invAb)(C6-NH)-X | 800 |
| AM08120-SS | Y-(S-C6)scsaacguaaCfGfAfuuu$^{z}$ca$^{z}$ug$^{z}$aa$^{z}$sa(invAb)(C6-NH)-X | 801 |
| AM08121-SS | Y-(S-C6)scsaacguaaCfGfAfuuuca$^{z}$u$^{z}$ga$^{z}$a$^{z}$sa(invAb)(C6-NH)-X | 802 |
| AM08122-SS | Y-(S-C6)scsa$^{z}$ac$^{z}$gu$^{z}$aa$^{z}$CfGfAfuuucaugaasa(invAb)(C6-NH)-X | 803 |
| AM08123-SS | Y-(S-C6)scsa$^{z}$a$^{z}$cg$^{z}$u$^{z}$aaCfGfAfuuucaugaasa(invAb)(C6-NH)-X | 804 |
| AM08124-SS | (Z)$_3$-(TriAlk14)s(invAb)scacauucuCfUfAfuguacuaugus(invAb)(C6-S)-X | 805 |
| AM08125-SS | (Z)$_3$-(TriAlk14)s(invAb)scacauucuCfUfAfugu$^{z}$ac$^{z}$ua$^{z}$ug$^{z}$us(invAb)(C6-S)-X | 806 |
| AM08126-SS | (Z)$_3$-(TriAlk14)s(invAb)sca$^{z}$ca$^{z}$uu$^{z}$cu$^{z}$CfUfAfuguacuaugus(invAb)(C6-S)-X | 807 |
| AM08127-SS | (Z)$_3$-(TriAlk14)s(invAb)scacauucuCfUfAfuguac$^{z}$u$^{z}$au$^{z}$g$^{z}$us(invAb)(C6-S)-X | 808 |
| AM08128-SS | (Z)$_3$-(TriAlk14)s(invAb)sacacaacuGfUfCfcauacuaacas(invAb)(C6-S)-X | 809 |
| AM08129-SS | (Z)$_3$-(TriAlk14)s(invAb)sacacaacuGfUfCfcau$^{z}$ac$^{z}$ua$^{z}$ac$^{z}$as(invAb)(C6-S)-X | 810 |
| AM08130-SS | (Z)$_3$-(TriAlk14)s(invAb)sac$^{z}$ac$^{z}$aa$^{z}$cu$^{z}$GfUfCfcauacuaacas(invAb)(C6-S)-X | 811 |
| AM08131-SS | (Z)$_3$-(TriAlk14)s(invAb)sacacaacuGfUfCfcauac$^{z}$u$^{z}$aa$^{z}$c$^{z}$as(invAb)(C6-S)-X | 812 |
| AM08132-SS | (Z)$_3$-(TriAlk14)scsaacguaaCfGfAfuuucaug$^{z}$aa$^{z}$sa(invAb)(C6-S)-X | 813 |
| AM08133-SS | (Z)$_3$-(TriAlk14)scsaacguaaCfGfAfuuuca$^{z}$ug$^{z}$aasa(invAb)(C6-S)-X | 814 |
| AM08134-SS | (Z)$_3$-(TriAlk14)scsaacguaaCfGfAfuuu$^{z}$ca$^{z}$ugaasa(invAb)(C6-S)-X | 815 |
| AM08135-SS | (Z)$_3$-(TriAlk14)scsaacguaaCfGfAfuuu$^{z}$caugaa$^{z}$sa(invAb)(C6-S)-X | 816 |
| AM08233-SS | (Z)$_3$-(TriAlk14)scsaacguaaCfGfAfuuuAlkcaAlkugAlkaaAlksa(invAb)-X | 817 |
| AM08234-SS | (Z)$_3$-(TriAlk14)scsaacguaaCfGfAfuuuAlkcaAlkugAlkaaAlksa(invAb)-X | 818 |
| AM08372-SS | (Z)$_3$-(TriAlk14)scsaacguaaCfGfAfuuuAlkcaAlkugAlkaaAlksa(invAb)-X | 819 |
| AM08394-SS | (Z)$_3$-(TriAlk14)scsaacguaaCfGfAfuuuAlkcaAlkugAlkaaAlksa(invAb)-X | 820 |
| AM08395-SS | (Z)$_3$-(TriAlk14)scsaacguaaCfGfAfuuuAlkcaAlkugAlkaaAlksa(invAb)-X | 821 |
| AM08396-SS | (Z)$_3$-(TriAlk14)scsaacguaaCfGfAfuuuAlkcaAlkugAlkaaAlksas(invAb)-X | 822 |
| AM08397-SS | (Z)$_3$-(TriAlk14)scsasacguaaCfGfAfuuuAlkcaAlkugAlkaaAlksas(invAb)-X | 823 |
| AM08398-SS | (Z)$_3$-(TriAlk14)s(invAb)scsasacguaaCfGfAfuuuAlkcaAlkugAlkaaAlksas(invAb)-X | 824 |
| AM08399-SS | (Z)$_3$-(TriAlk14)scsasacguaaCfGfAfuuuAlkcaAlkugAlkaaAlksas(invAb)-X | 825 |
| AM10024-SS | (Z)$_3$-(NH2-C6)scsaacguaaCfGfAfuuucaugaasa(invAb)(C6-S)-X | 826 |

The HIF-2 alpha RNAi agents described herein are formed by annealing an antisense strand with a sense strand. A sense strand containing a sequence listed in Table 2 or Table 4 (or 4.1, 4.2, or 4.3) can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of a HIF-2 alpha RNAi agent disclosed herein differs by 0, 1, 2, or 3 nucleotides from any of the antisense strand sequences in Table 3. In some embodiments, the sense strand of a HIF-2 alpha RNAi agent disclosed herein differs by 0, 1, 2, or 3 nucleotides from any of the sense strand sequences in Table 4.

In some embodiments, a HIF-2 alpha RNAi agent antisense strand comprises a nucleotide sequence of any of the sequences in Table 2 or Table 3. In some embodiments, a HIF-2 alpha RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2 or Table 3. In certain embodiments, a HIF-2 alpha RNAi agent antisense strand comprises or consists of a modified sequence of any one of the modified sequences in Table 3.

In some embodiments, a HIF-2 alpha RNAi agent sense strand comprises the nucleotide sequence of any of the sequences in Table 2 or Table 4 (or Table 4.1, 4.2, or 4.3). In some embodiments, a HIF-2 alpha RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24 of any of the sequences in Table 2 or Table 4 (or Table 4.1, 4.2, or 4.3). In certain embodiments, a HIF-2 alpha RNAi agent sense strand comprises or consists of a modified sequence of any one of the modified sequences in Table 4 (or Table 4.1, 4.2, or 4.3).

For the HIF-2 alpha RNAi agents disclosed herein, the nucleotide at position 1 of the antisense strand (from 5' end→3' end) can be perfectly complementary to a HIF-2 alpha gene, or can be non-complementary to a HIF-2 alpha gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

In some embodiments, a HIF-2 alpha RNAi agent antisense strand comprises the sequence of nucleotides (from 5' end→3' end) 2-18 or 2-19 of any of the antisense strand sequences in Table 2 or Table 3. In some embodiments, a HIF-2 alpha RNAi sense strand comprises the sequence of nucleotides (from 5' end→3' end) 1-17 or 1-18 of any of the sense strand sequences in Table 2 or Table 4 (or Table 4.1, 4.2, or 4.3).

In some embodiments, a HIF-2 alpha RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4 (or Table 4.1, 4.2, or 4.3).

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the HIF-2 alpha RNAi agent has a sense strand consisting of the modified sequence of any of the modified sequences in Table 4 (or Table 4.1, 4.2, or 4.3), and an antisense strand consisting of the modified sequence of any of the modified sequences in Table 3. Certain representative sequence pairings are exemplified by the Duplex ID Nos. shown in Table 5.

In some embodiments, a HIF-2 alpha RNAi agent comprises, consists of, or consists essentially of a duplex represented by any one of the Duplex ID Nos. presented herein. In some embodiments, a HIF-2 alpha RNAi agent comprises the sense strand and antisense strand nucleotide sequences of any of the duplexes represented by any of the Duplex ID Nos. presented herein. In some embodiments, a HIF-2 alpha RNAi agent comprises the sense strand and antisense strand nucleotide sequences of any of the duplexes represented by any of the Duplex ID Nos. presented herein and a targeting ligand, targeting group, and/or linking group wherein the targeting ligand, targeting group, and/or linking group is covalently linked (conjugated) to the sense strand or the antisense strand. In some embodiments, a HIF-2 alpha RNAi agent includes the sense strand and antisense strand modified nucleotide sequences of any of the Duplex ID Nos. presented herein. In some embodiments, a HIF-2 alpha RNAi agent comprises the sense strand and antisense strand modified nucleotide sequences of any of the Duplex ID Nos. presented herein and a targeting ligand, targeting group, and/or linking group, wherein the targeting ligand, targeting group, and/or linking group is covalently linked to the sense strand or the antisense strand.

In some embodiments, a HIF-2 alpha RNAi agent comprises an antisense strand and a sense strand having the nucleotide sequences of any of the antisense strand/sense strand duplexes of Table 2 or Table 5, and further comprises a targeting group. In some embodiments, a HIF-2 alpha RNAi agent comprises an antisense strand and a sense strand having the nucleotide sequences of any of the antisense strand/sense strand duplexes of Table 5, and further comprises an integrin receptor ligand targeting group.

In some embodiments, a HIF-2 alpha RNAi agent comprises an antisense strand and a sense strand having the nucleotide sequences of any of the antisense strand/sense strand duplexes of Table 5, and further comprises one or more linking groups selected from the group consisting of (NH2-C6), (C6-NH2), (C6-SS-C6), (6-SS-6), (TriAlk1), (TriAlk1)s, (TriAlk2), (TriAlk2)s, (TriAlk3), (TriAlk3)s, (TriAlk4), (TriAlk4)s, (TriAlk5), (TriAlk5)s, (TriAlk6), (TriAlk6)s, (TriAlk7), (TriAlk7)s, (TriAlk8), (TriAlk8)s, (TriAlk9), (TriAlk9)s, (TriAlk10), (TriAlk10)s, (TriAlk11), (TriAlk11)s, (TriAlk12), (TriAlk12)s, (TriAlk13), (TriAlk13)s, (TriAlk14), or (TriAlk14)s, each as defined in Table 7.

In some embodiments, a HIF-2 alpha RNAi agent comprises an antisense strand and a sense strand having the modified nucleotide sequence of any of the antisense strand and/or sense strand nucleotide sequences in Table 3 or Table 4, 4.1, 4.2, or 4.3.

In some embodiments, a HIF-2 alpha RNAi agent comprises an antisense strand and a sense strand having a modified nucleotide sequence of any of the antisense strand and/or sense strand nucleotide sequences of any of the duplexes Table 5, and further comprises an integrin targeting group.

In some embodiments, a HIF-2 alpha RNAi agent comprises, consists of, or consists essentially of any of the duplexes of Table 5.

TABLE 5

HIF-2 alpha RNAi Agents Duplexes with Corresponding Sense and Antisense Strand ID Numbers

| Duplex ID | Antisense Strand ID | Sense Strand ID |
|---|---|---|
| AD04169 | AM03465-AS | AM05339-SS |
| AD04545 | AM05815-AS | AM05814-SS |
| AD04546 | AM05815-AS | AM05816-SS |
| AD04999 | AM06491-AS | AM06490-SS |
| AD05000 | AM06493-AS | AM06492-SS |
| AD05001 | AM06495-AS | AM06494-SS |
| AD05002 | AM06497-AS | AM06496-SS |
| AD05003 | AM06499-AS | AM06498-SS |
| AD05004 | AM06501-AS | AM06500-SS |
| AD05005 | AM06503-AS | AM06502-SS |
| AD05006 | AM06505-AS | AM06504-SS |
| AD05018 | AM06525-AS | AM06524-SS |
| AD05019 | AM06527-AS | AM06526-SS |
| AD05020 | AM06529-AS | AM06528-SS |
| AD05021 | AM06531-AS | AM06530-SS |
| AD05022 | AM06533-AS | AM06532-SS |
| AD05023 | AM06535-AS | AM06534-SS |
| AD05024 | AM06537-AS | AM06536-SS |
| AD05025 | AM06539-AS | AM06538-SS |
| AD05034 | AM06551-AS | AM06550-SS |
| AD05035 | AM06553-AS | AM06552-SS |
| AD05036 | AM06555-AS | AM06554-SS |
| AD05037 | AM06557-AS | AM06556-SS |
| AD05038 | AM06559-AS | AM06558-SS |
| AD05039 | AM06561-AS | AM06560-SS |
| AD05040 | AM06563-AS | AM06562-SS |
| AD05041 | AM06565-AS | AM06564-SS |
| AD05042 | AM06567-AS | AM06566-SS |
| AD05043 | AM06569-AS | AM06568-SS |
| AD05224 | AM06878-AS | AM06877-SS |
| AD05225 | AM06880-AS | AM06879-SS |
| AD05226 | AM06882-AS | AM06881-SS |
| AD05227 | AM06884-AS | AM06883-SS |
| AD05228 | AM06886-AS | AM06885-SS |
| AD05229 | AM06888-AS | AM06887-SS |
| AD05230 | AM06890-AS | AM06889-SS |
| AD05231 | AM06892-AS | AM06891-SS |
| AD05232 | AM06894-AS | AM06893-SS |
| AD05233 | AM06896-AS | AM06895-SS |
| AD05234 | AM06898-AS | AM06897-SS |
| AD05235 | AM06900-AS | AM06899-SS |
| AD05236 | AM06902-AS | AM06901-SS |
| AD05237 | AM06904-AS | AM06903-SS |
| AD05238 | AM06906-AS | AM06905-SS |
| AD05295 | AM06982-AS | AM06981-SS |
| AD05296 | AM06982-AS | AM06983-SS |
| AD05297 | AM06985-AS | AM06984-SS |
| AD05298 | AM06982-AS | AM06986-SS |
| AD05351 | AM05815-AS | AM07071-SS |
| AD05403 | AM05815-AS | AM07138-SS |
| AD05404 | AM07140-AS | AM07139-SS |

TABLE 5-continued

HIF-2 alpha RNAi Agents Duplexes with Corresponding Sense and Antisense Strand ID Numbers

| Duplex ID | Antisense Strand ID | Sense Strand ID |
|---|---|---|
| AD05405 | AM07140-AS | AM07141-SS |
| AD05406 | AM07143-AS | AM07142-SS |
| AD05407 | AM07144-AS | AM07142-SS |
| AD05408 | AM07143-AS | AM07145-SS |
| AD05409 | AM07143-AS | AM07146-SS |
| AD05479 | AM05815-AS | AM07224-SS |
| AD05480 | AM05815-AS | AM07225-SS |
| AD05481 | AM07140-AS | AM07226-SS |
| AD05482 | AM07140-AS | AM07227-SS |
| AD05483 | AM07143-AS | AM07228-SS |
| AD05484 | AM07144-AS | AM07228-SS |
| AD05485 | AM07143-AS | AM07229-SS |
| AD05486 | AM07143-AS | AM07230-SS |
| AD05507 | AM05815-AS | AM07268-SS |
| AD05508 | AM05815-AS | AM07269-SS |
| AD05509 | AM05815-AS | AM07270-SS |
| AD05510 | AM05815-AS | AM07271-SS |
| AD05511 | AM05815-AS | AM07272-SS |
| AD05512 | AM05815-AS | AM07273-SS |
| AD05513 | AM05815-AS | AM07274-SS |
| AD05514 | AM05815-AS | AM07275-SS |
| AD05527 | AM05815-AS | AM07301-SS |
| AD05528 | AM05815-AS | AM07302-SS |
| AD05529 | AM05815-AS | AM07303-SS |
| AD05530 | AM05815-AS | AM07304-SS |
| AD05531 | AM05815-AS | AM07305-SS |
| AD05532 | AM05815-AS | AM07306-SS |
| AD05533 | AM05815-AS | AM07307-SS |
| AD05534 | AM05815-AS | AM07308-SS |
| AD05551 | AM05815-AS | AM07231-SS |
| AD05614 | AM05815-AS | AM07403-SS |
| AD05615 | AM05815-AS | AM07404-SS |
| AD05616 | AM05815-AS | AM07405-SS |
| AD05617 | AM05815-AS | AM07406-SS |
| AD05620 | AM05815-AS | AM07407-SS |
| AD05621 | AM05815-AS | AM07408-SS |
| AD05681 | AM05815-AS | AM07493-SS |
| AD05716 | AM05815-AS | AM07528-SS |
| AD05718 | AM07531-AS | AM07530-SS |
| AD05719 | AM07533-AS | AM07532-SS |
| AD05720 | AM07535-AS | AM07534-SS |
| AD05721 | AM07537-AS | AM07536-SS |
| AD05722 | AM07539-AS | AM07538-SS |
| AD05723 | AM07541-AS | AM07540-SS |
| AD05724 | AM07543-AS | AM07542-SS |
| AD05725 | AM07545-AS | AM07544-SS |
| AD05726 | AM07547-AS | AM07546-SS |
| AD05727 | AM07549-AS | AM07548-SS |
| AD05728 | AM07551-AS | AM07550-SS |
| AD05729 | AM07553-AS | AM07552-SS |
| AD05730 | AM07555-AS | AM07554-SS |
| AD05731 | AM07557-AS | AM07556-SS |
| AD05732 | AM07559-AS | AM07558-SS |
| AD05733 | AM07561-AS | AM07560-SS |
| AD05734 | AM07563-AS | AM07562-SS |
| AD05735 | AM07565-AS | AM07564-SS |
| AD05736 | AM07567-AS | AM07566-SS |
| AD05737 | AM07569-AS | AM07568-SS |
| AD05738 | AM07571-AS | AM07570-SS |
| AD05739 | AM07573-AS | AM07572-SS |
| AD05759 | AM07596-AS | AM05816-SS |
| AD05760 | AM07597-AS | AM05816-SS |
| AD05770 | AM07603-AS | AM05816-SS |
| AD05786 | AM05815-AS | AM07619-SS |
| AD05788 | AM05815-AS | AM07621-SS |
| AD05856 | AM05815-AS | AM07705-SS |
| AD05857 | AM05815-AS | AM07706-SS |
| AD05858 | AM05815-AS | AM07707-SS |
| AD05859 | AM05815-AS | AM07708-SS |
| AD05860 | AM05815-AS | AM07709-SS |
| AD05861 | AM07555-AS | AM07721-SS |
| AD05862 | AM07723-AS | AM07722-SS |
| AD05863 | AM07725-AS | AM07724-SS |
| AD05864 | AM07727-AS | AM07726-SS |

TABLE 5-continued

HIF-2 alpha RNAi Agents Duplexes with Corresponding Sense and Antisense Strand ID Numbers

| Duplex ID | Antisense Strand ID | Sense Strand ID |
|---|---|---|
| AD05865 | AM07729-AS | AM07728-SS |
| AD05866 | AM07555-AS | AM07730-SS |
| AD05867 | AM07727-AS | AM07731-SS |
| AD05868 | AM07733-AS | AM07732-SS |
| AD05869 | AM07735-AS | AM07734-SS |
| AD05870 | AM07737-AS | AM07736-SS |
| AD05871 | AM07739-AS | AM07738-SS |
| AD05872 | AM07741-AS | AM07740-SS |
| AD05873 | AM07743-AS | AM07742-SS |
| AD05874 | AM07745-AS | AM07744-SS |
| AD05875 | AM07747-AS | AM07746-SS |
| AD05899 | AM07545-AS | AM07776-SS |
| AD05900 | AM07539-AS | AM07777-SS |
| AD05901 | AM07557-AS | AM07778-SS |
| AD05915 | AM05815-AS | AM07710-SS |
| AD05916 | AM05815-AS | AM07711-SS |
| AD05917 | AM05815-AS | AM07712-SS |
| AD05918 | AM05815-AS | AM07713-SS |
| AD05919 | AM05815-AS | AM07801-SS |
| AD05930 | AM05815-AS | AM07813-SS |
| AD05932 | AM05815-AS | AM07817-SS |
| AD05933 | AM07199-AS | AM07224-SS |
| AD05934 | AM05815-AS | AM07814-SS |
| AD05935 | AM05815-AS | AM07816-SS |
| AD05936 | AM05815-AS | AM07818-SS |
| AD05954 | AM05815-AS | AM07822-SS |
| AD05955 | AM05815-AS | AM07823-SS |
| AD05956 | AM05815-AS | AM07824-SS |
| AD05957 | AM05815-AS | AM07825-SS |
| AD05958 | AM05815-AS | AM07826-SS |
| AD05959 | AM05815-AS | AM07827-SS |
| AD05960 | AM05815-AS | AM07828-SS |
| AD05961 | AM05815-AS | AM07829-SS |
| AD05962 | AM05815-AS | AM07830-SS |
| AD05963 | AM05815-AS | AM07831-SS |
| AD05964 | AM05815-AS | AM07832-SS |
| AD05965 | AM05815-AS | AM07833-SS |
| AD05966 | AM05815-AS | AM07834-SS |
| AD05967 | AM05815-AS | AM07835-SS |
| AD05968 | AM05815-AS | AM07836-SS |
| AD05969 | AM05815-AS | AM07837-SS |
| AD05970 | AM05815-AS | AM07838-SS |
| AD05971 | AM05815-AS | AM07839-SS |
| AD05972 | AM05815-AS | AM07840-SS |
| AD05979 | AM07891-AS | AM07890-SS |
| AD05980 | AM07893-AS | AM07892-SS |
| AD05981 | AM07895-AS | AM07894-SS |
| AD06056 | AM05815-AS | AM08018-SS |
| AD06057 | AM05815-AS | AM08019-SS |
| AD06058 | AM05815-AS | AM08020-SS |
| AD06059 | AM05815-AS | AM08021-SS |
| AD06060 | AM05815-AS | AM08022-SS |
| AD06061 | AM05815-AS | AM08023-SS |
| AD06062 | AM05815-AS | AM08024-SS |
| AD06063 | AM05815-AS | AM08025-SS |
| AD06064 | AM05815-AS | AM08026-SS |
| AD06065 | AM05815-AS | AM08027-SS |
| AD06066 | AM05815-AS | AM08028-SS |
| AD06067 | AM05815-AS | AM08029-SS |
| AD06068 | AM05815-AS | AM08030-SS |
| AD06069 | AM05815-AS | AM08031-SS |
| AD06070 | AM05815-AS | AM08032-SS |
| AD06071 | AM05815-AS | AM08033-SS |
| AD06072 | AM05815-AS | AM08034-SS |
| AD06073 | AM05815-AS | AM08035-SS |
| AD06074 | AM05815-AS | AM08036-SS |
| AD06075 | AM05815-AS | AM08037-SS |
| AD06076 | AM05815-AS | AM08038-SS |
| AD06113 | AM05815-AS | AM08092-SS |
| AD06114 | AM05815-AS | AM08093-SS |
| AD06129 | AM07199-AS | AM07839-SS |
| AD06136 | AM05815-AS | AM08108-SS |
| AD06137 | AM05815-AS | AM08109-SS |
| AD06138 | AM05815-AS | AM08110-SS |

TABLE 5-continued

| HIF-2 alpha RNAi Agents Duplexes with Corresponding Sense and Antisense Strand ID Numbers | | |
|---|---|---|
| Duplex ID | Antisense Strand ID | Sense Strand ID |
| AD06139 | AM05815-AS | AM08111-SS |
| AD06140 | AM05815-AS | AM08112-SS |
| AD06141 | AM05815-AS | AM08113-SS |
| AD06142 | AM05815-AS | AM08114-SS |
| AD06143 | AM05815-AS | AM08115-SS |
| AD06144 | AM05815-AS | AM08116-SS |
| AD06145 | AM05815-AS | AM08117-SS |
| AD06146 | AM05815-AS | AM08118-SS |
| AD06147 | AM05815-AS | AM08119-SS |
| AD06148 | AM05815-AS | AM08120-SS |
| AD06149 | AM05815-AS | AM08121-SS |
| AD06150 | AM05815-AS | AM08122-SS |
| AD06151 | AM05815-AS | AM08123-SS |
| AD06152 | AM07555-AS | AM08124-SS |
| AD06153 | AM07555-AS | AM08125-SS |
| AD06154 | AM07555-AS | AM08126-SS |
| AD06155 | AM07555-AS | AM08127-SS |
| AD06156 | AM07745-AS | AM08128-SS |
| AD06157 | AM07745-AS | AM08129-SS |
| AD06158 | AM07745-AS | AM08130-SS |
| AD06159 | AM07745-AS | AM08131-SS |
| AD06160 | AM05815-AS | AM08132-SS |
| AD06161 | AM05815-AS | AM08133-SS |
| AD06162 | AM05815-AS | AM08134-SS |
| AD06163 | AM05815-AS | AM08135-SS |
| AD06294 | AM05815-AS | AM08395-SS |
| AD06296 | AM05815-AS | AM08397-SS |
| AD06297 | AM05815-AS | AM08398-SS |
| AD06299 | AM08400-AS | AM08395-SS |
| AD07267 | AM05815-AS | AM10024-SS |

In some embodiments, a HIF-2 alpha RNAi agent, either before or after being optionally linked or conjugated to one or more targeting ligands, targeting groups, and/or PK enhancers, is prepared or provided as a salt, mixed salt, or a free-acid. The RNAi agents described herein, upon delivery to a cell expressing a HIF-2 alpha gene, inhibit or knockdown expression of one or more HIF-2 alpha genes in vivo and/or in vitro.

Targeting Ligands and Targeting Groups

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers. In some embodiments, a targeting group comprises an integrin targeting ligand.

In some embodiments, RNAi agents described herein are conjugated to targeting groups. In some embodiments, a targeting ligand enhances the ability of the RNAi agent to bind to a particular cell receptor on a cell of interest. In some embodiments, the targeting ligands conjugated to RNAi agents described herein have affinity for integrin receptors. In some embodiments, a suitable targeting ligand for use with the HIF-2 alpha RNAi agents disclosed herein has affinity for integrin alpha-v-beta 3, integrin alpha-v-beta-5, or both of these integrins.

In some embodiments, a HIF-2 alpha RNAi agent disclosed herein is linked to one or more integrin targeting ligands that include a compound of the formula:

(Formula I)

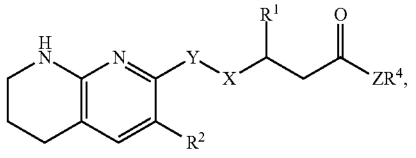

wherein,

X is $—C(R^3)_2—$, $—NR^3—$,

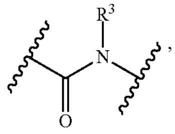,
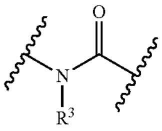, or

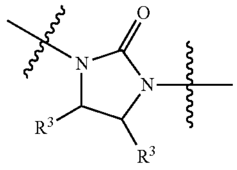;

Y is optionally substituted alkylene with 1 to 8 carbon atoms in the alkylene chain;

Z is O, $NR^3$, or S;

$R^1$ is optionally substituted aryl, optionally substituted heteroaryl, optionally substituted heterocyclyl, optionally substituted cycloalkyl or $R^1$ comprises the RNAi agent;

$R^2$ is H, optionally substituted alkyl, or $R^2$ comprises the RNAi agent; each instance of $R^3$ is independently selected from the group consisting of H and optionally substituted alkyl, or $R^3$ comprises the RNAi agent;

$R^4$ is H or optionally substituted alkyl; and wherein at least one of Y, $R^1$, $R^2$, any instance of $R^3$, and $R^4$ comprises the RNAi agent.

In some embodiments, a HIF-2 alpha RNAi agent disclosed herein is linked to one or more integrin targeting ligands that include one of the following structures:

(Structure 1a)
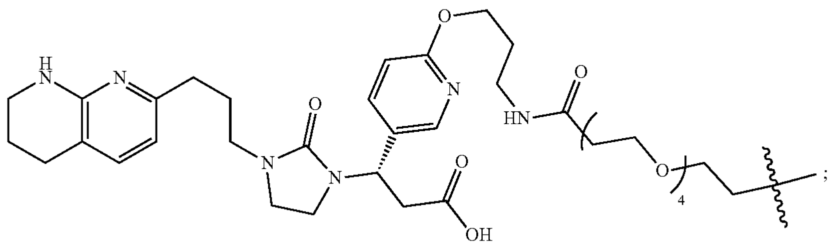
(Structure 2a)
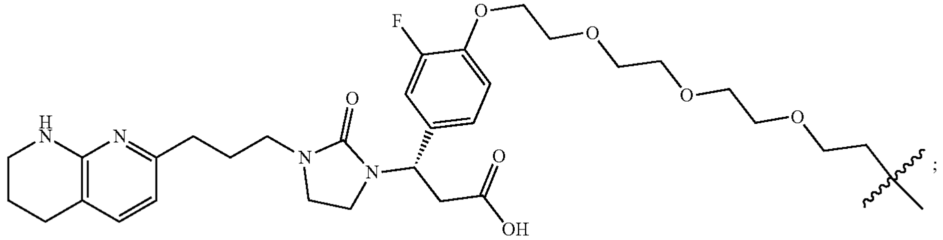
(Structure 2.1a)
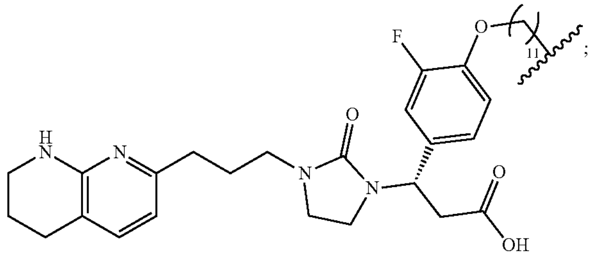
(Structure 2.2a)
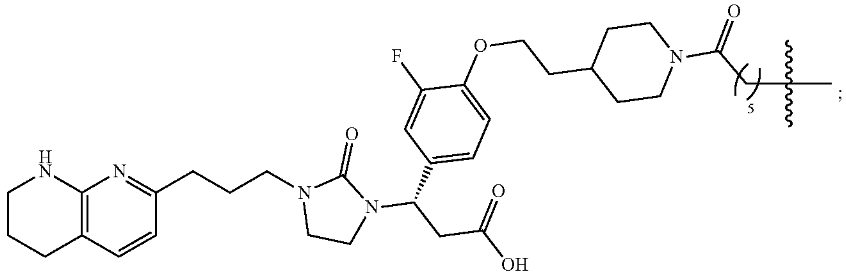
(Structure 2.3a)
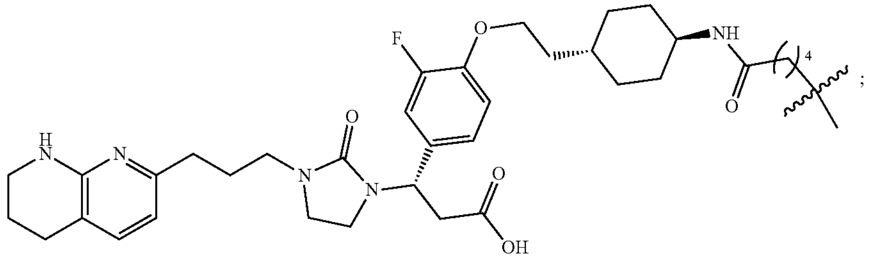
(Structure 2.4a)
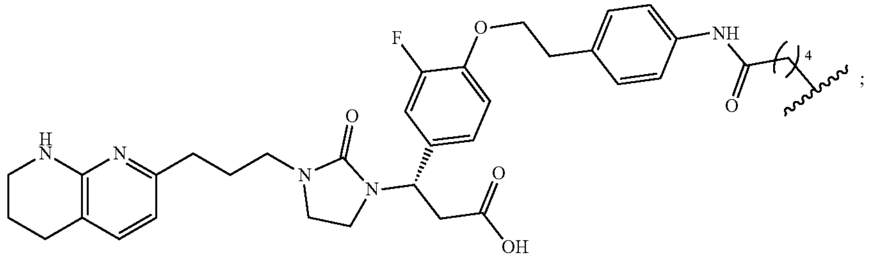

-continued
(Structure 2.5a)
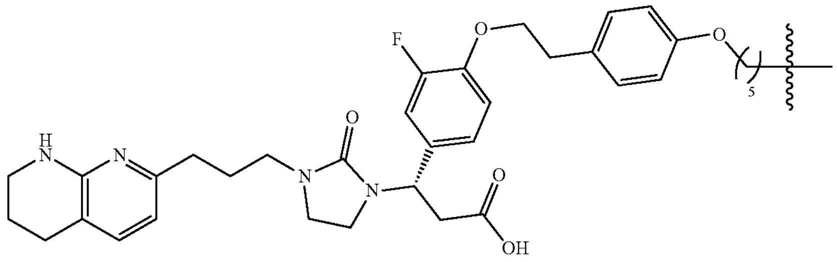
;
(Structure 2.6a)
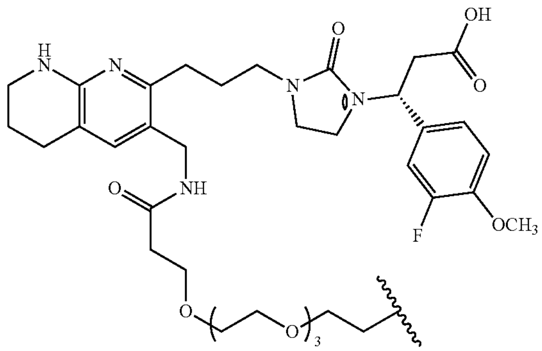
;
(Structure 2.7a)
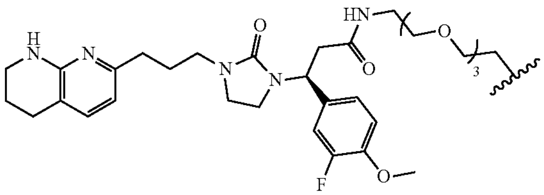
;
(Structure 2.8a)
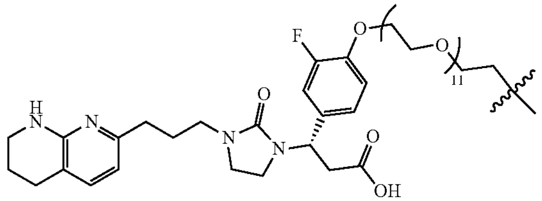
;
(Structure 2.9a)
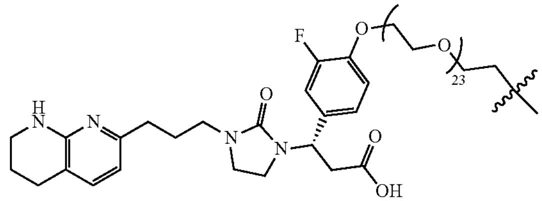
;
(Structure 2.10a)
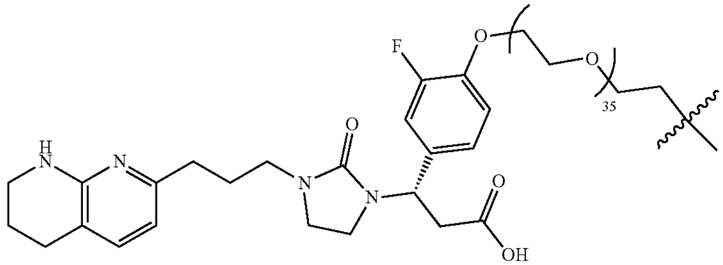
;
(Structure 2.11a)
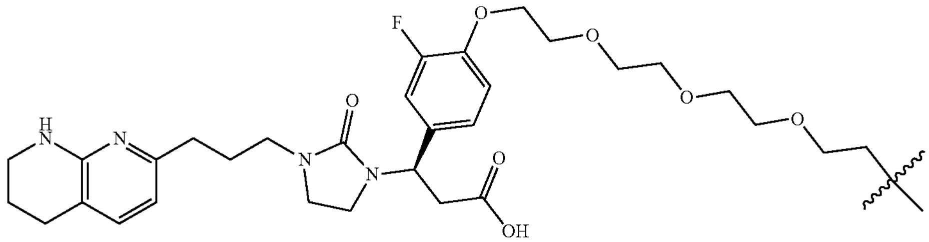
;

-continued
(Structure 28a)
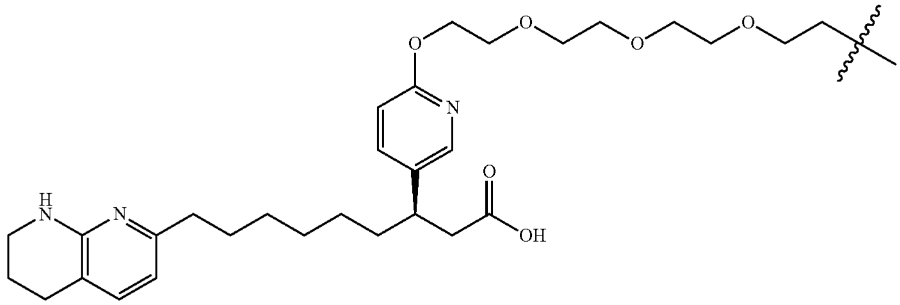
;
(Structure 29a)
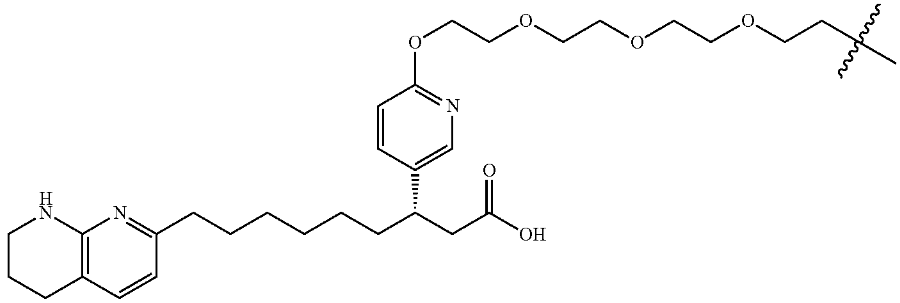
;
(Structure 30a)
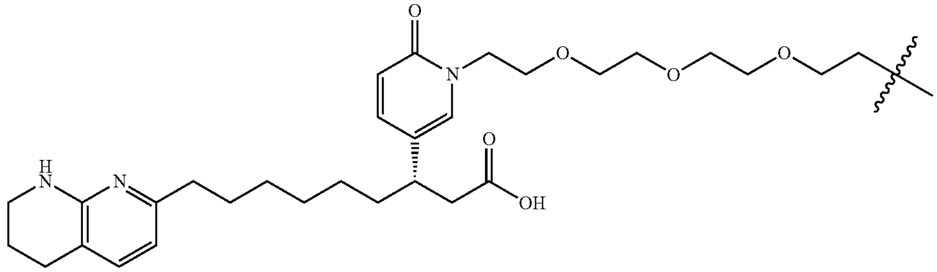
;
(Structure 31a)
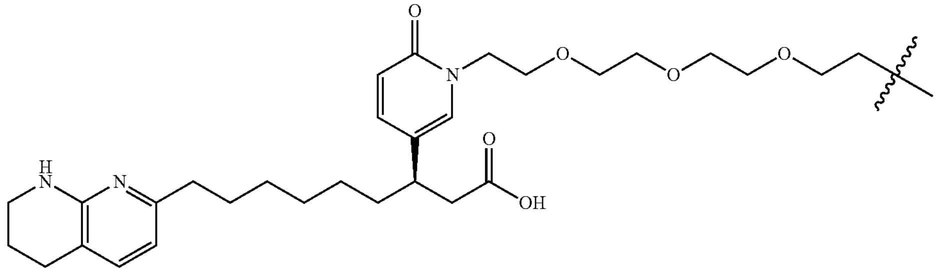
;

-continued
(Structure 32a)
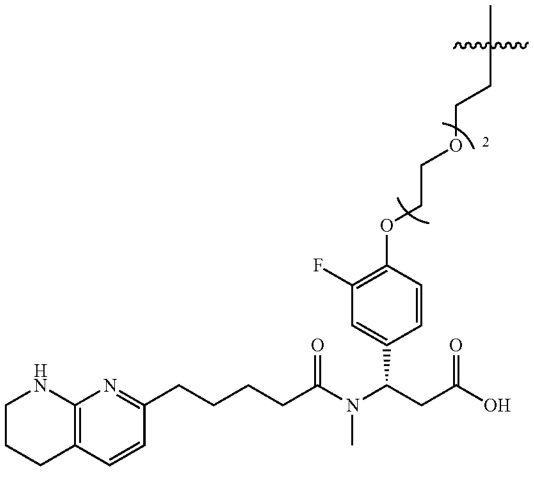
;
(Structure 33a)
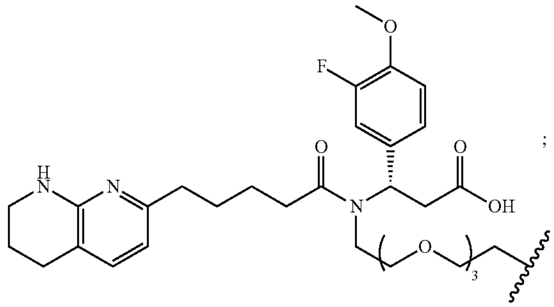
;
(Structure 34a)
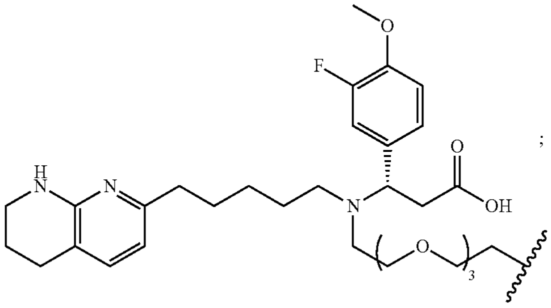
;
(Structure 36a)
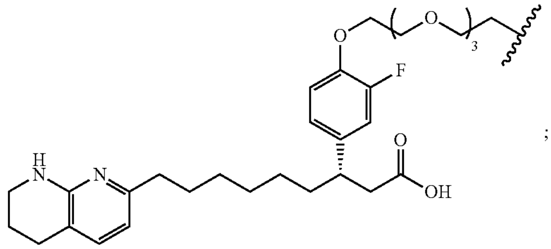
;
(Structure 37a)
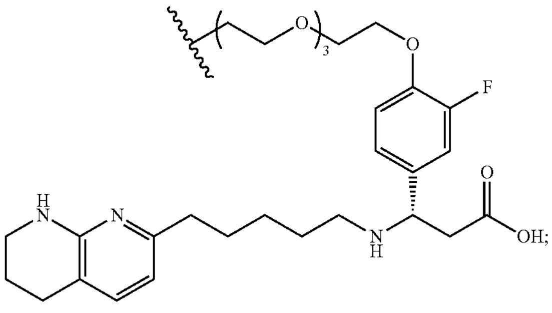
(Structure 38a)
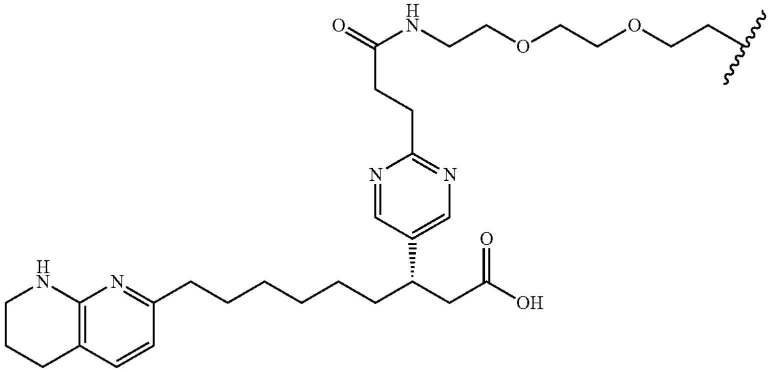
;

-continued (Structure 39a)

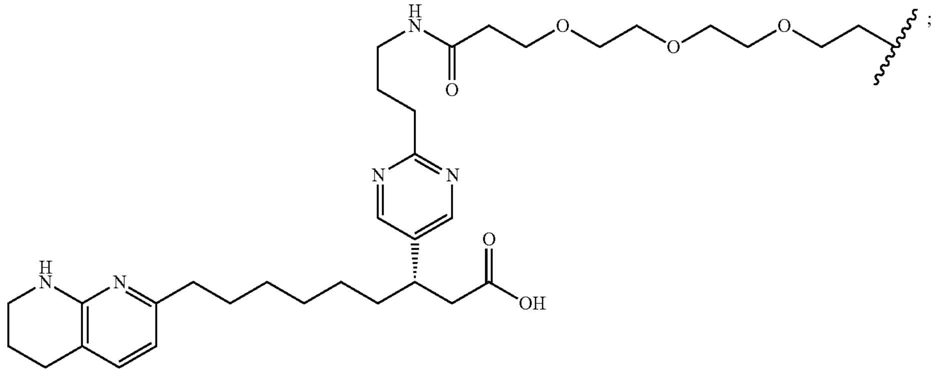

(Structure 40a)

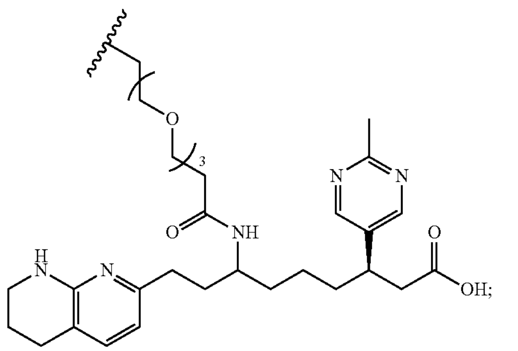

and (Structure 41a)

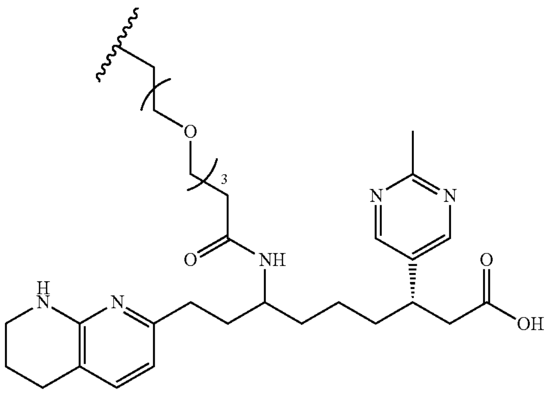

wherein  indicates the point of connection to a HIF-2 alpha RNAi agent

In some embodiments, targeting groups are conjugated to an RNAi agent using a "click" chemistry reaction. In some embodiments, RNAi agents are functionalized with one or more alkyne-containing groups, and targeting ligands include azide-containing groups. Upon reaction, azides and alkynes form triazoles. An example reaction scheme is shown below:

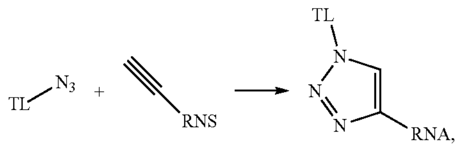

wherein TL comprises a targeting ligand, and RNA comprises an RNAi agent.

HIF-2 alpha RNAi agents may comprise more than one targeting ligand. In some embodiments, HIF-2 alpha RNAi agents comprise 1-20 targeting ligands. In some embodiments, HIF-2 alpha RNAi agents comprise from 1, 2, 3, 4, 5, 6, 7, 8, 9, 10, 11, 12, 13, 14, 15, 16, 17, 18, or 19 targeting ligands to 2, 3, 4, 5, 6, 7, 8, 9, 10, 11, 12, 13, 14, 15, 16, 17, 18, 19 or 20 targeting ligands.

In some embodiments, HIF-2 alpha RNAi agents comprise a targeting group, which includes 2 or more targeting ligands. In some embodiments, a targeting group may be conjugated at the 5' or 3' end of the sense strand of a HIF-2 alpha RNAi agent. In some embodiments, a targeting group may be conjugated to an internal nucleotide on a HIF-2 RNAi agent. In some embodiments, a targeting group may consist of two targeting ligands linked together, referred to as a "bidentate" targeting group. In some embodiments, a targeting group may consist of three targeting ligands linked together, referred to as a "tridentate" targeting group. In some embodiments, a targeting group may consist of four targeting ligands linked together, referred to as a "tetradentate" targeting group.

In some embodiments, HIF-2 alpha RNAi agents may comprise both a targeting group conjugated to the 3' or 5' end of the sense strand, and additionally targeting ligands conjugated to internal nucleotides. In some embodiments a tridentate targeting group is conjugated to the 5' end of the sense strand of a HIF-2 alpha RNAi agent, and at least one targeting ligand is conjugated to an internal nucleotide of the sense strand. In further embodiments, a tridentate targeting group is conjugated to the 5' end of the sense strand of a HIF-2 alpha RNAi agent, and four targeting ligands are conjugated to internal nucleotides of the sense strand. In some embodiments, the four targeting ligands are conjugated to the 2, 4, 6, and 8 nucleotide positions of the sense strand.

In some embodiments, the HIF-2 alpha RNAi agents are linked to one or more targeting groups of the following formula:

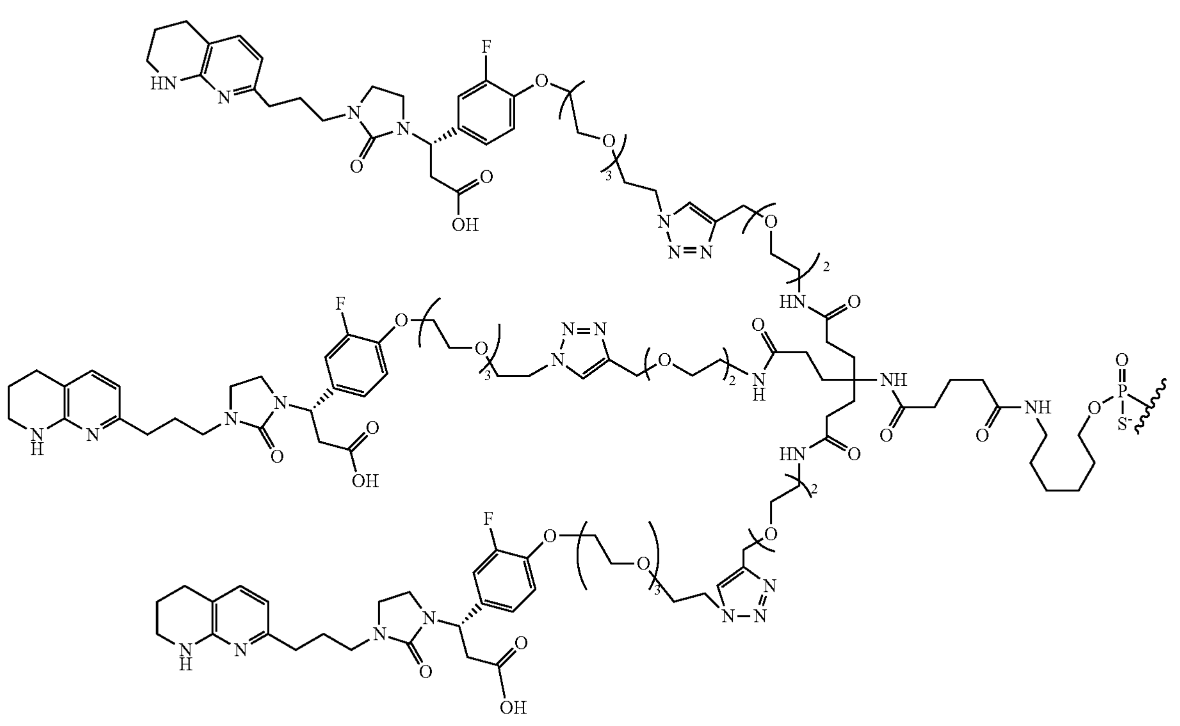

wherein ⌇ indicates the point of connection. In some embodiments the point of connection is the 5' end of the sense strand of a HIF-2 alpha RNAi agent.

Internally Linked Targeting Ligands

Some embodiments of HIF-2 alpha RNAi agents described herein include targeting ligands conjugated to internal nucleotides of the sense strand or antisense strand. In some embodiments, up to 15 targeting ligands may be conjugated to internal nucleotides of the sense strand of a HIF-2 alpha RNAi agent. In some embodiments, 1, 2, 3, 4, 5, 6, 7, 8, 9, 10, 11, 12, 13, 14, or 15 targeting ligands may be conjugated to internal nucleotides of the sense strand of a HIF-2 alpha RNAi agent. In some embodiments, 1 to 5 (for example, 1, 2, 3, 4, or 5) targeting ligands are conjugated to internal nucleotides of the sense strand of a HIF-2 alpha RNAi agent. In some embodiments, 3 to 4 targeting ligands are conjugated to internal nucleotides of the sense strand of a HIF-2 alpha RNAi agent.

In some embodiments, placement of internal targeting ligands may impact the efficacy or potency of a HIF-2 alpha RNAi agent. In some embodiments of HIF-2 alpha RNAi agents, a targeting group is conjugated to the 5' end of the sense strand, and at least 10 nucleotides are positioned between the tridentate targeting group located on the 5' end of the sense strand and the next closest targeting ligand located of the sense strand. In some embodiments, at least 5 nucleotides are positioned between the tridentate targeting group located on the 5' end of the sense strand and the next closest targeting ligand located of the sense strand.

In some embodiments where two or more targeting ligands are conjugated to internal nucleotides located of the sense strand of a HIF-2 alpha RNAi agent, there is a space of at least one nucleotide that is not conjugated to a targeting ligand positioned between two internal nucleotides that are conjugated to targeting ligands. In some embodiments where two or more targeting ligands are conjugated to the sense strand of a HIF-2 alpha RNAi agent, at least two nucleotides that are not conjugated to a targeting ligand are positioned between two internal nucleotides that are conjugated to targeting ligands.

In some embodiments, targeting ligands are conjugated to the 2, 4, and 6 nucleotides of the sense strand as numbered from 3' to 5', starting from the furthest 3' nucleotide that forms a base pair with the 5' terminal nucleotide on the antisense strand. In some embodiments, targeting ligands are conjugated to the 2, 4, 6 and 8 nucleotides (3'→5') from the 3' terminal nucleotide that forms a base pair with the 5' terminal nucleotide on the antisense strand.

Pharmacokinetic Enhancers

In some embodiments, a pharmacokinetic (PK) enhancer is linked to the HIF-2 alpha RNAi agents disclosed herein to facilitate the delivery of the RNAi agent to the desired cells or tissues. PK enhancing compounds can be synthetized having reactive groups, such as maleimide or azido groups, readily present to facilitate linkage to one or more linkers on the HIF-2 alpha RNAi agent. In some embodiments, PK enhancers may be synthesized as maleimides and conjugated to RNAi agents using reactions described herein. Other conjugation reactions such as “click” chemistry or amide conjugation may also be used.

In some embodiments, PK enhancers may include molecules that are fatty acids, lipids, albumin-binders, antibody-binders, polyesters, polyacrylates, poly-amino acids, and linear or branched polyethylene glycol (PEG) moieties having about 20-1000 ethylene oxide ($CH_2$—$CH_2$—O) units.

In some embodiments, a HIF-2 RNAi agent is linked to a PK enhancer that includes a compound having the structure of the following formula:

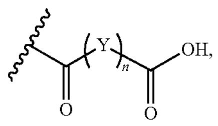

wherein Y is an optionally substituted saturated or unsaturated aliphatic chain, and n is an integer from 5-25.

In some embodiments, a HIF-2 RNAi agent is linked to a PK enhancer that includes a compound having the following structure:

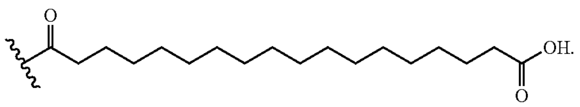 [SMILES: *C(=O)CCCCCCCCCCCCCCCCC(=O)O]

In some embodiments, a HIF-2 RNAi agent is linked to a PK enhancer that includes a compound having the following structure:

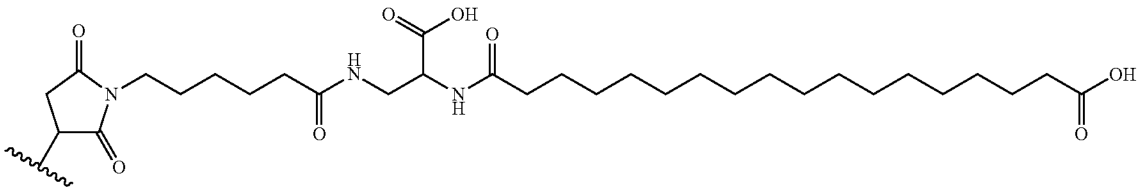 [SMILES: *C1CC(=O)N(CCCCCC(=O)NCC(NC(=O)CCCCCCCCCCCCCCCCC(=O)O)C(=O)O)C1=O]

Table 6, below, shows certain exemplary PK enhancing compounds that can be used as starting materials to link to the HIF-2 alpha RNAi agents disclosed herein. The PK enhancing compounds may be added to a HIF-2 alpha RNAi agent using any known method in the art.

TABLE 6

| Exemplary PK Enhancer Compounds Suitable for Linking to HIF-2 alpha RNAi Agents |
|---|
| 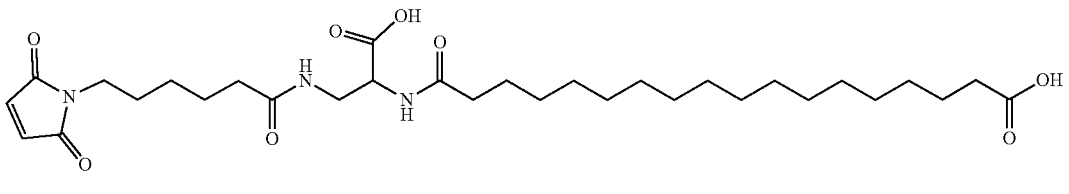 [SMILES: O=C(O)CCCCCCCCCCCCCCCCC(=O)NC(CNC(=O)CCCCCN1C(=O)C=CC1=O)C(=O)O] |
| Mal-$C_{18}$-diacid |
| 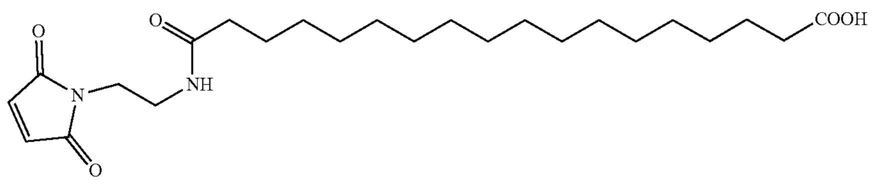 [SMILES: O=C(O)CCCCCCCCCCCCCCCCC(=O)NCCN1C(=O)C=CC1=O] |
| Mal-$C_{18}$-acid |

TABLE 6-continued
| Exemplary PK Enhancer Compounds Suitable for Linking to HIF-2 alpha RNAi Agents |
| --- |
| 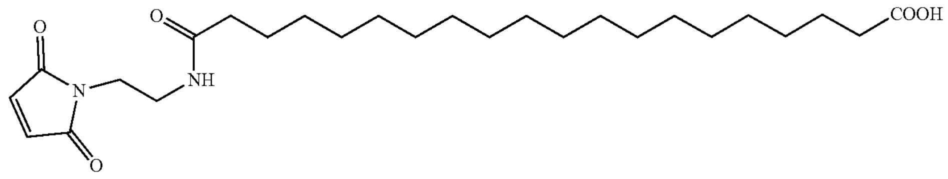 [SMILES: O=C(O)CCCCCCCCCCCCCCCCCCC(=O)NCCN1C(=O)C=CC1=O] |
| Mal-$C_{20}$-acid |
| 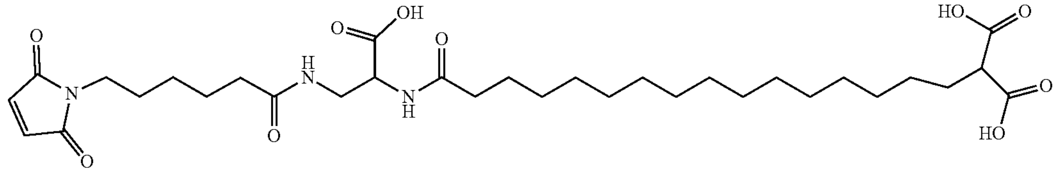 [SMILES: O=C(CCCCCN1C(=O)C=CC1=O)NCC(NC(=O)CCCCCCCCCCCCCCCC(C(=O)O)C(=O)O)C(=O)O] |
| Mal-$C_{18}$-triacid |
| 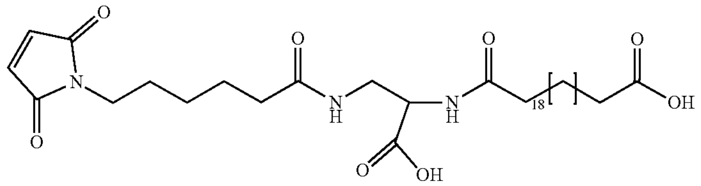 |
| Mal-$C_{22}$-diacid |
| 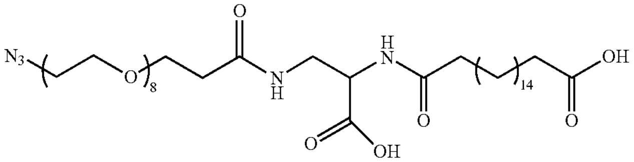 |
| $C_{18}$-diacid-$N_3$ |
| 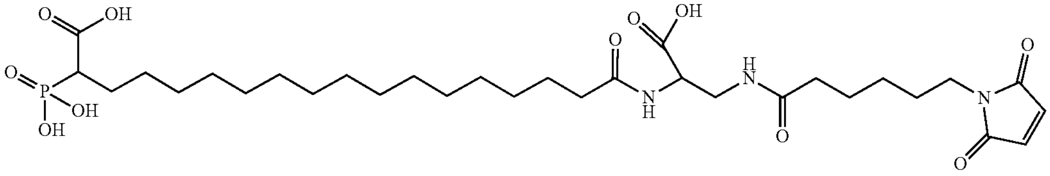 [SMILES: O=C(CCCCCN1C(=O)C=CC1=O)NCC(NC(=O)CCCCCCCCCCCCCCCC(C(=O)O)P(=O)(O)O)C(=O)O] |
| Mal-$C_{18}$-diacid-$PO_3$ |
| 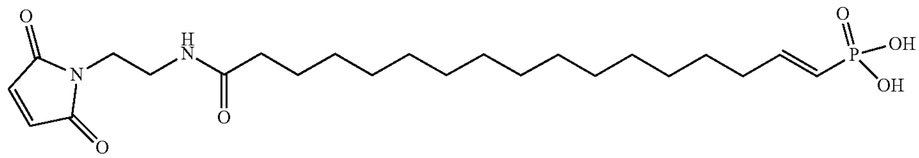 [SMILES: O=C(CCCCCCCCCCCCCC/C=C/P(=O)(O)O)NCCN1C(=O)C=CC1=O] |
| Mal-$C_{17}$-$PO_3$ |
| 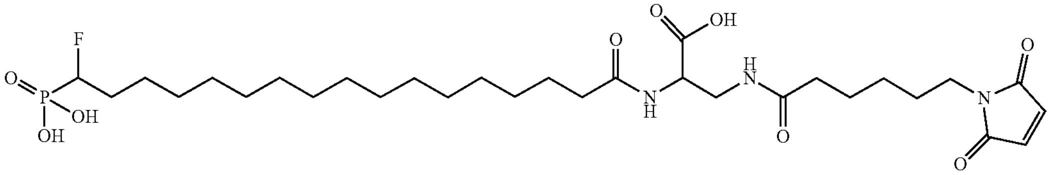 [SMILES: O=C(CCCCCN1C(=O)C=CC1=O)NCC(NC(=O)CCCCCCCCCCCCCCCC(F)P(=O)(O)O)C(=O)O] |
| Mal-$C_{17}$-Fluoro-$PO_3$ Monoacid |

TABLE 6-continued
| Exemplary PK Enhancer Compounds Suitable for Linking to HIF-2 alpha RNAi Agents |
| --- |
| 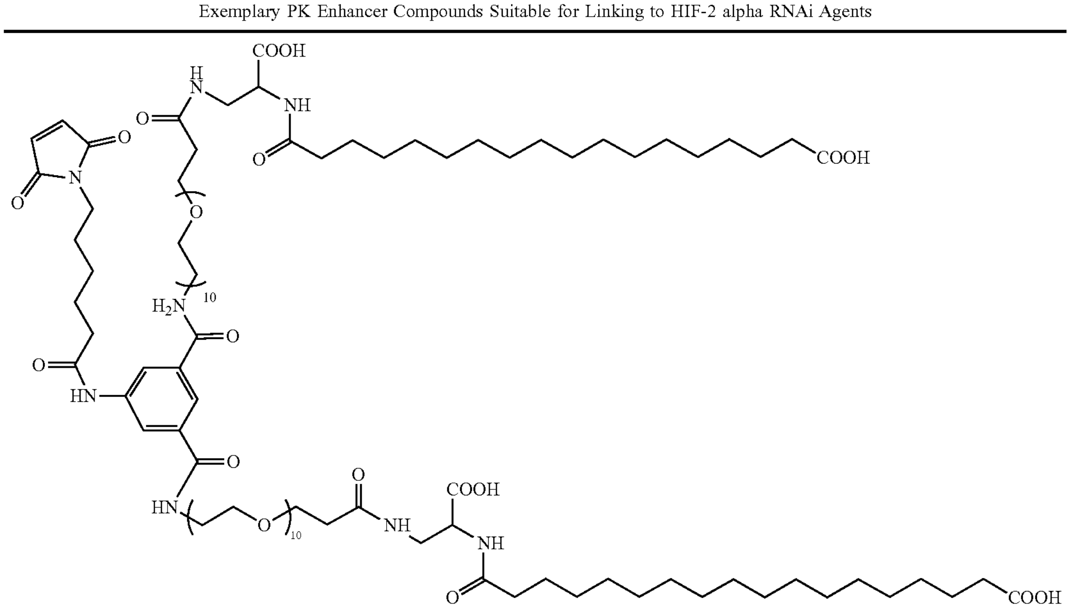 |
| Mal-BisC18-diacid |
| 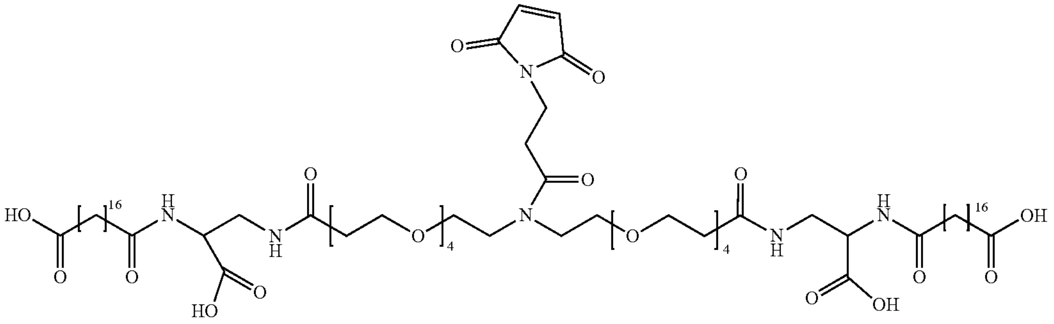 |
| Dual C18-diacid |
| 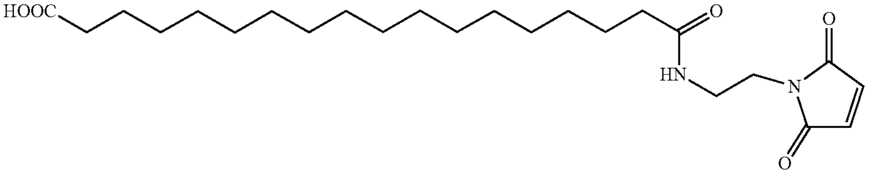 [SMILES: O=C(O)CCCCCCCCCCCCCCCCC(=O)NCCN1C(=O)C=CC1=O] |
| Mal-C18 Acid |
| 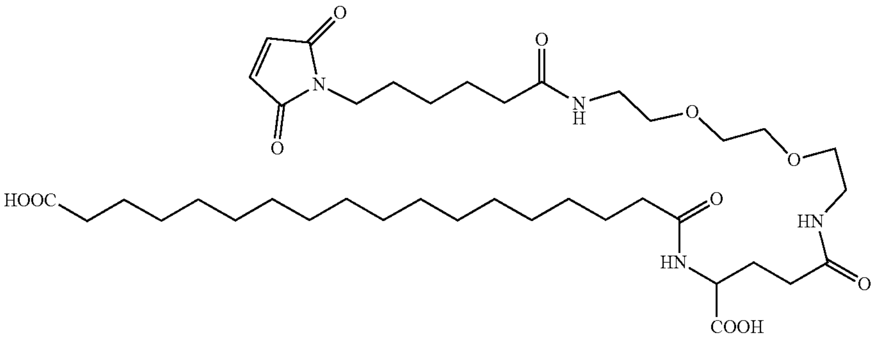 [SMILES: O=C(O)CCCCCCCCCCCCCCCCC(=O)NC(CCC(=O)NCCOCCOCCNC(=O)CCCCCN1C(=O)C=CC1=O)C(=O)O] |
| Mal-C6-PEG2-C18 Diacid |

TABLE 6-continued
Exemplary PK Enhancer Compounds Suitable for Linking to HIF-2 alpha RNAi Agents
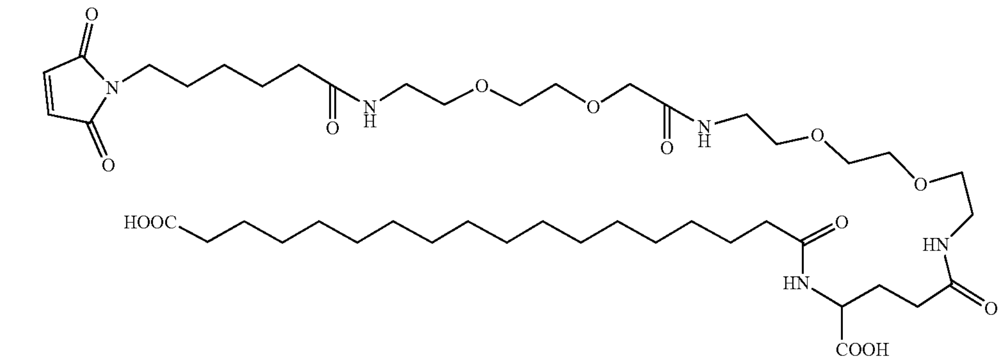 [SMILES: O=C(O)CCCCCCCCCCCCCCCCC(=O)NC(CCC(=O)NCCOCCOCCNC(=O)COCCOCCNC(=O)CCCCCN1C(=O)C=CC1=O)C(=O)O]
Mal-C6-PEG4-C18 Diacid
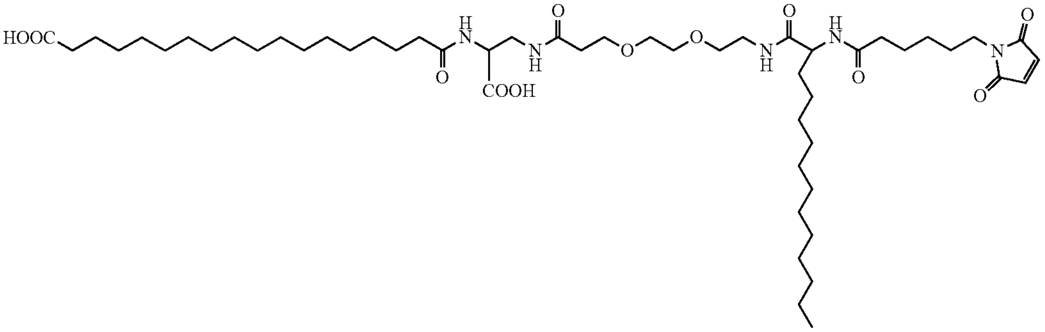 [SMILES: CCCCCCCCCCCCC(NC(=O)CCCCCN1C(=O)C=CC1=O)C(=O)NCCOCCOCCC(=O)NCC(NC(=O)CCCCCCCCCCCCCCCCC(=O)O)C(=O)O]
Mal-C6-C12-PEG2-C18 Diacid
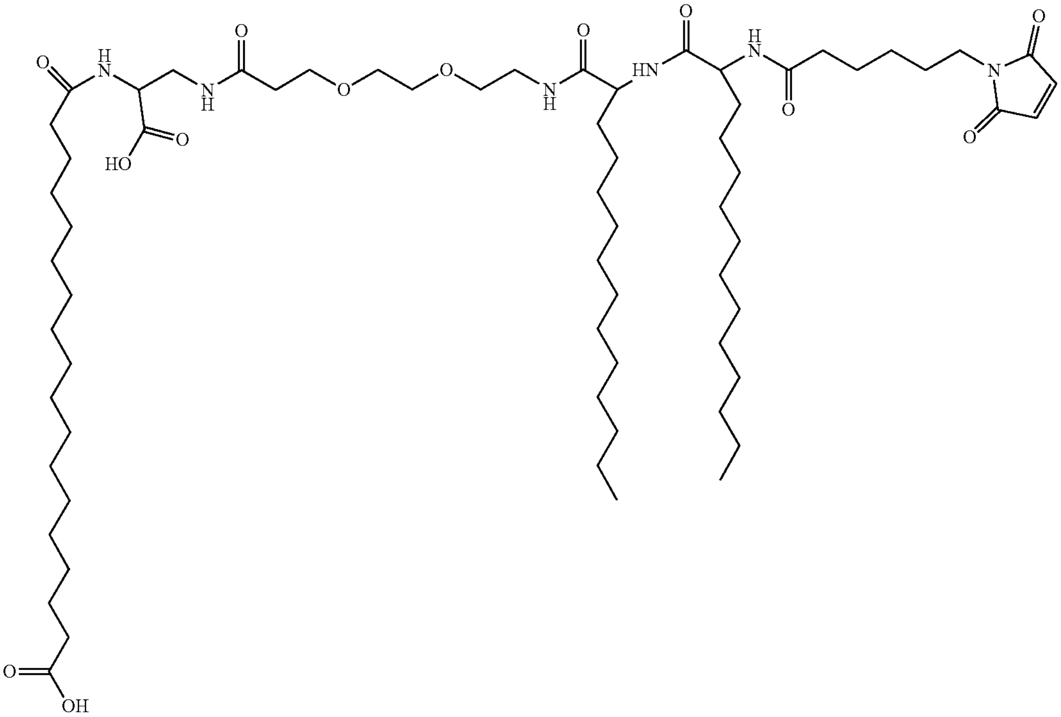 [SMILES: CCCCCCCCCCCCC(NC(=O)CCCCCN1C(=O)C=CC1=O)C(=O)NC(CCCCCCCCCCCC)C(=O)NCCOCCOCCC(=O)NCC(NC(=O)CCCCCCCCCCCCCCCCC(=O)O)C(=O)O]
Mal-C6-C12-C12-PEG2-C18 Diacid TABLE 6-continued
| Exemplary PK Enhancer Compounds Suitable for Linking to HIF-2 alpha RNAi Agents |
|---|
| 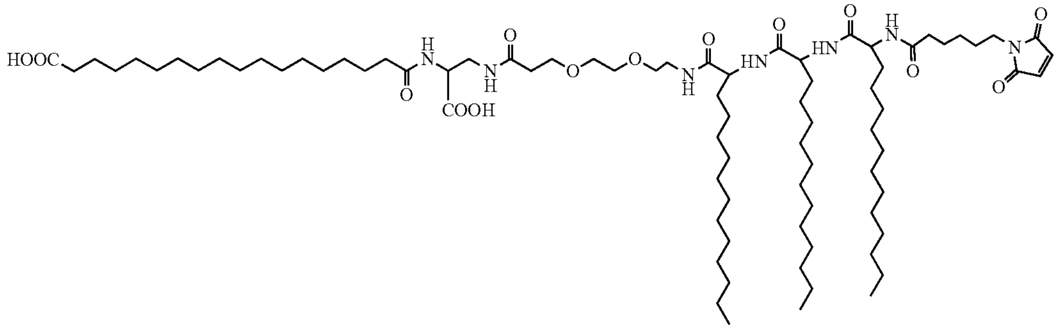 [SMILES: CCCCCCCCCCCCC(NC(=O)CCCCCN1C(=O)C=CC1=O)C(=O)NC(CCCCCCCCCCCC)C(=O)NC(CCCCCCCCCCCC)C(=O)NCCOCCOCCC(=O)NCC(NC(=O)CCCCCCCCCCCCCCCCC(=O)O)C(=O)O] |
| Mal-C6-C12-C12-C12-PEG2-C18 Diacid |
| 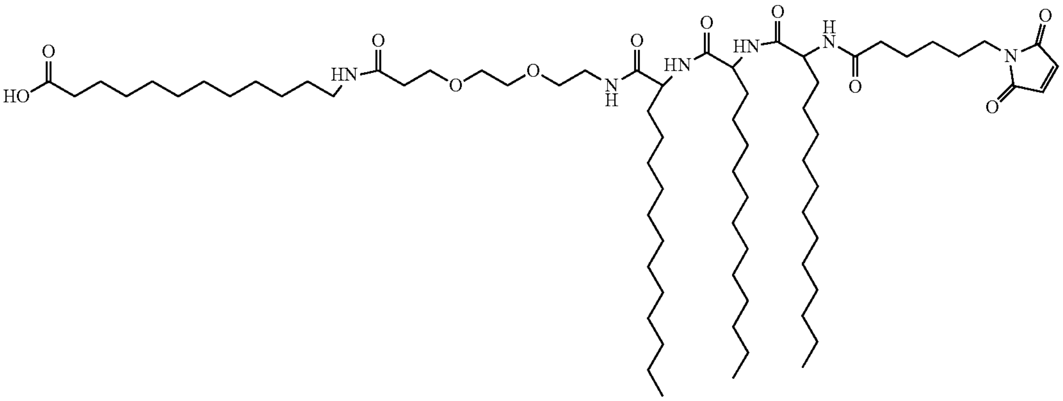 [SMILES: CCCCCCCCCCCCC(NC(=O)CCCCCN1C(=O)C=CC1=O)C(=O)NC(CCCCCCCCCCCC)C(=O)NC(CCCCCCCCCCCC)C(=O)NCCOCCOCCC(=O)NCCCCCCCCCCCC(=O)O] |
| Mal-C6-C12-C12-C12-PEG2-C12 acid |
| 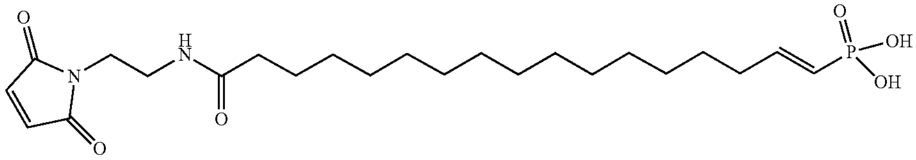 [SMILES: O=C(CCCCCCCCCCCCCC/C=C/P(=O)(O)O)NCCN1C(=O)C=CC1=O] |
| Mal-$C_{17}$-vinyl-$PO_3$ |
| 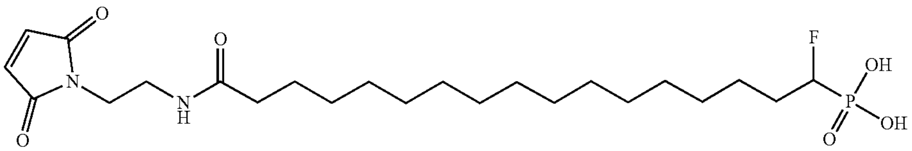 [SMILES: O=C(CCCCCCCCCCCCCCCC(F)P(=O)(O)O)NCCN1C(=O)C=CC1=O] |
| Mal-$C_{17}$-Fluoro-$PO_3$ |
| 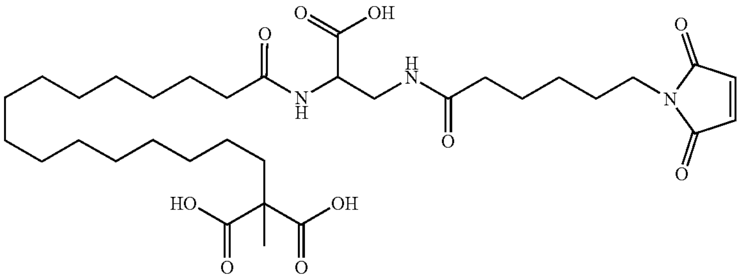 [SMILES: CC(CCCCCCCCCCCCCCCC(=O)NC(CNC(=O)CCCCCN1C(=O)C=CC1=O)C(=O)O)(C(=O)O)C(=O)O] |
| Mal-$C_{18}$-methyl-triacid |

TABLE 6-continued

Exemplary PK Enhancer Compounds Suitable for Linking to HIF-2 alpha RNAi Agents

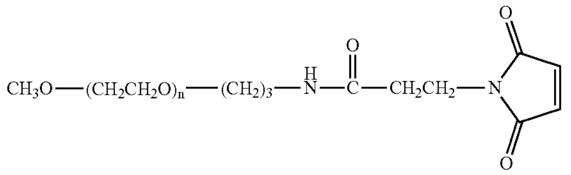

PEG40K,
wherein n is an integer, and the molecular weight of the PEG groups is about 40 kilodaltons
NOF, Sunbright ® ME-400MA

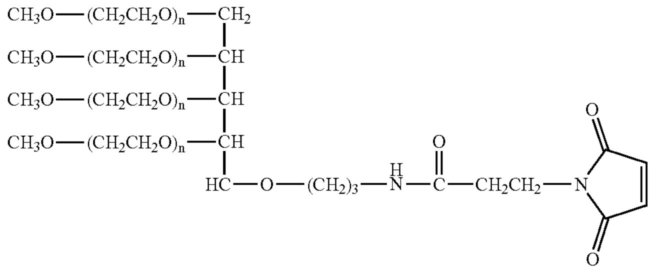

PEG40K (4-arm),
wherein n is an integer, and the molecular weight of the PEG groups is about 40 kilodaltons
NOF, Sunbright ® XY4-400MA In some embodiments, HIF-2 alpha RNAi agents may comprise one or more PK enhancers. In some embodiments, HIF-2 alpha RNAi agents comprise one, two, three, four, five, six, seven or more PK enhancers.

PK enhancers may be conjugated to a HIF-2 alpha RNAi agent using any known method in the art. In some embodiments, PK enhancers may include a maleimide moiety and be reacted with an RNAi agent comprising a disulfide linkage to form an RNAi agent comprising a PK enhancer. The disulfide may be reduced, and added to a maleimide by way of a Michael-Addition reaction. An example reaction scheme is shown below:

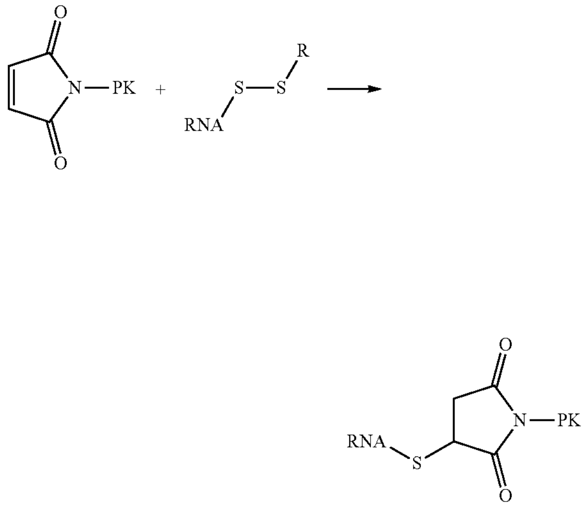

wherein PK comprises a PK enhancer, RNA comprises an RNAi agent, and R may be any suitable group known in the art. In some instances of the reaction scheme above, R is an alkyl group such as hexyl ($C_6H_{13}$).

In some embodiments, PK enhancers may include an azide moiety and be reacted with an RNAi agent comprising an alkyne to form an RNAi agent comprising a PK enhancer. The pair may be reacted using a "click" reaction of the general reaction scheme below:

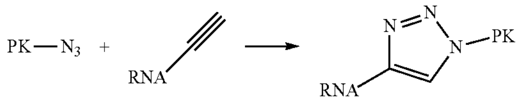

wherein PK comprises a PK enhancer, RNA comprises an RNAi agent.

In some embodiments, PK enhancers may be conjugated to the 5' end of the sense or antisense strand, the 3' end of the sense or antisense strand, or to an internal nucleotide of a HIF-2 alpha RNAi agent. In some embodiments, a HIF-2 alpha RNAi agent is synthesized with a disulfide-containing moiety at the 3' end of the sense strand, and a PK enhancer may be conjugated to the 3' end of the sense strand using the general synthetic scheme shown above. In some embodiments a HIF-2 alpha RNAi agent is synthesized to include a 2'-O-propargyl modified nucleotide (see, for example, Table 7), and a PK enhancer may be conjugated to an internal nucleotide using the general synthetic scheme shown above.

In some embodiments, after the PK enhancer has been conjugated to the RNAi agent, the PK enhancer may have the formula:

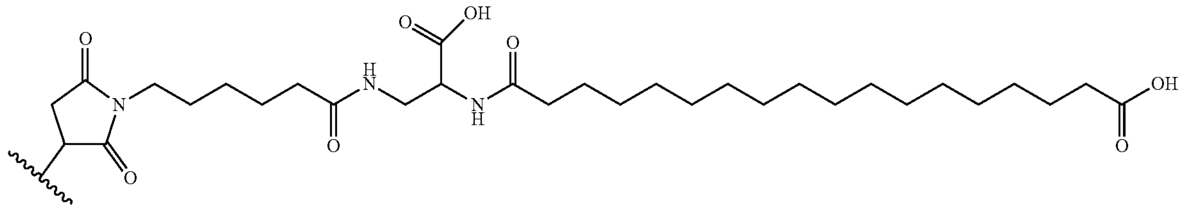
Mal-$C_{18}$-diacid
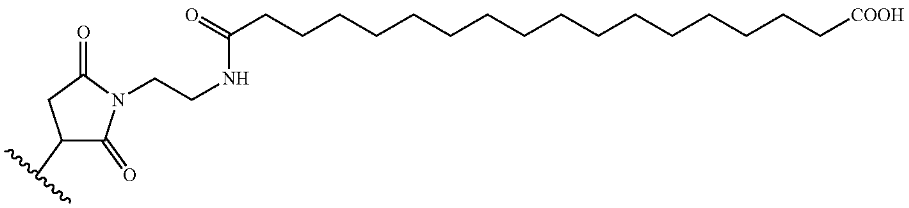
Mal-$C_{18}$-acid
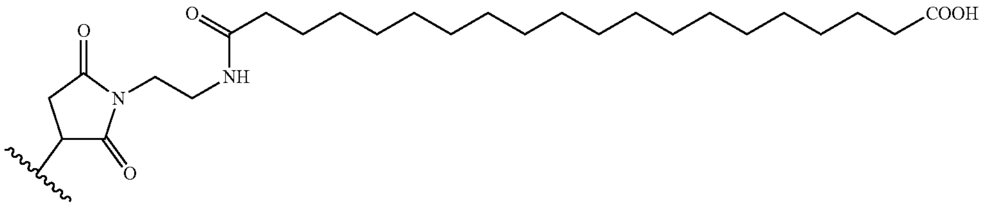
Mal-$C_{20}$-acid
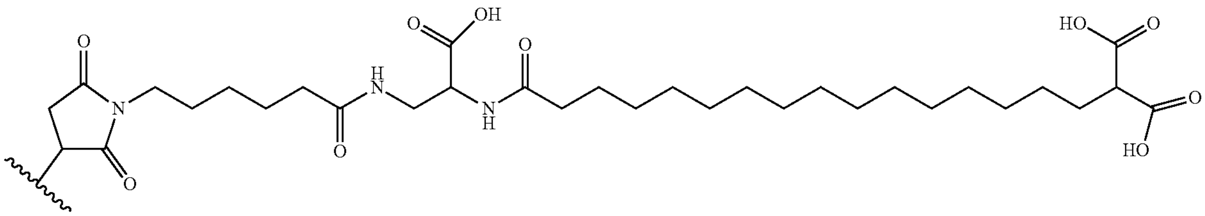
Mal-$C_{18}$-triacid
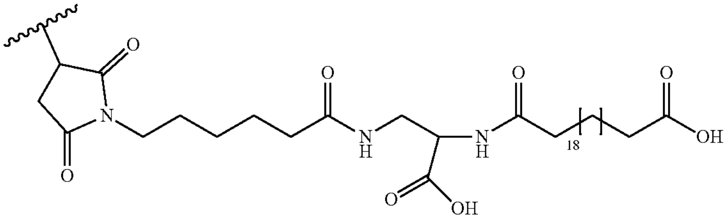
Mal-$C_{22}$-diacid
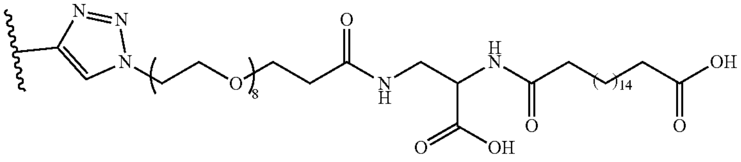
$C_{18}$-diacid-$N_3$ -continued
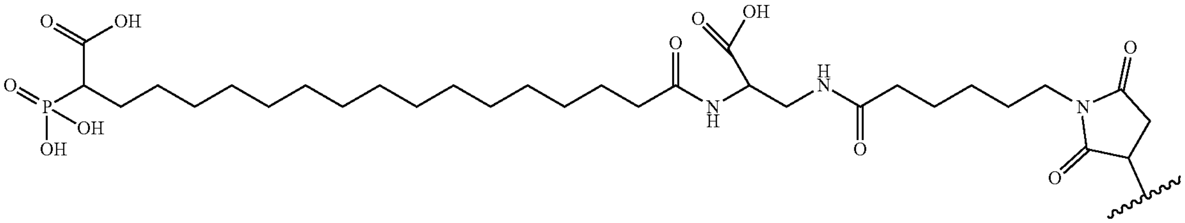
Mal-$C_{18}$-diacid-$PO_3$
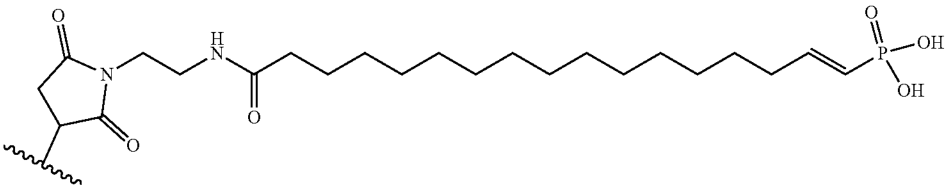
Mal-$C_{17}$-$PO_3$
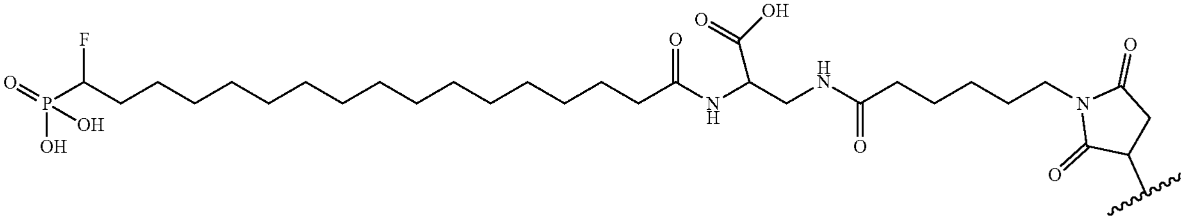
Mal-$C_{17}$-Fluoro-$PO_3$ Monoacid
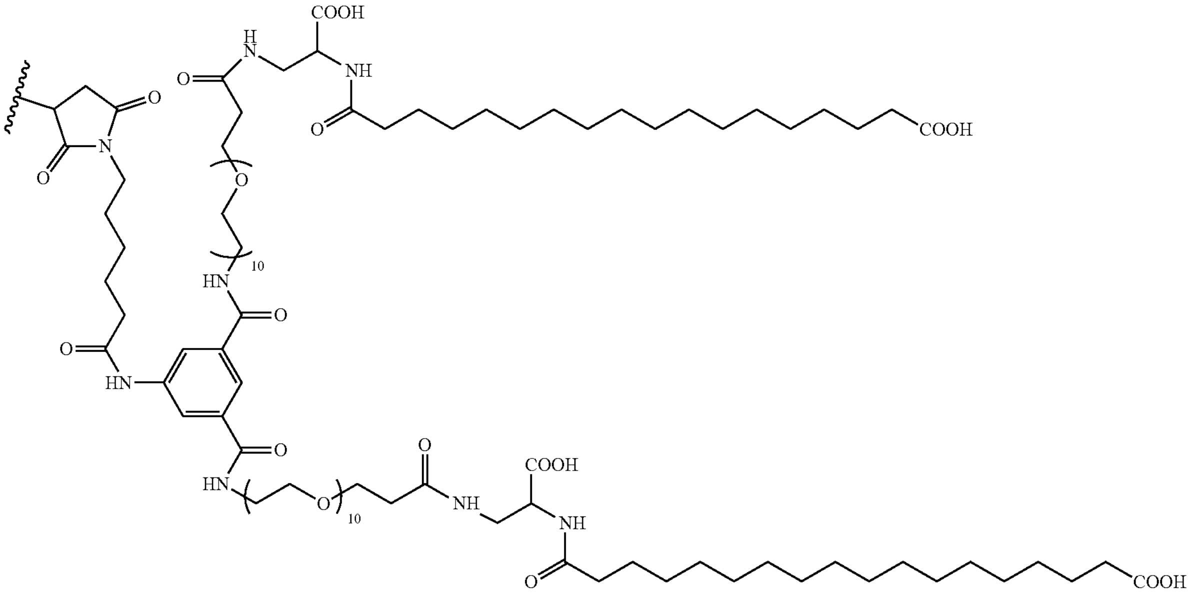
Mal-BisC18-diacid -continued
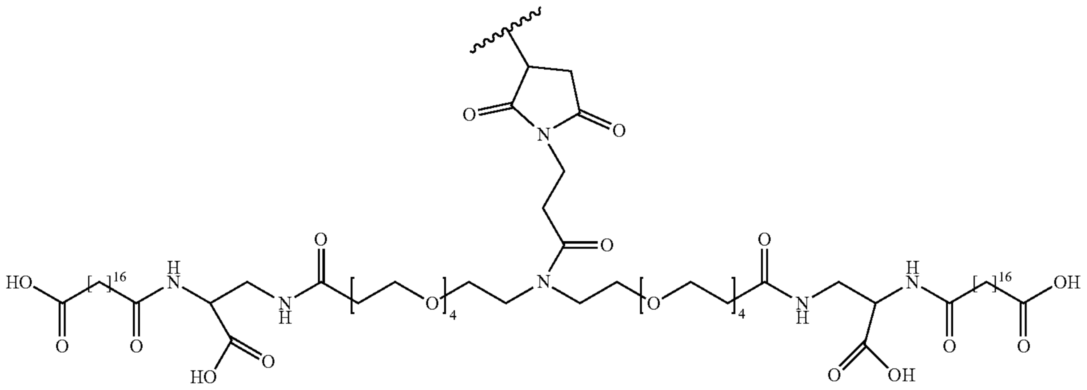
Dual C18-diacid
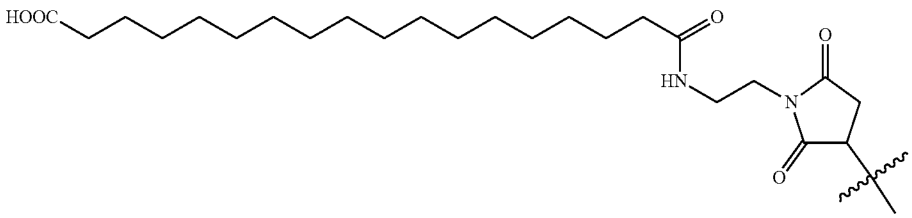
Mal-C18 Acid
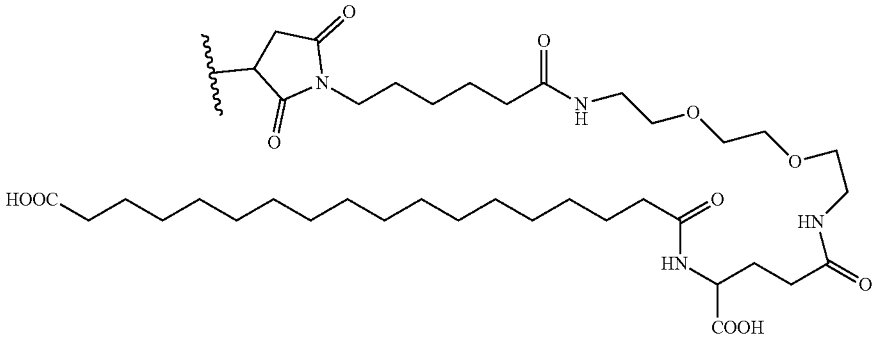
Mal-C6-PEG2-C18 Diacid
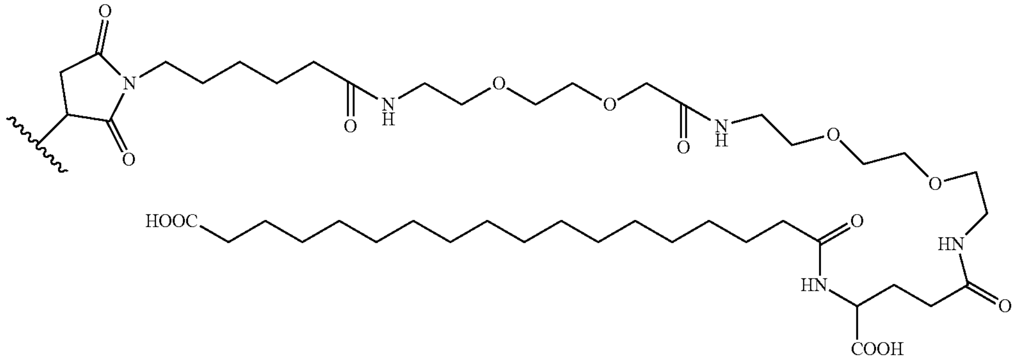
Mal-C6-PEG4-C18 Diacid -continued
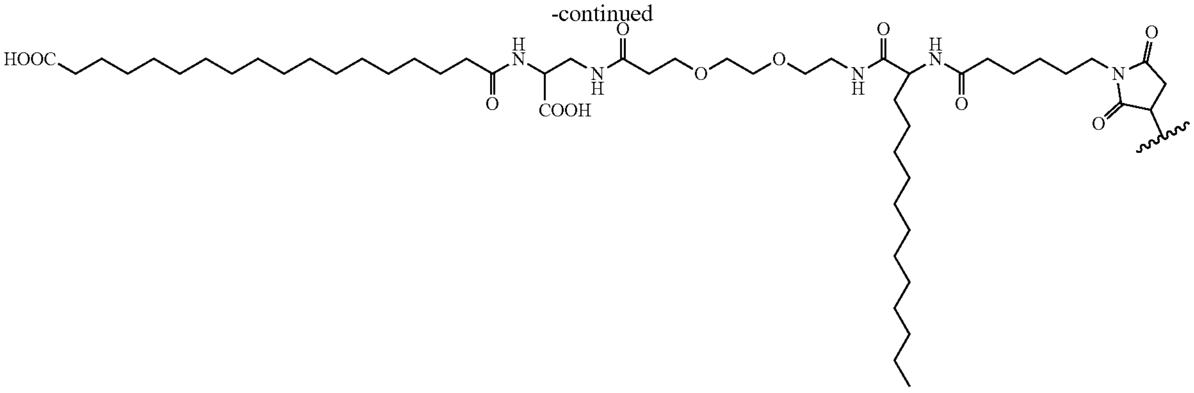
MAl-C6-C12-PEG2-C18 Diacid
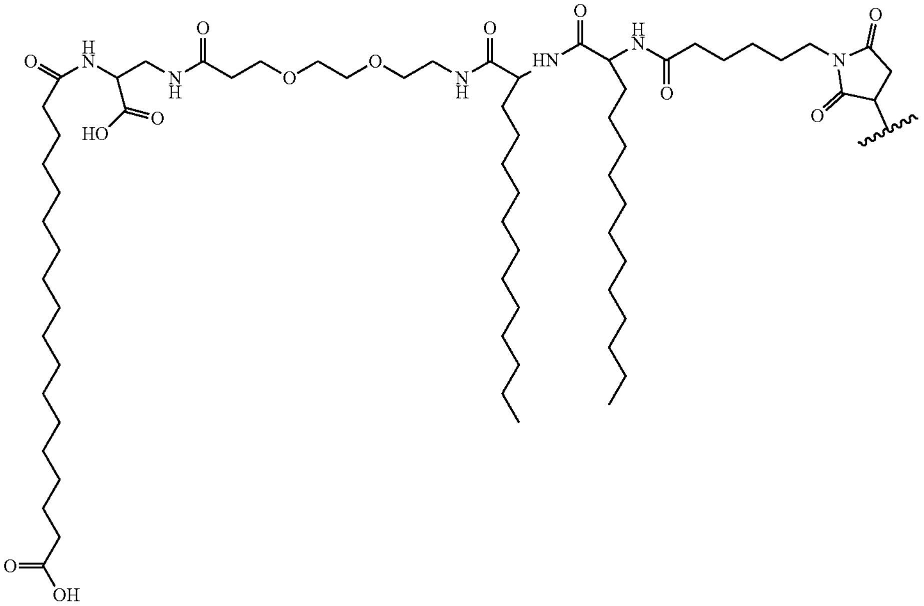
MAl-C6-C12-C12-PEG2-C18 Diacid
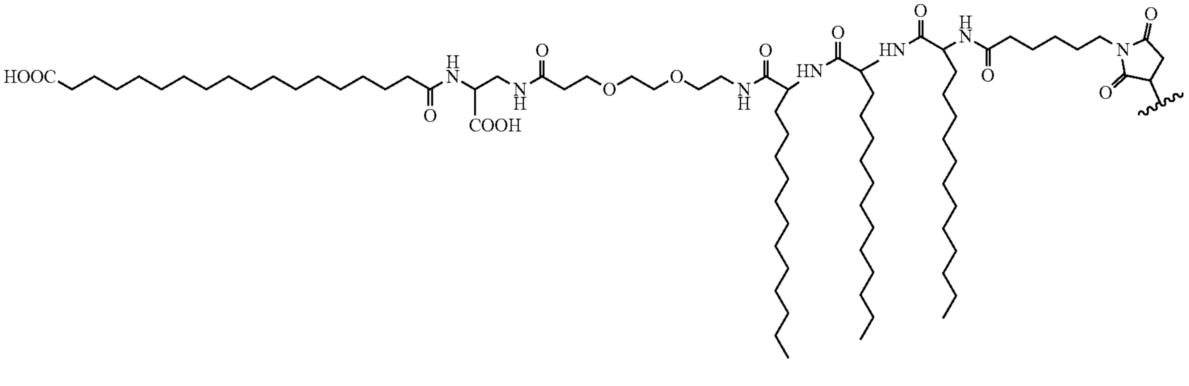
MAl-C6-C12-C12-C12-PEG2 C18 Diacid -continued
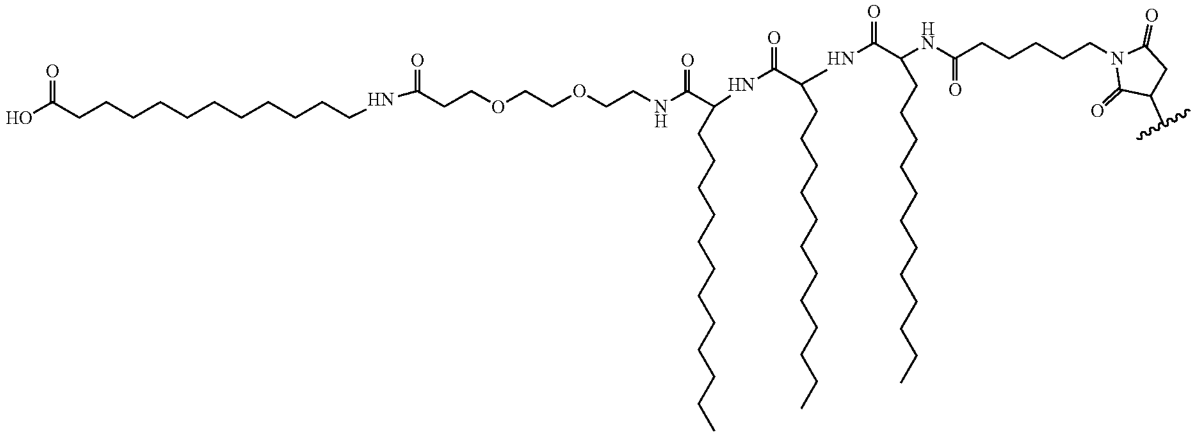
MAl-C6-C12-C12-C12-PEG2-C12 acid
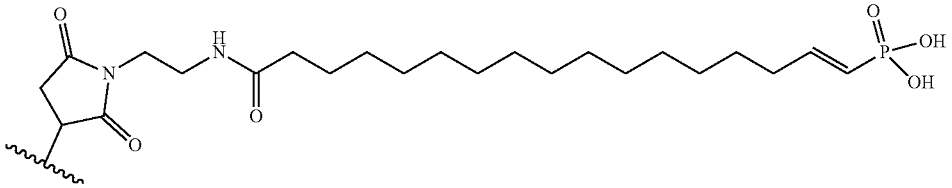
Mal-$C_{17}$-vinyl-$PO_3$
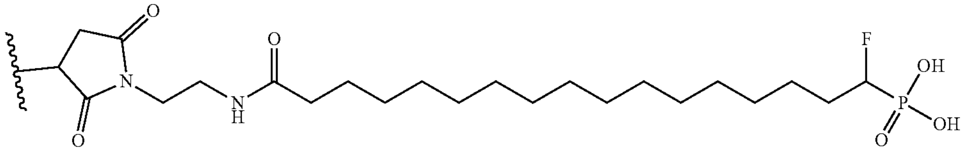
Mal-$C_{17}$-Fluoro-$PO_3$
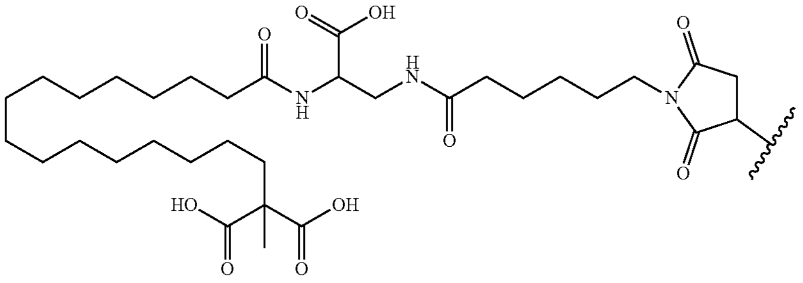
Mal-$C_{18}$-methyl-triacid
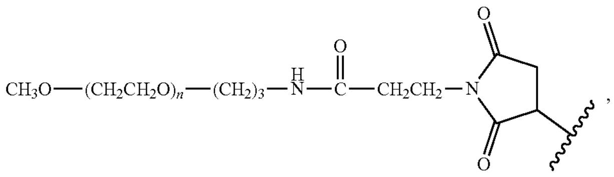
, wherein n is an integer, and the molecular weight of the PEG groups is about 40 kilodaltons
PEG40K
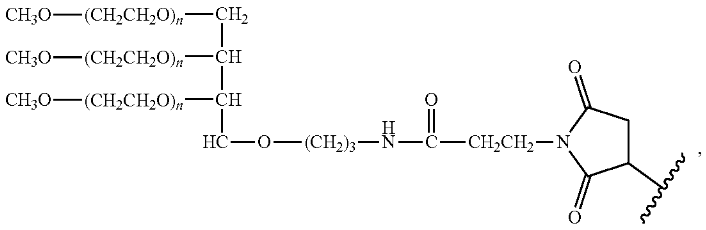
, wherein n is an integer, and the molecular weight of the PEG groups is about 40 kilodaltons
PEG40K (4-arm)

wherein ⌇ indicates the point of attachment to the RNAi agent.

Linking Groups and Delivery Vehicles

In some embodiments, a HIF-2 alpha RNAi agent contains or is conjugated to one or more non-nucleotide groups including, but not limited to a linking group, or a delivery vehicle. The non-nucleotide group can enhance targeting, delivery, or attachment of the RNAi agent. Non-limiting examples of linking groups are provided in Table 7. The non-nucleotide group can be covalently linked to the 3' and/or 5' end of either the sense strand and/or the antisense strand. In some embodiments, a HIF-2 alpha RNAi agent contains a non-nucleotide group linked to the 3' and/or 5' end of the sense strand. In some embodiments, a non-nucleotide group is linked to the 5' end of a HIF-2 alpha RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

The HIF-2 alpha RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the HIF-2 alpha RNAi agents disclosed herein are synthesized having an $NH_2$-$C_6$ group at the 5'-terminus of the sense strand of the RNAi agent. The terminal amino group subsequently can be reacted to form a conjugate with, for example, a group that includes a compound having affinity for one or more integrins (an integrin targeting ligand) or a PK enhancer. In some embodiments, the HIF-2 alpha RNAi agents disclosed herein are synthesized having one or more alkyne groups at the 5'-terminus of the sense strand of the RNAi agent. The terminal alkyne group(s) can subsequently be reacted to form a conjugate with, for example, a group that includes a targeting ligand.

In some embodiments, a targeting group comprises an integrin targeting ligand. In some embodiments, an integrin targeting ligand includes a compound that has affinity to integrin alpha-v-beta 3 and/or integrin alpha-v-beta 5. The use of an integrin targeting ligands can facilitate cell-specific targeting to cells having the respective integrin on its respective surface, and binding of the integrin targeting ligand can facilitate entry of the HIF-2 alpha RNAi agent, to which it is linked, into cells such as ccRCC cells. Targeting ligands, targeting groups, and/or PK enhancers can be attached to the 3' and/or 5' end of the HIF-2 alpha RNAi agent, and/or to internal nucleotides on the HIF-2 alpha RNAi agent, using methods generally known in the art. The preparation of targeting ligand and targeting groups, such as integrin $\alpha v \beta 3$/$\alpha v \beta 5$ is described, for example, in U.S. Provisional Patent Application No. 62/663,763, the contents of which is incorporated herein in its entirety.

Embodiments of the present disclosure include pharmaceutical compositions for delivering a HIF-2 alpha RNAi agent to a ccRCC cell in vivo. Such pharmaceutical compositions can include, for example, a HIF-2 alpha RNAi agent conjugated to a targeting group that comprises an integrin targeting ligand that has affinity for integrin $\alpha v \beta 3$ and/or integrin $\alpha v \beta 5$. In some embodiments, the targeting ligand is comprised of a compound having affinity for integrin $\alpha v \beta 3$ and/or integrin $\alpha v \beta 5$.

In some embodiments, the HIF-2 alpha RNAi agent is synthesized having a linking group, which can then facilitate covalent linkage of the HIF-2 alpha RNAi agent to a targeting ligand, a targeting group, a PK enhancer, or another type of delivery vehicle such as a delivery polymer. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include, but are not limited to: Alk-SMPT-C6, Alk-SS-C6, DBCO-TEG, Me-Alk-SS-C6, and C6-SS-Alk-Me, reactive groups such a primary amines and alkynes, alkyl groups, abasic residues/nucleotides, amino acids, trialkyne functionalized groups, ribitol, and/or PEG groups.

A linker or linking group is a connection between two atoms that links one chemical group (such as an RNAi agent) or segment of interest to another chemical group (such as a targeting ligand, targeting group, PK enhancer, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, targeting groups are linked to the HIF-2 alpha RNAi agents without the use of an additional linker. In some embodiments, the targeting group is designed having a linker readily present to facilitate the linkage to a HIF-2 alpha RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Any of the HIF-2 alpha RNAi agent nucleotide sequences listed in Tables 2, 3, and 4 (or Table 4.1, 4.2, or 4.3), whether modified or unmodified, may contain 3' and/or 5' targeting group(s), linking group(s), and/or pharmacokinetic enhancer(s). Any of the HIF-2 alpha RNAi agent sequences listed in Tables 3 and 4, or are otherwise described herein, which contain a 3' or 5' targeting ligand, targeting group, PK enhancer, or linking group, can alternatively contain no 3' or 5' targeting ligand, targeting group, linking group, or PK enhancer, or can contain a different 3' or 5' targeting ligand, targeting group, linking group, or PK enhancer including, but not limited to, those depicted in Tables 6 and 7. Any of the HIF-2 alpha RNAi agent duplexes listed in Table 5, whether modified or unmodified, can further comprise a targeting ligand, targeting group, linking group, or PK enhancer, including, but not limited to, those depicted in Tables 6 and 7, and the targeting group or linking group can be attached to the 3' or 5' terminus of either the sense strand or the antisense strand of the HIF-2 alpha RNAi agent duplex.

In some embodiments, a linking group may be conjugated synthetically to the 5' or 3' end of the sense strand of a HIF-2 alpha RNAi agent described herein. In some embodiments, a linking group is conjugated synthetically to the 5' end of the sense strand of a HIF-2 alpha RNAi agent. In some embodiments, a linking group conjugated to a HIF-2 alpha RNAi agent may be a trialkyne linking group.

In some embodiments, the HIF-2 alpha RNAi agents are linked to one or more tridentate targeting groups having the following formula:

Formula II

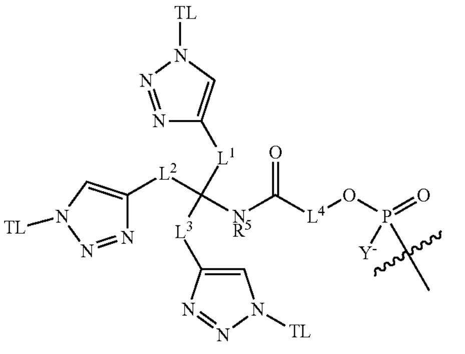

or a pharmaceutically acceptable salt thereof, wherein, $L^1$, $L^2$ and $L^3$ are each independently linkers comprising an optionally substituted alkylene;

$L^4$ is a linker comprising an optionally substituted alkylene, optionally substituted aryl, or optionally substituted cycloalkyl;

$R^5$ is H or optionally substituted alkyl;

TL is a targeting ligand; and

Y is O or S.

In other embodiments, the HIF-2 alpha RNAi agents are linked to one or more tridentate targeting groups using a linker having the formula of any one of TriAlk 1-14 as shown in Table 7, below. Methods of synthesizing compounds of Formula II are described in PCT Application No. PCT/US19/18232, entitled "Trialkyne Linking Agents and Methods of Use."

Examples of certain modified nucleotides and linking groups, are provided in Table 7.

TABLE 7

| Structures Representing Various Modified Nucleotides and Linking Groups | |
|---|---|
| 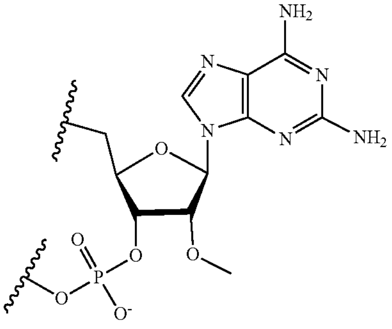<br>a_2N | 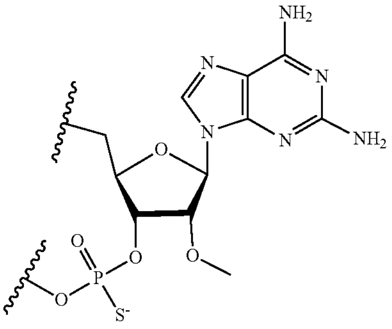<br>a_2Ns |
| 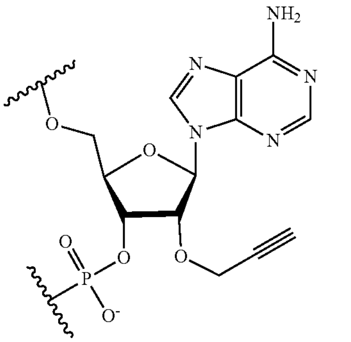<br>aAlk | 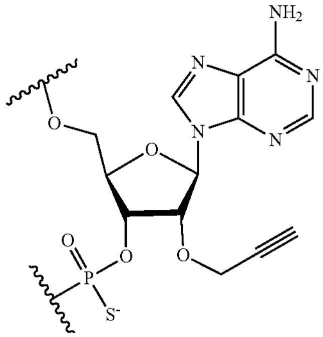<br>aAlks |

TABLE 7-continued
Structures Representing Various Modified Nucleotides and Linking Groups
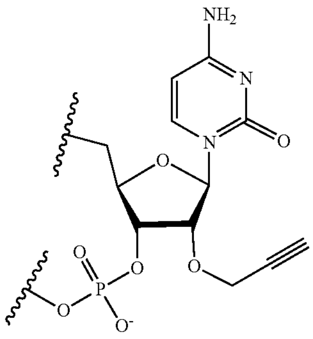
cAlk
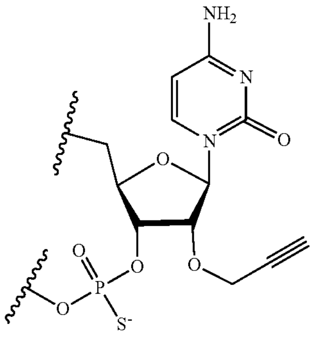
cAlks
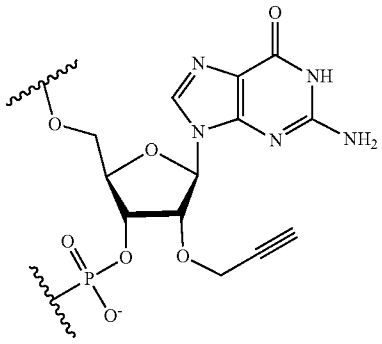
gAlk
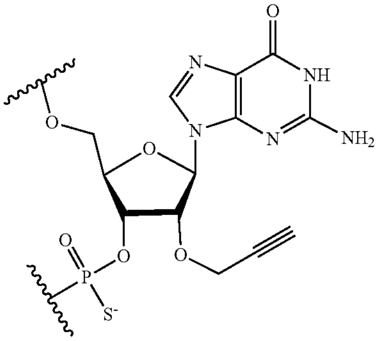
gAlks
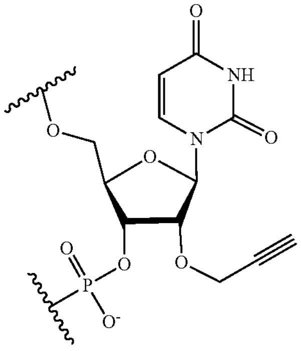
uAlk
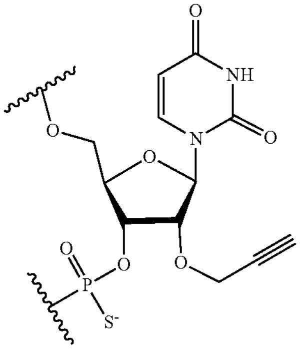
uAlks TABLE 7-continued Structures Representing Various Modified Nucleotides and Linking Groups When positioned internally in oligonucleotide:

linkage towards 5′ end

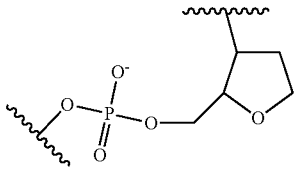

linkage towards 3′ end (invAb)

When positioned internally:

linkage towards 5′ end

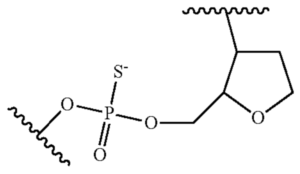

linkage towards 3′ end (invAb)s

When positioned at the 3' terminal end:

linkage towards 5′ end

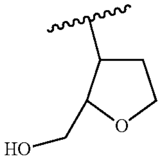

(invAb)

When positioned at the 3' terminal end:

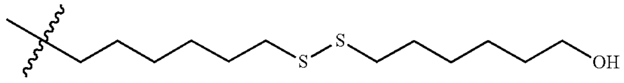 [SMILES: *CCCCCCSSCCCCCCO]

(C6-SS-C6)

When positioned internally:

linkage towards 3′ end

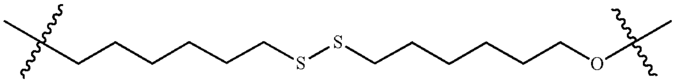

(C6-SS-C6)

TABLE 7-continued
Structures Representing Various Modified Nucleotides and Linking Groups
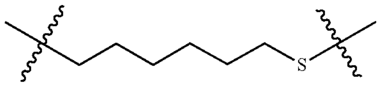 [SMILES: *CCCCCCS*]
(C6-S)
When positioned at the 3' terminal end:
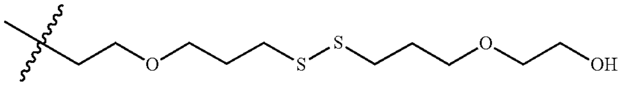 [SMILES: *CCOCCCSSCCCOCCO]
(6-SS-6)
When positioned internally:
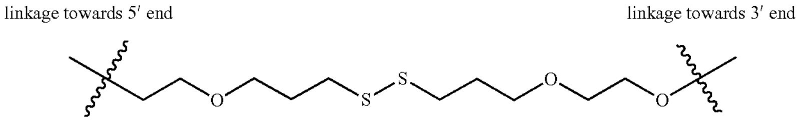 [SMILES: *CCOCCCSSCCCOCCO*]
(6-SS-6)
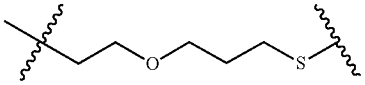 [SMILES: *CCOCCCS*]
(6-S)
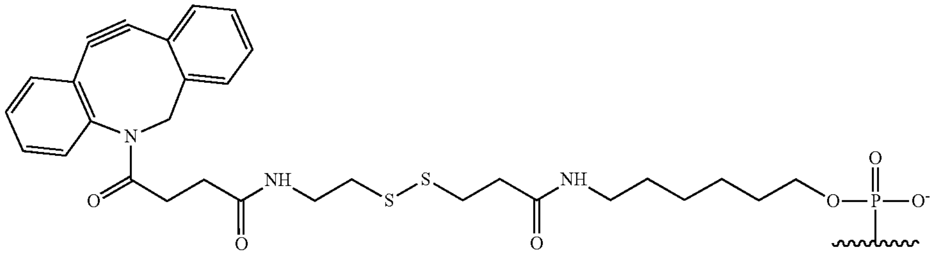 [SMILES: *P(=O)([O-])OCCCCCCNC(=O)CCSSCCNC(=O)CCC(=O)N1Cc2ccccc2C#Cc2ccccc21]
(C6-SS-Alk) or (Alk-SS-C6)
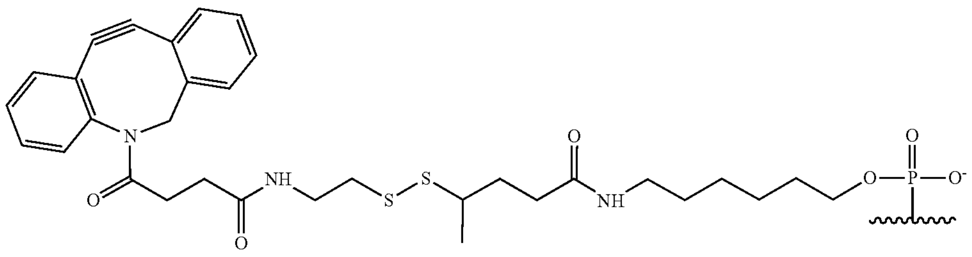 [SMILES: *P(=O)([O-])OCCCCCCNC(=O)CCC(C)SSCCNC(=O)CCC(=O)N1Cc2ccccc2C#Cc2ccccc21]
(C6-SS -Alk-Me)
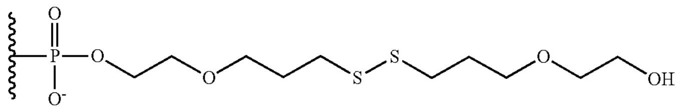 [SMILES: *P(=O)([O-])OCCOCCCSSCCCOCCO]
(PEG-C3-SS)

TABLE 7-continued
Structures Representing Various Modified Nucleotides and Linking Groups
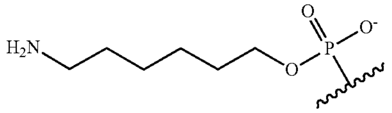 [SMILES: *P(=O)([O-])OCCCCCCN]
(NH2-C6)
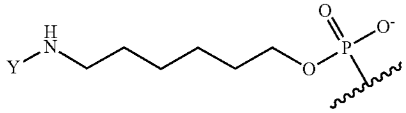
Y-(NH-C6)
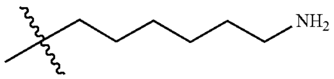 [SMILES: *CCCCCCN]
(C6-NH2)
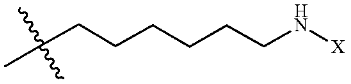
(C6-NH)-X
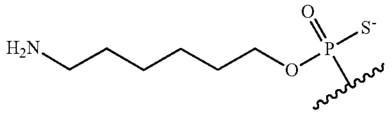 [SMILES: *P(=O)([S-])OCCCCCCN]
(NH2-C6)s
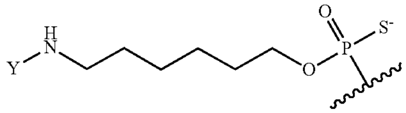
Y-(NH-C6)s
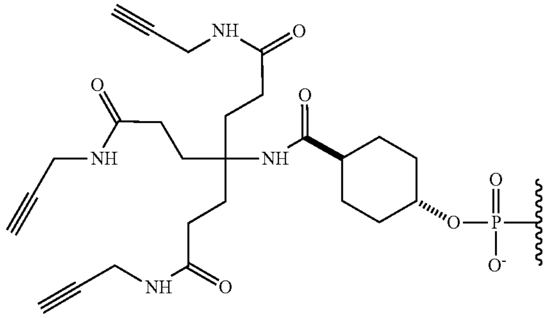
(TriAlk1)

TABLE 7-continued
Structures Representing Various Modified Nucleotides and Linking Groups
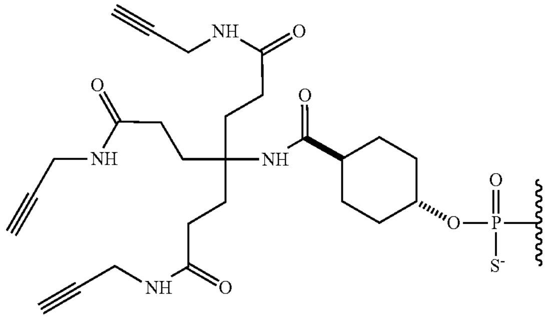 [SMILES: *P(=O)([O-])O[C@H]1CC[C@H](C(=O)NC(CCC(=O)NCC#C)(CCC(=O)NCC#C)CCC(=O)NCC#C)CC1]
(TriAlk1)s
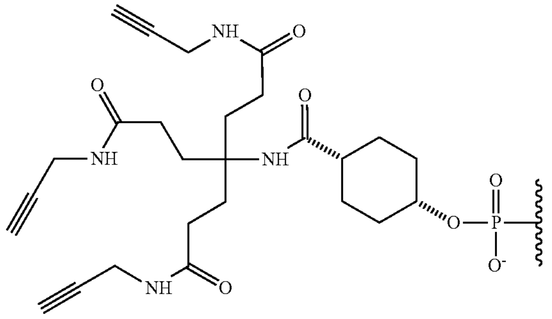
(TriAlk2)
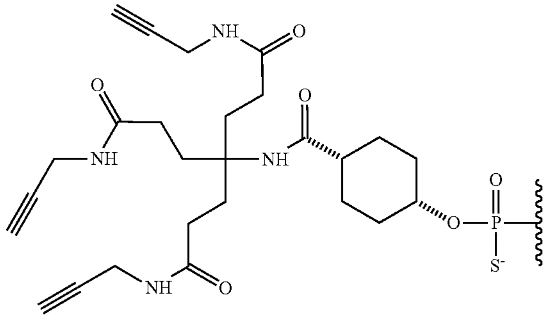 [SMILES: *P(=O)([O-])O[C@H]1CC[C@@H](C(=O)NC(CCC(=O)NCC#C)(CCC(=O)NCC#C)CCC(=O)NCC#C)CC1]
(TriAlk2)s
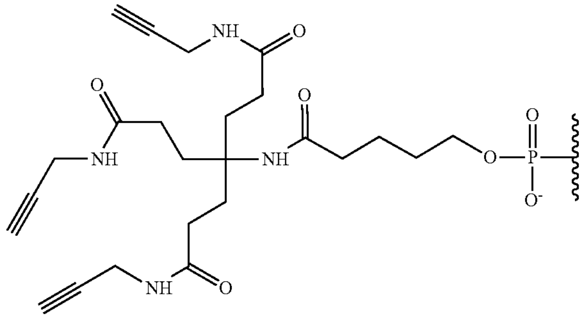 [SMILES: *P(=O)([S-])OCCCCC(=O)NC(CCC(=O)NCC#C)(CCC(=O)NCC#C)CCC(=O)NCC#C]
(TriAlk3)

TABLE 7-continued
Structures Representing Various Modified Nucleotides and Linking Groups
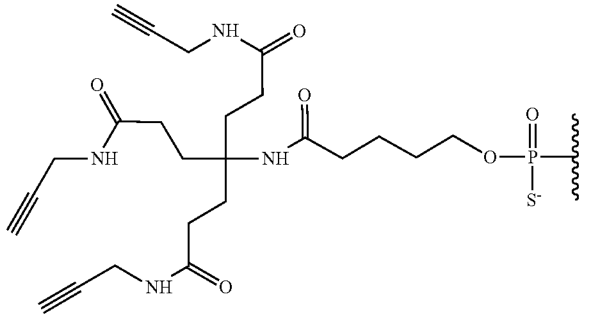
(TriAlk3)s
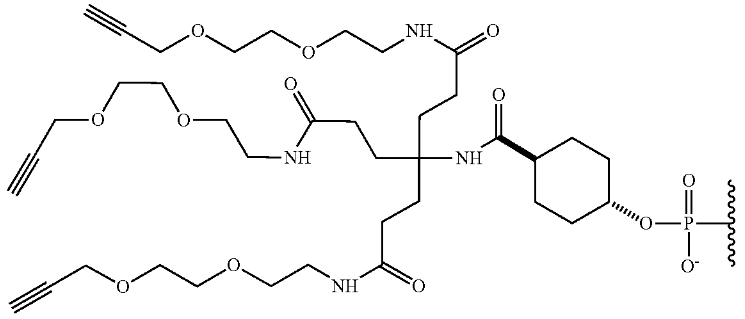 [SMILES: *P(=O)([S-])O[C@H]1CC[C@H](C(=O)NC(CCC(=O)NCCOCCOCC#C)(CCC(=O)NCCOCCOCC#C)CCC(=O)NCCOCCOCC#C)CC1]
(TriAlk4)
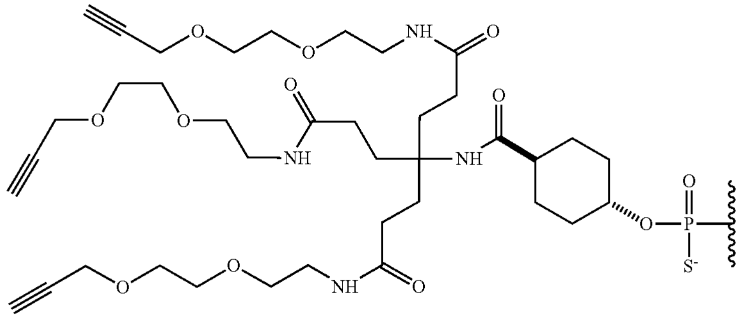
(TriAlk4)s
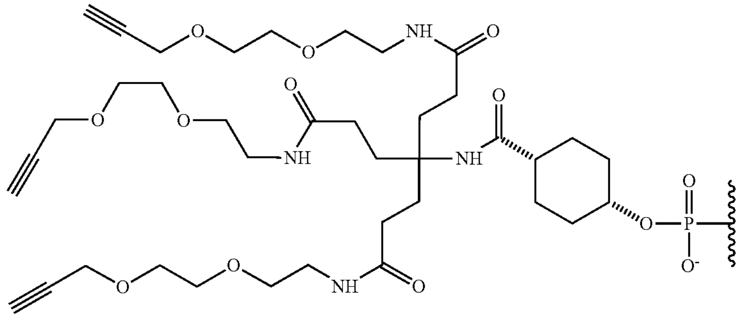
(TriAlk5)

TABLE 7-continued
Structures Representing Various Modified Nucleotides and Linking Groups
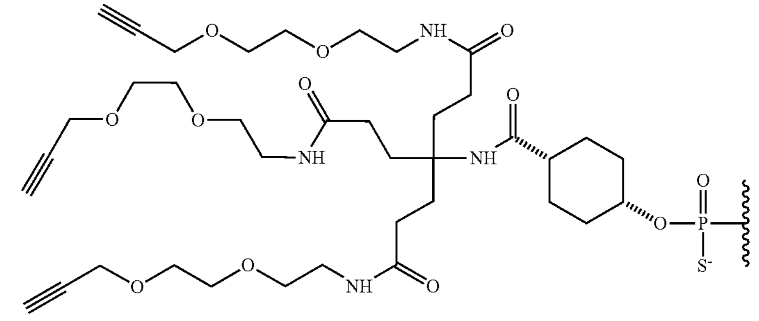 [SMILES: *P(=O)([O-])O[C@H]1CC[C@@H](C(=O)NC(CCC(=O)NCCOCCOCC#C)(CCC(=O)NCCOCCOCC#C)CCC(=O)NCCOCCOCC#C)CC1]
(TriAlk5)s
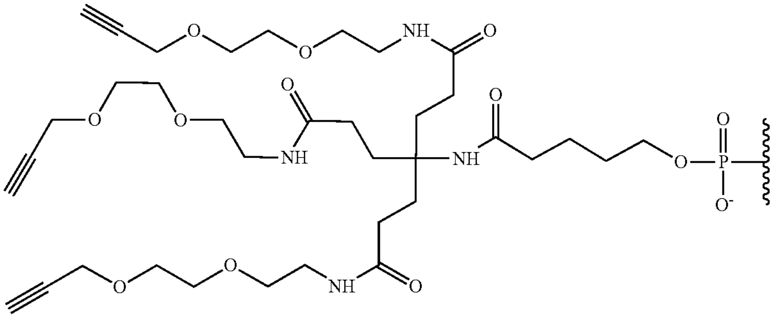 [SMILES: *P(=O)([O-])OCCCCC(=O)NC(CCC(=O)NCCOCCOCC#C)(CCC(=O)NCCOCCOCC#C)CCC(=O)NCCOCCOCC#C]
(TriAlk6)
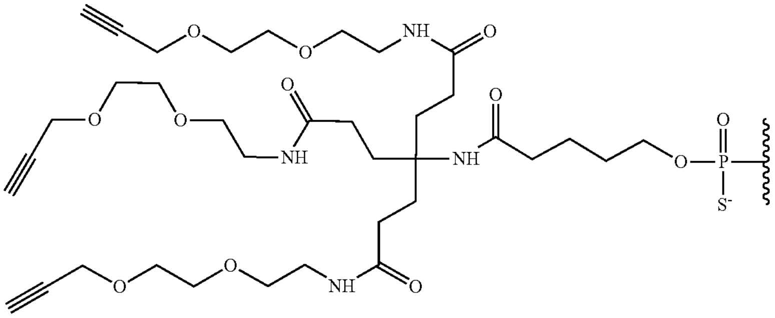
(TriAlk6)s
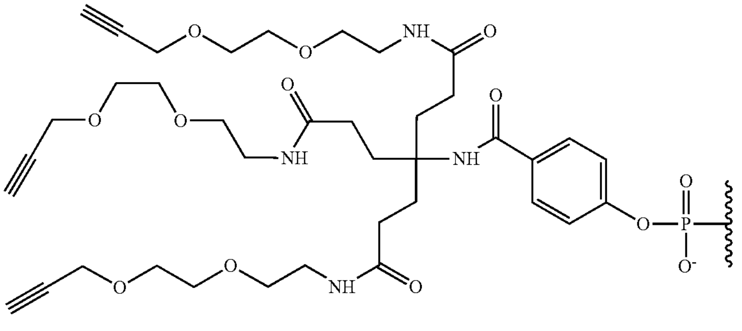
(TriAlk7)

TABLE 7-continued
Structures Representing Various Modified Nucleotides and Linking Groups
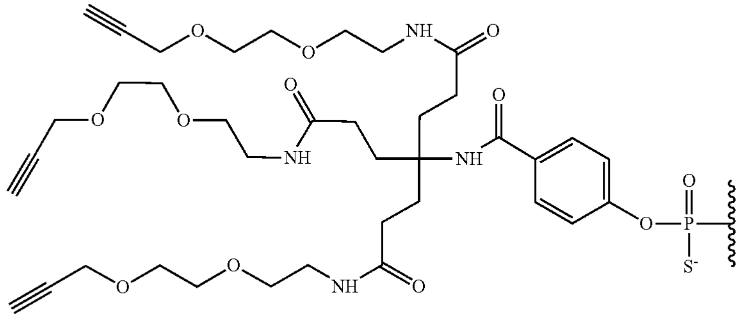 [SMILES: *P(=O)([O-])Oc1ccc(C(=O)NC(CCC(=O)NCCOCCOCC#C)(CCC(=O)NCCOCCOCC#C)CCC(=O)NCCOCCOCC#C)cc1]
(TriAlk7)s
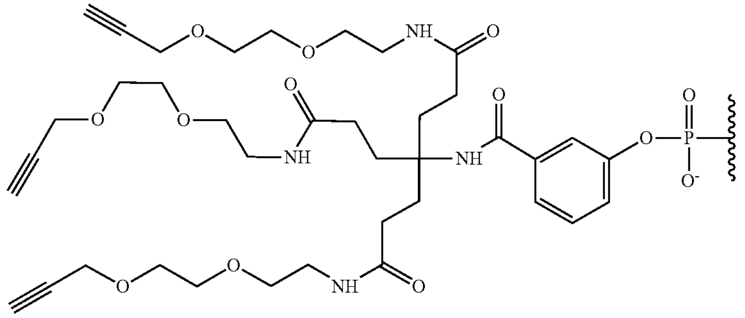 [SMILES: *P(=O)([O-])Oc1cccc(C(=O)NC(CCC(=O)NCCOCCOCC#C)(CCC(=O)NCCOCCOCC#C)CCC(=O)NCCOCCOCC#C)c1]
(TriAlk8)
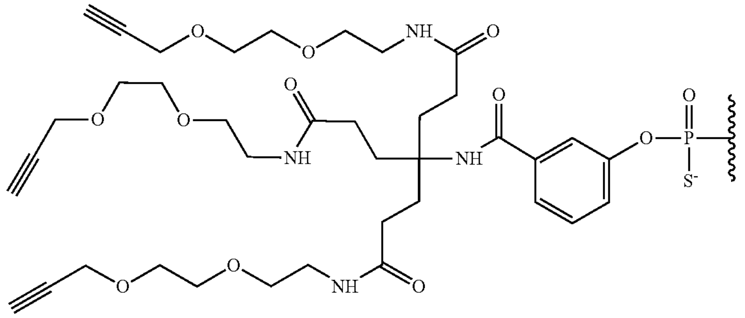 [SMILES: *P(=O)([S-])Oc1cccc(C(=O)NC(CCC(=O)NCCOCCOCC#C)(CCC(=O)NCCOCCOCC#C)CCC(=O)NCCOCCOCC#C)c1]
(TriAlk8)s
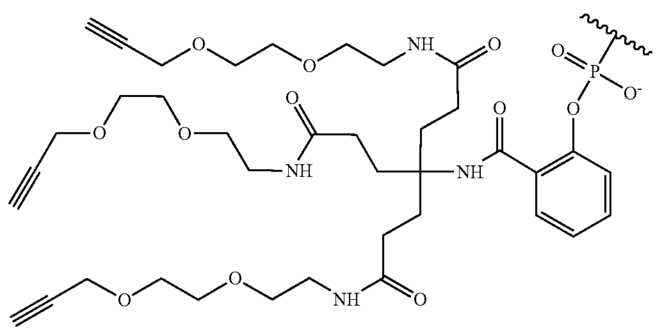
(TriAlk9)

TABLE 7-continued
Structures Representing Various Modified Nucleotides and Linking Groups
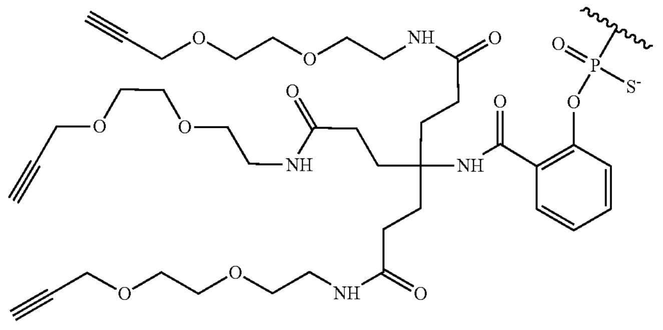 [SMILES: *P(=O)([S-])Oc1ccccc1C(=O)NC(CCC(=O)NCCOCCOCC#C)(CCC(=O)NCCOCCOCC#C)CCC(=O)NCCOCCOCC#C]
(TriAlk9)s
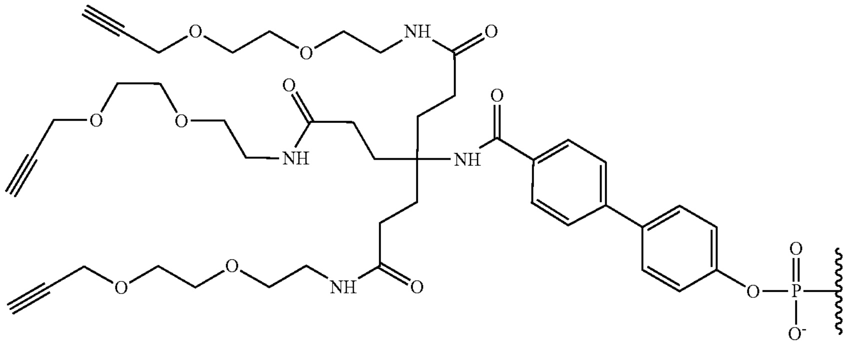
(TriAlk10)
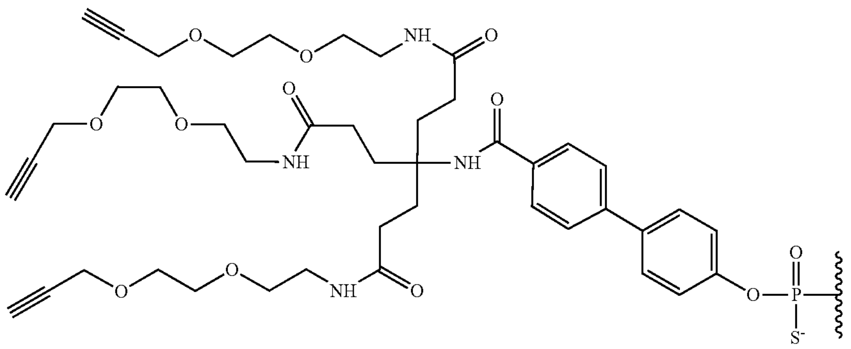 [SMILES: *P(=O)([S-])Oc1ccc(-c2ccc(C(=O)NC(CCC(=O)NCCOCCOCC#C)(CCC(=O)NCCOCCOCC#C)CCC(=O)NCCOCCOCC#C)cc2)cc1]
(TriAlk10)s
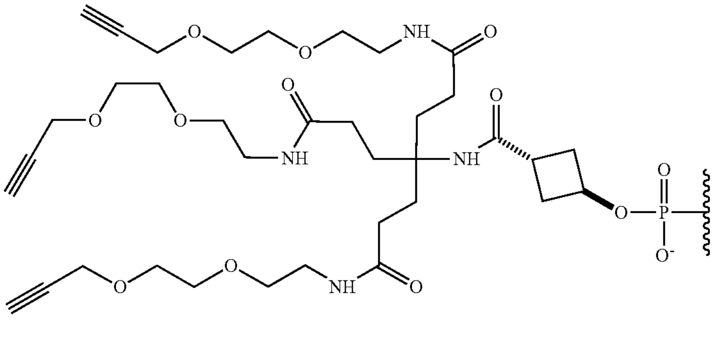 [SMILES: *P(=O)([O-])O[C@H]1C[C@H](C(=O)NC(CCC(=O)NCCOCCOCC#C)(CCC(=O)NCCOCCOCC#C)CCC(=O)NCCOCCOCC#C)C1]
(TriAlk11)

TABLE 7-continued
| Structures Representing Various Modified Nucleotides and Linking Groups |
| --- |
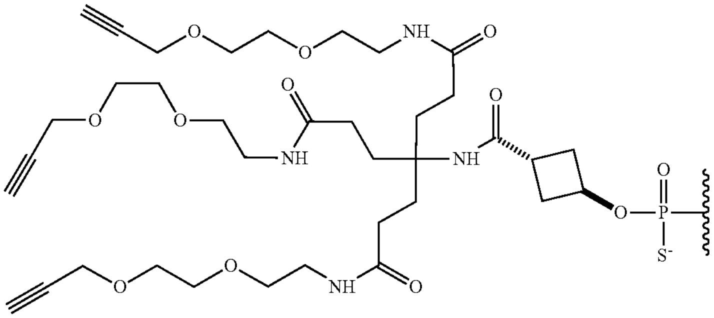
(TriAlk11)s
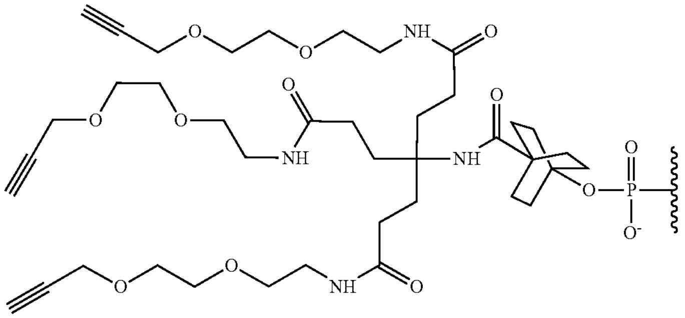
(TriAlk12)
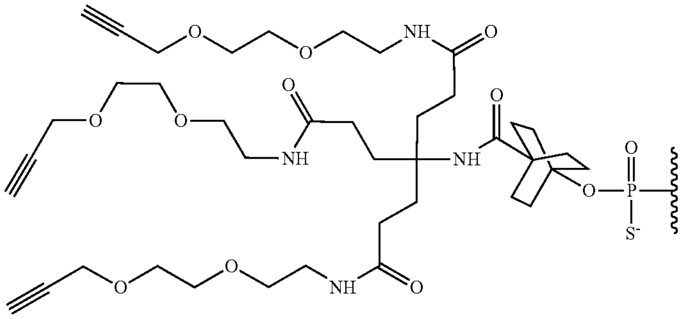 [SMILES: *P(=O)([O-])OC12CCC(C(=O)NC(CCC(=O)NCCOCCOCC#C)(CCC(=O)NCCOCCOCC#C)CCC(=O)NCCOCCOCC#C)(CC1)CC2]
(TriA1k12)s
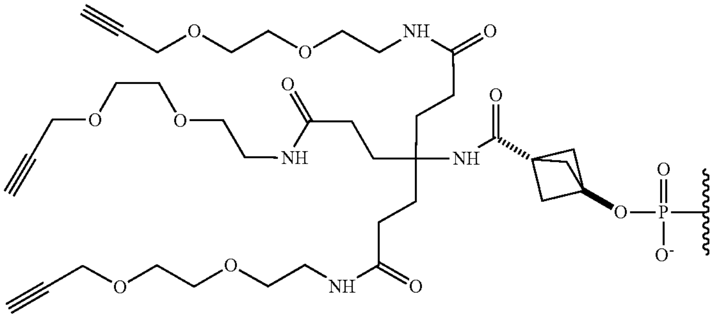 [SMILES: *P(=O)([O-])O[C@]12C[C@@](C(=O)NC(CCC(=O)NCCOCCOCC#C)(CCC(=O)NCCOCCOCC#C)CCC(=O)NCCOCCOCC#C)(C1)C2]
(TriAlk13)

TABLE 7-continued
Structures Representing Various Modified Nucleotides and Linking Groups
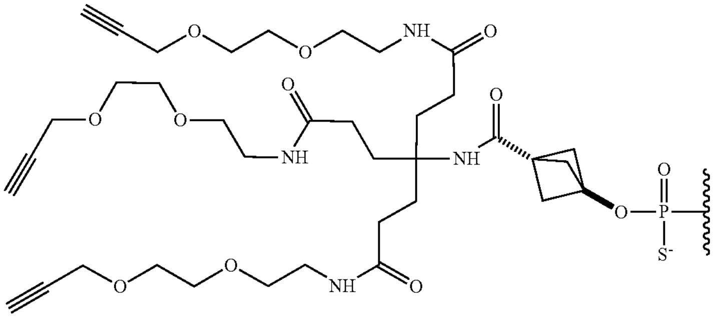
(TriA1k13)s
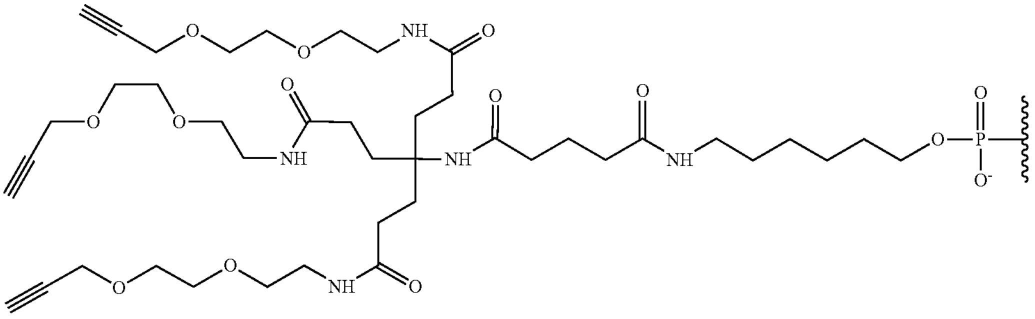
(TriAlk14)
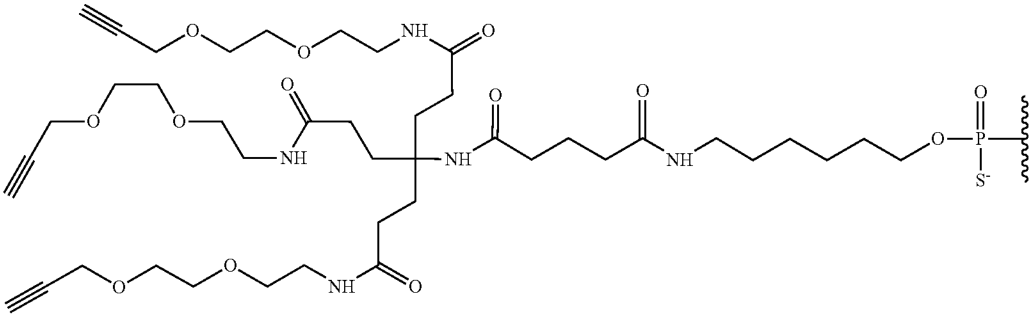 [SMILES: *P(=O)([O-])OCCCCCCNC(=O)CCCC(=O)NC(CCC(=O)NCCOCCOCC#C)(CCC(=O)NCCOCCOCC#C)CCC(=O)NCCOCCOCC#C]
(TriA1k14)s In some embodiments, an RNAi agent includes a linker having the structure of TriAlk 14:

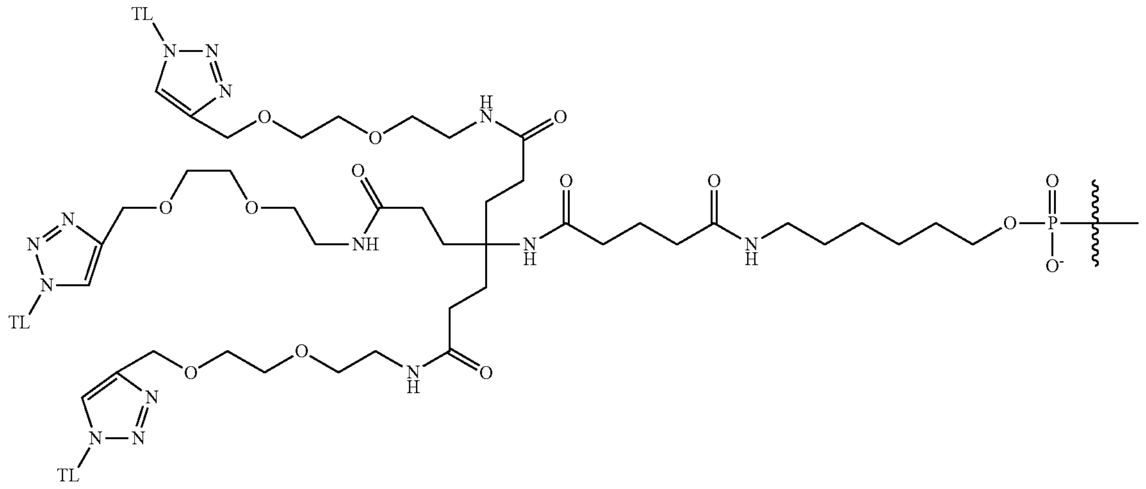

or TriAlk 14s:

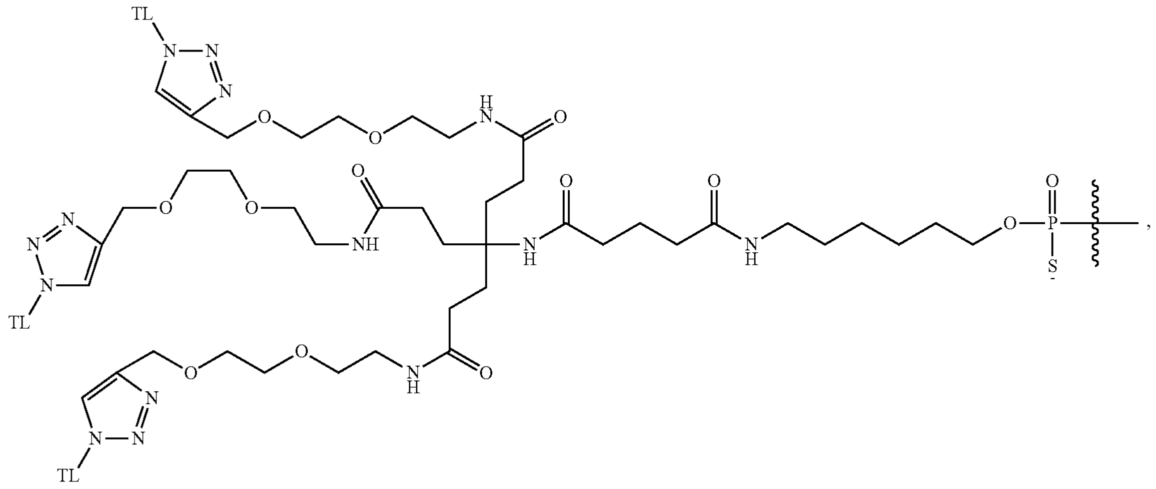

TL comprises a targeting ligand, which is the result of a "click" reaction with a compound of (TriAlk14), or (Trialk14)s and a targeting ligand comprising an azide.

Alternatively, other linking groups known in the art may be used.

In addition or alternatively to linking a HIF-2 alpha RNAi agent to one or more targeting ligands, targeting groups, and/or PK enhancers, in some embodiments, a delivery vehicle may be used to deliver an RNAi agent to a cell or tissue. A delivery vehicle is a compound that can improve delivery of the RNAi agent to a cell or tissue, and can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/022309, WO 2011/104169, and WO 2012/083185, WO 2013/032829, WO 2013/158141, each of which is incorporated herein by reference), or other delivery systems available in the art.

Pharmaceutical Compositions

In some embodiments, the present disclosure provides pharmaceutical compositions that include, consist of, or consist essentially of, one or more of the HIF-2 alpha RNAi agents disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (for example, antihistamine, diphenhydramine, etc.), small molecule drug, antibody, antibody fragment, aptamers, and/or vaccines.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agent with a known therapeutic benefit.

The pharmaceutical compositions can be administered in a number of ways depending upon whether local or systemic treatment is desired and upon the area to be treated. Administration can be made by any way commonly known in the art, such as, but not limited to, topical (for example, by a transdermal patch), pulmonary (for example, by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (for example, via an implanted device), intracranial, intraparenchymal, intrathecal, and intraventricular, administration. In some embodiments, the pharmaceutical compositions described herein are administered by subcutaneous injection. The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (for example, antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing a HIF-2 alpha RNAi agent are also an object of the present invention, as are processes for the manufacture of such medicaments, which processes comprise bringing one or more compounds containing a HIF-2 alpha RNAi agent, and, if desired, one or more other substances with a known therapeutic benefit, into a pharmaceutically acceptable form.

The described HIF-2 alpha RNAi agents and pharmaceutical compositions comprising HIF-2 alpha RNAi agents disclosed herein may be packaged or included in a kit, container, pack, or dispenser. The HIF-2 alpha RNAi agents and pharmaceutical compositions comprising the HIF-2 alpha RNAi agents may be packaged in pre-filled syringes or vials.

Methods of Treatment and Inhibition of Expression

The HIF-2 alpha RNAi agents disclosed herein can be used to treat a subject (for example, a human or other mammal) having a disease or disorder that would benefit from administration of the RNAi agent. In some embodiments, the RNAi agents disclosed herein can be used to treat a subject (for example, a human) that would benefit from reduction and/or inhibition in expression of HIF-2 alpha mRNA and/or HIF-2 alpha (EPAS1) protein levels, for example, a subject that has been diagnosed with or is suffering from symptoms related to cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preeclampsia, inflammation, chronic inflammation, neovascular diseases, and rheumatoid arthritis.

In some embodiments, the subject is administered a therapeutically effective amount of any one or more HIF-2 alpha RNAi agents. Treatment of a subject can include therapeutic and/or prophylactic treatment. The subject is administered a therapeutically effective amount of any one or more HIF-2 alpha RNAi agents described herein. The subject can be a human, patient, or human patient. The subject may be an adult, adolescent, child, or infant. Administration of a pharmaceutical composition described herein can be to a human being or animal.

The HIF-2 alpha RNAi agents described herein can be used to treat at least one symptom in a subject having a HIF-2 alpha-related disease or disorder, or having a disease or disorder that is mediated at least in part by HIF-2 alpha gene expression. In some embodiments, the HIF-2 alpha RNAi agents are used to treat or manage a clinical presentation of a subject with a disease or disorder that would benefit from or be mediated at least in part by a reduction in HIF-2 alpha mRNA. The subject is administered a therapeutically effective amount of one or more of the HIF-2 alpha RNAi agents or HIF-2 alpha RNAi agent-containing compositions described herein. In some embodiments, the methods disclosed herein comprise administering a composition comprising a HIF-2 alpha RNAi agent described herein to a subject to be treated. In some embodiments, the subject is administered a prophylactically effective amount of any one or more of the described HIF-2 alpha RNAi agents, thereby treating the subject by preventing or inhibiting the at least one symptom.

In certain embodiments, the present disclosure provides methods for treatment of diseases, disorders, conditions, or pathological states mediated at least in part by HIF-2 alpha gene expression, in a patient in need thereof, wherein the methods include administering to the patient any of the HIF-2 alpha RNAi agents described herein.

In some embodiments, the gene expression level and/or mRNA level of a HIF-2 alpha gene in a subject to whom a described HIF-2 alpha RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the HIF-2 alpha RNAi agent or to a subject not receiving the HIF-2 alpha RNAi agent. The gene expression level and/or mRNA level in the subject may be reduced in a cell, group of cells, and/or tissue of the subject.

In some embodiments, the HIF-2 alpha protein level in a subject to whom a described HIF-2 alpha RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HIF-2 alpha RNAi agent or to a subject not receiving the HIF-2 alpha RNAi agent. The protein level in the subject may be reduced in a cell, group of cells, tissue, blood, and/or other fluid of the subject.

A reduction in HIF-2 alpha mRNA levels and HIF-2 alpha protein levels can be assessed by any methods known in the art. As used herein, a reduction or decrease in HIF-2 alpha mRNA level and/or protein level are collectively referred to herein as a reduction or decrease in HIF-2 alpha or inhibiting or reducing the expression of HIF-2 alpha. The Examples set forth herein illustrate known methods for assessing inhibition of HIF-2 alpha gene expression.

In some embodiments, HIF-2 alpha RNAi agents may be used in the preparation of a pharmaceutical composition for use in the treatment of a disease, disorder, or symptom that is mediated at least in part by HIF-2 alpha gene expression. In some embodiments, the disease, disorder, or symptom that is mediated at least in part by HIF-2 alpha gene expression is cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preeclampsia, inflammation, chronic inflammation, neovascular diseases, or rheumatoid arthritis.

In some embodiments, methods of treating a subject are dependent on the body weight of the subject. In some embodiments, HIF-2 alpha RNAi agents may be administered at a dose of about 3 mg/kg to about 80 mg/kg of body weight of the subject. In other embodiments HIF-2 alpha RNAi agents may be administered at a dose of about 5 mg/kg to about 20 mg/kg of body weight of the subject.

In some embodiments, HIF-2 alpha RNAi agents may be administered in a split dose, meaning that two doses are given to a subject in a short (for example, less than 24 hour) time period. In some embodiments, about half of the desired daily amount is administered in an initial administration, and the remaining about half of the desired daily amount is administered approximately four hours after the initial administration.

In some embodiments, HIF-2 alpha RNAi agents may be administered once a week (weekly). In other embodiments, HIF-2 alpha RNAi agents may be administered biweekly (once every other week).

In some embodiments, the dose of the HIF-2 alpha RNAi agent administered is a fixed dose of 225 mg administered weekly. In some embodiments, the dose of the HIF-2 alpha RNAi agent administered is a fixed dose of 525 mg administered weekly. In some embodiments, the dose of the HIF-2 alpha RNAi agent administered is a fixed dose of 1,050 mg administered weekly. In some embodiments, the HIF-2 alpha RNAi agent is administered by intravenous infusion.

In some embodiments, HIF-2 alpha RNAi agents or compositions containing HIF-2 alpha RNAi agents may be used for the treatment of a disease, disorder, or symptom that is mediated at least in part by HIF-2 alpha (EPAS1) gene expression. In some embodiments, the disease, disorder or symptom that is mediated at least in part by HIF-2 alpha (EPAS1) gene expression is ccRCC.

Cells, Tissues, and Non-Human Organisms

Cells, tissues, and non-human organisms that include at least one of the HIF-2 alpha RNAi agents described herein is contemplated. The cell, tissue, or non-human organism is made by delivering the HIF-2 alpha RNAi agent to the cell, tissue, or non-human organism by any means available in the art. In some embodiments, the cell is a mammalian cell, including, but not limited to, a human cell.

The above provided embodiments and items are now illustrated with the following, non-limiting examples.

EXAMPLES

The following examples are not limiting and are intended to illustrate certain embodiments disclosed herein.

Example 1. Syntheses of HIF-2 Alpha RNAi Agents and Compositions Containing HIF-2 Alpha RNAi Agents The following describes the general procedures for the syntheses of certain HIF-2 alpha RNAi agents, and conjugates thereof, that are illustrated in the non-limiting Examples set forth herein.

Synthesis of RNAi Agents. RNAi agents can be synthesized using methods generally known in the art. For the synthesis of the RNAi agents illustrated in the Examples set forth herein, the sense and antisense strands of the RNAi agents were synthesized according to phosphoramidite technology on solid phase used in oligonucleotide synthesis. Depending on the scale, a MerMade96E® (Bioautomation), a MerMade12® (Bioautomation), or an Oligopilot 100 (GE Healthcare) was used. Syntheses were performed on a solid support made of controlled pore glass (CPG, 500 Å or 600 Å, obtained from Prime Synthesis, Aston, PA, USA) or polystyrene (obtained from Kinovate, Oceanside, CA, USA). All RNA and 2'-modified RNA phosphoramidites were purchased from Thermo Fisher Scientific (Milwaukee, WI, USA), ChemGenes (Wilmington, MA, USA), or Hongene Biotech (Morrisville, NC, USA). Specifically, the following 2'-O-methyl phosphoramidites that were used include the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites and 2'-O-propargyl phosphoramidites carried the same protecting groups as the 2'-O-methyl phosphoramidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes. The following UNA phosphoramidites that were used included the following: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile or a 200 mM solution of xanthane hydride (TCI America, Portland, OR, USA) in pyridine was employed.

TFA aminolink phosphoramidites were also commercially purchased (ThermoFisher) to introduce the (NH2-C6) reactive group linkers. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETr, 250 mM in acetonitrile) was used as activator solution. Coupling times were 10 min (RNA), 90 sec (2' O-Me), and 60 sec (2' F). Trialkyne-containing phosphoramidites were synthesized to introduce the respective (TriAlk #) linkers. When used in connection with the RNAi agents presented in certain Examples herein, trialkyne-containing phosphoramidites were dissolved in anhydrous dichloromethane or anhydrous acetonitrile (50 mM), while all other amidites were dissolved in anhydrous acetonitrile (50 mM), and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F).

For some RNAi agents, a linker, such as a C6-SS-C6 or a 6-SS-6 group, was introduced at the 3' terminal end of the sense strand. Pre-loaded resin was commercially acquired with the respective linker. Alternatively, for some sense strands, a dT resin was used and the respective linker was then added via standard phosphoramidite synthesis.

Cleavage and deprotection of support bound oligomer. After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

Purification. Crude oligomers were purified by anionic exchange HPLC using a TSKgel SuperQ-5PW 13 µm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G25 fine with a running buffer of 100 mM ammonium bicarbonate, pH 6.7 and 20% Acetonitrile or filtered water.

Annealing. Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.037 mg/(mL·cm) or was calculated from an experimentally determined extinction coefficient.

Synthesis of Linking Agent TriAlk 14

In some embodiments, linking agents such as TriAlk 14 may be attached to the RNAi agent in the form of phosphoramidites, by reacting a phosphoramidite comprising the trialkyne, or by synthesizing an RNAi agent comprising a reactive group such as a terminal amine and reacting the RNAi agent with a trialkyne moiety comprising an activated ester after the RNAi agent has been cleaved from the resin. The following procedures provide a method for synthesizing an activated ester version of TriAlk 14 (compound 22) or a phosphoramidite version of TriAlk 14 (compound 14)

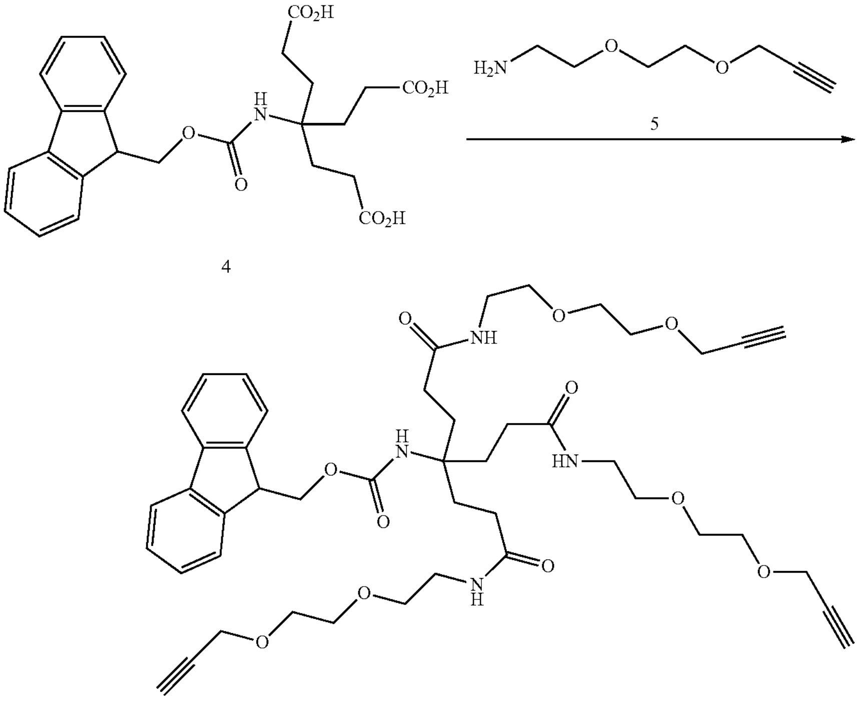

4

6

To a 3-L jacketed reactor was added 500 mL DCM and 4 (75.0 g, 0.16 mol). The internal temperature of the reaction was cooled to 0° C. and TBTU (170.0 g, 0.53 mol) was added. The suspension was then treated with the amine 5 (75.5 g, 0.53 mol) dropwise keeping the internal temperature less than 5° C. The reaction was then treated with DIPEA (72.3 g, 0.56 mol) slowly, keeping the internal temperature less than 5° C. After the addition was complete, the reaction was warmed up to 23° C. over 1 hour, and allowed to stir for 3 hours. A 10% kicker charge of all three reagents were added and allowed to stir an additional 3 hours. The reaction was deemed complete when <1% of 4 remained. The reaction mixture was washed with saturated ammonium chloride solution (2×500 mL) and once with saturated sodium bicarbonate solution (500 mL). The organic layer was then dried over sodium sulfate and concentrated to an oil. The mass of the crude oil was 188 g which contained 72% 6 by QNMR. The crude oil was carried to the next step. Calculated mass for $C_{46}H_{60}N_4O_{11}$=845.0 m/z. Found [M+H]=846.0.

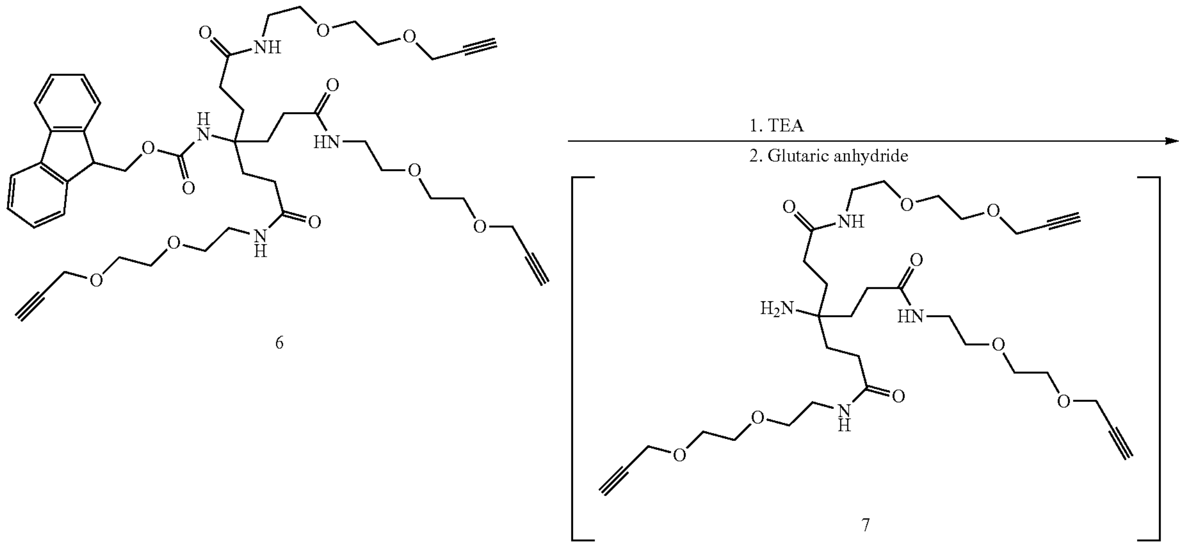

6

7

-continued

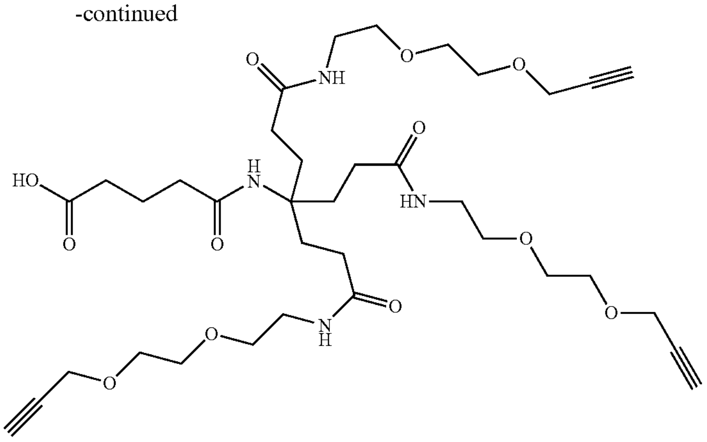

8

Figure 2:
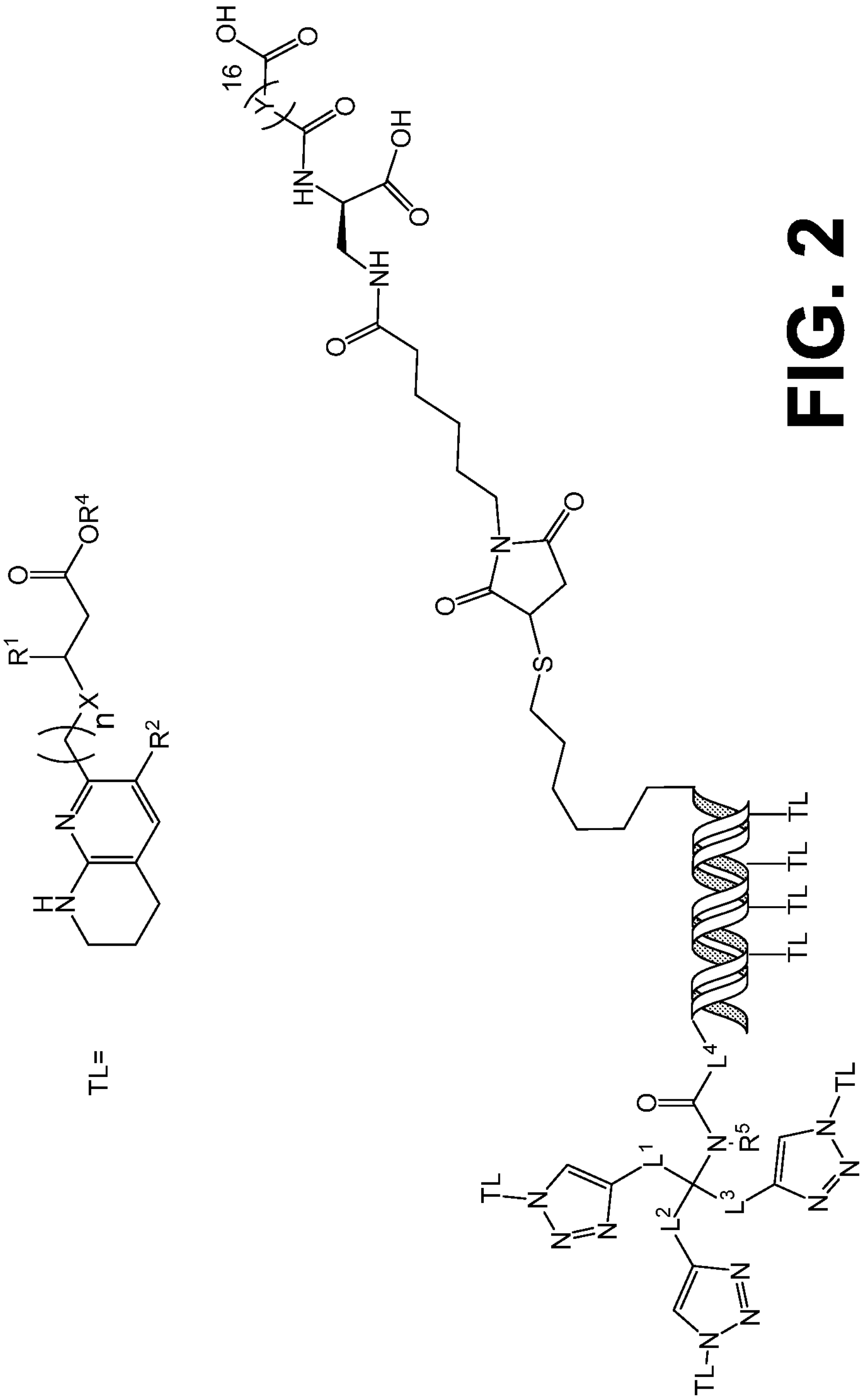
FIG. 2. Schematic diagram of a HIF-2 alpha RNAi agent (shown as the double-helix) shown linked to a PK enhancer on one end, and a tridentate scaffold suitable for forming a tridentate targeting group that includes three targeting ligands on the other end. The HIF-2 alpha RNA agent diagram further shows certain possible sites for linking targeting ligands (represented as "TL" in FIG. 2) to the HIF-2 alpha RNAi agent, including showing four targeting ligands linked to internal nucleotides.
Figure 3A:
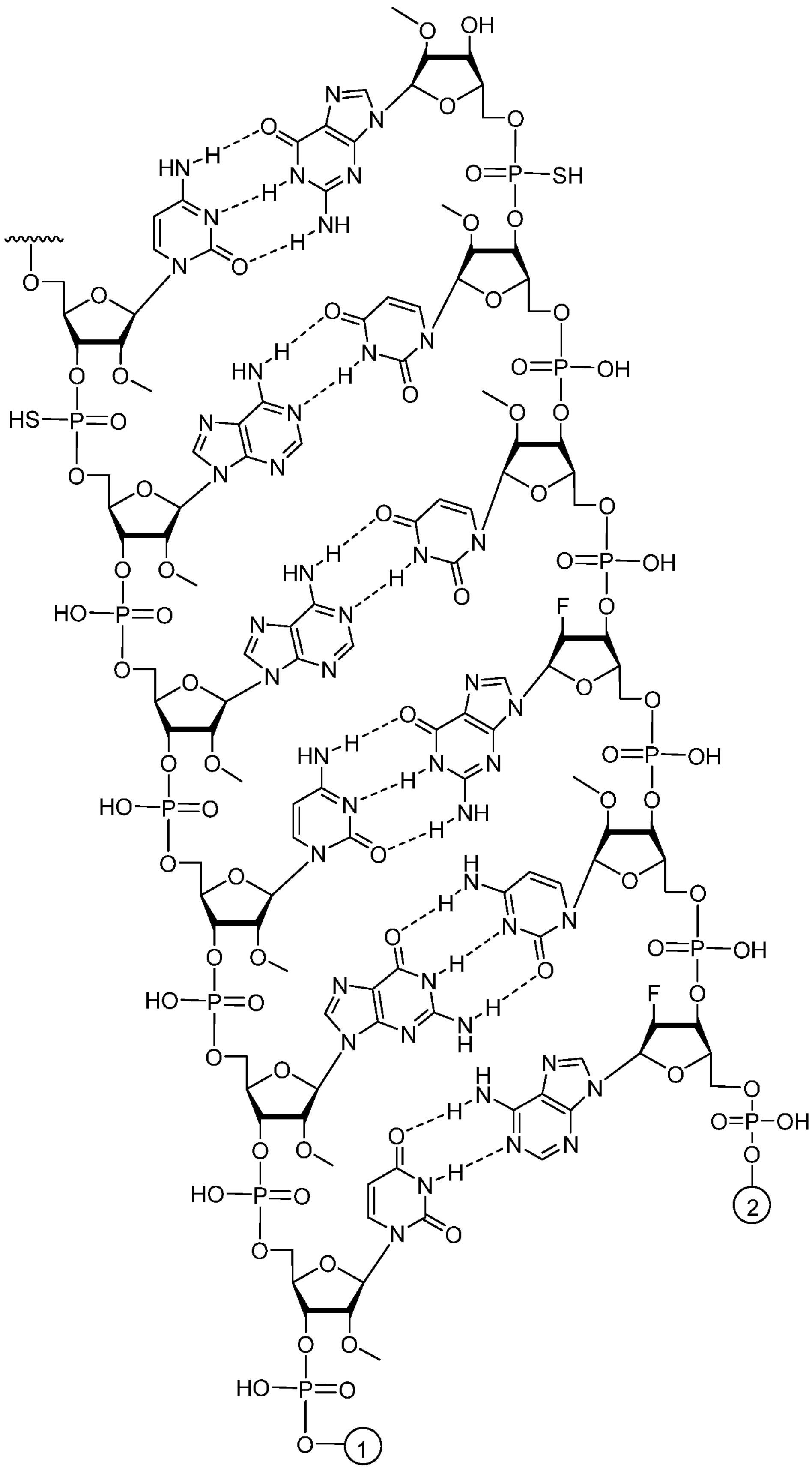
FIG. 3A to 3D. Chemical structure representation of HIF-2 alpha RNAi agent AD06299, in a free acid form, showing "TL" at the 2' position of nucleotides 2, 4, 6, and 8 (3'→5') of the sense strand starting from the first nucleotide that forms a base pair with the antisense strand (starting on FIG. 3D and continuing to FIG. 3C). "TL" represents the site of conjugation of a targeting ligand on these internal nucleotides.
Figure 3B:
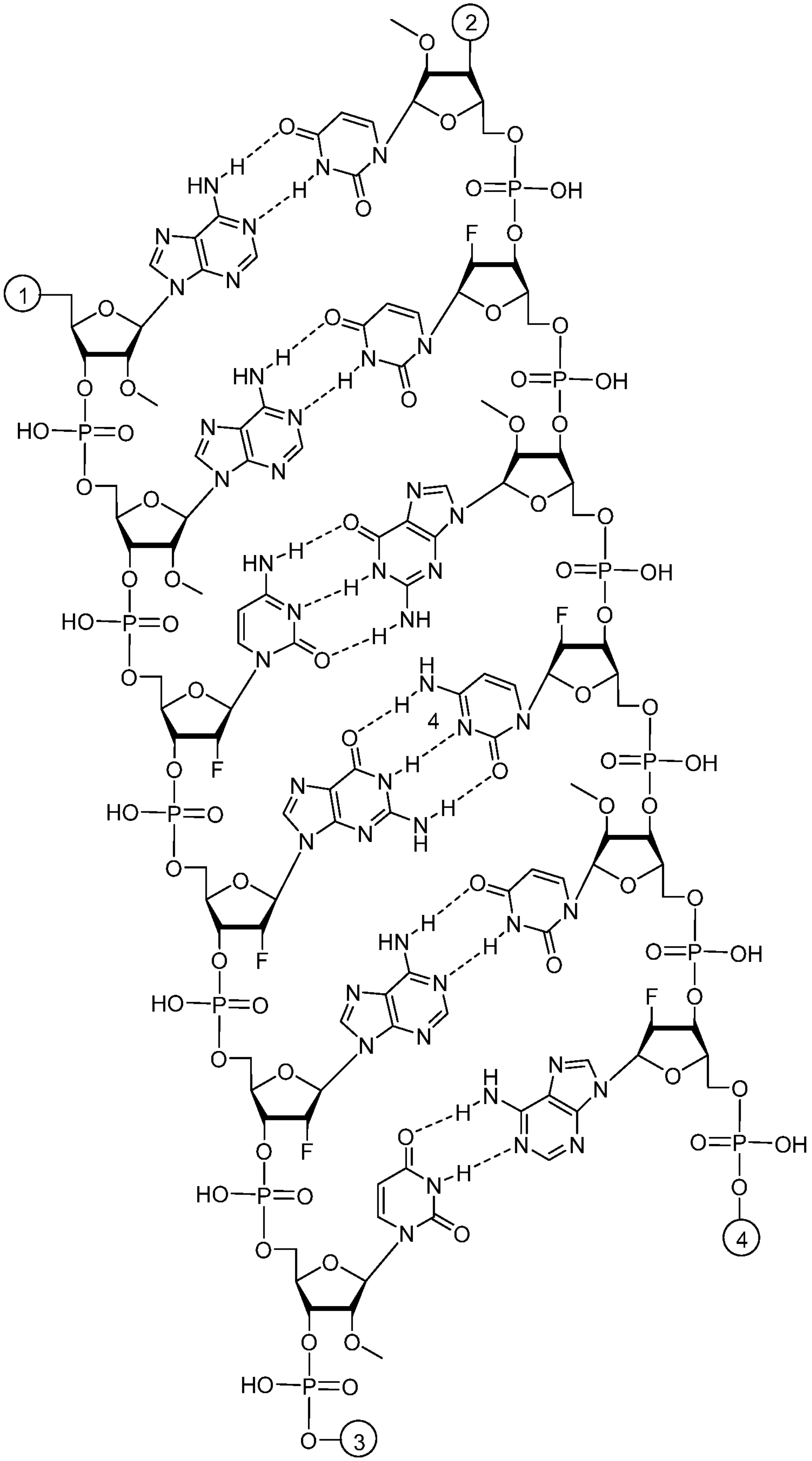
Figure 3C:
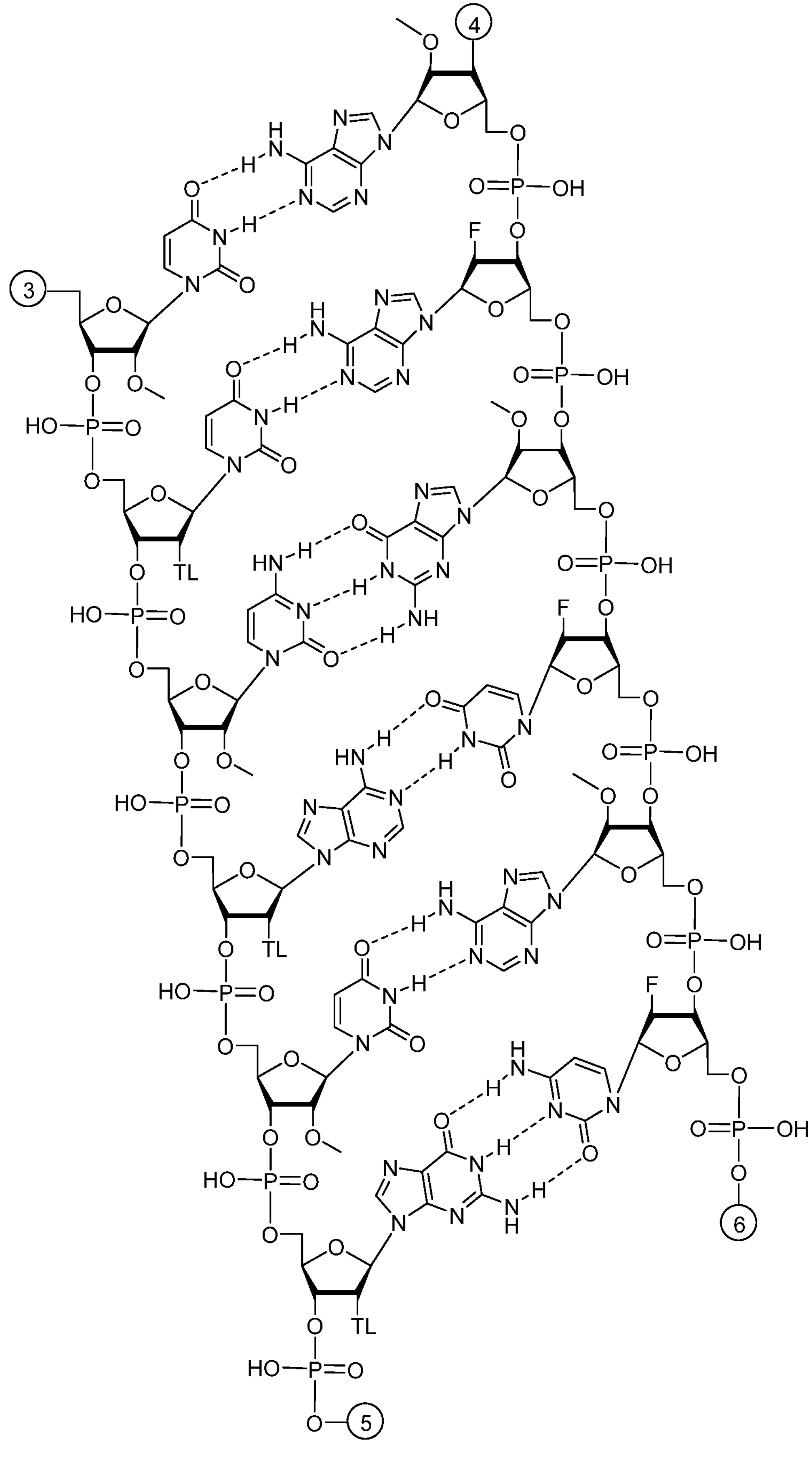
Figure 3D:
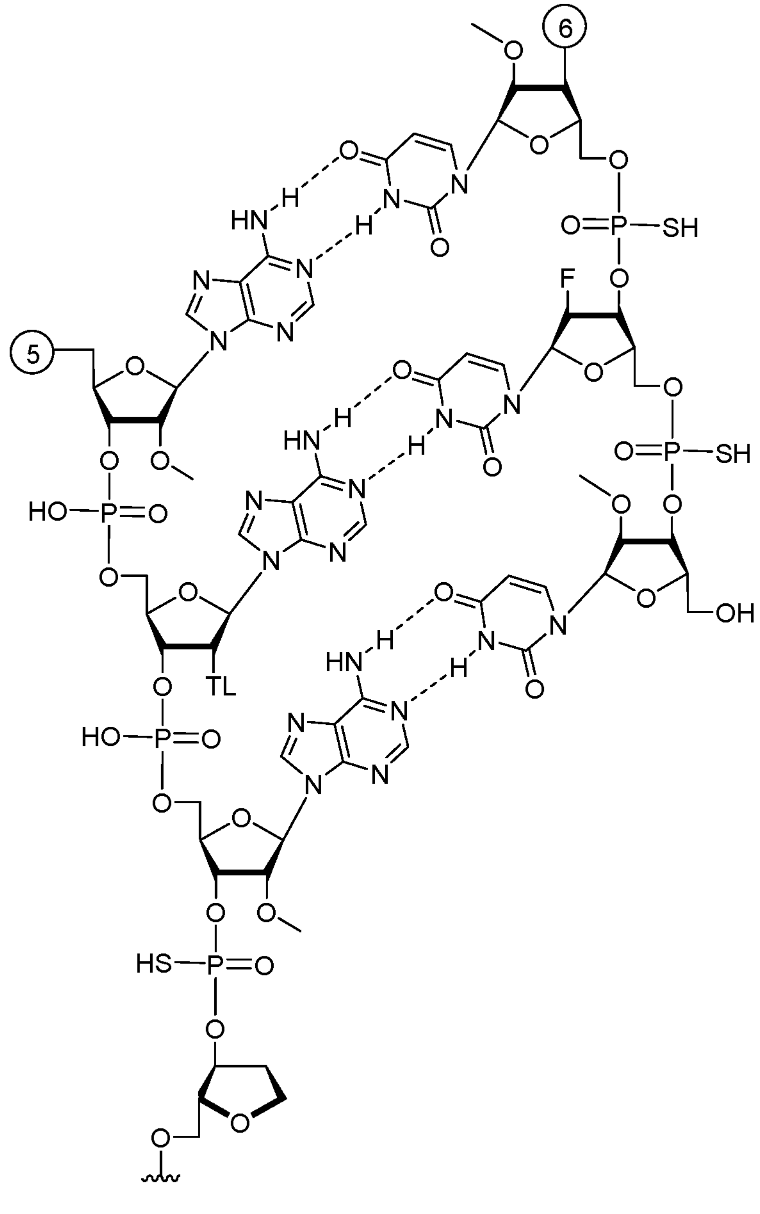

The 121.2 g of crude oil containing 72 wt % compound 6 (86.0 g, 0.10 mol) was dissolved in DMF (344 mL) and treated with TEA (86 mL, 20 v/v %), keeping the internal temperature below 23° C. The formation of dibenzofulvene (DBF) relative to the consumption of Fmoc-amine 6 was monitored via HPLC method 1 (FIG. 2) and the reaction was complete within 10 hours. To the solution was added glutaric anhydride (12.8 g, 0.11 mol) and the intermediate amine 7 was converted to compound 8 within 2 hours. Upon completion, the DMF and TEA were removed at 30° C. under reduced pressure resulting in 100 g of a crude oil. Due to the high solubility of compound 7 in water, an aqueous workup could not be used, and chromatography is the only way to remove DBF, TMU, and glutaric anhydride. The crude oil (75 g) was purified on a Teledyne ISCO Combi-Flash® purification system in three portions. The crude oil (25 g) was loaded onto a 330 g silica column and eluted from 0-20% methanol/DCM over 30 minutes resulting in 42 g of compound 8 (54% yield over 3 steps). Calculated mass for $C_{36}H_{55}N_4O_{12}$=736.4 m/z. Found [M+H]=737.0.

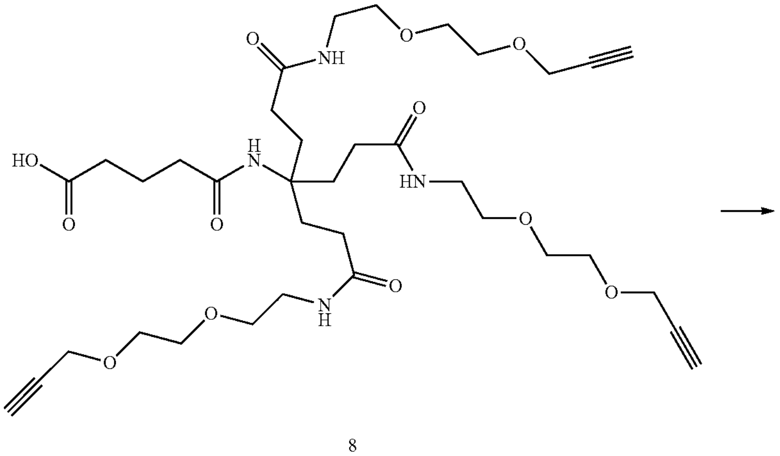

8

-continued

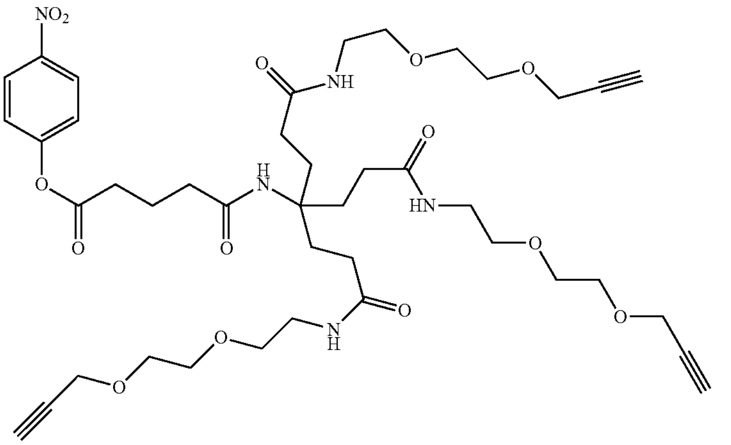

9

Compound 22

Compound 8 (42.0 g, 0.057 mol) was co-stripped with 10 volumes of acetonitrile prior to use to remove any residual methanol from chromatography solvents. The oil was redissolved in DMF (210 mL) and cooled to 0° C. The solution was treated with 4-nitrophenol (8.7 g, 0.063 moL) followed by EDC-hydrochloride (12.0 g, 0.063 mol) and found to reach completion within 10 hours. The solution was cooled to 0° C. and 10 volumes ethyl acetate was added followed by 10 volumes saturated ammonium chloride solution, keeping the internal temperature below 15° C. The layers were allowed to separate and the ethyl acetate layer was washed with brine. The combined aqueous layers were extracted twice with 5 volumes ethyl acetate. The combined organic layers were dried over sodium sulfate and concentrated to an oil. The crude oil (55 g) was purified on a Teledyne ISCO Combi-Flash® purification system in three portions. The crude oil (25 g) was loaded onto a 330 g silica column and eluted from 0-10% methanol/DCM over 30 minutes resulting in 22 g of pure 9 (Compound 22) (50% yield). Calculated mass for $C_{42}H_{59}N_5O_{14}$=857.4 m/z. Found [M+H]=858.0.

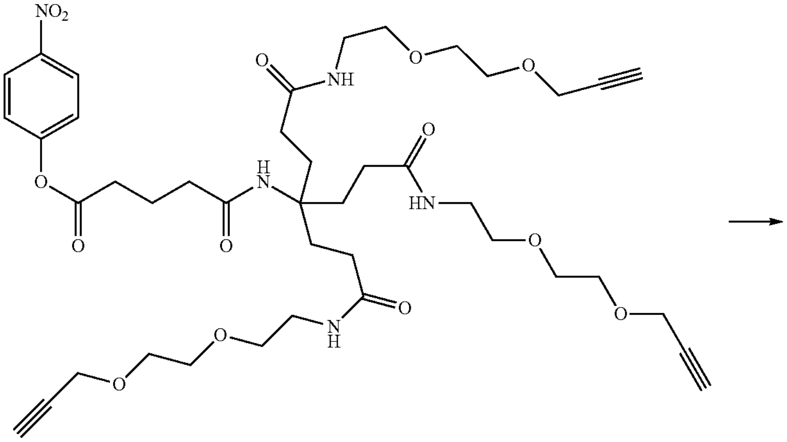

9

-continued

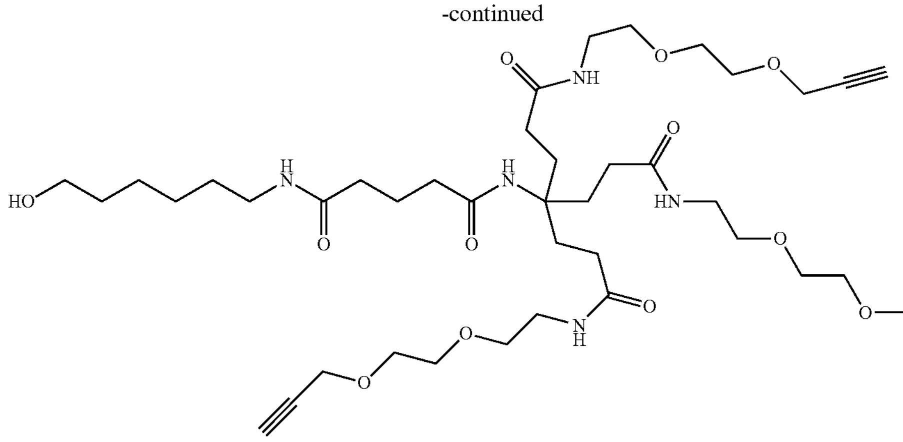

10

A solution of ester 9 (49.0 g, 57.1 mmol) and 6-amino-1-hexanol (7.36 g, 6.28 mmol) in dichloromethane (3 volumes) was treated with triethylamine (11.56 g, 111.4 mmol) dropwise. The reaction was monitored by observing the disappearance of compound 9 on HPLC Method 1 and was found to be complete in 10 minutes. The crude reaction mixture was diluted with 5 volumes dichloromethane and washed with saturated ammonium chloride (5 volumes) and brine (5 volumes). The organic layer was dried over sodium sulfate and concentrated to an oil. The crude oil was purified on a Teledyne ISCO Combi-Flash® purification system using a 330 g silica column. The 4-nitrophenol was eluted with 100% ethyl acetate and 10 was flushed from the column using 20% methanol/DCM resulting in a colorless oil (39 g, 81% yield). Calculated mass for $C_{42}H_{69}N_5O_{12}$=836.0 m/z. Found [M+H]=837.0.

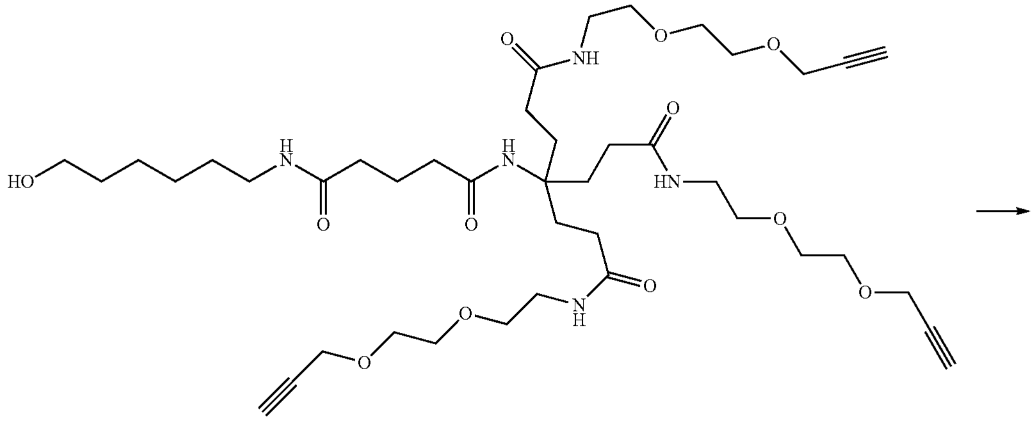

10

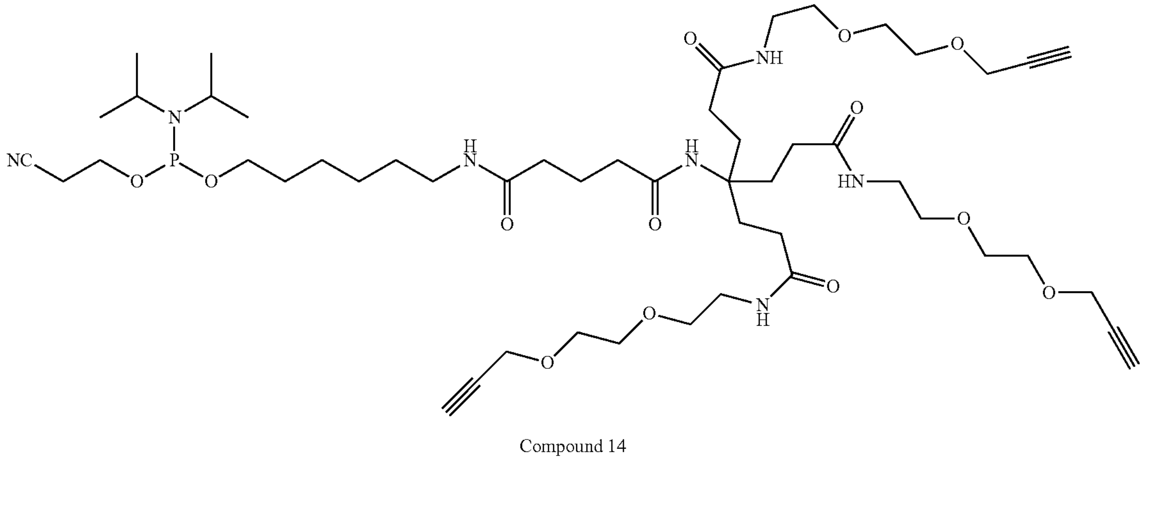

Compound 14

Alcohol 10 was co-stripped twice with 10 volumes of acetonitrile to remove any residual methanol from chromatography solvents and once more with dry dichloromethane (KF<60 ppm) to remove trace water. The alcohol 10 (2.30 g, 2.8 mmol) was dissolved in 5 volumes dry dichloromethane (KF<50 ppm) and treated with diisopropylammonium tetrazolide (188 mg, 1.1 mmol). The solution was cooled to 0° C. and treated with 2-cyanoethyl N,N,N',N'-tetraisopropylphosphoramidite (1.00 g, 3.3 mmol) dropwise. The solution was removed from ice-bath and stirred at 20° C. The reaction was found to be complete within 3-6 hours. The reaction mixture was cooled to 0° C. and treated with 10 volumes of a 1:1 solution of saturated ammonium bicarbonate/brine and then warmed to ambient over 1 minute and allowed to stir an additional 3 minutes at 20° C. The biphasic mixture was transferred to a separatory funnel and 10 volumes of dichloromethane was added. The organic layer was separated, and washed with 10 volumes of saturated sodium bicarbonate solution to hydrolyze unreacted bis-phosphorous reagent. The organic layer was dried over sodium sulfate and concentrated to an oil resulting in 3.08 g of 94 wt % Compound 14. Calculated mass for $C_{51}H_{86}N_7O_{13}P$=1035.6 m/z. Found [M+H]=1036.

Post-Synthetic Conjugation of Trialkyne scaffold. Either prior to or after annealing, the 5' or 3' amine functionalized sense strand of an RNAi agent can be conjugated to a trialkyne scaffold. The following describes the conjugation of trialkyne scaffold to the annealed duplex: Amine functionalized duplex was dissolved in 90% DMSO/10% $H_2O$, at ~50-70 mg/mL. 40 eq triethylamine was added, followed by 3 eq trialkyne-PNP. Once complete, the conjugate was precipitated twice in a solvent system of 1× phosphate buffered saline/acetonitrile (1:14 ratio), and dried.

Conjugation of Targeting Ligands to the HIF-2 RNAi Agents. Either prior to or after annealing and prior to or after conjugation of a PK enhancer, one or more targeting ligands can be linked to the HIF-2 RNAi agents disclosed herein. The following describes the general conjugation process used to link integrin targeting ligands to an alkyne-functionalized linker (for example, (TriAlk) or a 2'-O-propargyl group on an internal nucleotide). The procedure describes the addition of three targeting ligands to a tridentate targeting group scaffold. The same procedure may be used to link targeting ligands to internal nucleotides, though the number of equivalents of targeting ligands may be adjusted in view of the number of targeting ligands to be added: Stock solutions of 0.5M Tris(3-hydroxypropyltriazolylmethyl) amine (THPTA), 0.5M of Cu(II) sulfate pentahydrate (Cu (II)$SO_4$·5$H_2O$) and 2M solution of sodium ascorbate were prepared in deionized water. A 75 mg/mL solution in DMSO of the desired integrin ligand was made. In a vial containing the sense strand (75 mg/mL in deionized water), integrin ligands were added to the reaction (2 eq/alkyne) with stirring. Triethylamine (40 eq/sense strand) was added to the reaction vial. In a separate vial, 5 parts 0.5M THPTA was mixed with 1 part 0.5M Cu(II)$SO_4$·5$H_2O$, vortexed, and incubated at room temp for 5 min. After 5 min, THPTA/Cu solution (0.5 eq Cu/alkyne) was added to the reaction vial. Immediately afterwards, 2M ascorbate (5 eq/Cu) was added to the reaction vial. Once the reaction was complete (typically complete in 0.5-1 h), the reaction was immediately purified by non-denaturing anion exchange chromatography. Unless otherwise specified, all constructs described in the examples below including a tridentate targeting group include a group having the structure TriAlk14:

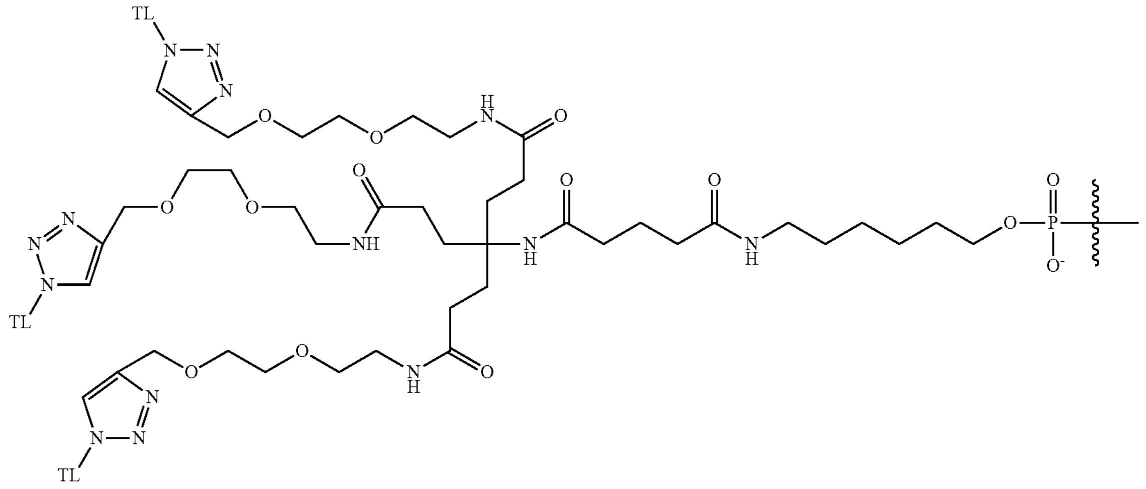

TriAlk14s:

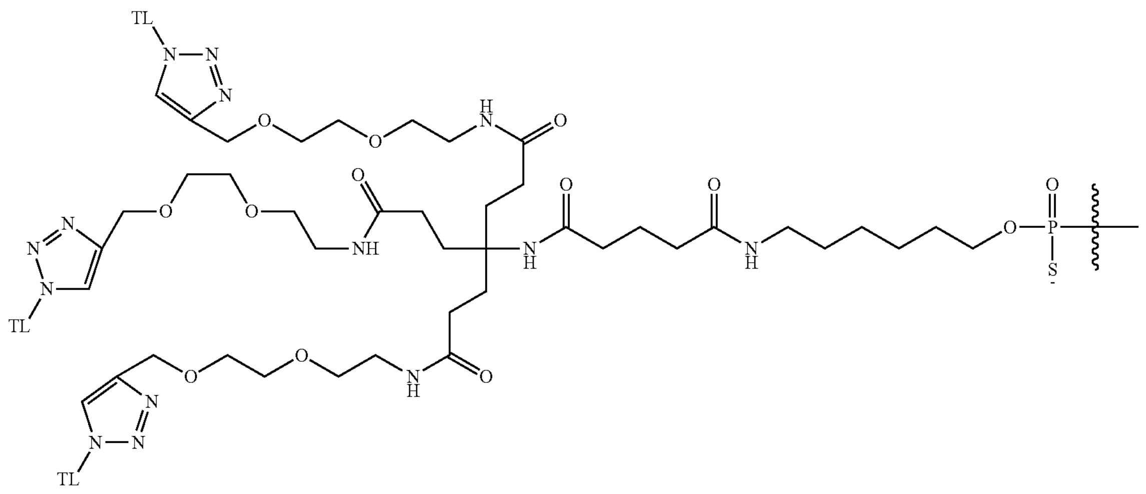

wherein TL comprises a targeting ligand and  indicates the point of connection to the RNAi agent.

Conjugation of PK Enhancers to the HIF-2 RNAi Agents. Either prior to or after annealing and prior to or after conjugation of one or more targeting ligands, one or more PK enhancers can be linked to the HIF-2 alpha RNAi agents disclosed herein. The following describes the general conjugation process used to link PK enhancers to the constructs set forth in the Examples depicted herein. The following describes the general process used to link the maleimide-functionalized PK enhancer to the (C6-SS-C6) or (6-SS-6) functionalized sense strand of a HIF-2 alpha RNAi agent by undertaking a dithiothreitol reduction of disulfide followed by a thiol-Michael Addition of the respective PK enhancer: In a vial, functionalized sense strand was dissolved at 75 mg/mL in 0.1M Hepes pH 8.5 buffer, and 25 eq of dithiothreitol was added. Once the reaction was complete (typically complete in 0.5-1 h), the conjugate was precipitated three times in a solvent system of 1× phosphate buffered saline/acetonitrile (1:40 ratio), and dried. A 75 mg/mL solution of maleimide functionalized PK enhancer in DMSO was then made. The disulfide-reduced (3' C6-SH, 5' HS-C6, or 3' 6-SH functionalized) sense strand was dissolved 100 mg/mL in deionized water, and three equivalents of maleimide-functionalized PK enhancer was added. Once the reaction was complete (typically complete in 1 h-3 h), the conjugate was precipitated in a solvent system of 1× phosphate buffered saline/acetonitrile (1:40 ratio), and dried.

Methods of Making Targeting Ligands

Some of the abbreviations used in the following experimental details of the synthesis of the examples are defined as follows: h or hr=hour(s); min=minute(s); mol=mole(s); mmol=millimole(s); M=molar; μM=micromolar; g=gram(s); sg=microgram(s); rt or RT=room temperature; L=liter(s); mL=milliliter(s); wt=weight; $Et_2O$=diethyl ether; THF=tetrahydrofuran; DMSO=dimethyl sulfoxide; EtOAc=ethyl acetate; $Et_3N$ or TEA=triethylamine; i-$Pr_2NEt$ or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl or TBDMSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; $N_2$=nitrogen; $SiO_2$=silica; RT=retention time; PTSA=para-toluenesulfonic acid; PPTS=pyridiniumpara-toluenesulfonate.

Synthesis of Structure 1c ((S)-3-(6-((1-azido-15-oxo-3,6,9,12-tetraoxa-16-azanonadecan-19-yl)oxy)pyridin-3-yl)-3-(2-oxo-3-(3-(5,6,7,8-tetrahydro-1,8-naphthyridin-2-yl)propyl)imidazolidin-1-yl)propanoic acid)

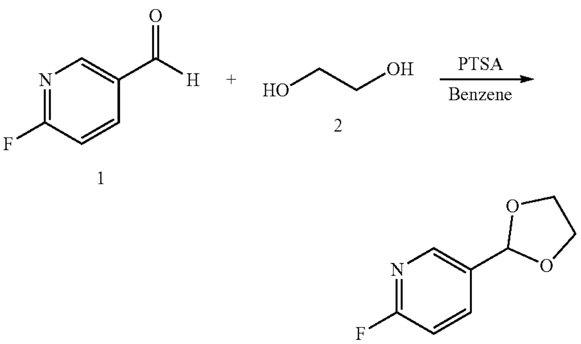

1 2 3

A mixture containing compound 1 (1.03 g, 8.23 mmol), compound 2 (0.92 g 14.8 mol), and PTSA hydrate (156 mg, 0.82 mmol) in benzene (25 mL) was refluxed in a Dean Stark apparatus overnight. The following morning, the reaction mixture was poured into saturated sodium bicarbonate, and ethyl acetate was subsequently added. The organic phase was separated, filtered over sodium sulfate, and concentrated to afford compound 3 in 95% yield, which was subsequently used without further purification.

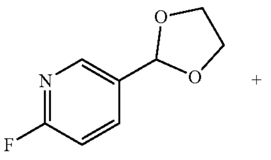

3

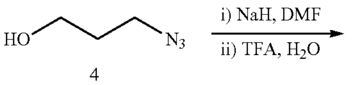

4

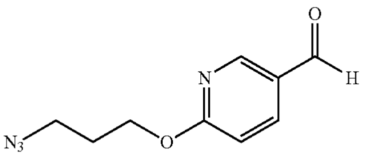

5

To a solution containing compound 4 (5.39 g, 53.3 mmol) and 3 Å molecular sieves in DMF (100 mL) was added sodium hydride (60 wt %, 2.13 g, 53.3 mmol), and the reaction was agitated for 1 hour. A solution of compound 3 (7.52 g, 7.52 g) in DMF (20 mL) was subsequently added and the suspension was heated at 80° C. overnight. Upon completion, the suspension was filtered over a cotton plug and concentrated under reduced pressure. The residue was partitioned between diethyl ether and water, and the organic phase was separated, filtered over sodium sulfate, and concentrated under reduced pressure. The residue was treated with 20 ml of 10% $H_2O$ in TFA and stirred for 30 minutes. Upon completion, the solution was chilled to 0° C. and the pH was adjusted to 11 with 6M NaOH, upon which the product precipitated as an oil. Compound 5 was extracted three times from the oily suspension with diethyl ether. The organic phases were combined, filtered over sodium sulfate, and concentrated. Compound 5 was then isolated in 26% yield by separation on silica eluting a gradient of ethyl acetate in hexanes.

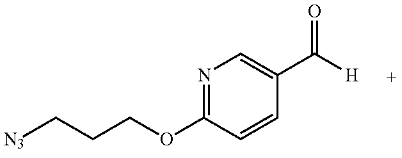

5

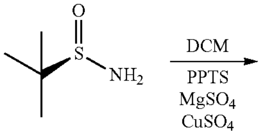

6

-continued

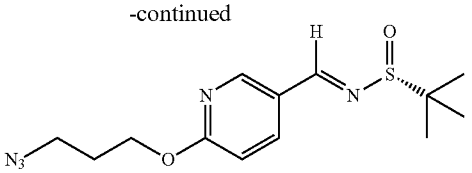

7

A mixture containing compound 5 (2.29 g, 9.94 mmol), compound 6 (4.82 g, 39.8 mmol), PPTS (125 mg, 0.50 mmol), magnesium sulfate (3 g, 24.9 mmol), copper sulfate (3.97 g, 24.9 mmol), and 3 angstrom molecular sieves in DCM (22 mL) was heated to reflux overnight. Upon completion, the mixture was filtered and concentrated under reduced pressure. Compound 7 was then isolated in 76% yield by separation on silica eluting a gradient of ethyl acetate in hexanes.

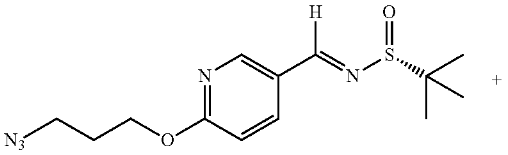

7

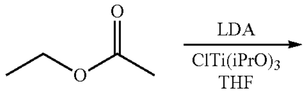

8

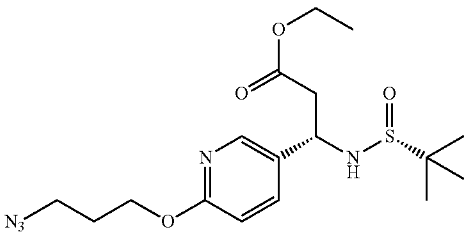

9

A flame dried flask was charged with THF (40 mL) and diisopropylamine (2.29 g, 22.6 mmol). It was cooled to −20° C. and n-BuLi (2.5 M, 8.64 mL, 21.6 mmol) was added via cannula. The solution was stirred for 10 min at −20° C. then cooled to −78° C. Compound 8 (2.02 mL, 20.6 mmol) was added dropwise with vigorous stirring. After addition, the solution was stirred for 30 min at −78° C. Next, $ClTi(iPrO)_3$ (11.26 g, 43.2 mmol) as a solution in THF (10 mL) was added via addition funnel over approximately 10 minutes with vigorous stirring. The reaction was stirred for 30 minutes at −78° C. Finally, compound 7 (2.29 g. 6.86 mmol) was added dropwise as a suspension in THF and stirred at −78° C. for 1.25 hours until the reaction was complete. To the reaction at −78° C. was added saturated aqueous ammonium chloride. The reaction was then removed from cooling and the aqueous phase was allowed to gradually thaw and quench (yellow orange color disappears). The mixture was portioned between EtOAc and saturated aqueous ammonium chloride. The organic phase was separated and aqueous phase was extracted two times with EtOAc. The organic phases were combined and dried over brine, then over sodium sulfate, and then filtered and concentrated. The residue was purified over silica eluting a gradient of ethyl acetate in hexanes. Compound 9 was obtained in 75% yield as single diastereomer after purification.

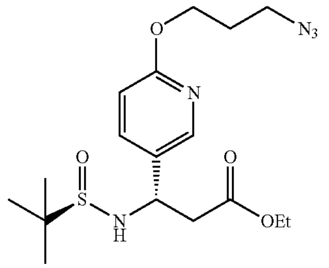

9

HCl

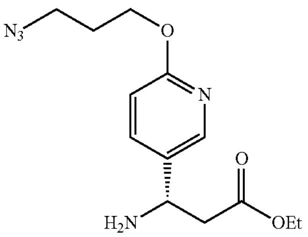

10

Compound 9 (1.28 g, 3.21 mmol) in MeOH (3.2 mL) was treated with HCl in dioxane (4M, 3.2 mL, 12.9 mmol) and stirred at room temperature for 30 minutes. Upon completion, the reaction mixture was diluted with water and washed with diethyl ether. Subsequently, the pH was adjusted to 11 using 2 N aqueous NaOH and the product was extracted with ethyl acetate. The organic phase was dried over sodium sulfate, filtered, and concentrated, yielding corn und 10 in 92% yield which was subsequently used without further purification.

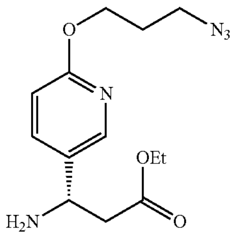

10

+

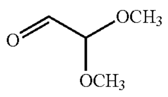

11

STAB—H

-continued

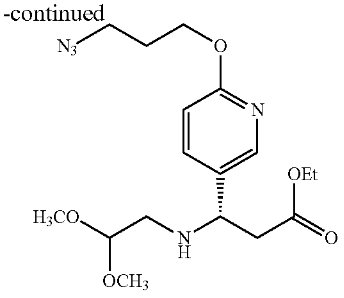

12

To a mixture of compound 10 (0.78 g, 2.67 mmol) and compound 11 (0.60 g, 3.46 mmol) in THF (6 mL) at 15° C. was added STAB-H (1.29 g, 6.12 mmol) portion-wise as solid. After the addition, cooling was removed and the mixture was stirred for approximately 2.5 hours to completion. The reaction was quenched by addition of saturated aqueous sodium bicarbonate and pH was brought to 9. The product was extracted three times with EtOAc, the organic phases were combined, dried with brine, then filtered over sodium sulfate and concentrated. Compound 12 was isolated in 85% yield by separation on silica eluting a gradient of ethyl acetate in hexanes.

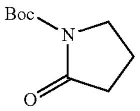

13

LDA $(MeO)_2POMe$

THF

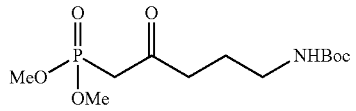

14

To DIPEA (7.53 mL, 53.75 mmol) in THF (35 mL) was added n-BuLi (2.5 M, 19.9 mL, 49.8 mmol) via oven dried gastight syringe over 2 minutes at −10 TC. The mixture was stirred for 10 minutes at −10° C., then cooled to −60° C. and a solution of dimethyl methylphosphonate (6.42 g, 51.8 mmol) in THF (8 mL) was added dropwise over 5-10 minutes. After aging at −60° C. for about 1 hour, compound 13 (7.37 g. 39.82 mmol) was added as solution in THF (15 mL) dropwise over 5 minutes at −60° C. The reaction mixture was stirred at −60° C. for 1 hour and then −41° C. for about 1.5 hours. The reaction was quenched by addition of 2.6 equivalents of $H_2SO_4$ (2.0 M) and extracted three times with ethyl acetate (~50 mL). The organic phases were combined and dried with brine, filtered over sodium sulfate, and concentrated briefly to determine crude weight and take sample for NMR. Upon determination of dry weight, compound 14 was dissolved in MeOH for use in next reaction without further purification. Calculated to be 75.83% yield. Crude wt/wt % 76.3% by NMR. $^1H$ NMR: 400 MHz $CDCl_3$ δ 4.75 (s, 1H), 3.81 (s, 3H), 3.78 (s, 3H), 3.10-3.14 (m, 2H), 3.04-3.09 (m, 2H), 2.68 (t, 2H), 1.82-1.75 (m, 2H), 1.44 (s, 9H).

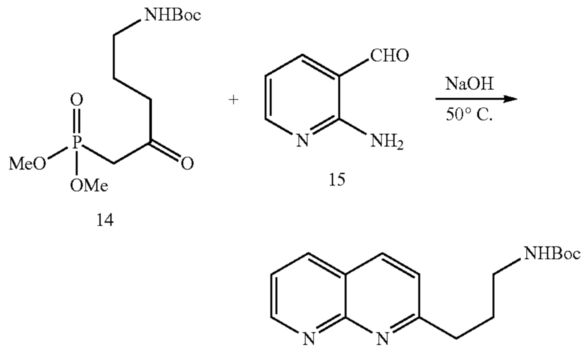

14 15 16

To compound 14 (9.33 g by weight from NMR of ~12 g crude, 30.16 mmol) in MeOH (40 mL), was added solution of NaOH (1.45 g, 36.2 mmol) in water (1.5 mL). The mixture was heated to 50° C. and compound 15 (2.76 g, 22.62 mmol) was added. After stirring for 30 minutes, a second portion of compound 15 (736 mg, 6.03 mmol) was added, and the reaction mixture was stirred overnight at 50° C. The reaction mixture was then concentrated to an oil and partitioned between 2 volumes EtOAc and 1 volume $H_2O$. The organic phase was separated and washed with 1 volume of water. The aqueous washes were combined and back extracted (2×, 1 vol) with EtOAc. The combined organic phase was dried over sodium sulfate, filtered, and concentrated. The crude was dried onto approximately 20 g of silica compound 16 was isolated in 69% yield by separation on silica eluting a gradient of ethyl acetate in hexanes containing 1% triethylamine. $^1H$ NMR: 400 MHz $CDCl_3$ δ 9.09 (dd, 1H), 8.17 (dd, 1H), 8.12 (d, 1H), 7.46 (dd, 1H), 7.41 (d, 1H), 4.78 (s, 1H), 3.24 (q, 2H), 3.10 (t, 2H), 2.12 (quin, 2H), 1.43 (s, 9H).

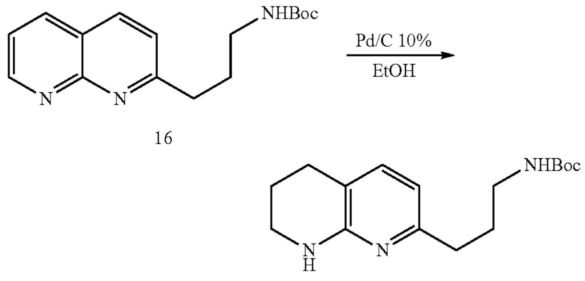

16 17

To a solution of compound 16 (5.98 g, 20.8 mmol) in EtOH (50 mL) was charged with palladium (10% on Carbon, 2.22 g, 2.08 mmol) and hydrogen at 1 atmosphere. The reaction mixture was stirred at room temperature overnight. Upon completion, the reaction mixture was filtered over Celite® and concentrated. Compound 17 was isolated in 79% yield by separation on silica eluting a gradient of ethyl acetate in hexanes containing 1% triethylamine. $^1H$ NMR: 400 MHz $CDCl_3$ δ 7.05 (d, 1H), 6.34 (d, 1H), 5.48 (s, 1H), 4.81 (s, 1H), 3.36-3.43 (m, 2H), 3.16 (q, 2H), 2.68 (t, 2H), 2.59 (t, 2H), 1.90 (dt, 2H), 1.83 (quin, 2H), 1.44 (s, 9H).

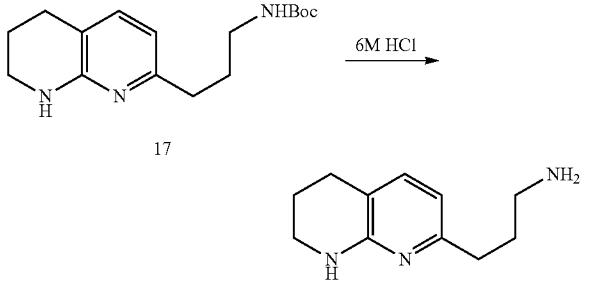

17 18

Compound 17 (4.81 g, 16.53 mmol) was dissolved in aqueous 6 M HCl (16.4 mL) and heated at 42° C. for 2 hours. An additional portion of 6 M HCl (2.8 mL) was then added and the reaction mixture was stirred for an additional 2 hours. To the reaction was added sodium chloride followed by aqueous 2 N NaOH until the product precipitated as an oil (pH was greater than 12). The mixture was extracted three times with 2-Butanol. The combined organic phase was dried over sodium sulfate, filtered and concentrated. Compound 18 was obtained in 85% yield and subsequently used without further purification. $^1H$ NMR: 400 MHz $CDCl_3$ δ 7.06 (d, 1H), 6.35 (d, 1H), 4.83 (s, 1H), 3.35-3.46 (m, 2H), 2.75-2.67 (m, 4H), 2.58 (t, 2H), 1.88-1.95 (m, 2H) 1.84-1.76 (m, 4H).

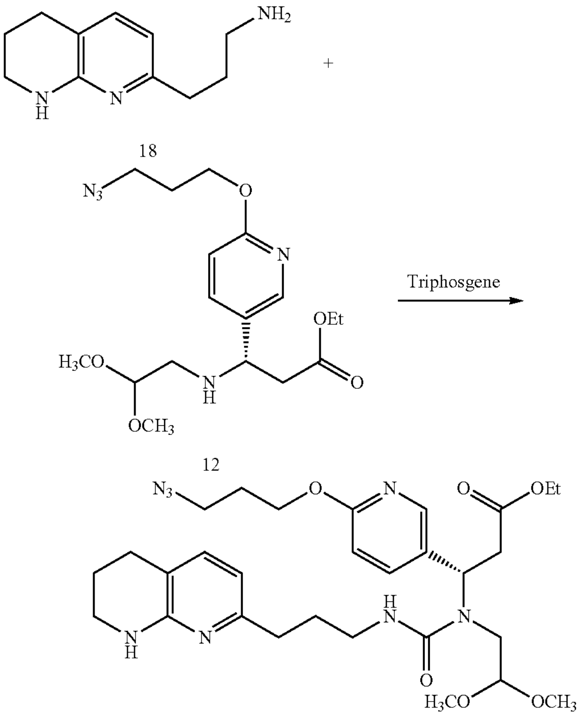

18 12 19

To a solution of triphosgene (85 mg, 0.28 mmol) in THF (0.9 mL) in a flame dried flask at −10° C. was added dropwise a solution of compound 18 (236 mg, 0.62 mmol) and TEA (0.134 mL, 0.96 mmol) in THF (0.5 mL). The reaction mixture was warmed to room temperature. After TLC indicated a complete reaction, additional TEA (0.134 mL) was added followed by addition of compound 12 (166 mg, 0.87 mmol) as a solid. The heterogenous mixture was heated at 50° C. for 2 hours with vigorous stirring. Upon completion, the reaction mixture was quenched with 1 volume of water and extracted three times with EtOAc. The combined organic phase was dried with brine, filtered over sodium sulfate and concentrated. Compound 19 was obtained assuming 100% yield and subsequently used without further purification.

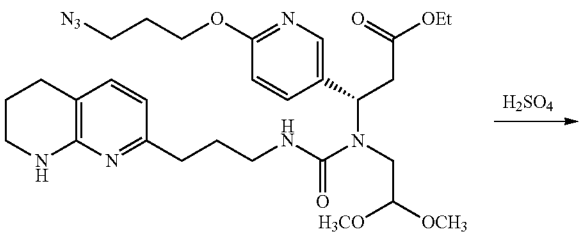

19

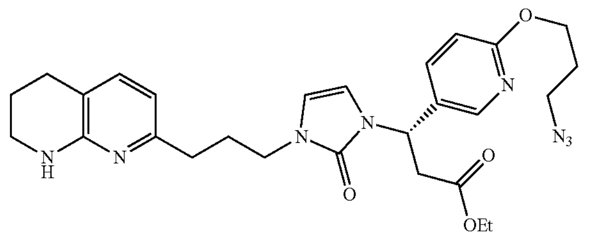

20

To crude compound 19 (400 mg, 0.62 mmol assumed) dissolved in THF (37 mL) was added $H_2SO_4$ (2M, 0.6 mL) and the mixture was stirred at room temperature overnight. The following morning, an additional portion of $H_2SO_4$ (0.65 equivalents) was added. Four hours later the reaction was complete. The reaction mixture was diluted with ethyl acetate. The organic phase was separated and the aqueous phase was back extracted once with ethyl acetate. The combined organic phase was filtered over sodium sulfate and concentrated. Compound 20 was isolated in 75% yield by separation over silica eluting a gradient of MeOH in DCM.

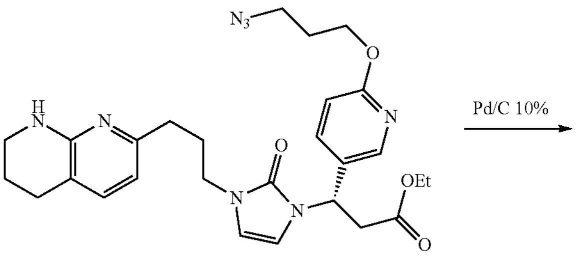

20

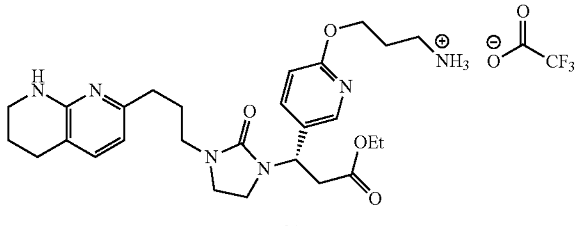

21

To a suspension of compound 20 (251 mg, 0.47 mmol) and Pd/C (10 wt %, 100 mg, 0.094 mmol) in ethanol (9 mL) was charged $H_2$ to 1 atmosphere and stirred at 35° C. overnight. Upon completion, palladium was removed by filtration over Celite®. Compound 21 was isolated in 20% yield as TFA salt by reverse phase HPLC using a $C_{18}$ 5 u 19×250 mm BEH column Waters Cor. eluting a gradient of acetonitrile in $H_2O$ containing 1% TFA.

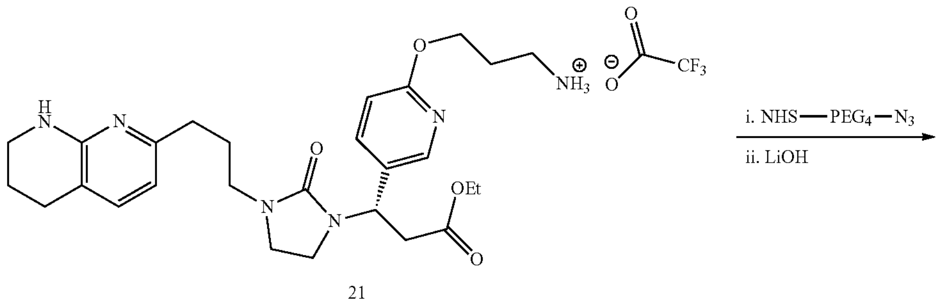

21

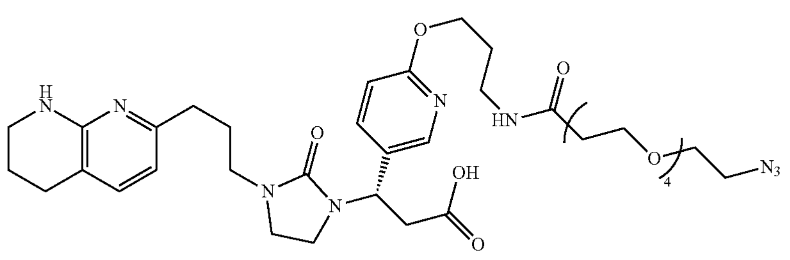

22

To a solution of compound 21 (61 mg, 0.097 mmol) in DCM (250 uL) was added TEA (8 uL, 0.24 mmol) followed by addition of NHS-$PEG_4$-$N_3$ (41.4 mg, 0.11 mmnol) as a solution in DCM (275 μL). The reaction mixture was stirred for 15 minutes and checked by LC-MS, which showed that the reaction was complete. All volatiles were removed, and the residue was dissolved in EtOH (0.4 mL) and water (0.4 mL). LiOH (11.2 mg, 0.47 mmol) was added and the reaction mixture was heated at 40° C. for 2 hours. Upon completion, the reaction mixture was concentrated under reduced pressure. Compound 22 (Structure 1c) was isolated in 42% yield by reverse phase HPLC using a $C_{18}$ 5 u 19x250 mm BEH column (Waters Corp.) eluting a gradient of acetonitrile in $H_2O$ containing 1% TFA.

Synthesis of Structure 2c ((S)-3-(4-(2-(2-(2-(2-azidoethoxy)ethoxy)ethoxy)ethoxy)-3-fluorophenyl)$_3$-(2-oxo-3-(3-(5,6,7,8-tetrahydro-1,8-naphthyridin-2-yl)propyl)imidazolidin-1-yl)propanoic acid)

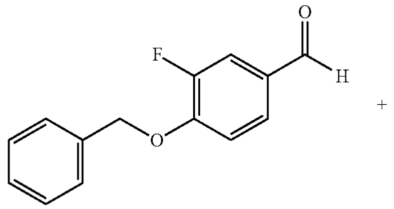

23

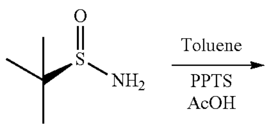

6

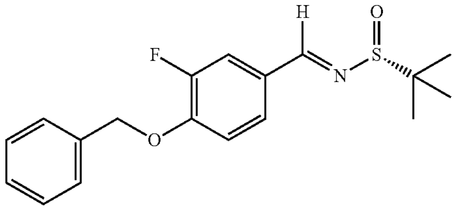

24

To a solution of compound 23 (10 g, 43.4 mmol) in toluene (80 mL) was added compound 6 (21.1 g, 0.17 mol), PPTS (0.55 g, 2.2 mmol), and then acetic acid (1.24 mL, 21.7 mmol)). The reaction vessel was equipped with a Dean Stark trap and then heated to reflux overnight. Upon completion the reaction mixture was concentrated and dried onto 60 grams of silica and purified over $SiO_2$ with a gradient of ethyl acetate in hexanes, yielding compound 24 in 66% yield. $^1$H NMR: 400 MHz $CDCl_3$ δ 8.47 (s, 1H), 7.68 (d, 1H), 7.31-7.56 (m, 6H), 6.98-7.16 (m, 1H), 5.23 (s, 2H), 1.26 (s, 9H).

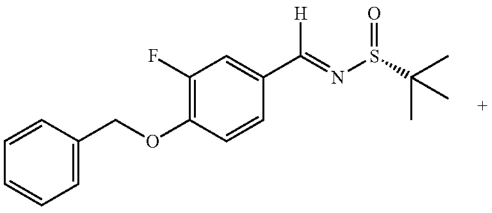

24

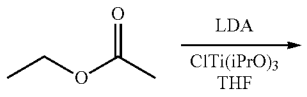

8

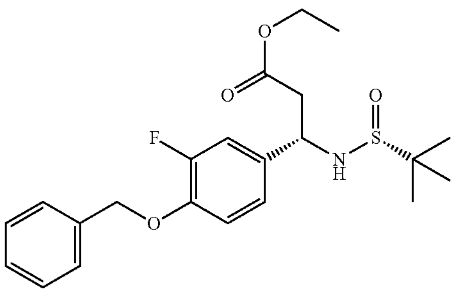

25

A flame dried flask was charged with THF (190 mL) and DIPEA (9.07 g, 89.7 mmol), cooled to −20° C., and then charged with n-BuLi (2.5M, 34.2 mL, 85.6 mmol) via cannula. The solution was stirred for 10 min at −20° C. then cooled to −78° C. Compound 8 (8 mL, 81.5 mmol) was added dropwise with vigorous stirring. After addition, stirred for 30 min at −78° C. Next, $ClTi(iPrO)_3$ (44.6 g, 0.171 mol) as solution in THF (40 mL) was added via addition funnel over 10 minutes. The reaction was stirred for 30 minutes at −78° C. Finally, compound 24 (9.06 g, 27.2 mmol) was added dropwise as a suspension in THF (20 mL) and stirred at −78° C. for 1.25 hour until the reaction was complete. To the reaction at −78° C. was added saturated aqueous ammonium chloride. The reaction was then removed from cooling and the aqueous phase was allowed to gradually thaw and quench (yellow orange color disappears). The mixture was partitioned between EtOAc and saturated aqueous ammonium chloride. The organic phase was separated and the aqueous phase was washed two times with EtOAc. The organic phases were combined and dried over brine, then over sodium sulfate, filtered, and concentrated. Compound 25 was obtained in 70% yield as a single diastereomer by separation on silica eluting a gradient of ethyl acetate in hexanes. $^1$H NMR: 400 MHz $CDCl_3$ δ 7.31-7.48 (m, 5H), 7.09 (dd, 1H), 6.89-7.04 (m, 2H), 5.13 (s, 2H), 4.59-4.76 (m, 2H), 4.13 (q, 2H), 2.81 (dd, 2H), 1.21-1.25 (m, 12H).

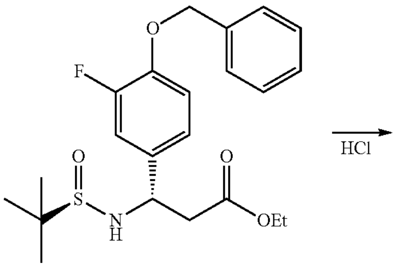

25

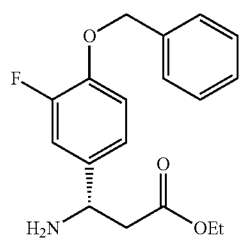

26

To compound 25 (8.07 g, 19.1 mmol) was added aqueous HCl (6M, 20.7 mL, 0.124 mol) followed by MeOH (60 mL). THF was added until homogenous solution was obtained and the reaction mixture was stirred for 6 hours at room temperature. The reaction mixture was basified to a of pH 10 with aqueous 2 N NaOH and then was extracted three times with EtOAc. The combined organic phases were dried with brine, filtered over sodium sulfate, and concentrated. Compound 26 was obtained in 95% yield and was subsequently used without further purification. $^1H$ NMR: 400 MHz $CDCl_3$ δ 7.28-7.46 (m, 6H), 7.18 (d, 1H), 6.99 (t, 1H), 5.11 (s, 2H), 4.57 (t, 1H), 4.09 (q, 2H), 2.97-3.09 (m, 1H), 2.81-2.93 (m, 1H), 1.18 (t, 3H)

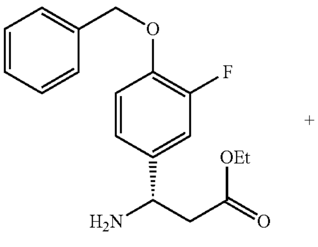

26

+

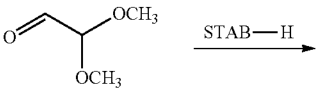

27

-continued

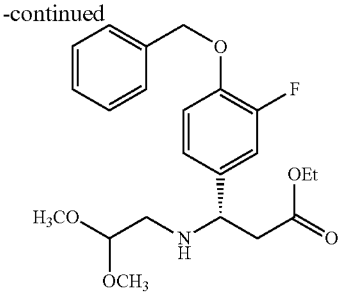

28

To a mixture of compound 26 (5.76 g, 18.2 mmol) and compound 27 (4.09 g, 23.6 mmol) in THF (40 mL) at 0° C. was added STAB-H (8.85 g, 41.8 mmol) portionwise as solid. After final addition cooling was removed and the mixture was stirred for approximately 2.5 hours to completion. The reaction mixture was quenched by addition of saturated aqueous sodium bicarbonate. The mixture was extracted three times with EtOAc. The combined organic phases were dried with brine, filtered over sodium sulfate, and concentrated. Compound 28 was isolated in 73% yield by separation on silica eluting a gradient of ethyl acetate in hexanes. $^1H$ NMR: 400 MHz $CDCl_3$ δ 7.30-7.49 (m, 5H), 7.11 (dd, 1H), 6.88-7.02 (m, 2H), 5.13 (s, 2H), 4.40 (t, 1H), 4.10 (q, 2H), 4.00 (dd, 1H), 3.35 (s, 3H), 3.31 (s, 3H), 2.47-2.75 (m, 4H), 1.20 (t, 3H).

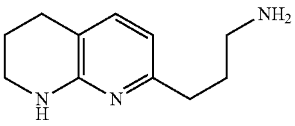

+

19

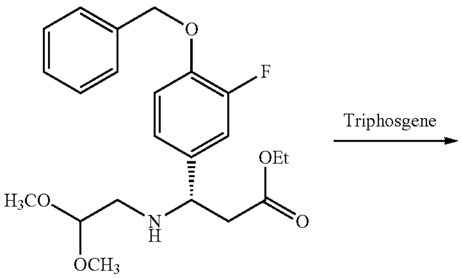

28

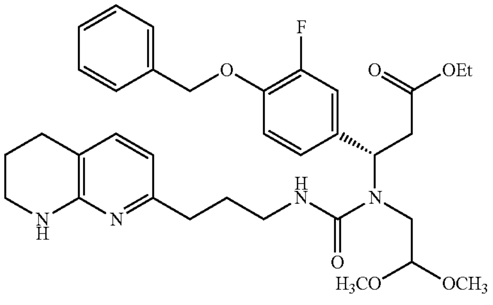

29

To a solution of triphosgene (1.2 g, 4.04 mmol) in THF (24 mL) in flame dried flask at −10° C. was added dropwise a solution of compound 19 (3.64 g, 8.99 mmol) and TEA (1.94 mmol, 13.9 mmol) in THF (6 mL). The reaction mixture was warmed to room temperature. After TLC indicated a complete reaction, additional TEA (3.3 mL, 23.6 mmol) was added followed by the addition of compound 28 (2.61 g, 13.7 mmol) as a solid. The heterogenous mixture was heated at 50° C. for 2 hours with vigorous stirring. Upon completion, the reaction mixture was quenched with 1 volume of water and extracted three times with EtOAc. The combined organic phase was dried with brine, filtered over sodium sulfate and concentrated. Compound 29 was obtained assuming 100% yield and the crude was subsequently used without further purification.

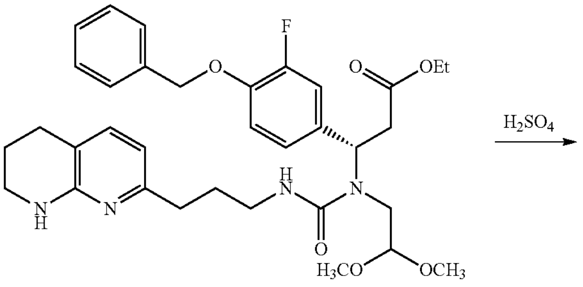

29

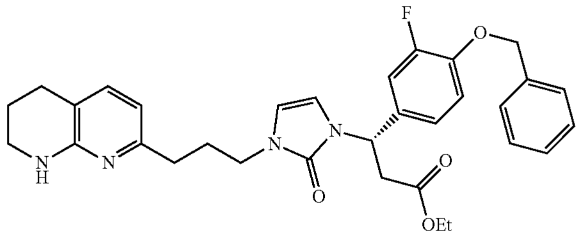

30

To compound 29 (5.59 g, 8.97 mmol) dissolved in THF (37 mL) was added water (0.8 mL) and $H_2SO_4$ (2M, 8.07 ml, 16.2 mmol) and the reaction mixture was stirred at 28° C. overnight. The following morning, the pH of the mixture was adjusted to 9 using sodium bicarbonate and extracted three times with DCM. The combined organic phases were dried with brine, filtered over sodium sulfate, and concentrated. Compound 30 was isolated in 82% yield by separation on silica eluting a gradient of MeOH in DCM containing 1% TEA.

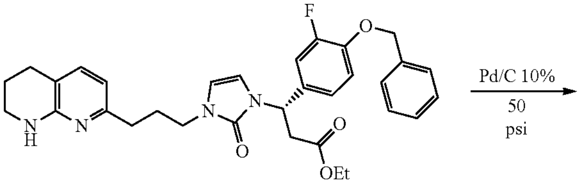

30

-continued

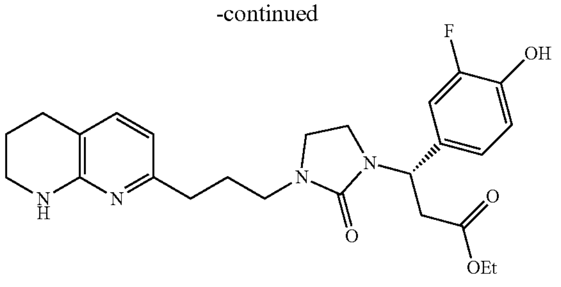

31

To compound 30 (4.13 g, 7.39 mmol) dissolved in EtOH (30 mL) was charged Degussa® palladium (10 wt %, 3.15 g, 2.96 mmol) and hydrogen to 50 psi. The mixture was stirred at room temperature overnight. The next day, reaction was 64% complete. The reaction mixture was filtered over Celite® and concentrated. The residue was dissolved in EtOH and charged with palladium (10 wt %, 1.57 g, 1.48 mmol)) and hydrogen to 50 psi. After stirring for 48 hours the reaction mixture was heated to 30° C. and stirred for a further 24 hours. Upon completion the suspension was filtered over Celite® and all volatiles were removed in vacuo. The residue was purified over silica eluting a gradient of MeOH in DCM, yielding compound 31 in 72% yield. $^1$H NMR: 400 MHz DMSO-$d_6$ δ 9.88 (s, 1H), 7.02-7.14 (m, 2H), 6.86-6.93 (m, 2H), 6.50-6.76 (m, 1H), 6.31 (d, 1H), 5.17 (t, 1H), 4.00 (q, 2H), 3.23-3.28 (m, 4H), 2.79-3.18 (m, 7H), 2.61 (t, 2H), 2.41 (t, 2H), 1.65-1.78 (m, 4H), 1.09 (t, 3H).

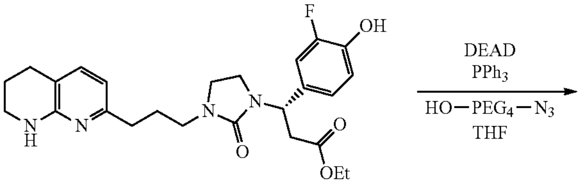

31

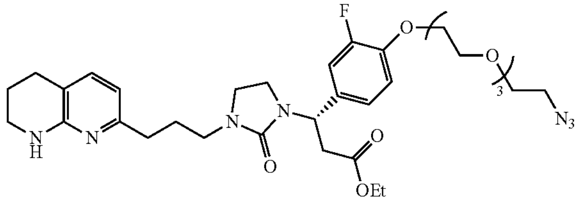

32

To a solution of $PPh_3$ (699 mg, 2.66 mmol) in THF (0.47 mL) at −10° C. was added dropwise a solution of DEAD. The mixture was warmed to room temperature and added to a neat mixture of compound 31 (600 mg, 1.33 mmol) and HO-$PEG_4$-$N_3$, (466 mg, 3.06 mmol) and stirred overnight. The reaction mixture was then concentrated under reduced pressure, and the residue was purified over silica eluting a gradient of MeOH in DCM, yielding compound 32 in 50% yield. $^1$H NMR: 400 MHz DMSO-$d_6$ δ 7.10-7.19 (m, 2H), 6.97-7.06 (m, 2H), 6.18-6.31 (m, 2H), 5.20 (t, 1H), 4.13-4.16 ((m, 1H), 3.98-4.04 (m, 2H), 3.71-3.80 ((m, 2H), 3.52-3.61 (m, 8H), 3.38-3.37 (m, 5H), 3.10-3.25 (m, 5H), 2.79-3.08 (m, 5H), 2.59 (t, 2H), 2.31-2.42 (m, 2H), 1.65-1.75 (m, 4H), 1.10 (t, 3H).

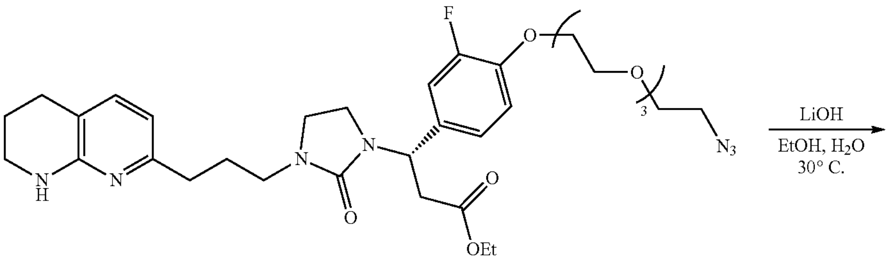

32

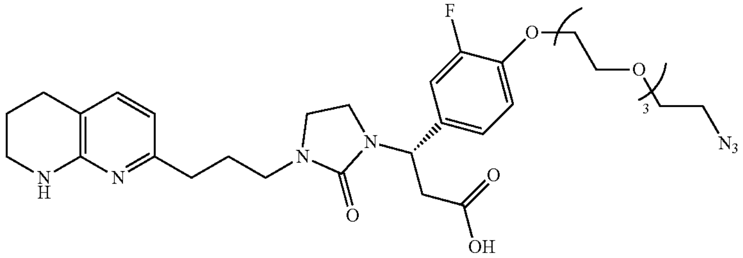

33

To compound 32 (826 mg, 1.23 mmol) was added EtOH (3 mL) and $H_2O$ (3 mL), followed by LiOH (97 mg, 4.05 mmol). The mixture was stirred at 30° C. overnight. Upon completion the mixture was neutralized to pH=5 using 6 M aqueous HCl and concentrated. The residue was purified by reverse phase HPLC with a Phenomenex Gemini C18, 50×250 mm, 10 μm column eluting a gradient of acetonitrile in water containing 0.1%, yielding compound 33 (Structure 2c) in 81% yield. $^1H$ NMR: 400 MHz $D_2O$ δ 7.30 (d, 1H), 7.01-7.19 (m, 3H), 6.45 (d, 1H), 5.24 (t, 1H), 4.14-4.32 (m, 2H), 3.84-3.92 (m, 2H), 3.59-3.77 (m, 10H), 3.14-3.45 (m, 8H), 0.02-3.12 (m, 1H), 2.97 (d, 2H), 2.85 (q, 1H), 2.50-2.72 (m, 4H), 1.68-1.94 (m, 4H).

Synthesis of Structure 2.1c ((S)-3-(4-((11-azidoundecyl)oxy)-3-fluorophenyl)-3-(2-oxo-3-(3-(5,6,7,8-tetrahydro-1,8-naphthyridin-2-yl)propyl)imidazolidin-1-yl)propanoic acid)

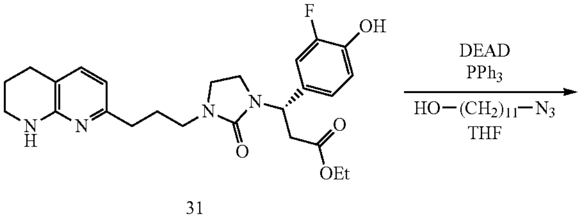

31

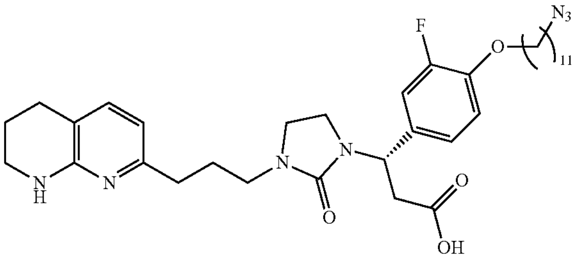

34

To a solution of $PPh_3$ in THF was added dropwise a solution of DEAD at room temperature. The mixture was transferred to a vial containing mixture of compound 31 and $OH—(CH_2)_{11}—N_3$, and the reaction mixture was stirred at room temperature overnight. Volatiles were removed from the reaction mixture and the crude was dissolved in EtOH. LiOH was added as a solution in $H_2O$, and additional water/EtOH was added until the reaction mixture became homogenous. After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution).

Synthesis of Structure 2.2c ((S)-3-(4-(2-(1-(6-azidohexanoyl)piperidin-4-yl)ethoxy)-3-fluorophenyl)-3-(2-oxo-3-(3-(5,6,7,8-tetrahydro-1,8-naphthyridin-2-yl)propyl)imidazolidin-1-yl)propanoic acid)

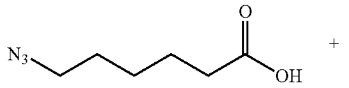

35

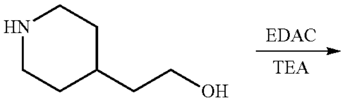

36

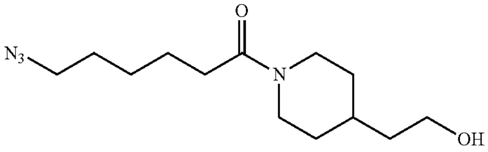

37

Compound 35 dissolved in DCM at 0° C. was treated with EDAC and acetonitrile was added to aid in solubility. After 5 minutes, TEA and compound 36 were added, cooling was removed, and stirring continued for 2 hours. Upon completion, saturated ammonium chloride was added and the organic phase was separated, filtered over sodium sulfate, and concentrated. The crude obtained was used subsequently without further purification.

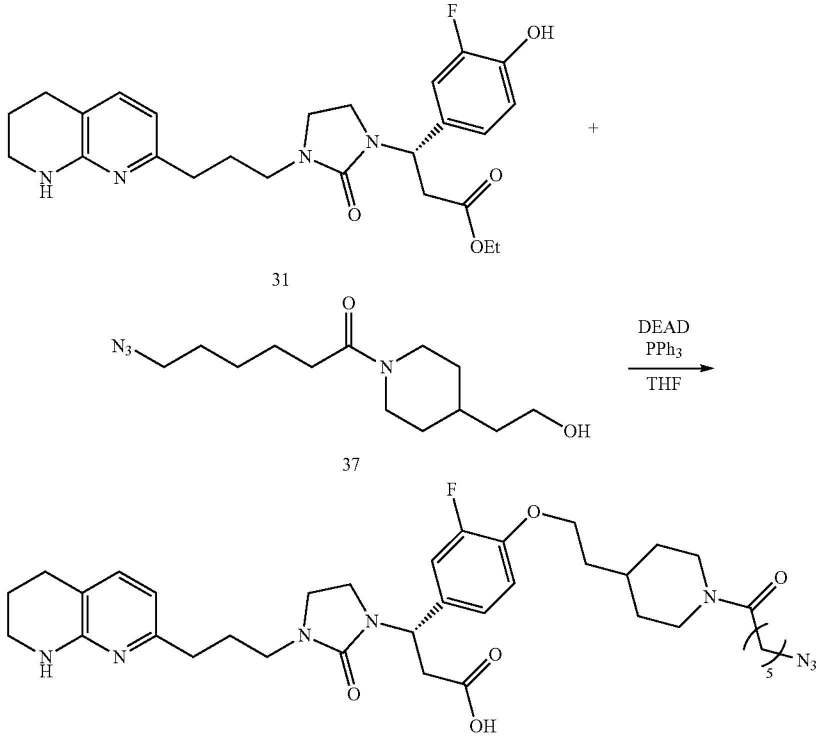

31

37

38

To a solution of $PPh_3$ in THF was added dropwise a solution of DEAD at room temperature with vigorous stirring. The mixture was transferred to a vial containing a mixture of compound 31 and compound 37, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous. After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 38 (Structure 2.2c).

Synthesis of Structure 2.3c ((S)-3-(4-(2-((1r,4S)-4-(5-azidopentanamido)cyclohexylthoxy)-3-fluorophenyl)-3-(2-oxo-3-(3-(5,6,7,8-tetrahydro-1,8-naphthyridin-2-yl)propyl)imidazolidin-1-yl)propanoic acid)

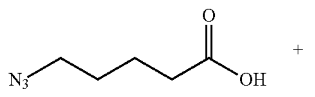

35

-continued

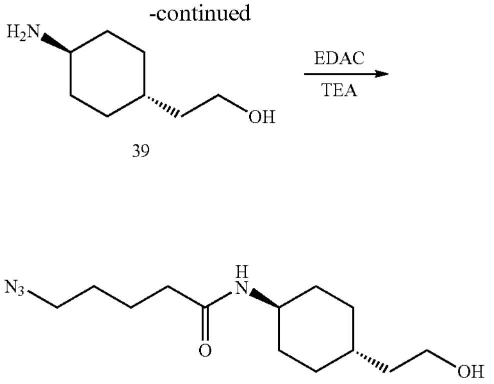

39

40

To a suspension of compound 35 in DCM at 0° C. was added EDAC as a solution in DCM. After 5 minutes, cooling was removed and compound 39 was added, followed by the addition of TEA. The heterogeneous mixture was stirred overnight at room temperature. The next day, the reaction was diluted with DCM and the precipitate dissolved. The mixture was washed twice with 5% $KHSO_4$ and once with brine. The organic phase was filtered over sodium sulfate and concentrated. The crude residue containing compound 40 was used without further purification.

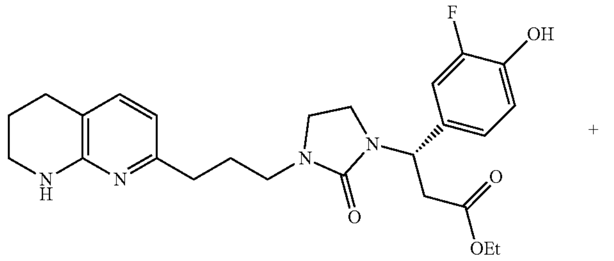

31

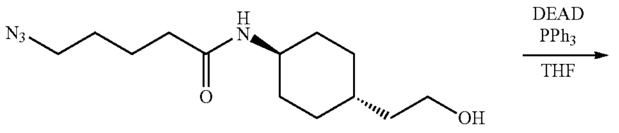

40

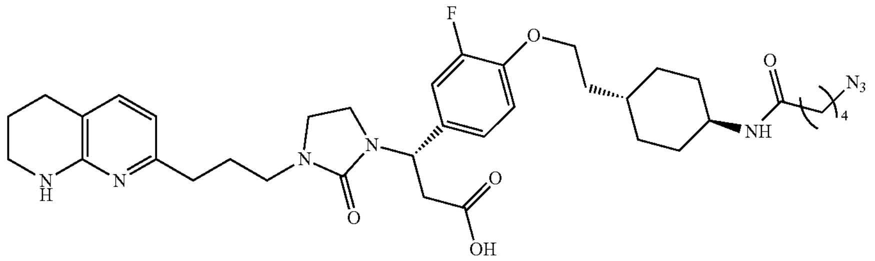

41

To a solution of $PPh_3$ in THF was added dropwise a solution of DEAD at room temperature with vigorous stirring. The mixture was transferred to a vial containing a mixture of compound 31 and compound 40, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 41 (Structure 2.3c).

Synthesis of Structure 2.4c ((S)-3-(4-(4-(5-azidopentanamido)phenethoxy)-3-fluorophenyl)-3-(2-oxo-3-(3-(5,6,7,8-tetrahydro-1,8-naphthyridin-2-yl)propyl)imidazolidin-1-yl)propanoic acid)

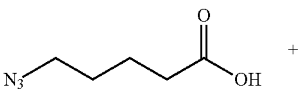

35

-continued

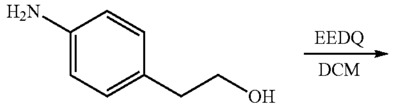

42

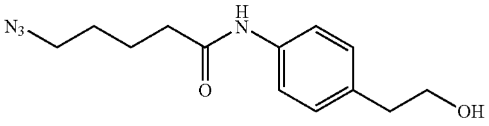

43

To a mixture of compound 35 and compound 42 in DCM was added EEDQ, and the solution was stirred at room temperature overnight. The reaction mixture was then diluted with DCM, washed three times with 1M HCl, and washed once with brine. The organic phase was dried over sodium sulfate, filtered, and concentrated. Compound 43 was then used without further purification.

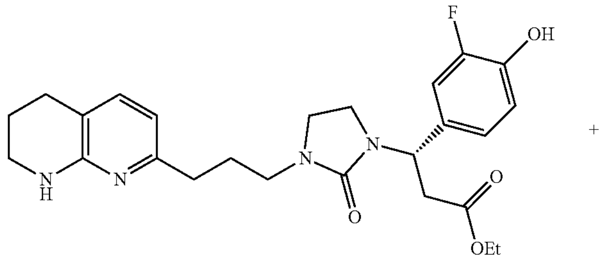

31

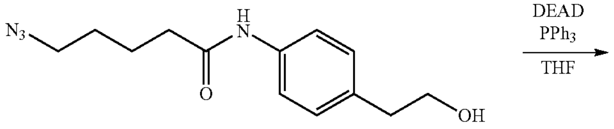

43

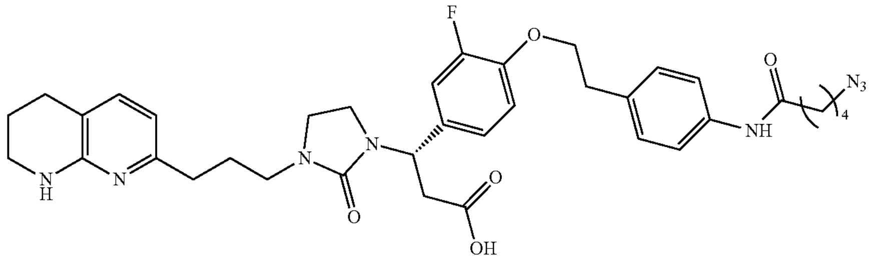

44

To a solution of $PPh_3$ in THF was added dropwise a solution of DEAD at room temperature with vigorous stirring. The mixture was transferred to a vial containing a mixture of compound 31 and compound 43, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous. After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 44 (Structure 2.4c).

Synthesis of Structure 2.5c ((S)-3-(4-(4-((5-azidopentyl)oxy)phenethoxy)-3-fluorophenyl)-3-(2-oxo-3-(3-(5,6,7,8-tetrahydro-1,8-naphthyridin-2-yl)propyl)imidazolidin-1-yl)propanoic acid)

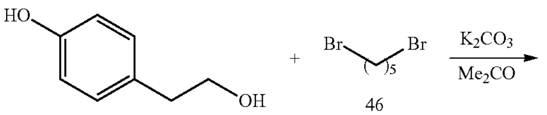

45 46

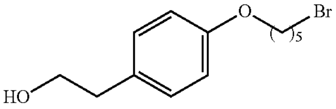

47

To a solution of compound 45 and compound 46 in acetone was added potassium carbonate. The mixture was heated to 65° C. in a sealed vial as a suspension with vigorous stirring overnight under $N_2$ protection. The reaction was then filtered, concentrated, and purified over silica eluting a gradient of ethyl acetate in hexanes, yielding compound 47.

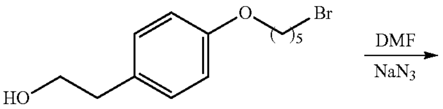

47

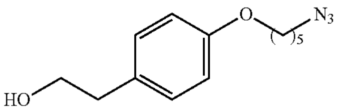

48

To a solution of compound 47 in DMF was added sodium azide and the mixture was stirred at 80° C. in a sealed vial under nitrogen protection overnight. Upon completion, 1 volume of water was added and the product was extracted with ethyl acetate. The separated organic phase was filtered over sodium sulfate and concentrated. Crude of compound 48 was used without further purification.

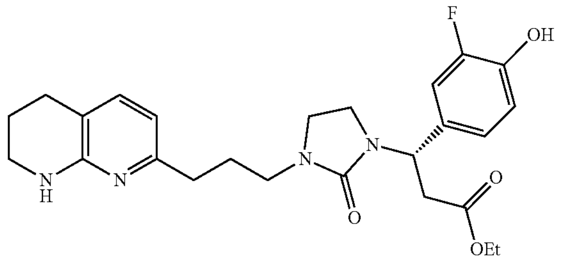

31

+

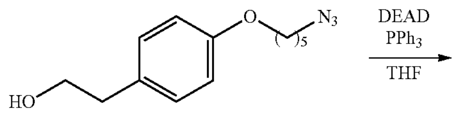

48

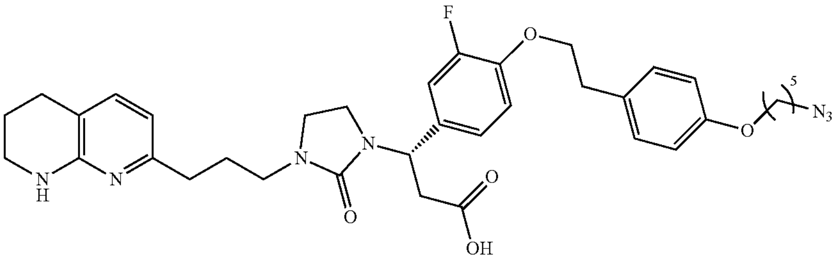

49

To a solution of $PPh_3$ in THF was added dropwise a solution of DEAD at room temperature with vigorous stirring. The mixture was transferred to a vial containing a mixture of compound 31 and compound 48, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous. After stirring at room temperature for 1.5 hours, the mixture was acidified to a pH of 3 with $H_2SO_4$, concentrated, and purified by reverse phase HPLC (Phenomenex Gemini C18, 50×250 mm, 10 μm, 0.1% TFA in acetonitrile/water, gradient elution), yielding compound 49 (Structure 2.5c).

Synthesis of Structure 2.6c ((S)-3-(3-(3-(3-(17-azido-3-oxo-6,9,12,15-tetraoxa-2-azaheptadecyl)-5,6,7,8-tetrahydro-1,8-naphthyidin-2-yl)propyl)-2-oxoimidazolidin-1-yl)-3-(3-fluoro-4-methoxyphenyl) propanoic acid)

-continued

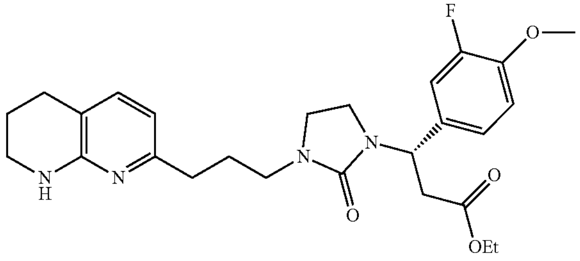

50

To a solution of $PPh_3$ in THF was added dropwise a solution of DEAD at 0° C. After complete addition, the mixture was transferred to a vial containing a neat mixture of compound 31 and MeOH. The vial was capped with $N_2$ and stirred at room temperature overnight. Upon completion all volatiles were removed and the crude obtained was purified over silica eluting a gradient of MeOH in DCM, yielding compound 50.

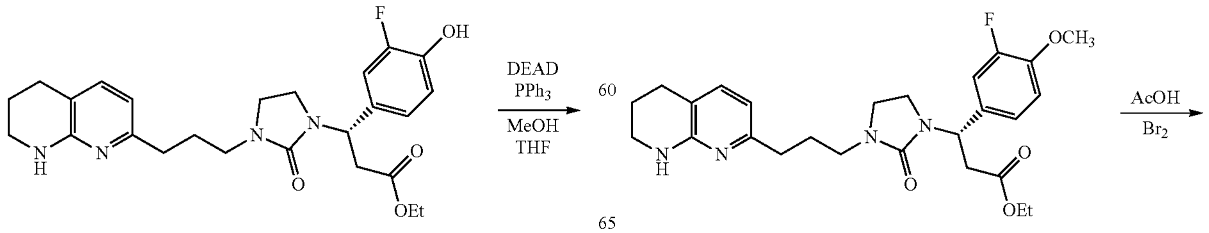

31 50

-continued

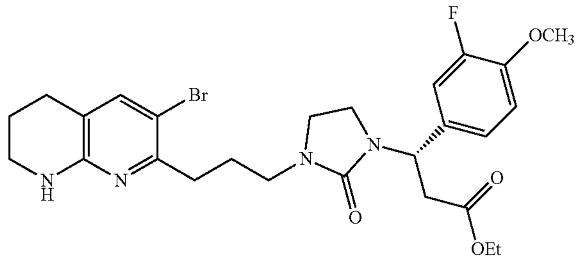

51

To a solution of compound 50 in AcOH was added bromine, and the mixture was stirred for 0.5 hours. Upon completion, the reaction was diluted with 5 volumes of ethyl acetate and 2.5 volumes of water. The aqueous layer was neutralized to pH 7 with saturated aqueous sodium bicarbonate, and the organic phase was separated. The aqueous layer was extracted two additional times with ethyl acetate. The combined organic phases were dried over sodium sulfate, filtered, and concentrated. Crude obtained of compound 51 was subsequently used without further purification.

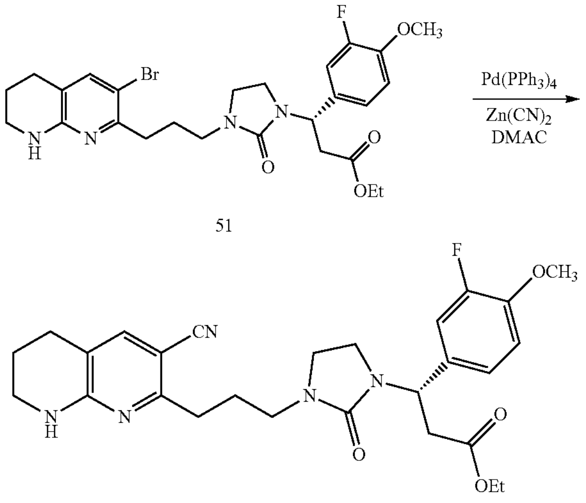

51

52

A solution of compound 51, $Pd(PPh_3)_4$, and $Zn(CN)_2$ in DMAC was degassed with nitrogen for 30 minutes The mixture was heated at 128° C. in a sealed vial overnight. Upon completion, mixture was diluted with 5 volumes of EtOAc. The organic phase was separated then washed two times with water, washed two times with brine, and then the organic phase was filtered over sodium sulfate and concentrated. The residue was purified over silica eluting 100% EtOAc, yielding compound 52.

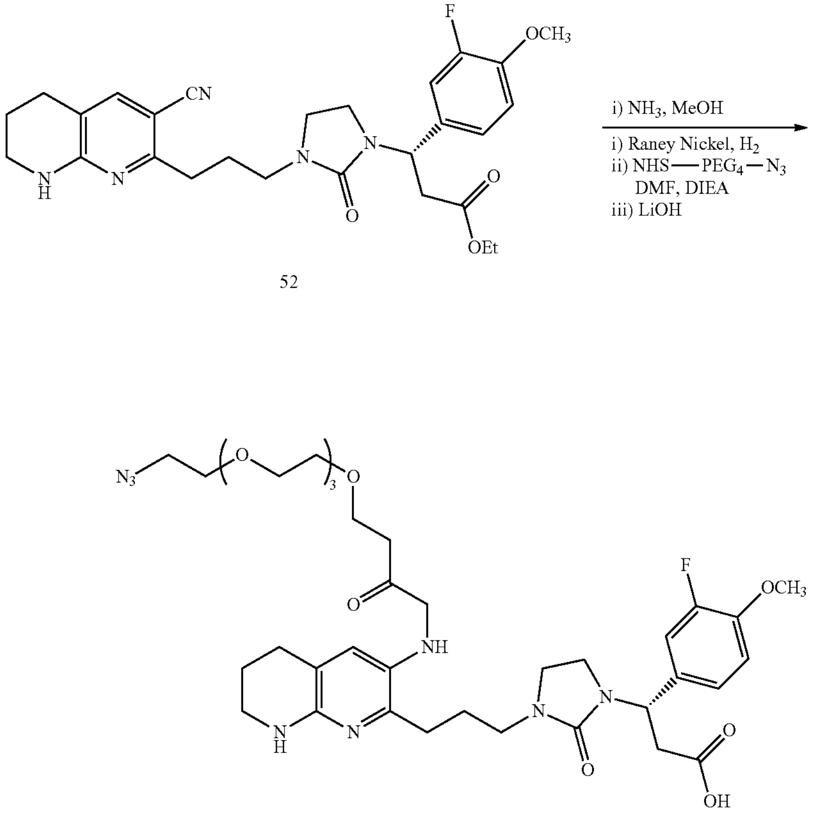

52

53

To a solution of compound 52 in MeOH was added ammonia, then a slurry of Raney nickel that was pre-rinsed three times with methanol. A Parr® flask was charged to 60 psi with hydrogen and stirred at room temperature for 16 hours. Upon completion, the suspension was filtered and concentrated. The crude residue obtained was redissolved in DMF. DIEA and NHS-$PEG_4$-$N_3$ were added and the mixture was stirred for one hour. Upon completion, all volatiles were removed and the crude residue was redissolved in a mixture of MeOH and THF. LiOH in $H_2O$ was added and the mixture was stirred at room temperature for 17 hours. Upon reaction completion, the pH was adjusted to 3 with TFA and the mixture was directly injected onto semi-preparative reverse phase HPLC (Phenomenex Gemini C18, 250×21.2 mm, 5 μm, 0.1% TFA in water/ACN, gradient elution), yielding compound 53 (Structure 2.6c).

Synthesis of Structure 2.7c ((S)—N-(2-(2-(2-(2-azidoethoxy)ethoxy)ethoxy)ethyl)-3-(3-fluoro-4-methoxyphenyl)-3-(2-oxo-3-(3-(5,6,7,8-tetrahydro-1,8-naphthyridin-2-yl)propyl)imidazolidin-1-yl)propanamide), Structure 2.8c, Structure 2.9c, and Structure 2.10c

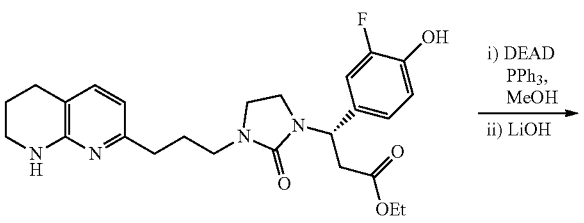

31

-continued

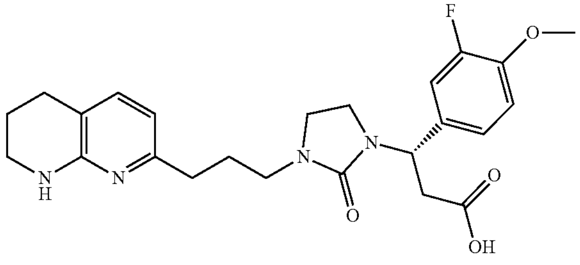

54

To compound 31 was added sequentially THF, $PPh_3$, and a solution of DEAD dropwise at 0° C. The mixture was stirred for 16 hours at room temperature. The mixture was then cooled to −20° C. for 1 hour and filtered to remove triphenylphosphine oxide. The filtrate was concentrated and intermediate of O-alkylation isolated by purification on silica eluting a gradient of ethyl acetate in hexanes containing 1% TEA. Isolated intermediate was then suspended in a mixture of THF and $H_2O$, treated with LiOH in $H_2O$, and stirred at 35° C. for 16 hours. Upon completion, the pH was adjusted to 7 with 2 M HCl and all volatiles were removed. Crude was suspended in $H_2O$; sodium chloride was added and compound 54 was extracted with ethyl acetate five times. The organic phases were combined, filtered over sodium sulfate and concentrated. Compound 54 was subsequently used without further purification.

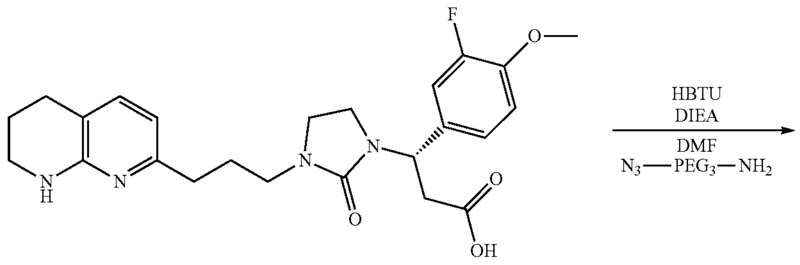

54

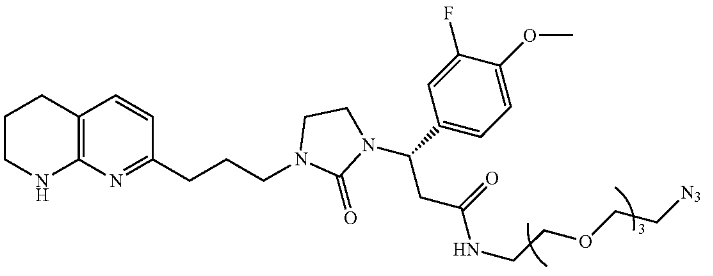

55

A solution of compound 54 in DMF was treated with HBTU and stirred for 5 minutes. DIEA and $N_3$-$PEG_3$-$NH_2$ were subsequently added, and the mixture was stirred at room temperature for 16 hours. Upon completion, the pH was adjusted to 3 with TFA and compound 55 was isolated by direct injection into semi-preparative reverse phase HPLC (Phenomenex Gemini C18, 250×21.2 mm, 5 μm, 0.1% TFA in water/ACN, gradient elution), yielding compound 55.

Similar procedures were used to synthesize compounds 2.8c, 2.9c and 2.10c, using $N_3$-$PEG_{11}$-$NH_2$, $N_3$-$PEG_{23}$-$NH_2$ and $N_3$-$PEG_{35}$-$NH_2$, respectively.

Synthesis of Structure 2.11c ((R)-3-(4-(2-(2-(2-(2-azidoethoxy)ethoxy)ethoxy)ethoxy)-3-fluorophenyl)-3-(2-oxo-3-(3-(5,6,7,8-tetrahydro-1,8-naphthyridin-2-yl)propyl)imidazolidin-1-yl)propanoic acid)

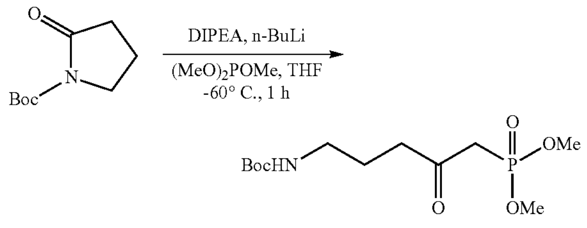

174

Into a 3-L 4-necked round-bottom flask purged and maintained with an inert atmosphere of nitrogen, was placed THF (1.50 L), DIPEA (150.00 mL, 716.000 mmol, 0.88 equiv.), n-BuLi (430.00 mL, 680.000 mmol, 0.84 equiv.) This was followed by the addition of trimethyl phosphite (195.00 mL) at −60° C. and stirred for 1 h at −60° C. To this was added tert-butyl 2-oxopyrrolidine-1-carboxylate (150.00 g, 809.835 mmol, 1.00 equiv.) at −60° C. The resulting solution was stirred for 1 h at −60° C. in a liquid nitrogen bath. The reaction was then quenched by the addition of 350 mL of $H_2SO_4$ (2N) and diluted with 1.5 L of $H_2O$. The resulting solution was extracted with 2×1 L of ethyl acetate. The resulting mixture was washed with 1×1 L of $H_2O$, dried over anhydrous sodium sulfate and concentrated under vacuum. This resulted in 200 g (crude) of tert-butyl N-[5-(dimethoxyphosphoryl)-4-oxopentyl]carbamate as yellow oil.

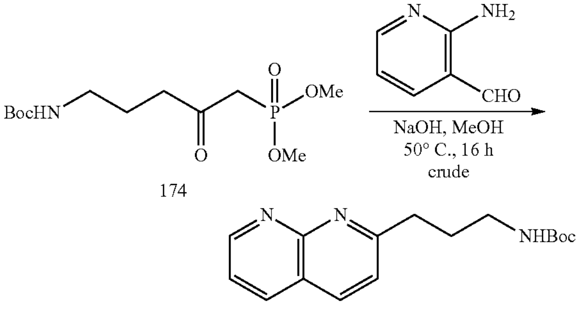

174

175

Into a 3-L round-bottom flask, was placed tert-butyl N-[5-(dimethoxyphosphoryl)-4-oxopentyl]carbamate (200.00 g, 1500.00 mmol, 1.50 equiv.), MeOH (1.50 L), 2-aminopyridine-3-carbaldehyde (53.00 g, 1000.00 mmol, 1.00 equiv.), NaOH (50.00 g, 1500.00 mmol, 1.50 equiv.). The resulting solution was stirred for 16 h at 50° C. in an oil bath. The pH value of the solution was adjusted to 8 with $NaHCO_3$ (aq.). The resulting mixture was concentrated. The reaction was then quenched by the addition of 1.5 L of water and extracted with 2×1.5 L of ethyl acetate. The combined organic layers were dried over anhydrous sodium sulfate and concentrated under vacuum. This resulted in 160 g (crude) of tert-butyl N-[3-(1,8-naphthyridin-2-yl)propyl]carbamate as yellow oil.

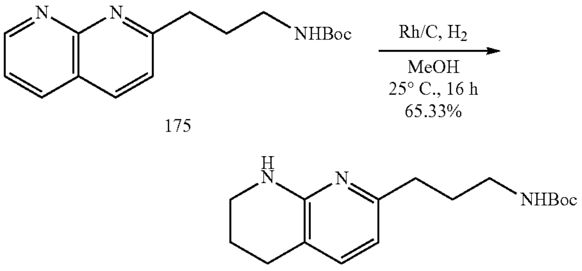

175

176

Into a 5-L round-bottom flask, was placed tert-butyl N-[3-(1,8-naphthyridin-2-yl)propyl]carbamate (160.00 g, 556.787 mmol, 1.00 equiv.), MeOH (2.00 L), Rh/C (140.00 g, 1.360 mmol), $H_2$ (40 Psi). The resulting solution was stirred for 16 h at 25° C. The solids were filtered out. The resulting mixture was concentrated. This resulted in 106 g (65.33%) of tert-butyl N-[3-(5,6,7,8-tetrahydro-1,8-naphthyridin-2-yl)propyl]carbamate as a yellow solid.

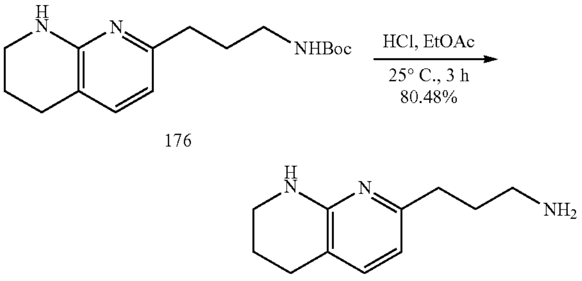

176

177

Into a 1-L round-bottom flask, was placed tert-butyl N-[3-(5,6,7,8-tetrahydro-1,8-naphthyridin-2-yl)propyl]carbamate (106.00 g, 363.767 mmol, 1.00 equiv.), EtOAc (500.00 mL), HCl in EtOAc (4M, 400.00 mL). The resulting solution was stirred for 3 h at 25° C. The resulting solution was diluted with 1 L of $H_2O$. NaOH (aq.) was employed to adjust the pH to 11. The resulting solution was extracted with 2×1 L of ethyl acetate. The combined organic layers were dried over anhydrous sodium sulfate and concentrated under vacuum. This resulted in 56 g (80.48%) of 3-(5,6,7,8-tetrahydro-1,8-naphthyridin-2-yl)propan-1-amine as a yellow solid.

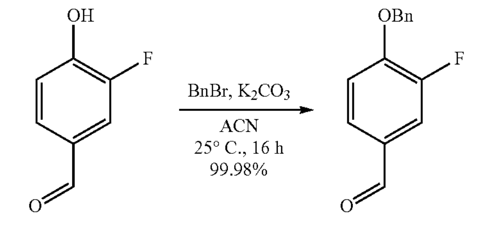

178

Into a 2-L round-bottom flask, was placed 3-fluoro-4-hydroxybenzaldehyde (140.00 g, 999.194 mmol, 1.00 equiv.), ACN (1000 mL), (bromomethyl)benzene (205.08 g, 1199.039 mmol, 1.20 equiv.), $K_2CO_3$ (414.28 g, 2997.581 mmol, 3.00 equiv.). The resulting solution was stirred for 16 h at 25° C. The solids were filtered out. The resulting mixture was concentrated. This resulted in 230 g (99.98%) of 4-(benzyloxy)-3-fluorobenzaldehyde as a white solid.

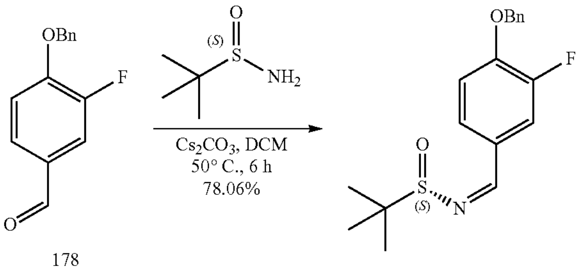

178 179

Into a 3-L round-bottom flask, was placed 4-(benzyloxy)-3-fluorobenzaldehyde (230.00 g, 998.966 mmol, 1.00 equiv.), DCM (1600 mL), (S)-2-methylpropane-2-sulfinamide (145.29 g, 1198.762 mmol, 1.20 equiv.), $Cs_2CO_3$ (650.97 g, 1997.933 mmol, 2.00 equiv.). The resulting solution was stirred for 6 h at 50° C. in an oil bath. The solids were filtered out. The resulting mixture was concentrated. This resulted in 260 g (78.06%) of (S)—N-[[4-(benzyloxy)-3-fluorophenyl]methylidene]-2-methylpropane-2-sulfinamide as a white solid.

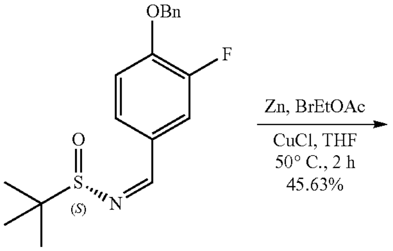

179

-continued

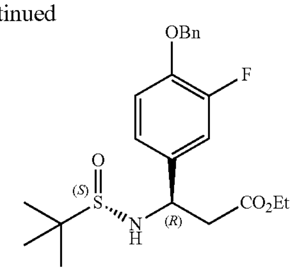

180

Into a 3-L round-bottom flask purged and maintained with an inert atmosphere of nitrogen, was placed THF (2.0 L), Zn (1.02 kg, 15595.945 mmol, 20.00 equiv.), CuCl (115.80 g, 1169.696 mmol, 1.50 equiv.), ethyl 2-bromoacetate (325.57 g, 1949.498 mmol, 2.50 equiv.), (S)—N-[[4-(benzyloxy)-3-fluorophenyl]methylidene]-2-methylpropane-2-sulfinamide (260.00 g, 779.797 mmol, 1.00 equiv.). The resulting solution was stirred for 30 min at 0° C. in a water/ice bath. The resulting solution was allowed to react, with stirring, for an additional 2 h while the temperature was maintained at 50° C. in an oil bath. The solids were filtered out. The resulting mixture was concentrated. The reaction was then quenched by the addition of 2 L of water and extracted with 2×2 L of ethyl acetate. The combined organic layers were dried over anhydrous sodium sulfate and concentrated under vacuum. This resulted in 150 g (45.63%) of ethyl (3R)-3-[4-(benzyloxy)-3-fluorophenyl]-3-[[(S)-2-methylpropane-2-sulfinyl]amino]propanoate as yellow oil.

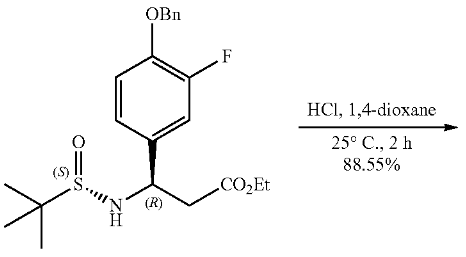

180

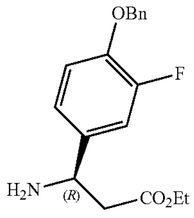

181

Into a 1-L round-bottom flask, was placed ethyl (3R)-3-[4-(benzyloxy)-3-fluorophenyl]-3-[[(S)-2-methylpropane-2-sulfinyl]amino]propanoate (150.00 g, 355.847 mmol, 1.00 equiv.), HCl in 1,4-dioxane (400.00 mL, 4M). The resulting solution was stirred for 2 h at 25° C. The resulting mixture was concentrated. The reaction was then quenched by the addition of 1 L of water. $NaHCO_3$ (aq.) was employed to adjust the pH to 8. The resulting solution was extracted with 2×1 L of ethyl acetate dried over anhydrous sodium sulfate and concentrated. This resulted in 100 g (88.55%) of ethyl (3R)-3-amino-3-[4-(benzyloxy)-3-fluorophenyl]propanoate as yellow oil.

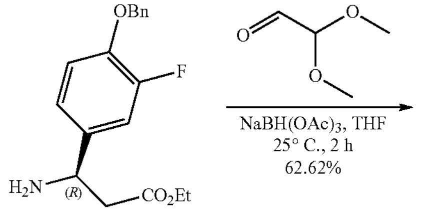

181

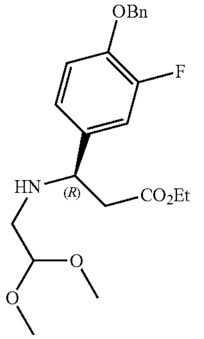

182

Into a 2-L round-bottom flask, was placed ethyl (3R)-3-amino-3-[4-(benzyloxy)-3-fluorophenyl]propanoate (100.00 g, 315.100 mmol, 1.00 equiv.), THF (1.00 L), 2,2-dimethoxyacetaldehyde (49.21 g, 472.696 mmol, 1.50 equiv.), $NaBH(OAc)_3$ (133.57 g, 630.199 mmol, 2.00 equiv.). The resulting solution was stirred for 2 h at 25° C. The reaction was then quenched by the addition of 1 L of water. The resulting solution was extracted with 2×1 L of ethyl acetate dried over $Na_2SO_4$ and concentrated under vacuum. This resulted in 80 g (62.62%) of ethyl (3R)-3-[4-(benzyloxy)-3-fluorophenyl]-3-[(2,2-dimethoxyethyl)amino]propanoate as yellow oil.

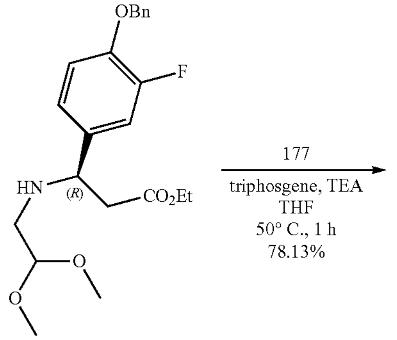

182

-continued

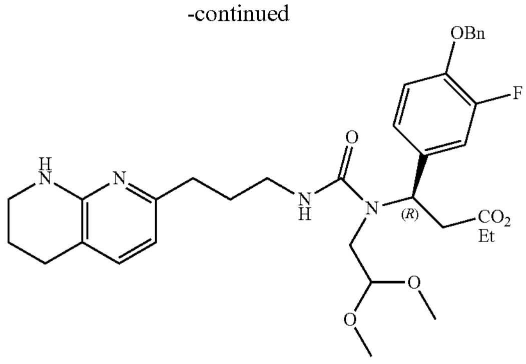

183

Into a 2-L 3-necked round-bottom flask, was placed Triphosgene (22.25 g, 74.975 mmol, 0.38 equiv.), THF (500 mL), ethyl (3R)-3-[4-(benzyloxy)-3-fluorophenyl]-3-[(2,2-dimethoxyethyl)amino]propanoate (80.00 g, 197.304 mmol, 1.00 equiv.), TEA (29.95 g, 295.956 mmol, 1.50 equiv.), 3-(5,6,7,8-tetrahydro-1,8-naphthyridin-2-yl)propan-1-amine (Compound 177, 33.97 g, 177.573 mmol, 0.90 equiv.). The resulting solution was stirred for 1 h at 50° C. in an oil bath. The reaction was then quenched by the addition of 1 L of water. $NaHCO_3$ (aq.) was employed to adjust the pH to 8. The resulting solution was extracted with 2×1 L of ethyl acetate dried over anhydrous sodium sulfate and concentrated. This resulted in 96 g (78.13%) of ethyl (3R)-3-[4-(benzyloxy)-3-fluorophenyl]-3-[(2,2-dimethoxyethyl)([[3-(5,6,7,8-tetrahydro-1,8-naphthyridin-2-yl)propyl]carbamoyl])amino]propanoate as yellow crude oil.

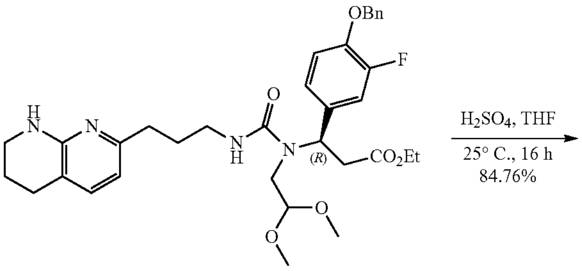

183

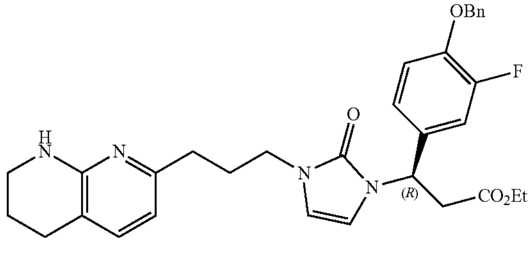

184

Into a 1000-mL round-bottom flask, was placed ethyl (3R)-3-[4-(benzyloxy)-3-fluorophenyl]-3-[(2,2-dimethoxyethyl)([[3-(5,6,7,8-tetrahydro-1,8-naphthyridin-2-yl)propyl]carbamoyl])amino]propanoate (96.00 g, 154.158 mmol, 1.00 equiv.), THF (500.00 mL), $H_2SO_4$ (180.00 mL, 2M). The resulting solution was stirred for 16 h at 25° C. NaOH (5M) was employed to adjust the pH to 8. The resulting solution was extracted with 2×1 L of dichloromethane dried over anhydrous sodium sulfate and concentrated. The residue was applied onto a silica gel column with dichloromethane/methanol (50/1). The collected fractions were combined and concentrated. This resulted in 73 g (84.76%) of ethyl (3R)-3-[4-(benzyloxy)-3-fluorophenyl]-3-[2-oxo-3-[3-(5,6,7,8-tetrahydro-1,8-naphthyridin-2-yl)propyl]-2,3-dihydro-1H-imidazol-1-yl]propanoate as yellow oil.

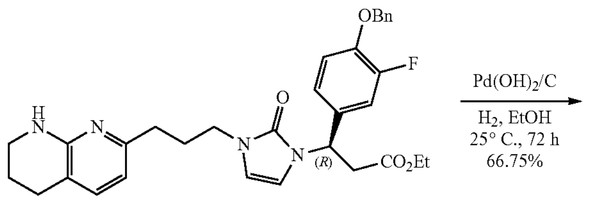

184

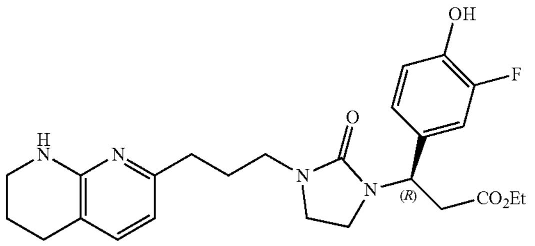

185

Into a 3-L round-bottom flask, was placed ethyl (3R)-3-[4-(benzyloxy)-3-fluorophenyl]-3-[2-oxo-3-[3-(5,6,7,8-tetrahydro-1,8-naphthyridin-2-yl)propyl]-2,3-dihydro-1H-imidazol-1-yl]propanoate (73.00 g, 130.671 mmol, 1.00 equiv.), EtOH (1.50 L), Pd(OH)$_2$/C (60.00 g, 427.259 mmol, 3.27 equiv.), H$_2$ (50 atm). The resulting solution was stirred for 72 h at 25° C. The solids were filtered out. The residue was applied onto a silica gel column with dichloromethane/methanol (9/1). The collected fractions were combined and concentrated. This resulted in 41.0415 g (66.75%) of ethyl (3R)-3-(3-fluoro-4-hydroxyphenyl)-3-[2-oxo-3-[3-(5,6,7,8-tetrahydro-1,8-naphthyridin-2-yl)propyl]imidazolidin-1-yl]propanoate as yellow oil.

LCMS-PH-ARP-052-0: [MS+1]+=471

Rotation Optical $[a]_D^{20.0}$=+37.5° (C=1 g/100 ml in MeOH) H-NMR: (300 MHz, DMSO-d$_6$, ppm) δ 9.84 (s, 1H), 7.07-7.00 (m, 2H), 6.95-6.850 (m, 2H), 6.24 (d, 2H), 5.18 (t, 1H), 4.06-3.96 (m, 2H), 3.32-2.75 (m, 10H), 2.60 (t, 2H), 2.37 (t, 2H), 1.77-1.67 (m, 4H), 1.10 (t, 3H).

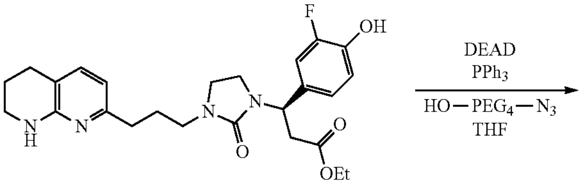

185

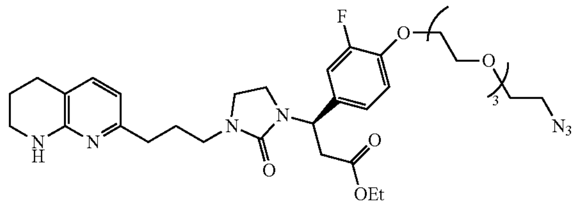

186

To a solution of PPh$_3$ in THF at −10° C. was added dropwise a solution of DEAD. The mixture was warmed to room temperature and added to a neat mixture of compound 185 and HO-PEG$_4$-N$_3$, and stirred overnight. The reaction mixture was then concentrated under reduced pressure, and the residue was purified over silica eluting a gradient of MeOH in DCM, yielding compound 186.

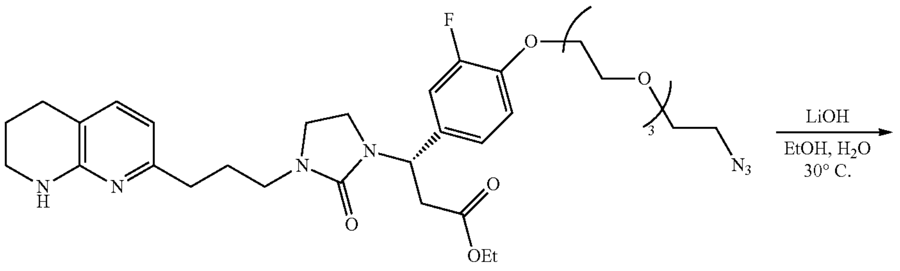

186

-continued

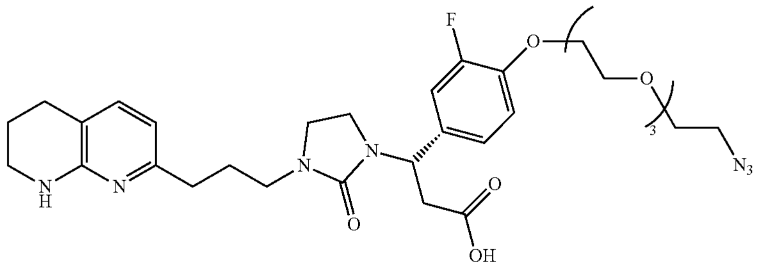

187

To compound 186 was added EtOH and $H_2O$, followed by LiOH. The mixture was stirred at 30° C. overnight. Upon completion the mixture was neutralized to pH=5 using 6 M aqueous HCl and concentrated. The residue was purified by reverse phase HPLC with a Phenomenex Gemini C18, 50×250 mm, 10 μm column eluting a gradient of acetonitrile in water containing 0.1%, yielding compound 187 (Structure 2.11c).

Synthesis of Structure 28c (Compound 118a) Structure 29c (Compound 118b), Structure 31c (Compound 119a), and Structure 30c (Compound 119b)

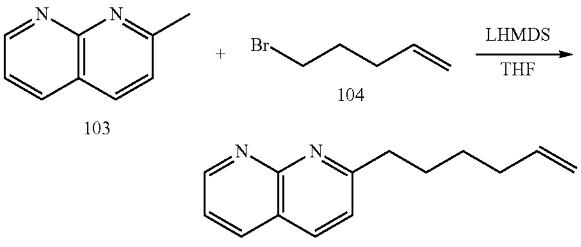

105

To a solution of LHMDS (1.0 M in THF, 95 mL, 95 mmol) and THF (60 mL) was added a solution of compound 103 (2-methyl-[1,8]naphthyridine (12.5 g, 86.7 mmol)) in THF (180 mL) dropwise at −78° C. After stirring for 30 minutes, a solution of compound 104 (5-bromo-1-pentene (19.4 g, 130 mmol)) in THF (120 mL) was added to the reaction mixture dropwise. The reaction mixture was warmed to 0° C. and stirred for 4 hours. The reaction mixture was quenched with saturated aqueous $NH_4Cl$ solution (100 mL) and deionized water (100 mL), then extracted with ethyl acetate (2×400 mL). The combined organic phase was dried over $Na_2SO_4$, filtered, concentrated, and compound 105 was isolated by CombiFlash® eluting a gradient of 50-100% ethyl acetate in hexanes. Yield of compound 105: 7.93 g (43%).

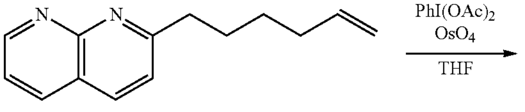

105

-continued

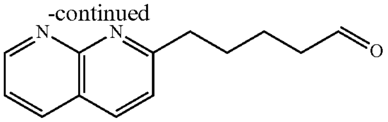

106

To a solution of compound 105 (2.50 g, 11.8 mmol) in acetone (67.5 mL), water (7.5 mL), and 2,6 lutidine (2.74 mL, 23.6 mmol) was added 4-methylmorpholine N-oxide (2.07 g, 17.7 mmol) and osmium tetroxide (2.5 wt % in t-butanol, 2.40 g, 0.24 mmol) at room temperature. After stirring for 75 minutes, (diacetoxyiodo)benzene (5.69 g, 17.7 mmol) was added to the reaction mixture. The reaction mixture was stirred for 2 hours then quenched with saturated aqueous sodium thiosulfate solution (100 mL) and extracted with ethyl acetate (2×100 mL). The combined organic phase was dried over $Na_2SO_4$, filtered, concentrated, and compound 106 was isolated by CombiFlash® eluting a gradient of 0-5% methanol in ethyl acetate. Yield of compound 106: 1.12 g (44%).

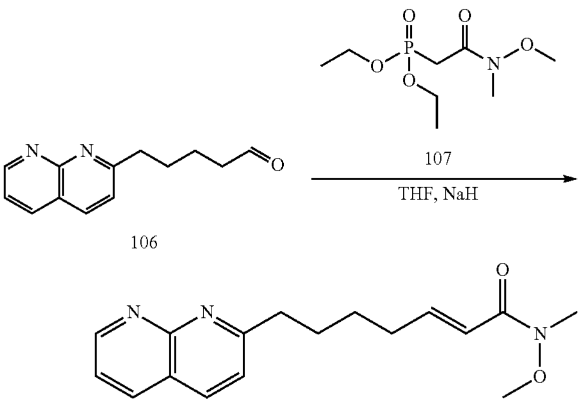

108

To a suspension of sodium hydride (60% dispersion in mineral oil, 0.185 g, 4.64 mmol) in THF (9 mL) was added a solution of compound 107 (diethyl (N-methoxy-N-methylcarbamoylmethyl)phosphonate) (1.06 g, 4.43 mmol) in THF (5 mL) at 0° C. After stirring for 30 minutes, a solution of compound 106 (0.903 g, 4.21 mmol) in THF (9 mL) was added dropwise. The reaction mixture was stirred for 10 minutes at 0° C. then quenched with saturated aqueous $NH_4Cl$ solution (30 mL) and extracted with ethyl acetate (3×30 mL). The combined organic phase was washed twice with half saturated aqueous $NaHCO_3$ solution. The organic phase was dried over $Na_2SO_4$, filtered, and concentrated. Yield of compound 108: 1.40 g (assumed 100% yield and used in the subsequent step without further purification).

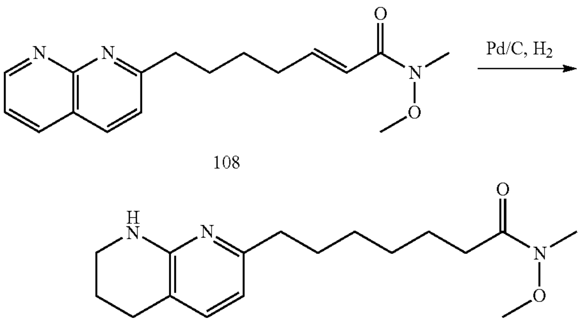

108

109

To a solution of compound 108 (1.31 g, 4.38 mmol) in ethyl acetate (20 mL) was added Pd/C (10% loading, 0.466 g, 0.44 mmol). The reaction vessel was pressurized with $H_2$ to 50 PSI. After stirring for 3.5 hours, the reaction mixture was filtered over Celite® and rinsed with methanol. The filtrate was concentrated and compound 109 was isolated by CombiFlash® eluting a gradient of 50-100% ethyl acetate in hexanes containing 1% triethylamine. Yield of compound 109: 0.833 g (62%).

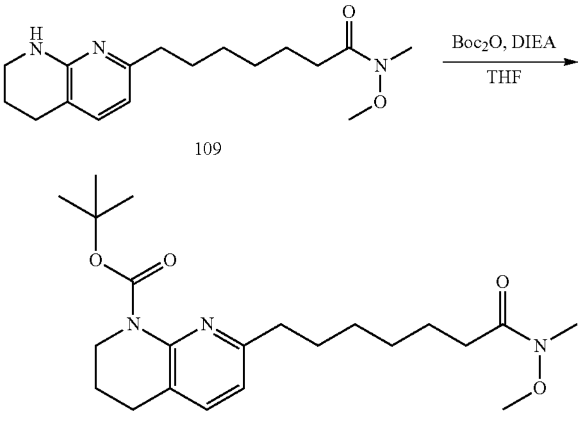

109

110

To a solution of compound 109 (0.833 g, 2.73 mmol) in THF (10 mL) was added DIEA (0.590 mL, 3.41 mmol) and di-tert-butyl dicarbonate (0.744 g, 3.41 mmol). The reaction mixture was heated to 50° C. for 5 hours. The reaction was incomplete based on LC/MS and additional portions of DIEA (0.590 mL, 3.41 mmol) and di-tert-butyl dicarbonate (0.744 g, 3.41 mmol) were added. The reaction mixture was heated at 50° C. for an additional 16 hours. The reaction mixture was concentrated and compound 110 was isolated by CombiFlash® eluting a gradient of 50-100% ethyl acetate in hexanes. Yield of compound 110: 0.934 g (84%).

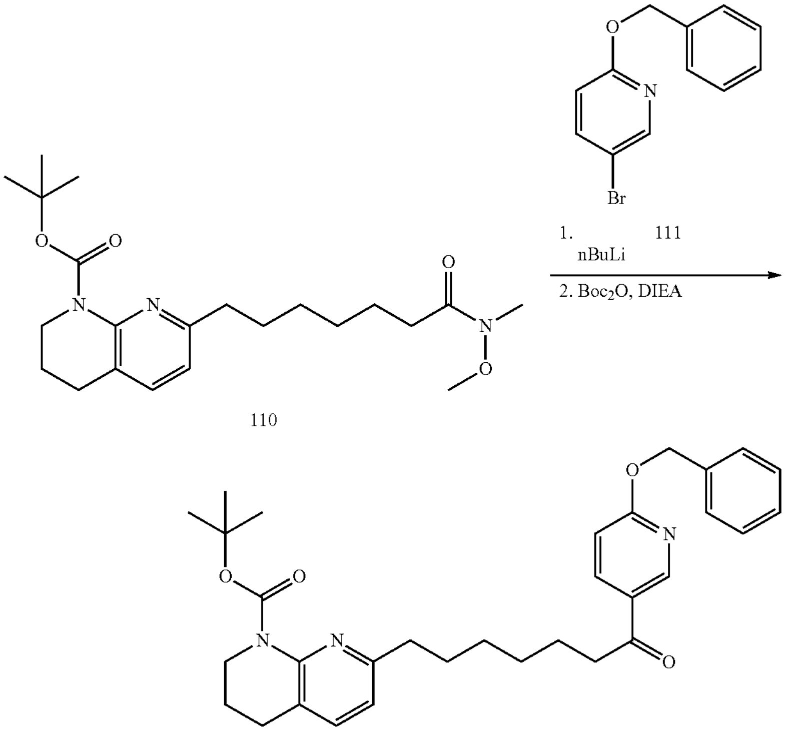

110

112

To a solution of n-butyl lithium (2.5 M in hexanes, 0.70 mL, 1.8 mmol) and THF (1.5 mL) was added compound 111 (5-bromo-2-(phenylmethoxy)-pyridine) (0.465 g, 1.8 mmol) as a solution in THF (0.8 mL) dropwise over 3 minutes at −78° C. Compound 110 (0.535 g, 1.3 mmol) was then added as a solution in THF (1 mL). After stirring for 30 minutes, the reaction was warmed to 0° C., quenched with saturated aqueous $NH_4Cl$ solution (10 mL), and acidified further with 6 M aqueous HCl to a pH of 7. The mixture was extracted with ethyl acetate (3×10 mL). The combined organic phase was dried over $Na_2SO_4$, filtered, and concentrated. To a solution of the crude in THF (8 mL) was added DIEA (0.94 mL, 5.4 mmol) and di-tert-butyl dicarbonate (1.18 g, 5.4 mmol). The mixture was stirred at 40° C. overnight. The reaction mixture was concentrated and compound 112 was isolated by CombiFlash® eluting a gradient of 0-40% ethyl acetate in hexanes. Yield of compound 112: 471 mg (50%).

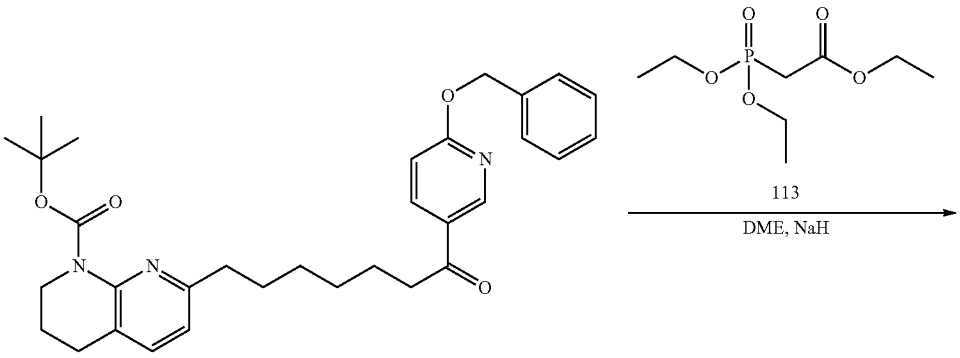

112

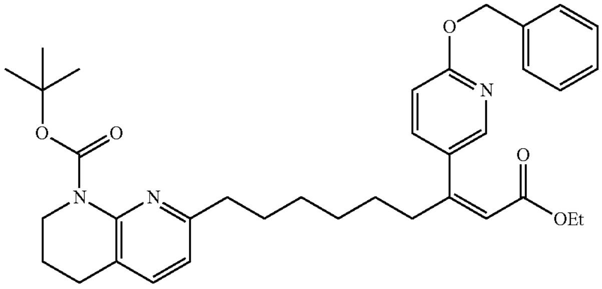

114

To a suspension of sodium hydride (60% dispersion in mineral oil, 0.106 g, 2.65 mmol) in dimethoxyethane (2 mL) was added compound 113 (triethyl phosphonoacetate) (0.593 g, 2.65 mmol) as a solution in dimethoxyethane (1 mL) at 0° C. After stirring for 20 minutes, the reaction mixture was warmed to room temperature and a solution of compound 112 (0.467 g, 0.88 mmol) in dimethoxyethane (2 mL) was added. The reaction mixture was heated at 70° C. for 4 hours. The reaction was quenched with saturated aqueous $NH_4Cl$ solution (10 mL) and the product was extracted with ethyl acetate (3×15 mL). The organic phase was dried over $Na_2SO_4$, filtered, concentrated, and compound 114 was isolated as a 1:1 mixture of cis:trans isomers by CombiFlash® eluting a gradient of 0-30% ethyl acetate in hexanes. Yield of compound 114: 392 mg (74%).

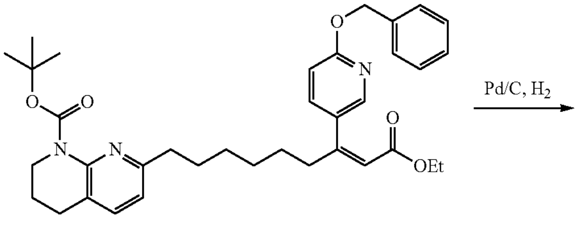

114

-continued

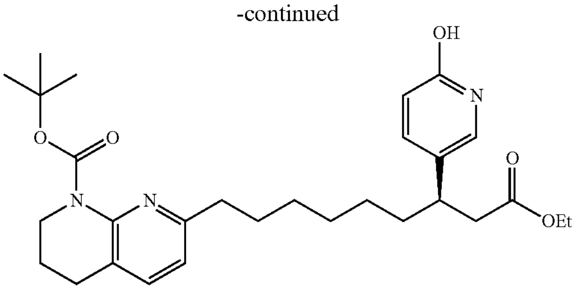

115a

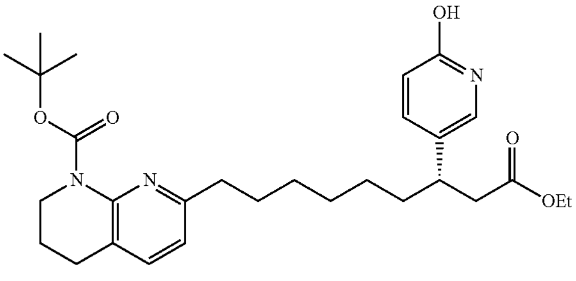

115b

To a solution of compound 114 (390 mg, 0.65 mmol) in ethanol (6 mL) was added Pd/C (10% loading, 69 mg, 0.07 mmol). The reaction vessel was pressurized with $H_2$ to 50 PSI. After stirring for 4 hours, the reaction mixture was filtered over Celite® and rinsed with methanol. The filtrate was concentrated and compound 115 was isolated as a racemic mixture by CombiFlash® eluting a gradient of 0-10% methanol in DCM. Yield of compound 115: 95 mg (29%). Chiral semi-preparative HPLC (250×21 mm Chiralpak® AD column, 5 μm, 90/10 hexanes/EtOH, 40 mL/min) was used to isolate 42 mg of the first eluting R-isomer (RT=12-14 m, >99% ee, compound 115a) and 40 mg of the second eluting S-isomer (RT=15-18 m, >98% ee, compound 115b). The identity of the R- and S-isomers were assigned based on the order of elution of a structurally similar compound reported by Coleman et al. 47 J. Med. Chem. 4834 (2004).

Structures 28c ((R)-3-(6-(2-(2-(2-(2-azidoethoxy)ethoxy)ethoxy)ethoxy)pyridin-3-yl-9-(5,6,7,8-tetrahydro-1,8-naphthyridin-2-yl)nonanoic acid) and 31c ((R)-3-(1-(2-(2-(2-(2-azidoethoxy)ethoxy)ethoxy)ethoxy-6-oxo-1,6-dihydropyridin-3-yl)-9-(5,6,7,8-tetrahydro-1,8-naphthyridin-2-yl)nonanoic acid

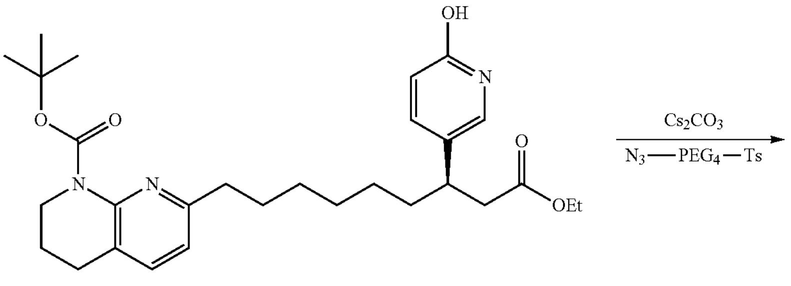

115a

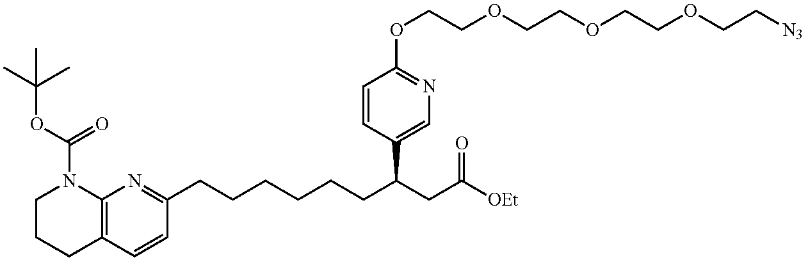

116a

+

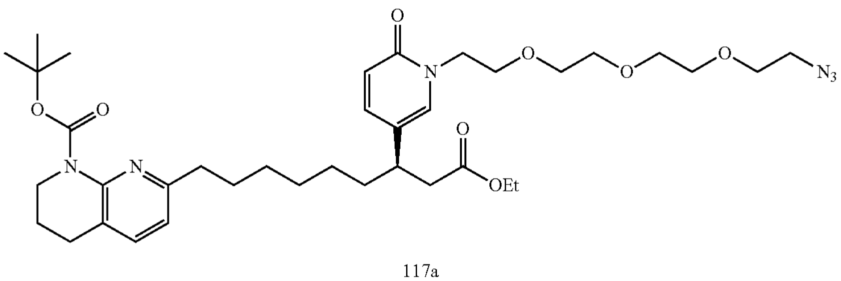

117a

To a solution of compound 115a (41 mg, 0.08 mmol) and $N_3$-$PEG_4$-OTs (61 mg, 0.16 mmol) in DMF (0.5 mL) was added cesium carbonate (53 mg, 0.16 mmol). The reaction mixture was stirred at 40° C. for 1 hour. The reaction mixture was quenched with aqueous $NaHCO_3$ solution (1 mL) then extracted with ethyl acetate (3×3 mL). The organic phase was concentrated under reduced pressure. The crude mixture of N- and O-alkylated regioisomers was subsequently used without further purification.

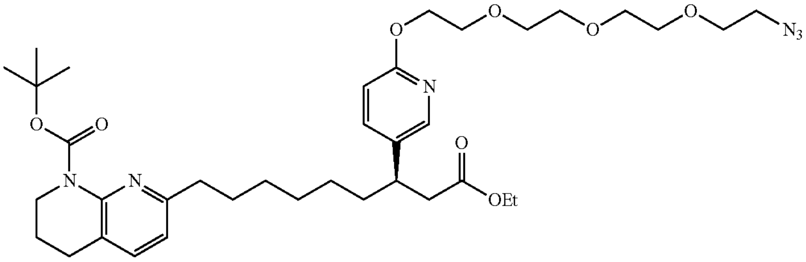

116a

+

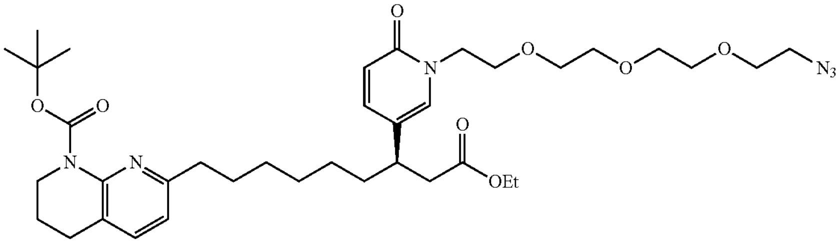

117a

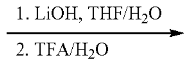

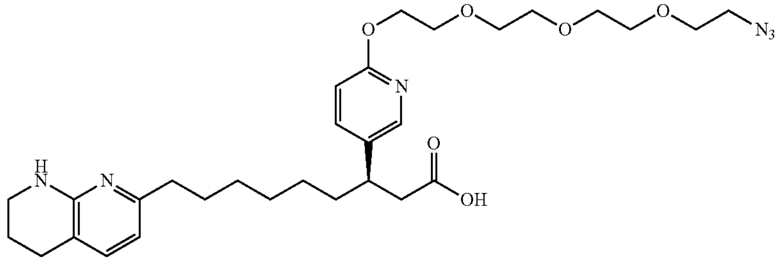

118a

+

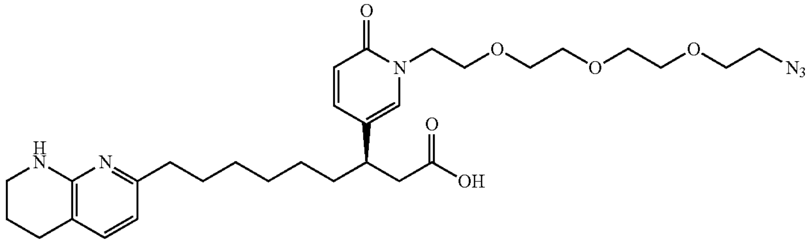

119a

To a solution of compounds 116a and 117a (58 mg, 0.08 mmol, 4:6 mixture of 9a:10a) in THF (1.0 mL) and deionized water (1.0 mL) was added lithium hydroxide (6 mg, 0.25 mmol). The reaction mixture was stirred at room temperature for 1 hour and then at 35° C. for 2 hours. An additional portion of lithium hydroxide (4 mg, 0.16 mmol) was added and the reaction temperature was increased to 40° C. After stirring for 3 hours, a final portion of lithium hydroxide (4 mg, 0.25 mmol, total 16 mg, 0.66 mmol) was added. The reaction mixture was stirred at 50° C. for 3 hours. The reaction mixture was acidified to a pH of 7 with 6 N aqueous HCl and concentrated under reduced pressure. The regioisomers, compounds 118a and 119a, were separated by CombiFlash® eluting a gradient of 0-5% methanol in DCM containing 0.5% acetic acid. Compound 118a was further purified by reverse phase HPLC (Thermo Scientific™ Aquasil™ C18, 250×21.2 mm, 5 µm, 20 mL/min, 0.1% TFA in water/ACN, gradient elution), yielding 13 mg of compound 118a (Structure 28c). Compound 119a was purified under the same conditions, yielding 16 mg of compound 119a (Structure 31c).

Structures 29c ((S)-3-(6-(2-(2-(2-(2-azidoethoxy)ethoxy)ethoxy)ethoxy)pyridin-3-yl)-9-(5,6,7,8-tetrahydro-1,8-naphthyridin-2-yl)nonanoic acid) and 30c ((S)-3-(1-(2-(2-(2-(2-azidoethoxy)ethoxy)ethoxy)ethyl)-6-oxo-1,6-dihydropyridin-3-yl)-9-(5,6,7,8-tetrahydro-1,8-naphthyridin-2-yl)nonanoic acid)

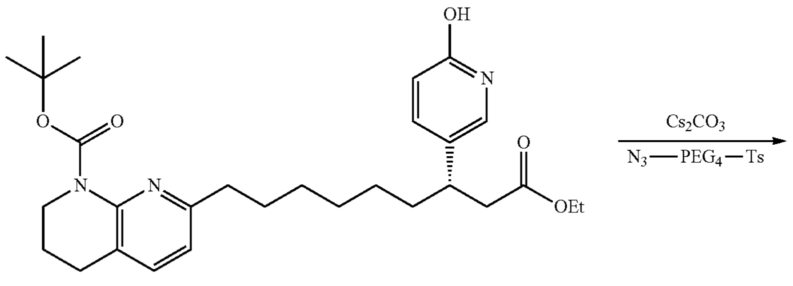

115b

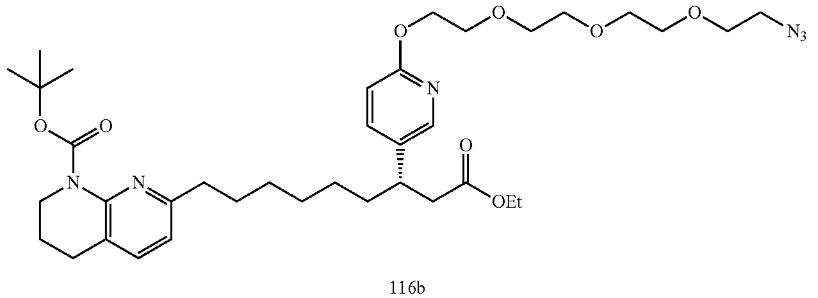

116b

+

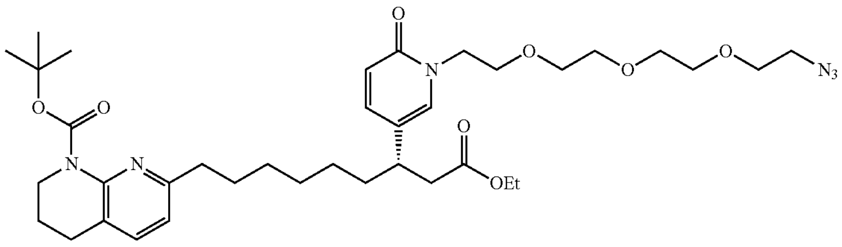

117b

To a solution of compound 115b (40 mg, 0.08 mmol) and $N_3$-$PEG_4$-OTs (58 mg, 0.16 mmol) in DMF (0.5 mL) was added cesium carbonate (51 mg, 0.16 mmol). The reaction mixture was stirred at 40° C. for 30 minutes. The reaction mixture was quenched with aqueous $NaHCO_3$ solution (1 mL) then extracted with ethyl acetate (3×3 mL). The organic phase was concentrated under reduced pressure. The crude mixture of N- and O-alkylated regioisomers was subsequently used without further purification.

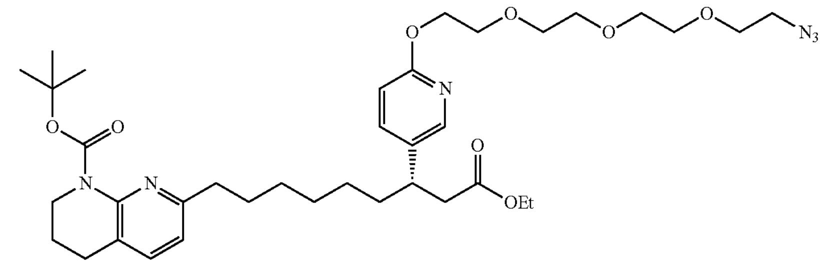

116b

+

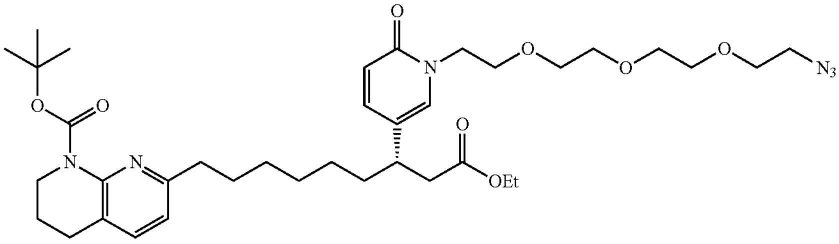

117b

1. LiOH, THF/$H_2O$
2. TFA/$H_2O$

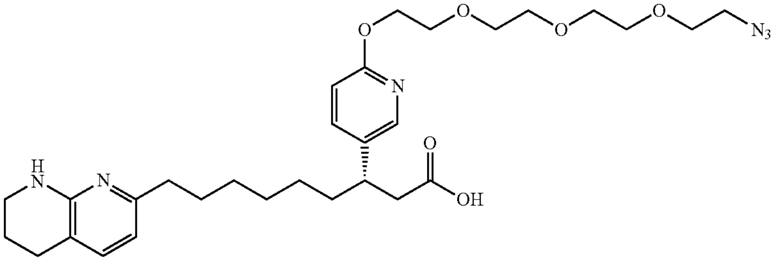

118b

+

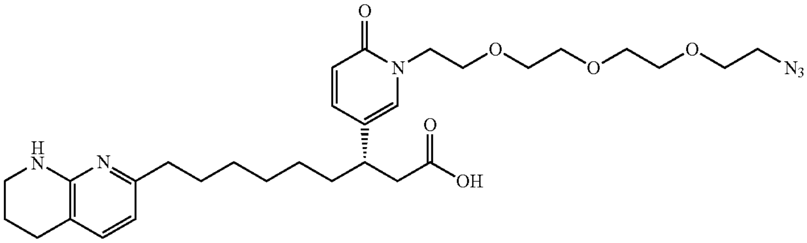

119b

To a solution of compounds 116b and 117b (56 mg, 0.08 mmol, 4:6 mixture of 9a:10a) in THF (0.75 mL) and deionized water (0.75 mL) was added lithium hydroxide (6 mg, 0.25 mmol). The reaction mixture was stirred at 45° C. for 2.5 hours. An additional portion of lithium hydroxide (6 mg, 0.25 mmol) was added and the reaction mixture was stirred for 2.5 hours. The reaction temperature was lowered to 35° C. and the mixture was stirred overnight. The reaction mixture was acidified to pH=7 with 6 N aqueous HCl and concentrated under reduced pressure. The regioisomers, compounds 118b and 119b, were separated by CombiFlash eluting a gradient of 0-5% methanol in DCM containing 0.5% acetic acid. Compound 118b was further purified by reverse phase HPLC (Thermo Scientific™ Aquasil™ C18, 250×21.2 mm, 5 μm, 20 mL/min, 0.1% TFA in water/ACN, gradient elution), yielding 14 mg of compound 118b (Structure 29c). Compound 119b was purified under the same conditions, yielding 18 mg of compound 119b (Structure 30c).

Synthesis of Structure 32c ((R)-3-(4-(2-(2-(2-azidoethoxy)ethoxy)ethoxy)-3-fluorophenyl)-3-(N-methyl-5-(5,6,7,8-tetrahydro-1,8-naphthyridin-2-yl)pentanamido)propanoic acid)

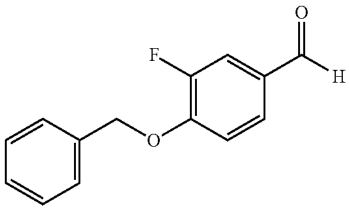

120

+

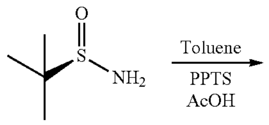

121

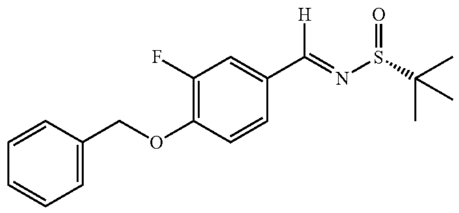

122

To compound 120 (2.75 g, 11.94 mmol) in toluene (80 mL) over 3 Å sieves was added compound 121 (5.79 g, 47.78 mmol), followed by PPTS (300 mg, 1.19 mmol) then AcOH (683 uL, 11.94 mmol). The reaction was brought to reflux overnight. Upon completion the reaction was quenched by addition of saturated sodium bicarbonate. The organic layer was diluted with 2 volumes of ethyl acetate, separated, and filtered over sodium sulfate. The product was isolated over silica eluting a gradient of ethyl acetate (0-30%) in hexane to yield 2.054 g (54%).

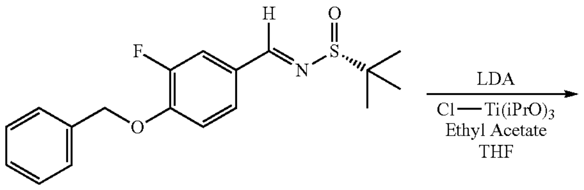

122

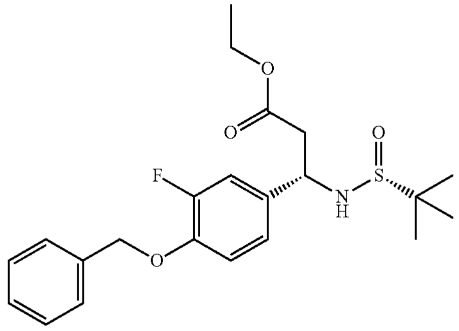

123

To DIA (2.85 mL, 20.33 mmol) in THF (15 mL) at −78° C. was added a 2.5M solution of n-BuLi (7.76 mL, 19.41 mmol) was added dropwise. Stirring was continued for 5 minutes at −78 C and ethyl acetate (1.81 mL, 18.48 mmol) was added dropwise. Stirring was continued for a further 10 minutes at −78° C. and a solution of chloro titanium triisopropoxide (9.27 mL, 38.381 mmol) in THF (10 mL) was added dropwise. Stirring was continued for a further 15 minutes at −78° C. and a solution of compound 122 (2.054 g, 6.16 mmol) in THF (10 mL) was added dropwise. Stirring was continued for 1.5 hours at −78° C. Upon completion the reaction was quenched by addition of saturated ammonium bicarbonate. The suspension was diluted with 6 volumes of ethyl acetate and the organic layer was separated, dried over sodium sulfate, filtered and concentrated. The product was isolated over silica eluting a gradient of ethyl acetate in hexanes to yield 1.043 g (53%).

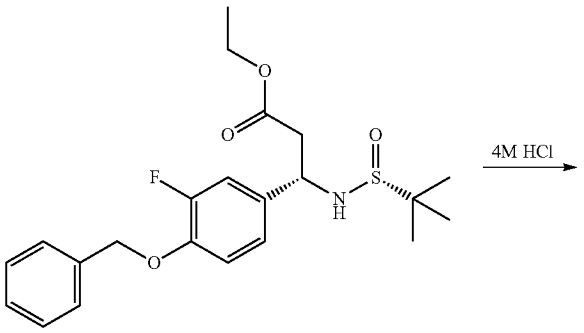

123

-continued

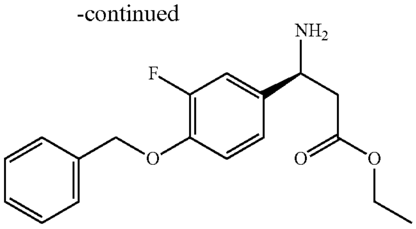

124

To compound 123 (1.043 g, 2.47 mmol) stirring in MeOH (3 mL) was added a 4M HCl solution in dioxane (3.09 mL, 12.37 mmol). Upon completion of deprotection the solution was diluted with water (8 mL) and washed twice with diethyl ether (6 mL). The aqueous layer was subsequently adjusted to a pH of 11 with sodium hydroxide. The precipitate was extracted with ethyl acetate, and the combined organic extracts were dried over sodium sulfate, filtered, and concentrated yielding 0.616 g (78.5%) of product 124 that was used without further purification.

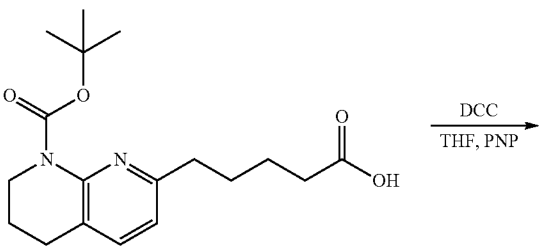

125

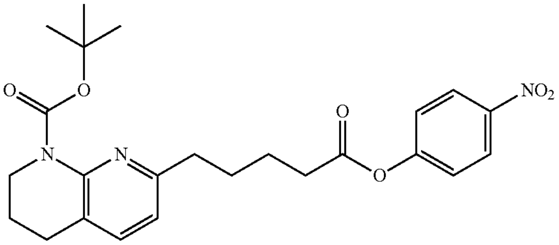

126

To compound 125 (92.1 mg, 0.275 mmol) in THF (1.5 mL) at 0° C. was added DCC (68.1 mg, 0.331 mmol). After 5 minutes PNP (106.1 mg, 0.331 mmol) was added, the ice bath was removed, and stirring continued for 1 hour. Upon completion the suspension was chilled to −20° C. for 1 hour and the precipitate was removed by filtration. The supernatant was concentrated and yielded 129 mg (103%) of crude product 126 that was subsequently used without further purification.

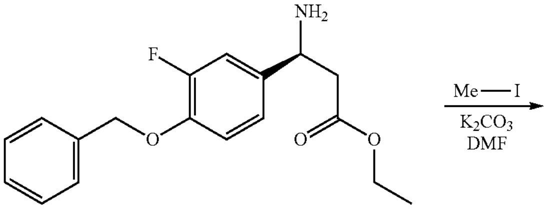

124

-continued

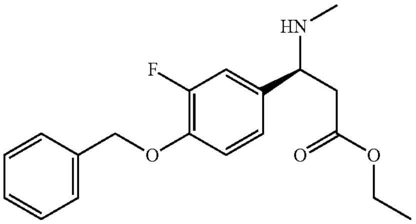

127

A mixture containing compound 124 (148.6 mg, 0.468 mmol) and potassium carbonate (129 mg, 0.937 mmol) in DMF (2 mL) was treated with methyl iodide (66.5 mg, 0.468 mmol) and stirred at 50° C. for 3 hours. Upon completion of alkylation all volatiles were removed and the product was isolated over silica eluting a gradient of ethyl acetate in hexanes, each buffered with 1% TEA, to yield 94.6 mg (61%).

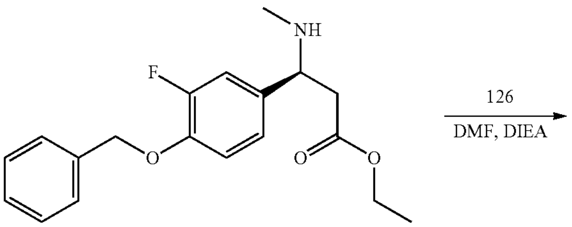

127

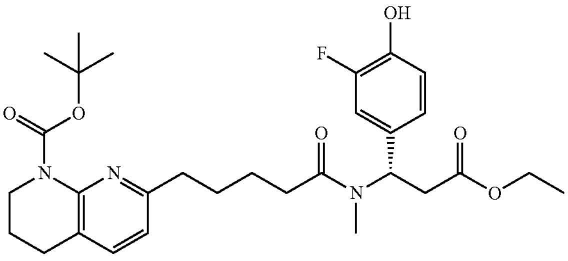

128

To compound 127 (94.5 mg, 0.285 mmol) in DMF (2 mL) was added DIEA (149 uL, 0.856 mmol) followed by Compound 126 (129.9 mg, 0.285 mmol) and the mixture was stirred for 1 hour at 80° C. Upon completion all volatiles were removed and the crude was dissolved in MeOH, treated with 10% palladium on carbon (20 mg), and the flask was charged with 60 PSI of hydrogen. Upon completion the suspension was filtered. The supernatant was concentrated and the crude product obtained was used subsequently without further purification.

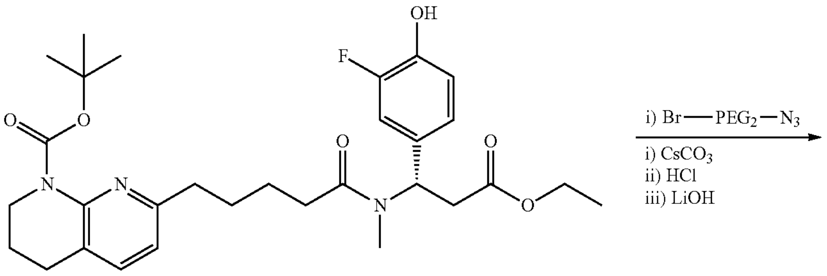

128

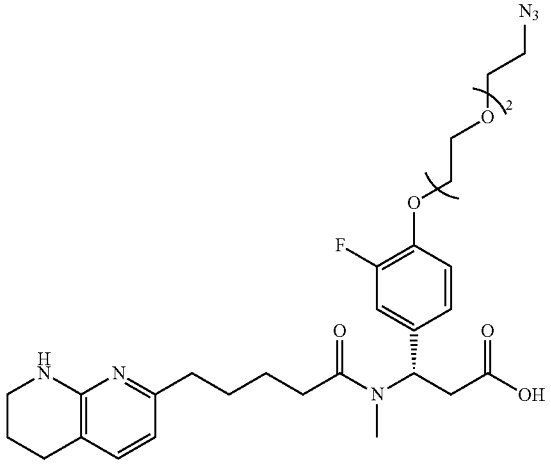

129

A mixture containing compound 128 (159 mg, 0.285 mmol), Bromo-PEG$_2$-Azide (74.7 mg, 0.314 mmol) and cesium carbonate (204 mg, 0.627 mmol) in DMF (2 mL) was heated to 60° C. for 2 hours. Upon completion all volatiles were removed and the crude was treated with 4M HCl in dioxane (0.5 mL, 2 mmol) and heated to 40° C. for 3 hours. Upon completion all volatiles were removed. The crude was suspended in a mixture of THF (1 mL), MeOH (1.5 mL) and $H_2O$ (1.5 mL), treated with lithium hydroxide (83.5 mg, 3.48 mmol) and heated to 40° C. for 16 hours. Upon completion the pH was adjusted to 3 with TFA, and the product was isolated by separation over a Phenomenex® Gemini® C18 column (21.2×250 mm, 5 micron) eluting a gradient of acetonitrile in water containing 0.1% TFA to yield 33.1 mg (20%).

Synthesis of Structure 33c ((R)-1-azido-13-(3-fluoro-4-methoxyphenyl)-12-(5-(5,6,7,8-tetrahydro-1,8-naphthyridin-2-yl)pentanoyl)-3,6,9-trioxa-12-azapentadecan-15-oic acid)

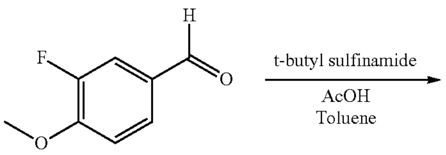

130

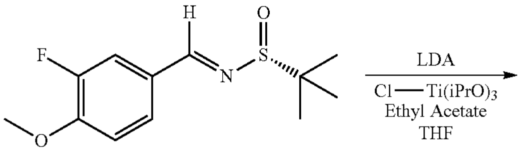

131

-continued

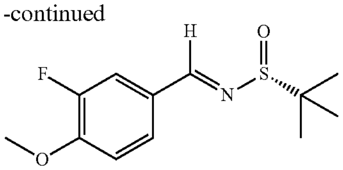

131

A mixture containing compound 130 (1.5 g, 9.73 mmol), (R) t-butyl sulfinamide (2.36 g, 19.46 mmol), and AcOH (0.14 mL) in toluene (45 mL) was refluxed in a flask fitted with a Dean-Stark trap for 16 hours. Upon completion the reaction was quenched by addition of saturated sodium bicarbonate. The organic layer was separated, dried over sodium sulfate, filtered and concentrated. The product was isolated by separation over silica eluting a gradient of ethyl acetate in hexanes to yield 1.714 g (68.4%).

-continued

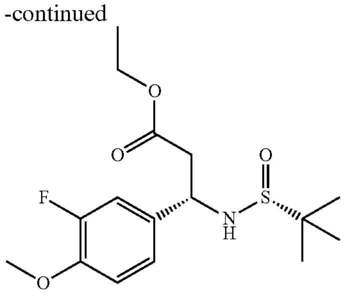

132

To DIA (3.056 mL, 21.80 mmol) in THF (18 mL) at −78° C. was added a 2.5M solution of n-BuLi (8.324 mL, 20.81 mmol) was added dropwise. Stirring was continued for 5 minutes at −78° C. and ethyl acetate (1.94 mL, 19.82 mmol) was added dropwise. Stirring was continued for a further 10 minutes at −78° C. and a solution of chloro titanium triisopropoxide (9.94 mL, 41.62 mmol) in THF (10 mL) was added dropwise. Stirring was continued for a further 15 minutes at −78° C. and a solution of compound 131 (1.70 g, 6.61 mmol) in THF (12 mL) was added dropwise. Stirring was continued for 1.5 hours at −78° C. Upon completion the reaction was quenched by addition of saturated ammonium bicarbonate. The suspension was diluted with 7 volumes of ethyl acetate and the organic layer was separated, dried over sodium sulfate, filtered and concentrated. The product was isolated over silica eluting a gradient of ethyl acetate in hexanes to yield 0.984 g (43%).

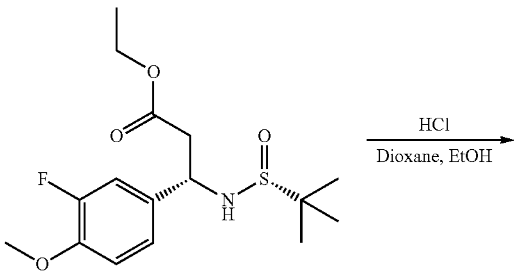

132

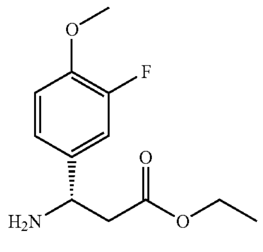

133

To compound 132 (0.975 g, 2.82 mmol) in EtOH (6 mL) at 0° C. was added 4 M HCl (2.12 mL, 8.47 mmol) in dioxane and stirred for 30 minutes. Upon completion the reaction was diluted with water (15 mL) and washed with diethyl ether. The organic layer was separated and the pH of the aqueous layer was adjusted to 12 with sodium hydroxide. The aqueous layer was washed with 5 volumes of ethyl acetate and the organic layer was separated, filtered over sodium sulfate and concentrated. The product was isolated by separation over silica eluting a gradient of ethyl acetate in hexanes containing 1% TEA to yield 0.434 g (64%).

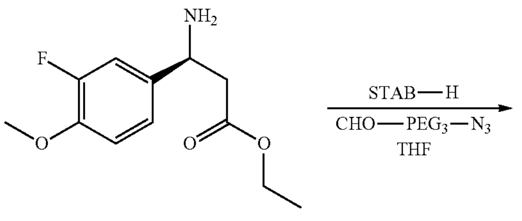

133

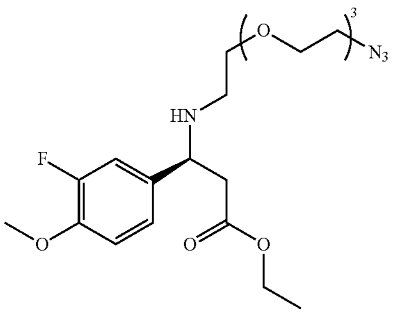

134

To a mixture of compound 133 (0.120 g, 0.497 mmol) and PEG (0.151 g, 0.696 mmol) in THF (2 mL) over 3 Å molecular sieves was added STAB-H (0.253 g, 1.19 mmol) and the suspension was stirred for 16 hours at room temperature. Upon completion the reaction was quenched by addition of saturated sodium bicarbonate and the crude was extracted with three portions of ethyl acetate. The separated organic extracts were combined, dried over sodium sulfate, filtered and concentrated. The crude obtained was used subsequently without further purification.

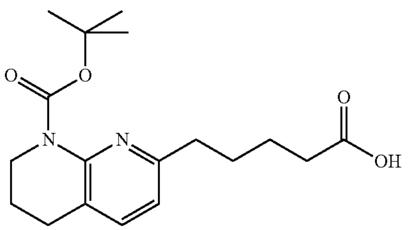

125

+

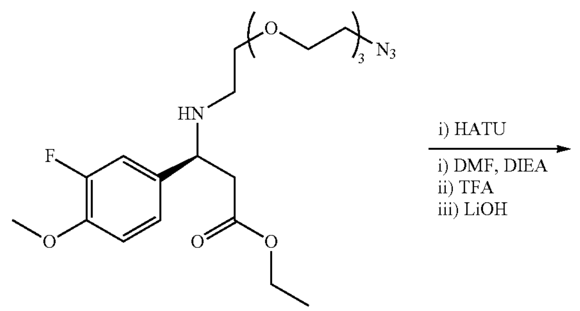

134

-continued

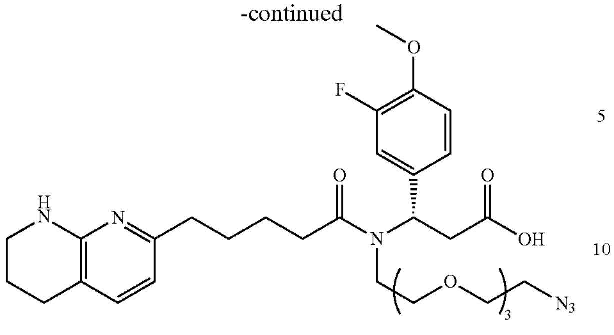

135

Compound 134 (0.200 g, 0.597 mmol) in DMF (2 mL) was treated with HATU (0.227 g, 0.597 mmol) and stirred for 5 minutes. To the activated ester was added DIEA (0.259 mL, 1.49 mmol) followed by compound 125 (0.220 g, 0.497 mmol) in DMF (1 mL) and the resulting mixture was stirred for 1 hour. All volatiles were removed and the resulting crude was treated with neat TFA (3.8 mL) and stirred for 3 hours at 40° C. Upon completion of BOC removal all volatiles were removed and the crude was suspended in a mixture of THF (4 mL), water (8 mL), and MeOH (8 mL). The resulting mixture was treated with LiOH (71.6 mg, 2.98 mmol) and heated to 40° C. for 16 hours. Upon completion the pH was adjusted to 3 with TFA, and the product was isolated by separation over a Phenomenex® Gemini® c18 column (21.2×250 mm, 5 micron) eluting a gradient of acetonitrile in water containing 0.1% TFA to yield 56.2 mg (18%, 3-Steps).

Synthesis of Structure 34c ((S)-1-azido-13-(3-fluoro-4-methoxyphenyl)-12-(5-(5,6,7,8-tetrahydro-1,8-naphthyridin-2-yl)pentyl)-3,6,9-trioxa-12-aza-pentadecan-15-oic acid)

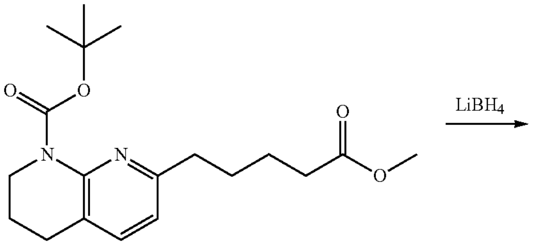

136

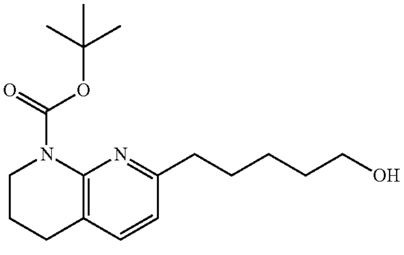

137

Compound 136 (0.500 g, 1.45 mmol) in a mixture of THF (9.0 mL) and MeOH (0.5 mL) at 0° C. was treated with lithium borohydride (94.5 mg, 4.34 mmol). Cooling was removed and stirring was continued until gas evolution ceased. The reaction mixture was diluted with 5 volumes of EtOAc. The organic layer was washed with ammonium bicarbonate, dried over sodium sulfate, filtered, and concentrated. The product was isolated by elution over silica using a gradient of ethyl acetate in hexanes to yield 309 mg (67%).

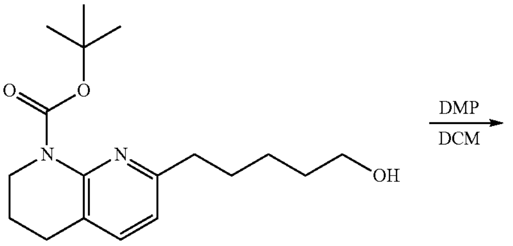

137

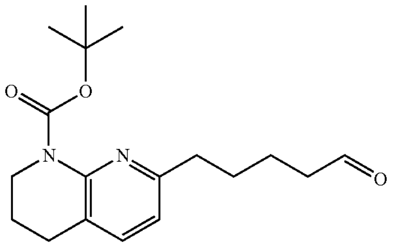

138

To a solution containing compound 137 (0.305 g, 0.952 mmol) in DCM (9 mL) at 0° C. was added Martin's reagent in several portions. Several drops of water were added, cooling was removed, and the reaction was stirred for 3 hours. Upon completion the mixture was washed with saturated sodium bicarbonate then saturated sodium thiosulfate. The separated organic was dried over sodium sulfate, filtered and concentrated. The product 138 was separated over silica eluting a gradient of MeOH in DCM to yield 140 mg (46%).

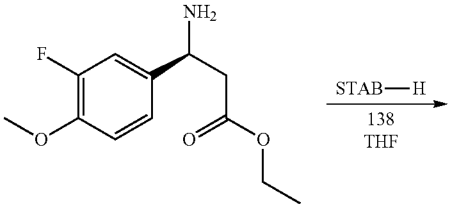

139

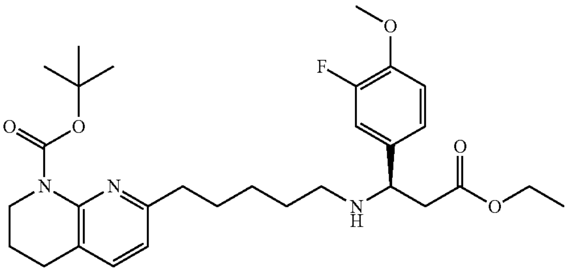

140

To a mixture containing compound 1 (85.2 mg, 0.353 mmol) and 138 (134.9 mg, 0.424 mmol) in THF (2.5 mL) over 3 Å molecular sieves was added STAB-H (0.150 g, 0.706 mmol) and the resulting suspension was heated to 40° C. for 16 hours. Upon completion the reaction was diluted with 5 volumes of ethyl acetate and treated with saturated sodium bicarbonate. The organic layer was separated, dried over sodium sulfate, filtered and concentrated. The product was isolated by separation over silica eluting a gradient of MeOH in DCM containing 1% TEA to yield 64 mg (33%).

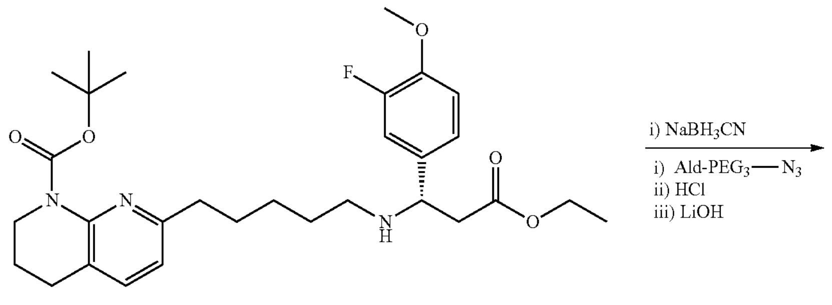

140

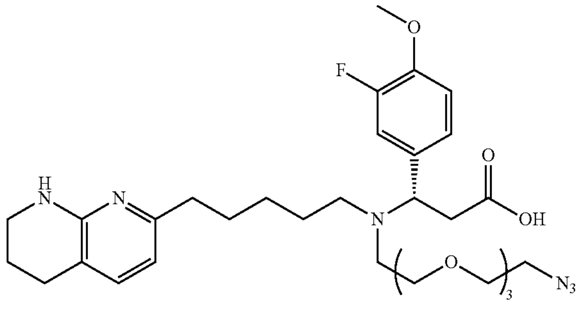

141

To a mixture containing compound 140 (60 mg, 0.110 mmol), Ald-$PEG_3$-$N_3$ (71.9 mg, 0.331 mmol) and AcOH (3 µL, 0.0276 mmol) in MeOH (1 mL) over 3 Å molecular sieves was added sodium cyanoborohydride (28.9 mg, 0.276 mmol) and the reaction was stirred at 40° C. for 3 hours. Upon completion the mixture was cooled to 0° C., water was added (0.15 mL) and the solution was acidified to a pH of 7 using HCl (4M) in dioxane. All methanol was subsequently removed, 4M HCl (0.138 mL, 0.552 mmol) in dioxane was added and the mixture was stirred at 40° C. for 2 hours. Upon completion of BOC removal all volatiles were removed and the crude was suspended in a mixture of THF (1 mL), water (2 mL) and MeOH (2 mL) and treated with lithium hydroxide (26.5 mg, 1.104 mmol). Upon completion of ester removal the pH was adjusted to 3 by addition of TFA and the product was isolated by separation on a Phenomenex® (21.2x250 mm) C18 column eluting a gradient of acetonitrile in water containing 0.1% TFA to yield 16.4 mg (24%, 3-Steps).

Synthesis of Structure 36c ((S)-3-(4-(2-(2-(2-(2-azidoethoxy)ethoxy)ethoxy)ethoxy)-3-fluorophenyl)-9-(5,6,7,8-tetrahydro-1,8-naphthyridin-2-yl) nonanoic acid)

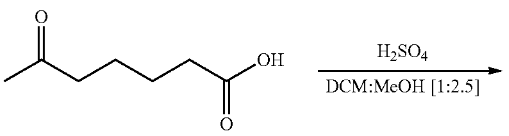

-continued

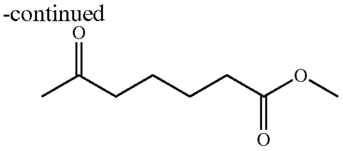

141

To a solution of 6-oxoheptanoic acid (9.74 g, 68 mmol) in DCM (30 mL) and MeOH (75 mL) was added conc. $H_2SO_4$ (0.18 mL, 3.4 mmol) at room temperature. The reaction mixture was refluxed overnight. The reaction mixture was then concentrated to an oil, redissolved in DCM (150 mL), and washed with sat. aq. $NaHCO_3$ (2x40 mL) and brine (40 mL). The organic layer was dried over $Na_2SO_4$, filtered, and concentrated. The product was used in the next step without further purification. Yield of compound 141: 10.2 g (95%). $^1$H NMR (400 MHz, DMSO-d6): δ 3.58 (s, 3H), 2.43 (t, 2H), 2.29 (t, 2H), 1.46 (m, 4H).

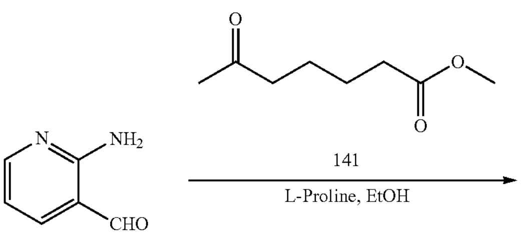

-continued

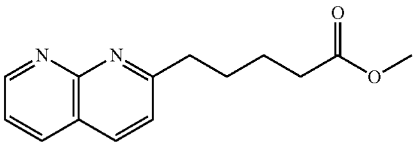

142

To a solution of compound 141 (10.2 g, 65 mmol) and 2-amino-3-formylpyridine (7.89 g, 65 mmol) in EtOH (80 mL) was added L-proline (3.72 g, 32 mmol). The reaction mixture was heated at reflux overnight. The reaction mixture was then concentrated, dissolved in EtOAc (50 mL), and washed with water (3x30 mL). The organic phase was dried over $Na_2SO_4$, filtered, and concentrated. The residue was purified by CombiFlash using silica gel as the stationary phase and was eluted with a gradient of EtOAc in DCM (10-100%). Yield of compound 142: 6.08 g (39%). Mass calculated for $C_{14}H_{16}N_2O_2$ $[M+H]^+$: 245.13, found: 245.21.

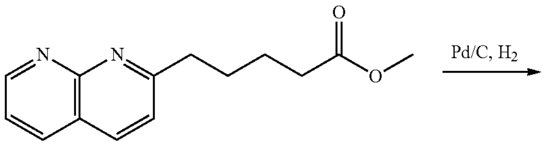

142

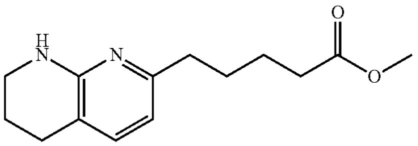

143

To a solution of compound 142 (6.08 g, 24.9 mmol) in MeOH (50 mL) was added Pd/C (10% loading, Degussa type, 1.99 g, 1.87 mmol). The reaction flask was charged with nitrogen, evacuated, and backfilled with nitrogen three times. This process was repeated with hydrogen, and the reaction vessel was finally charged with hydrogen (1 atm) and stirred overnight at room temperature. The reaction mixture was filtered over Celite®, the pad rinsed with MeOH, and the filtrate concentrated. The product, compound 143, was used in the next step without further purification assuming 100% yield. Mass calculated for $C_{14}H_{20}N_2O_2$ $[M+H]^+$: 249.16, found: 249.08.

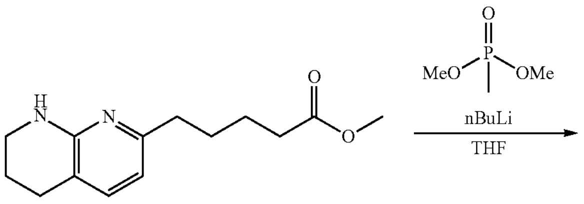

143

-continued

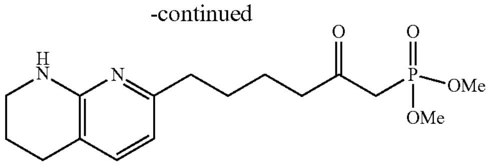

144

To a solution of dimethyl methylphosphonate (12.3 g, 100 mmol) in anhydrous THF (120 mL) was added n-BuLi solution (2.5 M in hexanes, 40 mL, 100 mmol) via syringe pump over 1 h at −78° C. A solution of compound 143 (6.175 g, 24.9 mmol) in THF (40 mL) was added to the reaction mixture over 45 m at −78° C. After stirring for 20 m at −78° C., the reaction mixture was quenched with sat. aq. $NH_4Cl$ solution (200 mL), warmed to rt, and extracted with EtOAc (400 mL). The organic layer was washed with water (200 mL) and brine (200 mL). The organic phase was separated, dried over $Na_2SO_4$, filtered, and concentrated. The product was used in the next step without further purification. Yield of compound 144: 7.86 g (93%). Mass calculated for $C_{16}H_{25}N_2O_4P$ $[M+H]^+$: 341.17, found: 341.17.

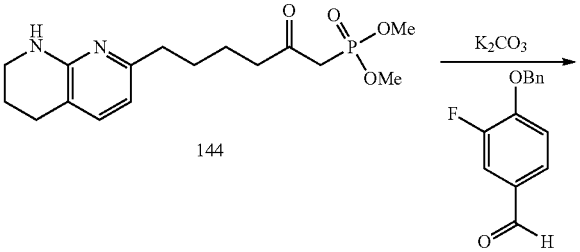

144

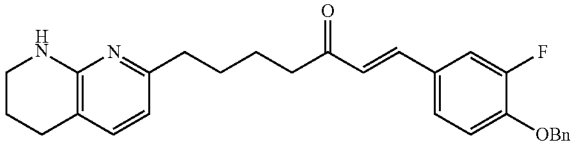

145

A suspension of 3-fluoro-4-(phenylmethoxy)-benzaldehyde (0.38 g, 1.65 mmol), compound 144 (0.67 g, 1.98 mmol), and anhydrous potassium carbonate (0.547 g, 3.96 mmol) in THF (13.5 mL) was heated at reflux overnight. Additional 3-fluoro-4-(phenylmethoxy)-benzaldehyde (0.19 g, 0.83 mmol) and potassium carbonate (0.23 g, 1.65 mmol) were added and the reaction mixture was refluxed for an additional 4 h. The mixture was diluted with EtOAc (100 mL) and washed with water (30 mL) and brine (30 mL). The organic phase was separated, dried over $Na_2SO_4$, filtered, and concentrated. The residue was purified by CombiFlash using silica gel as the stationary phase and was eluted with a gradient of MeOH in DCM (0-10%). Yield of compound 145: 446 mg (61%). Mass calculated for $C_{28}H_{29}FN_2O_2$ $[M+H]^+$: 445.23, found: 445.41.

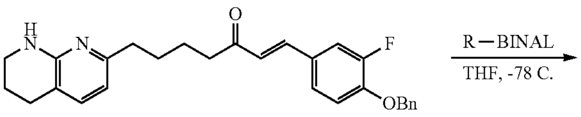

145

-continued

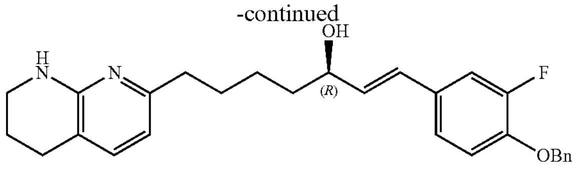

146

Preparation of R-BINAL: To a slurry of LAH (0.396 g, 10.4 mmol, 0.98 eq) dry THF (34 mL) was added EtOH (0.492 g, 10.65 mmol, 1.00 eq) as a solution in THF (3.2 mL) over 10 m while maintaining an internal temperature <35° C. After aging for 30 m, R-BINOL (3.05 g, 10.65 mmol, 1.00 eq) was added as a solution in THF (10 mL), maintaining an internal temperature <35° C. (ca 10 minutes). After stirring for 2 h at room temperature, the reaction mixture was cooled on a dry ice/acetone bath to −78° C.

Compound 145 (1.18 g, 2.65 mmol) was dried azeotropically with anhydrous toluene (50 mL) and was dissolved in anhydrous THF (12 mL). The solution of compound 145 was added dropwise to the solution of R-BINAL via syringe pump over 45 m at −78° C. After 1.5 h, the reaction vessel was transferred to a very large dewer, filled with dry ice/acetone, and covered with aluminum foil. The reaction mixture was stirred ON at −78° C. The majority of the reduction occurred within the first 1.5 h with only a small amount additional conversion overnight. The reaction was quenched by addition of sat. aq. $NH_4Cl$ (150 mL) and warmed to room temperature. The mixture was further acidified to pH=7 using 6 N HCl then extracted with EtOAc (2×250 mL). The combined organic phase was washed with water (125 mL) and brine (125 mL). The organic phase was dried over $Na_2SO_4$, filtered, and concentrated. The residue was purified by CombiFlash using silica gel as the stationary phase and was eluted with a gradient of MeOH in DCM (0-5%). Yield of compound 146: 634 mg (53%). Chiral purity was determined by analytical chiral HPLC, Chiralpak AD-H column 4.6×250 mm, 5 micron, EtOH 0.1% diethylamine isocratic, 1.75 mL/min. The first eluting R isomer was 86 area % pure, corresponding to 72% ee. Compound 146 was further purified by chiral semi-preparative HPLC (Chiralpak AD-H 21.2×250 mm, 5 micron, EtOH 0.1% diethylamine, 20 mL/min). Final yield of compound 146: 445 mg (98% ee). Mass calculated for $C_{28}H_{31}FN_2O_2$ $[M+H]^+$: 447.25, found: 447.30.

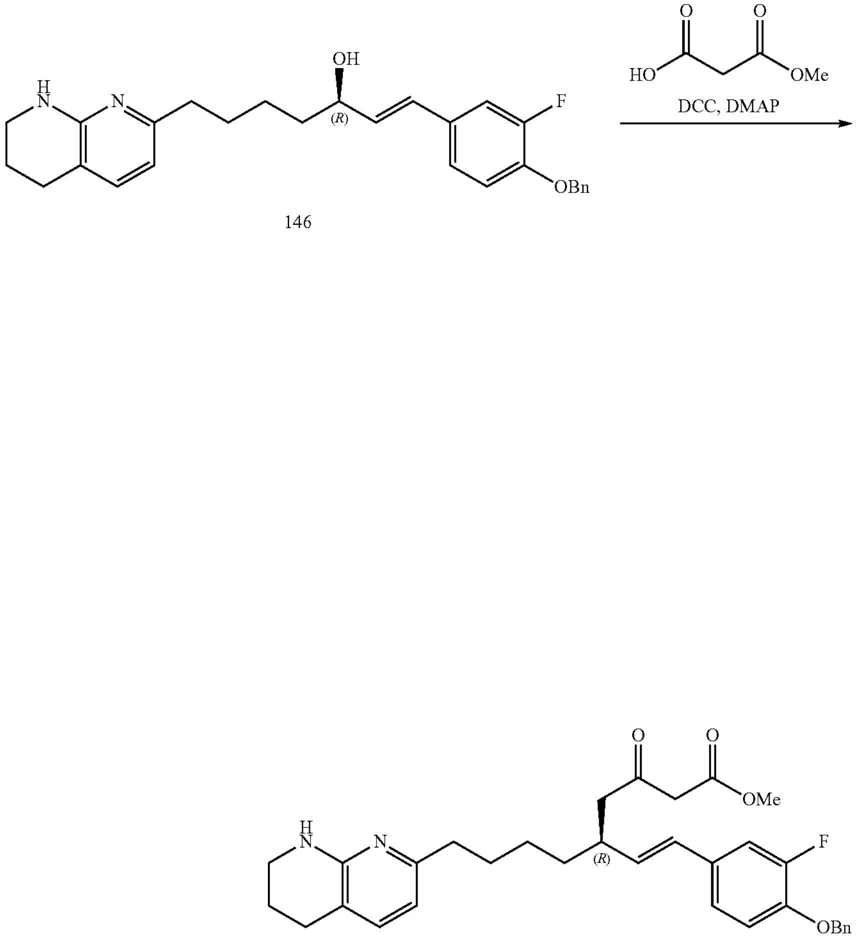

146

147

To a solution of compound 146 (0.325 g, 0.73 mmol) and malonic acid monomethyl ester (0.103 g, 0.87 mmol) in DCM (3 mL) was added a solution of DMAP (9 mg, 0.073 mmol) in DCM. The mixture was cooled to 0° C. and DCC (0.180 g, 0.87 mmol) was added. The cooling bath was removed, and the reaction was stirred at rt ON. The reaction mixture was then diluted with DCM (10 mL) and filtered. The filtrate was concentrated and purified by CombiFlash using silica gel as the stationary phase, eluting with a gradient of MeOH (0-5%) in DCM. Yield of compound 147: 142 mg (37%). Mass calculated for $C_{32}H_{35}FN_2O_5$ $[M+H]^+$: 547.26, found: 547.58.

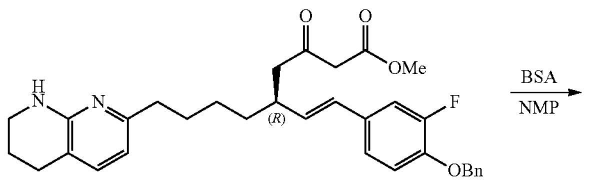

147

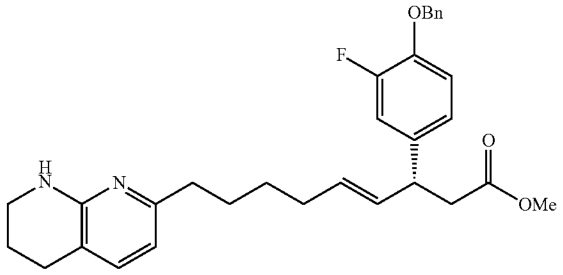

148

To a solution of compound 147 (0.232 g, 0.42 mmol) in NMP (0.5 mL) was added N,O-bis(trimethylsilyl)acetamide (0.229 g, 1.12 mmol) at room temperature. The mixture was heated at 60° C. for 30 m. Brine (58 μL) was added in two portions over 5 m. The reaction mixture was then heated at 90° C. for 3 h then room temperature overnight. The reaction mixture was diluted with EtOAc (12 mL) and washed with water (3 mL). The aqueous layer was back extracted with EtOAc (12 mL). The combined organic layer was concentrated. The residue was purified by CombiFlash using silica gel as the stationary phase and was eluted with a gradient of MeOH in DCM. Yield of compound 148: 140 mg (66%). Mass calculated for $C_{31}H_{35}FN_2O_3$ $[M+H]^+$: 503.27, found: 503.29.

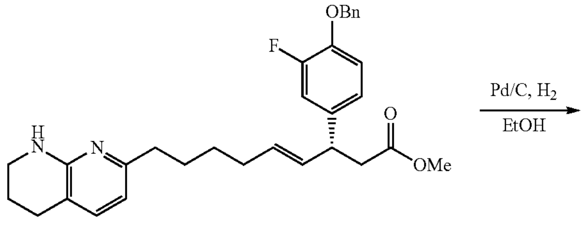

148

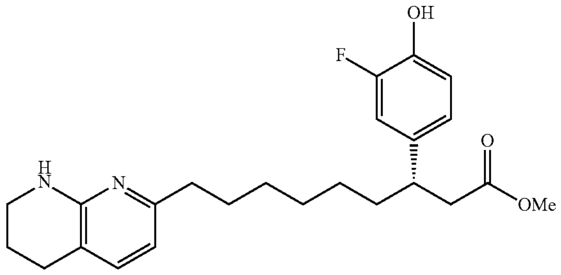

149

To a solution of compound 148 (0.169 g, 0.34 mmol) in EtOH (3 ML) was added a slurry of Pd/C (10% loading, 36 mg, 0.034 mmol) in EtOH (1 mL). The reaction vessel was pressurized and vented with hydrogen three times. The reaction vessel was repressurized to 55 psi for 3 h. The reaction mixture was diluted with MeOH (5 mL) and filtered. The filtrate was concentrated and the product, compound 149, was used in the next step without further purification assuming 100% yield. Mass calculated for $C_{24}H_{31}FN_2O_3$ $[M+H]^+$: 415.24, found: 415.07.

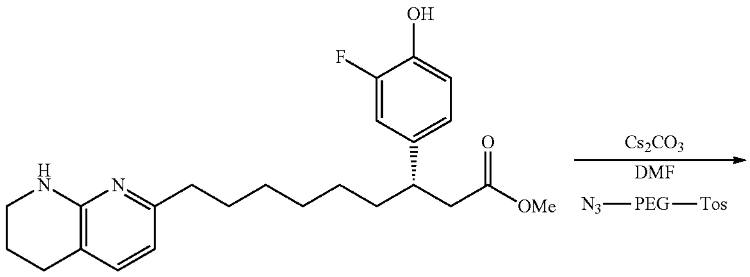

149

-continued

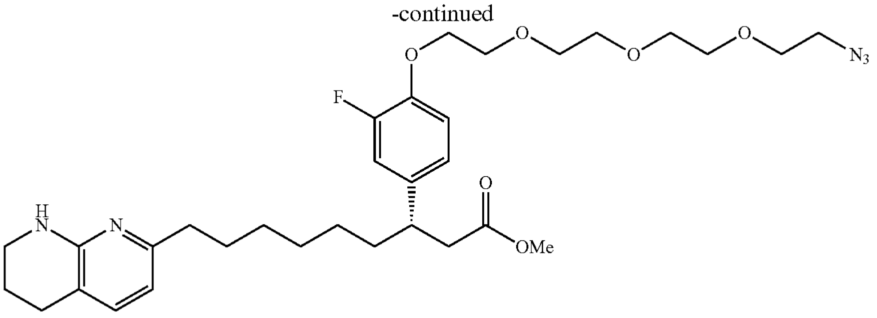

150

To a solution of compound 149 (139 mg, 0.34 mmol) and azido-PEG$_4$-tosylate (0.188 mg, 0.50 mmol) in DMF (2.5 mL) was added cesium carbonate (164 mg, 0.50 mmol). The reaction mixture was heated at 40° C. for 1 h then quenched with sat. aq. $NaHCO_3$ (3 mL). The mixture was extracted with EtOAc, (3×10 mL). The combined organic phase was washed with water (2×5 mL). The organic phase was dried over $Na_2SO_4$, filtered, concentrated, and used in the next step without further purification. Mass calculated for $C_{32}H_{46}FN_5O_6$ $[M+H]^+$: 616.35, found: 616.90.

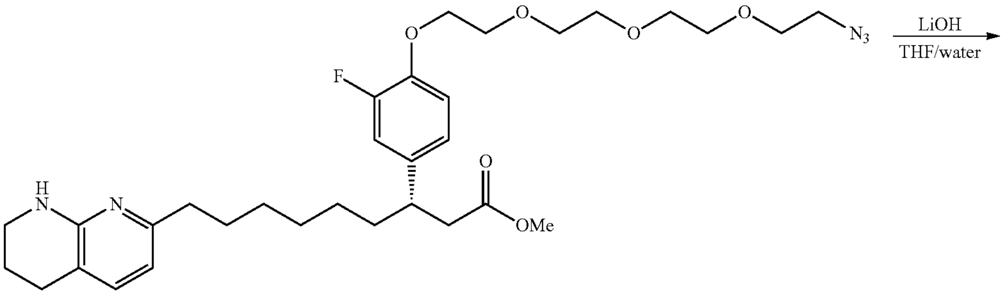

150

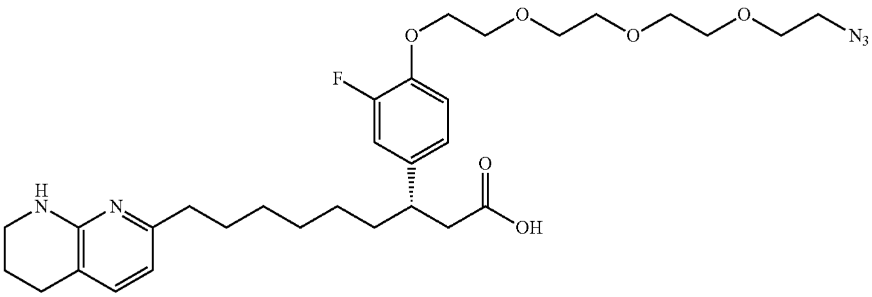

151

To a solution of compound 150 (0.207 mg, 0.34 mmol) in THF (1.5 mL) and water (1.5 mL) was added lithium hydroxide (0.040 g, 1.68 mmol). The reaction mixture was heated to 40° C. overnight. The next morning the reaction mixture was acidified with 6 N HCl to pH=7 and concentrated under reduced pressure. The residue was dissolved in 35% ACN in $H_2O$, 0.1% TFA, and purified by RP-HPLC (Thermo Aquasil C18, 250×21 mm, 5 μm, 20 mL/min, gradient of ACN in $H_2O$ containing 0.1% TFA). Yield of compound 151 (SM 36): 125 mg (52% over 3 steps). Mass calculated for $C_{31}H_{44}FN_5O_6$ $[M+H]^+$: 602.34, found: 602.85.

Synthesis of Structure 37c ((S)-3-(42-(2-(2-(2-azidoethoxy)ethoxy)ethoxy)ethoxy)-3-fluorophenyl)-3-(5-(5,6,7,8-tetrahydro-1,8-naphthyridin-2-yl)pentanamido)propanoic acid)

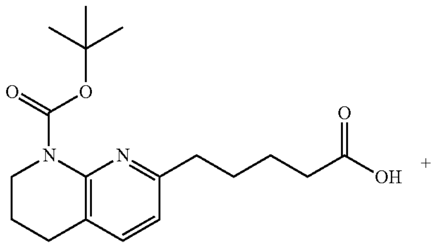

169

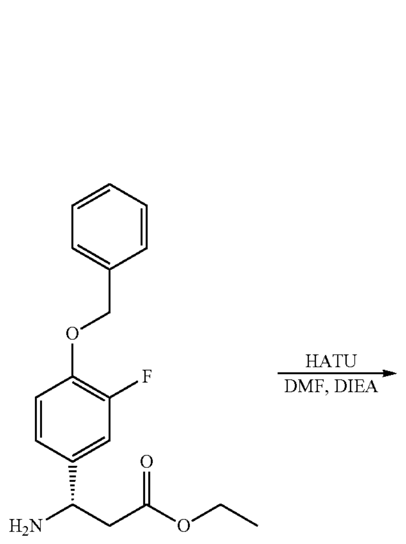

170

-continued

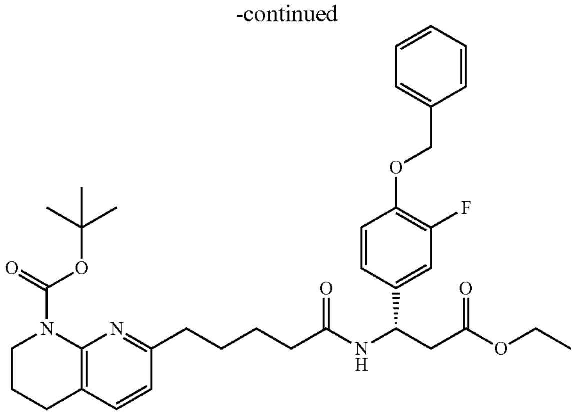

171

Compound 169 (90 mg, 0.268 mmol) in DMF (1.5 mL) was treated with HATU (112 mg, 0.295 mmol) and stirred for 5 minutes. A mixture containing compound 170 (94 mg, 0.295 mmol) and DIEA (0.154 mL, 0.884 mmol) in DMF (0.5) was subsequently added and stirring was continued for 1 hour. Upon completion all volatiles were removed and compound 171 was isolated by separation over silica eluting a gradient of MeOH in DCM yielding 123 mg (72%).

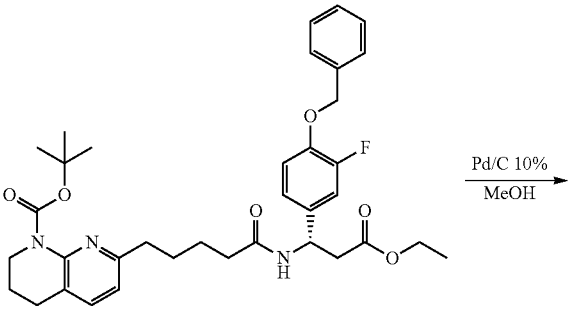

171

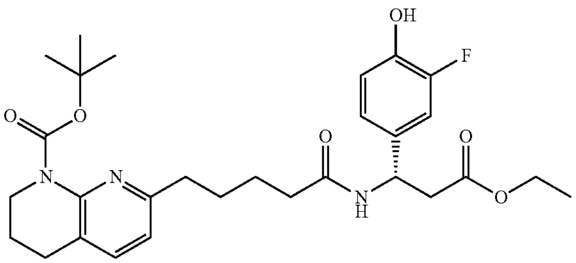

172

A suspension containing 10% palladium on carbon (21 mg, 0.0194 mmol) and compound 171 (123 mg, 0.194 mmol) in MeOH (2 mL) was charged with 60 PSI hydrogen and stirred for 1 hour. Upon completion the suspension was filtered over Celite® and concentrated to yield 88 mg (83%) of crude that was used subsequently without further purification.

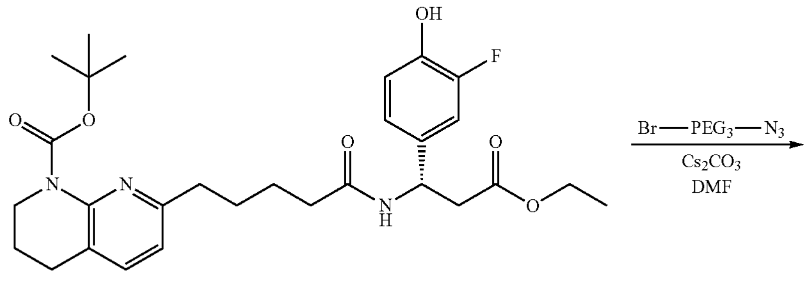
172
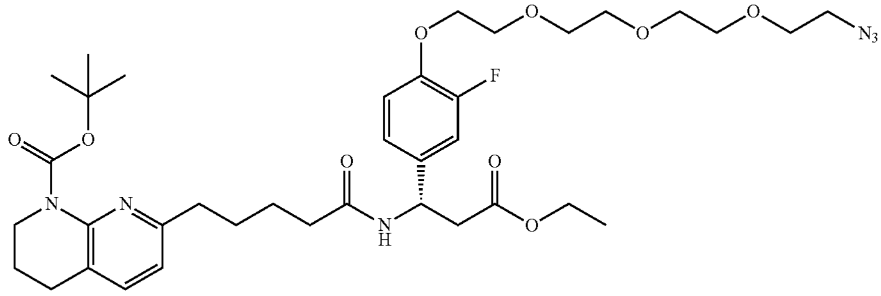
173
A suspension containing compound 172 (87 mg, 0.160 mmol), Br-$PEG_3$-$N_3$ (50 mg, 0.176 mmol) and cesium carbonate (115 mg, 0.352 mmol) in DMF (1 mL) was heated to 60° C. and stirred for 2 hours. Upon completion all volatiles were removed and compound 173 was isolated by separation over silica eluting a gradient of MeOH in DCM yielding 91 mg (76%).
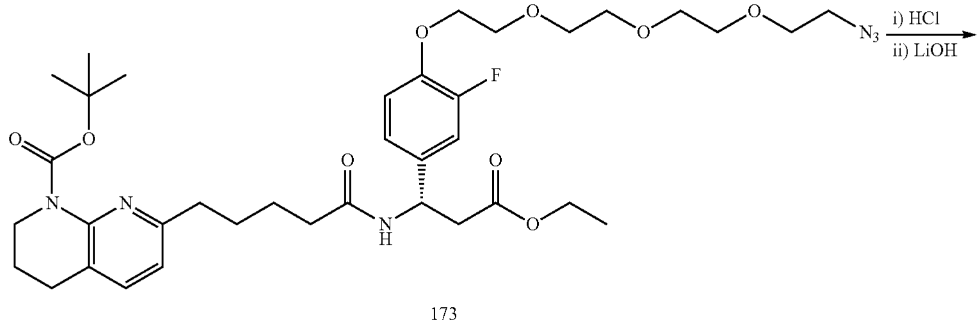
173
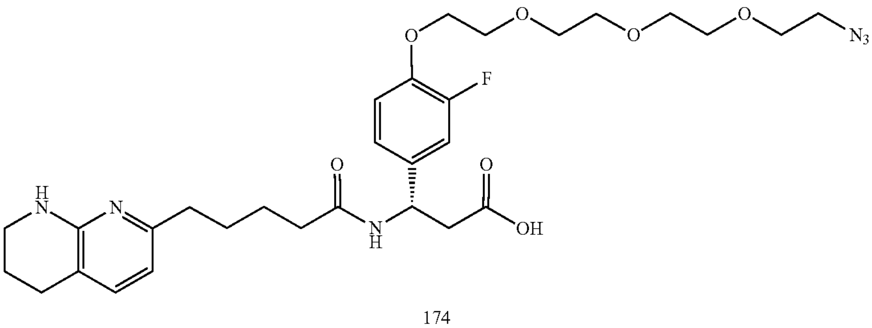
174

Compound 173 (50 mg, 0.067 mmol) in dioxane (0.5 mL) was treated with a 4M HCl (0.671 mmol, 0.168 mL) solution in dioxane and stirred at 40° C. for 3 hours. Upon completion all volatiles were removed. The crude was dissolved in a mixture of $H_2O$ (0.4 mL), THF (0.2 mL) and MeOH (0.4 mL), treated with LiOH (8 mg, 0.356 mmol), and stirred at 40° C. for 16 hours. Upon completion the pH was adjusted to 3 with TFA and the product was isolated by separation over a Phenomenx Gemini C18 column (21.2x250 mm, 5 micron) eluting a gradient of acetonitrile in water containing 0.1% TFA to yield 25 mg (60%, 2-Steps).

Synthesis of Structure 38c ((S)-3-(2-(3-((2-(2-(2-azidoethoxy)ethoxy)ethyl)amino)-3-oxopropyl)pyrimidin-5-yl)-9-(5,6,7,8-tetrahydro-1,8-naphthyridin-2-yl)nonanoic acid) and Structure 39c ((S)-3-(2-(1-azido-12-oxo-3,6,9-trioxa-13-azahexadecan-16-yl)pyrimidin-5-yl)-9-(5,6,7,8-tetrahydro-1,8-naphthyridin-2-yl)nonanoic acid)

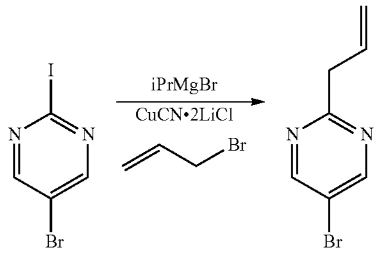

152

To a solution of 5-bromo-2-iodo-pyrimidine (8.00 g, 28.1 mmol) in anhydrous THF (95 mL) was added a solution of i-PrMgBr in THF (0.75 M, 56 mL, 42.0 mmol) at −78° C. while maintaining an internal temperature <−70° C. (ca. 15 m). The resulting solution was then stirred for 15 minutes before adding CuCN·2LiCl solution in THF (1 M, 31 mL, 31.0 mmol) and then allyl bromide (5.10 g, 42 mmol) as a solution in THF (10 mL). The reaction mixture was warmed to room temperature and stirred for 1 h. The reaction mixture was quenched with MeOH (40 mL) and concentrated. The residue was purified by CombiFlash using silica gel as the stationary phase and was eluted with a gradient of EtOAc in hexanes (0-20%). Yield of compound 152: 4.13 g (74%). Mass calculated for $C_7H_7BrN_2$ $[M+H]^+$: 198.99, found: 199.05.

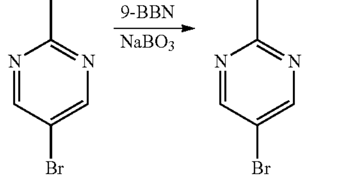

152 153

To a solution of compound 152 (7.70 g, 38.7 mmol) in THF (115 mL) was added a solution of 9-BBN in THF (0.5 M, 131 mL, 65.8 mmol) at 0° C. over 30 m. The reaction mixture was warmed to room temperature and stirred overnight. To the reaction mixture was added a slurry of $NaHCO_3$ (48.7 g, 580 mmol) in water (100 mL) followed by a slurry of $NaBO_3$ monohydrate (46.3 g, 464 mmol) in water (100 mL) at 0° C. The cooling bath was removed, and the mixture was stirred vigorously for 1 h. The reaction mixture was transferred to a separatory funnel and the layers were separated. The aqueous layer was extracted with EtOAc (200 mL). The organic phases were combined and washed with brine (100 mL). The brine layer was back extracted with EtOAc (100 mL). The combined organic phase was dried over $Na_2SO_4$, filtered, and concentrated to yield ~15 g crude, yellow oil. The crude was purified by CombiFlash using silica gel as the stationary phase and was eluted with a gradient of EtOAc in hexanes (50-100%). Yield of compound 153: 3.44 g (41%). Mass calculated for $C_7H_9BrN_2O$ $[M+H]^+$: 217.00, found: 216.97.

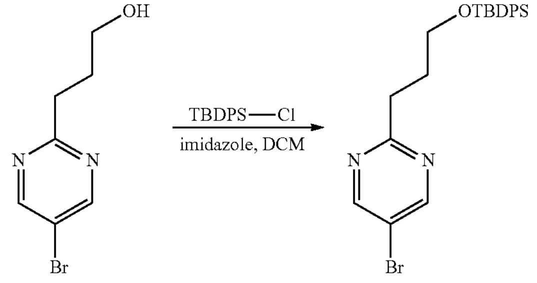

153 154

To a solution of compound 153 (3.44 g, 15.8 mmol) in DCM (40 mL) was added imidazole (1.73 g, 25.4 mmol) and a solution of TBDPSCl (5.23 g, 19.0 mmol) in DCM (12 mL) at 0° C. The reaction was warmed to room temperature and stirred overnight. The reaction mixture was diluted with DCM (75 mL) and washed with water (50 mL) and brine (50 mL). The organic layer was dried over $Na_2SO_4$, filtered, and concentrated. The residue was purified by CombiFlash using silica gel as the stationary phase and was eluted with a gradient of EtOAc (0-8%) in hexanes. Yield of compound 154: 5.56 g (77%). Mass calculated for $C_{23}H_{27}BrN_2OSi$ $[M+H]^+$: 455.12, found: 455.44.

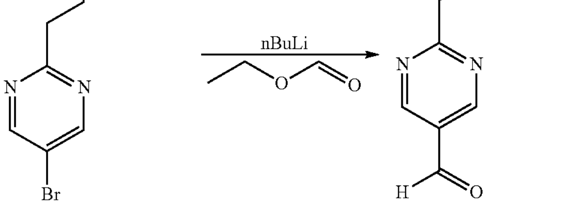

154 155

To a solution of compound 154 (6.07 g, 13.3 mmol) in THF (150 mL) at −75° C. was added a solution of nBuLi in THF (2.5 M, 5.6 mL, 14.0 mmol) dropwise, maintaining an internal temperature <−70° C. (ca. 10 m). After 3 m, a solution of ethyl formate (1.04 g, 1.13 mL, 14.0 mmol) in THF (5 mL) was added dropwise, maintaining an internal temperature <−70° C. The mixture was stirred at −78° C. for 20 m then quenched with HCl in dioxane (4 M, 3.67 mL, 14.7 mmol) that was further diluted with THF (5 mL), maintaining an internal temperature <−65° C. The cooling bath was removed, and the reaction was warmed to ambient temperature and concentrated. The residue was purified by CombiFlash using silica gel as the stationary phase and was eluted with a gradient of EtOAc in hexanes (0-20%). Yield of compound 155: 1.79 g (33%). $^1$H NMR (400 MHz, $CDCl_3$): δ 10.09 (s, 1H), 9.06 (s, 2H), 7.64 (m, 4H), 7.38 (m, 6H), 3.77 (t, 2H), 3.20 (t, 2H), 2.17 (q, 2H), 1.03 (s, 9H).

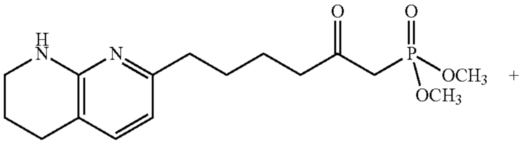

144

-continued

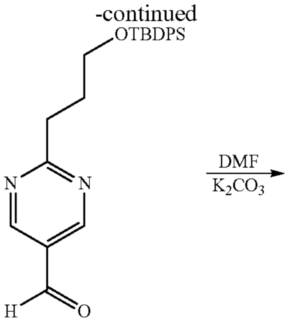

155

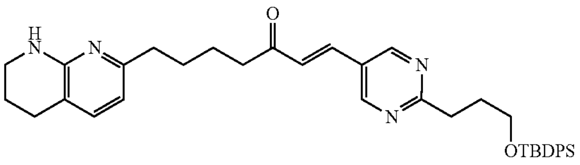

156

To a solution of compound 144 (1.68 g, 4.15 mmol) and compound 155 (1.70 g, 4.98 mmol) in THF (25 mL) was added $K_2CO_3$ (0.861 g, 6.23 mmol). The reaction mixture was heated to 40° C. for 2.5 h then 50° C. for 12 h. The reaction mixture was diluted with EtOAc (100 mL) and washed with water (50 mL) and brine (50 mL). The organic phase was dried over $Na_2SO_4$, filtered, and concentrated. The residue was purified by CombiFlash using silica gel as the stationary phase and was eluted with a gradient of EtOAc (0-100%) in hexanes containing 1% triethylamine. Yield of compound 156: 2.04 g (79%). Mass calculated for $C_{38}H_{46}N_4O_2Si$ [M+H]$^+$: 619.35, found: 619.69.

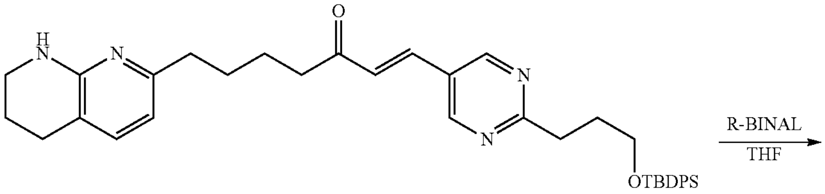

156

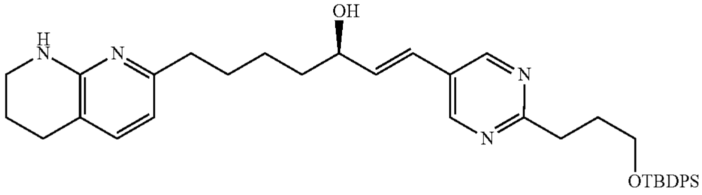

157

Preparation of R-BINAL: LAH (1.169 g, 30.8 mmol) was slurried in dry THF (90 mL). To the slurry was added EtOH as a solution in THF (6 M, 5.2 mL, 31.4 mmol) keeping $T_{int}$<40° C. The mixture was aged at 35° C. for 40 m then cooled to 30° C. A solution of R-(BINOL) (9.00 g, 31.4 mmol) in THF (45 mL) was added, keeping $T_{int}$<40° C. The mixture was aged at 50° C. for 1 h, cooled to ambient temperature, then heated to 50° C. and TMEDA (14.1 mL, 11.0 g, 94.3 mmol) was added. The mixture was aged at 50° C. for 1 h, cooled to ambient temperature, and then used with compound 156.

To a solution of R-BINAL (~0.2 M, 110 mL, 22.0 mmol) in THF was added a solution of compound 16 (1.16 g, 1.88 mmol) in THF (12 mL) at −78° C. over 5 m. After 30 m, the reaction mixture was quenched with sat. aq. $NH_4Cl$, warmed to rt, and the product was extracted with EtOAc (3×125 mL). The organic layer was dried over $Na_2SO_4$, filtered, and concentrated. The residue was purified by CombiFlash using silica gel as the stationary phase and was eluted with a gradient of MeOH (0-5%) in EtOAc containing 1% triethylamine. Yield of compound 157: 0.96 g (82%). Chiral purity was determined by analytical chiral HPLC, Chiralpak AD-H column 4.6×250 mm, 5 micron, 25% EtOH, 75% hexanes, 0.1% diethylamine isocratic, 2 mL/min). The second eluting R isomer was ~95 area % pure, corresponding to ~90% ee. Mass calculated for $C_{38}H_{48}N_4O_2Si$ $[M+H]^+$: 621.36, found: 621.71.

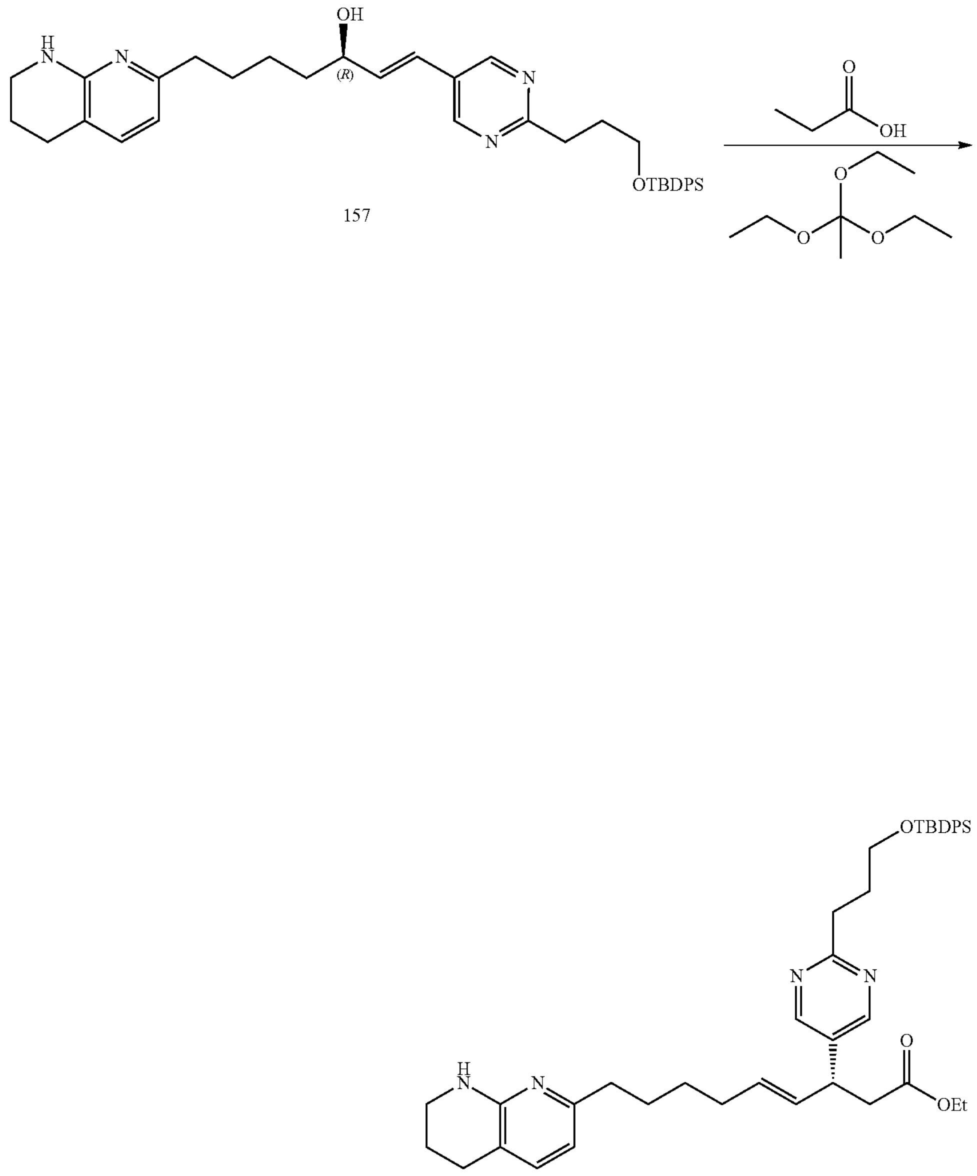

157

158

To a solution of compound 157 (0.925 g, 1.49 mmol) in triethylorthoacetate (9.25 mL) was added a solution of propionic acid in trimethylorthoacetate (0.15 M, 0.55 mL, 0.08 mmol). The reaction mixture was heated at 140° C. in a sealed vial for 1.5 h. The reaction mixture was concentrated, and the residue was purified by CombiFlash using silica gel as the stationary phase, eluting with a gradient of EtOAc (0-50%) in hexanes containing 1% triethylamine. Yield of compound 158: 0.898 g (87%). Mass calculated for $C_{42}H_{54}N_4O_3Si$ $[M+H]^+$: 691.41, found: 691.93.

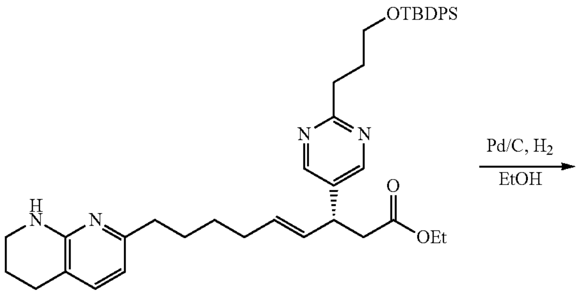

158

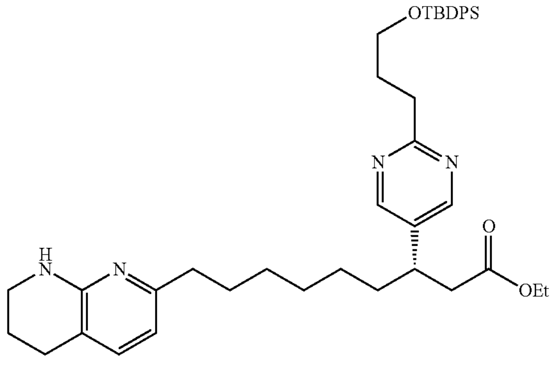

159

To a solution of compound 158 (0.893 g, 1.30 mmol) in EtOH (10 mL) was added a slurry of Pd/C (extent of loading: 10 wt %, 0.138 g, 0.13 mmol) in EtOH (4 mL). The reaction mixture was charged 50 psi $H_2$ and stirred for 4.5 h. The reaction mixture was filtered, concentrated, and used in the next step without further purification. Yield of compound 159: 0.885 g (99%). Mass calculated for $C_{42}H_{56}N_4O_3Si$ $[M+H]^+$: 693.42, found: 693.82.

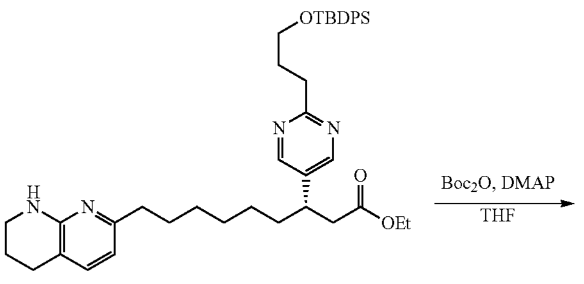

159

-continued

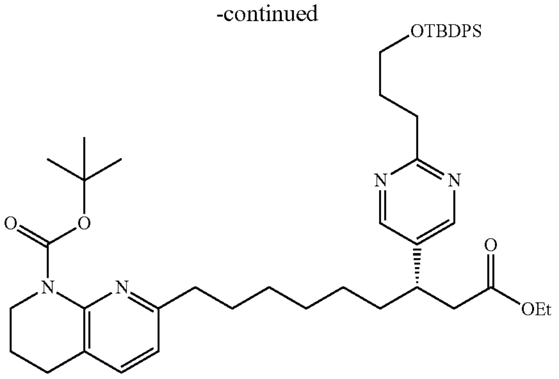

160

A solution of Boc anhydride (0.836 g, 3.83 mmol) in THF (2.5 mL) was added to compound 159 (0.885 g, 1.28 mmol) followed by a solution of DMAP (20 mg/mL in THF, 155 uL, 0.0031 g, 0.026 mmol). The mixture was heated to 60° C. for 6 h. The reaction mixture was concentrated and the residue was purified by CombiFlash using silica gel as the stationary phase, eluting with a gradient of EtOAc (0-50%) in hexanes. Yield of compound 160: 0.721 g (71%). Mass calculated for $C_{47}H_{64}N_4O_5Si$ $[M+H]^+$: 793.47, found: 794.28.

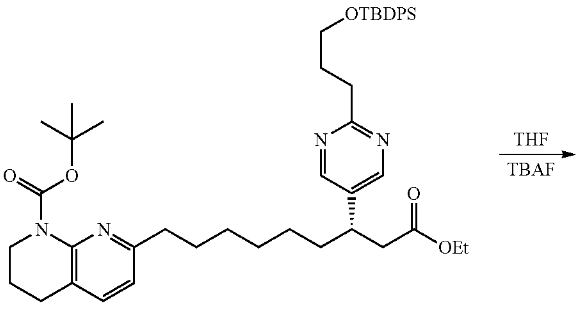

160

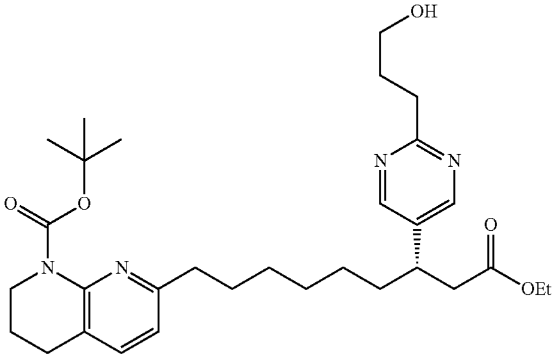

161

To a solution of compound 160 (0.621 g, 0.783 mmol) in THF (6 mL) was added a solution of TBAF in THF (1 M, 1.2 mL, 1.2 mmol) at 0° C. The reaction mixture was warmed to room temperature and stirred for 2 h. The reaction mixture was diluted with EtOAc (30 mL) and washed with sat. aq. $NH_4Cl$ (2×10 mL). The organic layer was concentrated. The residue was purified by CombiFlash using silica gel as the stationary phase and was eluted with a gradient of EtOAc (50-100%) in hexanes. Yield of compound 21: 0.362 g (83%). Chiral purity was determined by analytical chiral HPLC, Chiralpak AD-H column 4.6×250 mm, 5 micron, 20% EtOH, 80% hexanes, 0.1% diethylamine, isocratic, 1.5 mL/min. The second eluting R isomer was 93% pure, corresponding to 86% ee. was Compound 161 was further purified by chiral semi-preparative HPLC (Chiralpak AD-H 21.2×250 mm, 5 micron, 20% EtOH, 80% hexanes, 0.1% diethylamine, 60 mL/min). Final yield of compound 161: 308 mg (99% ee). Mass calculated for $C_{31}H_{46}N_4O_5$ $[M+H]^+$: 555.36, found: 555.72.

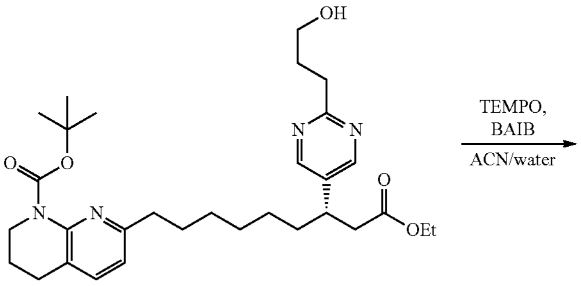

161

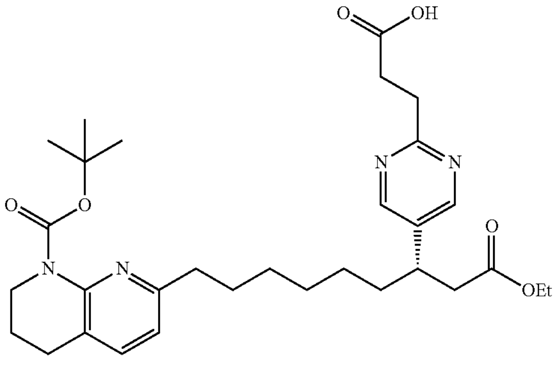

162

To a solution of compound 161 (0.030 g, 0.054 mmol) in ACN (0.30 mL) was added BAIB (0.042 g, 0.130 mmol) and TEMPO (2.5 mg, 0.016 mmol) followed by water (0.30 mL) at room temperature. After 2 hr, the reaction mixture was concentrated. The residue was purified by RP-HPLC (Phenomenex Gemini C18 21.2×250 mm, 5 micron, 0.1% TFA water/ACN, 30-80% ACN gradient). Yield of compound 162: 0.030 g (97%). Mass calculated for $C_{31}H_{44}N_4O_6$ $[M+H]^+$: 569.34, found: 569.68.

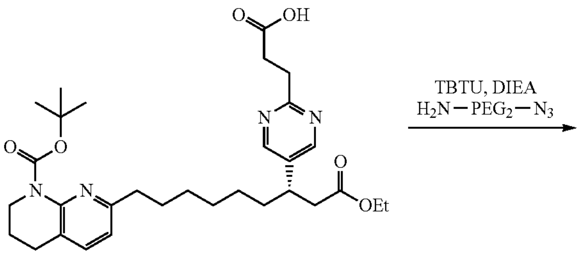

162

-continued

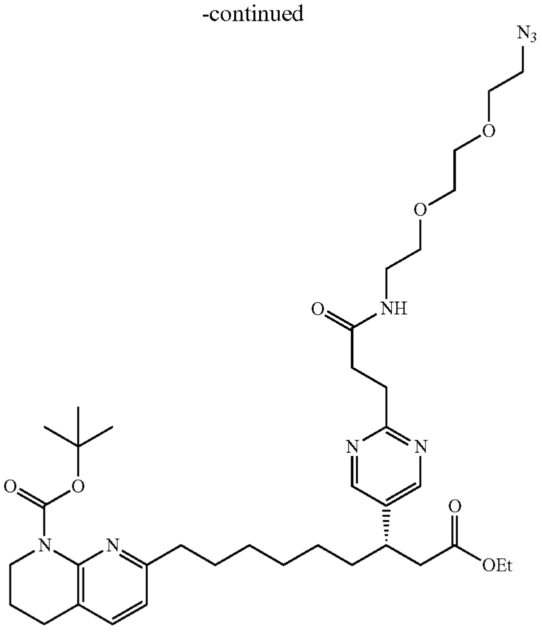

163

To a solution of compound 162 (33 mg, 0.058 mmol) and amino-$PEG_2$-azide (15 mg, 0.087 mmol) in DMF (0.5 mL) was added TBTU (32 mg, 0.099 mmol) then DIEA (35 μL, 26 mg, 0.203 mmol) at 0° C. The reaction mixture was warmed to room temperature and stirred for 30 m. The reaction mixture was concentrated, and the product, compound 163, was used in the next step without purification. Mass calculated for $C_{37}H_{56}N_8O_7$$[M+H]^+$: 725.44, found: 725.77.

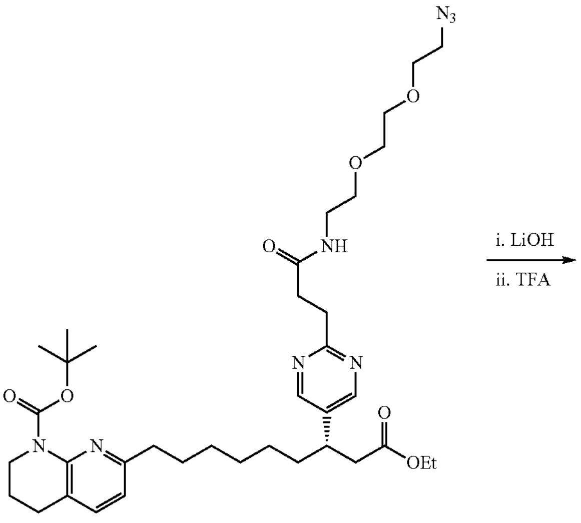

163

-continued

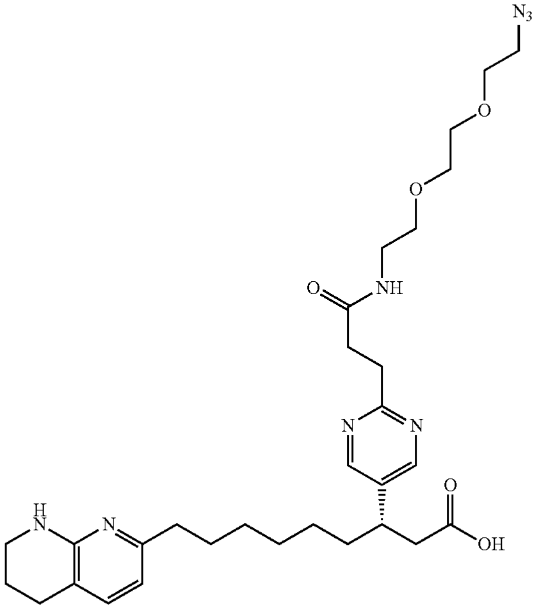

164

To a solution of compound 163 (42 mg, 0.058 mmol) in THF (0.30 mL) was added a 1 M solution of LiOH (0.174 mL, 0.174 mmol). The reaction mixture was heated at 40° C. for 1 hr. An additional portion of LiOH was added (0.174 mL, 0.174 mmol). After 3 h, the reaction stalled, and an additional portion of LiOH was added (0.174 mL, 0.174 mmol). The reaction was stirred for an additional 2 hr (9 eq LiOH, 5 hr total). The reaction mixture was neutralized to pH=5 using 3 N HCl and concentrated. The residue was dissolved in TFA:water [95:5] and stirred for 2 hours at room temperature. The reaction mixture was concentrated, and the residue was purified by RP-HPLC (Phenomenex Gemini C18 21.2x250 mm, 5 micron, water/ACN containing 0.1% TFA, 20-50% ACN gradient). Yield of compound 164 (Structure 38c): 23 mg (66%). Mass calculated for $C_{30}H_{44}N_8O_5$ $[M+H]^+$: 597.35, found: 597.85.

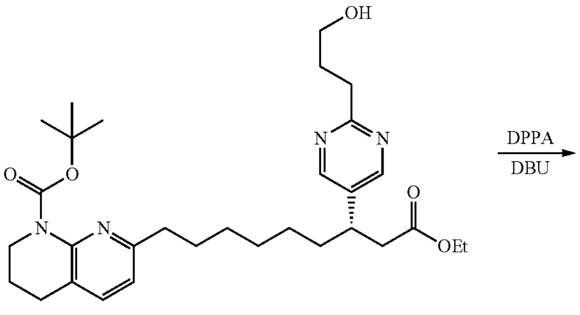

161

-continued

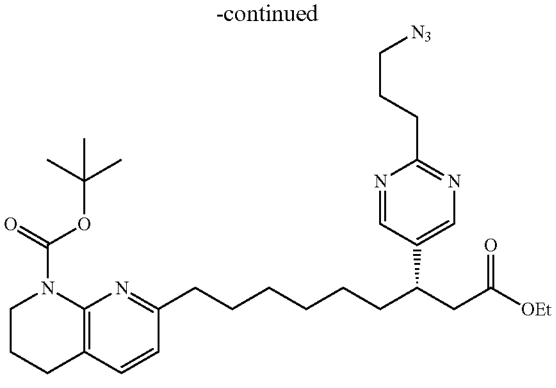

165

To a solution of compound 161 (30 mg, 0.054 mmol) in THF (150 µL) was added diphenyl phosphoryl azide (35 µL, 45 mg, 0.162 mmol) followed by DBU (12 µL, 12 mg, 0.081 mmol) at 0° C. The reaction mixture was warmed to rt and stirred overnight. The next morning, the reaction mixture was heated at 60° C. for 7 h. The reaction mixture was concentrated and purified by RP-HPLC (Phenomenex Gemini C18 21.2x250 mm, 5 micron, 0.1% TFA water/ACN, 32-60% ACN gradient). Yield of compound 165: 14 mg (44%). Mass calculated for $C_{31}H_{45}N_7O_4$ $[M+H]^+$: 580.36, found: 580.66.

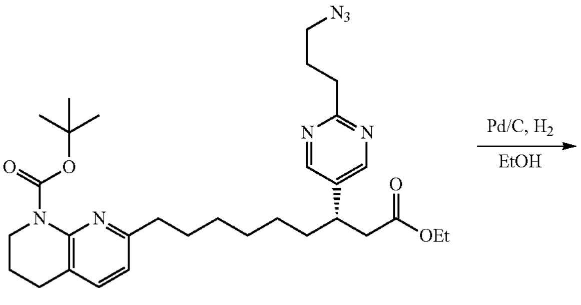

165

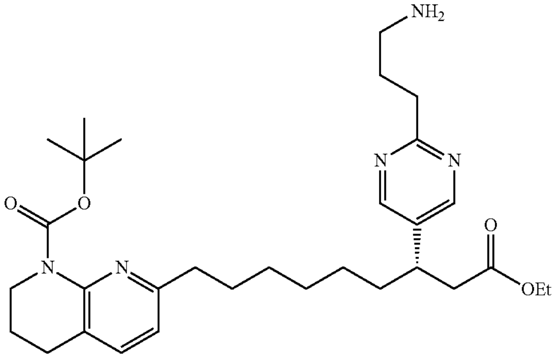

166

To a solution of compound 165 (18 mg, 0.031 mmol) in EtOH (100 µL) was added a slurry of Pd/C (10% loading, 3.3 mg, 0.003 mmol) in EtOH (170 µL). The reaction vessel was charged with $H_2$ then evacuated three times and then charged with $H_2$ (1 atm). After 30 m, the reaction mixture was filtered, concentrated, and used in the next step without further purification. Yield of compound 166: 17 mg (99%). Mass calculated for $C_{31}H_{47}N_5O_4$ $[M+H]^+$: 554.37, found: 554.73.

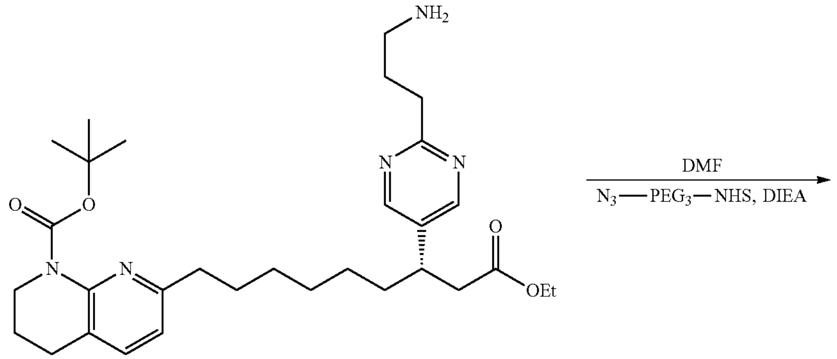
166
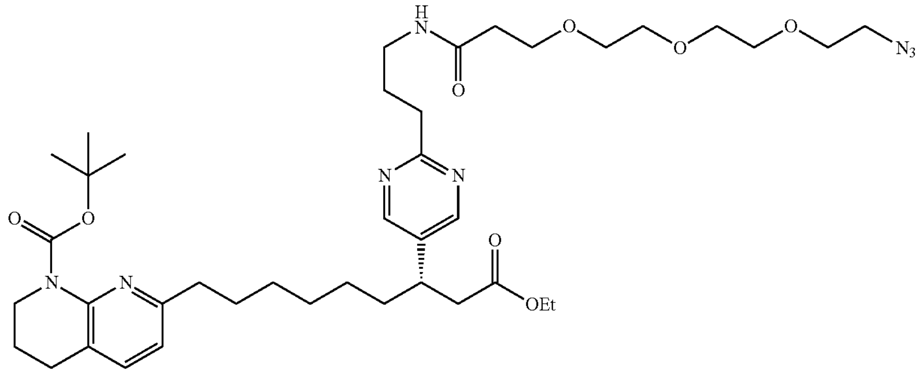
167
To a solution of compound 166 (17 mg, 0.031 mmol) and azido-PEG$_3$-NHS ester (14 mg, 0.040 mmol) in DMF (170 μL) was added DIEA (16 μL, 12 mg, 0.092 mmol) at room temperature. The reaction mixture was stirred for 1 h at room temperature, concentrated, and then used in the next step without purification. Mass calculated for $C_{40}H_{62}N_8O_8$ $[M+H]^+$: 783.48, found: 783.84.
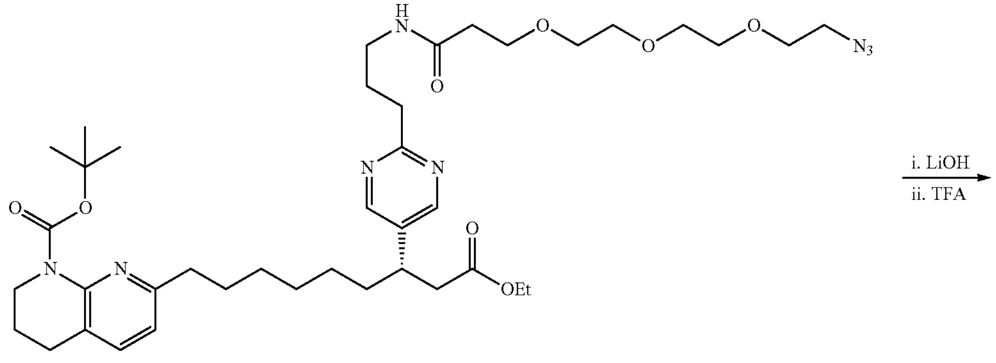
167

-continued

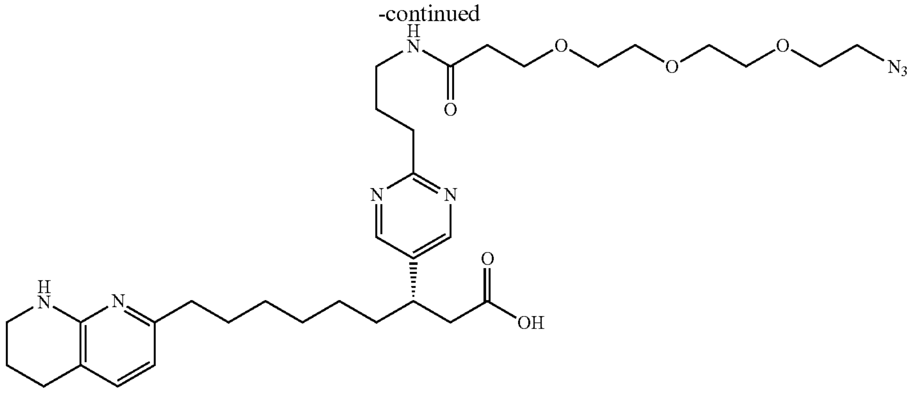

168

To a solution of compound 167 (24 mg, 0.031 mmol) in THF (180 µL) was added a 1 M solution of LiOH (153 µL, 0.153 mmol). The reaction mixture was heated at 40° C. After 1 hr, an additional portion of LiOH was added (153 uL, 0.153 mmol, 5 eq). The reaction mixture was stirred for 3 h at 40° C. then room temperature overnight. The reaction mixture was neutralized to pH=5 using 3 N HCl and concentrated. The residue was dissolved in TFA:water [95:5] and stirred for 3 hours at room temperature. The reaction mixture was concentrated, and the residue was purified by RP-HPLC (Phenomenex Gemini C18 21.2×250 mm, 5 micron, water/ACN containing 0.1% TFA, 15-45% ACN gradient). Yield of compound 168 (Structure 39c): 9.8 mg (49%). Mass calculated for $C_{33}H_{50}N_6O_6$ $[M+H]^+$: 655.40, found: 656.01.

Synthesis of Pharmacokinetic Enhancers

Mal-C22-Diacid

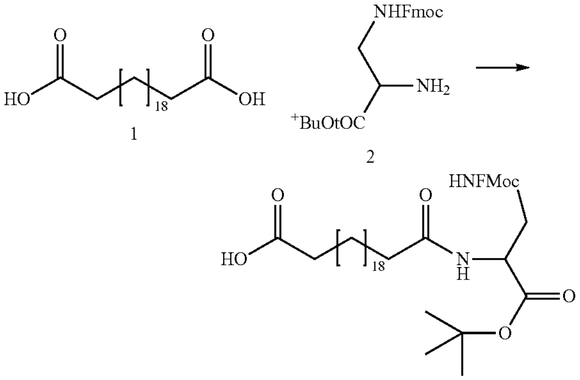

1 2 3

Compound 1 (0.200 g) was mixed with TBTU (0.182 g) in 2 mL of DMF. DIPEA (0.207 mL) was added dropwise. Then Compound 2 (0.227 g) was added after 5 minutes. The mixture was stirred for 1 hour. The mixture was then diluted with 40 mL of DCM and washed with 5% citric acid (4×30 mL) and dried over $Na_2SO_4$, filtered and concentrated. The product was dried on rotary evaporator and high vacuum. The resulting solid was dry-loaded onto 12 G Redi-Sep® Rf column on CombiFlash® in Hex:EtOAc 0=>80% over 30 minutes. Yield: 53 mg (39.2%)

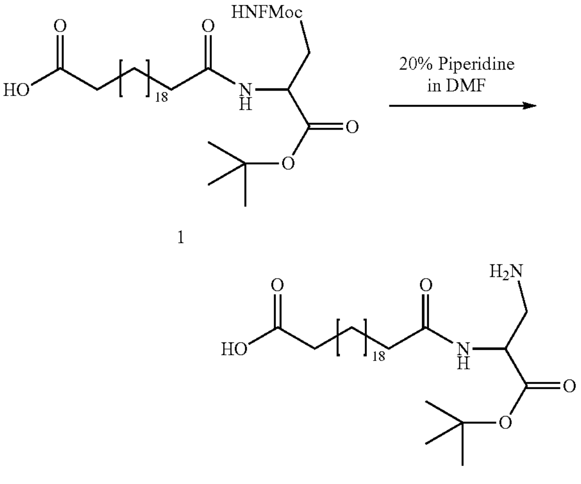

1 2

Compound 1 was azeotropically distilled with toluene, 20% piperidine in DMF, and $Et_3N$ mixture twice. The yield was 50 mg.

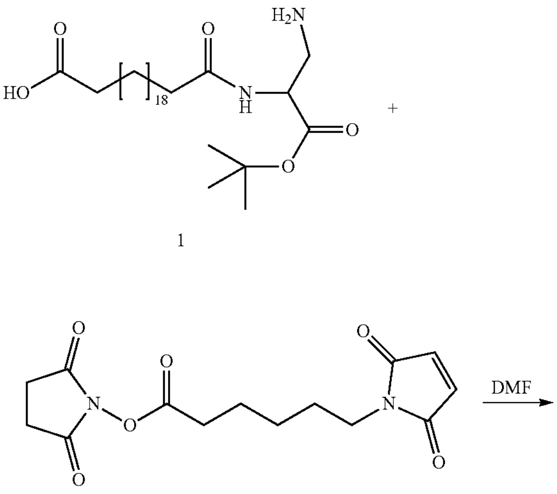

1 2

-continued

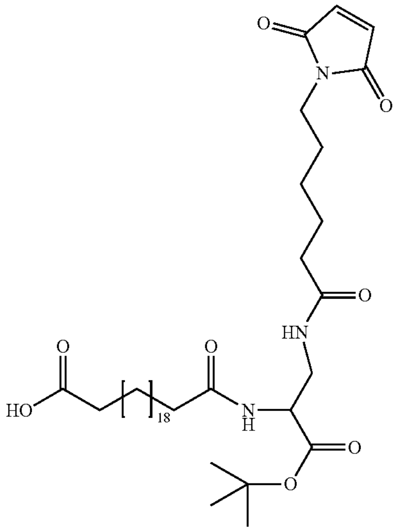

3

Compounds 1 (0.0350 g) and 2 (0.105 g) were combined in DMF and $Et_3N$ (0.095 mL) was added. The reaction was complete after one hour. The mixture was then diluted with DCM and washed with 5% citric acid (3×8 mL) and dried with $Na_2SO_4$, filtered and concentrated. The product was brought up in 1 mL of toluene and loaded onto a 4G Redi-Sep Rf column on CombiFlash®, with Hex:EtOAc 0=>100% EtOAc over 15 minutes. Then the mobile phase was switched to DCM:DCM with 20% MeOH 0=>100% over 20 minutes. Yield: 12 mg (24.9%)

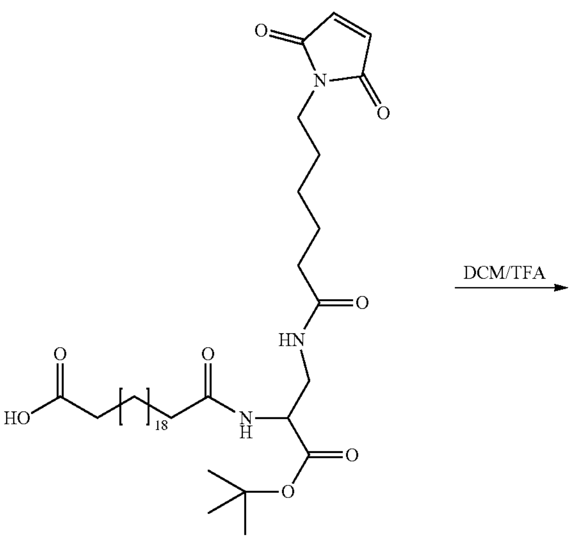

1

-continued

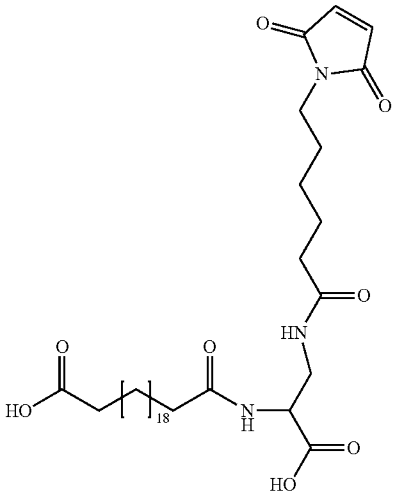

2

Compound 1 (0.012 g) was dissolved in 1 mL of a 1:1 mixture of DCM/TFA. The reaction was allowed to stir for 3 hours. The product was dried on rotary evaporator and high vacuum. Yield: 0.0110 g (99.6%.)

C18-diacid-N3

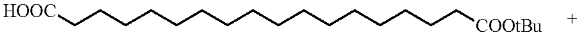

1

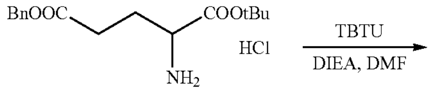

2

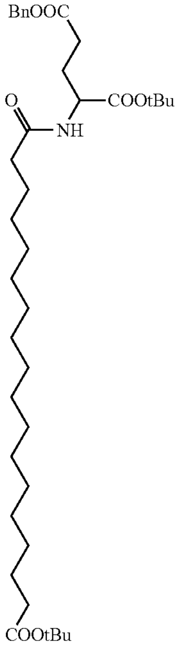

Compound 1 (0.500 g, Asta Tech.® #64704) and compound 2 (0.454 g, Chem-Impex #16167) were dissolved in DMF and TBTU (0.442 g) and DIPEA (0.586 mL) were added. The mixture was allowed to stir for two hours. The mixture was then diluted with DCM (40 mL) and washed with $H_2O$ (4×40 mL), dried over $Na_2SO_4$, filtered and concentrated. The product was brought up in 2 mL of DCM and loaded onto Redi-Sep Rf column on CombiFlash® (Mobile phase DCM:DCM with 20% MeOH 0=>20% over 25 minutes.) The product was concentrated on high vacuum. Yield: 740 mg (85%)

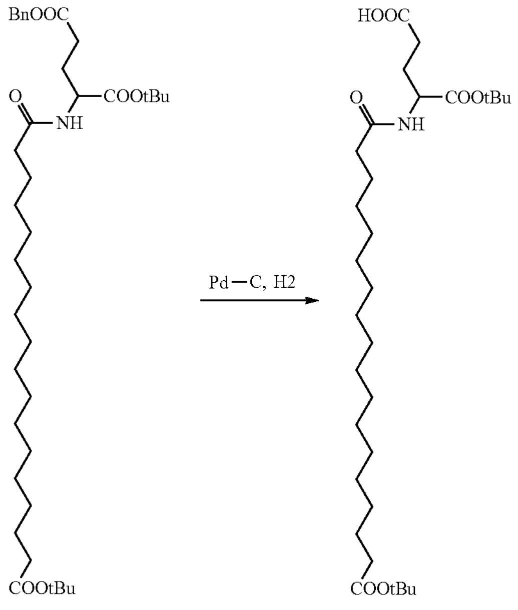

1 2

Compound 1 (0.720 g) was dissolved in 5 mL of MeOH in a flask. A septum was put on the flask and the atmosphere was evacuated and replaced with nitrogen two times. Then Pd/C 30% (0.200 g) was added via weighing papers. The septum was replaced, then the atmosphere was evacuated and replaced with hydrogen two times. The reaction was allowed to stir at room temperature for one hour. The mixture was filtered, and the filtrate dried on rotary evaporator and high vacuum. Yield: 665 mg.

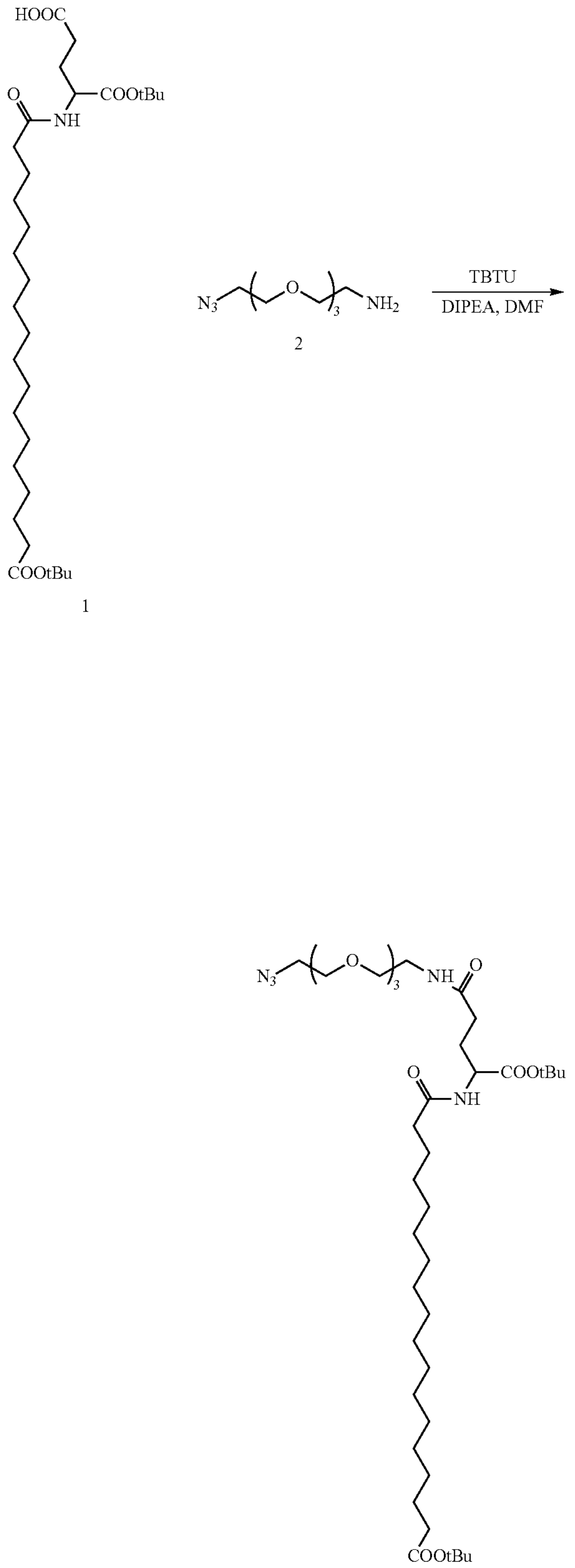

1 2

Compound 1 (0.150 g) and Compound 2 (0.0618 g) were dissolved in DMF and TBTU (0.0884 g) and DIPEA (0.117 mL) were added to the mixture. The reaction was allowed to stir at room temperature for one hour. The mixture was then diluted with DCM (12 mL), washed with water (4×8 mL), dried over $Na_2SO_4$, filtered and concentrated on high vacuum. The product was brought up in DCM (1 mL) and loaded onto 4G Redi-Sep Rf column on CombiFlash® (mobile phase DCM:DCM with 20% methanol 0=>50% over 25 minutes.) Yield: 162 mg (79%)

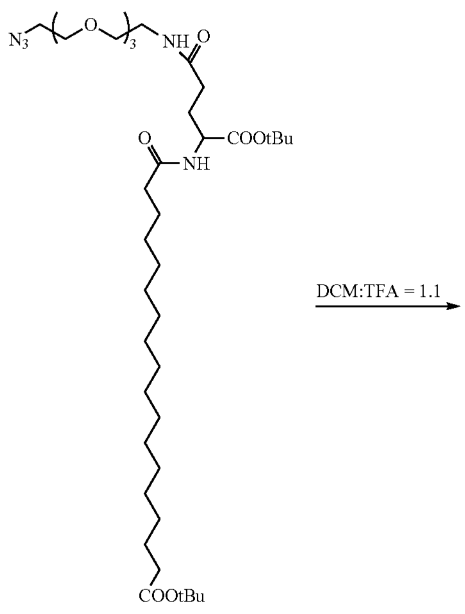

1

-continued

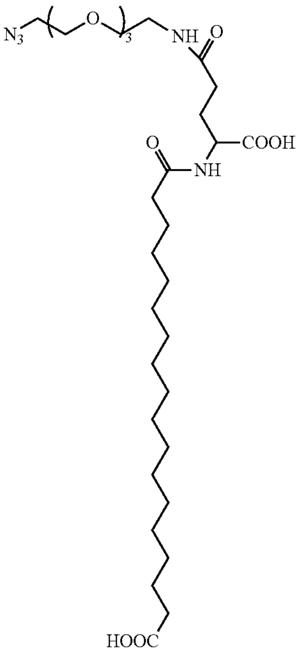

Compound 1 (0.155 g) was dissolved in a 1:1 mixture of DCM:TFA. The reaction was allowed to stir at room temperature for two hours. The product was concentrated on rotary evaporator and placed on high vacuum. Yield: 129 mg (97%.)

Mal-C18-Diacid (D-Version)

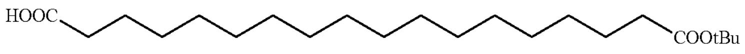

1

+

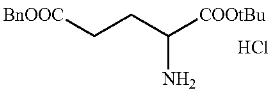

2

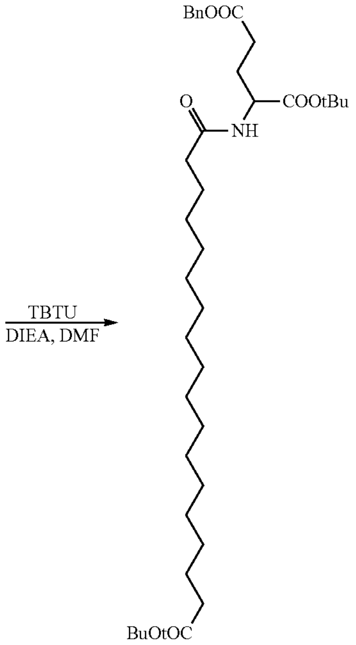

Compound 1 (0.500 g) and Compound 2 (0.4539 g) were dissolved in DMF and TBTU (0.4418 g) and DIPEA (0.586 mL) were added to the mixture. The reaction was allowed to stir at room temperature for two hours. The mixture was then diluted with DCM (40 mL), washed with water (4×40 mL), dried over $Na_2SO_4$, filtered and concentrated on high vacuum. The product was brought up in DCM (2 mL) and loaded onto 4G Redi-Sep Rf column on CombiFlash® (mobile phase DCM:DCM with 20% methanol 0=>50% over 25 minutes.) Yield: 740 mg (85%)

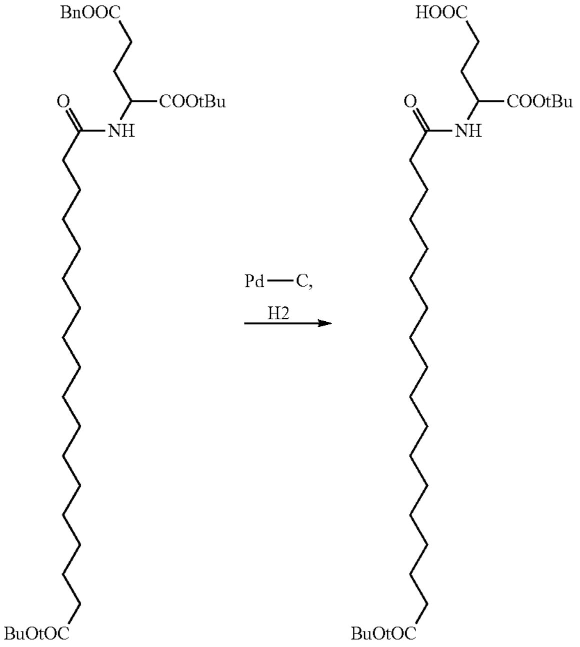

Compound 1 (0.720 g) was dissolved in 5 mL of MeOH, then a septum was placed on the flask and $N_2$ was applied two times. Then, Pd/C (0.200 g) was added via weighing papers, then the septum was replaced and vacuum followed by $H_2$ was applied two times. The reaction was allowed to stir at room temperature for 1 hour. The product was filtered and the filtrate was dried on rotavap and high vacuum. Yield: 655 mg.

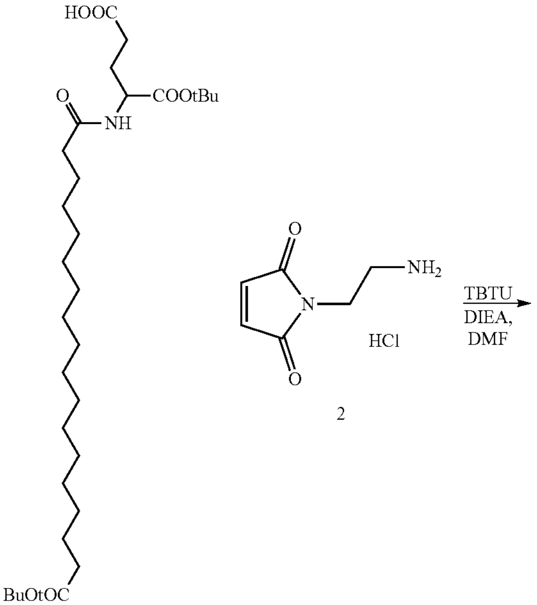

1

2

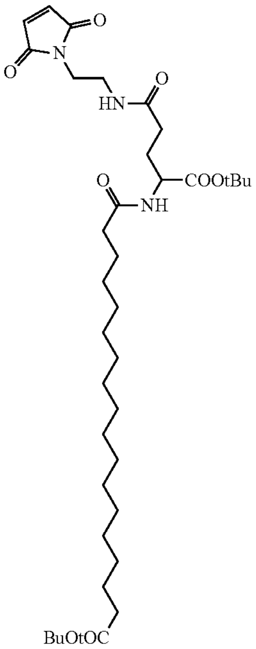

Compound 1 (0.100 g) and Compound 2 (0.0318 g) were dissolved in DMF and TBTU (0.0589 g) and DIPEA (0.078 mL) were added to the mixture. The reaction was allowed to stir at room temperature for one hour. The mixture was then diluted with DCM (10 mL), washed with water (4×7 mL), dried over $Na_2SO_4$, filtered and concentrated on high vacuum. The product was brought up in DCM (0.5 mL) and loaded onto 4G Redi-Sep Rf column on CombiFlash® (mobile phase DCM:DCM with 20% methanol 0=>50% over 25 minutes.) Yield: 100 mg (82%)

-continued
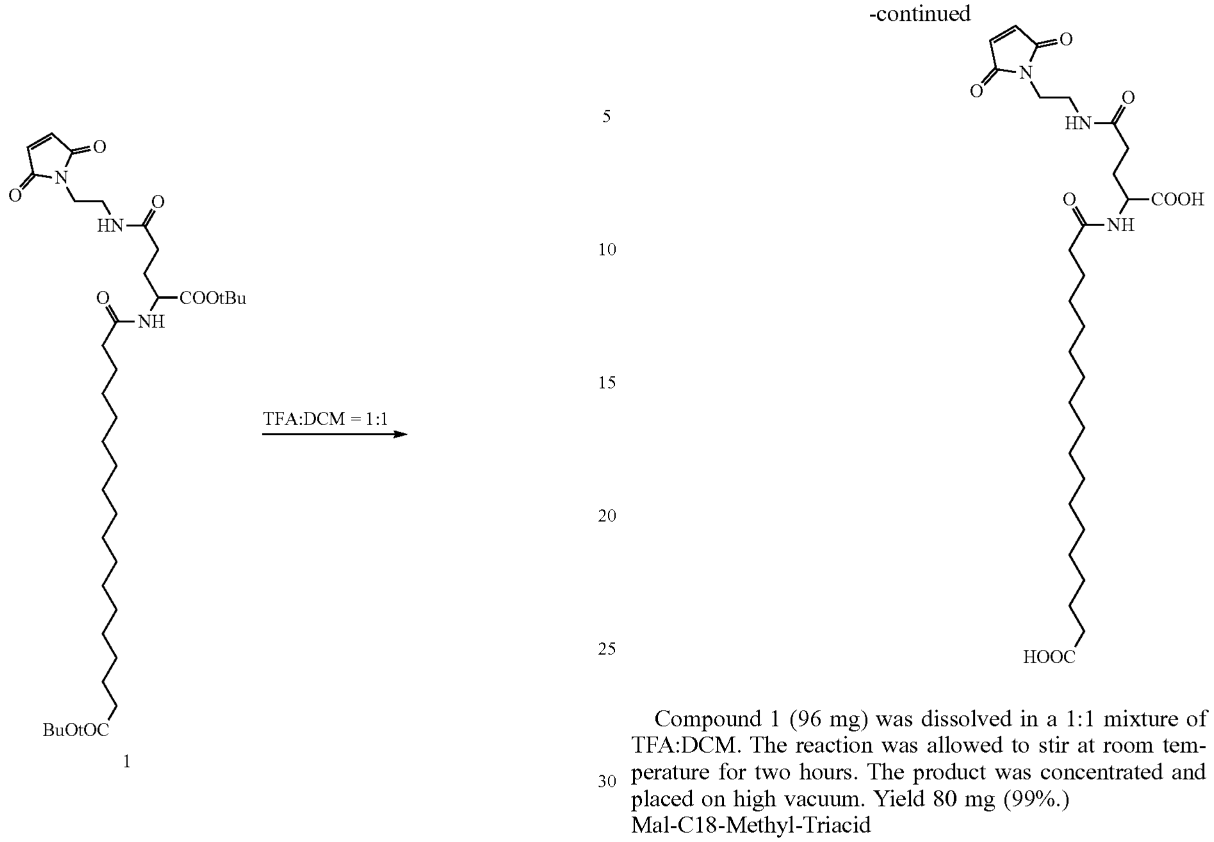
1
Compound 1 (96 mg) was dissolved in a 1:1 mixture of TFA:DCM. The reaction was allowed to stir at room temperature for two hours. The product was concentrated and placed on high vacuum. Yield 80 mg (99%.)
Mal-C18-Methyl-Triacid
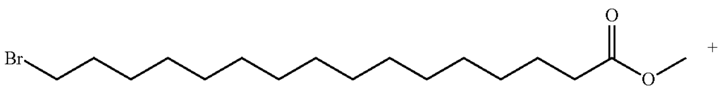
1
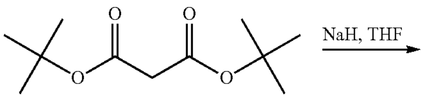
2
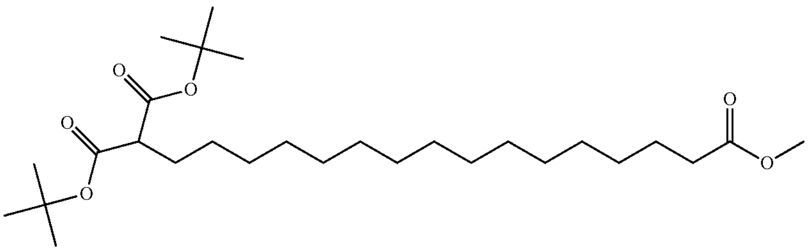
3

Compound 2 (Sigma® #254487, 0.405 g) in 1 mL of THF was added to a suspension of NaH in THF (3.5 mL) at 0° C. The reaction was warmed to room temperature and stirred for 20 minutes. The reaction was mixed until it became clear. Then compound 1 (Sigma®#684511, 0.436 g) in 2 mL THF was added dropwise at 0° C. and stirred for 0.5 h. Then the ice bath was removed and the reaction was allowed to stir at room temperature overnight. The reaction was then diluted with DCM (35 mL) and washed with $NH_4Cl$ solution (1×8 mL.) The organics was back-extracted with DCM (1×8 mL.) The organics were combined and washed with $H_2O$ (2×8 mL.) The organic phase was dried over $Na_2SO_4$, filtered and concentrated. The product was purified via chromatography (wet-loaded in toluene (1 mL) onto a CombiFlash® 12 G RediSep Rf Gold, mobile phase Hexane:Hexane with 10% EA=>0=>50% over 25 minutes.) Yield: 390 mg (64.5%)

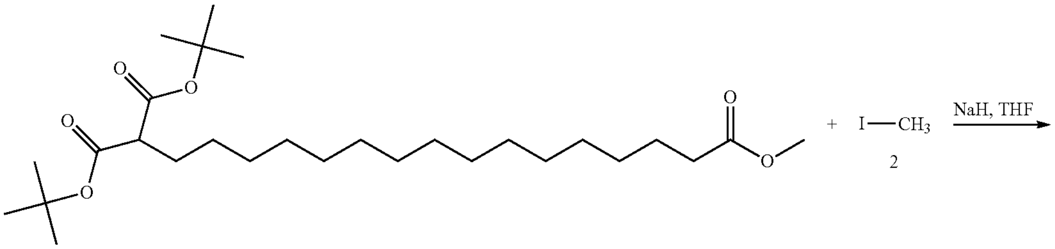

1

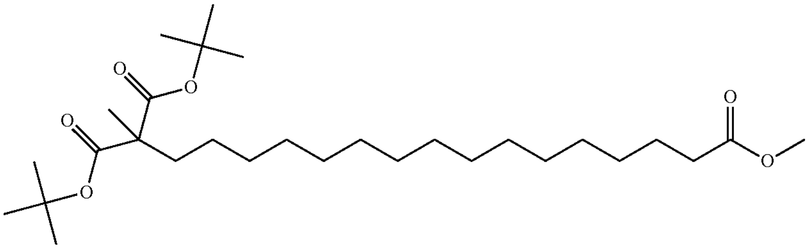

3

Compound 1 (0.100 g in 0.5 mL THF) was added to a suspension of NaH in 0.75 mL THF at 0° C. The reaction was warmed to room temperature and stirred for 20 minutes. The reaction mixture became clear. Then compound 2 (Sigma® 67692, 0.016 mL in 0.5 mL THF) was added dropwise at 0° C. and stirred for 0.5 h. The ice bath was removed and the reaction was allowed to stir at room temperature overnight. The reaction was diluted with DCM (20 mL) and washed with $NH_4Cl$ (1×5 mL.) The organic layer was back-extracted with DCM (1×5 mL). The organics were combined and washed with $H_2O$ (2×5 mL.) The organic phase was dried over $Na_2SO_4$, filtered and concentrated. The product was purified via chromatography (wet-loaded in toluene (1 mL) onto a CombiFlash® 12 G RediSep Rf Gold, mobile phase Hexane:Hexane with 10% EA 0=>50% over 25 minutes.) Yield: 30 mg (29.2%)

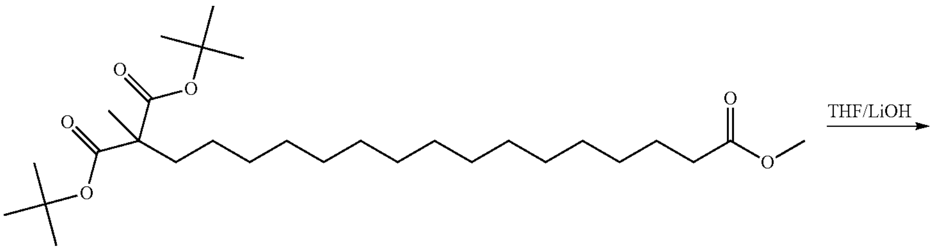

1

-continued
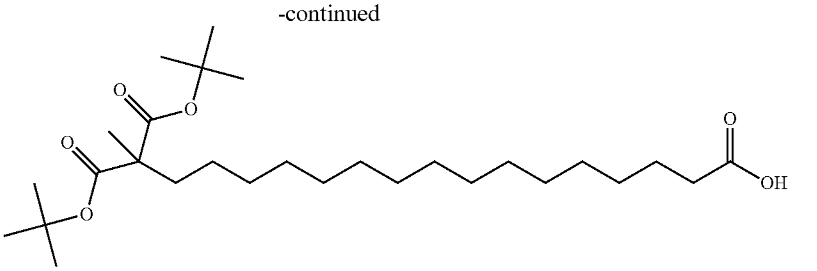
2
Compound 1 (0.0300 g) was dissolved in 0.4 mL of THF. Then LiOH (480 mg in 10 mL of THF) was added. The reaction was allowed to stir for 16 hours. The reaction was acidified to pH=3 with citric acid. The organic layer was extracted with 2×6 mL of DCM, and the organics were combined and dried over $Na_2SO_4$, filtered and concentrated. Yield: 25 mg (85.7%)
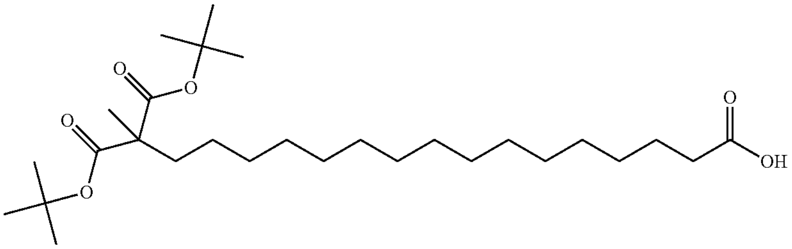
1
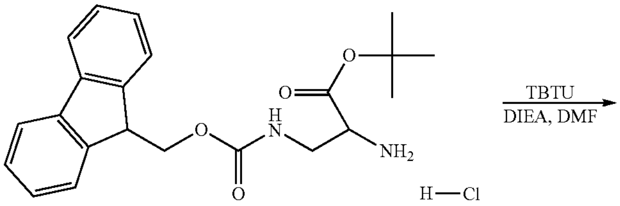
2
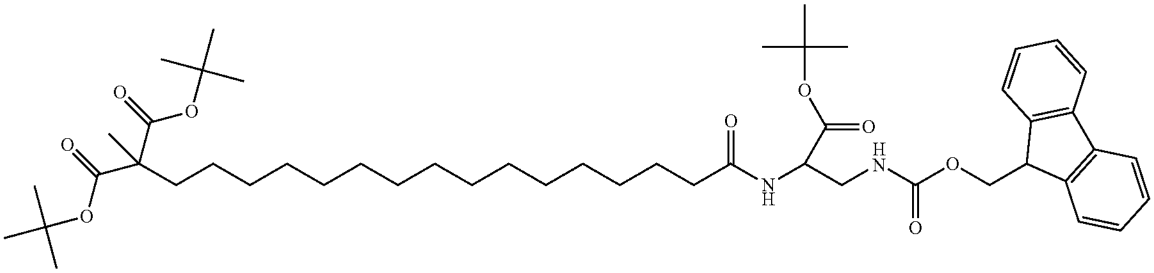
3

Compound 1 (0.0250 g) and Compound 2 (Chem Impex® #30487, 0.0238 g) were dissolved in DMF and TBTU (0.0190 g) and DIPEA (0.022 mL) were added to the mixture. The reaction was allowed to stir at room temperature for one hour. The mixture was then diluted to 9 mL with DCM, washed with water (3×7 mL), dried over $Na_2SO_4$, filtered and concentrated on high vacuum. The product was brought up in DCM (0.5 mL) and loaded onto 4G Redi-Sep Rf column on CombiFlash® (mobile phase DCM:DCM with 20% methanol 0=>25% over 15 minutes.) Yield: 37.1 mg (84.7%)

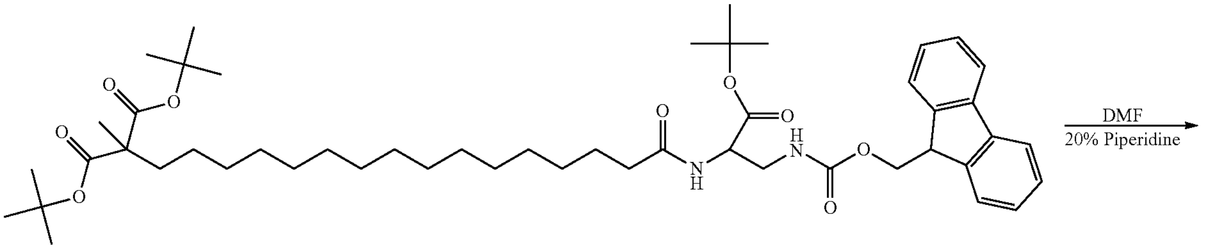

1

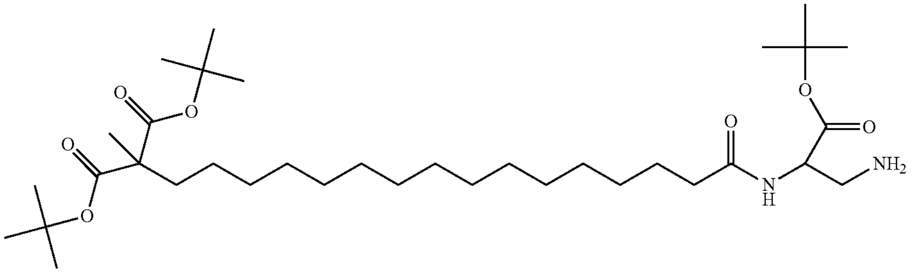

2

Compound 1 (0.0320 g) was dissolved in 0.5 mL of 20% piperidine in DMF. The reaction was allowed to stir at room temperature for one hour. The product was concentrated on high vacuum, then dissolved in toluene and concentrated on high vacuum. The product was brought up in 0.5 mL of DCM with 2×0.25 mL rinses and wet-loaded onto pre-equilibrated 4 g RediSep Gold Rf column on CombiFlash®, mobile phase DCM=>DCM with 20% MeOH 0=>50% over 20 minutes. Yield: 0.020 g (84.7%)

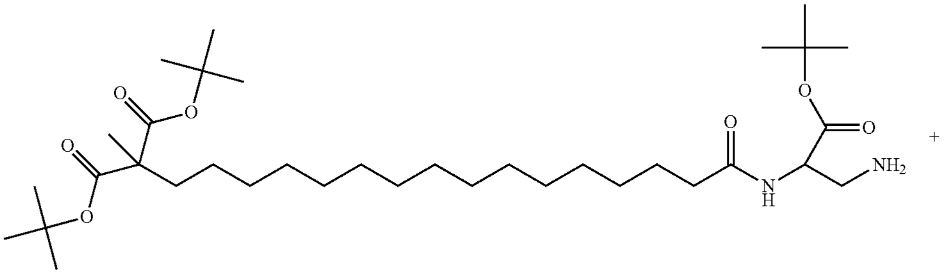

1

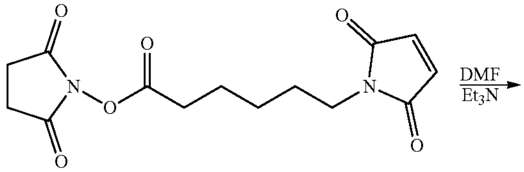

2

-continued

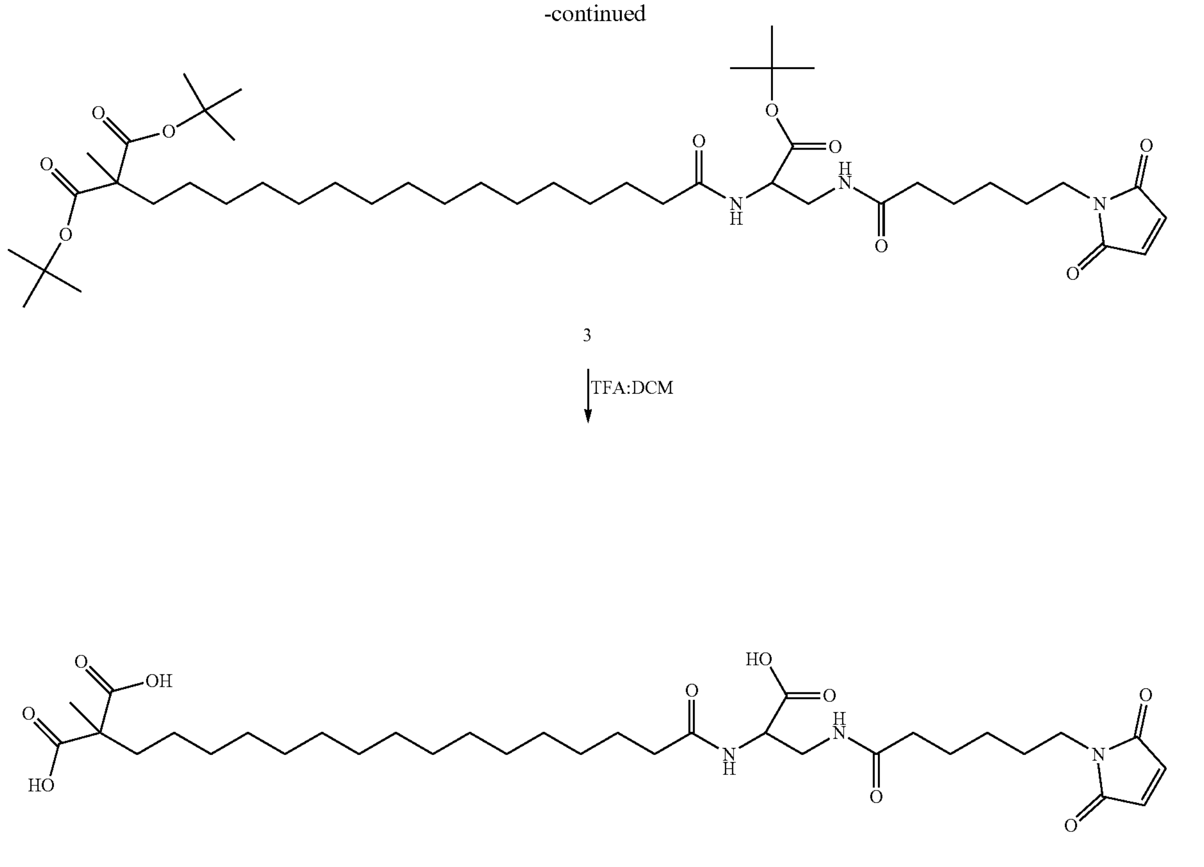

3

4

Compound 1 (0.0200 g) was added to a solution of $Et_3N$ (0.022 mL) in DMF (0.4 mL.) Then compound 2 (Asta Tech® #24%61, 0.0246 g) was added. The Reaction was allowed to stir at room temperature for one hour. The reaction was diluted to 10 mL with DCM and washed with 5% citric acid in water (3×5 mL), dried over $Na_2SO_4$, filtered and concentrated on high vacuum. The product was wet-loaded in 0.5 mL DCM with 2×0.3 mL rinses onto pre-equilibrated 4 g Redi Sep Gold Rf Column, mobile phase DCM=>20% MeOH in DCM 0=>30% over 20 minutes. Yield: 20 mg.

The product was then brought up in 2 mL of a 1:1 mixture of TFA:DCM and allowed to stir for two hours. The product was concentrated on rotary evaporator and high vacuum. Yield: 13 mg.

Mal-$C_{17}$-Fluoro-$PO_3$ Monoacid

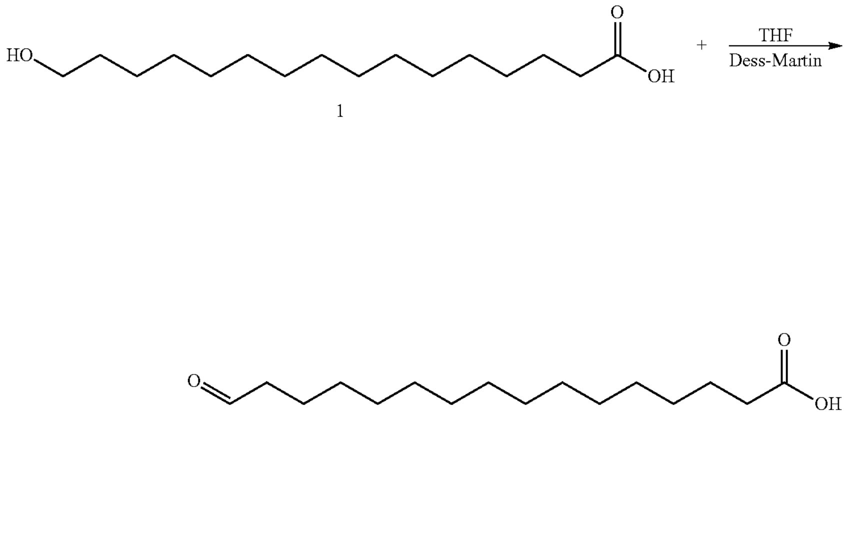

1

Compound 1 (Sigma® #177490, 5.00 g) was dissolved in a mixture of 70 mL THF and 20 mL of DMF. Then Dess-Martin Periodinane (Sigma® #274623, 11.7 g) was added. The reaction was allowed to stir for three hours. The mixture was concentrated on rotary evaporator and high vacuum, then dry-loaded onto 120 g Redi-Sep Gold Rf column on CombiFlash®, mobile phase hexane with 10% DCM:EtOAc, 0=>30% over 30 minutes. Yield: 2.86 g.

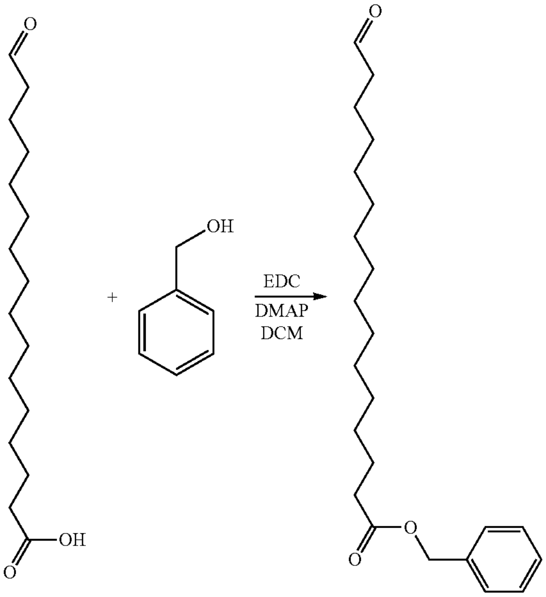

1

2

Compound 1 (2.85 g) and benzyl alcohol (1.36 mL) were mixed in 50 mL of DCM, and cooled to 0° C. Then EDC (2.53 g) and DMAP (0.257 g) were added sequentially. The reaction was allowed to warm to room temperature, then stirred for two hours while monitored by TLC. The mixture was extracted with $NH_4Cl$ (1×50 mL) solution and DCM. The organic phase was dried over $Na_2SO_4$, concentrated and dry-loaded on 80 g RediSep Gold Rf column, mobile phase Ethyl Acetate:Hexane, 0=>15% over 30 minutes. Yield: 2.31 g (61.0%)

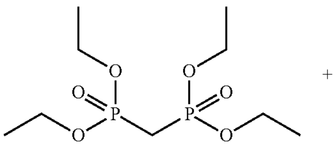

1

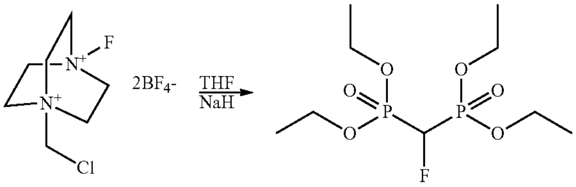

2

3

NaH (60% in oil, 0.047 mL) was added to a flask and the flask was charged with 15 mL THF. The flask was cooled to 0° C., and compound 1 (AK Scientific #J91196, 0.500 g) in 2 mL THF was added dropwise. The reaction was stirred for five minutes, then the ice was removed and the reaction was allowed to stir for 15 minutes at room temperature. The reaction was cooled to 0° C., and compound 2 (Tokyo Chemical Industry Co. #f0358, 0.768 g) was added as one solid portion. Then 0.3 mL of anhydrous DMF was added, followed by removal of the ice bath. The reaction was allowed to stir at room temperature overnight. The reaction was then diluted with DCM (50 mL) and washed with saturated $NH_4Cl$ (1×12 mL.) The aqueous layer was washed with DCM (1×10 mL.) The organics were combined and washed with $H_2O$ (2×10 mL), dried over $Na_2SO_4$, filtered and concentrated on rotary evaporator and high vacuum. The product was loaded in 1.5 mL DCM onto 4G Redi-Sep Gold Rf column on CombiFlash, mobile phase DCM:DCM with 20% MeOH, 0=>30% over 20 minutes. Yield 157 mg (36.2%)

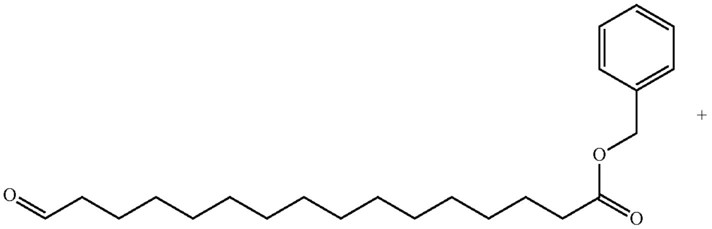

1

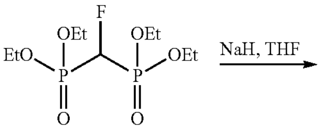

2

-continued

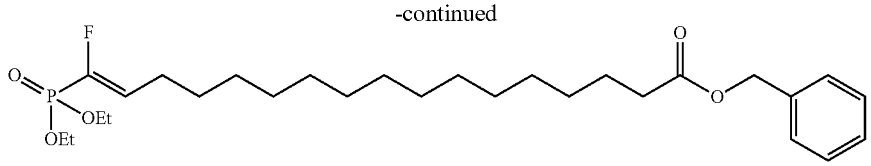

3

Compound 2 (0.149 g in 0.5 mL THF) was added to a suspension of NaH in THF (0.75 mL) at 0° C. The reaction was warmed to room temperature and stirred for 20 minutes. A solution of compound 1 (0.140 g) in 1.25 mL THF was added gradually at 0° C. and stirred for 0.5 h. The reaction was then diluted with DCM (20 mL) and washed with sat. $NH_4Cl$ (1×5 mL). The product was back-extracted with DCM (1×5 mL.) The combined organic layers were washed with $H_2O$ (2×5 mL.) The organic phase was dried over $Na_2SO_4$, filtered and concentrated. The product was dry loaded onto 1 g silica, 4G RediSep Rf Gold, mobile phase Hexane:EtOAc 0=>50%. Yield 67 mg (33.7%)

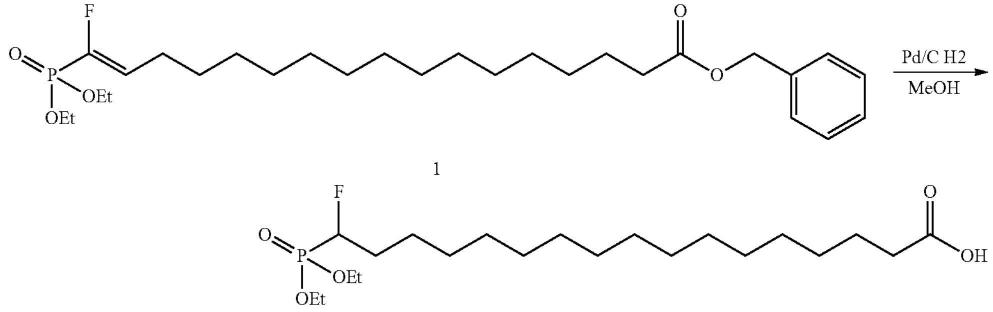

1

2

Compound 1 (0.0530 g) was dissolved in 2 mL MeOH, then a septum was placed on the flask and $N_2$ was applied two times. Then, Pd/C (0.0250 g) was added via weighing papers, then the septum was replaced and vacuum followed by $H_2$ was applied two times. The reaction was allowed to stir at room temperature for 2 hours. The product was filtered with a syringe filter and the filtrate was dried on rotavap and high vacuum. Yield: 36 mg (82.0%)

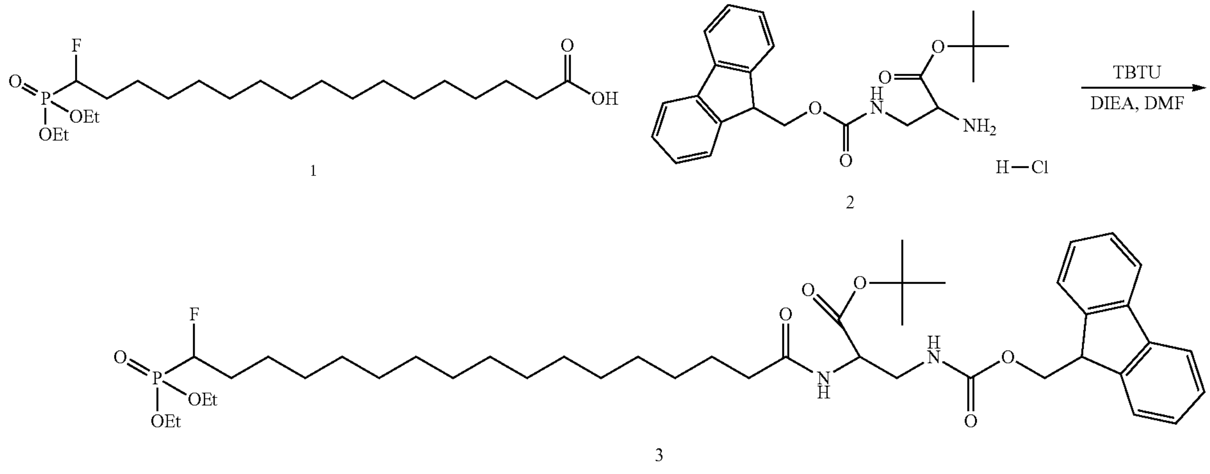

1

2

3

Compound 1 (0.0200 g) was dissolved in 0.3 mL of DMF, then TBTU (0.0174 g) followed by DIPEA 0.021 mL were added. The mixture was allowed to stir for 5 minutes, and then compound 2 (Chem Impex® #30487, 0.0217 g) was added. The reaction was allowed to stir at room temperature for one hour. Then the mixture was diluted with 6 mL DCM and washed with $H_2O$ (3×3 mL), and dried over $Na_2SO_4$, filtered and concentrated on rotary evaporator and high vacuum. The product was loaded in 1 mL DCM onto RediSep 4G Gold Rf column on CombiFlash®, mobile phase DCM:DCM with 20% MeOH, 0=>30% over 15 minutes. Yield 10 mg (88.8%)

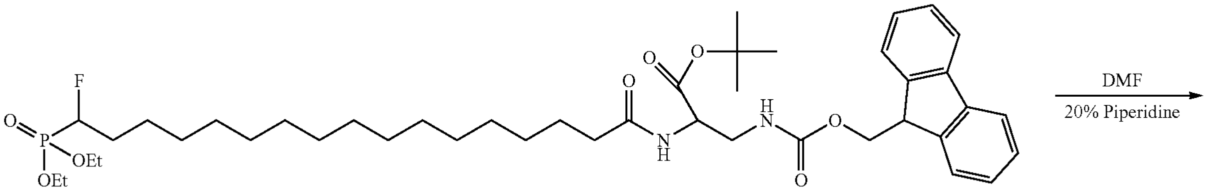

1

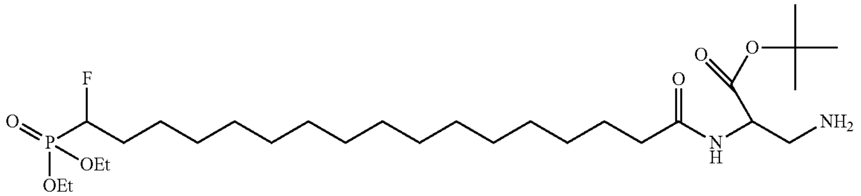

2

Compound 1 (0.0330 g) was dissolved in 0.5 mL DMF with 20% piperidine. The reaction was allowed to stir at room temperature for one hour. The reaction was concentrated on rotary evaporator and high vacuum. The product was loaded in 1 mL DCM onto 4G RediSep Gold Rf column on CombiFlash, mobile phase DCM:DCM with 20% MeOH, 0=>50% over 20 minutes. Yield: 11.5 mg (48.5%)

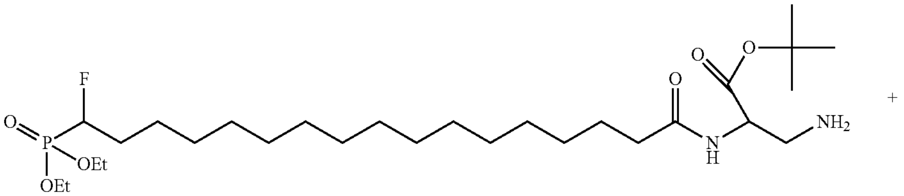

1

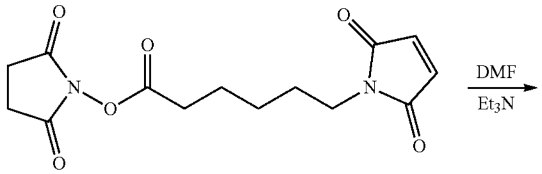

2

-continued

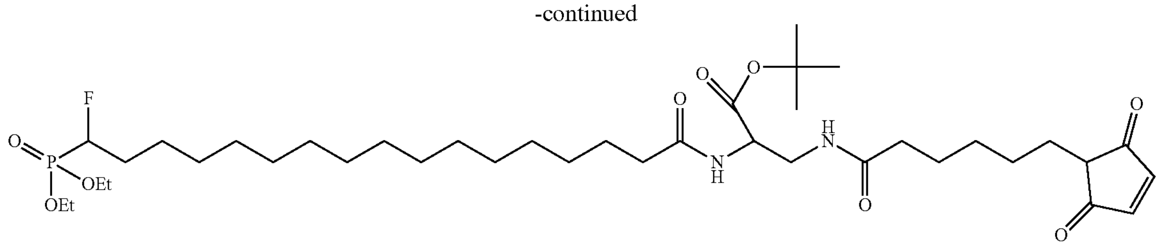

3

Compound 1 (0.0115 g) was dissolved in 0.3 L DMF, and Compound 2 (Asta Tech® #24961, 0.0156 g) and $Et_3N$ (0.014 mL) were added. The reaction was allowed to stir at room temperature overnight. The reaction was then diluted with DCM (6 mL) and washed with 5% citric acid (3×3 mL), dried over $Na_2SO_4$, filtered and concentrated. The product was loaded in 1 mL DCM onto 4G RediSep Gold R column on CombiFlash, mobile phase DCM:DCM with 20% MeOH from 0=>35% over 20 minutes. Yield: 10 mg (64.9%)

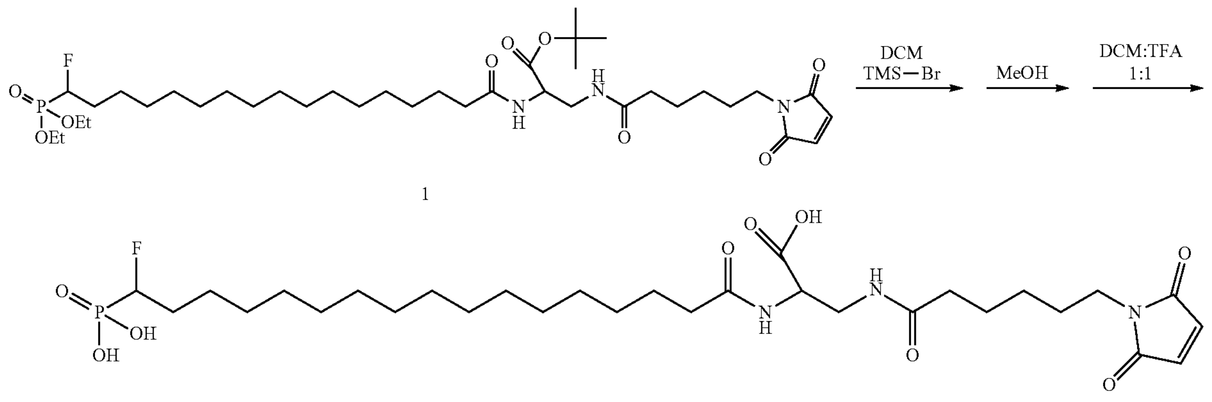

1

2

Compound 1 (0.0100 g) was dissolved in 0.3 mL of DCM and the mixture was cooled to 0° C. Then 0.051 mL of TMS-Br was added and the reaction was allowed to stir at 0° C. for 4 hours, followed by 3 hours at room temperature. The reaction was dried and 1 mL of MeOH was added. The reaction was allowed to stir overnight. The product was dried on rotary evaporator and high vacuum with toluene azeotroping (3×1 mL.) The reaction was then brought up in DCM:TFA 1:1 (1 mL) and set stirring at room temperature. After 1.5 h, the reaction was concentrated on rotary evaporator and high vacuum. Yield: 8.5 mg (99%.)

Mal-$C_{17}$-Fluoro-$PO_3$

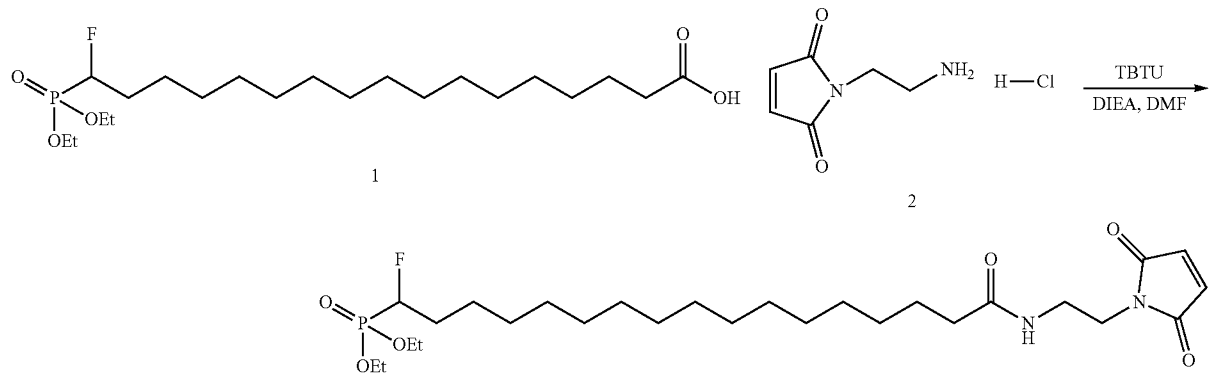

1

2

3

Compound 1 (0.0150 g) was dissolved in 0.25 mL of DMF. Then TBTU (0.0125) was added to the mixture, followed by DIEA (0.015 mL), and the mixture was allowed to stir for 5 minutes. Then, compound 2 (0.0062 g) was added to the mixture, and the reaction was stirred at room temperature for one hour. Then the reaction was diluted with DCM (6 mL) and washed with $H_2O$ (3x3 mL), dried over $Na_2SO_4$, filtered and concentrated on rotary evaporator and high vacuum. The product was loaded in 1 mL DCM onto 4G RediSep Gold Rf column on CombiFlash, mobile phase DCM:DCM with 20% MeOH from 0=>30% over 15 minutes. Yield: 12.5 mg (64.7%)

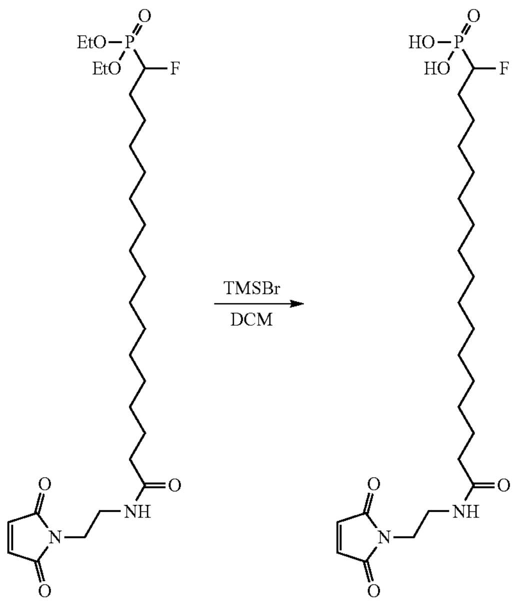

1 2

A solution of compound 1 (0.0125 g) in 0.4 mL DCM was cooled to 0° C. and TMSBr was added dropwise. The reaction was stirred at 0° C. for three hours. The volatiles were completely removed by rotary evaporator and high vacuum. The residue was stirred with MeOH for 2 hours to remove TMS. The mixture was dried on rotary evaporator and high vacuum. Yield: 11.5 mg (98.8%.)

Synthesis of Mal-C18-Diacid and Related Compounds

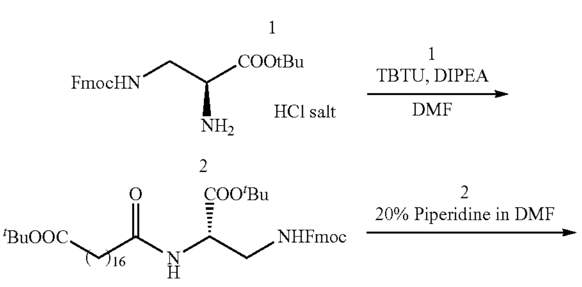

-continued

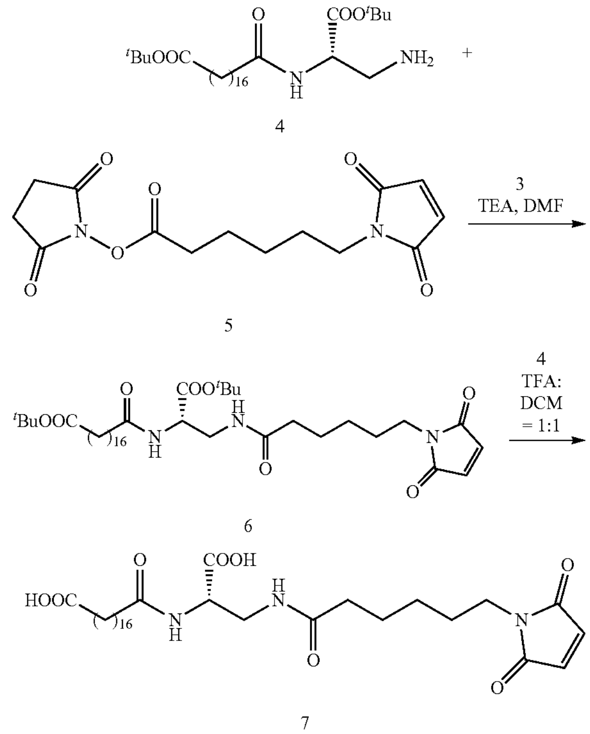

Step 1: Compound 1 (MW=370.57, 0.741 g, 2 mmol) was dissolved in 10 mL DMF. TBTU (Mw=321, 0.642 g, 2 mmol) and DIPEA (Mw=129, 0.87 ml, 5 mmol) were sequentially added and the mixture was stirred for 5 minutes. Compound 2 was added (Mw=418.9, 0.838 g, 2 mmol). The solution was stirred for 1 hour. The solution was diluted by 40 ml DCM and washed with water 3 times (40 mL each time). The organic phase was evaporated and purified using column chromatography (EA:HEX=0%-100%) to provide compound 3 (80% yield). (Mass Observed, M+1=736).

Step 2: Compound 3 was treated with 20% Piperidine in DMF for half an hour. The solvent was evaporated and the residue was purified through chromatography (MeOH: DCM=0%-10%). (Mass Observed, M+1=514). (Mass Observed, M+1=707).

Step 3: Compound 4 (Mw=513, 50 mg, 0.0975 mmol) was dissolved in 1 ml DMF. Compound 5 (Mw=308, 36 mg, 1.2 equiv) and TEA (0.041 ml, 3 equiv) were added. The reaction was stirred for 2 hours. The solution was diluted by DCM and washed with water 3 times. The organic phase was evaporated and purified by chromatography (EA:HEX=0%-100%) to provide compound 6. (Mass Observed, M+1=594).

Step 4: Compound 6 was treated with 50% TFA in DCM for 2 hours. The solvent was evaporated to provide compound 7 (Mal-C18-diacid) (Mass Observed, M+1=594.)

Mal-C18-Triacid

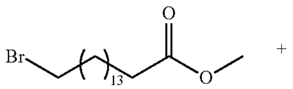

8

-continued

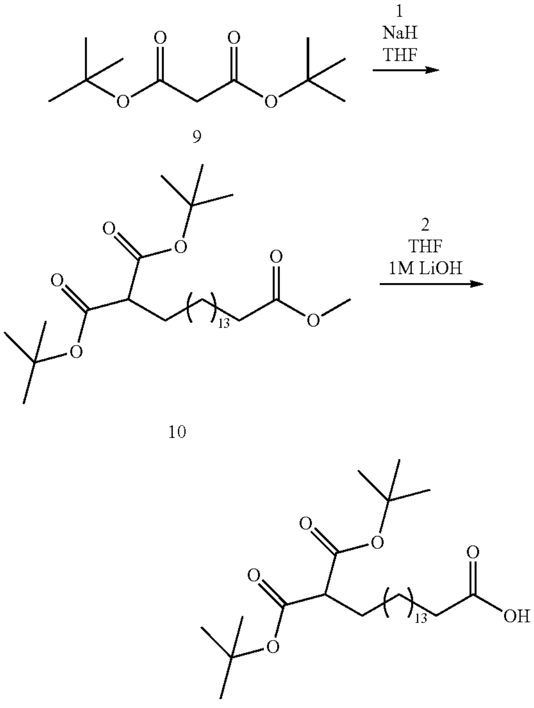

9

10

11

Step 1: Compound 9 (1.2 eq) was added to a solution of NaH (1.2 eq) in 3 ml of THF at 0° C., stir at room temperature for 0.5 hr. Compound 8 (1 mmol, 1 eq) in 1 ml of THF was then added to the mixture dropwise at 0° C. The mixture was stirred at 0° C. for 0.5 h, until the solution was clear. The solution was then raised to room temperature, and the solution slowly became a slurry. After 5 h, the reaction was quenched with $NH_4Cl$, and extracted with DCM. The product was purified on column (Hex: 10% EtOAc in Hexanes), peaks come out around 0%-3% of EtOAc. (42% Yield, 200 mg) (Mass Observed, M+1=486).

Step 2: Compound 10 was dissolved in THF (3 mL) and 1M LiOH (3 mL) was added. The reaction was stirred 16 hr at 25° C. Then, the solution was acidified to pH=3 with Citric Acid, and extracted with DCM (3×10 mL). The organic phases were combined and concentrated in vacuo, no further purification. (Mass Observed, M+1=472).

Mal-C18-Triacid was synthesized by using Compound 11 in place of compound 1 in the same synthesis as described for Mal-C18-diacid. (Mass Observed, M+1=638).

Mal-$C_{18}$-Diacid-$PO_3$

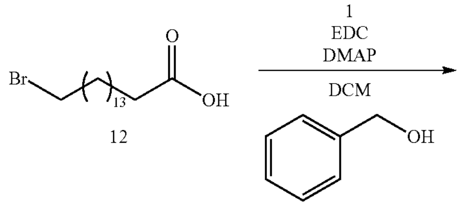

12

13

-continued

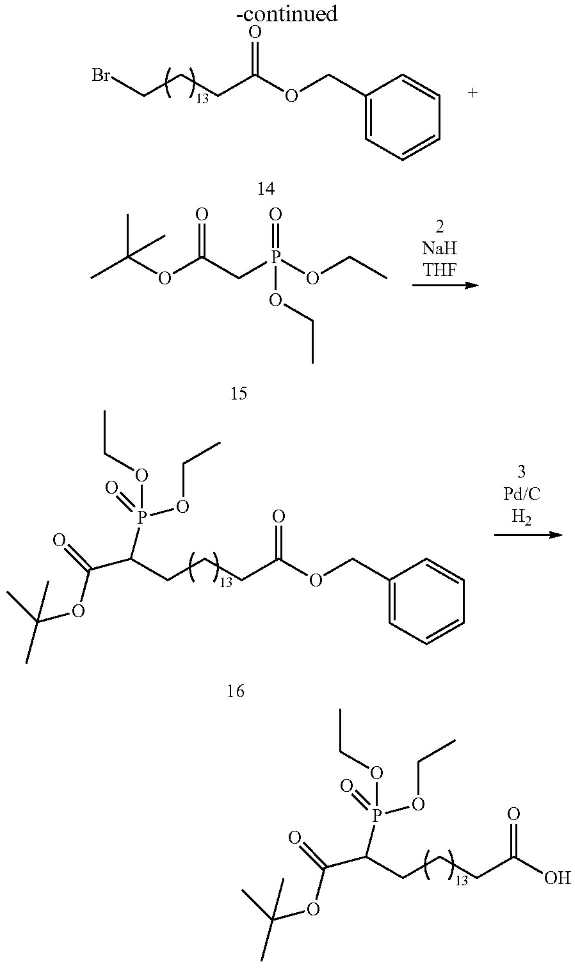

14

15

16

17

Step 1: Compound 12 (2.64 mmol, 1 eq) and Compound 13 (2.909 mmol, 1.1 eq) were mixed together in DCM, and the mixture was cooled to 0° C. EDC (1.1 eq) and DMAP (0.2 eq) were added sequentially. The reaction was warmed to room temperature. The reaction was stirred for 2 hours and was monitored by TLC Hexane:EtOAc 8:2. The organics were extracted with $NH_4Cl$ solution and DCM. The organic phase was dried over $Na_2SO_4$, concentrated, and purified using chromatography (EA:HEX=0% to 10%). The product spot comes out around 2% of EA. (Mass Observed, M+1=426).

Step 2: Compound 15 (1.2 eq) was added to a solution of NaH (1.2 eq) in 3 mL of THF at 0° C., and stirred at room temperature for 0.5 hr. Compound 14 (0.470 mmol, 1 eq) in 1 ml of THF was added to the mixture dropwise at 0° C. The reaction was stirred at 0° C. for 0.5 h, and the solution was clear. Then the mixture was raised to room temperature, and the solution slowly became a slurry. After 5 h, the reaction was quenched with $NH_4Cl$, and extracted with DCM. Column (Hex: 10% EtOAc in Hexanes), peaks come out around 3% of EtOAc. (16% Yield, 45 mg) (Mass Observed, M+1=598).

Step 3: Compound 16 (0.0519 mmol, 1 eq) was dissolved in MeOH. Then Pd/C (60 mg) was added to the reaction and several purge and refill cycles were performed with $H_2$. The reaction was stirred at 25° C. for 12 hrs. The mixture was filtered through silica and concentrated in vacuo to provide product. (24 mg, 92% Yield) (Mass Observed, M+1=508).

Mal-$C_{18}$-diacid-$PO_3$ was synthesized in the same manner as Mal-C18-diacid by substituting Compound 17 for compound 1 in the synthesis of Mal-C18-diacid. (Mass Observed, M+1=674).
Mal-C6-PEG2-C18-Diacid
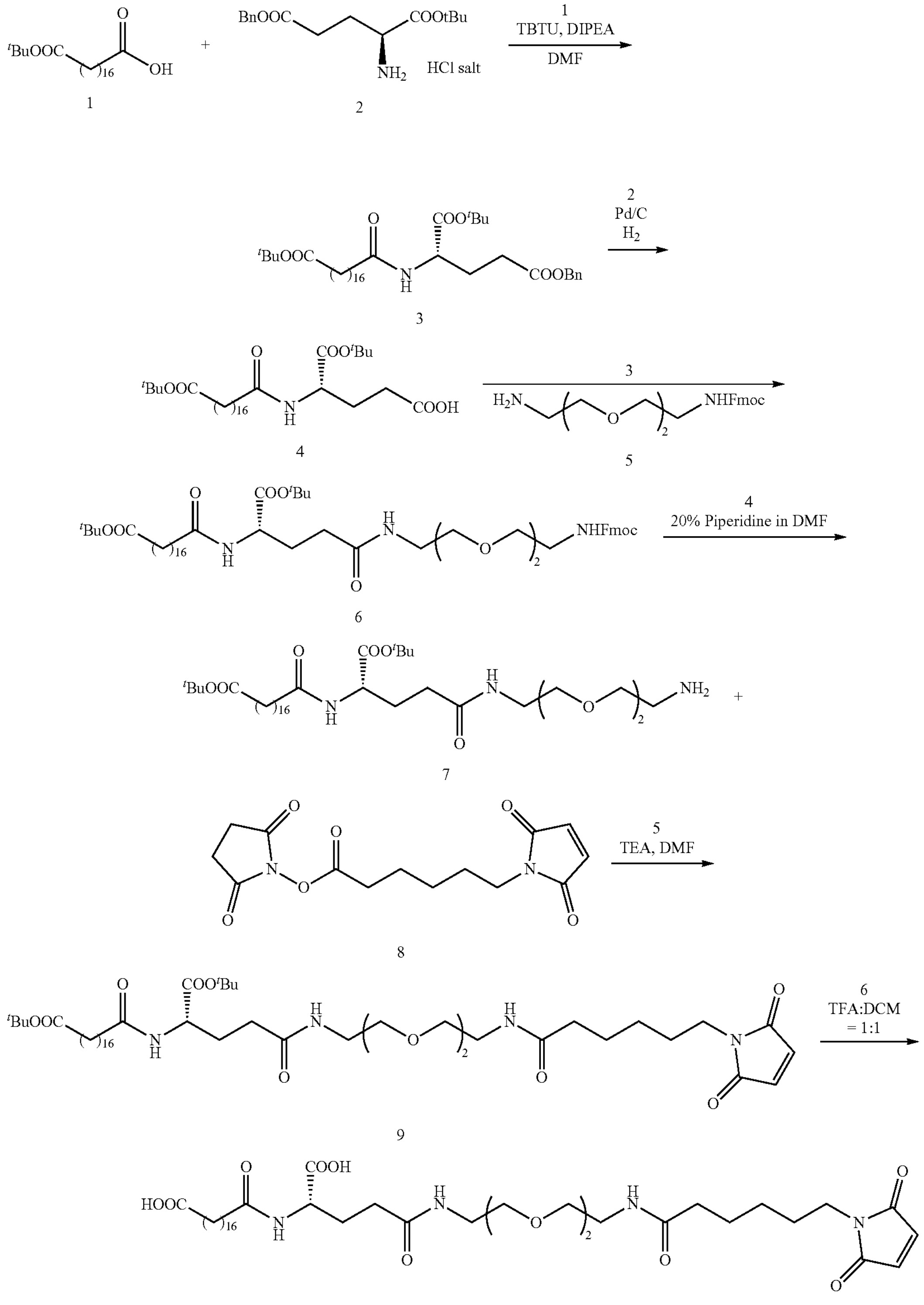
10

Step 1: Compound 1 (1 eq, 2 mmol) was dissolved in 10 mL DMF. TBTU (1 eq, 2 mmol) and DIPEA (2.5 eq, 5 mmol) were sequentially added and the mixture was stirred for 5 minutes. Compound 2 was added (1 eq, 2 mmol). The solution was stirred for 1 hour. The solution was diluted by 40 mL DCM and washed with water 3 times (40 mL each time). The organic phase was evaporated and purified by chromatography (DCM:DCM with 20% MeOH=0%-25%) to provide compound 3 (80% yield). (Mass Observed, M+1=647). (Mass Observed, M+1=767.)

Step 2: Compound 3 (1.6 mmol, 1 eq) was dissolved in MeOH. Pd/C (150 mg) was added to the reaction and several purge and refill cycles were performed with $H_2$. The reaction was stirred at 25° C. for 12 hrs. The reaction was filtered through silica and concentrated in vacuo to provide product. (1.5 mmol, 94% Yield) (Mass Observed, M+1=557).

Step 3: Compound 4 (1 eq, 1.5 mmol) was dissolved in 10 ml DMF. TBTU (1 eq) and DIPEA (2.5 eq) were sequentially added and the mixture was stirred for 5 minutes. Compound 5 (1 eq, 1.5 mmol) was added. The solution was stirred for 1 hour. The solution was diluted with 40 mL DCM and washed with water 3 times (40 mL each time). The organic phase was evaporated and chromatography (DCM: DCM with 20% MeOH=0%-25%) to provide compound 6 (80% yield). (Mass Observed, M+1=909).

Step 4: Compound 6 (1 eq, 1.2 mmol) was treated with 20% Piperidine in DMF for 30 mins. The solvent was evaporated and the residue was purified through chromatography (DCM:DCM with 20% MeOH=0%-30%) to provide Compound 7 (0.984 mmol, 82% yield) (Mass Observed, M+1=687).

Step 5: Compound 7 (1 eq, 0.984 mmol) was dissolved in 1 mL DMF. Compound 8 (1.2 eq, 1.18 mmol) and TEA (3 eq, 2.952 mmol) were added. The reaction was stirred for 2 hours. The solution was diluted by DCM (30 mL) and washed with water 3 times (15 mL each time). The organic phase was evaporated and chromatography (DCM:DCM with 20% MeoH=0%-30%) to provide compound 9 (0.738 mmol, 75% yield). (Mass Observed, M+1=880).

Step 6: Compound 9 was treated with 50% TFA in DCM for 2 hours. The mixture was concentrated in vacuo to provide compound 10. (Mass Observed, M+1=768).

Mal-C6-PEG4-C18-Diacid

Mal-C6-PEG4-C18-diacid was synthesized in the same manner as Mal-C18-diacid, but compound 7 was subjected to treatment with NHFmoc-$PEG_2$-$NH_2$. The Fmoc protecting group was removed with 20% piperidine deprotection as described in Step 4, then the steps 5 and 6 were repeated as described above (Mass Observed, M+1=912.)

Mal-Bis C18-Diacid

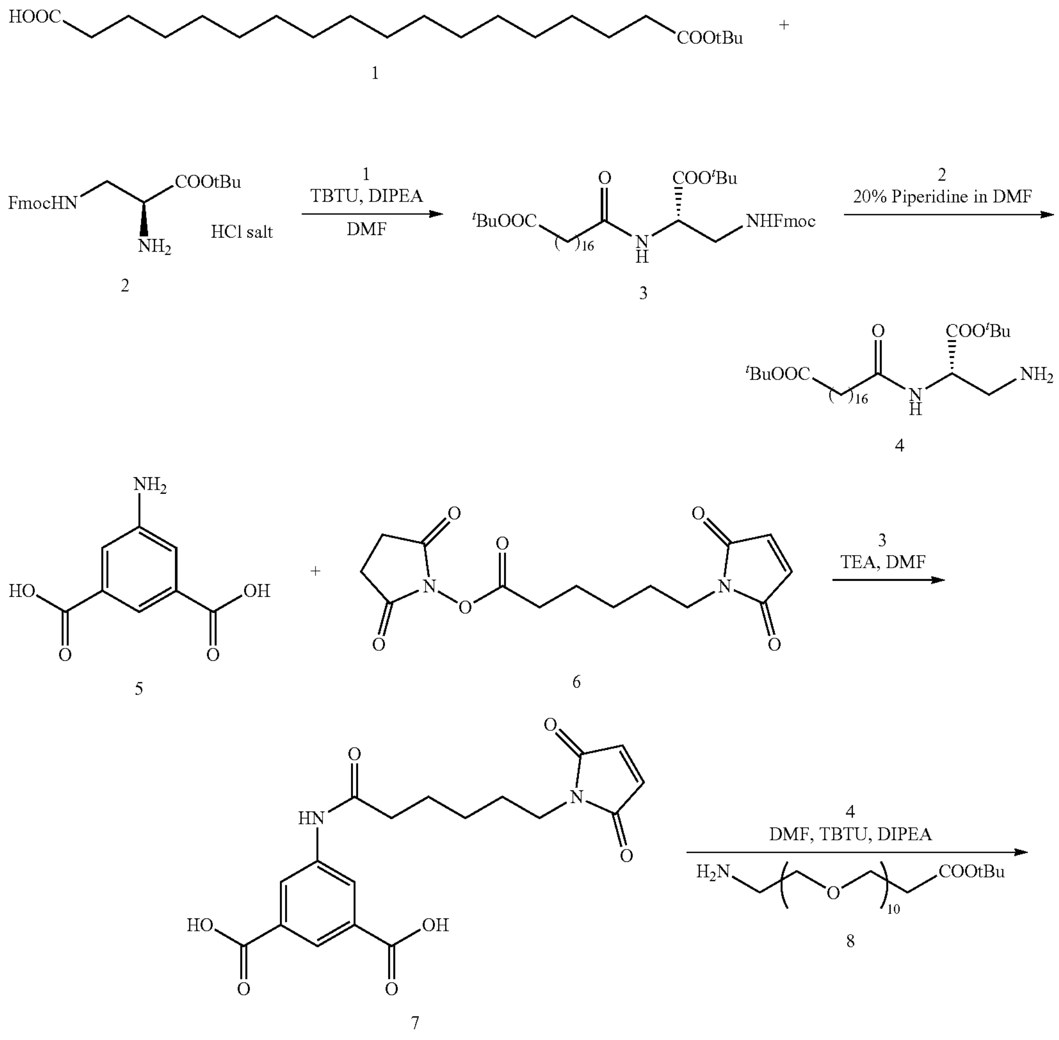

-continued

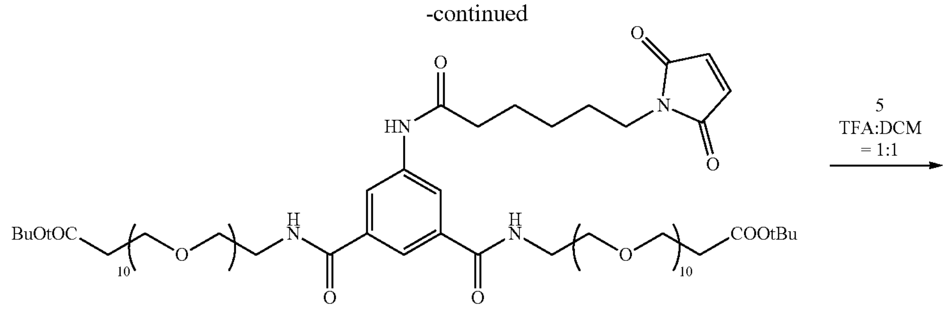

9

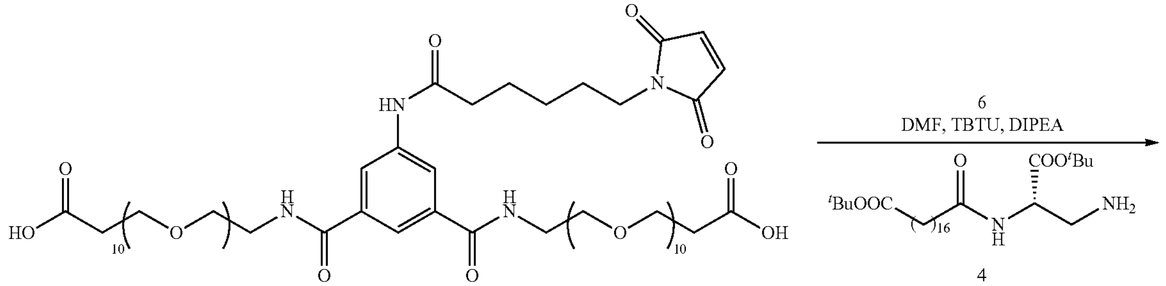

4

10

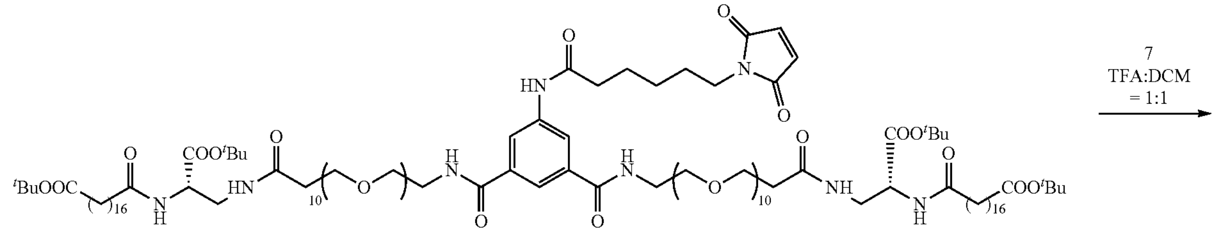

11

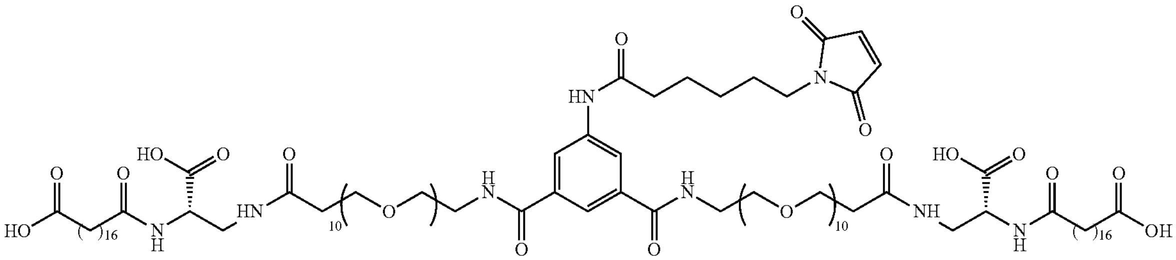

12

Steps 1 & 2: Compound 4 was synthesized as described in the synthesis of Mal-C18-Diacid, above.

Step 3: Compound 5 (1.0 mmol, 1 eq), compound 6 (1.3 eq) and TEA (5.0 eq) were well mixed in 3 mL DMF. The reaction was stirred overnight. The mixture was concentrated on rotary evaporator and purified via column chromatography. The product elutes around 4% MeOH in 1% HOAc in DCM. LC-MS shows desired peak with impurities. The final product was 170 mg with 45% yield.

Step 4: Compound 7 (0.12 mmol, 1 eq), compound 8 (2.4 eq), TBTU (2.4 eq) and DIPEA (5.0 eq) were well mixed in 1 mL DMF. The reaction was stirred overnight. LC-MS shows product as well as one major side product (more than product) and three small impurities. The mixture was concentrated by rotary evaporator and purified on column by DCM/MeOH. The product elutes around 6-12% of MeOH. The final product was obtained as 78 mg (oil) with 42% yield.

Step 5: Compound 9 (0.05 mmol) was dissolved in 2 mL DCM/TFA (1/1, v/v). The reaction was stirred for 1 hr. The solvents were evaporated to obtain compound 10 72 mg with 99% yield.

Step 6: Compound 10 (0.05 mmol, 1 eq), compound 4 (2.2 eq), TBTU (2.2 eq) and DIPEA (8.0 eq) were well mixed in 0.5 mL DMF. The reaction was stirred for 1 h. LC-MS shows product as well as one major side product (nonpolar TFA method). The mixture was concentrated by rotary evaporator and purified on column by DCM/MeOH. The product elutes around 8-12% of MeOH. Compound 11 was obtained as 60 mg with 49% yield.

Step 7: Compound 11 (0.025 mmol) was dissolved in 0.5 mL DCM/TFA (1/1, v/v). The reaction was stirred for 1 hr. The solvents were evaporated to obtain compound 12, 53 mg with 97% yield.

Synthesis of Mal-C18-Acid and Related Compounds

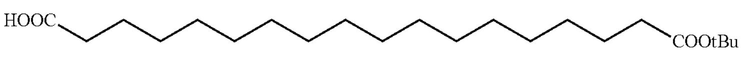

1

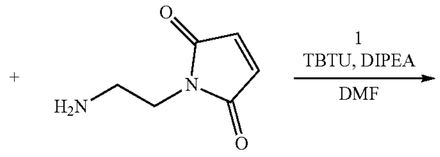

2

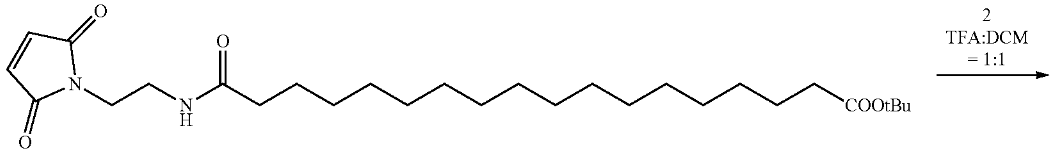

3

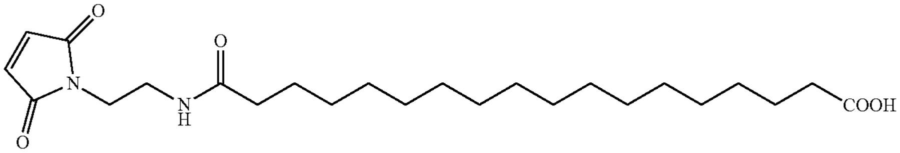

4

Step 1: Compound 1 (0.27 mmol, 1 eq) was dissolved in 1 mL DMF. TBTU (1 eq) and DIPEA (2.5 eq) were sequentially added and the mixture was stirred for 5 minutes. Compound 2 was added (1 eq). The solution was stirred for 1 hour. The solution was diluted with 40 ml DCM and washed with water 3 times (40 mL each time). The organic phase was concentrated using rotary evaporator and purified using column chromatography (EA:HEX=0%-100%) to provide compound 3. (Mass Observed, M+1=494).

Step 2: Compound 3 was treated with 50% TFA in DCM for 2 hours. The product was concentrated using rotary evaporator to provide compound 4. (Mass Observed, M+1=437).

Mal-$C_{20}$-Acid

Mal-$C_{20}$-acid was synthesized in the same manner as Mal-C18-acid using commercially available $C_{20}$ starting material in place of compound 1 (Mass Observed, M+1=465).

Mal-$C_{17}$—$PO_3$

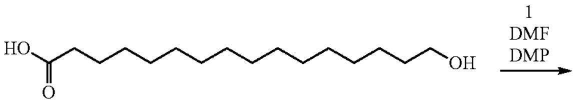

5

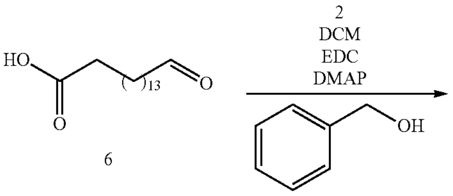

6

7

-continued

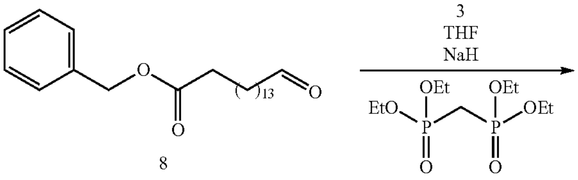

8

9

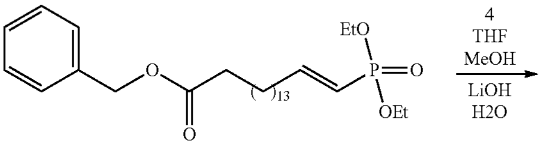

10

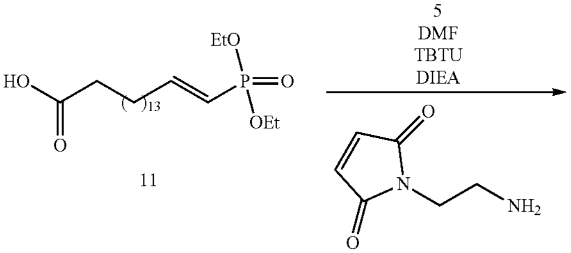

11

2

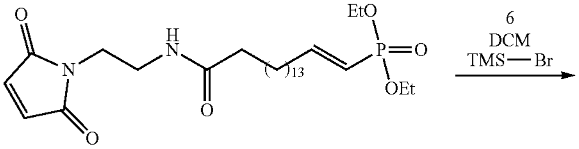

12

-continued

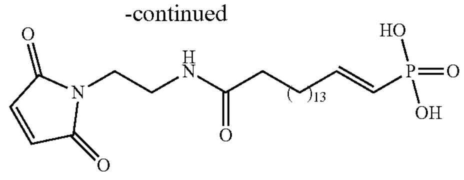

13

Step 1: DMP (1.3 eq, 4.78 mmol) and compound 5 (1 eq, 3.68 mmol) were mixed in DMF (15 mL). After 2 hours, the reaction was finished as shown by TLC. Some solid precipitate formed. Workup: filtration to get rid of solids, rinse with DCM. The product was concentrated in vacuo and purified using chromatography (Hex with 10% DCM: EtOAC=>0%-20%), product elutes at 5%-10%. (0.8136 mmol, 22% Yield) (Mass Observed, M+1=271).

Step 2: Compound 6 (1 eq, 0.8136 mmol) and Compound 7 (1.1 eq, 0.8949 mmol) were mixed in DCM (5 mL), cool to 0° C. EDC (1.1 eq) and DMAP (0.2 eq) were added sequentially. The reaction was warmed to room temperature. The reaction was stirred for 2 hours and was monitored by TLC Hexane:EtOAc 8:2. The product was extracted with $NH_4Cl$ solution and DCM. The organic phase was dried over $Na_2SO_4$, concentrated, and purified through chromatography (Hex:EtOAC=0% to 10%). The product spot comes out at 4% of EtOAc (0.4438 mmol, 54.5% Yield). (Mass Observed, M+1=361).

Step 3: Compound 9 (1.4 eq) was added to a solution of NaH (1.2 eq) in 1.5 ml of THF at 0° C. and stirred at room temperature for 0.5 hr. Compound 8 (1 eq, 0.4438 mmol) in 1 ml of THF was added to the mixture dropwise at 0° C. The reaction was stirred at 0° C. for 0.5 h, and the solution was clear. The mixture was warmed to room temperature, and the solution slowly became a slurry. After 5 h, the reaction was quenched with $NH_4Cl$, and extracted with DCM. Column (Hex:EtOAc=>0% to 50%), product comes out at 35% of EtOAc. (0.2020 mmol, 45.5% Yield) (Mass Observed, M+1=496).

Step 4: Compound 10 (1 eq, 0.2020 mmol) was dissolved in a mixture of 1:1:1 of MeOH, THF, and 1M LiOH (3 mL total solution). The mixture was stirred for 2 hr at 25° C. The reaction was acidified to pH=3 with Citric Acid, and extracted with DCM (3×10 mL). The organic phases were combined, dried over $Na_2SO_4$, filtered and concentrated in vacuo. No further purification was necessary. (Mass Observed, M+1=405).

Step 5: Compound 11 (1 eq, 0.0938 mmol) was dissolved in 1 mL DMF. TBTU (1 eq) and DIPEA (2.5 eq) were sequentially added and the mixture was stirred for 5 minutes. Compound 2 was added (1 eq). The solution was stirred for 1 hour. The solution was diluted by 10 mL with DCM and washed with water 3 times (5 mL each time). The organic phase was evaporated and purified by chromatography (DCM:DCM with 20% MeOH=0%-30%) to provide compound 12 (0.0683, 73% Yield) (Mass Observed, M+1=528).

Step 6: A solution of compound 12 in DCM was cooled to 0° C. and TMS-Br was added dropwise. The reaction was stirred at 0° C. and monitored by LC-MS. The reaction was complete within 2.5 hours. The volatiles were completely removed by rotary evaporator and high vacuum (to completely remove acid). The residue was stirred with MeOH for 2 hours to remove TMS. The product was concentrated in vacuo to provide desired product. (Assume 100% Yield) (Mass Observed, M+1=471).

Mal-$C_{18}$-Diacid (L-Version)

Mal-C18-diacid (L-version) was synthesized in the same manner as Mal-C18-acid Mal-C18-Glu (L)-Diacid, but Glu (D) was used in place of Glu(L) (Mass Observed, M+1=567)

Synthesis of Mal-C6-C12-PEG2-C18 Diacid and Related Compounds

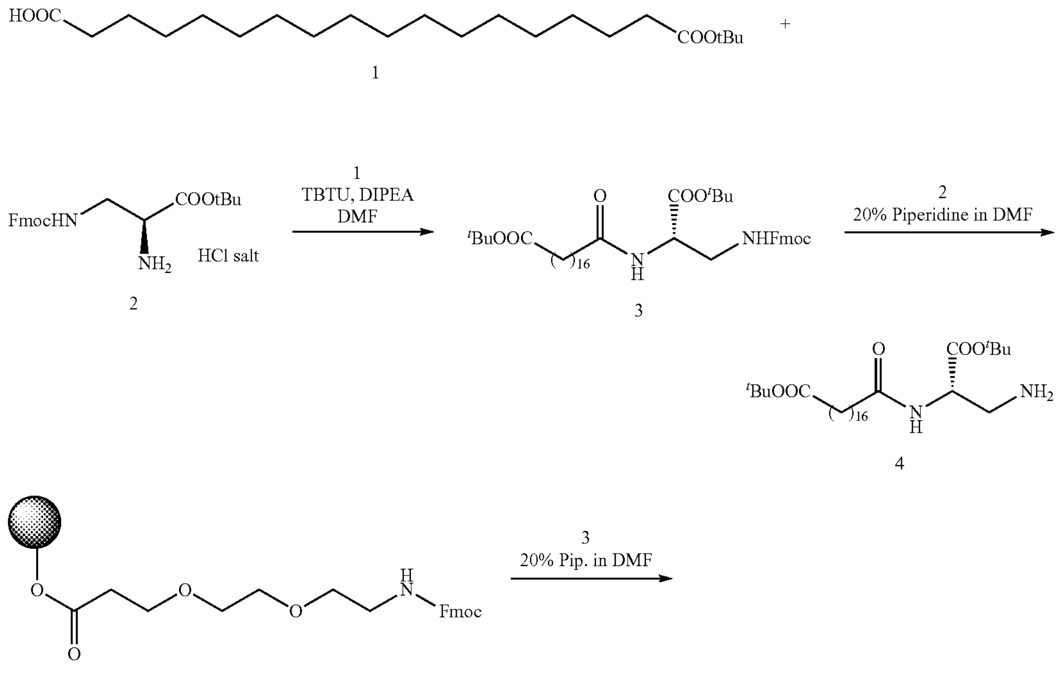

1 2 3 4 5

-continued
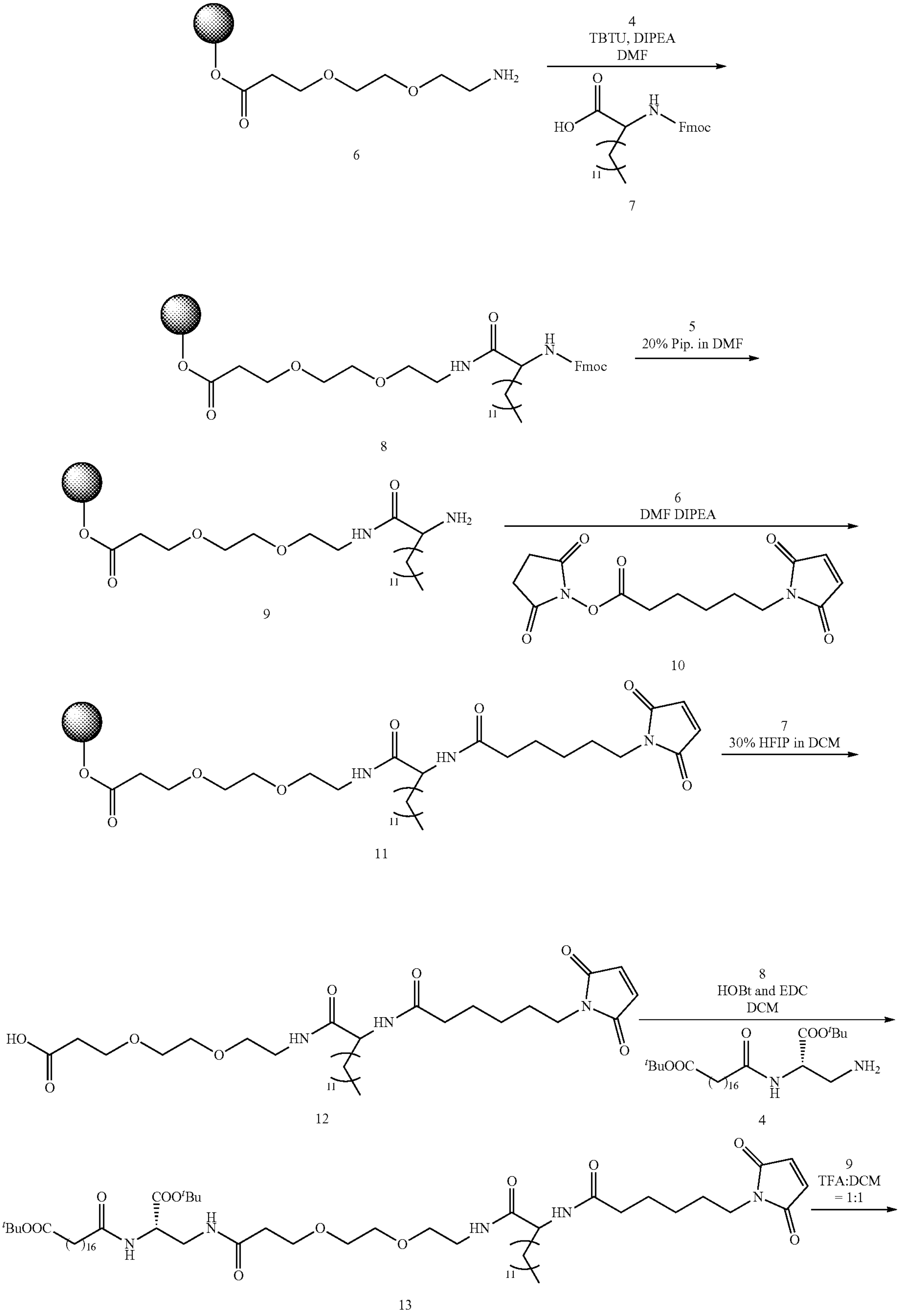

-continued

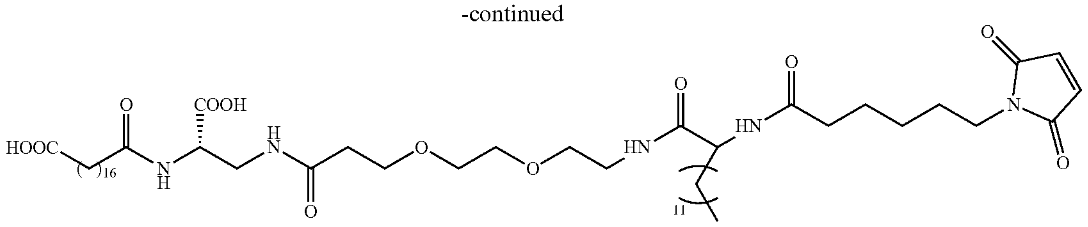

14

Steps 1 & 2: Compound 4 was synthesized as described in the synthesis of Mal-C18-Diacid, above.

Step 3: Compound 5 (1 mmol, 1 eq) was treated with 3 mL 20% piperidine in DMF for 20 mins. Then the resin was rinsed 3 times with DMF and used in the next step without further purification.

Step 4: To compound 6 was added a mixture of TBTU (2 eq), compound 7 (2 eq), DIPEA (6 eq) in 3 mL of DMF, and stirred for 1 hr. The solvents were removed under vacuum and the resin was rinsed 3 times with 3 mL of DMF.

Step 5: Compound 8 was treated with 3 ml 20% piperidine in DMF for 20 mins. Then the resin was rinsed 3 times with DMF and used in the next step without further purification.

Step 6: To compound 9 was added a mixture of compound 10 (2 eq) and DIPEA (6 eq) in 3 mL of DMF and stirred overnight. The solvents were removed under vacuum and the resin was rinsed 3 times with 3 mL of DMF.

Step 7: Compound 11 was treated with 3 ml 30% HFIP in DCM for 30 mins. The solution was filtered, and the filtrate was collected and evaporated to provide compound 12.

Step 8: To compound 10 (1 eq) in DCM was added EDC (1 eq), followed by HOBt (1 eq) and stirred for 15 mins. Compound 4 was then added, and the reaction was further stirred for another 4 hrs. The solvent was evaporated, and the crude material was purified through chromatogram in DCM and MeOH.

Step 9: Compound 13 was treated with 3 ml 50% TFA in DCM for 1 hr. The solvents evaporated to provide compound 14. Mal-C6-C12-Peg2-C18 Diacid (Mass Observed, M+1=979).

Mal-C6-C12-C12-PEG2-C18-Diacid

Mal-C6-C12-C12-PEG2-C18-Diacid was synthesized using the same procedure as Mal-C6-C12-PEG2-C18 diacid, though compound 9 was subjected to the reactions of steps 4 and 5 before continuing to further steps. (Mass Observed, M+1=1204).

Mal-C6-C12-C12-C12-PEG2-C18 Diacid

Mal-C6-C12-C12-C12-PEG2-C18 Diacid was synthesized using the same procedure as Mal-C6-C12-PEG2-C18 diacid, though compound 9 was subjected to the reactions of steps 4 and 5 twice before continuing to further steps. (Mass Observed, M+1=1429.)

Mal-C6-C12-C12-C12-PEG2-C12 Acid

Mal-C6-C12-C12-C12-PEG2-C12 acid was synthesized using the same procedure as Mal-C6-C12-PEG2-C18 diacid, though compound 9 was subjected to the reactions of steps 4 and 5 twice before continuing to further steps, followed by use of a commercially available C12 analog of compound 4. (Mass Observed, M+1=1245).

Example 2. Orthotopic Clear Cell Renal Cell Carcinoma (ccRCC) Tumor-Bearing Mouse Model Using Human A-498 Cells Creation of SEAP-expressing clear cell renal cell carcinoma (ccRCC) A498 cells. A pCR3.1 expression vector expressing the reporter gene secreted alkaline phosphatase (SEAP) under the CMV promoter was prepared by directional cloning of the SEAP coding sequence PCR amplified from Clontech's pSEAP2-basic vector. Convenient restriction sites were added onto primers used to amplify the SEAP coding sequence for cloning into the pCR3.1 vector (Invitrogen). The resultant construct pCR3-SEAP was used to create a SEAP-expressing A498 ccRCC cell line. Briefly, pCR3-SEAP plasmid was transfected into A498 ccRCC cells by electroporation following manufacturer's recommendation. Stable transfectants were selected by G418 resistance. Selected A498-SEAP clones were evaluated for SEAP expression and integration stability.

Implantation of SEAP-expressing clear cell renal cell carcinoma (ccRCC) A498 cells. Female athymic (immunodeficient) nude mice were anesthetized with ~3% isoflourane and placed in the right lateral decubitus position. A small, 0.5-1 cm, longitudinally abdominal incision in the left flank was made. Using a moist cotton swab, the left kidney was lifted out of the peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 μl aliquot of 2:1 (vol:vol) cell/matrigel mixture containing about 300,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Serum was collected every 7-14 days after implantation to monitor tumor growth using a commercial SEAP assay kit. For most studies, tumor mice were used 5-6 weeks after implantation, when tumor measurements were typically around 4-8 mm.

Determination of HIF2 mRNA Expression. For the studies reported in the Examples herein, mice were euthanized the identified day after injection and total RNA was isolated from kidney tumor using Trizol reagent following manufacturer's recommendation. Relative HiF2α mRNA levels were determined by RT-qPCR as described below and compared to mice treated with delivery buffer (isotonic glucose) only. In preparation for quantitative PCR, total RNA was isolated from tissue samples homogenized in TriReagent (Molecular Research Center, Cincinnati, OH) following the manufacturer's protocol. Approximately 500 ng RNA was reverse-transcribed using the High Capacity cDNA Reverse Transcription Kit (Life Technologies). For human (tumor) Hif2a (EPAS1) expression, pre-manufactured TaqMan gene expression assays for human Hif2a (Catalog #4331182) and CycA (PPIA) Catalog #: 4326316E) were used in biplex reactions in triplicate using TaqMan Gene Expression Master Mix (Life Technologies) or VeriQuest Probe Master Mix (Affymetrix). Quantitative PCR was performed by using a 7500 Fast or StepOnePlus Real-Time PCR system (Life Technologies). The $\Delta\Delta C_T$ method was used to calculate relative gene expression.

Example 3. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according dosing Groups that included the following:

TABLE 8

Dosing Groups of Tumor-Bearing Mice in Example 3.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD04545 (without any targeting ligand), formulated in isotonic glucose. | Single IV injection on day 1 |
| 3 | 7.5 mg/kg of HIF-2 alpha RNAi agent AD04546, linked at the 3' terminal end of the sense strand to a branched (4 arm) 40 kilodalton (kD) polyethylene glycol (PEG) PK enhancer, formulated in isotonic glucose. | Single IV injection on day 1 |
| 4 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to a branched (4 arm) 40 kilodalton (kDa) polyethylene glycol (PEG) PK enhancer, formulated in isotonic glucose. | Single IV injection on day 1 |
| 5 | 7.5 mg/kg of HIF-2 alpha RNAi agent AD04546, linked at the 3' terminal end of the sense strand to PK enhancer Mal-C6-C12-C12-C12-PEG2-C12 acid, formulated in isotonic glucose. | Single IV injection on day 1 |
| 6 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C6-C12-C12-C12-PEG2-C12 acid, formulated in isotonic glucose. | Single IV injection on day 1 |

In Groups 5 and 6, the PK enhancer having the following structure was linked to the 3' terminal end of the sense strand by reducing the disulfide and undertaking a Michael Addition reaction to link the maleimide reactive group of the PK enhancer compound:

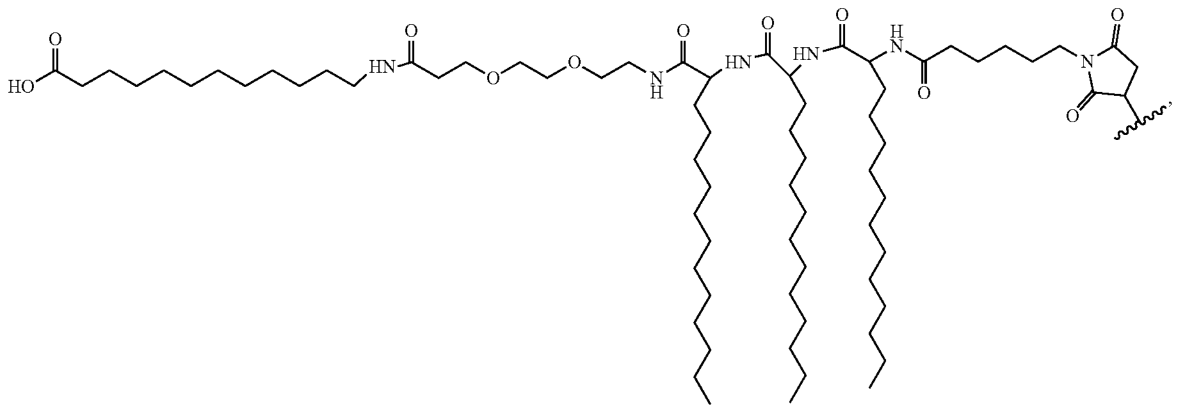 [SMILES: *C1CC(=O)N(CCCCCC(=O)NC(CCCCCCCCCCCC)C(=O)NC(CCCCCCCCCCCC)C(=O)NC(CCCCCCCCCCCC)C(=O)NCCOCCOCCC(=O)NCCCCCCCCCCCC(=O)O)C1=O]

wherein  indicates the point of attachment to the RNAi agent at the C6-S group as indicated in Table 4.3 (See also Example 1).

In Groups 4 and 6, the tridentate integrin targeting group (which included three integrin ligands having affinity for alpha-v-beta-3 of the structure of Structure 2a-avb3) was linked to the 5' terminal end of the sense strand by coupling to the functionalized amine linker (NH2-C6):

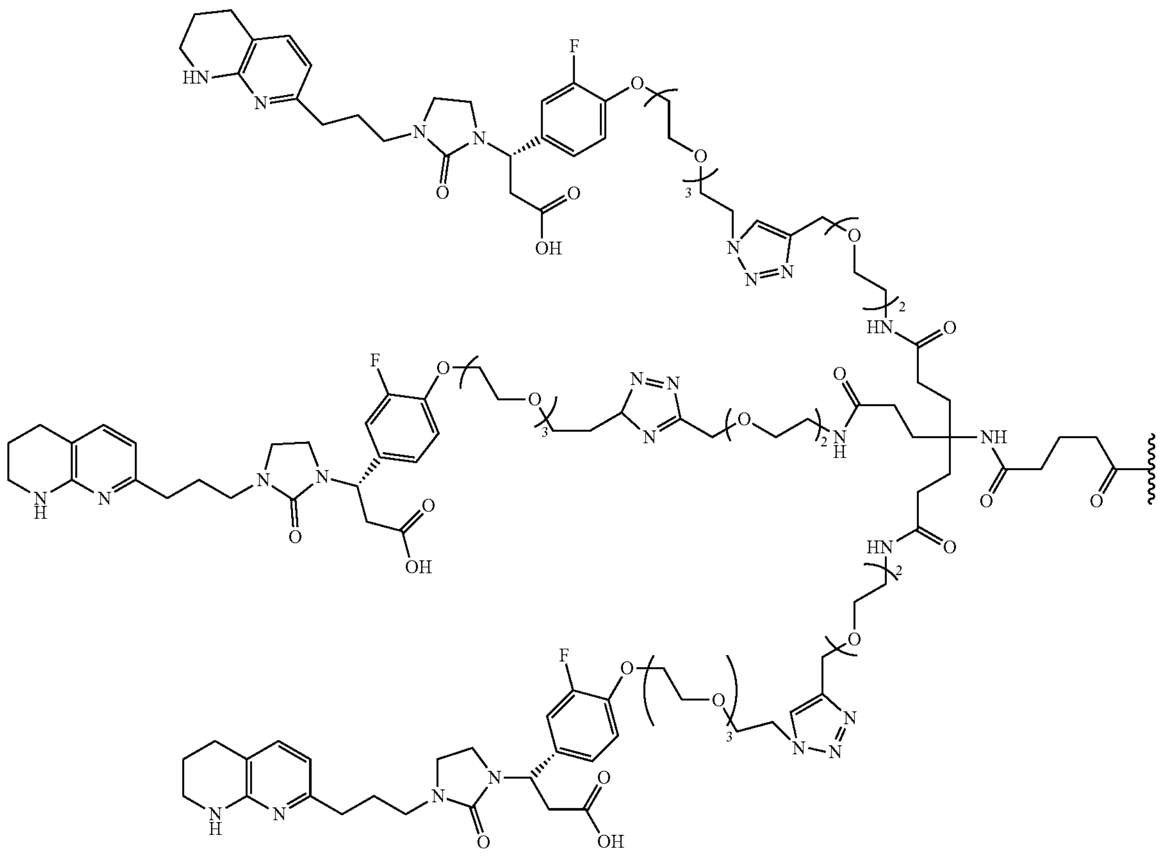

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 9

Average Relative huHIF-2 alpha mRNA Expression at Sacrifice (Day 8) in Example 3.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.162 | 0.193 |
| Group 2 (7.5 mg/kg AD04545 (no ligand)) | 3 | 1.030 | 0.058 | 0.061 |
| Group 3 (7.5 mg/kg AD04546-40 kDa PEG) | 3 | 0.638 | 0.083 | 0.095 |

TABLE 9-continued

Average Relative huHIF-2 alpha mRNA Expression at Sacrifice (Day 8) in Example 3.

| Group ID | Number of animals (n=) | Average Relative HIF-2 alpha mRNA expression | Low (error) | High (error) |
|---|---|---|---|---|
| Group 4 (7.5 mg/kg Tri-Structure 2a-avb3-AD04546-40-kDa PEG) | 3 | 0.308 | 0.028 | 0.030 |
| Group 5 (7.5 mg/kg AD04546-Mal-C6-C12-C12-C12-PEG2-C12 acid) | 3 | 0.630 | 0.049 | 0.053 |
| Group 6 (7.5 mg/kg Tri-Structure 2a-avb3-AD04546-Mal-C6-C12-C12-C12-PEG2-C12 acid) | 3 | 0.456 | 0.068 | 0.079 |

As shown in Table 9 above, only minimal knockdown was observed for Group 2 (AD04545, showing approximately 0% knockdown (1.030) compared to vehicle control), which was a HIF-2 alpha RNAi agent that was not linked to a targeting ligand or to a PK enhancer. Groups 4 and 6, which each included tridentate targeting groups, showed greater activity compared to constructs without a targeting ligand present indicating a targeting ligand dependence. Further, additional inhibitory activity was observed in the Groups that included both a targeting ligand and a PK enhancer. (See, for example, Group 4 (showing approximately 70% knockdown (0.308) and Group 6 (showing approximately 55% knockdown (0.456)).

Example 4. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to dosing Groups that included the following:

TABLE 10

Dosing Groups of Tumor-Bearing Mice in Example 4.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to a branched (4 arm) 40 kilodalton (kDa) polyethylene glycol (PEG) PK enhancer, formulated in isotonic glucose. | Single IV injection on day 1 |
| 3 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C6-C12-C12-C12-PEG2-C12 acid, formulated in isotonic glucose. | Single IV injection on day 1 |
| 4 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C6-C12-PEG2-C18-diacid, formulated in isotonic glucose. | Single IV injection on day 1 |
| 5 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C6-C12-C12-PEG2-C18-diacid, formulated in isotonic glucose. | Single IV injection on day 1 |

TABLE 10-continued

| Dosing Groups of Tumor-Bearing Mice in Example 4. | | |
|---|---|---|
| Group | RNAi Agent and Dose | Dosing Regimen |
| 6 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C6-C12-C12-C12-PEG2-C18-diacid, formulated in isotonic glucose. | Single IV injection on day 1 |
| 7 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-diacid, formulated in isotonic glucose. | Single IV injection on day 1 |
| 8 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-acid, formulated in isotonic glucose. | Single IV injection on day 1 |
| 9 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C20-acid, formulated in isotonic glucose. | Single IV injection on day 1 |

In Groups 3-9, the respective PK enhancers having the following structures were linked to the 3' terminal end of the sense strand:

Group 3

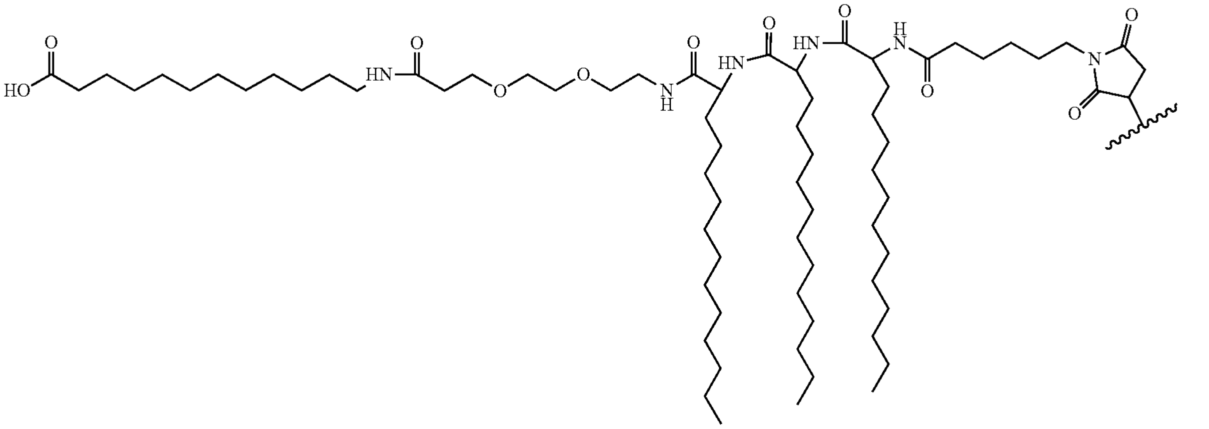

Group 4

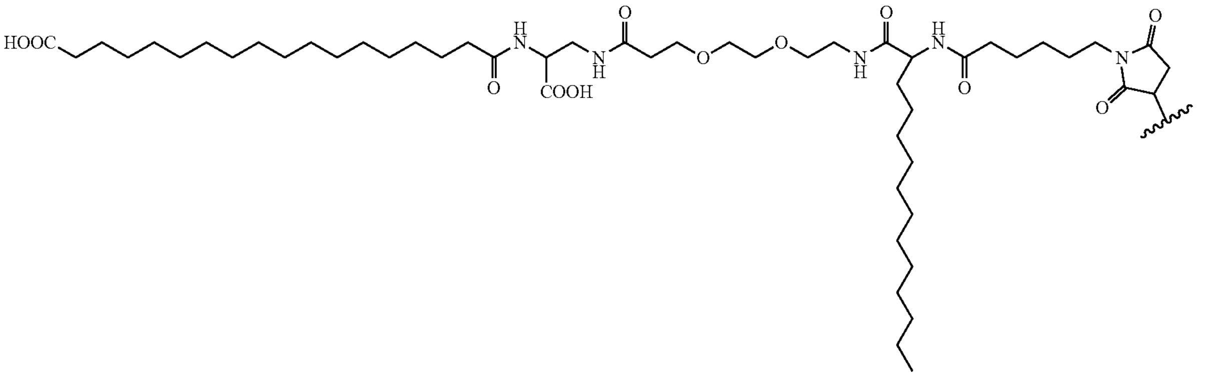

-continued
Group 5
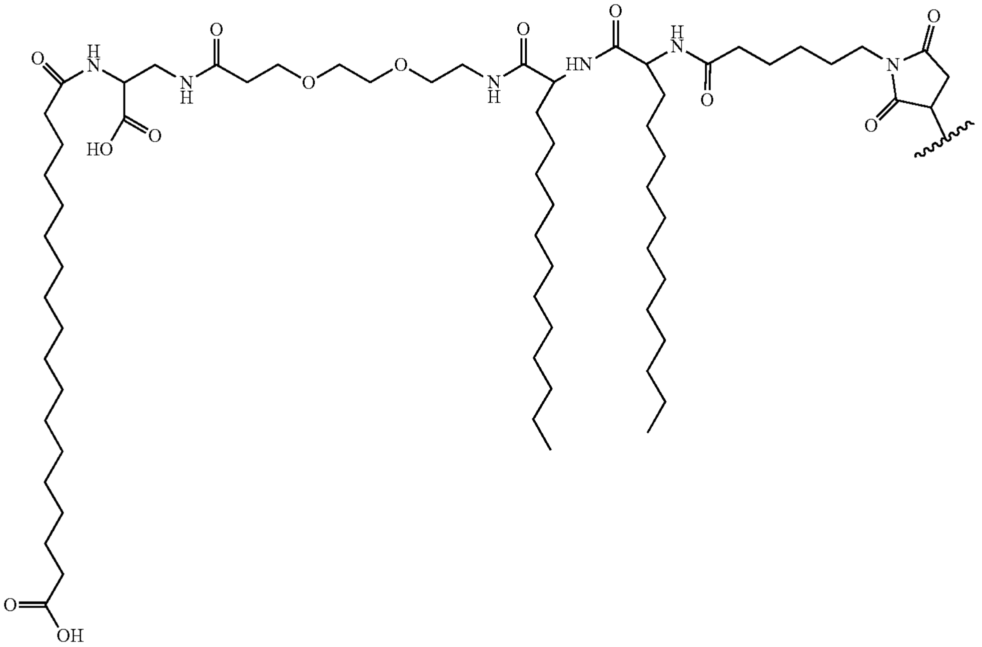
Group 6
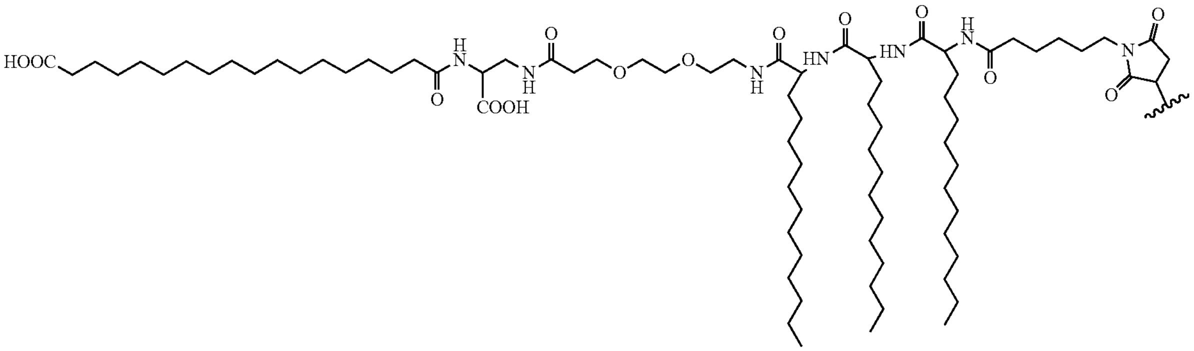
Group 7
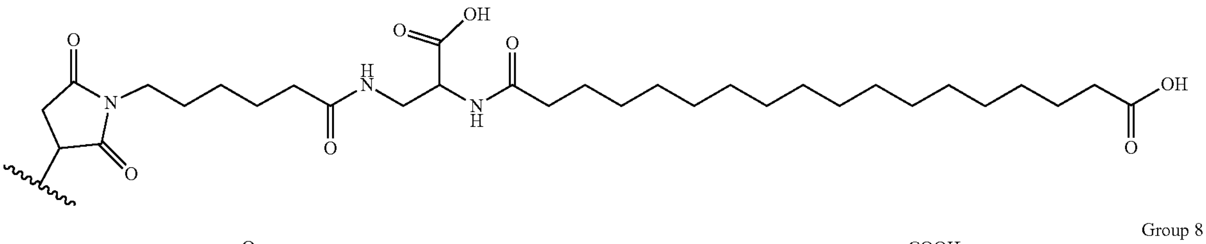
Group 8
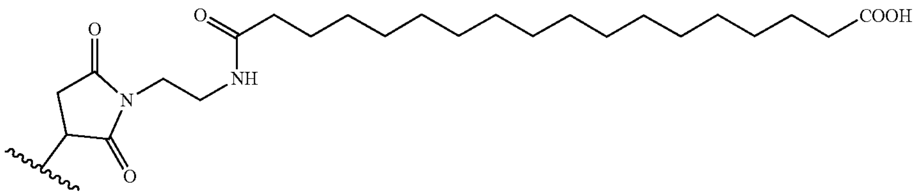

-continued

Group 9

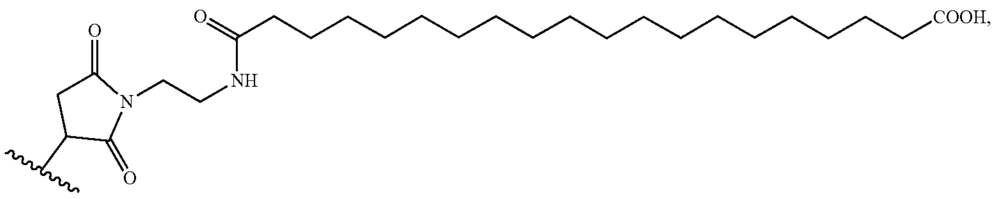

wherein ⸾ indicates the point of attachment to the RNAi agent at the C6-S group as indicated in Table 4.3.

In Groups 2-9, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 11

Average Relative huHIF-2 alpha mRNA Expression at Sacrifice (Day 8) in Example 4.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.130 | 0.150 |
| Group 2 (7.5 mg/kg Tri-Structure 2a-avb3-AD04546-40 kDa PEG) | 3 | 0.206 | 0.018 | 0.020 |
| Group 3 (7.5 mg/kg Tri-Structure 2a-avb3-AD04546-Mal-C6-C12-C12-C12-PEG2-C12 acid) | 3 | 0.381 | 0.052 | 0.060 |
| Group 4 (7.5 mg/kg Tri-Structure 2a-avb3-AD04546-Mal-C6-C12-PEG2-C18 diacid) | 3 | 0.343 | 0.028 | 0.030 |
| Group 5 (7.5 mg/kg Tri-Structure 2a-avb3-AD04546-Mal-C6-C12-C12-PEG2-C18 diacid) | 3 | 0.279 | 0.034 | 0.039 |
| Group 6 (7.5 mg/kg Tri-Structure 2a-avb3-AD04546-Mal-C6-C12-C12-C12-PEG2-C18 Diacid) | 3 | 0.454 | 0.122 | 0.167 |
| Group 7 (7.5 mg/kg Tri-Structure 2a-avb3-AD04546-Mal-$C_{18}$-diacid) | 3 | 0.306 | 0.041 | 0.048 |
| Group 8 (7.5 mg/kg Tri-Structure 2a-avb3-AD04546-Mal-$C_{18}$-acid) | 3 | 0.363 | 0.053 | 0.062 |
| Group 9 (7.5 mg/kg Tri-Structure 2a-avb3-AD04546-Mal-$C_{20}$-acid) | 3 | 0.354 | 0.036 | 0.039 |

As shown in Table 11 above, each of the HIF-2 alpha RNAi agents linked to tridentate targeting groups (Groups 2 through 9) showed substantial inhibitory activity compared to control.

Example 5. In Vivo Administration of HIF-2 Alpha RNAi Agent in ccRCC Tumor-Bearing Mice The tumor-bearing mouse model of Example 2 was used to evaluate HIF-2 alpha RNAi agents in vivo. On study day 1, mice in Groups 1 through 6 listed herein were dosed via tail vein intravenous (IV) injection with approximately 300 microliters volume of injection, according to the following dosing Groups in Table 12, below. Additionally, mice in Group 7 listed herein were dosed via subcutaneous (SQ) injection between the skin and muscle into the loose skin over the neck and shoulder area. The Groups dosed included the following:

TABLE 12

Dosing Groups of Tumor-Bearing Mice in Example 5.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-$C_{18}$-diacid, formulated in isotonic glucose | Single IV injection on day 1 |
| 3 | 7.5 mg/kg of HIF-2 alpha RNAi agent AD04546, linked at the 5' terminal end of the sense strand to a tridentate targeting group having three integrin targeting ligands of Structure 6.1-avb6, and also linked at the 3' terminal end of the sense strand to PK enhancer Mal-C18-diacid, formulated in isotonic glucose | Single IV injection on day 1 |
| 4 | 7.5 mg/kg of HIF-2 alpha RNAi agent AD04546, linked at the 5' terminal end of the sense strand to a tridentate targeting group having three integrin targeting ligands of Structure 14-avb6, and also linked at the 3' terminal end of the sense strand to PK enhancer Mal-C18-diacid, formulated in isotonic glucose | Single IV injection on day 1 |
| 6 | 7.5 mg/kg of HIF-2 alpha RNAi agent AD04545, linked at the 5' terminal end of the sense strand to a tridentate targeting group having three integrin targeting ligands of Structure 2a-avb3, formulated in isotonic glucose. | Single IV injection on day 1 |
| 7 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C18-diacid, formulated in isotonic glucose | Single SQ injection on day 1 |

In Groups 2-5 and 7, the PK enhancer having the structures indicated in previous examples for Mal-$C_{18}$-diacid was linked to the 3' terminal end of the sense strand.

In Groups 2 and 5-7, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above. In Group 3, a tridentate integrin targeting group (which included three integrin ligands having affinity for alpha-v-beta-6 of the structure of Structure 6.1-avb6) was linked to the 5' terminal end of the sense strand by coupling to the functionalized amine reactive group linker (NH2-C6), and in Group 4, a tridentate integrin targeting group (which included three integrin ligands having affinity for alpha-v-beta-6 of the structure of Structure 14-avb6) was linked to the 5' terminal end of the sense strand by coupling to the functionalized amine reactive group linker (NH2-C6). The structures for the tridentate targeting groups that include the integrin targeting ligands Structure 6.1-avb6 and Structure 14-avb6 are shown below:

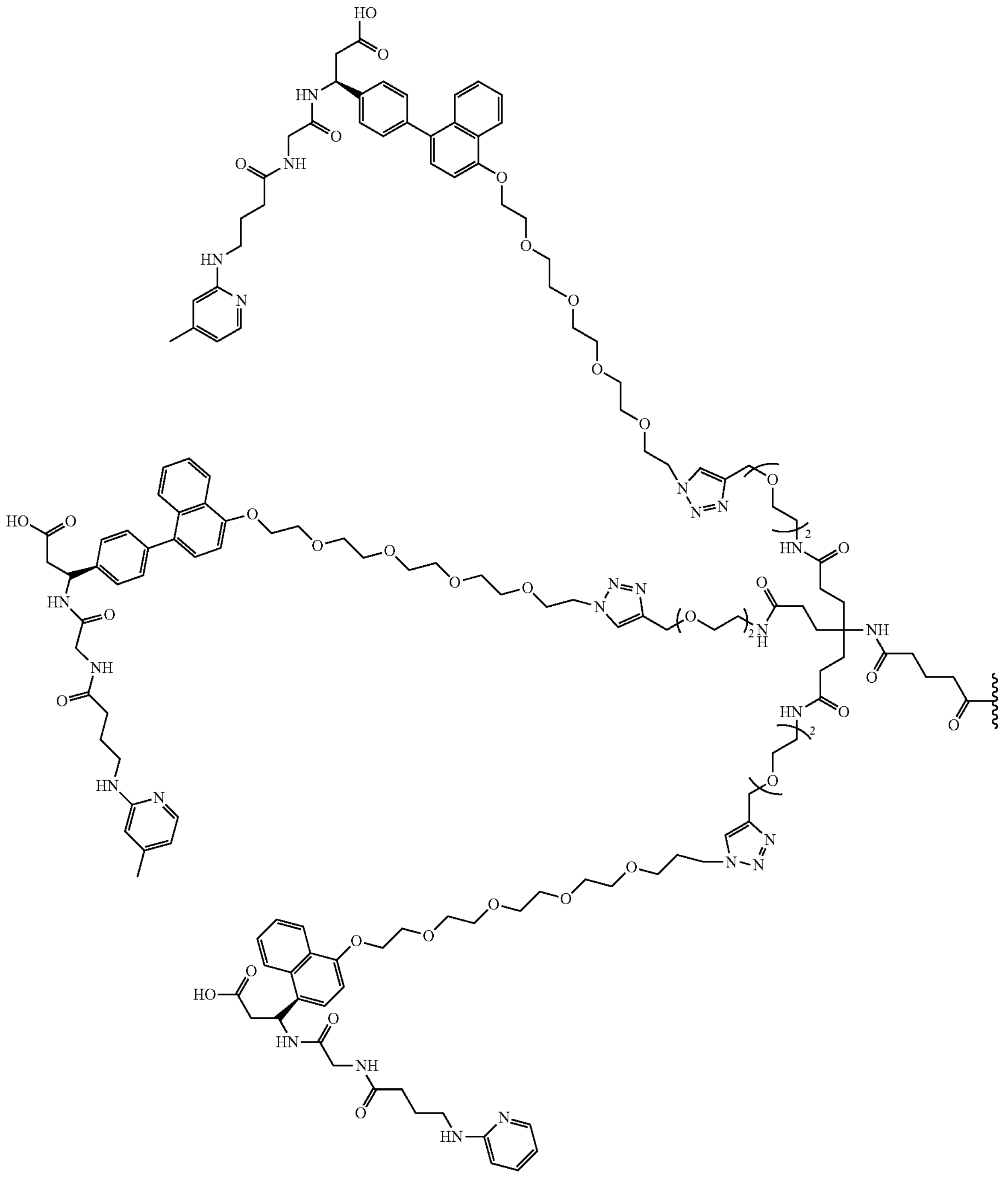

Targeting group for Structure 6.1-avb6,

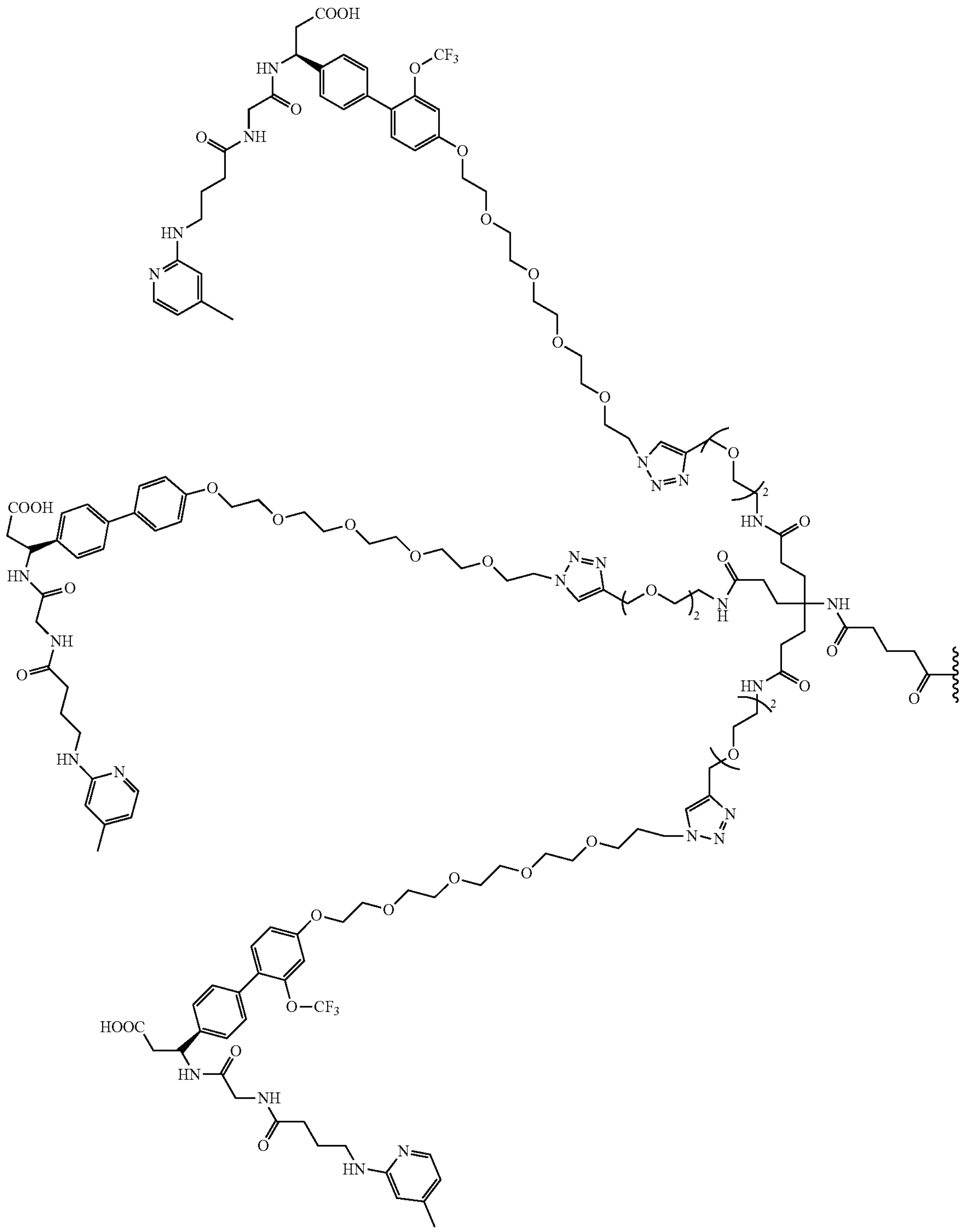

Targeting group for Structure 14-avb6, wherein ⌇ indicates the point of connection to the functionalized amine linker.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 13

| Average Relative huHIF-2 alpha mRNA Expression at Sacrifice (Day 8) in Example 5. | | | | |
|---|---|---|---|---|
| Group ID | Number of animals (n=) | Average Relative HIF-2 alpha mRNA expression | Low (error) | High (error) |
| Group 1 (isotonic glucose vehicle) | 3 | 1.000 | 0.108 | 0.122 |
| Group 2 (7.5 mg/kg Tri-Structure 2a-avb3-AD04546-Mal-C18 diacid) (IV) | 3 | 0.437 | 0.054 | 0.062 |
| Group 3 (7.5 mg/kg Tri-Structure 6.1-avb6-AD04546-Mal-C18 diacid) | 3 | 0.691 | 0.056 | 0.060 |
| Group 4 (7.5 mg/kg Tri-Structure 14-avb6-AD04546-Mal-C18 diacid) | 3 | 0.582 | 0.170 | 0.241 |
| Group 6 (7.5 mg/kg Tri-Structure 2a-avb3-AD04545) | 3 | 0.751 | 0.125 | 0.150 |
| Group 7 (7.5 mg/kg Tri-Structure 2a-avb3-AD04546-Mal-C18 diacid) (SQ) | 3 | 0.427 | 0.035 | 0.038 |

As shown in Table 13 above, the preference for linking one or more targeting ligands and a PK enhancer showed improved potency in silencing HIF-2 alpha expression. (See, for example, Group 6 (without PK enhancer) achieving only approximately 25% knockdown (0.751). Further, the data shows a preference for targeting groups that include targeting ligands that have affinity for integrin alpha-v-beta-3, compared to targeting ligands having affinity for alpha-v-beta-6. (Compare Group 3 (approximately 31% knockdown (0.691) using alpha-v-beta-6 ligand) and Group 4 (approximately 42% knockdown (0.582) using alpha-v-beta-6 ligand) with Group 2 (approximately 56% knockdown (0.437) using alpha-v-beta-3 ligand) and Group 5 (approximately 58% knockdown (0.413) using alpha-v-beta-3 ligand). Additionally, as shown in Groups 7 and 2, comparable efficacy can be achieved for dosing both IV and SQ using the PK enhancer of C18-diacid (C18diacid).

Example 6. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 14

| Dosing Groups of Tumor-Bearing Mice in Example 6. | | |
|---|---|---|
| Group | RNAi Agent and Dose | Dosing Regimen |
| 1 | Isotonic glucose (D5W) (no RNAi agent) | Single IV injection on day 1 |
| 2 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-diacid, formulated in isotonic glucose. | Single IV injection on day 1 |
| 3 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C18-triacid, formulated in isotonic glucose. | Single IV injection on day 1 |
| 4 | 7.5 mg/kg of HIF-2 alpha RNAi agent AD05786, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] When viewing 5' → 3' on the sense strand of AD05786, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, 16, and 20 of the sense strand). | Single IV injection on day 1 |
| 5 | 7.5 mg/kg of HIF-2 alpha RNAi agent AD05915, linked at the 5' terminal end of the sense strand to a tridentate targeting group having three integrin targeting ligands of Structure 2a-avb3, having a Azide-C18-Diacid PK enhancer linked internally at the 2' position of nucleotide 6 (3'→ 5') from the first nucleotide that forms a base pair with the antisense strand[(ii)], and further linked at the 3' terminal | Single IV injection on day 1 |

TABLE 14-continued

| Dosing Groups of Tumor-Bearing Mice in Example 6. | | |
|---|---|---|
| Group | RNAi Agent and Dose | Dosing Regimen |
| | end of the sense strand to PK enhancer Mal-C18-diacid, formulated in isotonic glucose. (ii) When viewing 5' → 3' on the sense strand of AD05915, the C18-diacid PK enhancer is linked to the 2'-O-propargyl nucleotide (represented by aAlk in the modified sense strand sequence), which when viewed 5' → 3' on the sense strand sequence is at nucleotide 16 of the sense strand). | |
| 6 | 7.5 mg/kg of HIF-2 alpha RNAi agent AD05916, linked at the 5' terminal end of the sense strand to a tridentate targeting group having three integrin targeting ligands of Structure 2a-avb3, having a Azide-C18-Diacid PK enhancer linked internally at the 2' position of nucleotide 15 (3'→ 5') from the first nucleotide that forms a base pair with the antisense strand(iii), and further linked at the 3' terminal end of the sense strand to PK enhancer Mal-C18-diacid, formulated in isotonic glucose. (iii) When viewing 5' → 3' on the sense strand of AD05916, the C18-diacid PK enhancer is linked to the 2'-O-propargyl nucleotide (represented by aAlk in the modified sense strand sequence for AD005916), which when viewed 5' → 3' on the sense strand sequence is at nucleotide 7 of the sense strand). | Single IV injection on day 1 |
| 7 | 7.5 mg/kg of HIF-2 alpha RNAi agent AD05917, linked at the 5' terminal end of the sense strand to a tridentate targeting group having three integrin targeting ligands of Structure 2a-avb3, having a Azide-C18-Diacid PK enhancer linked internally at the 2' position of each of nucleotides 6 and 15 (3'→ 5') from the first nucleotide that forms a base pair with the antisense strand(iv), and further linked at the 3' terminal end of the sense strand to PK enhancer Mal-C18-diacid, formulated in isotonic glucose. (iv) When viewing 5' → 3' on the sense strand of AD05917, the C18-diacid PK enhancers are linked to the 2'-O-propargyl nucleotides (represented by aAlk in the modified sense strand sequence), which when viewed 5' → 3' on the sense strand sequence are at nucleotides 7 and 16 of the sense strand). | Single IV injection on day 1 |
| 10 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C17-vinyl-PO3, formulated in isotonic glucose. | Single IV injection on day 1 |
| 11 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal-C17-fluoro-PO3, formulated in isotonic glucose. | Single IV injection on day 1 |

In Groups 2, 4-7, the PK enhancer having the structures indicated in previous examples for Mal-$C_{18}$-diacid was linked to the 3' terminal end of the sense strand. Group 3 included the PK enhancer linked to 3' terminal end of the sense strand of the following structure:

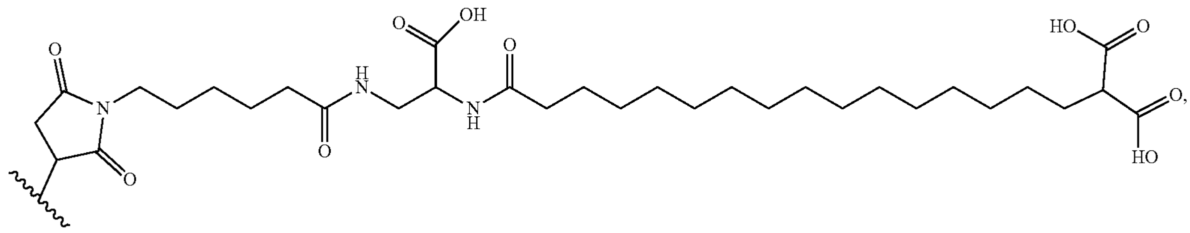 [SMILES: *C1CC(=O)N(CCCCCC(=O)NCC(NC(=O)CCCCCCCCCCCCCCCC(C(=O)O)C(=O)O)C(=O)O)C1=O]
, wherein indicates the point of attachment to the RNAi agent at the C6-S group as indicated in Table 4.3.

Group 10 included the PK enhancer linked to 3' terminal end of the sense strand of the following structure:

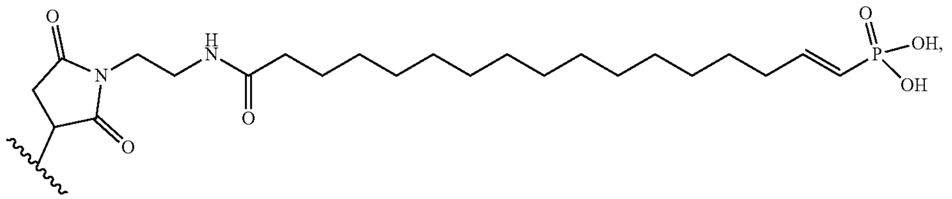 [SMILES: *C1CC(=O)N(CCNC(=O)CCCCCCCCCCCCCC/C=C/P(=O)(O)O)C1=O]

wherein indicates the point of attachment to the RNAi agent at the C6-S group as indicated in Table 4.3.

Group 11 included the PK enhancer linked to 3' terminal end of the sense strand of the following structure:

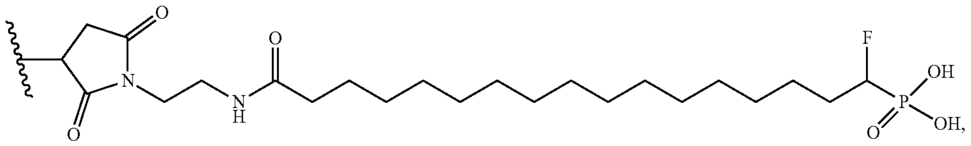 [SMILES: *C1CC(=O)N(CCNC(=O)CCCCCCCCCCCCCCCC(F)P(=O)(O)O)C1=O]

wherein indicates the point of attachment to the RNAi agent at the C6-S group as indicated in Table 4.3.

In Groups 5-7, PK enhancers were conjugated to internal nucleotides. Nucleotides as indicated included a 2'-O-propargyl group, and azide-containing PK enhancers (C18-di-acid-$N_3$) were added to form a triazole. Groups 5-7 included a PK enhancer of the structure:

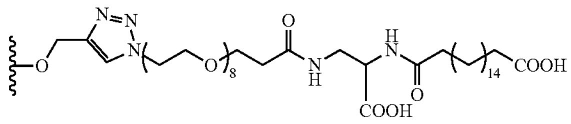

wherein indicates the point of attachment to the RNAi agent at the 2' position of the indicated nucleotide.

In Groups 2-11, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 15

Average Relative huHIF-2 alpha mRNA Expression at Sacrifice (Day 8) in Example 6.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.148 | 0.173 |
| Group 2 (7.5 mg/kg Tri-Structure 2a-avb3-AD04546-C18 diacid)) | 3 | 0.345 | 0.056 | 0.067 |
| Group 3 (7.5 mg/kg Tri-Structure 2a-avb3- AD04546-C18 triacid) | 3 | 0.302 | 0.085 | 0.118 |
| Group 4 (7.5 mg/kg Tri-Structure 2a-avb3-AD05786 (Int Structure 2a-avb3)$_4$-C18-diacid) | 3 | 0.228 | 0.050 | 0.065 |
| Group 5 (7.5 mg/kg Tri-Structure 2a-avb3-AD05915 (Int C18-diacid)-C18-diacid) | 3 | 0.414 | 0.120 | 0.169 |

TABLE 15-continued

Average Relative huHIF-2 alpha mRNA Expression at Sacrifice (Day 8) in Example 6.

| Group ID | Number of animals (n=) | Average Relative HIF-2 alpha mRNA expression | Low (error) | High (error) |
|---|---|---|---|---|
| Group 6 (7.5 mg/kg Tri-Structure 2a-avb3-AD05916 (Int C18-diacid)-C18-diacid) | 3 | 0.524 | 0.091 | 0.111 |
| Group 7 (7.5 mg/kg Tri-Structure 2a-avb3-AD05917 (Int C18-diacid)-C18-diacid) | 3 | 0.391 | 0.124 | 0.182 |
| Group 10 (7.5 mg/kg Tri-Structure 11-avb3-AD04546-C17-vinyl-PO3) | 3 | 0.318 | 0.082 | 0.111 |
| Group 11 (7.5 mg/kg Tri-Structure 11-avb3-AD04546-C17-fluoro-PO3) | 3 | 0.388 | 0.087 | 0.112 |

As shown in Table 15 above, each of the HIF-2 alpha RNAi agents linked to tridentate targeting groups (Groups 2 through 11) showed substantial inhibitory activity compared to control.

Example 7. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, which included the following dosing Groups:

TABLE 16

Dosing Groups of Tumor-Bearing Mice in Example 7.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-diacid, formulated in isotonic glucose. | Single IV injection on day 1 |
| 3 | 7.5 mg/kg of HIF-2 alpha RNAi agent AD05786, having a Structure 2a-avb3 targeting ligand linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose. | Single IV injection on day 1 |
| 4 | 7.5 mg/kg of HIF-2 alpha RNAi agent AD05786, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] See Example 6. | Single IV injection on day 1 |
| 6 | 7.5 mg/kg of HIF-2 alpha RNAi agent AD04546, linked at the 5' terminal end of the sense strand to a tridentate targeting group having three integrin targeting ligands of Structure 2a-avb3, and further linked at the 3' terminal end of the sense strand to PK enhancer Mal-C18-diacid-PO3, formulated in isotonic glucose. | Single IV injection on day 1 |
| 7 | 7.5 mg/kg of HIF-2 alpha RNAi agent AD04546, linked at the 5' terminal end of the sense strand to a tridentate targeting group having three integrin targeting ligands of Structure 2a-avb3, and further linked at the 3' terminal end of the sense strand to PK enhancer Mal-C22-diacid, formulated in isotonic glucose. | Single IV injection on day 1 |

TABLE 16-continued

| Dosing Groups of Tumor-Bearing Mice in Example 7. | | |
|---|---|---|
| Group | RNAi Agent and Dose | Dosing Regimen |
| 8 | 7.5 mg/kg of HIF-2 alpha RNAi agent AD04546, linked at the 5' terminal end of the sense strand to a tridentate targeting group having three integrin targeting ligands of Structure 2a-avb3, and further linked at the 3' terminal end of the sense strand to PK enhancer Mal-C18-triacid, formulated in isotonic glucose. | Single IV injection on day 1 |
| 9 | 7.5 mg/kg of HIF-2 alpha RNAi agent AD04546, linked at the 5' terminal end of the sense strand to a tridentate targeting group having three integrin targeting ligands of Structure 10-avb6, and further linked at the 3' terminal end of the sense strand to PK enhancer Mal-C18-diacid, formulated in isotonic glucose. | Single IV injection on day 1 |
| 10 | 7.5 mg/kg of HIF-2 alpha RNAi agent AD04546, linked at the 5' terminal end of the sense strand to a tridentate targeting group having three integrin targeting ligands of Structure 26-avb6, and further linked at the 3' terminal end of the sense strand to PK enhancer Mal-C18-diacid, formulated in isotonic glucose. | Single IV injection on day 1 |

In Groups 2-4, 9 and 10, the PK enhancer having the structures indicated in previous examples for Mal-$C_{18}$-diacid was linked to the 3' terminal end of the sense strand.

Group 6 includes a PK enhancer on the 3' end of the sense strand having the structure:

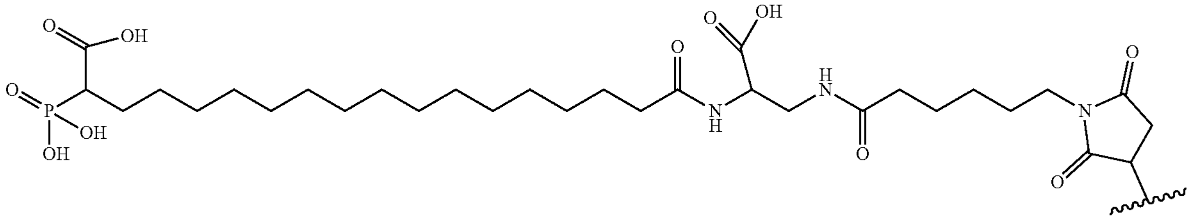 [SMILES: *C1CC(=O)N(CCCCCC(=O)NCC(NC(=O)CCCCCCCCCCCCCCCC(C(=O)O)P(=O)(O)O)C(=O)O)C1=O]

wherein indicates the point of attachment to the RNAi agent at the C6-S group as indicated in Table 4.3.

Group 7 includes a PK enhancer on the 3' end of the sense strand having the structure:

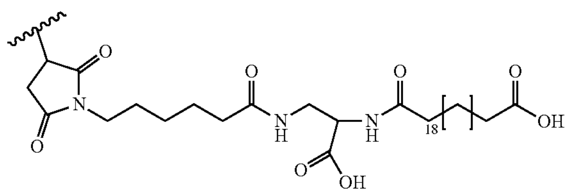

wherein indicates the point of attachment to the RNAi agent at the C6-S group as indicated in Table 4.3.

Group 8 includes a PK enhancer formed by the Michael addition of Mal-Cis-triacid to the 3' end of the sense strand comprising a disulfide, as shown in Example 6.

In Groups 2, 4-8, and 10, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above. Group 9 included the tridentate integrin targeting group (which included three integrin ligands having affinity for alpha-v-beta-6 of the structure of Structure 10-avb6) linked to the 5' terminal end of the sense strand by coupling to the functionalized amine reactive group linker (NH2-C6), the structure of which is shown below:

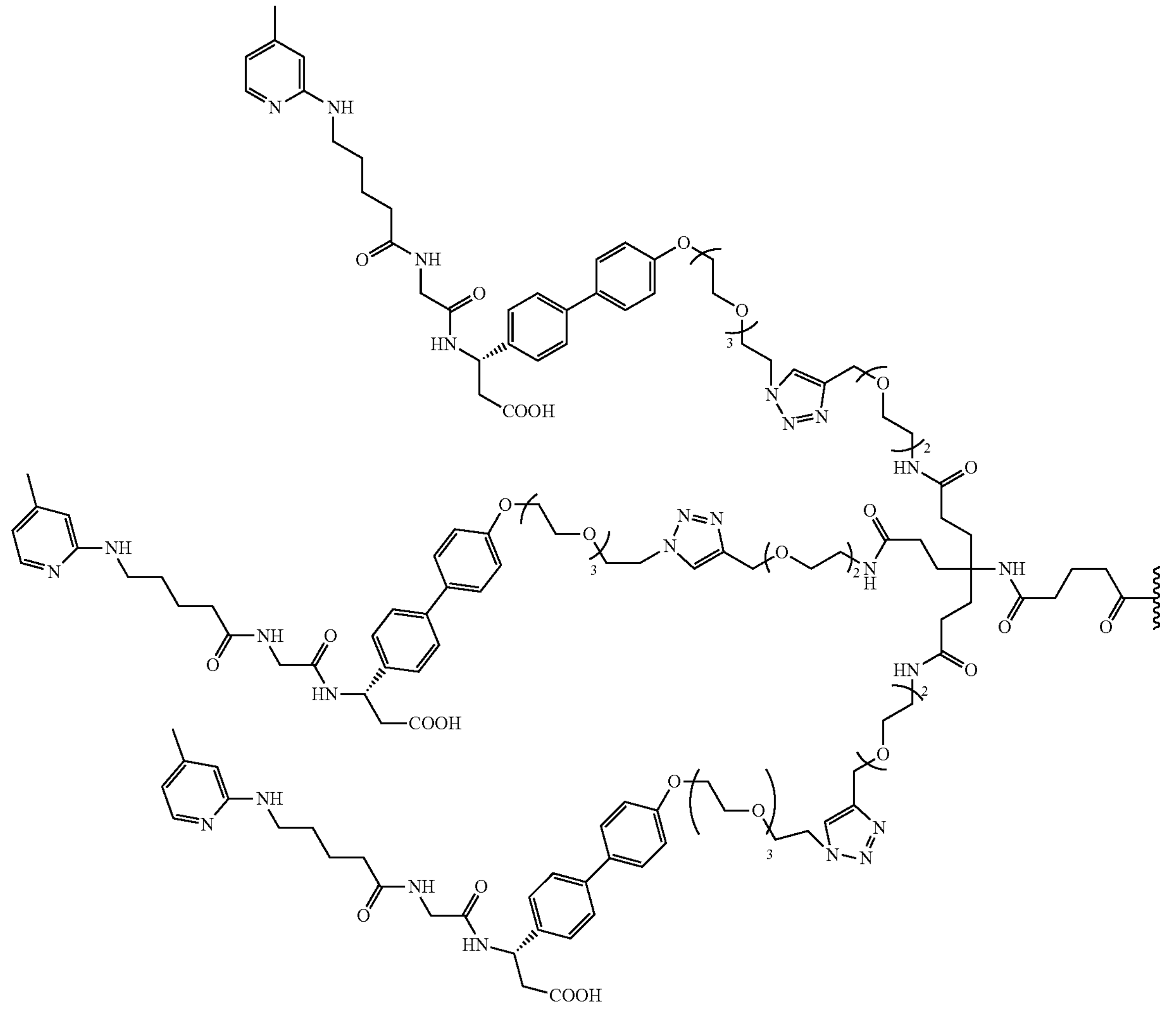

Group 10 included the tridentate integrin targeting group (which included three integrin ligands having affinity for alpha-v-beta-6 of the structure of Structure 26-avb6) linked to the 5' terminal end of the sense strand by coupling to the functionalized amine reactive group linker (NH2-C6), the structure of which is shown below:

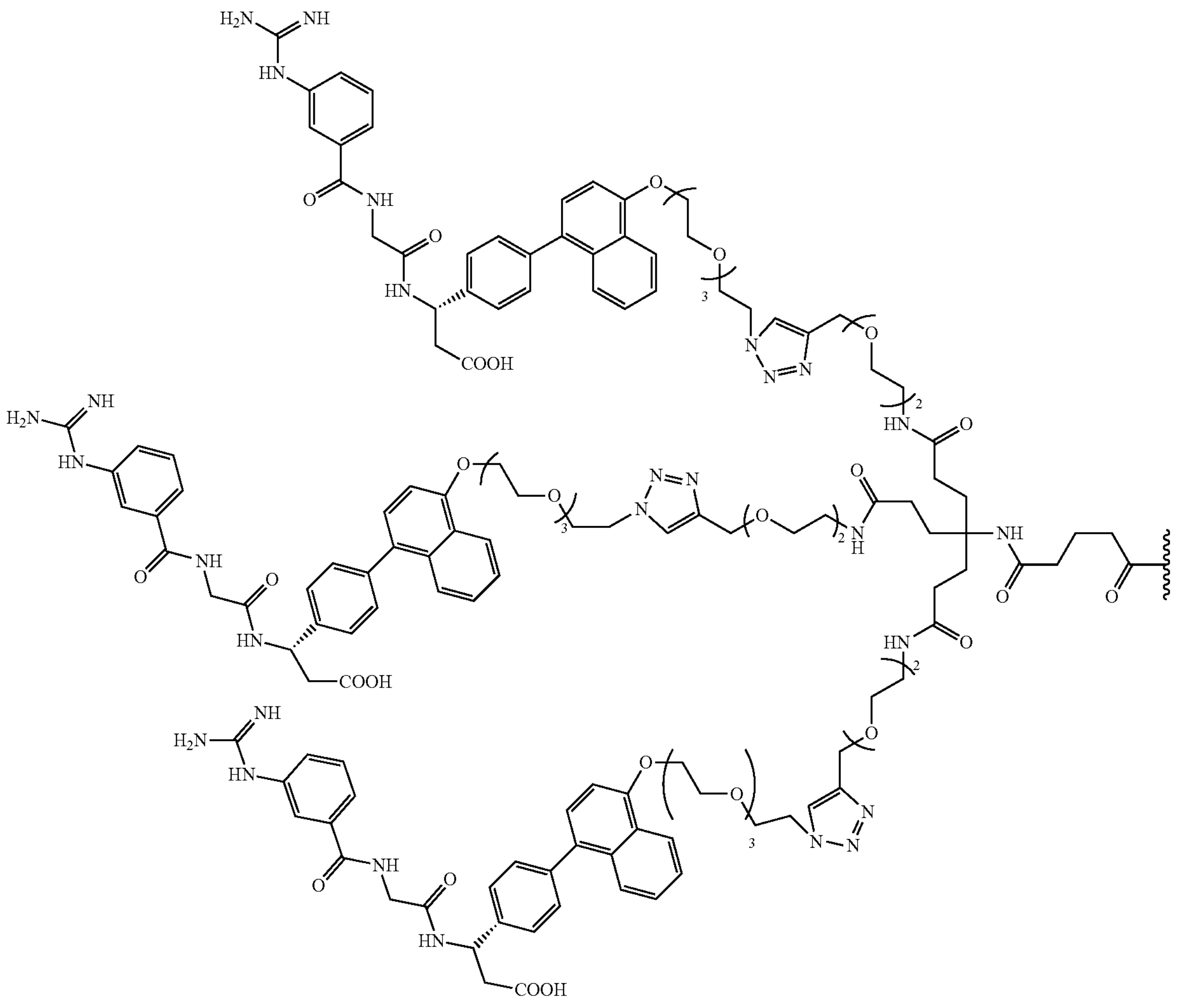

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 17

Average Relative huHIF-2 alpha mRNA Expression at Sacrifice (Day 8) in Example 7.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.119 | 0.135 |
| Group 2 (7.5 mg/kg Tri-Structure 2a-avb3-AD04546-C18 diacid) | 3 | 0.433 | 0.085 | 0.106 |

TABLE 17-continued

Average Relative huHIF-2 alpha mRNA Expression at Sacrifice (Day 8) in Example 7.

| Group ID | Number of animals (n=) | Average Relative HIF-2 alpha mRNA expression | Low (error) | High (error) |
|---|---|---|---|---|
| Group 3 (7.5 mg/kg AD05786 (Int-Structure 2a-avb3)4-C18 diacid) | 3 | 0.336 | 0.059 | 0.072 |
| Group 4 (7.5 mg/kg Tri-Structure 2a-avb3-AD05786 (Int-Structure 2a-avb3)4-C18 diacid) | 3 | 0.224 | 0.028 | 0.032 |
| Group 6 (7.5 mg/kg Tri-Structure 2a-avb3-AD04546-Mal-C18 diacid-$PO_3$) | 3 | 0.412 | 0.085 | 0.107 |
| Group 7 (7.5 mg/kg Tri-Structure 2a-avb3-AD04546-Mal-C22-diacid) | 3 | 0.595 | 0.067 | 0.075 |
| Group 8 (7.5 mg/kg Tri-Structure 2a-avb3-AD04546-Mal-C18-triacid) | 3 | 0.300 | 0.041 | 0.048 |
| Group 9 (7.5 mg/kg Tri-Structure 10-avb6-AD04546-Mal-C18-diacid) | 3 | 0.607 | 0.072 | 0.082 |
| Group 10 (7.5 mg/kg Tri-Structure 26-avb6-AD04546-Mal-C18-diacid) | 3 | 0.819 | 0.179 | 0.229 |

As shown in Table 17 above, Group 4, which included four (4) internally placed Structure 2a-avb3 ligands on the sense strand of the HIF-2 alphaRNAi agent, exhibited approximately 78% knockdown of huHIF-2 alpha mRNA (0.228).

Example 8. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 18

Dosing Groups of Tumor-Bearing Mice in Example 8.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD05930, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose. <br>[(i)] When viewing 5' → 3' on the sense strand of AD05930, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, 16, and 20 of the sense strand). | Single IV injection on day 1 |
| 3 | 7.5 mg/kg of HIF-2 alpha RNAi agent AD05930, linked at the 5' terminal end of the sense strand to a single integrin targeting ligand having the structure of Structure 2a-avb3 and also with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose. <br>[(i)] When viewing 5' → 3' on the sense strand of AD05930, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, 16, and 20 of the sense strand). | Single IV injection on day 1 |

TABLE 18-continued

Dosing Groups of Tumor-Bearing Mice in Example 8.

| Group | RNAi Agent and Dose | Dosing Regimen |
| --- | --- | --- |
| 4 | 7.5 mg/kg of HIF-2 alpha RNAi agent AD05930, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-triacid, formulated in isotonic glucose.<br>[(i)] When viewing 5' → 3' on the sense strand of AD05930, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, 16, and 20 of the sense strand). | Single IV injection on day 1 |
| 5 | 7.5 mg/kg of HIF-2 alpha RNAi agent AD05932, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 3, 5, 6, 15, 16, 19, and 20 (3'→ 5') from the first nucleotide that forms a base pair with the antisense strand[(ii)], and further linked at the 3' terminal end of the sense strand to PK enhancer Mal-C18-diacid, formulated in isotonic glucose.<br>[(ii)] When viewing 5' → 3' on the sense strand of AD05932, the Structure 2a-avb3 targeting ligands are linked to the 2'-O-propargyl nucleotides (represented by aAlk and uAlk in the modified sense strand sequence), which when viewed 5' → 3' on the sense strand sequence are at nucleotides 2, 3, 6, 7, 16, 17, 19, and 20 of the sense strand). | Single IV injection on day 1 |
| 6 | 7.5 mg/kg of HIF-2 alpha RNAi agent AD05786, with an integrin targeting ligand of Structure 2a-avb3 linked internally at the 2' position of each of nucleotides 2, 6, 15, and 19 (3'→ 5') from the first nucleotide that forms a base pair with the antisense strand[(iii)], and further linked at the 3' terminal end of the sense strand to PK enhancer Mal-C18-diacid, formulated in isotonic glucose.<br>[(iii)] See Example 6. | Single IV injection on day 1 |
| 7 | 7.5 mg/kg of HIF-2 alpha RNAi agent AD05934, linked at the 5' terminal end of the sense strand to PK enhancer Mal-C18-diacid, with an integrin targeting ligand of Structure 2a-avb3 linked internally at the 2' position of each of nucleotides 2, 6, 15, and 19 (3'→ 5') from the first nucleotide that forms a base pair with the antisense strand[(iii)], and further linked at the 3' terminal end of the sense strand to PK enhancer Mal-C18-diacid, formulated in isotonic glucose.<br>[(iii)] When viewing 5' → 3' on the sense strand of AD05934, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, 16, and 20 of the sense strand). | Single IV injection on day 1 |
| 8 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-diacid, formulated in isotonic glucose. | Single IV injection on day 1 |
| 9 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-triacid, formulated in isotonic glucose. | Single IV injection on day 1 |
| 10 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-diacid-$PO_3$, formulated in isotonic glucose. | Single IV injection on day 1 |
| 11 | 7.5 mg/kg of HIF-2 alpha RNAi agent AD04546, linked at the 5' terminal end of the sense strand to a tridentate targeting group having three integrin targeting ligands of Structure 2a-avb3, and also linked at the 3' terminal end of the sense strand to PK enhancer Mal- C18-methyl-triacid, formulated in isotonic glucose. | Single IV injection on day 1 |

In Groups 2, 3 and 5-8, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction. Groups 4 and 9 included a PK enhancer having the structure indicated in Example 6. Group 10 included a PK enhancer having the structure indicated in Example 7. Group 11 includes a PK enhancer on the 3' end of the sense strand having the structure:

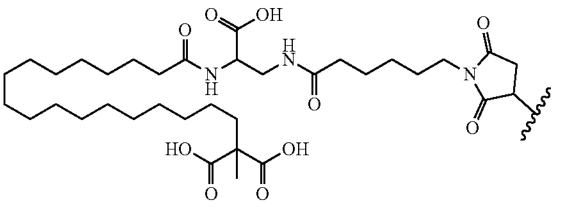 [SMILES: *C1CC(=O)N(CCCCCC(=O)NCC(NC(=O)CCCCCCCCCCCCCCCCCC(C)(C(=O)O)C(=O)O)C(=O)O)C1=O]

wherein  indicates the point of attachment to the RNAi agent at the C6-S group as indicated in Table 4.3.

In Groups 2, 4-5, and 8-11, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above. In Group 2, a single Structure 2a-avb3 targeting ligand was linked to the 5' terminal end of the sense strand by coupling to the functionalized amine reactive group linker (NH2-C6). In Group 7, PK enhancer C18-diacid was linked to the (C6-SS-C6) disulfide linker located on the 5' terminal end of the sense strand as well as the to the 3' terminal end of the sense strand.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 19

Average Relative huHIF-2 alpha mRNA Expression at Sacrifice (Day 8) in Example 8.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.208 | 0.263 |
| Group 2 (7.5 mg/kg Tri-Structure 2a-avb3-AD05930-(Int Structure 2a-avb3)$_4$-Mal-C18 diacid) | 3 | 0.183 | 0.023 | 0.026 |
| Group 3 (7.5 mg/kg Structure 2a-avb3-AD05930-(Int Structure 2a-avb3)$_4$-Mal-C18-diacid) | 3 | 0.311 | 0.042 | 0.049 |
| Group 4 (7.5 mg/kg Tri-Structure 2a-avb3-AD05930-(Int Structure 2a-avb3)$_4$-Mal-C18-triacid) | 3 | 0.209 | 0.043 | 0.054 |
| Group 5 (7.5 mg/kg Tri-Structure 2a-avb3-AD05932-(Int Structure 2a-avb3)$_8$-Mal-C18-diacid) | 3 | 0.136 | 0.014 | 0.016 |
| Group 6 (7.5 mg/kg AD05786 (Int Structure 2a-avb3)-Mal-C18-diacid) | 3 | 0.488 | 0.055 | 0.062 |
| Group 7 (7.5 mg/kg C18-diacid-AD05934 (Int Structure 2a-avb3)$_4$-Mal-C18-diacid) | 3 | 0.314 | 0.028 | 0.031 |
| Group 8 (7.5 mg/kg Tri-Structure 2a-avb3-AD04546-Mal-C18-diacid) | 3 | 0.516 | 0.060 | 0.068 |
| Group 9 (7.5 mg/kg Tri-Structure 2a-avb3-AD04546-Mal-C18-triacid) | 3 | 0.541 | 0.120 | 0.155 |
| Group 10 (7.5 mg/kg Tri-Structure 2a-avb3-AD04546-Mal-C18-diacid-PO3) | 3 | 0.477 | 0.058 | 0.067 |
| Group 11 (7.5 mg/kg Tri-Structure 2a-avb3-AD04546-Mal-C18-methyl-triacid) | 3 | 0.495 | 0.042 | 0.046 |

As shown in Table 19 above, inclusion of internal targeting ligand located on the sense strand of the HIF-2 alpha RNAi agents shows additional improvement in knockdown. (See, for example, Group 2 (four (4) internally positioned targeting ligands showing approximately 82% knockdown (0.183), and Group 8 (with no internally positioned targeting ligands showing approximately 49% knockdown (0.516).

Example 9. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 20

Dosing Groups of Tumor-Bearing Mice in Example 9.

| Group | RNAi Agent and Dose | Dosing Regimen |
|---|---|---|
| 1 | Isotonic glucose (D5W) (no RNAi agent) | Single IV injection on day 1 |
| 2 | 7.5 mg/kg of HIF-2 alpha RNAi agent AD05930, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[i], and further linked at the 3' terminal end of the sense strand to PK enhancer Mal-C18-diacid, formulated in isotonic glucose. [i] See Example 8. | Single IV injection on day 1 |
| 3 | 7.5 mg/kg of HIF-2 alpha RNAi agent AD05954, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, and 15 (3'→ 5') from the first nucleotide that forms a base pair with the antisense strand[ii], and further linked at the 3' terminal end of the sense strand to PK enhancer Mal-C18-diacid, formulated in isotonic glucose. [ii] When viewing 5' → 3' on the sense strand of AD05954, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, and 16 of the sense strand). | Single IV injection on day 1 |
| 4 | 7.5 mg/kg of HIF-2 alpha RNAi agent AD05955, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 15, and 19 (3'→ 5') from the first nucleotide that forms a base pair with the antisense strand[iii], and further linked at the 3' terminal end of the sense strand to PK enhancer Mal-C18-diacid, formulated in isotonic glucose. [iii] When viewing 5' → 3' on the sense strand of AD05955, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 7, and 20 of the sense strand). | Single IV injection on day 1 |
| 5 | 7.5 mg/kg of HIF-2 alpha RNAi agent AD05956, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, and 19 (3'→ 5') from the first nucleotide that forms a base pair with the antisense strand[iv], and further linked at the 3' terminal end of the sense strand to PK enhancer Mal-C18-diacid, formulated in isotonic glucose. [iv] When viewing 5' → 3' on the sense strand of AD05956, the Structure 2a-avb3 targeting ligands are linked to the 2'-O-propargyl nucleotides (represented by aAlk in the modified sense strand sequence), which when viewed 5' → 3' on the sense strand sequence are at nucleotides 3, 16, and 20 of the sense strand). | Single IV injection on day 1 |

TABLE 20-continued

Dosing Groups of Tumor-Bearing Mice in Example 9.

| Group | RNAi Agent and Dose | Dosing Regimen |
|---|---|---|
| 6 | 7.5 mg/kg of HIF-2 alpha RNAi agent AD05957, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 6, 15, and 19 (3'→ 5') from the first nucleotide that forms a base pair with the antisense strand[v], and further linked at the 3' terminal end of the sense strand to PK enhancer Mal-C18-diacid, formulated in isotonic glucose.<br>[v] When viewing 5' → 3' on the sense strand of AD05957, the Structure 2a-avb3 targeting ligands are linked to the 2'-O-propargyl nucleotides (represented by aAlk in the modified sense strand sequence), which when viewed 5' → 3' on the sense strand sequence are at nucleotides 7, 16, and 20 of the sense strand). | Single IV injection on day 1 |
| 7 | 7.5 mg/kg of HIF-2 alpha RNAi agent AD05958, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 15 and 19 (3'→ 5') from the first nucleotide that forms a base pair with the antisense strand[vi], and further linked at the 3' terminal end of the sense strand to PK enhancer Mal-C18-diacid, formulated in isotonic glucose.<br>[vii] when viewing 5' → 3' on the sense strand of AD05958, the Structure 2a-avb3 targeting ligands are linked to the 2'-O-propargyl nucleotides (represented by aAlk in the modified sense strand sequence), which when viewed 5' → 3' on the sense strand sequence are at nucleotides 16 and 20 of the sense strand). | Single IV injection on day 1 |
| 8 | 7.5 mg/kg of HIF-2 alpha RNAi agent AD05959, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 6 (3'→ 5') from the first nucleotide that forms a base pair with the antisense strand[vii], and further linked at the 3' terminal end of the sense strand to PK enhancer Mal-C18-diacid, formulated in isotonic glucose.<br>[vii] When viewing 5' → 3' on the sense strand of AD05959, the Structure 2a-avb3 targeting ligands are linked to the 2'-O-propargyl nucleotides (represented by aAlk in the modified sense strand sequence), which when viewed 5' → 3' on the sense strand sequence are at nucleotides 3 and 7 of the sense strand). | Single IV injection on day 1 |
| 9 | 7.5 mg/kg of HIF-2 alpha RNAi agent AD05960, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 19 (3'→ 5') from the first nucleotide that forms a base pair with the antisense strand[viii], and further linked at the 3' terminal end of the sense strand to PK enhancer Mal-C18-diacid, formulated in isotonic glucose.<br>[viii] When viewing 5' → 3' on the sense strand of AD05960, the Structure 2a-avb3 targeting ligands are linked to the 2'-O-propargyl nucleotides (represented by aAlk in the modified sense strand sequence), which when viewed 5' → 3' on the sense strand sequence are at nucleotides 3 and 20 of the sense strand). | Single IV injection on day 1 |
| 10 | 7.5 mg/kg of HIF-2 alpha RNAi agent AD05961, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 6 and 19 (3'→ 5') from the first nucleotide that forms a base pair with the antisense strand[ix], and further linked at the 3' terminal end of the sense strand to PK enhancer Mal-C18-diacid, formulated in isotonic glucose.<br>[ix] When viewing 5' → 3' on the sense strand of AD05961, the Structure 2a-avb3 targeting ligands are linked to the 2'-O-propargyl nucleotides (represented by aAlk in the modified sense strand sequence), which when viewed 5' → 3' on the sense strand sequence are at nucleotides 7 and 20 of the sense strand). | Single IV injection on day 1 |
| 11 | 7.5 mg/kg of HIF-2 alpha RNAi agent AD05962, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 15 (3'→ 5') from the first nucleotide that forms a base pair with the antisense strand[x], and further linked at the 3' terminal end of the sense strand to PK enhancer Mal-C18-diacid, formulated in isotonic glucose.<br>[x] When viewing 5' → 3' on the sense strand of AD05962, the Structure 2a-avb3 targeting ligands are linked to the 2'-O-propargyl | Single IV injection on day 1 |

TABLE 20-continued

Dosing Groups of Tumor-Bearing Mice in Example 9.

| Group | RNAi Agent and Dose | Dosing Regimen |
|---|---|---|
| | nucleotides (represented by aAlk in the modified sense strand sequence), which when viewed 5' → 3' on the sense strand sequence are at nucleotides 3 and 16 of the sense strand). | |
| 12 | 7.5 mg/kg of HIF-2 alpha RNAi agent AD05917, linked at the 5' terminal end of the sense strand to a tridentate targeting group having three integrin targeting ligands of Structure 2a-avb3, having a C18-diacid PK enhancer linked internally at the 2' position of each of nucleotides 6 and 15 (3'→ 5') from the first nucleotide that forms a base pair with the antisense strand[(xi)], and further linked at the 3' terminal end of the sense strand to PK enhancer Mal-C18-diacid, formulated in isotonic glucose. [(xi)] See Example 6. | Single IV injection on day 1 |
| 13 | 7.5 mg/kg of HIF-2 alpha RNAi agent AD05932, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 3, 5, 6, 15, 16, 19, and 20 (3'→ 5') from the first nucleotide that forms a base pair with the antisense strand[(xii)], and further linked at the 3' terminal end of the sense strand to PK enhancer Mal-C18-diacid, formulated in isotonic glucose. [(xii)] See Example 8. | Single IV injection on day 1 |

In Groups 2-13, the enhancer having the structure indicated in previous examples for Mal-$C_{18}$-diacid was linked to the 3' terminal end of the sense strand by linking the maleimide reactive group by reducing the disulfide and undertaking a Michael Addition reaction In Groups 2-13, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 21

Average Relative huHIF-2 alpha mRNA Expression at Sacrifice (Day 8) in Example 9.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.197 | 0.246 |
| Group 2 (7.5 mg/kg Tri-Structure 2a-avb3-AD05930-(Int Structure 2a-avb3)$_4$-Mal-C18-diacid) | 3 | 0.265 | 0.031 | 0.036 |
| Group 3 (7.5 mg/kg Structure 2a-avb3-AD05954-(Int Structure 2a-avb3)$_3$-Mal-C18-diacid) | 3 | 0.337 | 0.095 | 0.133 |
| Group 4 (7.5 mg/kg Tri-Structure 2a-avb3-AD05955-(Int Structure 2a-avb3)$_3$- Mal-C18-diacid) | 3 | 0.401 | 0.049 | 0.056 |
| Group 5 (7.5 mg/kg Tri-Structure 2a-avb3-AD05956-(Int Structure 2a-avb3)$_3$-Mal-C18-diacid) | 3 | 0.315 | 0.100 | 0.146 |
| Group 6 (7.5 mg/kg Tri-Structure 2a-avb3-AD05957-(Int Structure 2a-avb3)$_3$-Mal-C18-diacid) | 3 | 0.313 | 0.050 | 0.060 |
| Group 7 (7.5 mg/kg Tri-Structure 2a-avb3-AD05958-(Int Structure 2a-avb3)$_2$-Mal-C18-diacid) | 3 | 0.426 | 0.126 | 0.179 |
| Group 8 (7.5 mg/kg Tri-Structure 2a-avb3-AD05959-(Int Structure 2a-avb3)$_2$-Mal-C18-diacid) | 3 | 0.330 | 0.080 | 0.105 |
| Group 9 (7.5 mg/kg Tri-Structure 2a-avb3-AD05960-(Int Structure 2a-avb3)$_2$-Mal-C18-diacid) | 3 | 0.359 | 0.063 | 0.076 |

TABLE 21-continued

| Average Relative huHIF-2 alpha mRNA Expression at Sacrifice (Day 8) in Example 9. | | | | |
|---|---|---|---|---|
| Group ID | Number of animals (n=) | Average Relative HIF-2 alpha mRNA expression | Low (error) | High (error) |
| Group 10 (7.5 mg/kg Tri-Structure 2a-avb3-AD05961-(Int Structure 2a-avb3)$_2$-Mal-C18-diacid) | 3 | 0.515 | 0.082 | 0.098 |
| Group 11 (7.5 mg/kg Tri-Structure 2a-avb3-AD05962-(Int Structure 2a-avb3)$_2$-Mal-C18-diacid) | 3 | 0.433 | 0.142 | 0.212 |
| Group 12 (7.5 mg/kg Tri-Structure 2a-avb3-AD05917-(Int Structure 2a-avb3)$_2$-Mal-C18-diacid) | 3 | 0.460 | 0.100 | 0.128 |
| Group 13 (7.5 mg/kg Tri-Structure 2a-avb3-AD05932-(Int Structure 2a-avb3)$_8$-Mal-C18-diacid) | 3 | 0.135 | 0.029 | 0.037 |

Each of the HIF-2 alpha RNAi agents examined in Example 9 included at least 2 internal nucleotides that included an avb3 integrin targeting ligand attached at the 2' position of the nucleotide, and as shown in Table 21 above, each of the HIF-2 alpha RNAi agents tested exhibited nearly 50% or greater knockdown of HIF-2 alpha compared to vehicle control. Groups 2 (having 4 internal ligands, approximately 74% knockdown) and 13 (having 8 internal ligands, approximately 86% knockdown) showed particularly high reductions of huHIF-2 alpha mRNA expression.

Example 10. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 22

| Dosing Groups of Tumor-Bearing Mice in Example 10. | | |
|---|---|---|
| Group | RNAi Agent and Dose | Dosing Regimen |
| 1 | Isotonic glucose (D5W) (no RNAi agent) | Single IV injection on day 1 |
| 2 | 7.5 mg/kg of HIF-2 alpha RNAi agent AD05930, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, 15, and 19 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] See Example 8. | Single IV injection on day 1 |
| 3 | 7.5 mg/kg of HIF-2 alpha RNAi agent AD05963, linked at the 5' terminal end of the sense strand to a tridentate targeting group having three integrin targeting ligands of Structure 2a-avb3, with an integrin targeting ligand of Structure 2a-avb3 linked internally at the 2' position of nucleotide 2 (3'→ 5') from the first nucleotide that forms a base pair with the antisense strand[(ii)], and further linked at the 3' terminal end of the sense strand to PK enhancer Mal-C18-diacid, formulated in isotonic glucose.<br>[(ii)] When viewing 5' → 3' on the sense strand of AD05963, the Structure 2a-avb3 targeting ligands is linked to the 2'-O-propargyl nucleotide (represented by aAlk in the modified sense strand sequence), which when viewed 5' → 3' on the sense strand sequence at nucleotide 20 of the sense strand. | Single IV injection on day 1 |
| 4 | 7.5 mg/kg of HIF-2 alpha RNAi agent AD05915, linked at the 5' terminal end of the sense strand to a tridentate targeting group having three integrin targeting ligands of Structure 2a-avb3, with an integrin targeting ligand of Structure 2a-avb3 linked internally at the 2' position of nucleotide 6 (3'→ 5') from the first nucleotide that forms a base pair with the antisense strand[(iii)], and further linked at the 3' terminal end of the sense strand to PK enhancer Mal-C18-diacid, formulated in isotonic glucose.<br>[(iii)] See Example 6. | Single IV injection on day 1 |
| 5 | 7.5 mg/kg of HIF-2 alpha RNAi agent AD05916, linked at the 5' terminal end of the sense strand to a tridentate targeting group having three integrin targeting ligands of Structure 2a-avb3, with an | Single IV injection on day 1 |

TABLE 22-continued

| Dosing Groups of Tumor-Bearing Mice in Example 10. | | |
|---|---|---|
| Group | RNAi Agent and Dose | Dosing Regimen |
| | integrin targeting ligand of Structure 2a-avb3 linked internally at the 2' position of nucleotide 15 (3'→ 5') from the first nucleotide that forms a base pair with the antisense strand(iv), and further linked at the 3' terminal end of the sense strand to PK enhancer Mal-C18-diacid, formulated in isotonic glucose.<br>(iv) See Example 6. | |
| 6 | 7.5 mg/kg of HIF-2 alpha RNAi agent AD05964, linked at the 5' terminal end of the sense strand to a tridentate targeting group having three integrin targeting ligands of Structure 2a-avb3, with an integrin targeting ligand of Structure 2a-avb3 linked internally at the 2' position of nucleotide 19 (3'→ 5') from the first nucleotide that forms a base pair with the antisense strand(v), and further linked at the 3' terminal end of the sense strand to PK enhancer Mal-C18-diacid, formulated in isotonic glucose.<br>(v) When viewing 5' → 3' on the sense strand of AD05964, the Structure 2a-avb3 targeting ligands is linked to the 2'-O-propargyl nucleotide (represented by aAlk in the modified sense strand sequence), which when viewed 5' → 3' on the sense strand sequence at nucleotide 3 of the sense strand. | Single IV injection on day 1 |
| 7 | 7.5 mg/kg of HIF-2 alpha RNAi agent AD05966, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4, 8, 14, and 18 (3'→ 5') from the first nucleotide that forms a base pair with the antisense strand(vi), and further linked at the 3' terminal end of the sense strand to PK enhancer Mal-C18-diacid, formulated in isotonic glucose.<br>(vi) When viewing 5' → 3' on the sense strand of AD05966, the Structure 2a-avb3 targeting ligands are linked to the 2'-O-propargyl nucleotides (represented by aAlk, cAlk, gAlk, and uAlk in the modified sense strand sequence), which when viewed 5' → 3' on the sense strand sequence are at nucleotides 4, 8, 14, and 18 of the sense strand. | Single IV injection on day 1 |
| 8 | 7.5 mg/kg of HIF-2 alpha RNAi agent AD05967, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 7, 10, 14, and 17 (3'→ 5') from the first nucleotide that forms a base pair with the antisense strand(vii), and further linked at the 3' terminal end of the sense strand to PK enhancer Mal-C18-diacid, formulated in isotonic glucose.<br>(vii) when viewing 5' → 3' on the sense strand of AD05967, the Structure 2a-avb3 targeting ligands are linked to the 2'-O-propargyl nucleotides (represented by aAlk, gAlk, cAlk, and uAlk in the modified sense strand sequence), which when viewed 5' → 3' on the sense strand sequence are at nucleotides 5, 8, 12, and 15 of the sense strand. | Single IV injection on day 1 |
| 9 | 7.5 mg/kg of HIF-2 alpha RNAi agent AD05968, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 9, 10, 14, and 15 (3'→ 5') from the first nucleotide that forms a base pair with the antisense strand(viii), and further linked at the 3' terminal end of the sense strand to PK enhancer Mal-C18-diacid, formulated in isotonic glucose.<br>(vii) when viewing 5' → 3' on the sense strand of AD05968, the Structure 2a-avb3 targeting ligands are linked to the 2'-O-propargyl nucleotides (represented by aAlk and uAlk in the modified sense strand sequence), which when viewed 5' → 3' on the sense strand sequence are at nucleotides 7, 8, 12, and 13 of the sense strand. | Single IV injection on day 1 |
| 10 | 7.5 mg/kg of HIF-2 alpha RNAi agent AD05969, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 14, 16, 18, and 20 (3'→ 5') from the first nucleotide that forms a base pair with the antisense strand(ix), and further linked at the 3' terminal end of the sense strand to PK enhancer Mal-C18-diacid, formulated in isotonic glucose.<br>(ix) when viewing 5' → 3' on the sense strand of AD05969, the Structure 2a-avb3 targeting ligands are linked to the 2'-O-propargyl nucleotides (represented by aAlk, cAlk, and uAlk in the modified sense strand sequence), which when viewed 5' → 3' on the sense strand sequence are at nucleotides 2, 4, 6, and 8 of the sense strand. | Single IV injection on day 1 |

TABLE 22-continued

| Dosing Groups of Tumor-Bearing Mice in Example 10. | | |
|---|---|---|
| Group | RNAi Agent and Dose | Dosing Regimen |
| 11 | 7.5 mg/kg of HIF-2 alpha RNAi agent AD05970, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 17, 18, 19, and 20 (3'→ 5') from the first nucleotide that forms a base pair with the antisense strand[(x)], and further linked at the 3' terminal end of the sense strand to PK enhancer Mal-C18-diacid, formulated in isotonic glucose. [(x)] When viewing 5' → 3' on the sense strand of AD05970, the Structure 2a-avb3 targeting ligands are linked to the 2'-O-propargyl nucleotides (represented by aAlk, cAlk, and gAlk in the modified sense strand sequence), which when viewed 5' → 3' on the sense strand sequence are at nucleotides 2, 3, 4, and 5 of the sense strand. | Single IV injection on day 1 |
| 12 | 7.5 mg/kg of HIF-2 alpha RNAi agent AD05971, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(xi)], and further linked at the 3' terminal end of the sense strand to PK enhancer Mal-C18-diacid, formulated in isotonic glucose. [(xi)] when viewing 5' → 3' on the sense strand of AD05971, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single IV injection on day 1 |
| 13 | 7.5 mg/kg of HIF-2 alpha RNAi agent AD05972, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 3, 4, and 5 (3'→ 5') from the first nucleotide that forms a base pair with the antisense strand[(xii)], and further linked at the 3' terminal end of the sense strand to PK enhancer Mal-C18-diacid, formulated in isotonic glucose. [(xii)] When viewing 5' → 3' on the sense strand of AD05972, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 17, 18, 19, and 20 of the sense strand. | Single IV injection on day 1 |

In Groups 2-13, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction In Groups 2-13, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 23

| Average Relative huHIF-2 alpha mRNA Expression at Sacrifice (Day 8) in Example 10. | | | | |
|---|---|---|---|---|
| Group ID | Number of animals (n=) | Average Relative HIF-2 alpha mRNA expression | Low (error) | High (error) |
| Group 1 (isotonic glucose vehicle) | 3 | 1.000 | 0.204 | 0.256 |
| Group 2 (7.5 mg/kg Tri-Structure 2a-avb3-AD05930-(Int Structure 2a-avb3)$_4$- Mal-C18-diacid) | 3 | 0.267 | 0.046 | 0.055 |

TABLE 23-continued

| Average Relative huHIF-2 alpha mRNA Expression at Sacrifice (Day 8) in Example 10. | | | | |
|---|---|---|---|---|
| Group ID | Number of animals (n=) | Average Relative HIF-2 alpha mRNA expression | Low (error) | High (error) |
| Group 3 (7.5 mg/kg Structure 2a-avb3-AD05963-(Int Structure 2a-avb3)- Mal-C18-diacid) | 3 | 0.405 | 0.065 | 0.077 |
| Group 4 (7.5 mg/kg Tri-Structure 2a-avb3-AD05915-(Int Structure 2a-avb3)- Mal-C18-diacid) | 3 | 0.455 | 0.014 | 0.015 |
| Group 5 (7.5 mg/kg Tri-Structure 2a-avb3-AD05916-(Int Structure 2a-avb3)- Mal-C18-diacid) | 3 | 0.392 | 0.032 | 0.034 |
| Group 6 (7.5 mg/kg Tri-Structure 2a-avb3-AD05964-(Int Structure 2a-avb3)- Mal-C18-diacid) | 3 | 0.445 | 0.070 | 0.084 |
| Group 7 (7.5 mg/kg Tri-Structure 2a-avb3-AD05966-(Int Structure $2a\text{-}avb3)_4$- Mal-C18-diacid) | 3 | 0.166 | 0.020 | 0.023 |
| Group 8 (7.5 mg/kg Tri-Structure 2a-avb3-AD05967-(Int Structure $2a\text{-}avb3)_4$- Mal-C18-diacid) | 3 | 0.211 | 0.037 | 0.045 |
| Group 9 (7.5 mg/kg Tri-Structure 2a-avb3-AD05968-(Int Structure $2a\text{-}avb3)_4$- Mal-C18-diacid) | 3 | 0.505 | 0.065 | 0.075 |
| Group 10 (7.5 mg/kg Tri-Structure 2a-avb3-AD05969-(Int Structure $2a\text{-}avb3)_4$- Mal-C18-diacid) | 3 | 0.416 | 0.090 | 0.116 |
| Group 11 (7.5 mg/kg Tri-Structure 2a-avb3-AD05970-(Int Structure $2a\text{-}avb3)_4$- Mal-C18-diacid) | 3 | 0.469 | 0.028 | 0.030 |
| Group 12 (7.5 mg/kg Tri-Structure 2a-avb3-AD05971-(Int Structure $2a\text{-}avb3)_4$- Mal-C18-diacid) | 3 | 0.161 | 0.018 | 0.020 |
| Group 13 (7.5 mg/kg Tri-Structure 2a-avb3-AD05972-(Int Structure $2a\text{-}avb3)_4$- Mal-C18-diacid) | 3 | 0.193 | 0.025 | 0.029 |

Example 11. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 24

| Dosing Groups of Tumor-Bearing Mice in Example 11. | | |
|---|---|---|
| Group | RNAi Agent and Dose | Dosing Regimen |
| 1 | Isotonic glucose (D5W) (no RNAi agent) | Single IV injection on day 1 |
| 2 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] When viewing 5' → 3' on the sense strand of AD06294, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single IV injection on day 1 |

TABLE 24-continued

| Dosing Groups of Tumor-Bearing Mice in Example 11. | | |
|---|---|---|
| Group | RNAi Agent and Dose | Dosing Regimen |
| 3 | 2.0 mg/kg of HIF-2 alpha RNAi agent AD06058, linked at the 5' terminal end of the sense strand to a tridentate targeting group having three integrin targeting ligands of Structure 2a-avb3, with an integrin targeting ligand of Structure 2a-avb3 linked internally at the 2' position of nucleotide 4 (3'→ 5') from the first nucleotide that forms a base pair with the antisense strand[(ii)], and further linked at the 3' terminal end of the sense strand to PK enhancer Mal-C18-diacid, formulated in isotonic glucose. [(ii)] When viewing 5' → 3' on the sense strand of AD06058, the Structure 2a-avb3 targeting ligands is linked to the 2'-O-propargyl nucleotide (represented by gAlk in the modified sense strand sequence), which when viewed 5' → 3' on the sense strand sequence at nucleotide 18 of the sense strand. | Single IV injection on day 1 |
| 4 | 2.0 mg/kg of HIF-2 alpha RNAi agent AD06146, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4 and 8 (3'→ 5') from the first nucleotide that forms a base pair with the antisense strand[(iii)], and further linked at the 3' terminal end of the sense strand to PK enhancer Mal-C18-diacid, formulated in isotonic glucose. [(iii)] When viewing 5' → 3' on the sense strand of AD06146, the Structure 2a-avb3 targeting ligands is linked to the 2'-O-propargyl nucleotide (represented by gAlk and uAlk in the modified sense strand sequence), which when viewed 5' → 3' on the sense strand sequence at nucleotides 14 and 18 of the sense strand. | Single IV injection on day 1 |
| 5 | 2.0 mg/kg of HIF-2 alpha RNAi agent AD06160, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 4 (3'→ 5') from the first nucleotide that forms a base pair with the antisense strand[(iv)], and further linked at the 3' terminal end of the sense strand to PK enhancer Mal-C18-diacid, formulated in isotonic glucose. [(iv)] When viewing 5' → 3' on the sense strand of AD06160, the Structure 2a-avb3 targeting ligands are linked to the 2'-O-propargyl nucleotides (represented by aAlk and gAlk in the modified sense strand sequence), which when viewed 5' → 3' on the sense strand sequence are at nucleotides 18 and 20 of the sense strand. | Single IV injection on day 1 |
| 6 | 2.0 mg/kg of HIF-2 alpha RNAi agent AD06161, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4 and 6 (3'→ 5') from the first nucleotide that forms a base pair with the antisense strand[(v)], and further linked at the 3' terminal end of the sense strand to PK enhancer Mal-C18-diacid, formulated in isotonic glucose. [(v)] When viewing 5' → 3' on the sense strand of AD06161, the Structure 2a-avb3 targeting ligands are linked to the 2'-O-propargyl nucleotides (represented by aAlk and gAlk in the modified sense strand sequence), which when viewed 5' → 3' on the sense strand sequence are at nucleotides 16 and 18 of the sense strand. | Single IV injection on day 1 |
| 7 | 2.0 mg/kg of HIF-2 alpha RNAi agent AD06162, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 6 and 8 (3'→ 5') from the first nucleotide that forms a base pair with the antisense strand[(vi)], and further linked at the 3' terminal end of the sense strand to PK enhancer Mal-C18-diacid, formulated in isotonic glucose. [(vi)] When viewing 5' → 3' on the sense strand of AD06162, the Structure 2a-avb3 targeting ligands are linked to the 2'-O-propargyl nucleotides (represented by aAlk and uAlk in the modified sense strand sequence), which when viewed 5' → 3' on the sense strand sequence are at nucleotides 14 and 16 of the sense strand. | Single IV injection on day 1 |
| 8 | 2.0 mg/kg of HIF-2 alpha RNAi agent AD06163, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 8 (3'→ 5') from the first nucleotide that forms a base pair with the antisense strand[(vii)], and further linked at the 3' terminal end of the sense strand to PK enhancer Mal-C18-diacid, formulated in isotonic glucose. [(vii)] when viewing 5' → 3' on the sense strand of AD06163, the Structure 2a-avb3 targeting ligands are linked to the 2'-O-propargyl | Single IV injection on day 1 |

TABLE 24-continued

| Dosing Groups of Tumor-Bearing Mice in Example 11. | | |
|---|---|---|
| Group | RNAi Agent and Dose | Dosing Regimen |
| | nucleotides (represented by aAlk and uAlk in the modified sense strand sequence), which when viewed 5' → 3' on the sense strand sequence are at nucleotides 14 and 20 of the sense strand. | |
| 9 | 2.0 mg/kg of HIF-2 alpha RNAi agent AD05959, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 6 (3'→ 5') from the first nucleotide that forms a base pair with the antisense strand[(viii)], and further linked at the 3' terminal end of the sense strand to PK enhancer Mal-C18-diacid, formulated in isotonic glucose. | Single IV injection on day 1 |

[(viii)] See Example 9.

In Groups 2-9, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction In Groups 2-9, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group, except for Group 2 in which only two (2) mice were dosed. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 25

Average Relative huHIF-2 alpha mRNA Expression at Sacrifice (Day 8) in Example 11.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.094 | 0.104 |
| Group 2 (7.5 mg/kg Tri-Structure 2a-avb3-AD06294-(Int Structure 2a-avb3)$_4$- Mal-C18-diacid) | 2 | 0.313 | 0.029 | 0.032 |
| Group 3 (7.5 mg/kg Structure 2a-avb3-AD06058-(Int Structure 2a-avb3)- Mal-C18-diacid) | 3 | 0.548 | 0.049 | 0.054 |
| Group 4 (7.5 mg/kg Tri-Structure 2a-avb3-AD06146-(Int Structure 2a-avb3)$_2$- Mal-C18-diacid) | 3 | 0.485 | 0.043 | 0.047 |
| Group 5 (7.5 mg/kg Tri-Structure 2a-avb3-AD06160-(Int Structure 2a-avb3)$_2$- Mal-C18-diacid) | 3 | 0.508 | 0.060 | 0.068 |
| Group 6 (7.5 mg/kg Tri-Structure 2a-avb3-AD06161-(Int Structure 2a-avb3)$_2$- Mal-C18-diacid) | 3 | 0.464 | 0.054 | 0.061 |
| Group 7 (7.5 mg/kg Tri-Structure 2a-avb3-AD06162-(Int Structure 2a-avb3)$_2$- Mal-C18-diacid) | 3 | 0.455 | 0.031 | 0.033 |
| Group 8 (7.5 mg/kg Tri-Structure 2a-avb3-AD06163-(Int Structure 2a-avb3)$_2$- Mal-C18-diacid) | 3 | 0.516 | 0.065 | 0.074 |
| Group 9 (7.5 mg/kg Tri-Structure 2a-avb3-AD05959-(Int Structure 2a-avb3)$_2$- Mal-C18-diacid) | 3 | 0.642 | 0.063 | 0.070 |

Example 12. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 26

Dosing Groups of Tumor-Bearing Mice in Example 12.

| Group | RNAi Agent and Dose | Dosing Regimen |
|---|---|---|
| 1 | Isotonic glucose (D5W) (no RNAi agent) | Single IV injection on day 1 |
| 2 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] See Example 11. | Single IV injection on day 1 |
| 3 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] See Example 11. | Single IV injection on day 1 |
| 4 | 2.0 mg/kg of HIF-2 alpha RNAi agent AD06065, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 and 6 (3'→ 5') from the first nucleotide that forms a base pair with the antisense strand[(ii)], and further linked at the 3' terminal end of the sense strand to PK enhancer Mal-C18-diacid, formulated in isotonic glucose.<br>[(ii)] When viewing 5' → 3' on the sense strand of AD06065, the Structure 2a-avb3 targeting ligands is linked to the 2'-O-propargyl nucleotide (represented by aAlk and gAlk in the modified sense strand sequence), which when viewed 5' → 3' on the sense strand sequence at nucleotides 16, 18, and 20 of the sense strand. | Single IV injection on day 1 |
| 5 | 4.0 mg/kg of HIF-2 alpha RNAi agent AD06065, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 and 6 (3'→ 5') from the first nucleotide that forms a base pair with the antisense strand[(ii)], and further linked at the 3' terminal end of the sense strand to PK enhancer Mal-C18-diacid, formulated in isotonic glucose.<br>[(ii)] When viewing 5' → 3' on the sense strand of AD06065, the Structure 2a-avb3 targeting ligands is linked to the 2'-O-propargyl nucleotide (represented by aAlk and gAlk in the modified sense strand sequence), which when viewed 5' → 3' on the sense strand sequence at nucleotides 16, 18, and 20 of the sense strand. | Single IV injection on day 1 |
| 6 | 2.0 mg/kg of HIF-2 alpha RNAi agent AD06066, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, and 8 (3'→ 5') from the first nucleotide that forms a base pair with the antisense strand[(iii)], and further linked at the 3' terminal end of the sense strand to PK enhancer Mal-C18-diacid, formulated in isotonic glucose.<br>[(iii)] When viewing 5' → 3' on the sense strand of AD06066, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14,18, and 20 of the sense strand. | Single IV injection on day 1 |
| 7 | 4.0 mg/kg of HIF-2 alpha RNAi agent AD06066, linked at the 5' terminal end of the sense strand to a tridentate targeting group having three integrin targeting ligands of Structure 2a-avb3, with an | Single IV injection on day 1 |

TABLE 26-continued

Dosing Groups of Tumor-Bearing Mice in Example 12.

| Group | RNAi Agent and Dose | Dosing Regimen |
|---|---|---|
| | integrin targeting ligand of Structure 2a-avb3 linked internally at the 2' position of each of nucleotides 2, 4, and 8 (3'→ 5') from the first nucleotide that forms a base pair with the antisense strand(iv), and further linked at the 3' terminal end of the sense strand to PK enhancer Mal-C18-diacid, formulated in isotonic glucose. (iv) When viewing 5' → 3' on the sense strand of AD06066, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14,18, and 20 of the sense strand. | |
| 8 | 2.0 mg/kg of HIF-2 alpha RNAi agent AD06067, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, and 8 (3'→ 5') from the first nucleotide that forms a base pair with the antisense strand(v), and further linked at the 3' terminal end of the sense strand to PK enhancer Mal-C18-diacid, formulated in isotonic glucose. (v) When viewing 5' → 3' on the sense strand of AD06067, the Structure 2a-avb3 targeting ligands are linked to the 2'-O-propargyl nucleotides (represented by aAlk and uAlk in the modified sense strand sequence), which when viewed 5' → 3' on the sense strand sequence are at nucleotides 14, 16, and 20 of the sense strand. | Single IV injection on day 1 |
| 9 | 4.0 mg/kg of HIF-2 alpha RNAi agent AD06067, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 6, and 8 (3'→ 5') from the first nucleotide that forms a base pair with the antisense strand(v), and further linked at the 3' terminal end of the sense strand to PK enhancer Mal-C18-diacid, formulated in isotonic glucose. (v) When viewing 5' → 3' on the sense strand of AD06067, the Structure 2a-avb3 targeting ligands are linked to the 2'-O-propargyl nucleotides (represented by aAlk and uAlk in the modified sense strand sequence), which when viewed 5' → 3' on the sense strand sequence are at nucleotides 14, 16, and 20 of the sense strand. | Single IV injection on day 1 |
| 10 | 2.0 mg/kg of HIF-2 alpha RNAi agent AD06068, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4, 6, and 8 (3'→ 5') from the first nucleotide that forms a base pair with the antisense strand(vi), and further linked at the 3' terminal end of the sense strand to PK enhancer Mal-C18-diacid, formulated in isotonic glucose. (vi) When viewing 5' → 3' on the sense strand of AD06068, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, and 18 of the sense strand. | Single IV injection on day 1 |
| 11 | 4.0 mg/kg of HIF-2 alpha RNAi agent AD06068, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4, 6, and 8 (3'→ 5') from the first nucleotide that forms a base pair with the antisense strand(vi), and further linked at the 3' terminal end of the sense strand to PK enhancer Mal-C18-diacid, formulated in isotonic glucose. (vi) When viewing 5' → 3' on the sense strand of AD06068, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, and 18 of the sense strand. | Single IV injection on day 1 |

In Groups 2-11, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction.

In Groups 2-11, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group, except for Group 6 in which only two (2) mice were dosed. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 27

Average Relative huHIF-2 alpha mRNA Expression at Sacrifice (Day 8) in Example 12.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.114 | 0.128 |
| Group 2 (2.0 mg/kg Tri-Structure 2a-avb3-AD06294-(Int Structure 2a-avb3)$_4$- Mal-C18-diacid) | 3 | 0.245 | 0.026 | 0.029 |
| Group 3 (4.0 mg/kg Structure 2a-avb3-AD06294-(Int Structure 2a-avb3)$_4$- Mal-C18-diacid) | 3 | 0.188 | 0.049 | 0.066 |
| Group 4 (2.0 mg/kg Tri-Structure 2a-avb3-AD06065-(Int Structure 2a-avb3)$_3$- Mal-C18-diacid) | 3 | 0.357 | 0.066 | 0.080 |
| Group 5 (4.0 mg/kg Tri-Structure 2a-avb3-AD06065-(Int Structure 2a-avb3)$_3$- Mal-C18-diacid) | 3 | 0.331 | 0.045 | 0.052 |
| Group 6 (2.0 mg/kg Tri-Structure 2a-avb3-AD06066-(Int Structure 2a-avb3)$_3$- Mal-C18-diacid) | 2 | 0.291 | 0.035 | 0.040 |
| Group 7 (4.0 mg/kg Tri-Structure 2a-avb3-AD06066-(Int Structure 2a-avb3)$_3$- Mal-C18-diacid) | 3 | 0.222 | 0.068 | 0.098 |
| Group 8 (2.0 mg/kg Tri-Structure 2a-avb3-AD06067-(Int Structure 2a-avb3)$_3$- Mal-C18-diacid) | 3 | 0.320 | 0.028 | 0.031 |
| Group 9 (4.0 mg/kg Tri-Structure 2a-avb3-AD06067-(Int Structure 2a-avb3)$_3$- Mal-C18-diacid) | 3 | 0.243 | 0.048 | 0.060 |
| Group 10 (2.0 mg/kg Tri-Structure 2a-avb3-AD06068-(Int Structure 2a-avb3)$_3$- Mal-C18-diacid) | 3 | 0.327 | 0.018 | 0.019 |
| Group 11 (4.0 mg/kg Tri-Structure 2a-avb3-AD06068-(Int Structure 2a-avb3)$_3$- Mal-C18-diacid) | 3 | 0.266 | 0.070 | 0.095 |

Example 13. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 28

Dosing Groups of Tumor-Bearing Mice in Example 13.

| Group | RNAi Agent and Dose | Dosing Regimen |
|---|---|---|
| 1 | Isotonic glucose (D5W) (no RNAi agent) | Single IV injection on day 1 |
| 2 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] See Example 11. | Single IV injection on day 1 |
| 3 | 2.0 mg/kg of HIF-2 alpha RNAi agent AD05972, linked at the 5' terminal end of the sense strand to a tridentate targeting group having three integrin targeting ligands of Structure 2a-avb3, with an integrin targeting ligand of Structure 2a-avb3 linked internally at | Single IV injection on day 1 |

TABLE 28-continued

Dosing Groups of Tumor-Bearing Mice in Example 13.

| Group | RNAi Agent and Dose | Dosing Regimen |
|---|---|---|
| | the 2' position of each of nucleotides 2, 3, 4, and 5 (3'→ 5') from the first nucleotide that forms a base pair with the antisense strand(ii), and further linked at the 3' terminal end of the sense strand to PK enhancer Mal-C18-diacid, formulated in isotonic glucose. (ii) See Example 10. | |
| 4 | 2.0 mg/kg of HIF-2 alpha RNAi agent AD06071, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, and 5 (3'→ 5') from the first nucleotide that forms a base pair with the antisense strand(iii), and further linked at the 3' terminal end of the sense strand to PK enhancer Mal-C18-diacid, formulated in isotonic glucose. (iii) When viewing 5' → 3' on the sense strand of AD06071, the Structure 2a-avb3 targeting ligands is linked to the 2'-O-propargyl nucleotide (represented by aAlk, gAlk, and uAlk in the modified sense strand sequence), which when viewed 5' → 3' on the sense strand sequence at nucleotides 17, 18, and 20 of the sense strand. | Single IV injection on day 1 |
| 5 | 4.0 mg/kg of HIF-2 alpha RNAi agent AD06072, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 3, 4, and 5 (3'→ 5') from the first nucleotide that forms a base pair with the antisense strand(iv), and further linked at the 3' terminal end of the sense strand to PK enhancer Mal-C18-diacid, formulated in isotonic glucose. (iv) When viewing 5' → 3' on the sense strand of AD06072, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 17, 18, and 19 of the sense strand. | Single IV injection on day 1 |
| 6 | 2.0 mg/kg of HIF-2 alpha RNAi agent AD06059, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 3, 4, 5, and 6 (3'→ 5') from the first nucleotide that forms a base pair with the antisense strand(v), and further linked at the 3' terminal end of the sense strand to PK enhancer Mal-C18-diacid, formulated in isotonic glucose. (v) When viewing 5' → 3' on the sense strand of AD06059, the Structure 2a-avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 16, 17, 18, and 19 of the sense strand. | Single IV injection on day 1 |
| 7 | 4.0 mg/kg of HIF-2 alpha RNAi agent AD06060, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 4, 5, 6, and 7 (3'→ 5') from the first nucleotide that forms a base pair with the antisense strand(vi), and further linked at the 3' terminal end of the sense strand to PK enhancer Mal-C18-diacid, formulated in isotonic glucose. (vi) When viewing 5' → 3' on the sense strand of AD06060, the Structure 2a-avb3 targeting ligands are linked to the 2'-O-propargyl nucleotides (represented by aAlk, cAlk, gAlk, and uAlk in the modified sense strand sequence), which when viewed 5' → 3' on the sense strand sequence are at nucleotides 15, 16, 17, and 18 of the sense strand. | Single IV injection on day 1 |
| 8 | 2.0 mg/kg of HIF-2 alpha RNAi agent AD06061, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 5, 6, 7, and 8 (3'→ 5') from the first nucleotide that forms a base pair with the antisense strand(vii), and further linked at the 3' terminal end of the sense strand to PK enhancer Mal-C18-diacid, formulated in isotonic glucose. (vii) When viewing 5' → 3' on the sense strand of AD06061, the Structure 2a-avb3 targeting ligands are linked to the 2'-O-propargyl nucleotides (represented by aAlk, cAlk, gAlk, and uAlk in the modified sense strand sequence), which when viewed 5' → 3' on the sense strand sequence are at nucleotides 14, 15, 16, and 17 of the sense strand. | Single IV injection on day 1 |
| 9 | 4.0 mg/kg of HIF-2 alpha RNAi agent AD06062, linked at the 5' terminal end of the sense strand to a tridentate targeting group | Single IV injection |

TABLE 28-continued

| Dosing Groups of Tumor-Bearing Mice in Example 13. | | |
|---|---|---|
| Group | RNAi Agent and Dose | Dosing Regimen |
| | having three integrin targeting ligands of Structure 2a-avb3, with an integrin targeting ligand of Structure 2a-avb3 linked internally at the 2' position of each of nucleotides 6, 7, 8, and 9 (3'→ 5') from the first nucleotide that forms a base pair with the antisense strand[(viii)], and further linked at the 3' terminal end of the sense strand to PK enhancer Mal-C18-diacid, formulated in isotonic glucose. [(viii)] When viewing 5' → 3' on the sense strand of AD06062, the Structure 2a-avb3 targeting ligands are linked to the 2'-O-propargyl nucleotides (represented by aAlk, cAlk, gAlk, and uAlk in the modified sense strand sequence), which when viewed 5' → 3' on the sense strand sequence are at nucleotides 13, 14, 15, and 16 of the sense strand. | on day 1 |
| 10 | 2.0 mg/kg of HIF-2 alpha RNAi agent AD06068, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 7, 8, 9, and 10 (3'→ 5') from the first nucleotide that forms a base pair with the antisense strand[(ix)], and further linked at the 3' terminal end of the sense strand to PK enhancer Mal-C18-diacid, formulated in isotonic glucose. [(ix)] When viewing 5' → 3' on the sense strand of AD06063, the Structure 2a-avb3 targeting ligands are linked to the 2'-O-propargyl nucleotides (represented by aAlk, cAlk, gAlk, and uAlk in the modified sense strand sequence), which when viewed 5' → 3' on the sense strand sequence are at nucleotides 12, 13, 14, and 15 of the sense strand. | Single IV injection on day 1 |

In Groups 2-10, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction.

In Groups 2-10, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 29

Average Relative huHIF-2 alpha mRNA Expression at Sacrifice (Day 8) in Example 13.

| Group ID | Number of animals (n=) | Average Relative HIF-2 alpha mRNA expression | Low (error) | High (error) |
|---|---|---|---|---|
| Group 1 (isotonic glucose vehicle) | 3 | 1.000 | 0.087 | 0.096 |
| Group 2 (2.0 mg/kg Tri-Structure 2a-avb3-AD06294-(Int Structure 2a-avb3)$_4$- Mal-C18-diacid) | 3 | 0.341 | 0.047 | 0.054 |
| Group 3 (2.0 mg/kg Structure 2a-avb3-AD05972-(Int Structure 2a-avb3)$_4$- Mal-C18-diacid) | 3 | 0.422 | 0.056 | 0.065 |
| Group 4 (2.0 mg/kg Tri-Structure 2a-avb3-AD06071-(Int Structure 2a-avb3)$_3$- Mal-C18-diacid) | 3 | 0.481 | 0.089 | 0.109 |
| Group 5 (2.0 mg/kg Tri-Structure 2a-avb3-AD06072-(Int Structure 2a-avb3)$_3$- Mal-C18-diacid) | 3 | 0.440 | 0.020 | 0.021 |
| Group 6 (2.0 mg/kg Tri-Structure 2a-avb3-AD06059-(Int Structure 2a-avb3)$_4$- Mal-C18-diacid) | 3 | 0.438 | 0.062 | 0.073 |
| Group 7 (2.0 mg/kg Tri-Structure 2a-avb3-AD06060-(Int Structure 2a-avb3)$_4$- Mal-C18-diacid) | 3 | 0.413 | 0.042 | 0.047 |

TABLE 29-continued

| Average Relative huHIF-2 alpha mRNA Expression at Sacrifice (Day 8) in Example 13. | | | | |
|---|---|---|---|---|
| Group ID | Number of animals (n=) | Average Relative HIF-2 alpha mRNA expression | Low (error) | High (error) |
| Group 8 (2.0 mg/kg Tri-Structure 2a-avb3-AD06061-(Int Structure 2a-avb3)$_4$- Mal-C18-diacid) | 3 | 0.459 | 0.069 | 0.081 |
| Group 9 (2.0 mg/kg Tri-Structure 2a-avb3-AD06062-(Int Structure 2a-avb3)$_4$- Mal-C18-diacid) | 3 | 0.513 | 0.138 | 0.189 |
| Group 10 (2.0 mg/kg Tri-Structure 2a-avb3-AD06063-(Int Structure 2a-avb3)$_4$- Mal-C18-diacid) | 3 | 0.602 | 0.049 | 0.053 |

Example 14. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, according to the following dosing Groups:

TABLE 30

| Dosing Groups of Tumor-Bearing Mice in Example 14. | | |
|---|---|---|
| Group | RNAi Agent and Dose | Dosing Regimen |
| 1 | Isotonic glucose (D5W) (no RNAi agent) | Single IV injection on day 1 |
| 2 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] See Example 11. | Single IV injection on day 1 |
| 3 | 5.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(ii)], and further linked at the 3' terminal end of the sense strand to PK enhancer Mal-C18-diacid, formulated in isotonic glucose. [(ii)] See Example 11. | Single IV injection on day 1 |
| 4 | 2.0 mg/kg of HIF-2 alpha RNAi agent AD06296, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 6, and 8 (3'→ 5') from the first nucleotide that forms a base pair with the antisense strand[(iii)], and further linked at the 3' terminal end of the sense strand to PK enhancer Mal-C18-diacid, formulated in isotonic glucose. [(iii)] When viewing 5' → 3' on the sense strand of each of AD06296, AD06297, and AD06299, the Structure 2a-avb3 targeting ligands is linked to the 2'-O-propargyl nucleotide (represented by aAlk, gAlk, and uAlk in the modified sense strand sequence), which when viewed 5' → 3' on the sense strand sequence at nucleotides 14, 16, 18, and 20 of the sense strand. | Single IV injection on day 1 |
| 5 | 5.0 mg/kg of HIF-2 alpha RNAi agent AD06296, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 6, and 8 (3'→ 5') from the first nucleotide that forms a base pair with the antisense strand[(iii)], and further linked at the 3' terminal end of the sense strand | Single IV injection on day 1 |

TABLE 30-continued

| Dosing Groups of Tumor-Bearing Mice in Example 14. | | |
|---|---|---|
| Group | RNAi Agent and Dose | Dosing Regimen |
| | to PK enhancer Mal-C18-diacid, formulated in isotonic glucose. (iii) When viewing 5' → 3' on the sense strand of each of AD06296, AD06297, and AD06299, the Structure 2a-avb3 targeting ligands is linked to the 2'-O-propargyl nucleotide (represented by aAlk, gAlk, and uAlk in the modified sense strand sequence), which when viewed 5' → 3' on the sense strand sequence at nucleotides 14, 16, 18, and 20 of the sense strand. | |
| 6 | 2.0 mg/kg of HIF-2 alpha RNAi agent AD06297, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 6, and 8 (3'→ 5') from the first nucleotide that forms a base pair with the antisense strand[iii], and further linked at the 3' terminal end of the sense strand to PK enhancer Mal-C18-diacid, formulated in isotonic glucose. (iii) When viewing 5' → 3' on the sense strand of each of AD06296, AD06297, and AD06299, the Structure 2a-avb3 targeting ligands is linked to the 2'-O-propargyl nucleotide (represented by aAlk, gAlk, and uAlk in the modified sense strand sequence), which when viewed 5' → 3' on the sense strand sequence at nucleotides 14, 16, 18, and 20 of the sense strand. | Single IV injection on day 1 |
| 7 | 2.0 mg/kg of HIF-2 alpha RNAi agent AD06299, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 6, and 8 (3'→ 5') from the first nucleotide that forms a base pair with the antisense strand[iii], and further linked at the 3' terminal end of the sense strand to PK enhancer Mal-C18-diacid, formulated in isotonic glucose. (iii) When viewing 5' → 3' on the sense strand of each of AD06296, AD06297, and AD06299, the Structure 2a-avb3 targeting ligands is linked to the 2'-O-propargyl nucleotide (represented by aAlk, gAlk, and uAlk in the modified sense strand sequence), which when viewed 5' → 3' on the sense strand sequence at nucleotides 14, 16, 18, and 20 of the sense strand. | Single IV injection on day 1 |

In Groups 2-7, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction.

In Groups 2-7, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 31

| Average Relative huHIF-2 alpha mRNA Expression at Sacrifice (Day 8) in Example 14. | | | | |
|---|---|---|---|---|
| Group ID | Number of animals (n=) | Average Relative HIF-2 alpha mRNA expression | Low (error) | High (error) |
| Group 1 (isotonic glucose vehicle) | 3 | 1.000 | 0.167 | 0.201 |
| Group 2 (2.0 mg/kg Tri-Structure 2a-avb3-AD06294-(Int Structure 2a-avb3)$_4$- Mal-C18-diacid) | 3 | 0.382 | 0.080 | 0.101 |
| Group 3 (5.0 mg/kg Structure 2a-avb3-AD06294-(Int Structure 2a-avb3)$_4$- Mal-C18-diacid) | 3 | 0.194 | 0.044 | 0.057 |
| Group 4 (2.0 mg/kg Tri-Structure 2a-avb3-AD06296-(Int Structure 2a-avb3)$_3$- Mal-C18-diacid) | 3 | 0.512 | 0.170 | 0.255 |
| Group 5 (5.0 mg/kg Tri-Structure 2a-avb3-AD06296-(Int Structure 2a-avb3)$_3$- Mal-C18-diacid) | 3 | 0.212 | 0.025 | 0.028 |

TABLE 31-continued

| Average Relative huHIF-2 alpha mRNA Expression at Sacrifice (Day 8) in Example 14. | | | | |
|---|---|---|---|---|
| Group ID | Number of animals (n=) | Average Relative HIF-2 alpha mRNA expression | Low (error) | High (error) |
| Group 6 (2.0 mg/kg Tri-Structure 2a-avb3-AD06297-(Int Structure 2a-avb3)$_4$- Mal-C18-diacid) | 3 | 0.404 | 0.081 | 0.102 |
| Group 7 (2.0 mg/kg Tri-Structure 2a-avb3-AD06299-(Int Structure 2a-avb3)$_4$- Mal-C18-diacid) | 3 | 0.282 | 0.057 | 0.072 |

Each of the HIF-2 alpha RNAi agents in Example 14 included a sense strand that comprised (i) a tridentate targeting group located at the 5' terminal end of the sense strand that comprised three targeting ligands; (ii) a total of four additional internal targeting ligands linked at the 2' position to each of the nucleotides located at positions 2, 4, 6, and 8 from the first nucleotide that forms a base pair with the antisense strand; and (iii) a PK enhancer linked to the 3' terminal end of the sense strand. As shown in Table 31 above, each of the RNAi agents, dosed at both 2.0 mg/kg and 5.0 mg/kg exhibited substantial reductions of huHIF-2 alpha mRNA compared to vehicle control.

Example 15. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study day 1, mice were dosed via tail vein intravenous (IV) injection with approximately 300 microliters volume of injection, which included the following dosing Groups:

TABLE 32

| Dosing Groups of Tumor-Bearing Mice in Example 15. | | |
|---|---|---|
| Group | RNAi Agent and Dose | Dosing Regimen |
| 1 | Isotonic glucose (D5W) (no RNAi agent) | Single IV injection on day 1 |
| 2 | 2.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] See Example 11. | Single IV injection on day 1 |
| 3 | 5.0 mg/kg of HIF-2 alpha RNAi agent AD06153, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2 and 8 (3'→ 5') from the first nucleotide that forms a base pair with the antisense strand[(ii)], and further linked at the 3' terminal end of the sense strand to PK enhancer Mal-C18-diacid, formulated in isotonic glucose. [(ii)] When viewing 5' → 3' on the sense strand of AD06153 the Structure 2a-avb3 targeting ligands are linked to the 2'-O-propargyl nucleotides (represented by aAlk and uAlk in the modified sense strand sequence), which when viewed 5' → 3' on the sense strand sequence at nucleotides 14 and 20 of the sense strand. | Single IV injection on day 1 |

TABLE 32-continued

| Dosing Groups of Tumor-Bearing Mice in Example 15. | | |
|---|---|---|
| Group | RNAi Agent and Dose | Dosing Regimen |
| 4 | 2.0 mg/kg of HIF-2 alpha RNAi agent AD06157, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4 6, and 8 (3'→ 5') from the first nucleotide that forms a base pair with the antisense strand[(iii)], and further linked at the 3' terminal end of the sense strand to PK enhancer Mal-C18-diacid, formulated in isotonic glucose. [(iii)] When viewing 5' → 3' on the sense strand of each of AD06157, the Structure 2a-avb3 targeting ligands are linked to the 2'-O-propargyl nucleotides (represented by aAlk, cAlk, and uAlk in the modified sense strand sequence), which when viewed 5' → 3' on the sense strand sequence at nucleotides 14, 16, 18, and 20 of the sense strand. | Single IV injection on day 1 |

In Groups 2-4, the PK enhancer having the structure indicated in previous examples for Mal-$C_{18}$-diacid was linked to the 3' terminal end of the sense strand by linking the maleimide reactive group by reducing the disulfide and undertaking a Michael Addition reaction.

In Groups 2-4, the tridentate integrin targeting group (which included three integrin ligands having affinity for alpha-v-beta-3 of the structure of Structure 2a-avb3) linked to the 5' terminal end of the sense strand by coupling to the functionalized amine reactive group linker (NH2-C6) has the structure set forth in Example 3, above.

Three (3) mice were dosed in each Group, except for the vehicle control group (Group 1), which only had 2 mice. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 33

Average Relative huHIF-2 alpha mRNA Expression at Sacrifice (Day 8) in Example 15.

| Group ID | Number of animals (n=) | Average Relative HIF-2 alpha mRNA expression | Low (error) | High (error) |
|---|---|---|---|---|
| Group 1 (isotonic glucose vehicle) | 2 | 1.000 | 0.057 | 0.061 |
| Group 2 (2.0 mg/kg Tri-Structure 2a-avb3-AD06294-(Int Structure 2a-avb3)$_4$- Mal-C18-diacid) | 3 | 0.397 | 0.044 | 0.049 |
| Group 3 (5.0 mg/kg Structure 2a-avb3-AD06153-(Int Structure 2a-avb3)$_4$- Mal-C18-diacid) | 3 | 0.470 | 0.076 | 0.091 |
| Group 4 (2.0 mg/kg Tri-Structure 2a-avb3-AD06157-(Int Structure 2a-avb3)$_3$- Mal-C18-diacid) | 3 | 0.451 | 0.105 | 0.137 |

Example 16. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. On study days 1, 2, 8, 9, 15, 22, and 29, mice were dosed via tail vein intravenous (IV) injection with approximately 300 microliters volume of injection of either 5.0 mg/kg of Tri-Structure 2a-avb3-AD05971-(Int Structure 2a-avb3)$_4$-C18-diacid, or isotonic glucose with no RNAi agent.

Figure 4A:
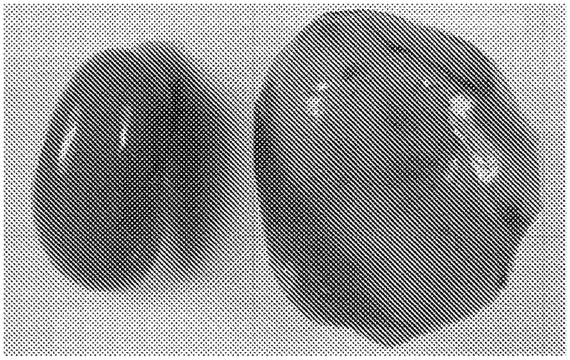
FIG. 4A to 4B. Images showing the tumor size from tumor-bearing mice on day 36 according to the study described in Example 16 herein.
Figure 4B:
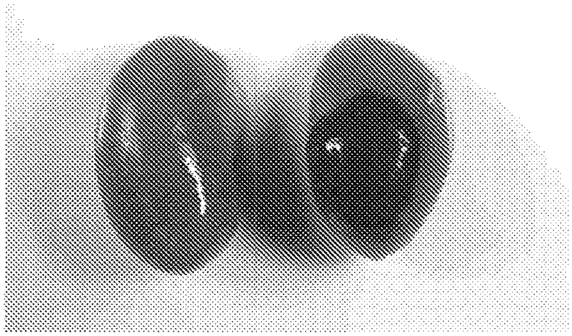
Figure 5A:
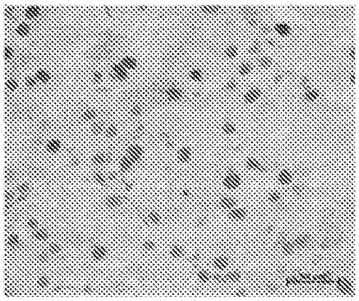
FIG. 5A to 5B. Images showing immunohistochemistry (IHC) staining of HIF-2 alpha protein from the tumor-bearing mice dosed according to Example 16 herein.
Figure 5B:
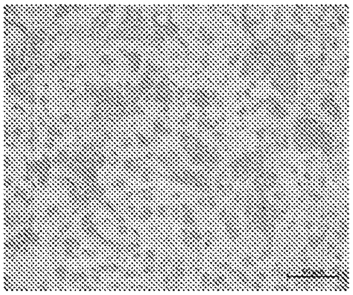

Six (6) mice were dosed in each Group. Mice were sacrificed on study day 36, kidney tumors were harvested. FIG. 4A shows the kidneys from a mouse in the untreated control group, with the tumor kidney shown on the right side of the image, and the contralateral kidney shown on the left. FIG. 4B shows the kidneys from a mouse in the group treated with RNAi agent, also with the tumor kidney shown on the right side of that image and the contralateral kidney shown on the left. As is evident from the images and confirmed by tumor weights, the HIF-2 alpha RNAi agent group inhibited tumor growth. Additionally, as shown in FIG. 5A, immunohistochemistry (IHC) staining of cells from a tumor-bearing mouse in the control group confirms the presence of HIF-2 alpha protein as is visible by the darkened spots, while no such darkened spots are evident on the image of FIG. 5B showing the cells of a tumor-bearing mouse treated with HIF-2 alpha RNAi agent.

Example 17. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. Mice were dosed via tail vein intravenous (IV) injection with approximately 300 microliters volume of injection according to the following dosing Groups:

TABLE 34

Dosing Groups of Tumor-Bearing Mice in Example 17.

| Group | RNAi Agent and Dose | Dosing/Sacrifice Regimen |
|---|---|---|
| 1 | Isotonic glucose (D5W) (no RNAi agent) | Single IV injection on days 1 and 8; day 22 harvest |
| 2 | 5.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | Single IV injection on days 1 and 8; day 15 harvest |
| 3 | 5.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | Single IV injection on days 1 and 8; day 22 harvest |
| 4 | Isotonic glucose (D5W) (no RNAi agent) | Single IV injection on day 1 and 15; day 29 harvest |
| 5 | 5.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | Single IV injection on day 1 and 15; day 22 harvest |
| 6 | 5.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | Single IV injection on day 1 and 15; day 29 harvest |

Four (4) mice were dosed in each Group. At the scheduled date of sacrifice as noted in Table 34, above, kidney tumors were harvested and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 35

Average Relative huHIF-2 alpha mRNA Expression at Sacrifice in Example 17.

| Group ID | Number of animals (n=) | Average Relative HIF-2 alpha mRNA expression | Low (error) | High (error) |
|---|---|---|---|---|
| Group 1 (isotonic glucose vehicle, Day 1 and 8 dosing; day 22 harvest) | 4 | 1.000 | 0.267 | 0.364 |
| Group 2 (5.0 mg/kg Tri-Structure 2a-avb3-AD06294-(Int Structure 2a-avb3)$_4$- Mal-C18-diacid, day 1 and 8 dosing; day 15 harvest) | 4 | 0.192 | 0.041 | 0.053 |
| Group 2 (5.0 mg/kg Tri-Structure 2a-avb3-AD06294-(Int Structure 2a-avb3)$_4$- Mal-C18-diacid, day 1 and 8 dosing; day 22 harvest) | 4 | 0.334 | 0.095 | 0.132 |
| Group 4 (isotonic glucose vehicle, Day 1 and 15 dosing; day 29 harvest) | 4 | 1.000 | 0.260 | 0.352 |
| Group 5 (5.0 mg/kg Tri-Structure 2a-avb3-AD06294-(Int Structure 2a-avb3)$_4$- Mal-C18-diacid, day 1 and 15 dosing; day 22 harvest) | 4 | 0.168 | 0.029 | 0.035 |
| Group 6 (5.0 mg/kg Tri-Structure 2a-avb3-AD06294-(Int Structure 2a-avb3)$_4$- Mal-C18-diacid, day 1 and 15 dosing; day 29 harvest) | 4 | 0.282 | 0.066 | 0.086 |

Example 18. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. Mice were dosed via tail vein intravenous (IV) injection with approximately 300 microliters volume of injection according to the following dosing Groups:

TABLE 36

Dosing Groups of Tumor-Bearing Mice in Example 18.

| Group | RNAi Agent and Dose | Dosing Regimen |
|---|---|---|
| 1 | Saline (no RNAi agent) | Single IV injection on day 1 |
| 2 | 20.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | Single IV injection on day 1 |
| 3 | 10.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in | An initial IV injection on day 1, and a second IV injection four hours later on day 1 [2 x 10 mg/kg injections on day 1] |

TABLE 36-continued

Dosing Groups of Tumor-Bearing Mice in Example 18.

| Group | RNAi Agent and Dose | Dosing Regimen |
|---|---|---|
| | isotonic glucose. [i] See Example 11. | |
| 4 | 10.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose. [i] See Example 11. | Single IV injection on day 1 |

Four (4) mice were dosed in each Group. Mice were sacrificed on study day 8, kidney tumors were harvested, and total human HIF-2 mRNA in the kidney tumors was isolated following collection and homogenization. HIF-2 alpha (huHIF-2 alpha) mRNA expression was quantitated by probe-based quantitative PCR, normalized to human Cyclophilin A (PPIA) expression and expressed as fraction of vehicle control group (geometric mean, +/−95% confidence interval).

TABLE 37

Average Relative huHIF-2 alpha mRNA Expression at Sacrifice in Example 18.

| Group ID | Number of animals (n=) | Average Relative HIF-2 alpha mRNA expression | Low (error) | High (error) |
|---|---|---|---|---|
| Group 1 (saline vehicle) | 4 | 1.000 | 0.065 | 0.069 |
| Group 2 (20.0 mg/kg Tri-Structure 2a-avb3-AD06294-(Int Structure 2a-avb3)$_4$- Mal-C18-diacid, single injection on day 1) | 4 | 0.191 | 0.040 | 0.050 |
| Group 3 (2 x 10.0 mg/kg Tri-Structure 2a-avb3-AD06294-(Int Structure 2a-avb3)$_4$- Mal-C18-diacid, two injections on day 1 (4 hours apart)) | 4 | 0.148 | 0.027 | 0.033 |
| Group 4 (10.0 mg/kg Tri-Structure 2a-avb3-AD06294-(Int Structure 2a-avb3)$_4$- Mal-C18-diacid, single injection on day 1) | 4 | 0.220 | 0.056 | 0.075 |

Example 19. In Vivo Administration of HIF-2 Alpha RNAi Agents in ccRCC Tumor-Bearing Mice The tumor-bearing mouse model of Example 2 was used to evaluate HIF-2 alpha RNAi agents in vivo. Mice were dosed via tail vein intravenous (IV) injection with approximately 300 microliters volume of injection according to the following dosing Groups:

TABLE 38

Dosing Groups of Tumor-Bearing Mice in Example 19.

| Group | RNAi Agent and Dose | Dosing Regimen |
|---|---|---|
| 1 | Saline (no RNAi agent) | Single IV injection weekly |
| 2 | 20.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked | Single IV injection weekly |

TABLE 38-continued

| Dosing Groups of Tumor-Bearing Mice in Example 19. | | |
|---|---|---|
| Group | RNAi Agent and Dose | Dosing Regimen |
| | internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | |
| 3 | 10.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | An initial IV injection followed by a second IV injection four hours later on day one [2 x 10 mg/kg injections], starting on day 1 and administered weekly |
| 4 | 10.0 mg/kg of HIF-2 alpha RNAi agent AD06294, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[i], and further linked at the 3' terminal end of the sense strand to PK enhancer Mal-C18-diacid, formulated in isotonic glucose.<br>[i] See Example 11. | An initial IV injection followed by a second IV injection four hours later on day one [2 x 10 mg/kg injections], starting on day 1 and administered biweekly (every other week). |

Figure 6:
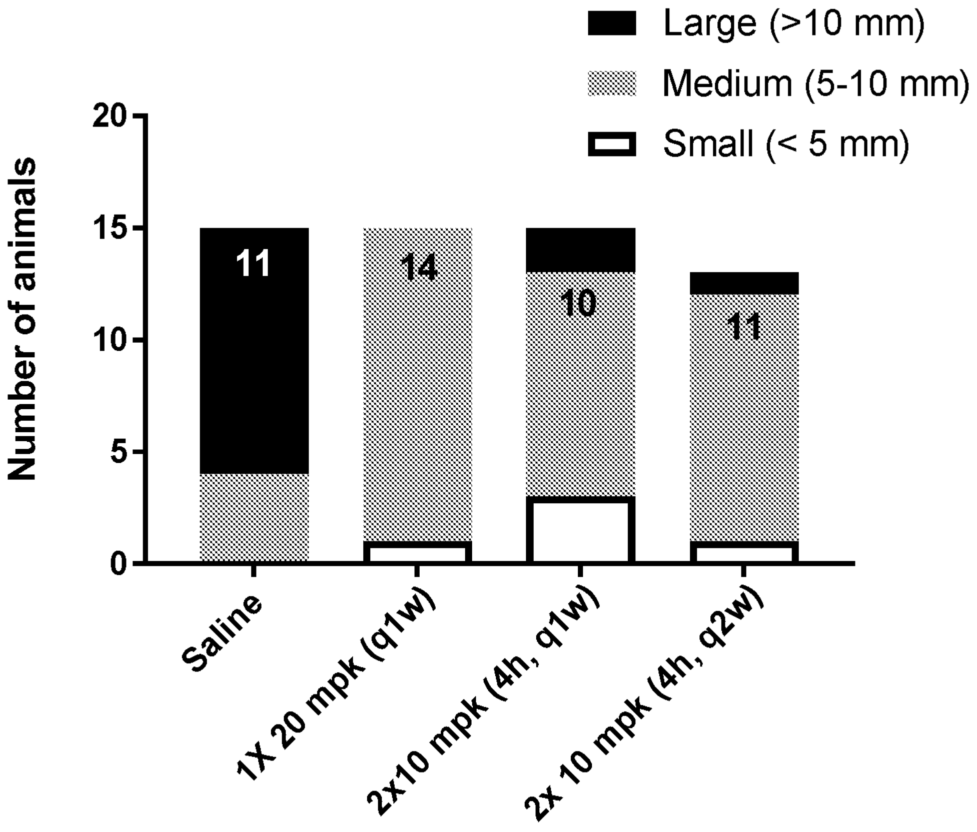
FIG. 6. Bar graph reflecting the tumor size of animals dosed according to Example 19 herein. Animals were categorized based on tumor size measurements on day 34.
Figures 7A, 7B, 7C:
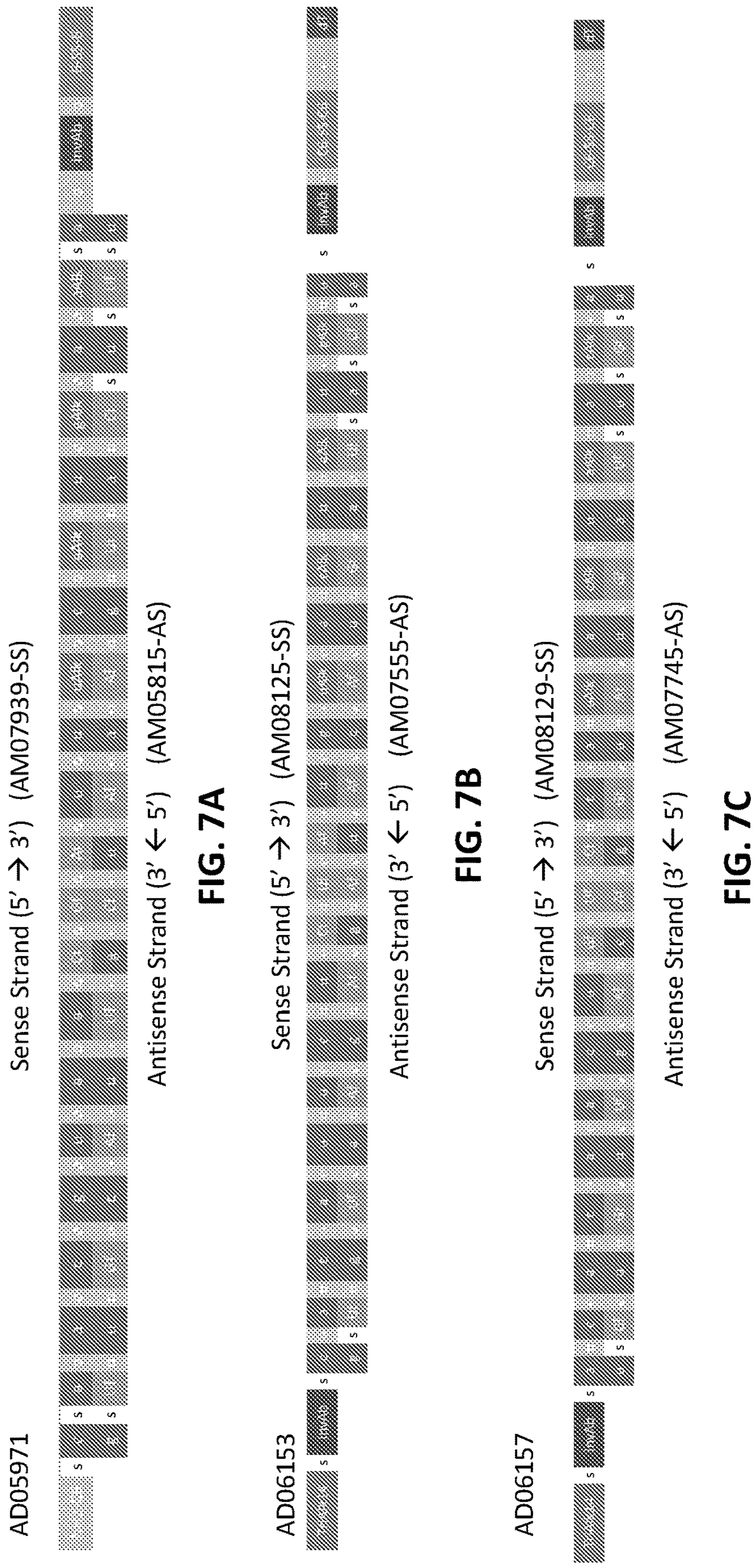
FIG. 7A. to 7G. Schematic showing nucleotides, internucleoside linkages, and sense strand modifications of AD05971, AD06153, AD06157, AD05930, AD05966, AD05967 and AD05972 as synthesized on solid support, wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; aAlk, cAlk, gAlk, and uAlk represent 2'-O-propargyl adenosine, cytidine, guanosine, and uridine, respectively, o represents a phosponate linkage, and s represents a phosphorothioate linkage, and invAb, 6-SS-6, C6-SS-C6, NH2-C6, and TriAlk14 are all as defined in Table 7. Further modifications to the RNAi agents of FIG. 7 may be effected following cleavage from the solid support, such as addition of targeting ligands and PK Enhancers.
Figures 7D, 7E, 7F, 7G:
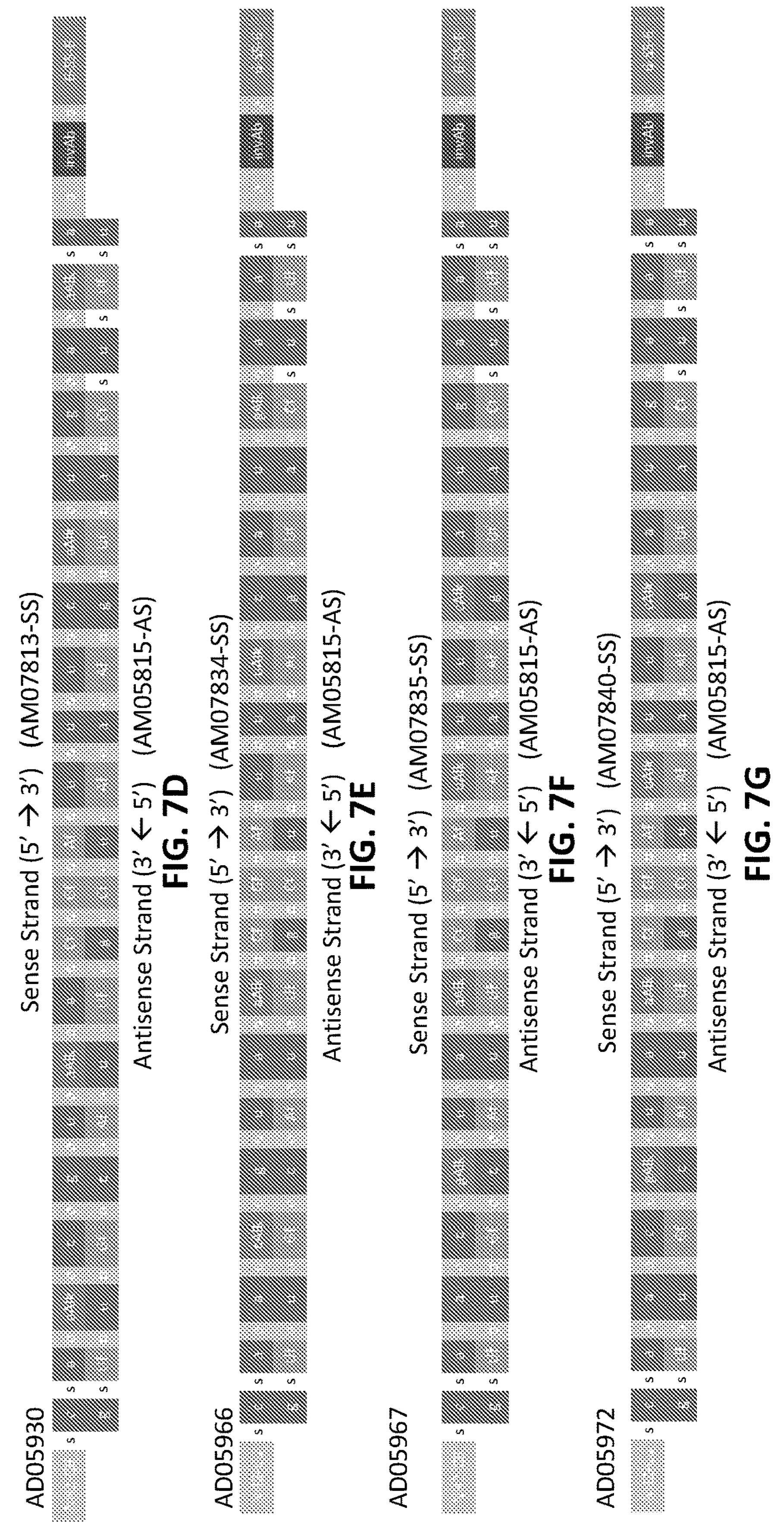

Fifteen (15) mice were dosed in each Group and body weight and tumor growth were monitored by palpation and caliper estimates weekly. One animal in Group 4 was found dead on day 21. FIG. 6 shows the effects on tumor growth up to study Day 34. As reported in FIG. 6, the data show an overall improvement in tumor size reduction when administered with a HIF-2 alpha RNAi agent compared to the saline vehicle control.

Example 20. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 1 herein. The RNAi agents had the respective modified nucleotide sequences set forth in Example 2 herein and were designed to target Hif2a (EPAS1).

On study day 1, kidney tumor bearing mice were dosed via tail vein injection according to the following dosing Groups:

TABLE 39

| Dosing Groups of Mice in Example 20. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 4 | 5.0 mg/kg of HIF-2 alpha RNAi agent AD05971, linked at the 5' terminal end of the sense strand to a tridentate targeting group having three integrin targeting ligands of Structure 2a-avb3, with an integrin | Single injection on day 1 |

TABLE 39-continued

| Dosing Groups of Mice in Example 20. | | |
|---|---|---|
| Group | RNAi Agent and Dose | Dosing Regimen |
| | targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | |
| 5 | 5.0 mg/kg of HIF-2 alpha RNAi agent AD05971, linked at the 5' terminal end of the sense strand to a tridentate targeting group having three integrin targeting ligands of Structure 32a-avb3, with an integrin targeting ligand of Structure 32a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 6 | 5.0 mg/kg of HIF-2 alpha RNAi agent AD05971, linked at the 5' terminal end of the sense strand to a tridentate targeting group having three integrin targeting ligands of Structure 33a-avb3, with an integrin targeting ligand of Structure 33a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 7 | 5.0 mg/kg of HIF-2 alpha RNAi agent AD05971, linked at the 5' terminal end of the sense strand to a tridentate targeting group having three integrin targeting ligands of Structure 34a-avb3, with an integrin targeting ligand of Structure 34a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |

Three (3) tumor bearing mice were dosed in each Group (n=3). Mice were sacrificed on study day 8 after injection, and total RNA was isolated from kidney tumor. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval).

TABLE 40

Average Relative Hif2α mRNA Expression at Sacrifice in Example 20.

| Group ID | Average Relative huHIF2α mRNA Expression | Low (error) | High (error) |
|---|---|---|---|
| Group 1 (isotonic glucose) | 1.000 | 0.077 | 0.083 |
| Group 4 (5.0 mg/kg RNAi agent-tridentate integrin targeting ligand of Structure 2a, three internal ligands of Structure 2a, and Mal-C18-diacid pk extender) | 0.245 | 0.048 | 0.059 |
| Group 5 (5.0 mg/kg RNAi agent-tridentate integrin targeting ligand of Structure 32a, three internal ligands of Structure 32a, and Mal-C18-diacid) | 0.213 | 0.065 | 0.094 |
| Group 6 (5.0 mg/kg RNAi agent-tridentate integrin targeting ligand of Structure 33a, three internal ligands of Structure 33a, and Mal-C18-diacid) | 0.603 | 0.117 | 0.146 |
| Group 7 (5.0 mg/kg RNAi agent-tridentate integrin targeting ligand of Structure 34a, three internal ligands of Structure 34a, and Mal-C18-diacid) | 0.528 | 0.067 | 0.077 |

As shown in Table 40 above, each of the Hif2a RNAi agent-integrin targeting ligand conjugates showed a reduction in mRNA expression in mice compared to control.

Example 21. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 1 herein. The RNAi agents had the respective modified nucleotide sequences set forth herein and were designed to target Hif2a (EPAS1).

On study day 1, kidney tumor bearing mice (see Example 4) were dosed via tail vein injection according to the following dosing Groups:

TABLE 41

Dosing Groups of Mice in Example 21.

| Group | RNAi Agent and Dose | Dosing Regimen |
|---|---|---|
| 1 | Isotonic glucose (d5w (5% dextrose in water)) (no RNAi agent) | Single injection on day 1 |
| 2 | 2.0 mg/kg of HIF-2 alpha RNAi agent AD05971, linked at the 5' terminal end of the sense strand to a tridentate targeting group having three integrin targeting ligands of Structure 2.11-avb3, with an integrin targeting ligand of Structure 2.11a-avb3 linked internally at the 2' position of each of nucleotides 2, 4, 6, and 8 (3'→ 5') from the first nucleotide that forms a base pair with the antisense strand(i), and further linked at the 3' terminal end of the sense strand to PK enhancer Mal-C18-diacid, formulated in isotonic glucose.<br>(1) The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 5 | 2.0 mg/kg of HIF-2 alpha RNAi agent AD05971, linked at the 5' terminal end of the sense strand to a tridentate targeting group having three integrin targeting ligands of Structure 36-avb3, with an integrin targeting ligand of Structure 36a-avb3 linked internally at the 2' position of each of nucleotides 2, 4, 6, and 8 (3'→ 5') from the first nucleotide that forms a base pair with the antisense strand(i), and further linked at the 3' terminal end of the sense strand to PK enhancer Mal-C18-diacid, formulated in isotonic glucose.<br>(i) The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 6 | 2.0 mg/kg of HIF-2 alpha RNAi agent AD05971, linked at the 5' terminal end of the sense strand to a tridentate targeting group having three integrin targeting ligands of Structure 37-avb3, with an integrin | Single injection on day 1 |

TABLE 41-continued

| Dosing Groups of Mice in Example 21. | | |
|---|---|---|
| Group | RNAi Agent and Dose | Dosing Regimen |
| | targeting ligand of Structure 37a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | |

Three (3) tumor bearing mice were dosed in each Group (n=3). Mice were sacrificed on study day 8 after injection, and total RNA was isolated from kidney tumor. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval).

TABLE 42

| Average Relative Hif2α mRNA Expression at Sacrifice in Example 21. | | | |
|---|---|---|---|
| Group ID | Average Relative huHIF2α mRNA Expression | Low (error) | High (error) |
| Group 1 (isotonic glucose) | 1.000 | 0.090 | 0.099 |
| Group 2 (5.0 mg/kg RNAi agent-tridentate integrin targeting ligand of Structure 2.11a, three internal ligands of Structure 2.11a, and Mal-C18-diacid) | 0.362 | 0.021 | 0.022 |
| Group 5 (5.0 mg/kg RNAi agent-tridentate integrin targeting ligand of Structure 36a, three internal ligands of Structure 36a, and Mal-C18-diacid) | 0.617 | 0.028 | 0.029 |

TABLE 42-continued

| Average Relative Hif2α mRNA Expression at Sacrifice in Example 21. | | | |
|---|---|---|---|
| Group ID | Average Relative huHIF2α mRNA Expression | Low (error) | High (error) |
| Group 6 (5.0 mg/kg RNAi agent-tridentate integrin targeting ligand of Structure 37a, three internal ligands of Structure 37a, and Mal-C18-diacid) | 0.375 | 0.081 | 0.103 |

As shown in Table 42 above, each of the Hif2α RNAi agent-integrin targeting ligand conjugates showed a reduction in mRNA expression in mice compared to control.

Example 22. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 1 herein. The RNAi agents had the respective modified nucleotide sequences set forth herein and were designed to target Hif2a (EPAS1).

On study day 1, kidney tumor bearing mice were dosed via tail vein injection according to the following dosing Groups:

TABLE 43

| Dosing Groups of Mice in Example 22. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 2.0 mg/kg of HIF-2 alpha RNAi agent AD05971, linked at the 5' terminal end of the sense strand to a tridentate targeting group having three integrin targeting ligands of Structure 2a-avb3, with an integrin targeting ligand of Structure 2a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and | Single injection on day 1 |

TABLE 43-continued

| Dosing Groups of Mice in Example 22. | | |
|---|---|---|
| Group | RNAi Agent and Dose | Dosing Regimen |
| | uAlk in the modified sense strand sequence), which when viewed 5' → 3 ' on the sense strand sequence are at nucleotides 14, 16, 18, and 20 of the sense strand. | |
| 3 | 4.0 mg/kg of HIF-2 alpha RNAi agent AD05971, linked at the 5' terminal end of the sense strand to a tridentate targeting group having three integrin targeting ligands of Structure 2a-avb3, with an integrin targeting ligand of Structure 2a-avb3 targeting ligand linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 6 | 2.0 mg/kg of HIF-2 alpha RNAi agent AD05971, linked at the 5' terminal end of the sense strand to a tridentate targeting group having three integrin targeting ligands of Structure 38-avb3, with an integrin targeting ligand of Structure 38a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 7 | 4.0 mg/kg of HIF-2 alpha RNAi agent AD05971, linked at the 5' terminal end of the sense strand to a tridentate targeting group having three integrin targeting ligands of Structure 38-avb3, with an integrin targeting ligand of Structure 38a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 8 | 2.0 mg/kg of HIF-2 alpha RNAi agent AD05971, linked at the 5' terminal end of the sense strand to a tridentate targeting group having three integrin targeting ligands of Structure 39-avb3, with an integrin targeting ligand of Structure 39a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 9 | 4.0 mg/kg of HIF-2 alpha RNAi agent AD05971, linked at the 5' terminal end of the sense strand to a tridentate targeting group having three integrin targeting ligands of Structure 39-avb3, with an integrin targeting ligand of Structure 39a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose. [(i)] The avb3 targeting ligands are linked to the 2'-O-propargyl nucleotides (represented by aAlk, gAlk, and | Single injection on day 1 |

TABLE 43-continued

| Dosing Groups of Mice in Example 22. | | |
|---|---|---|
| Group | RNAi Agent and Dose | Dosing Regimen |
| | uAlk in the modified sense strand sequence), which when viewed 5' → 3' on the sense strand sequence are at nucleotides 14, 16, 18, and 20 of the sense strand. | |
| 10 | 2.0 mg/kg of HIF-2 alpha RNAi agent AD05971, linked at the 5' terminal end of the sense strand to a tridentate targeting group having three integrin targeting ligands of Structure 40-avb3, with an integrin targeting ligand of Structure 40a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 11 | 4.0 mg/kg of HIF-2 alpha RNAi agent AD05971, linked at the 5' terminal end of the sense strand to a tridentate targeting group having three integrin targeting ligands of Structure 40-avb3, with an integrin targeting ligand of Structure 40a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 12 | 2.0 mg/kg of HIF-2 alpha RNAi agent AD05971, linked at the 5' terminal end of the sense strand to a tridentate targeting group having three integrin targeting ligands of Structure 41-avb3, with an integrin targeting ligand of Structure 41a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 13 | 4.0 mg/kg of HIF-2 alpha RNAi agent AD05971, linked at the 5' terminal end of the sense strand to a tridentate targeting group having the structure of integrin targeting ligand Structure 41-avb3, having a Structure 41a-avb3 linked internally at the 2' position of each of nucleotides 2, 4, 6, and 8 (3'→ 5') from the first nucleotide that forms a base pair with the antisense strand[(i)], and further linked at the 3' terminal end of the sense strand to PK enhancer Mal-C18-diacid, formulated in isotonic glucose.<br>[(i)] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval).

TABLE 44

Average Relative Hif2α mRNA Expression at Sacrifice in Example 22.

| Group ID | Average Relative huHIF2α mRNA Expression | Low (error) | High (error) |
|---|---|---|---|
| Group 1 (isotonic glucose) | 1.000 | 0.247 | 0.327 |
| Group 2 (2.0 mg/kg RNAi agent-tridentate integrin targeting ligand of Structure 2a, three internal ligands of Structure 2a, and Mal-C18-diacid) | 0.286 | 0.037 | 0.043 |
| Group 3 (4.0 mg/kg RNAi agent-tridentate integrin targeting ligand of Structure 2a, three internal ligands of Structure 2a, and Mal-C18-diacid) | 0.263 | 0.035 | 0.040 |
| Group 6 (2.0 mg/kg RNAi agent-tridentate integrin targeting ligand of Structure 38a, three internal ligands of Structure 38a, and Mal-C18-diacid) | 0.655 | 0.050 | 0.054 |
| Group 7 (4.0 mg/kg RNAi agent-tridentate integrin targeting ligand of Structure 38a, three internal ligands of Structure 38a, and Mal-C18-diacid) | 0.488 | 0.042 | 0.046 |
| Group 8 (2.0 mg/kg RNAi agent-tridentate integrin targeting ligand of Structure 39a, three internal ligands of Structure 39a, and Mal-C18-diacid) | 0.609 | 0.065 | 0.073 |
| Group 9 (4.0 mg/kg RNAi agent-tridentate integrin targeting ligand of Structure 39a, three internal ligands of Structure 39a, and Mal-C18-diacid) | 0.518 | 0.050 | 0.055 |

TABLE 44-continued

Average Relative Hif2α mRNA Expression at Sacrifice in Example 22.

| Group ID | Average Relative huHIF2α mRNA Expression | Low (error) | High (error) |
|---|---|---|---|
| Group 10 (2.0 mg/kg RNAi agent-tridentate integrin targeting ligand of Structure 40a, three internal ligands of Structure 40a, and Mal-C18-diacid) | 0.805 | 0.113 | 0.132 |
| Group 11 (4.0 mg/kg RNAi agent-tridentate integrin targeting ligand of Structure 40a, three internal ligands of Structure 40a, and Mal-C18-diacid) | 0.738 | 0.091 | 0.104 |
| Group 12 (2.0 mg/kg RNAi agent-tridentate integrin targeting ligand of Structure 41a, three internal ligands of Structure 41a, and Mal-C18-diacid) | 0.978 | 0.082 | 0.090 |
| Group 13 (4.0 mg/kg RNAi agent-tridentate integrin targeting ligand of Structure 41a, three internal ligands of Structure 41a, and Mal-C18-diacid) | 0.779 | 0.106 | 0.123 |

As shown in Table 44 above, each of the Hif2a RNAi agent-integrin targeting ligand conjugates showed a reduction in mRNA expression in mice compared to control.

Example 23. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 1 herein. The RNAi agents had the respective modified nucleotide sequences set forth in Example 2 herein and were designed to target Hif2a (EPAS1).

On study day 1, kidney tumor bearing mice were dosed via tail vein injection according to the following dosing Groups:

TABLE 45

Dosing Groups of Mice in Example 23.

| Group | RNAi Agent and Dose | Dosing Regimen |
|---|---|---|
| 1 | Saline (0.9%) (no RNAi agent) | Single injection on day 1 |
| 2 | 2.5 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with the antisense strand[i], and further linked at the 3' terminal end of the sense strand to PD modulator Mal-C18-diacid, formulated in isotonic glucose.<br>[i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 3 | 5.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→5') from the first nucleotide that forms a base pair with | Single injection on day 1 |

TABLE 45-continued

| Dosing Groups of Mice in Example 23. | | |
|---|---|---|
| Group | RNAi Agent and Dose | Dosing Regimen |
| | the antisense strand[i], and further linked at the 3' terminal end of the sense strand to PD modulator Mal-C18-diacid, formulated in isotonic glucose. [i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | |
| 4 | 10.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→ 5') from the first nucleotide that forms a base pair with the antisense strand[i], and further linked at the 3' terminal end of the sense strand to PD modulator Mal-C18-diacid, formulated in isotonic glucose. [i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16,18, and 20 of the sense strand. | Single injection on day 1 |
| 5 | 2.5 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→ 5') from the first nucleotide that forms a base pair with the antisense strand[i], and further linked at the 3' terminal end of the sense strand to PD modulator Mal-C18-diacid, formulated in isotonic glucose. [i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 6 | 5.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→ 5') from the first nucleotide that forms a base pair with the antisense strand[i], and further linked at the 3' terminal end of the sense strand to PD modulator Mal-C18-diacid, formulated in isotonic glucose. [i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 7 | 10.0 mg/kg of HIF-2 alpha RNAi agent AD05971, linked at the 5' terminal end of the sense strand to a tridentate targeting group having three integrin targeting ligands of Structure 2.11a, with an integrin targeting ligand of Structure 2.11a linked internally at the 2' position of each of nucleotides 2, 4, 6, and 8 (3'→ 5') from the first nucleotide that forms a base pair with the antisense strand[i], and further linked at the 3' terminal end of the sense strand to PD modulator Mal-C18-diacid, formulated in isotonic glucose. [i] The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 8 | 2.5 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→ 5') from the first nucleotide that forms a base pair with the antisense strand[i], and further linked at the 3' | Single injection on day 1 |

TABLE 45-continued

Dosing Groups of Mice in Example 23.

| Group | RNAi Agent and Dose | Dosing Regimen |
|---|---|---|
| | terminal end of the sense strand to PD modulator Mal-C18-diacid, formulated in isotonic glucose. (i) The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | |
| 9 | 5.0 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→ 5') from the first nucleotide that forms a base pair with the antisense strand(i), and further linked at the 3' terminal end of the sense strand to PD modulator Mal-C18-diacid, formulated in isotonic glucose. (i) The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |
| 10 | 10.0 mg/kg of HIF-2 alpha RNAi agent AD05971, linked at the 5' terminal end of the sense strand to a tridentate targeting group having three integrin targeting ligands of Structure 2a, with an integrin targeting ligand of Structure 2a linked internally at the 2' position of each of nucleotides 2, 4, 6, and 8 (3'→ 5') from the first nucleotide that forms a base pair with the antisense strand(i), and further linked at the 3' terminal end of the sense strand to PD modulator Mal-C18-diacid, formulated in isotonic glucose. (i) The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 of the sense strand. | Single injection on day 1 |

Four (4) tumor bearing mice were dosed in each Group (n=4), except for Group 4 which only had three (3) mice as one mouse was deemed to have a faulty injection. Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval).

TABLE 46

Average Relative Hif2α mRNA Expression at Sacrifice in Example 23.

| Group ID | Average Relative huHIF2α mRNA Expression | Low (error) | High (error) |
|---|---|---|---|
| Group 1 (isotonic glucose) | 1.000 | 0.180 | 0.220 |
| Group 2 (2.5 mg/kg RNAi agent-tridentate integrin targeting ligand of Structure 2.11a, three internal ligands of Structure 2.11a, and Mal-C18-diacid) | 0.278 | 0.068 | 0.091 |
| Group 3 (5.0 mg/kg RNAi agent-tridentate integrin targeting ligand of Structure 2.11a, three internal ligands of Structure 2.11a, and Mal-C18-diacid) | 0.229 | 0.062 | 0.086 |

TABLE 46-continued

Average Relative Hif2α mRNA Expression at Sacrifice in Example 23.

| Group ID | Average Relative huHIF2α mRNA Expression | Low (error) | High (error) |
|---|---|---|---|
| Group 4 (10.0 mg/kg RNAi agent-tridentate integrin targeting ligand of Structure 2.11a, three internal ligands of Structure 2.11a, and Mal-C18-diacid) | 0.202 | 0.014 | 0.015 |
| Group 5 (2.5 mg/kg RNAi agent-tridentate integrin targeting ligand of Structure 2.11a, three internal ligands of Structure 2.11a, and Mal-C18-diacid) | 0.324 | 0.035 | 0.040 |
| Group 6 (5.0 mg/kg RNAi agent-tridentate integrin targeting ligand of Structure 2.11a, three internal ligands of Structure 2.11a, and Mal-C18-diacid) | 0.308 | 0.018 | 0.019 |
| Group 7 (10.0 mg/kg RNAi agent-tridentate integrin targeting ligand of Structure 2.11a, three internal ligands of Structure 2.11a, and Mal-C18-diacid) | 0.197 | 0.041 | 0.052 |
| Group 8 (2.5 mg/kg RNAi agent-tridentate integrin targeting ligand of Structure 2a, three internal ligands of Structure 2a, and Mal-C18-diacid) | 0.218 | 0.048 | 0.062 |
| Group 9 (5.0 mg/kg RNAi agent-tridentate integrin targeting ligand of Structure 2a, three internal ligands of Structure 2a, and Mal-C18-diacid) | 0.160 | 0.065 | 0.109 |

TABLE 46-continued

| Average Relative Hif2α mRNA Expression at Sacrifice in Example 23. | | | |
|---|---|---|---|
| Group ID | Average Relative huHIF2α mRNA Expression | Low (error) | High (error) |
| Group 10 (10.0 mg/kg RNAi agent-tridentate integrin targeting ligand of Structure 2a, three internal ligands of Structure 2a, and Mal-C18-diacid) | 0.276 | 0.053 | 0.066 |

As shown in Table 46 above, each of the Hif2α RNAi agent-integrin targeting ligand conjugates showed a reduction in mRNA expression in mice compared to control.

Example 24. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice were dosed via tail vein injection according to the following dosing Groups:

TABLE 47

| Dosing Groups of Mice in Example 24. | | |
|---|---|---|
| Group | RNAi Agent and Dose | Dosing Regimen |
| 1 | Isotonic glucose (d5w (5% dextrose in water)) (no RNAi agent) | Single injection on day 1 |
| 2 | 7.5 mg/kg of Hif2α RNAi agent (AD04546) conjugated to a tridentate integrin targeting ligand of Structure 2a, and further including a C18-diacid moiety linked to the construct, formulated in isotonic glucose. | Single injection on day 1 |
| 6 | 7.5 mg/kg of Hif2α RNAi agent (AD04546) conjugated to a tridentate integrin targeting ligand of Structure 28a, and further including a Mal-C18-diacid moiety linked to the construct, formulated in isotonic glucose. | Single injection on day 1 |
| 7 | 7.5 mg/kg of Hif2α RNAi agent (AD04546) conjugated to a tridentate integrin targeting ligand of Structure 29a, and further including a Mal-C18-diacid moiety linked to the construct, formulated in isotonic glucose. | Single injection on day 1 |
| 8 | 7.5 mg/kg of Hif2α RNAi agent (AD04546) conjugated to a tridentate integrin targeting ligand of Structure 30a, and further including a Mal-C18-diacid moiety linked to the construct, formulated in isotonic glucose. | Single injection on day 1 |
| 9 | 7.5 mg/kg of Hif2α RNAi agent (AD04546) conjugated to a tridentate integrin targeting ligand of Structure 31a, and further including a Mal-C18-diacid moiety linked to the construct, formulated in isotonic glucose. | Single injection on day 1 |

The RNAi agents were synthesized having nucleotide sequences directed to target the human Hif2α gene, and included a functionalized amine reactive group ($NH_2$-$C_6$) at the 5' terminal end of the sense strand to facilitate conjugation to the integrin targeting ligands.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 4.

TABLE 48

Average Relative Hif2α mRNA Expression at Sacrifice in Example 24.

| Group ID | Average Relative huHIF2α mRNA Expression | Low (error) | High (error) |
|---|---|---|---|
| Group 1 (isotonic glucose) | 1.000 | 0.077 | 0.083 |
| Group 2 (7.5 mg/kg RNAi agent-tridentate integrin targeting ligand of Structure 2a, Mal-C18-diacid) | 0.456 | 0.113 | 0.150 |
| Group 6 (7.5 mg/kg RNAi agent-tridentate integrin targeting ligand of Structure 28a, Mal-C18-diacid) | 0.649 | 0.072 | 0.081 |
| Group 7 (7.5 mg/kg RNAi agent-tridentate integrin targeting ligand of Structure 29a, Mal-C18-diacid) | 0.426 | 0.054 | 0.062 |
| Group 8 (7.5 mg/kg RNAi agent-tridentate integrin targeting ligand of Structure 30a, Mal-C18-diacid) | 0.699 | 0.064 | 0.070 |
| Group 9 (7.5 mg/kg RNAi agent-tridentate integrin targeting ligand of Structure 31a, Mal-C18-diacid) | 0.580 | 0.069 | 0.079 |

As shown in Table 48 above, each of the Hif2α RNAi agent-integrin targeting ligand conjugates showed a reduction in mRNA expression compared to control.

Embodiments

Embodiment 1. An RNAi agent for inhibiting expression of a HIF-2 alpha (EPAS1) gene, comprising:

(i) an antisense strand comprising at least 17 contiguous nucleotides differing by 0 or 1 nucleotides from any one of the sequences provided in Table 3;

(ii) a sense strand comprising a nucleotide sequence that is at least partially complementary to the antisense strand; and (iii) one or more targeting ligands.

Embodiment 2. The RNAi agent of embodiment 1, wherein the antisense strand comprises nucleotides 2-18 of any one of the sequences provided in Table 3.

Embodiment 3. The RNAi agent of embodiment 1 or embodiment 2, wherein the sense strand comprises a nucleotide sequence of at least 17 contiguous nucleotides differing by 0 or 1 nucleotides from any one of the sense strand sequences provided in Table 4, 4.1, 4.2, or 4.3, and wherein the sense strand has a region of at least 85% complementarity over the 17 contiguous nucleotides to the antisense strand.

Embodiment 4. The RNAi agent of any one of embodiments 1-3, wherein all or substantially all of the nucleotides of the sense strand of the RNAi agent, the antisense strand of the RNAi agent, or both the sense strand and the antisense strand of the RNAi agent, are modified nucleotides.

Embodiment 5. The RNAi agent of embodiment 4, wherein at least one modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate deoxyribonucleotide, 2'-O-propargyl-modified nucleotide, 2'-O-triazole-modified nucleotides, and 3'-O-methyl nucleotide.

Embodiment 6. The RNAi agent of embodiment 5, wherein each modified nucleotide is independently selected from the group consisting of: 2'-O-methyl nucleotides, 2'-fluoro nucleotides, and 2'-O-triazole-modified nucleotides.

Embodiment 7. The RNAi agent of any one of embodiments 1-6, wherein the antisense strand comprises the nucleotide sequence of any one of the modified antisense strand sequences provided in Table 3.

Embodiment 8. The RNAi agent of any one of embodiments 1-7, wherein the sense strand comprises the nucleotide sequence of any of the modified sense strand sequences provided in Table 4.

Embodiment 9. The RNAi agent of any one of embodiments 1-8, wherein the antisense strand comprises the nucleotide sequence of any one of the modified sequences provided in Table 3 and the sense strand comprises the nucleotide sequence of any one of the modified sequences provided in Table 4, Table 4.1, Table 4.2, or Table 4.3.

Embodiment 10. The RNAi agent of any one of embodiments 1-9, wherein the antisense strand comprises nucleotides 2-18 of usUfsusCfaUfgAfaAfuCfgUfuAfcGfuUfsg (SEQ ID NO: 30) wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively.

Embodiment 11. The RNAi agent of embodiment 10, wherein the antisense strand comprises the sequence of usUfsusCfaUfgAfaAfuCfgUfuAfcGfuUfsg (SEQ ID NO: 30) wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively.

Embodiment 12. The RNAi agent of embodiment 1, wherein the sense strand comprises nucleotides 2-18 of the sequence of CAACGUAACGAUUUCAUGAAA (SEQ ID NO: 428).

Embodiment 13. The RNAi agent of embodiment 1, wherein the sense strand comprises the sequence of Y-(NH-C6) scsaacguaaCfGfAfuuu$^{Z}$ca$^{Z}$ug$^{Z}$aa$^{Z}$sa(invAb)(6-S)-X (SEQ ID NO: 761) wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively, and each Z independently represents a pharmacological moiety, Y-(NH-C6)s represents:

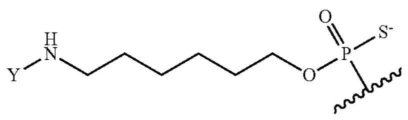

(invAb) represents:

linkage towards 5' end of oligonucleotide

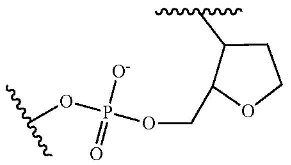 [SMILES: *OP(=O)([O-])OCC1OCCC1*]

linkage towards 3' end of oligonucleotide and (6-S) represents:

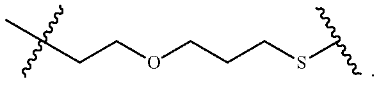 [SMILES: *CCOCCCS*]

Embodiment 14. The RNAi agent of any one of embodiments 12 or 13, wherein the antisense strand is at least substantially complementary to the sense strand.

Embodiment 15. The RNAi agent of any of embodiments 1-14, wherein the nucleotides of the sense strand consist of the sequence of Y-(NH-C6)scsaacguaaCfGfAfuuu$^{Z}$ca$^{Z}$ug$^{Z}$aa$^{Z}$sa(invAb)(6-S)-X (SEQ ID NO: 761) wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively, and each Z independently represent a pharmacological moiety, Y-(NH-C6)s represents:

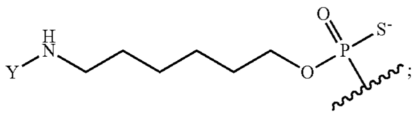

(invAb) represents:

linkage towards 5' end of oligonucleotide

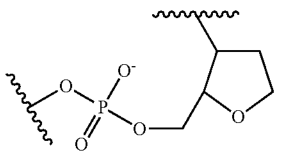 [SMILES: *OP(=O)([O-])OCC1OCCC1*]

linkage towards 3' end of oligonucleotide and (6-S) represents:

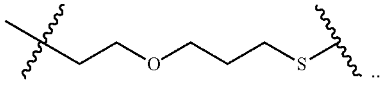 [SMILES: *CCOCCCS*]

Embodiment 16. The RNAi agent of embodiment 15 wherein the nucleotides of the antisense strand consist of the sequence of usUfsusCfaUfgAfaAfuCfgUfuAfcGfuUfsg (SEQ ID NO: 30) wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively.

Embodiment 17. The RNAi agent of any one of embodiments 1-16, wherein the sense strand of the RNAi agent is linked to at least one targeting ligand.

Embodiment 18. The RNAi agent of embodiment 17, wherein the targeting ligand comprises a compound having affinity for an integrin.

Embodiment 19. The RNAi agent of embodiment 18, wherein the targeting ligand comprises a compound that has affinity for integrin alpha-v-beta-3, alpha-v-beta-5, or both alpha-v-beta-3 and alpha-v-beta-5.

Embodiment 20. The RNAi agent of embodiment 19, wherein the targeting ligand is a compound of the formula:

(Formula I)

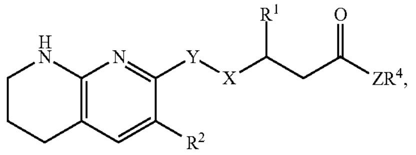

wherein,

X is —C($R^3$)$_2$—, —N$R^3$—,

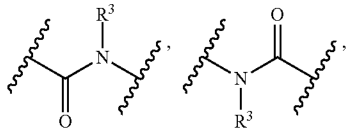

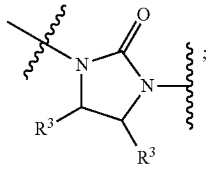

Y is optionally substituted alkylene with 1 to 8 carbon atoms in the alkylene chain;

Z is O, N$R^3$, or S;

$R^1$ is optionally substituted aryl, optionally substituted heteroaryl, optionally substituted heterocyclyl, optionally substituted cycloalkyl or $R^1$ comprises the RNAi agent;

$R^2$ is H, optionally substituted alkyl, or $R^2$ comprises the RNAi agent; each instance of $R^3$ is independently selected from the group consisting of H and optionally substituted alkyl, or $R^3$ comprises the RNAi agent;

$R^4$ is H or optionally substituted alkyl; and wherein at least one of Y, $R^1$, $R^2$, any instance of $R^3$, and $R^4$ comprises the RNAi agent.

Embodiment 21. The RNAi agent of embodiment 20, wherein the targeting ligand is selected from:

(Structure 1a)
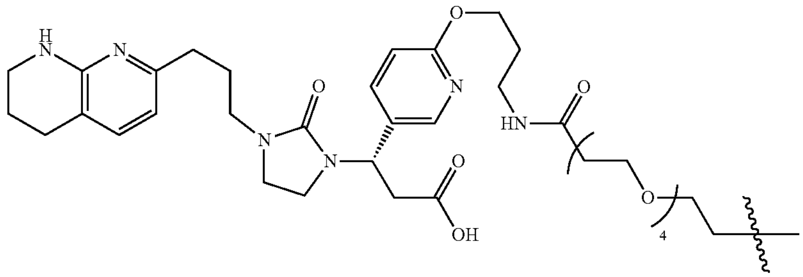
;
(Structure 2a)
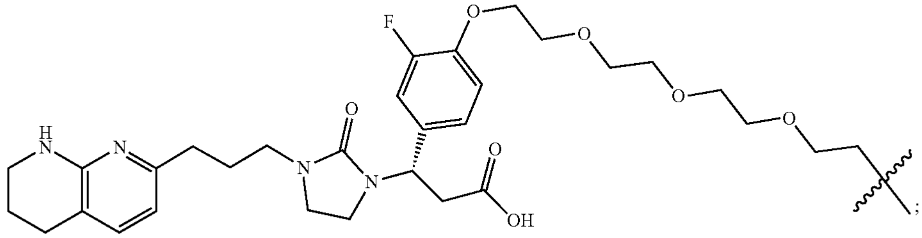
;
(Structure 2.1a)
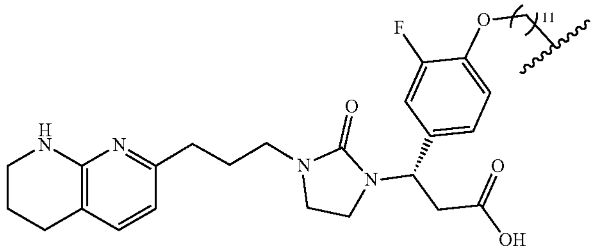
;
(Structure 2.2a)
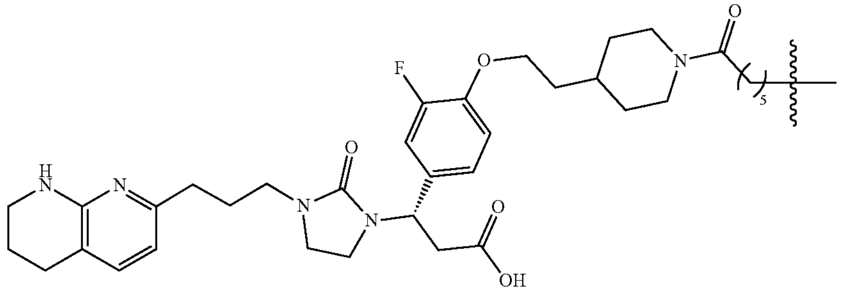
;
(Structure 2.3a)
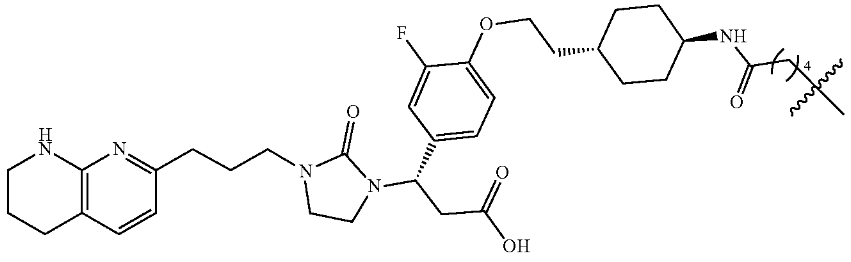
;

-continued
(Structure 2.4a)
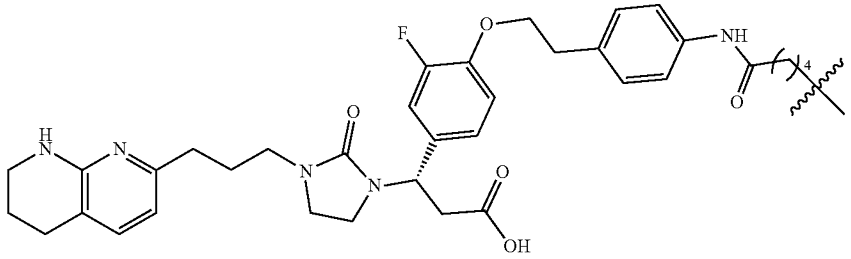
;
(Structure 2.5a)
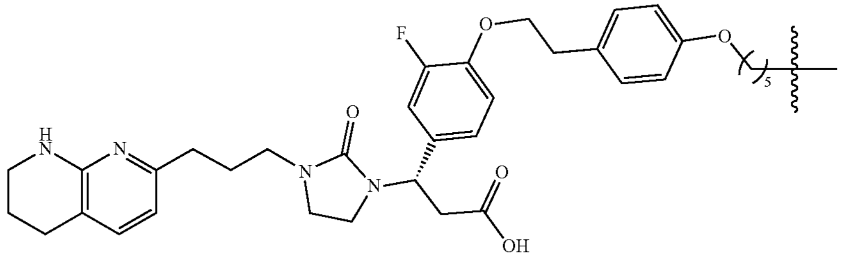
;
(Structure 2.6a)
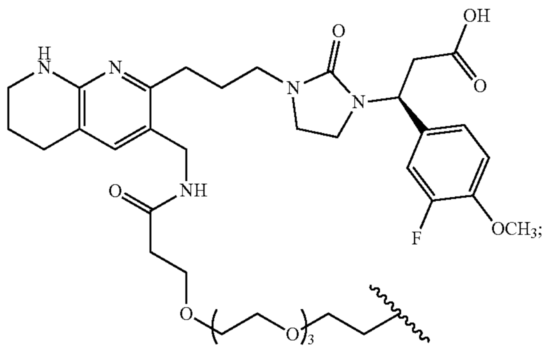
;
(Structure 2.7a)
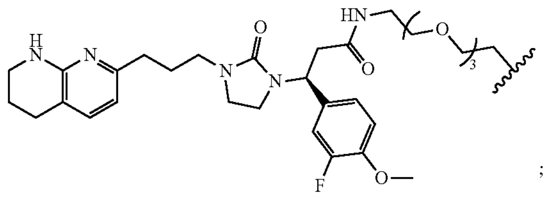
;
(Structure 2.8a)
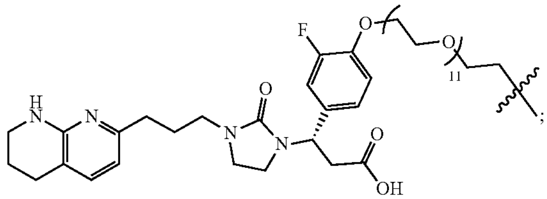
;
(Structure 2.9a)
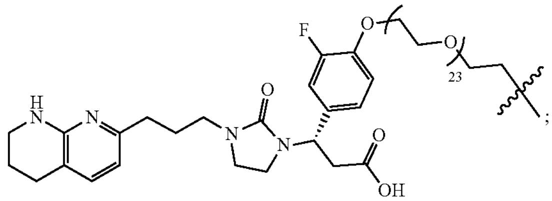
;
(Structure 2.10a)
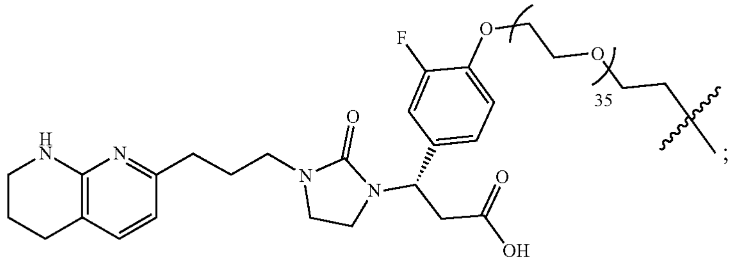
;
(Structure 2.11a)
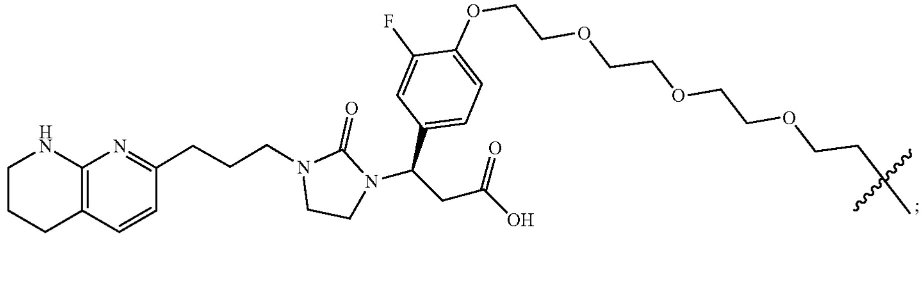
;

-continued
(Structure 28a)
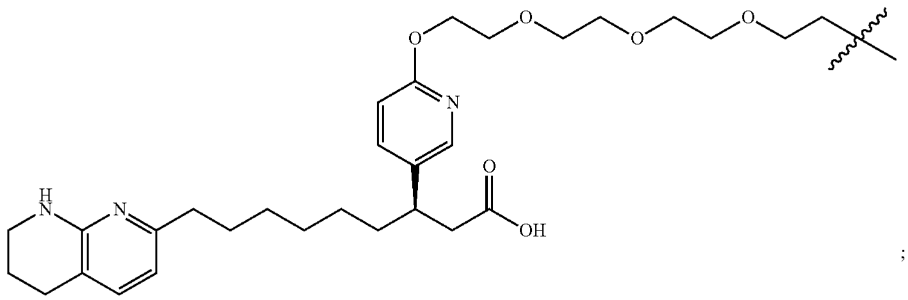
;
(Structure 29a)
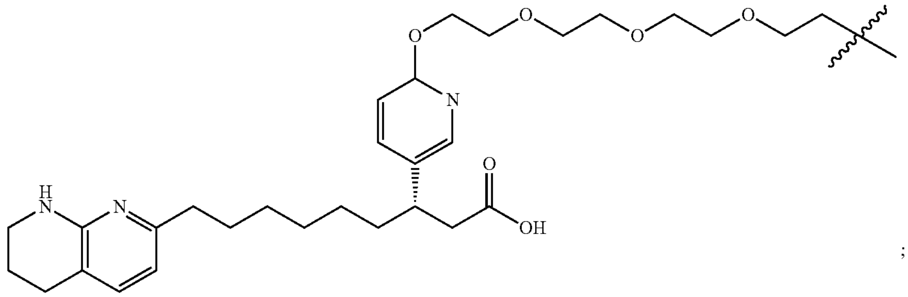
;
(Structure 30a)
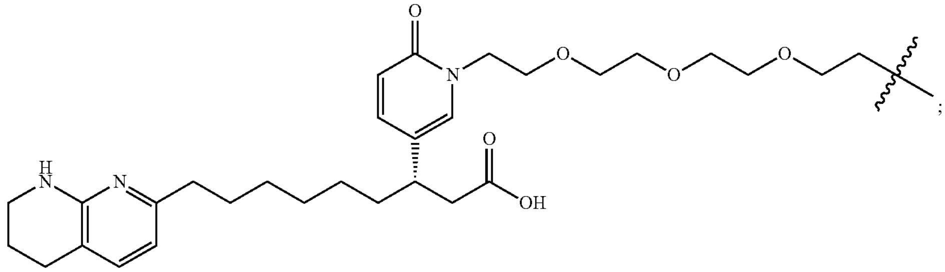
;
(Structure 31a)
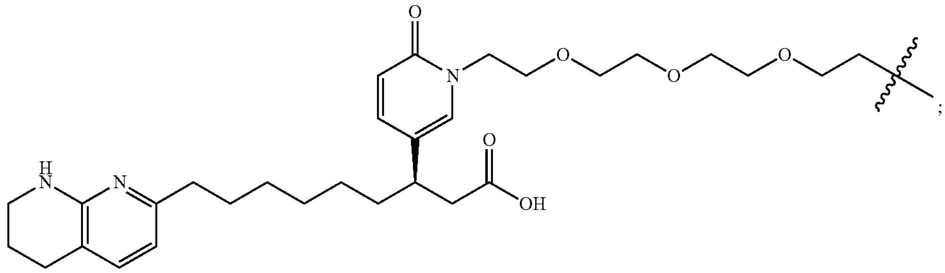
;

-continued
(Structure 32a)
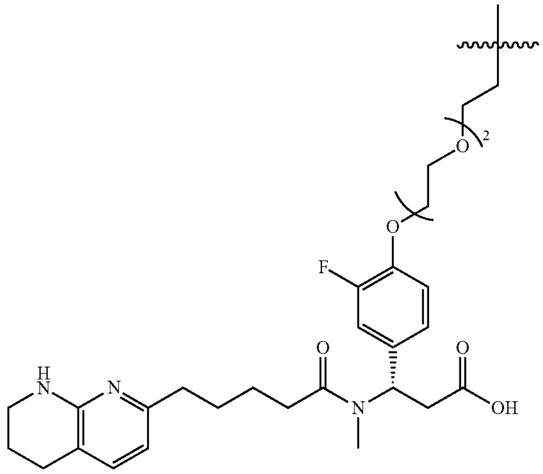
;
(Structure 33a)
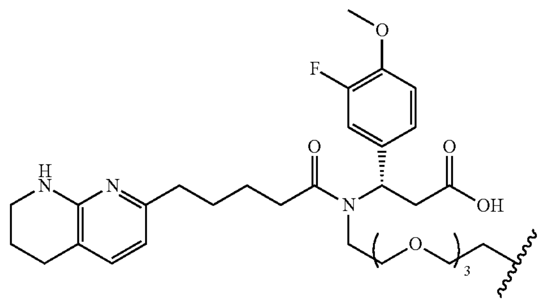
;
(Structure 34a)
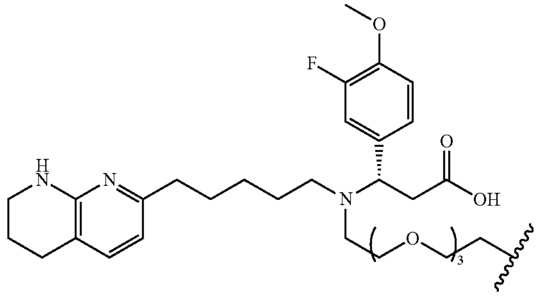
;
(Structure 36a)
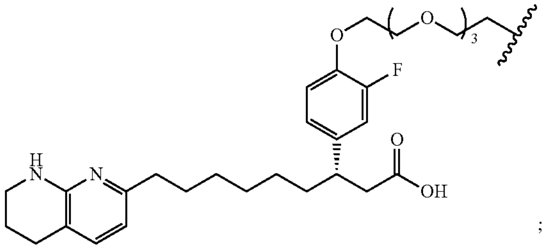
;
(Structure 37a)
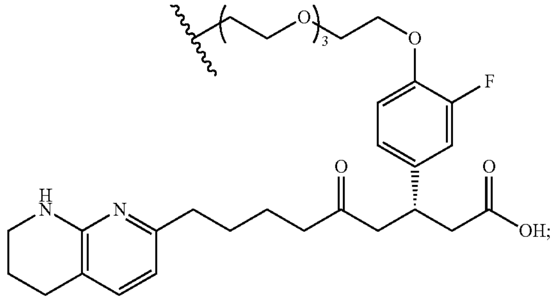
;
(Structure 38a)
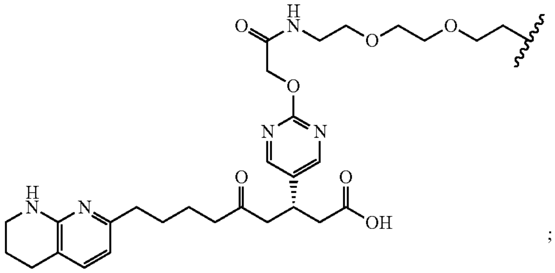
;
(Structure 39a)
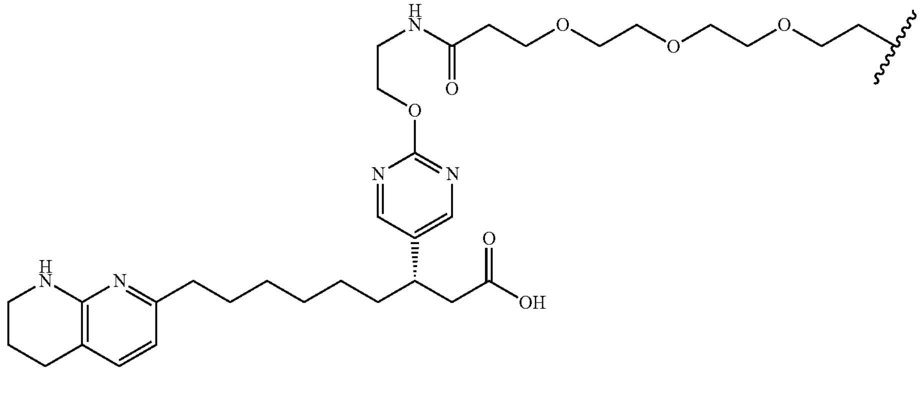
;

-continued (Structure 40a)

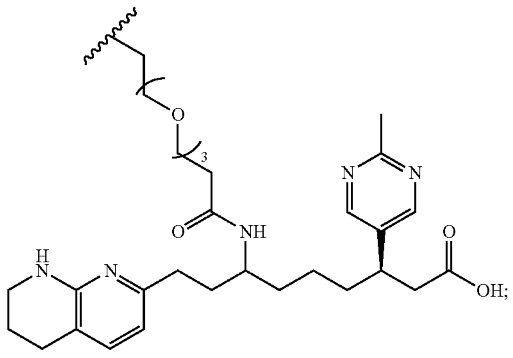

and (Structure 41a)

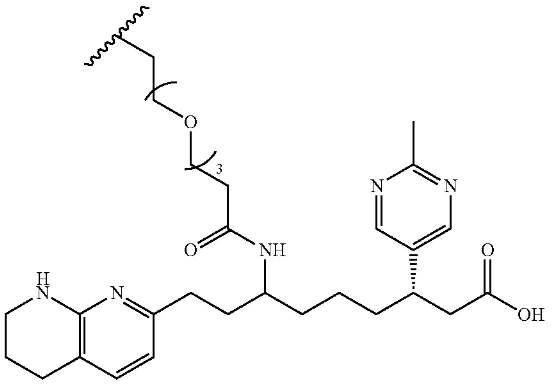

wherein  indicates the point of connection to the HIF-2 alpha RNAi agent.

Embodiment 22. The RNAi agent of any one of embodiments 1-21, wherein the targeting ligand is of the structure (Structure 2a)

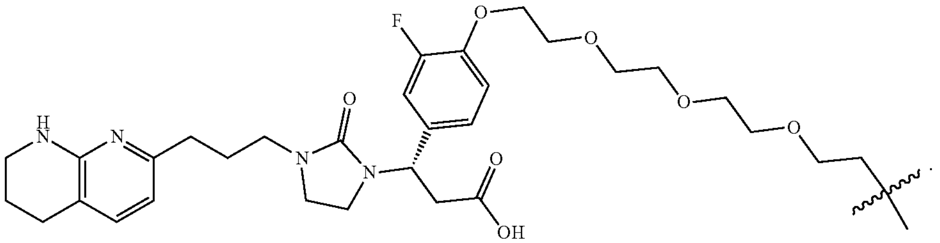

Embodiment 23. The RNAi agent of any one of embodiments 1-22, further comprising a pharmacokinetic (PK) enhancer.

Embodiment 24. The RNAi agent of embodiment 23, wherein the PK enhancer comprises the formula:

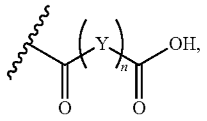

wherein Y is an optionally substituted saturated or unsaturated aliphatic chain and n is an integer from 5-25.

Embodiment 25. The RNAi agent of embodiment 24, wherein the PK enhancer comprises

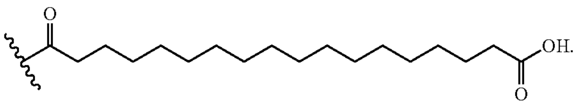 [SMILES: *C(=O)CCCCCCCCCCCCCCCCC(=O)O]

Embodiment 26. The RNAi agent of embodiment 23, wherein the PK enhancer is selected from the group consisting of:

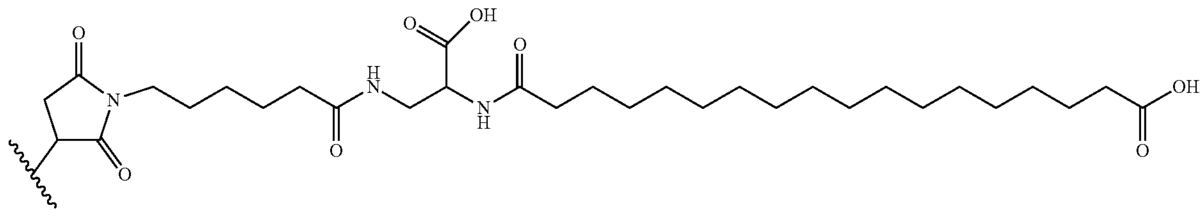

Mal-$C_{18}$-diacid

-continued
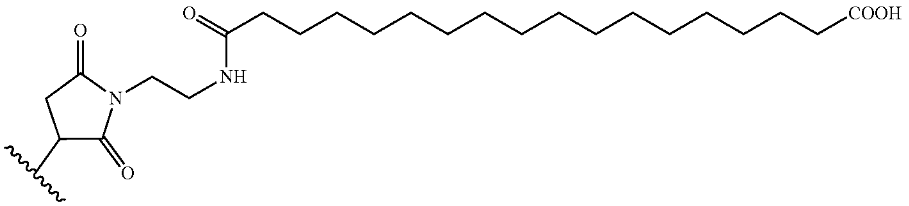
Mal-$C_{18}$-acid
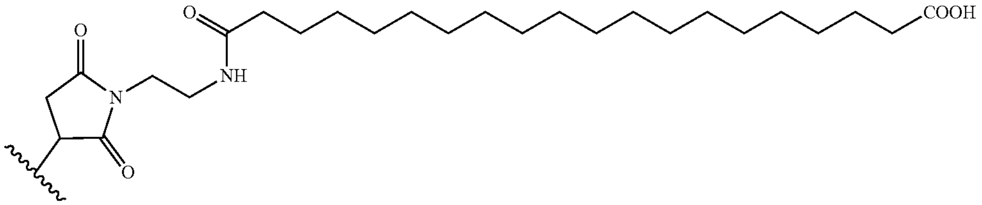
Mal-$C_{20}$-acid
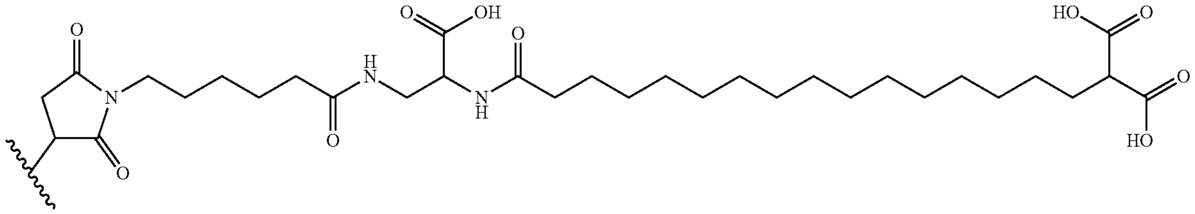
Mal-$C_{18}$-triacid
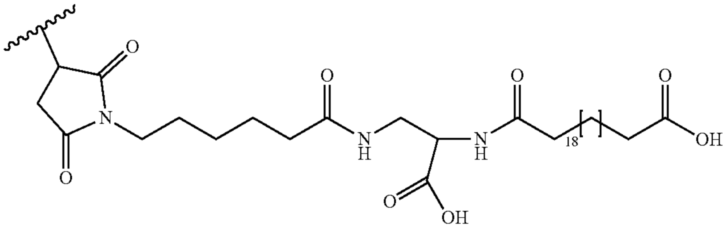
Mal-$C_{22}$-diacid
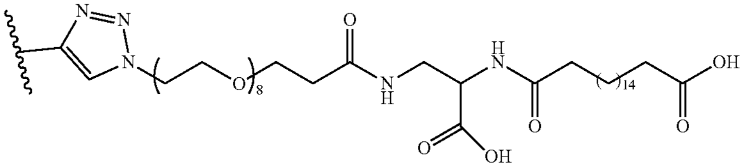
$C_{18}$-diacid-$N_3$
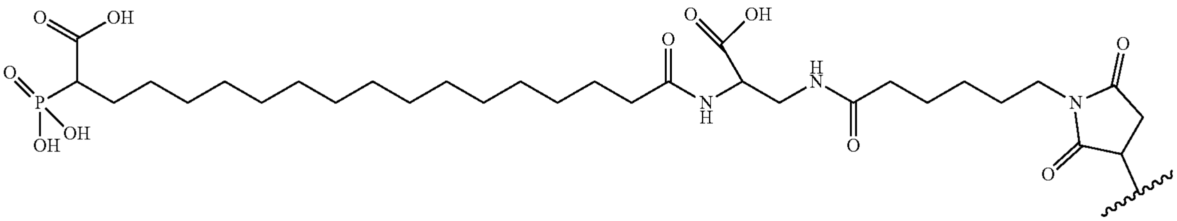
Mal-$C_{18}$-diacid-$N_3$
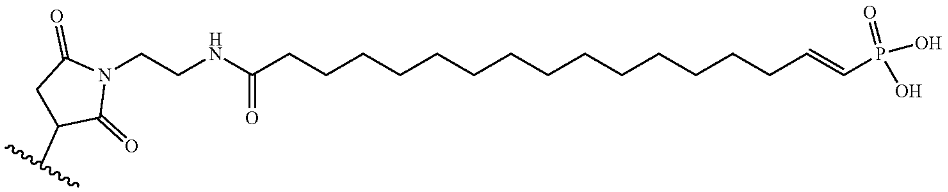
Mal-$C_{17}$-$PO_3$ -continued
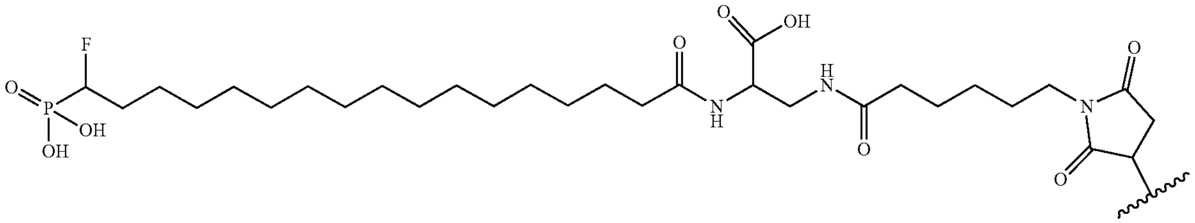
Mal-$C_{17}$-Fluoro-$PO_3$ Monoacid
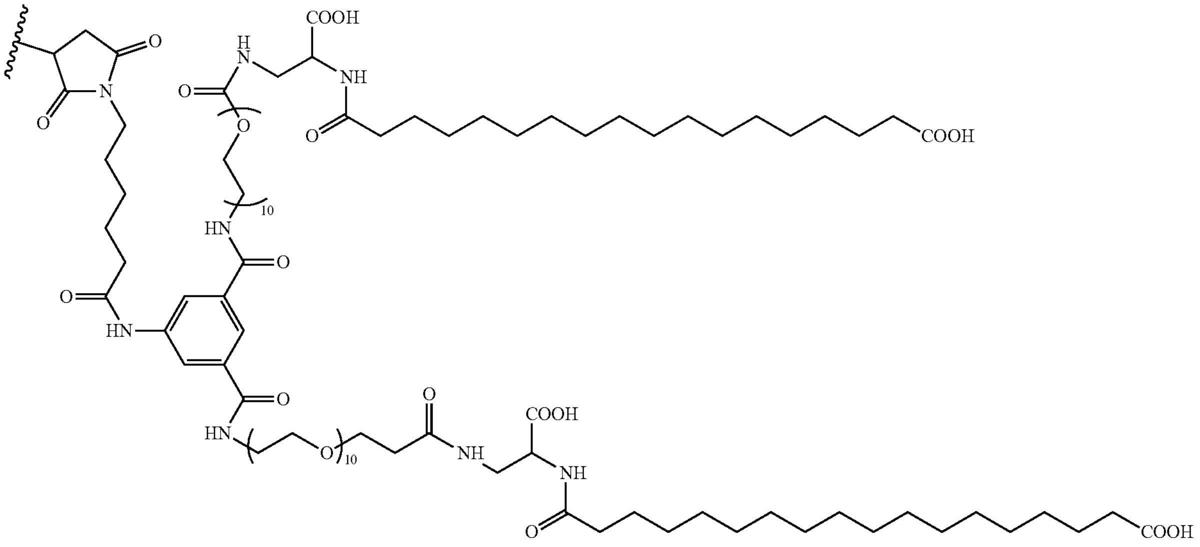
Mal-BisC18-diacid
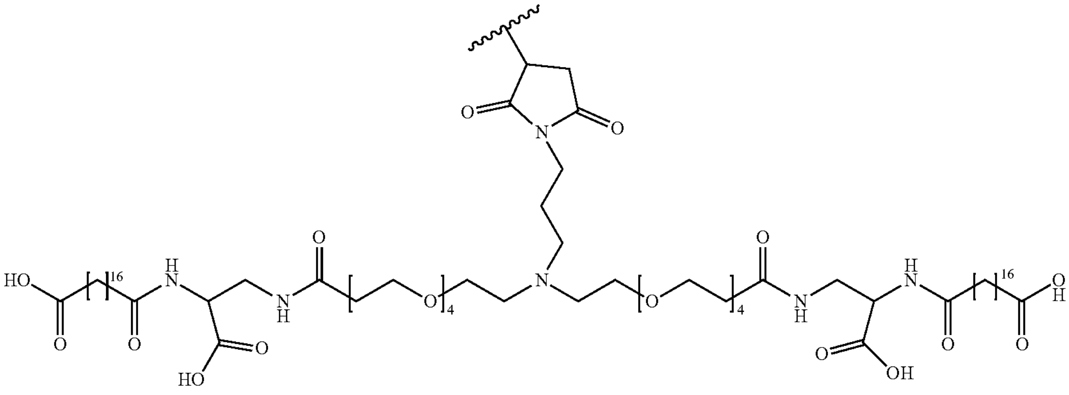
Dual C18-diacid
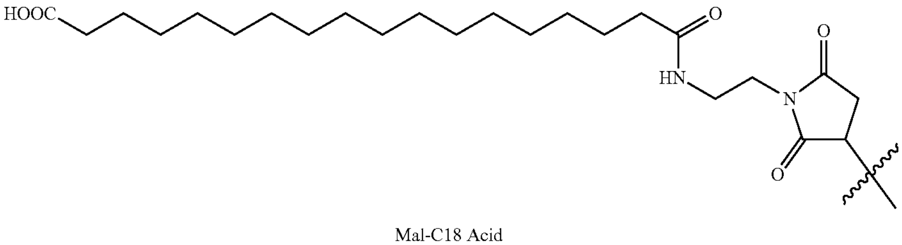
Mal-C18 Acid -continued
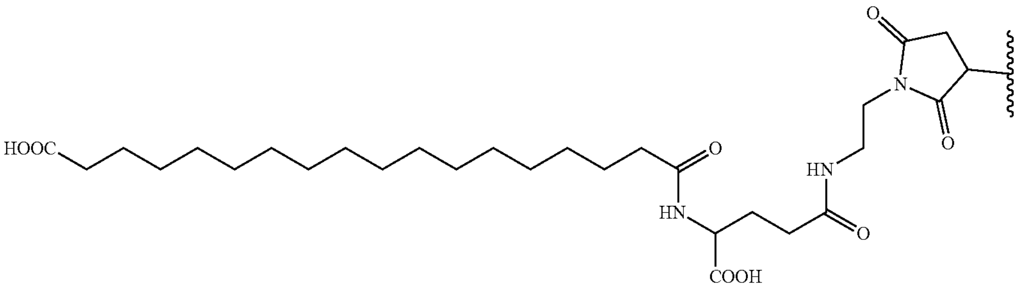
Mal-C18 Diacid
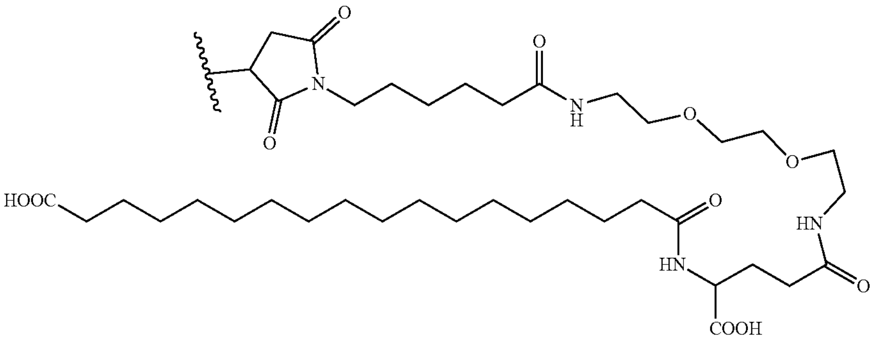
Mal-C6-PEG2-C18-Diacid
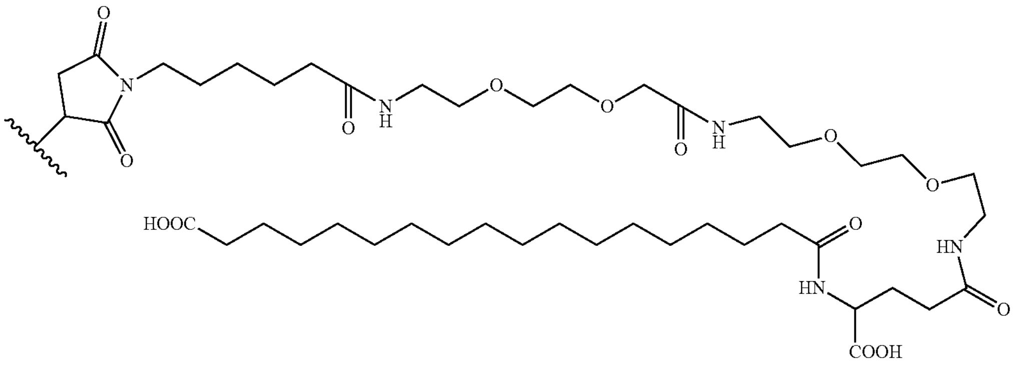
Mal-C6-PEG4-C18-Diacid
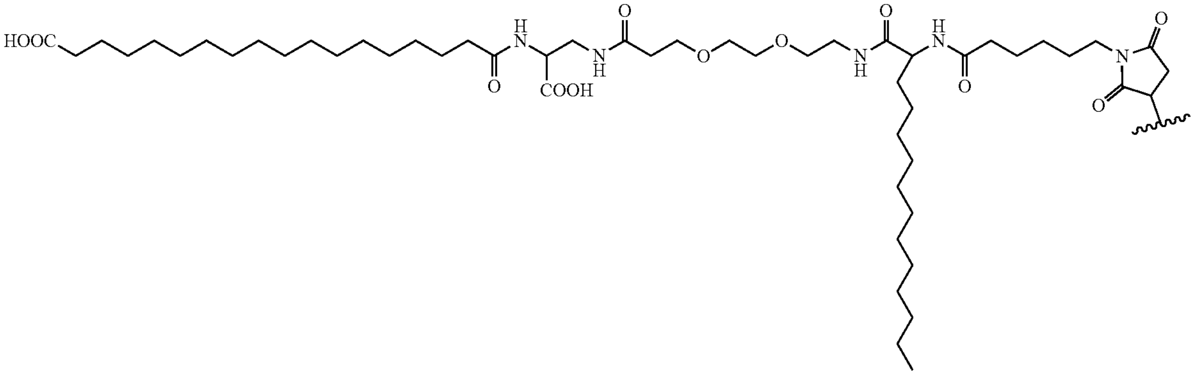
Mal-C6-C12-PEG2-C18 Diacid -continued
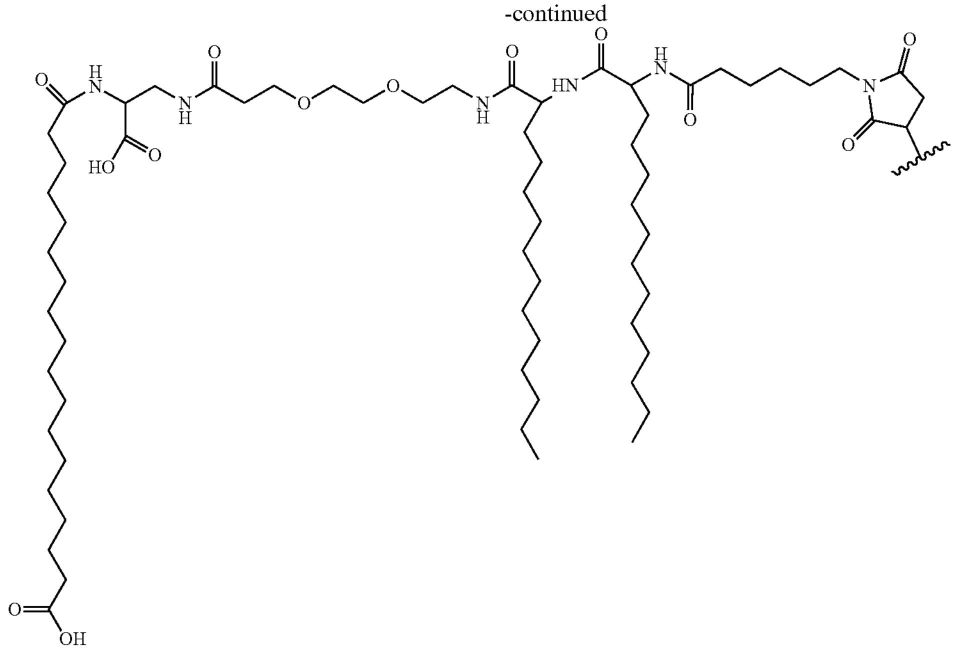
Mal-C6-C12-C12-PEG2-C18 Diacid
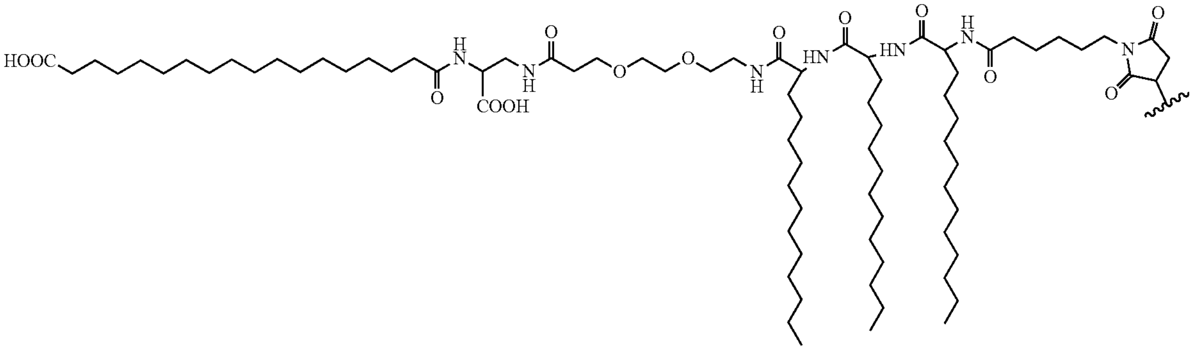
Mal-C6-C12-C12-C12-PEG2-C18-Diacid
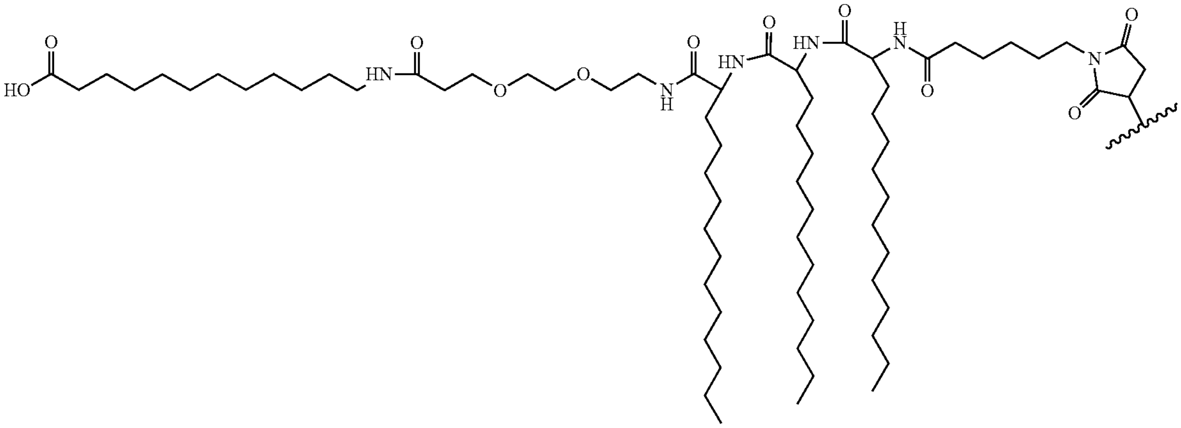
Mal-C6-C12-C12-C12-PEG2-C12 Diacid
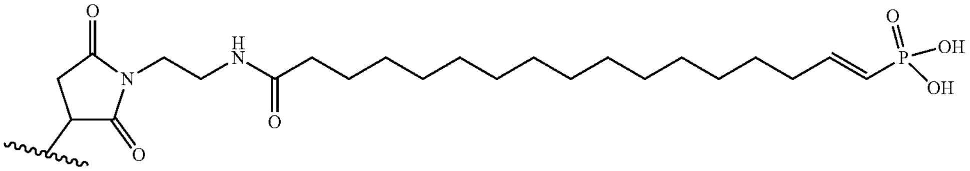
Mal-$C_{17}$-vinyl-$PO_3$ -continued

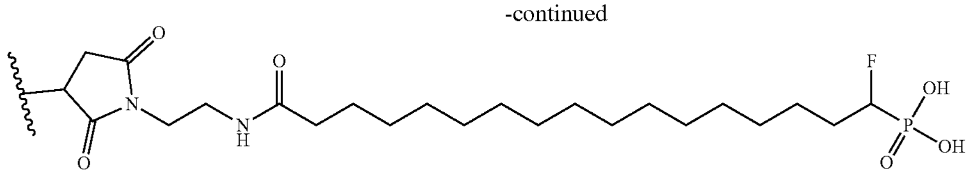

Mal-$C_{17}$-Fluoro-$PO_3$

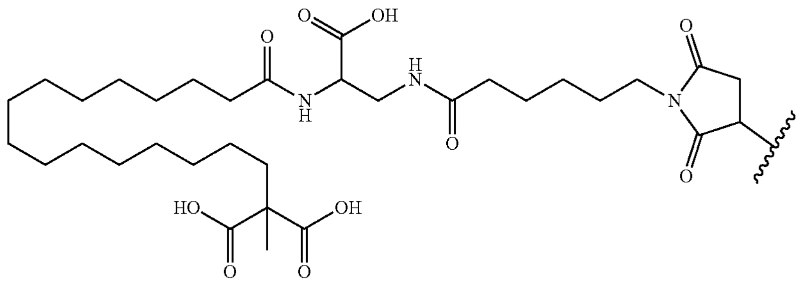

Mal-$C_{18}$-methyl-triacid

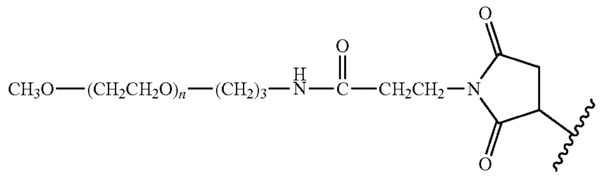

PEG40K,
wherein n is an integer, and the molecular weight of the PEG groups is about 40 kilodaltons

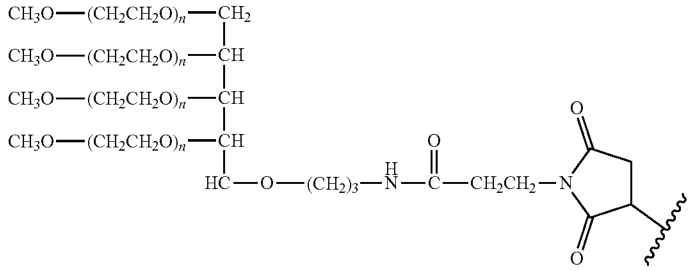

PEG40K (4-arm),
wherein n is an integer, and the molecular weight of the PEG groups is about 40 kilodaltons wherein indicates the point of attachment to the RNAi agent.

Embodiment 27. The RNAi agent of any one of embodiments 1-26, wherein the targeting ligand is linked to the sense strand.

Embodiment 28. The RNAi agent of any one of embodiments 23-27, wherein the PK enhancer is linked to the sense strand.

Embodiment 29. The RNAi agent of any one of embodiments 1-28, wherein the RNAi agent is linked to 2 to 10 targeting ligands.

Embodiment 30. The RNAi agent of any one of embodiments 1-29, wherein the RNAi agent is linked to a targeting group comprising two or more targeting ligands at the 5' terminal end of the sense strand.

Embodiment 31. The RNAi agent of any one of embodiments 1-30, wherein at least one targeting ligand is linked to the 5' terminal end of the sense strand, and at least one targeting ligand is linked to a non-terminal nucleotide of the sense strand.

Embodiment 32. The RNAi agent of any one of embodiments 1-31, linked to two or more targeting ligands, wherein the two or more targeting ligands are linked at a branch point to form a targeting group.

Embodiment 33. The RNAi agent of embodiment 32, wherein the targeting group comprises three targeting ligands and the targeting group is of the formula:

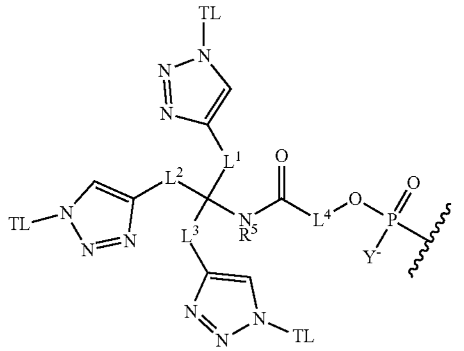

wherein, $L^1$, $L^2$ and $L^3$ are each independently linkers comprising an optionally substituted alkylene;

$L^4$ is a linker comprising an optionally substituted alkylene, optionally substituted aryl, or optionally substituted cycloalkyl;

$R^5$ is H or optionally substituted alkyl;

TL is a targeting ligand; and

Y is O or S.

Embodiment 34. The RNAi agent of embodiment 33, wherein the targeting group is of the formula:

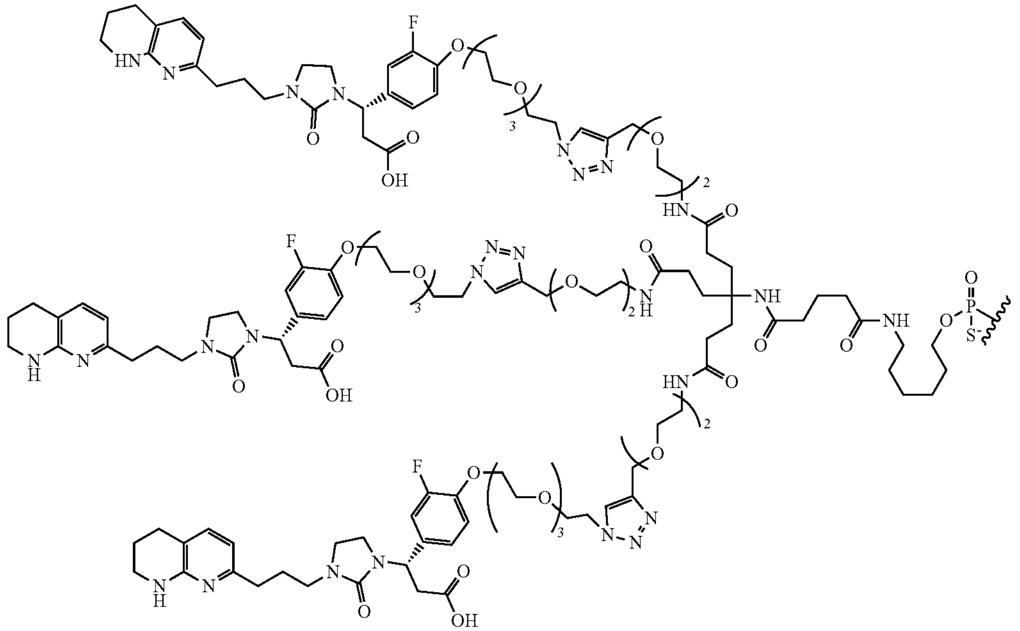

Embodiment 35. The RNAi agent of any one of embodiments 1-34, wherein a tridentate targeting group is linked to the 5' terminal end of the sense strand, and wherein at least two additional targeting ligands are linked to one or more nucleotides of the sense strand.

Embodiment 36. The RNAi agent of embodiment 31 or 35, wherein at least 10 nucleotides are positioned between the targeting group located on the 5' end of the sense strand and the targeting ligand located on the sense strand.

Embodiment 37. The RNAi agent of any one of embodiments 1-36, wherein at least one targeting ligand is linked to the 2' position of a nucleotide of the sense strand of the RNAi agent.

Embodiment 38. The RNAi agent of any one of embodiments 23-37, wherein the PK enhancer is linked to the 3' terminal end of the sense strand.

Embodiment 39. The RNAi agent of any one of embodiments 1-38, wherein 5 to 8 targeting ligands are linked to the sense strand.

Embodiment 40. The RNAi agent of embodiment 39, wherein the sense strand of the RNAi agent is linked to at least one tridentate targeting group and at least two targeting ligands linked to one or more nucleotides of the sense strand.

Embodiment 41. The RNAi agent of embodiment 40, wherein the sense strand of the RNAi agent is linked to (i) a tridentate targeting group at the 5' terminal end of the sense strand, and (ii) 2 to 4 targeting ligands linked to nucleotides other than the 5' terminal nucleotide of the sense strand.

Embodiment 42. The RNAi agent of any one of embodiments 29-41, wherein the targeting ligands are linked to the sense strand as follows: (i) a tridentate targeting group comprising 3 individual targeting ligands is located at the 5' terminal end of the sense strand; and (ii) the additional targeting ligands are individual targeting ligands linked to individual nucleotides of the sense strand that are at least 10 nucleotides away from the 5' terminal end of the sense strand.

Embodiment 43. The RNAi agent of embodiment 42, wherein the targeting ligands are linked to the sense strand nucleotides located at positions 2, 4, 6, and 8 (3'→5') from the 3' terminal nucleobase that forms a base pair with the 5' terminal nucleotide on the antisense strand.

Embodiment 44. The RNAi agent of embodiment 43, wherein at least one targeting ligand is linked to an individual nucleotide at the 2' position of the ribose ring, the 3' position of the ribose ring, the 1' position of the ribose ring or to the nucleobase of the nucleotide, the 4' position of the ribose ring, or the 5' position of the nucleotide.

Embodiment 45. The RNAi agent of embodiment 44, wherein at least one targeting ligand is linked to the 2' position of the ribose ring of an individual nucleotide.

Embodiment 46. The RNAi agent of any one of embodiments 1-45, wherein the sense strand is between 18 and 49 nucleotides in length, and the antisense strand is between 18 and 49 nucleotides in length.

Embodiment 47. The RNAi agent of embodiment 46, wherein the sense strand and the antisense strand are each between 18 and 27 nucleotides in length.

Embodiment 48. The RNAi agent of embodiment 47, wherein the sense strand and the antisense strand are each between 18 and 24 nucleotides in length.

Embodiment 49. The RNAi agent of embodiment 48, wherein the sense strand and the antisense strand are each 21 nucleotides in length.

Embodiment 50. The RNAi agent of any one of embodiments 46-49, wherein the RNAi agent has two blunt ends.

Embodiment 51. The RNAi agent of any one of embodiments 1-50, wherein the sense strand comprises one or two terminal caps.

Embodiment 52. The RNAi agent of any one of embodiments 1-51, wherein the sense strand comprises one or two inverted abasic residues.

Embodiment 53. The RNAi agent of any one of embodiments 1-52, wherein the RNAi agent is comprised of a sense strand and an antisense strand that form a duplex having the structure of any one of the duplexes in Table 5.

Embodiment 54. The RNAi agent of any one of embodiments 51-53, wherein the sense strand further includes inverted abasic residues at the 3' end of the nucleotide sequence, at the 5' end of the nucleotide sequence, or at both the 3' end and the 5' end of the nucleotide sequence.

Embodiment 55. A HIF-2 alpha RNAi agent comprising:

(i) an antisense strand comprising at least 17 contiguous nucleotides differing by 0 or 1 nucleotides from any one of the sequences provided in Table 3; and (ii) a sense strand comprising a nucleotide sequence that is at least partially complementary to the antisense strand.

Embodiment 56. An RNAi agent capable of inhibiting expression of a HIF-2 alpha (EPAS1) gene comprising:

(i) an antisense strand that is between 18 and 49 nucleotides in length that is at least partially complementary to a HIF-2 alpha (EPAS1) gene (SEQ ID NO:1);

(ii) a sense strand that is at least partially complementary to the antisense strand;

(iii) a targeting ligand linked to the sense strand; and (iv) a PK enhancer linked to the sense strand.

Embodiment 57. The RNAi agent of embodiment 56, wherein the targeting ligand is linked to the 5' terminal end of the sense strand.

Embodiment 58. The RNAi agent of embodiment 56 or 57, wherein the PK enhancer is linked to the 3' terminal end of the sense strand.

Embodiment 59. The RNAi agent of any one of embodiments 56-58, wherein one or more targeting ligands are linked to one or more nucleotides of the sense strand.

Embodiment 60. The RNAi agent of embodiment 59, wherein 2 to 12 targeting ligands are linked to nucleotides of the sense strand.

Embodiment 61. The RNAi agent of any one of embodiments 56-60, wherein a tridentate targeting group comprised of three targeting ligands is linked to the 5' terminal end of the sense strand; a PK enhancer is linked to the 3' terminal end of the sense strand; and between 2 to 12 targeting ligands are linked to individual nucleotides of the sense strand.

Embodiment 62. The RNAi agent of embodiment 61, wherein the targeting ligands that are linked to individual nucleotides of the sense strand are linked at the 2' position of each respective nucleotide.

Embodiment 63. The RNAi agent of any one of embodiments 56-62, wherein targeting ligands are linked to nucleotides located at positions 2, 6, 15, and 19 (3' 4 5') from the first nucleotide that forms a base pair with the antisense strand.

Embodiment 64. The RNAi agent of any one of embodiments 56-62, wherein targeting ligands are linked to nucleotides located at positions 2, 4, 6, and 8 (3'→5') from the first nucleotide that forms a base pair with the antisense strand.

Embodiment 65. The RNAi agent of any one of embodiments 56-62, wherein targeting ligands are linked to nucleotides of the sense strand that are across from nucleotides 2, 4, 6, and 8 (5'→3') of the antisense strand.

Embodiment 66. The RNAi agent of any one of embodiments 56-65, wherein a tridentate targeting group comprising three targeting ligands is located at the 5' terminal end of the sense strand, the sense strand further includes two to four targeting ligands that are linked to nucleotides of the sense strand, and there are at least 10 nucleotides separating the tridentate targeting group at the 5' terminal end of the sense strand and the next closest targeting ligand that is attached to nucleotide.

Embodiment 67. The RNAi agent of embodiment 66, wherein four targeting ligands are linked to individual nucleotides of the sense strand.

Embodiment 68. The RNAi agent of any one of embodiments 56-67, wherein the targeting ligand is an integrin targeting ligand that includes a compound that has affinity for integrin alpha-v-beta-3.

Embodiment 69. The RNAi agent of any one of embodiments 56-68, wherein the PK enhancer is of the formula:

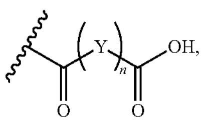

wherein Y is an optionally substituted saturated or unsaturated aliphatic chain and n is an integer from 5-25.

Embodiment 70. An RNAi agent comprising an antisense strand comprising the sequence usUfsusCfaUfgAfaAf-uCfgUfuAfcGfuUfsg (SEQ ID NO: 30), a sense strand comprising the sequence Y-(NH-C6)scsaacguaaCfGfA-fuuu$^{Z}$ca$^{Z}$ug$^{Z}$aa$^{Z}$sa(invAb)(6-S)-X (SEQ ID NO: 761), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; u$^{Z}$, a$^{Z}$, g$^{Z}$, and c$^{Z}$ represent uridine, adenosine, guanosine and cytidine, respectively, with a pharmacological moiety comprising Z linked at the 2' position of the nucleotide; Y-(NH-C6)s represents:

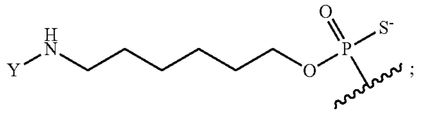

(invAb) represents:

linkage towards 5' end of oligonucleotide

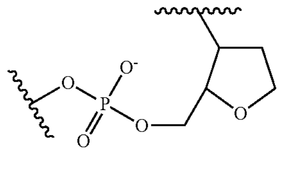 [SMILES: *OP(=O)([O-])OCC1OCCC1*]

linkage towards 3' end of oligonucleotide; (6-S) represents:

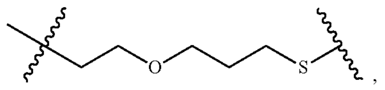 [SMILES: *CCOCCCS*]

and each X, Y and Z independently represents:

(i) a targeting group comprising one or more targeting ligands, wherein the targeting ligand is selected from the group consisting of: Structure 2a, Structure 2.11a, Structure 29a, and Structure 32a;

(ii) a targeting ligand having a structure selected from the group consisting of: Structure 2a, Structure 2.11a, Structure 29a, and Structure 32a; or (iii) a PK enhancer having a structure selected from the group consisting of C-18 diacid, C-18 triacid, Mal-$C_{17}$-vinyl-$PO_3$, and C20 acid.

Embodiment 71. The RNAi agent of embodiment 70, wherein each Z is a targeting ligand having a structure of Structure 2a:

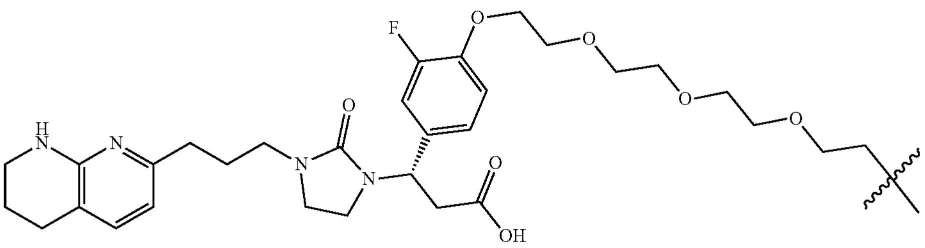 [SMILES: *CCOCCOCCOCCOc1ccc([C@H](CC(=O)O)N2CCN(CCCc3ccc4c(n3)NCCC4)C2=O)cc1F]

wherein  indicates the point of attachment.

Embodiment 72. The RNAi agent of embodiment 70, wherein each Z is a targeting ligand having a structure of Structure 2.11a:
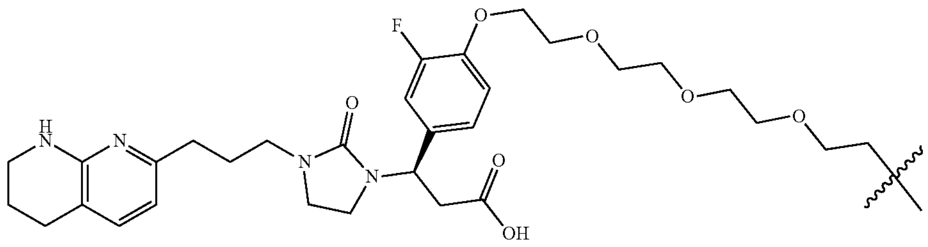 [SMILES: *CCOCCOCCOCCOc1ccc([C@@H](CC(=O)O)N2CCN(CCCc3ccc4c(n3)NCCC4)C2=O)cc1F]
wherein ⸾ indicates the point of attachment.
Embodiment 73. The RNAi agent of embodiment 70, wherein each Z is a targeting ligand having a structure of Structure 29a:
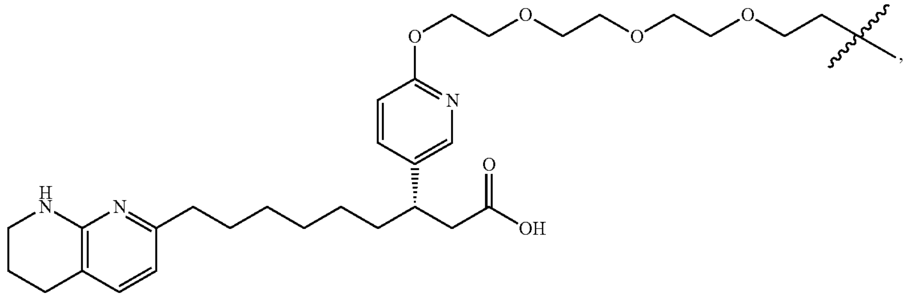 [SMILES: *CCOCCOCCOCCOc1ccc([C@@H](CCCCCCc2ccc3c(n2)NCCC3)CC(=O)O)cn1]
wherein ⸾ indicates the point of attachment.

Embodiment 74. The RNAi agent of embodiment 70, wherein each Z is a targeting ligand having a structure of Structure 32a:

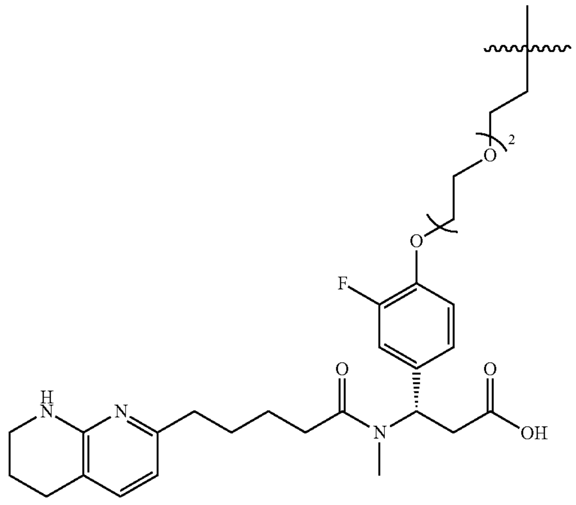

wherein ⌇ indicates the point of attachment.

Embodiment 75. The RNAi agent of any one of embodiments 70-74, wherein X is a PK enhancer having a structure of C-18 diacid:

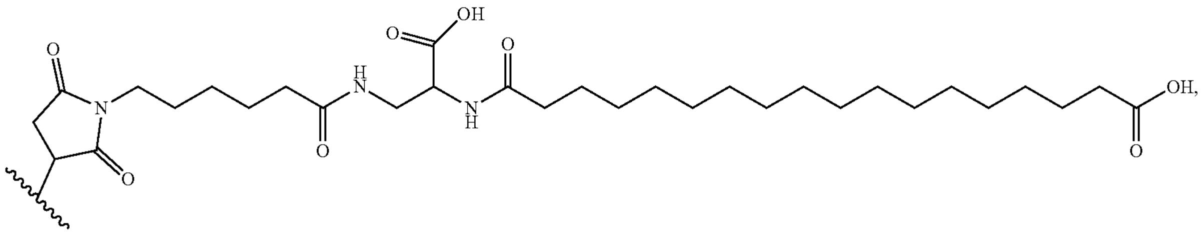 [SMILES: *C1CC(=O)N(CCCCCC(=O)NCC(NC(=O)CCCCCCCCCCCCCCCCC(=O)O)C(=O)O)C1=O]

wherein ⌇ indicates the point of attachment.

Embodiment 76. The RNAi agent of any one of embodiments 70-74, wherein X is a PK enhancer having a structure of Mal-C-18 triacid:

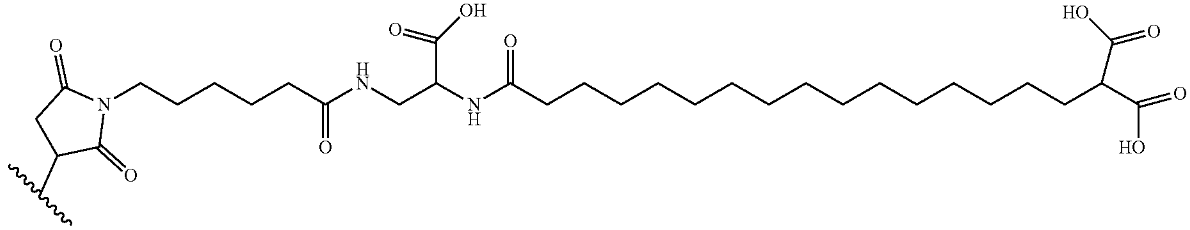 [SMILES: *C1CC(=O)N(CCCCCC(=O)NCC(NC(=O)CCCCCCCCCCCCCCCC(C(=O)O)C(=O)O)C(=O)O)C1=O]

wherein ⌇ indicates the point of attachment.

Embodiment 77. The RNAi agent of any one of embodiments 70-74, wherein X is a PK enhancer having a structure of Mal-C17-vinyl PO3:

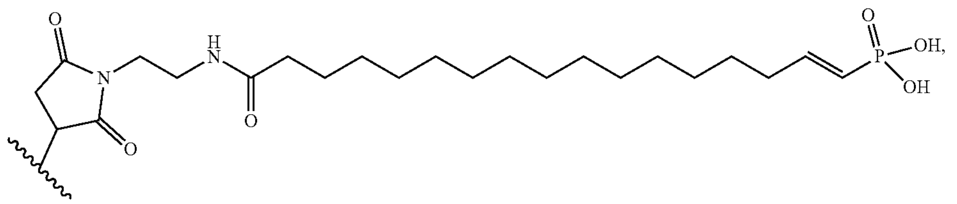 [SMILES: *C1CC(=O)N(CCNC(=O)CCCCCCCCCCCCCC/C=C/P(=O)(O)O)C1=O]

wherein ⌇ indicates the point of attachment.

Embodiment 78. The RNAi agent of any one of embodiments 70-74, wherein X is a PK enhancer having a structure of Mal-$C_{20}$ acid:

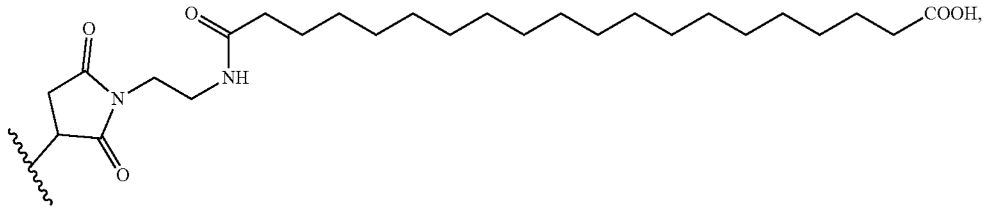 [SMILES: *C1CC(=O)N(CCNC(=O)CCCCCCCCCCCCCCCCCCC(=O)O)C1=O]

wherein ⌇ indicates the point of attachment.

Embodiment 79. The RNAi agent of any one of embodiments 70-78, wherein the RNAi agent includes 2, 3, 4, 5, 6, 7, 8, 9, or 10 targeting ligands.

Embodiment 80. The RNAi agent of embodiment 79, wherein the RNAi agent includes 7 targeting ligands.

Embodiment 81. The RNAi agent of embodiment 80, wherein Y is a targeting group having the structure of TriAlk 14:

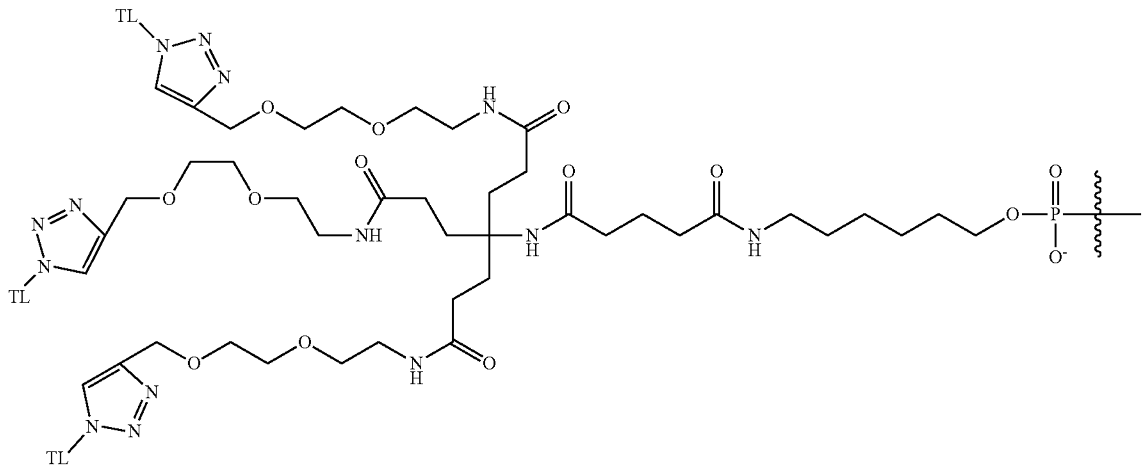

or TriAlk 14s:

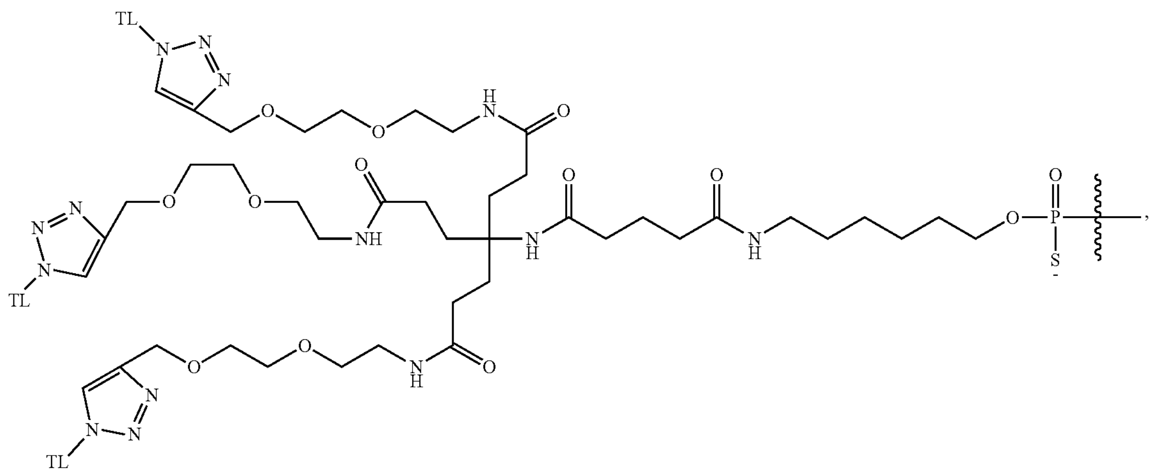

wherein TL comprises a targeting ligand selected from the group consisting of: Structure 2a, Structure 2.11a, Structure 29a, and Structure 32a.

Embodiment 82. The RNAi agent of embodiment 81, wherein each TL comprises Structure 2a:

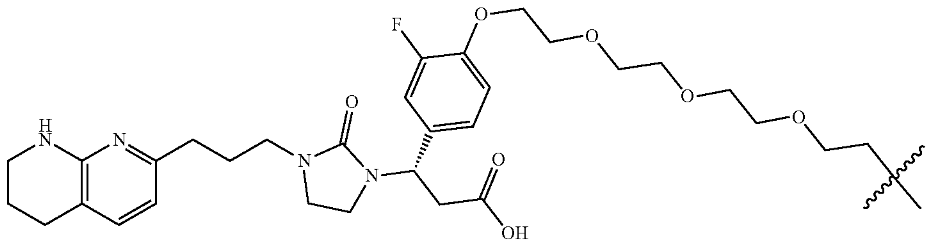 [SMILES: *CCOCCOCCOCCOc1ccc([C@H](CC(=O)O)N2CCN(CCCc3ccc4c(n3)NCCC4)C2=O)cc1F]

wherein ⌇ indicates the point of attachment.

Embodiment 83. The RNAi agent of embodiment 81, wherein each TL comprises Structure 2.11a:

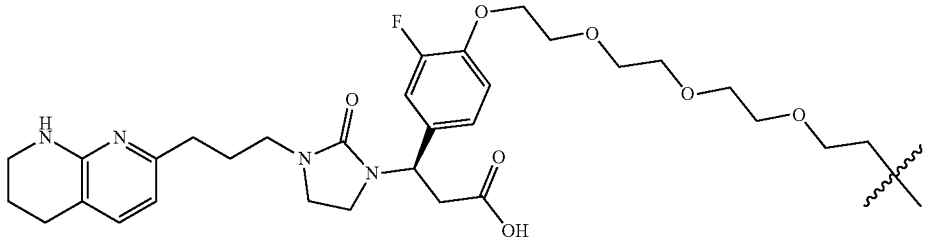 [SMILES: *CCOCCOCCOCCOc1ccc([C@@H](CC(=O)O)N2CCN(CCCc3ccc4c(n3)NCCC4)C2=O)cc1F]

wherein ⌇ indicates the point of attachment.

Embodiment 84. The RNAi agent of embodiment 81, wherein each TL comprises Structure 29a:

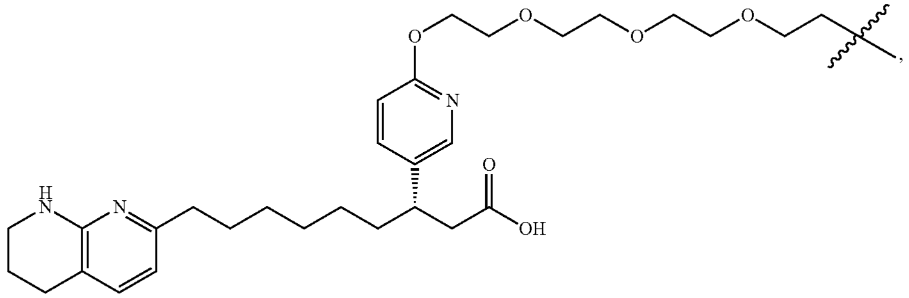 [SMILES: *CCOCCOCCOCCOc1ccc([C@@H](CCCCCCc2ccc3c(n2)NCCC3)CC(=O)O)cn1]

wherein indicates the point of attachment.

Embodiment 85. The RNAi agent of embodiment 81, wherein each TL comprises Structure 32a:

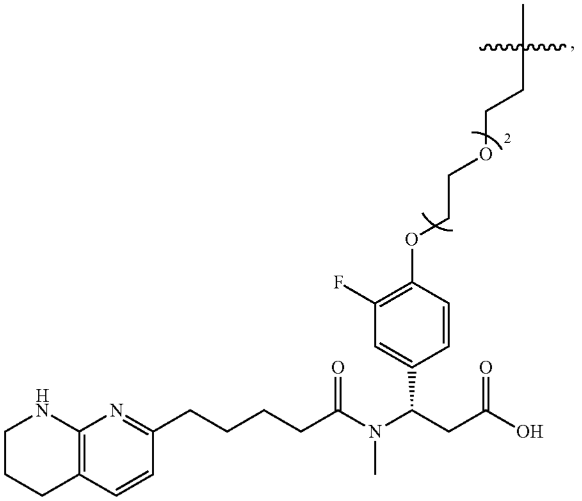

wherein indicates the point of attachment.

Embodiment 86. The RNAi agent of any one of embodiments 70-81, wherein the nucleotides of the antisense strand consist of the nucleotides of SEQ ID NO: 30.

Embodiment 87. The RNAi agent of any one of embodiments 70-82, wherein the nucleotides of the sense strand consist of the nucleotides of SEQ ID NO: 761.

Embodiment 88. A composition comprising the RNAi agent of any one of embodiments 1-88, wherein the composition comprises a pharmaceutically acceptable excipient.

Embodiment 89. The composition of embodiment 88, further comprising a second RNAi agent for inhibiting the expression of HIF-2 alpha.

Embodiment 90. The composition of embodiment 88 or 89, further comprising one or more additional therapeutics.

Embodiment 91. A method for inhibiting expression of a HIF-2 alpha (EPAS1) gene in a cell, the method comprising introducing into a cell an effective amount of an RNAi agent of any one of embodiments 1-88 or the composition of any one of embodiments 88-90.

Embodiment 92. The method of embodiment 91, wherein the cell is within a subject.

Embodiment 93. The method of embodiment 92, wherein the subject is a human subject.

Embodiment 94. The method of any one of embodiments 91-94, wherein the HIF2-alpha gene expression is inhibited by at least about 30%.

Embodiment 95. A method of treating a HIF2-alpha-related disease or disorder, the method comprising administering to a human subject in need thereof a therapeutically effective amount of the composition of any one of embodiments 88-90.

Embodiment 96. The method of embodiment 95, wherein the disease or disorder is cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preeclampsia, inflammation, chronic inflammation, neovascular diseases, or rheumatoid arthritis Embodiment 97. The method of embodiment 95 or 96, wherein the disease is clear cell renal cell carcinoma (ccRCC).

Embodiment 98. The method of any one of embodiments 91-97, wherein the RNAi agent is administered at a dose of about 3 mg/kg to about 80 mg/kg of body weight of the human subject.

Embodiment 99. The method of embodiment 98, wherein the RNAi agent is administered at a dose of about 5 mg/kg to about 20 mg/kg of body weight of the human subject.

Embodiment 100. The method of embodiment 98 or 99, wherein the RNAi agent is administered in a split dose, wherein about half of the desired daily amount is administered in an initial administration, and the remaining about half of the desired daily amount is administered approximately four hours after the initial administration.

Embodiment 101. The method of any one of embodiments 98-100, wherein the dose or doses of the RNAi agent is administered once a week.

Embodiment 102. The method of any one of embodiments 99-101, wherein the dose or split doses of the RNAi agent is administered biweekly (once every other week).

Embodiment 103. Use of the RNAi agent of any one of embodiments 1-88 or the composition according to any one of embodiments 88-90, for the treatment of a disease, disorder, or symptom that is mediated at least in part by HIF-2 alpha (EPAS1) gene expression.

Embodiment 104. Use according to embodiment 103, wherein the disease is ccRCC.

Embodiment 105. Use of the RNAi agent of any one of embodiments 1-88 or the composition according to any one of embodiments 88-90, for the preparation of a pharmaceutical composition for treating a disease, disorder, or symptom that is mediated at least in part by HIF-2 alpha (EPAS1) gene expression.

Embodiment 106. Use of embodiment 105, wherein the disease is ccRCC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent comprising an antisense strand comprising the sequence usUfsusCfaUfgAfaAfuCfgUfuAfcGfuUfsg (SEQ ID NO: 30), and a sense strand comprising the sequence Y-(NH-C6) scsaacguaaCfGfAfuuu$^{Z}$ca$^{Z}$ug$^{Z}$aa$^{Z}$sa (invAb) (6-S)-X (SEQ ID NO: 761), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; s represents a phosphorothioate linkage; $u^{Z}$, $a^{Z}$, $g^{Z}$, and $c^{Z}$ represent uridine, adenosine, guanosine and cytidine, respectively, with a pharmacological moiety comprising Z linked at the 2' position of the nucleotide; Y-(NH-C6) s represents:

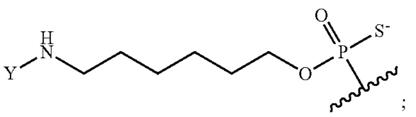
;

(invAb) represents:
linkage towards 5' end

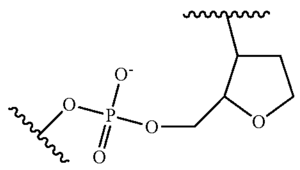 [SMILES: *OP(=O)([O-])OCC1OCCC1*]

linkage towards 3' end; (6-S) represents:

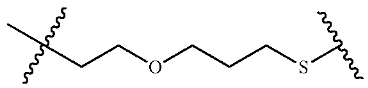
, and each X, Y and Z independently represents:

(i) a targeting group comprising one or more targeting ligands, wherein the targeting ligand is selected from the group consisting of: Structure 2a, Structure 2.11a, Structure 29a, and Structure 32a;

(ii) a targeting ligand having a structure selected from the group consisting of: Structure 2a, Structure 2.11a, Structure 29a, and Structure 32a; or (iii) a PK enhancer having a structure selected from the group consisting of C-18 diacid, C-18 triacid, Mal-$C_{17}$-vinyl-$PO_3$, and C20 acid.

2. The RNAi agent of claim 1, wherein each Z is a targeting ligand having a structure of Structure 2a:

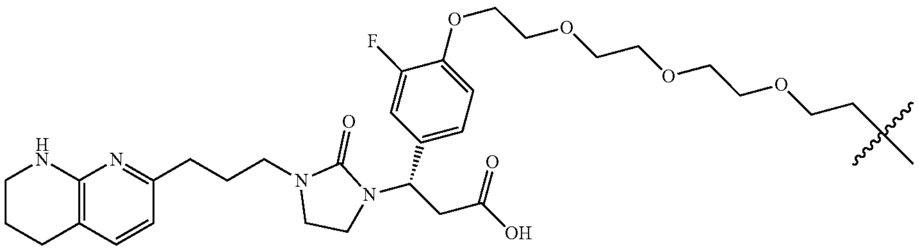 [SMILES: *CCOCCOCCOCCOc1ccc([C@H](CC(=O)O)N2CCN(CCCc3ccc4c(n3)NCCC4)C2=O)cc1F]

wherein ⌇ indicates the point of attachment.

3. The RNAi agent of claim 1, wherein each Z is a targeting ligand having a structure of Structure 2.11a:

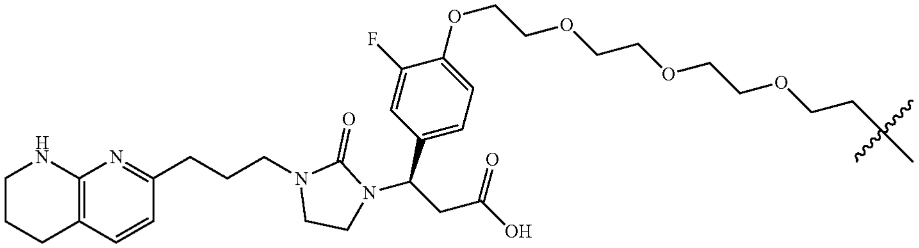 [SMILES: *CCOCCOCCOCCOc1ccc([C@@H](CC(=O)O)N2CCN(CCCc3ccc4c(n3)NCCC4)C2=O)cc1F]

wherein ⌇ indicates the point of attachment.

4. The RNAi agent of claim 1, wherein each Z is a targeting ligand having a structure of Structure 29a:

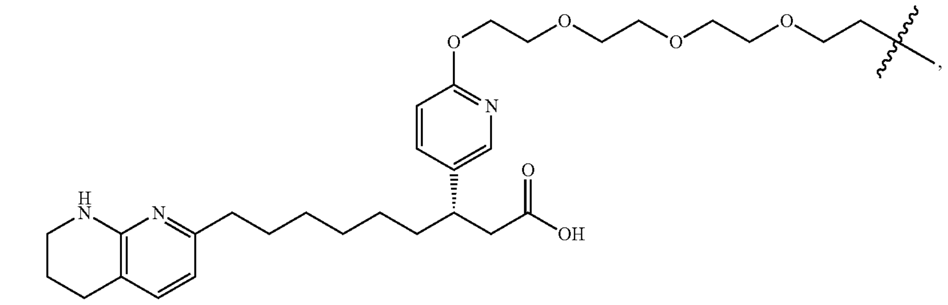 [SMILES: *CCOCCOCCOCCOc1ccc([C@@H](CCCCCCc2ccc3c(n2)NCCC3)CC(=O)O)cn1]

wherein ⌇ indicates the point of attachment.

5. The RNAi agent of claim 1, wherein each Z is a targeting ligand having a structure of Structure 32a:

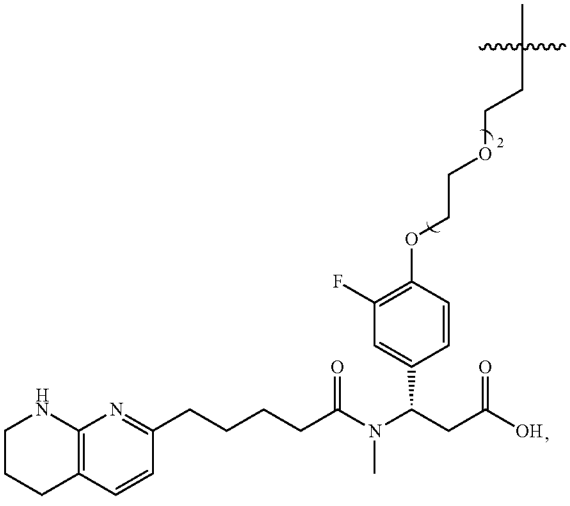 [SMILES: *CCOCCOc1ccc([C@H](CC(=O)O)N(C)C(=O)CCCCc2ccc3c(n2)NCCC3)cc1F]

wherein ⌇ indicates the point of attachment.

6. The RNAi agent of claim 1, wherein X is a PK enhancer having a structure of C-18 diacid:

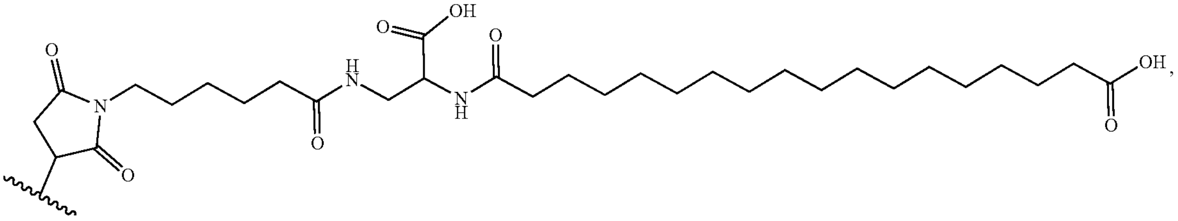 [SMILES: *C1CC(=O)N(CCCCCC(=O)NCC(NC(=O)CCCCCCCCCCCCCCCCC(=O)O)C(=O)O)C1=O]

wherein ⌇ indicates the point of attachment.

7. The RNAi agent of claim 1, wherein the RNAi agent includes 2, 3, 4, 5, 6, 7, 8, 9, or 10 targeting ligands.

8. The RNAi agent of claim 7, wherein the RNAi agent includes 7 targeting ligands.

9. The RNAi agent of claim 8, wherein Y is a targeting group having the structure of TriAlk 14:

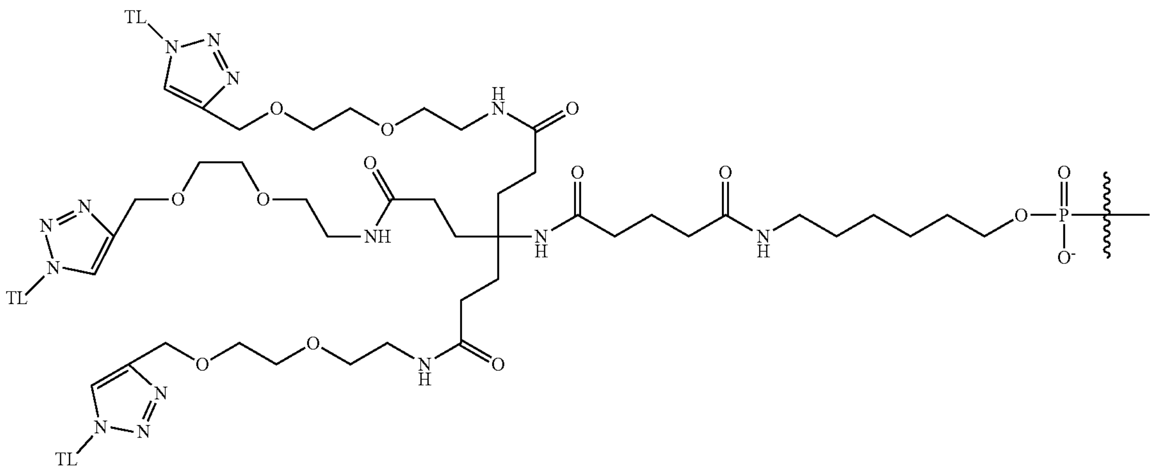

or TriAlk 14s:

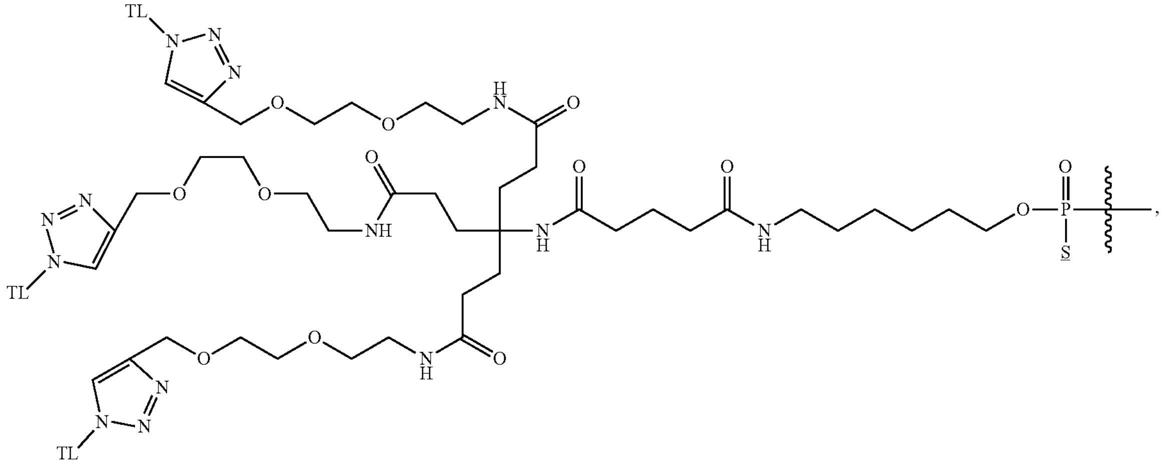

wherein TL comprises a targeting ligand selected from the group consisting of: Structure 2a, Structure 2.11a, Structure 29a, and Structure 32a.

10. The RNAi agent of claim 9, wherein each TL comprises Structure 2a:

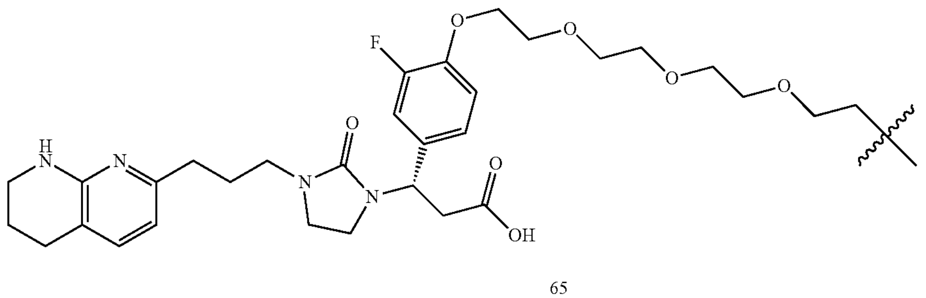

wherein ⌇ indicates the point of attachment.

11. The RNAi agent of claim 1, wherein the nucleotides of the antisense strand consist of the nucleotides of SEQ ID NO: 30.

12. The RNAi agent of claim 1, wherein the nucleotides of the sense strand consist of the nucleotides of SEQ ID NO: 761.

13. A composition comprising the RNAi agent of claim 1, wherein the composition comprises a pharmaceutically acceptable excipient.

14. The composition of claim 13, further comprising a second RNAi agent for inhibiting the expression of HIF-2 alpha.

15. The composition of claim 13, further comprising one or more additional therapeutics.

16. A method for inhibiting expression of a HIF-2 alpha (EPAS1) gene in a cell, the method comprising introducing into a cell an effective amount of an RNAi agent of claim 1.

17. The method of claim 16, wherein the HIF2-alpha gene expression is inhibited by at least about 30% in vivo.

18. A method of treating a HIF2-alpha-related disease or disorder, the method comprising administering to a human subject in need thereof a therapeutically effective amount of the composition of claim 13.

19. The method of claim 18, wherein the disease or disorder is cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preeclampsia, inflammation, chronic inflammation, neovascular diseases, or rheumatoid arthritis.

20. The method of claim 18, wherein the disease is clear cell renal cell carcinoma (ccRCC).

* * * * *